(12) United States Patent
Rose et al.

(10) Patent No.: US 11,929,171 B2
(45) Date of Patent: Mar. 12, 2024

(54) METHODS FOR EVALUATION AND TREATMENT OF GLYCEMIC DYSREGULATION AND ATHEROSCLEROTIC CARDIOVASCULAR DISEASE AND APPLICATIONS THEREOF

(71) Applicant: The Board of Trustees of the Leland Stanford Junior University, Stanford, CA (US)

(72) Inventors: Sophia Miryam Schüssler-Fiorenza Rose, Stanford, CA (US); Kevin Contrepois, Menlo Park, CA (US); Wenyu Zhou, Stanford, CA (US); Samson Mataraso, Stanford, CA (US); Tejaswini Mishra, Stanford, CA (US); Michael Snyder, Stanford, CA (US); Kegan Moneghetti, Stanford, CA (US); Francois Haddad, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 762 days.

(21) Appl. No.: 16/657,878

(22) Filed: Oct. 18, 2019

(65) Prior Publication Data
US 2020/0227166 A1    Jul. 16, 2020

Related U.S. Application Data

(60) Provisional application No. 62/845,161, filed on May 8, 2019, provisional application No. 62/814,746, filed (Continued)

(51) Int. Cl.
*G16H 50/20* (2018.01)
*G16B 5/00* (2019.01)
(Continued)

(52) U.S. Cl.
CPC .............. *G16H 50/20* (2018.01); *G16B 5/00* (2019.02); *G16H 10/40* (2018.01); *G16H 10/60* (2018.01);
(Continued)

(58) Field of Classification Search
CPC .................................................. G06Q 50/20–26
See application file for complete search history.

(56) References Cited

U.S. PATENT DOCUMENTS 5,045,694 A    9/1991 Beavis et al.
5,118,937 A    6/1992 Hillenkamp et al.
(Continued)

FOREIGN PATENT DOCUMENTS

WO    1993003151    2/1993
WO    WO-9410901 A1 *  5/1994    ......... A61B 5/14532
(Continued)

OTHER PUBLICATIONS

1000 Genomes Project Consortium, "A global reference for human genetic variation", Nature, vol. 526, Sep. 30, 2015, pp. 68-74, doi: 10.1038/nature15393.
(Continued)

*Primary Examiner* — Neal Sereboff
(74) *Attorney, Agent, or Firm* — KPPB LLP

(57) ABSTRACT

Methods to compute glycemia tests and applications thereof are described. Additional methods to compute risk of atherosclerotic cardiovascular disease and applications thereof are described. Generally, systems utilize analyte measurements to determine a glycemic status or cardiovascular disease risk, which can be used as a basis to treat individuals.

20 Claims, 37 Drawing Sheets
Specification includes a Sequence Listing.

Related U.S. Application Data on Mar. 6, 2019, provisional application No. 62/757,629, filed on Nov. 8, 2018, provisional application No. 62/747,488, filed on Oct. 18, 2018.

(51) Int. Cl.
| | |
|---|---|
| *G16H 10/40* | (2018.01) |
| *G16H 10/60* | (2018.01) |
| *G16H 20/10* | (2018.01) |
| *G16H 50/70* | (2018.01) |
| *G16H 70/60* | (2018.01) |

(52) U.S. Cl.
CPC ............. *G16H 20/10* (2018.01); *G16H 50/70* (2018.01); *G16H 70/60* (2018.01)

(56) References Cited

U.S. PATENT DOCUMENTS

| | | | |
|---|---|---|---|
| 5,565,332 A | 10/1996 | Hoogenboom et al. | |
| 5,981,180 A | 11/1999 | Chandler et al. | |
| 6,524,793 B1 | 2/2003 | Chandler et al. | |
| 7,445,844 B2 | 11/2008 | Chandler et al. | |
| 10,550,168 B2 | 2/2020 | Kim et al. | |
| 2019/0317079 A1* | 10/2019 | Trenholm | G16C 20/70 |

FOREIGN PATENT DOCUMENTS

| | | | |
|---|---|---|---|
| WO | 1994013804 | 6/1994 | |
| WO | WO-9532416 A1 * | 11/1995 | ......... A61B 5/14532 |
| WO | 2022104394 A1 | 5/2022 | |

OTHER PUBLICATIONS

Bolyen et al., "Reproducible, interactive, scalable and extensible microbiome data science using QIIME 2", Nature Biotechnology 37: 852-857, https://qiime2.org/, retrieved from: https://web.archive.org/web/20180924171644/https://qiime2.org/, Sep. 24, 2018, 2 pgs.

Brown et al., "A Novel Algorithm for Scalable and Accurate Bayesian Network Learning", MEDINFO, Studies in Health Technology and Informatics, vol. 107, 2004, pp. 711-715.

Buhr, "Apple's Watch isn't the first with an EKG reader but it will matter to more consumers", TechCrunch, Sep. 12, 2018, Retrieved from: https://techcrunch.com/2018/09/12/apples-watch-isnt-the-first-with-an-ekg-reader-but-it-will-matter-to-more-consumers/.

Callahan et al., "DADA2: High-resolution sample inference from Illumina amplicon data", Nature Methods, vol. 13, May 23, 2016, pp. 581-583, DOI:10.1038/NMETH.3869.

Callahan et al., "Exact sequence variants should replace operational taxonomic units in marker-gene data analysis", The ISME Journal, 2017, vol. 11, pp. 2639-2643, published online Jul. 21, 2017, doi:10.1038/ismej.2017.119.

Cano, "Bench-to-bedside review: Glucose production from the kidney", Critical Care, vol. 6, No. 4, Jun. 7, 2002, pp. 317-321.

Caporaso et al., "QIIME allows analysis of high-throughput community sequencing data", Nature Methods, May 2010, vol. 7, No. 5, published online Apr. 11, 2010, pp. 335-336, DOI:10.1038/NMETH.F303.

Cauwenberghs et al., "Relation of Insulin Resistance to Longitudinal Changes in Left Ventricular Structure and Function in a General Population", Journal of the American Heart Association, vol. 7, No. 7, e008315, Mar. 24, 2018, 24 pgs., DOI: 10.1161/JAHA.117.008315.

Cersosimo et al., "Assessment of Pancreatic β-Cell Function: Review of Methods and Clinical Applications", Current Diabetes Reviews, vol. 10, No. 1, Jan. 2014, pp. 2-42.

Chang et al., "Second-generation PLINK: rising to the challenge of larger and richer datasets", GigaScience, 2015, vol. 4, No. 7, published online, Feb. 25, 2015, 16 pgs., DOI:10.1186/s13742-015-0047-8.

Charbonneau et al., "Pretreatment Circulating Serum Cytokines Associated with Follicular and Diffuse Large B-Cell Lymphoma: A Clinic-Based Case-Control Study", Cytokine, vol. 60, No. 3, Dec. 2012, pp. 882-889, doi:10.1016/j.cyto.2012.08.028.

Chen et al., "Monocytes from Metabolic Syndrome Subjects Exhibit a Proinflammatory M1 Phenotype", Metabolic Syndrome and Related Disorders, vol. 12, No. 7, Aug. 25, 2014, pp. 362-366, DOI:10.1089/met.2014.0017.

Chen et al., "Personal Omics Profiling Reveals Dynamic Molecular and Medical Phenotypes", Cell, Mar. 16, 2012, vol. 148, pp. 1293-1307, DOI:10.1016/j.cell.2012.02.009.

Collins et al., "A New Initiative on Precision Medicine", The New England Journal of Medicine, Feb. 26, 2015, vol. 372, No. 9, pp. 793-795, DOI:10.1056/NEJMp1500523.

Coloma et al., "Design and production of novel tetravalent bispecific antibodies", Nature Biotechnology, Feb. 1997, vol. 15, pp. 159-163.

Contrepois et al., "Optimized Analytical Procedures for the Untargeted Metabolomic Profiling of Human Urine and Plasma by Combining Hydrophilic Interaction (HILIC) and Reverse-Phase Liquid Chromatography (RPLC)-Mass Spectrometry", Molecular & Cellular Proteomics, vol. 14, No. 6, Jun. 2015, pp. 1684-1695, DOI:10.1074/mcp.M114.046508.

Cote et al., "Generation of human monoclonal antibodies reactive with cellular antigens", Proceedings of the National Academy, vol. 80, Apr. 1983, pp. 2026-2030.

Cross et al., "Coronary risk assessment among intermediate risk patients using a clinical and biomarker based algorithm developed and validated in two population cohorts", Current Medical Research and Opinion, vol. 28, No. 11, Nov. 2012, pp. 1819-1830, doi:10.1185/03007995.2012.742878.

Ding et al., "CXCL9: evidence and contradictions for its role in tumor progression", Cancer Medicine, vol. 5, No. 11, Oct. 10, 2016, pp. 3246-3259, doi: 10.1002/cam4.934.

Dinneen et al., "Carbohydrate Metabolism in Non-Insulin-Dependent Diabetes Mellitus", The New England Journal of Medicine, vol. 327, No. 10, Sep. 3, 1992, pp. 707-713.

Douglas et al., "The Future of Cardiac Imaging: Report of a Think Tank Convened by the American College of Cardiology", JACC: Cardiovascular Imaging, vol. 9, No. 10, Oct. 2016, pp. 1211-1223, http://dx.doi.org/10.1016.02.027.

DPPR Group, "The Diabetes Prevention Program (DPP): Description of lifestyle intervention", Diabetes Care, vol. 25, No. 12, Dec. 2002, pp. 2165-2171.

Dutta et al., "Myocardial infarction accelerates atherosclerosis", Nature, Jul. 19, 2012, vol. 487, No. 7407, pp. 325-329, doi:10.1038/nature11260.

Eckhart et al., "Metabolomics as a Key Integrator for "Omic" Advancement of Personalized Medicine and Future Therapies", Clinical and Translational Science, vol. 5, No. 3, Jun. 11, 2012, pp. 285-288, DOI: 10.1111/j.1752-8062.2011.00388.

Elkind et al., "Interleukin-2 levels are associated with carotid artery intima-media thickness", Atherosclerosis, vol. 180, No. 1, May 1, 2005, pp. 181-187.

Fadini et al., "An unbalanced monocyte polarisation in peripheral blood and bone marrow of patients with type 2 diabetes has an impact on microangiopathy", Diabetologia, 2013, vol. 56, published online Apr. 26, 2013, pp. 1856-1866, DOI: 10.1007/s00125-013-2918-9.

Fruchterman et al., "Graph Drawing by Force-directed Placement", Journal of Software: Practice and Experience, vol. 21, No. 11, Nov. 1991, pp. 1129-1164.

Go et al., "Determining the Clinical Significance of Monoclonal Gammopathy of Undetermined Significance: A SEER-Medicare Population Analysis", Clinical Lymphoma, Myeloma, and Leukemia, vol. 15, No. 3, Mar. 1, 2015, pp. 177-186.e4, doi:10.1016/j.clml.2014.09.004.

Godsland et al., "Loss of beta cell function as fasting glucose increases in the non-diabetic range", Diabetologia, 2004, vol. 47, No. 7, pp. 1157-1166, published online Jul. 13, 2004, DOI: 10.1007/s00125-004-1454-z.

Goff et al., "2013 ACC/AHA Guideline on the Assessment of Cardiovascular Risk", Circulation, vol. 129[suppl 2], Jun. 24, 2014, pp. S49-S73, DOI: 10.1161/01.cir.0000437741.48606.98.

(56) References Cited

OTHER PUBLICATIONS

Haabeth et al., "Inflammation driven by tumour-specific Th1 cells protects against B-cell cancer", Nature Communications, vol. 2, No. 240, Mar. 15, 2011, 12 pgs., DOI:10.1038/ncomms1239.

Hall et al., "Glucotypes reveal new patterns of glucose dysregulation", PLOS Biology, vol. 16, No. 7, e2005143, Jul. 24, 2018, 23 pgs., https://doi.org/10.1371/journal.pbio.2005143.

Hall et al., "Polymorphisms in Catechol-O-Methyltransferase Modify Treatment Effects of Aspirin on Risk of Cardiovascular Disease", Arteriosclerosis, Thrombosis, and Vascular Biology, vol. 34, No. 9, Sep. 2014, pp. 2160-2167, DOI:10.1161/ATVBAHA.114.303845.

Hamilton, "GM-CSF in inflammation and autoimmunity", Cell Press: Trends in Immunology, vol. 23, No. 8, Aug. 1, 2002, pp. 403-408.

Hovorka et al., "ISEC: a program to calculate insulin secretion", Computer Methods and Programs in Biomedicine, vol. 50, No. 3, Aug. 1996, pp. 253-264.

Ahlqvist et al., "Novel subgroups of adult-onset diabetes and their association with outcomes: a data-driven cluster analysis of six variables", The Lancet Diabetes & Endocrinology, vol. 6, No. 5, May 1, 2018, pp. 361-369, published online Mar. 1, 2018, http://dx.doi.org/10.1016/s2213-8587(18)30051-2.

American Diabetes Association, "8. Pharmacologic Approaches to Glycemic Treatment: Standards of Medical Care in Diabetes", Diabetes Care, vol. 41, Supplement 1, Jan. 2018, pp. S73-S85, https://doi.org/10.2337/dc18-S008.

Andrus et al., "2013 ACC/AHA Guideline on the Assessment of Cardiovascular Risk", Journal of the American College of Cardiology, vol. 63, No. 25, Jul. 1, 2014, p. 2886s.

Arena et al., "Technical Considerations Related to the Minute Ventilation/Carbon Dioxide Output Slope in Patients with Heart Failure", Chest, vol. 124, No. 2, Aug. 2003, pp. 720-727.

Beckonert et al., "Metabolic profiling, metabolomic and metabonomic procedures for NMR spectroscopy of urine, plasma, serum and tissue extracts", Nature Protocols, vol. 2, No. 11, 2007, pp. 2692-2703, published online Oct. 25, 2007, doi:10.1038/nprot.200.376.

Bell et al., "Hepatocyte Growth Factor Is Positively Associated with Risk of Stroke: The MESA (Multi-Ethnic Study of Atherosclerosis)", Stroke, vol. 47, No. 11, Nov. 2016, pp. 2689-2694, DOI: 10.1161/STROKEAHA.116.014172.

Berry et al., "Xanthine oxidoreductase and cardiovascular disease: molecular mechanisms and pathophysiological implications", The Journal of Physiology, vol. 555, Part 3, Apr. 2004, pp. 589-606, first published online Dec. 23, 2003, DOI: 10.1113/jphysiol.2003.055913.

Bokulich et al., "Optimizing taxonomic classification of marker-gene amplicon sequences with QIIME 2's q2-feature-classifier plugin", Microbiome, vol. 6, No. 90, May 17, 2018, 17 pgs., https://doi.org/10.1186/s40168-018-0470-z.

International Search Report and Written Opinion for International Application No. PCT/US2021/072445, Search completed Feb. 17, 2022, dated Apr. 6, 2022, 27 Pgs.

Hu et al., "Elevated Risk of Cardiovascular Disease Prior to Clinical Diagnosis of Type 2 Diabetes", Diabetes Care, vol. 25, No. 7, Jul. 2002, pp. 1129-1134.

Hyotylainen, "Novel methodologies in metabolic profiling with a focus on molecular diagnostic applications", Expert Review of Molecular Diagnostics, vol. 12, No. 5, Jun. 2012, pp. 527-538, DOI: 10.1586/erm.12.33.

IHMP Research Network Consortium, "The Integrative Human Microbiome Project: Dynamic Analysis of Microbiome-Host Omics Profiles during Periods of Human Health and Disease", Cell Host & Microbe, vol. 16, No. 3, Sep. 10, 2014, pp. 276-289, DOI: http://dx.doi.org/10.1016/j.chom.2014.08.014.

Iikuni et al., "Leptin and Inflammation", Current Immunology Reviews, vol. 4, May 1, 2008, pp. 70-79, doi:10.2174/157339508784325046.

Johnson et al., "Histidine Rich Glycoprotein and Cancer: A Multifaceted Relationship", Anticancer Research, vol. 34, No. 2, Feb. 2014, pp. 593-603.

Kamburov et al., "Integrated pathway-level analysis of transcriptomics and metabolomics data with IMPaLA", Bioinformatics, 2011, vol. 27, No. 20, pp. 2917-2918, Advance Access publication Sep. 4, 2011, doi:10.1093bioinformatics/btr499.

Kaminsky et al., "Reference Standards for Cardiorespiratory Fitness Measured with Cardiopulmonary Exercise Testing Using Cycle Ergometry: Data from the Fitness Registry and the Importance of Exercise National Database (FRIEND) Registry", Mayo Clinic Proceedings, Feb. 2017, vol. 92, No. 2, Feb. 2017, pp. 1-6, http://dx.doi.org/10.1016/j.marocp.2016.10.003.

Kanat et al., "The Relationship Between β-Cell Function and Glycated Hemoglobin: Results from the Veterans Administration Genetic Epidemiology Study", Diabetes Care, Apr. 2011, vol. 34, No. 4, pp. 1006-1010, published online Feb. 25, 2011, DOI: 10.2337/dc10-1352.

Kang et al., "Antibody redesign by chain shuffling from random combinatorial immunoglobulin libraries", Proceedings of the National Academy of Sciences of the United States of America, Dec. 1991, vol. 88, pp. 11120-11123.

Kim et al., "Isolated Impaired Fasting Glucose and Peripheral Insulin Sensitivity: Not a simple relationship", Diabetes Care, Feb. 2008, vol. 31, No. 2, pp. 347-352, DOI: 10.2337/dc07-1574.

Kingsmore, "Multiplexed protein measurement: technologies and applications of protein and antibody arrays", Nature Reviews Drug Discovery, vol. 5, No. 4, Apr. 2006, pp. 310-321.

Klok et al., "The role of leptin and ghrelin in the regulation of food intake and body weight in humans: a review", Obesity Reviews, Aug. 24, 2006, vol. 8, No. 1, pp. 21-34, doi: 10.1111/j.1467-789X.2006.00270.x.

Kohler et al., "Continuous cultures of fused cells secreting antibody of predefined specificity", Nature, Aug. 7, 1975, vol. 256, pp. 495-497.

Kraly et al., "Review: Microfluidic applications in metabolomics and metabolic profiling", Analytica Chimica Acta, Oct. 19, 2009, vol. 653, No. 1, pp. 23-35, doi:10.1016/j.aca.2009.08.037.

Kusters et al., "Cytokines and Immune Responses in Murine Atherosclerosis", Methods in Molecular Biology, Jan. 2015, vol. 1339, pp. 17-40, DOI: 10.1007/978-1-4939-2929-0-2.

Kuznetsova et al., "Additive Prognostic Value of Left Ventricular Systolic Dysfunction in a Population-Based Cohort", Circulation: Cardiovascular Imaging, Jul. 2016, vol. 9, No. 7, 10 pgs., DOI: 10.1161/CIRCIMAGING.116.004661.j.

Kuznetsova et al., "Longitudinal Changes in Left Ventricular Diastolic Function in a General Population", Circulation: Cardiovascular Imaging, vol. 8, No. 4, Apr. 2015, 9 pgs., DOI: 10.1161/CIRCIMAGING.114.002882.

Kwo et al., "ACG Clinical Guideline: Evaluation of Abnormal Liver Chemistries", American Journal of Gastroenterology, Jan. 2017, vol. 112, pp. 18-35, published online Dec. 20, 2016, doi:10.1038/ajg.2016.517.

Lagani et al., "Feature Selection with the R Package MXM: Discovering Statistically Equivalent Feature Subsets", Journal of Statistical Software, Sep. 5, 2017, vol. 80, No. 7, 25 pgs., doi: 10.18637/jss.v080.i07.

Lam et al., "Detecting and annotating genetic variations using the HugeSeq pipeline", Nature Biotechnology, Mar. 7, 2012, vol. 30, pp. 226-229, doi:10.1038/nbt2134.

Lang et al., "Recommendations for Cardiac Chamber Quantification by Echocardiography in Adults: An Update from the American Society of Echocardiography and the European Association of Cardiovascular Imaging", Journal of the American Society of Echocardiography, Jan. 2015, vol. 28, No. 1, pp. 1-39, http://dx.doi.org/10.1016/j.echo.2014.10.003.

Lee et al., "Cost-Effectiveness of Using High-Sensitivity C-Reactive Protein to Identify Intermediate- and Low-Cardiovascular-Risk Individuals for Statin Therapy", Circulation, Oct. 12, 2010, vol. 122, pp. 1478-1487, DOI: 10.1161/CIRCULATIONAHA.110.947960.

Lee et al., "Validity of the international physical activity questionnaire short form (IPAQ-SF): A systematic review", International Journal of Behavioral Nutrition and Physical Activity, Oct. 21, 2011, vol. 8, No. 115, 11 pgs., http://ijbnpa.org/content/8/1/115.

(56) References Cited

OTHER PUBLICATIONS

Levy et al., "Prognostic Implications of Echocardiographically Determined Left Ventricular Mass in the Framingham Heart Study", The New England Journal of Medicine, May 31, 1990, vol. 322, No. 22, pp. 1561-1566.

Li et al., "Decoding the Genomics of Abdominal Aortic Aneurysm", Cell, Sep. 6, 2018, vol. 174, pp. 1361-1372, https://doi.org/10.1016/j.cell.2018.07.021.

Li et al., "Digital Health: Tracking Physiomes and Activity Using Wearable Biosensors Reveals Useful Health-Related Information", PLoS Biology, Jan. 12, 2017, vol. 15, No. 1, 30 pgs., DOI:10.1371/journal.pbio.2001402.

Malik et al., "Multiancestry genome-wide association study of 520,000 subjects identifies 32 loci associated with stroke and stroke subtypes", Nature Genetics, Mar. 12, 2018, vol. 50, No. 4, pp. 524-537, doi:10.1038/s41588-018-0058-3.

Mallender et al., "Construction, Expression, and Activity of a Bivalent Bispecific Single-chain Antibody", The Journal of Biological Chemistry, Jan. 7, 1994, vol. 269, No. 1, pp. 199-206.

Matsuda et al., "Insulin sensitivity indices obtained from oral glucose tolerance testing: comparison with the euglycemic insulin clamp", Diabetes Care, Sep. 1999, vol. 22, No. 9, pp. 1462-1470.

Mcclelland et al., "10-Year Coronary Heart Disease Risk Prediction Using Coronary Artery Calcium and Traditional Risk Factors: Derivation in the MESA (Multi-Ethnic Study of Atherosclerosis) With Validation in the HNR (Heinz Nixdorf Recall) Study and the DHS (Dallas Heart Study", Journal of the American College of Cardiology, Oct. 13, 2015, vol. 66, No. 15, pp. 1643-1653, http://dx.doi.org/10.1016/j.jacc.2015.08.035.

Mcconnell et al., "Feasibility of Obtaining Measures of Lifestyle From a Smartphone App: The MyHeart Counts Cardiovascular Health Study", JAMA Cardiology, Jan. 2017, vol. 2, No. 1, pp. 67-76, published online Dec. 14, 2016, doi:10.1001/jamacardio.2016.4395.

Mclaughlin et al., "Is There a Simple Way to Identify Insulin-Resistant Individuals at Increased Risk of Cardiovascular Disease?", The American Journal of Cardiology, Aug. 1, 2005, vol. 96, No. 3, pp. 399-404, doi:10.1016/j.amjcard.2005.03.085.

Mclaughlin et al., "Use of Metabolic Markers to Identify Overweight Individuals Who Are Insulin Resistant", Annals of Internal Medicine, Nov. 18, 2003, vol. 139, No. 10, pp. 802-809.

Mitchell et al., "Arterial Stiffness and Cardiovascular Events: The Framingham Heart Study", Circulation, Feb. 2, 2010, vol. 121, No. 4, pp. 505-511, DOI: 10.1161/CIRCULATIONAHA.109.886655.

Moneghetti et al., "Applying current normative data to prognosis in heart failure: The Fitness Registry and the Importance of Exercise National Database (FRIEND)", International Journal of Cardiology, Jul. 15, 2018, vol. 263, pp. 75-79, doi:10.1016/j.ijcard.2018.02.102.

Montagna, "Using SAS to Manage Biological Species Data and Calculate Diversity Indices", SCSUG Educational Forum, Nov. 2014, 5 pgs.

Morrison et al., "Chimeric human antibody molecules: Mouse antigen-binding domains with human constant region domains", Proceedings of the National Academy of Sciences of the United States of America, Nov. 1984, vol. 81, pp. 6851-6855.

Mothe-Satney et al., "Adipocytes Secrete Leukotrienes: Contribution to Obesity-Associated Inflammation and Insulin Resistance in Mice", Diabetes, Sep. 2012, vol. 61, pp. 2311-2319, DOI: 10.2337/db11-1455.

O'Connell, "Recent advances in metabolomics in oncology", Bioanalysis, Feb. 2012, vol. 4, No. 4, pp. 431-451, DOI:10.4155/BIO.11.326.

Omer et al., "Role of Cytokine Gene Score in Risk Prediction of Premature Coronary Artery Disease", Genetic Testing and Molecular Biomarkers, Nov. 1, 2016, vol. 20, No. 11, pp. 685-691, DOI: 10.1089/gtmb.2016.0108.

Orlandi et al., "Cloning immunoglobulin variable domains for expression by the polymerase chain reaction", Proceedings of the National Academy of Sciences of the United States of America, May 1989, vol. 86, pp. 3833-3837.

Parhofer, "Interaction between Glucose and Lipid Metabolism: More than Diabetic Dyslipidemia", Diabetes and Metabolism Journal, Oct. 22, 2015, vol. 39, pp. 353-362, http://dx.doi.org/10.4093/dmj.2015.39.5.353.

Pearson et al., "Genetic cause of hyperglycemia and response to treatment in diabetes", The Lancet: Mechanisms of Disease, Oct. 18, 2003, vol. 362, pp. 1275-1281.

Perkins et al., "Precision medicine screening using whole-genome sequencing and advanced imaging to identify disease risk in adults", Proceedings of the National Academy of Sciences of the United States of America, Apr. 3, 2018, vol. 115, No. 14, pp. 3686-3691, published online Mar. 19, 2018, www.pnas.org/cgi/doi/10.1073/pnas.1706096114.

Piening et al., "Integrative Personal Omics Profiles during Periods of Weight Gain and Loss", Cell Systems, Feb. 28, 2018, vol. 6, pp. 157-170, https://doi.org/10.1016/j.cels.2017.12.013.

Porez et al., "Bile acid receptors as targets for the treatment of dyslipidemia and cardiovascular disease", Journal of Lipid Research, Sep. 2012, vol. 53, pp. 1723-1737, published, JLR Papers in Press, May 1, 2012, DOI: 10.1194/jlr.R024794.

Price et al., "A wellness study of 108 individuals using personal, dense, dynamic data clouds", Nature Biotechnology, Aug. 2017, vol. 35, No. 8, pp. 747-756, doi:1038/nbt.3870.

Purcell et al., "PLINK: A Tool Set for Whole-Genome Association and Population-Based Linkage Analyses", The American Journal of Human Genetics, Sep. 2007, vol. 81, pp. 559-575, DOI: 10.1086/519795.

Reidy et al., "Leptin: an essential regulator of lipid metabolism", Comparative Biochemistry and Physiology Part A: Molecular & Integrative Physiology, Mar. 2000, vol. 125, pp. 285-298.

Ridker et al., "Antiinflammatory Therapy with Canakinumab for Atherosclerotic Disease", The New England Journal of Medicine, Sep. 21, 2017, vol. 377, No. 12, pp. 1119-1131, DOI: 10.1056/NEJMoa1707914.

Rolny et al., "HRG Inhibits Tumor Growth and Metastasis by Inducing Macrophage Polarization and Vessel Normalization through Downregulation of PlGF", Cancer Cell, Jan. 18, 2011, vol. 19, pp. 31-44, DOI: 10.1016/j.ccr.2010.11.009.

Rusling et al., "Measurement of biomarker proteins for point-of-care early detection and monitoring of cancer", Analyst, Jul. 8, 2010, vol. 135, pp. 2496-2511, DOI: 10.1039/c0an002041.

Sane et al., "Roles of transglutaminases in cardiac and vascular diseases", Frontiers in Bioscience, Jan. 1, 2007, vol. 12, pp. 2530-2545.

Schnitzler et al., "The Role of (Modified) Lipoproteins in Vascular Function: A Duet Between Monocytes and the Endothelium", Current Medicinal Chemistry, 2018, vol. 25, pp. 1-15, DOI: 10.2174/0929867325666180316121015.

Selvin et al., "Diabetes Mellitus, Prediabetes, and Incidence of Subclinical Myocardial Damage", Circulation, Oct. 14, 2014, vol. 130, pp. 1374-1382, DOI: 10.1161/CIRCULATIONAHA.114.010815.

Shannon et al., "Cytoscape: A Software Environment for Integrated Models of Biomolecular Interaction Networks", Genome Research, Dec. 2003, vol. 13, pp. 2498-2504, http://www.genome.org/cgi/doi/10.1101/gr.1239303.

Simmons et al., "Prophylactic and Therapeutic Efficacy of Human Monoclonal Antibodies against H5N1 Influenza", PLoS Medicine, May 29, 2007, vol. 4, No. 5, e178, pp. 0928-0936, doi:10.1371/journal.pmed.0040178.

Slavich et al., "Assessing Lifetime Stress Exposure Using the Stress and Adversity Inventory for Adults (Adult STRAIN): An Overview and Initial Validation", Psychosomatic Medicine, Jan. 2018, vol. 80, pp. 17-27, DOI:10.1097/PSY0000000000000534.

Smith, "In adults without CVD, the MESA score, including coronary artery calcium, predicted 10-y risk for CHD events", Annals of Internal Medicine, Mar. 15, 2016, vol. 164, No. 6, JC35, pp. 1643-1653, doi: 10.7326/ACPJC-2016-164-6-035.

Tsamardinos et al., "The max-min hill-climbing Bayesian network structure learning algorithm", Machine Learning, 2006, vol. 65, pp. 31-78, published online Mar. 28, 2006.

Turesson et al., "Monoclonal gammopathy of undetermined significance and risk of lymphoid and myeloid malignancies: 728 cases

(56) References Cited

OTHER PUBLICATIONS followed up to 30 years in Sweden", Blood, Jan. 16, 2014, vol. 123, No. 3, pp. 338-345, prepublished online as Blood First Edition paper, Nov. 12, 2013, DOI: 10.1182/blood-2013-05-505487.
Tyanova et al., "The Perseus computational platform for comprehensive analysis of (prote)omics data", Nature Methods, Jun. 27, 2016, vol. 13, No. 9, pp. 731-740, DOI: 10.1038/nmeth.3901.
Upadhya et al., "Atherogenic Effect of Interleukin-2 and Antiatherogenic Effect of Interleukin-2 Antibody in Apo-E-Deficient Mice", Angiology, May 1, 2004, vol. 55, No. 3, pp. 289-294.
Van Cauter et al., "Estimation of Insulin Secretion Rates from C-Peptide Levels: Comparison of Individual and Standard Kinetic Parameters for C-Peptide Clearance", Diabetes, Mar. 1992, vol. 41, No. 3, pp. 368-377.
Van Diepen et al., "Interactions between inflammation and lipid metabolism: Relevance for efficacy of anti-inflammatory drugs in the treatment of atherosclerosis", Atherosclerosis, 2013, vol. 228, No. 2, available online Mar. 1, 2013, pp. 306-315, http://dx.doi.org/10.1016/j.atherosclerosis.2013.02.028.
Varghese et al., "Mechanisms Underlying the Pathogenesis of Isolated Impaired Glucose Tolerance in Humans", The Journal of Clinical Endocrinology & Metabolism, Dec. 2016, vol. 101, No. 12, pp. 4816-4824, first published online Sep. 7, 2016, doi: 10.1210/jc.2016.1998.
Wang et al., "Carotid Intima-Media Thickness Is Associated with Premature Parental Coronary Heart Disease: The Framingham Heart Study", Circulation, Aug. 5, 2003, vol. 108, pp. 572-576, DOI: 10.1116/01.CIR000008174.35431.DE.
Whirl-Carrillo et al., "Pharmacogenomics Knowledge for Personalized Medicine", Perspectives, Oct. 2012, vol. 92, No. 4, pp. 414-417, doi:10.1038/cipt.3012.96.
Wilson et al., "Prediction of Coronary Heart Disease Using Risk Factor Categories", Circulation, May 12, 1998, vol. 97, No. 18, pp. 1837-1847.
Winter et al., "Man-made antibodies", Nature, Jan. 24, 1991, vol. 349, pp. 293-299.
Wollert et al., "Growth Differentiation Factor 15 as a Biomarker in Cardiovascular Disease", Clinical Chemistry, Jan. 1, 2017, vol. 63, No. 1, pp. 140-151, DOI: 10.1373/clinchem.2016.255174.
Zeisbrich et al., "Hypermetabolic macrophages in rheumatoid arthritis and coronary artery disease due to glycogen synthase kinase 3b inactivation", Annals of the Rheumatic Diseases, Jul. 2018, vol. 77, No. 7, pp. 1053-1062, doi:10.1136/annrheumids-2017-212647.
Ahmed et al., "Structural characterization of GASDALIE Fc bound to the activating Fc receptor FcγRIIIa", Journal of Structural Biology, vol. 194, No. 1, Apr. 2016, pp. 78-89, doi: https://doi.org/10.1016/j.jsb.2016.02.001.
Barry et al., "Efficacy and effectiveness of screen and treat policies in prevention of type 2 diabetes: systematic review and meta-analysis of screening tests and interventions", The BMJ, vol. 356, Jan. 4, 2017, 16 pgs., doi: https://doi.org/10.1136/bmj.i6538.
Betz et al., "mTOR complex 2-Akt signaling at mitochondria-associated endoplasmic reticulum membranes (MAM) regulates mitochondrial physiology", Proceedings of the National Academy of Sciences, vol. 110, No. 31, Jul. 30, 2013, pp. 12526-12534, doi: https://doi.org/10.1073/pnas.1302455110.
Biniecka et al., "Dysregulated bioenergetics: a key regulator of joint inflammation", Annals of the Rheumatic Diseases, vol. 75, No. 12, Nov. 10, 2016, pp. 2192-2200, doi: 10.1136/annrheumdis-2015-208476.
Borrok et al., "3S7G: Aglycosylated human igg1 fc fragment", Protein Data Bank, Deposited: May 26, 2011, Released: May 30, 2012, Retrieved from: https://www.rcsb.org/structure/3S7G, 5 pgs., DOI: 10.2210/pdb3S7G/pdb.
Carter et al., "Loss of OcaB Prevents Age-Induced Fat Accretion and Insulin Resistance by Altering B-Lymphocyte Transition and Promoting Energy Expenditure", Diabetes, vol. 67, No. 7, Jul. 2018, Electronic Publication: Mar. 1, 2018, pp. 1285-1296, doi: 10.2337/db17-0558.
Coleman, "Obese and diabetes: Two mutant genes causing diabetes-obesity syndromes in mice", Diabetologia, vol. 14, Mar. 1978, pp. 141-148, doi: https://doi.org/10.1007/BF00429772.
Crispin et al., "Crystal structure of sialylated IgG Fc: Implications for the mechanism of intravenous immunoglobulin therapy", Proceedings of the National Academy of Sciences, vol. 110, No. 38, Sep. 17, 2013, pp. E3544-E3546, doi: https://doi.org/10.1073/pnas.1310657110.
Defuria et al., "B cells promote inflammation in obesity and type 2 diabetes through regulation of T-cell function and an inflammatory cytokine profile", Proceedings of the National Academy of Sciences, vol. 110, No. 13, Mar. 26, 2013, pp. 5133-5138, doi: 10.1073/pnas.1215840110.
Ferrara et al., "Unique carbohydrate-carbohydrate interactions are required for high affinity binding between FcγRIII and antibodies lacking core fucose", Proceedings of the National Academy of Sciences, vol. 108, No. 31, Aug. 2, 2011, pp. 12669-12674, doi: https://doi.org/10.1073/pnas.1108455108.
Hahn et al., "Proinflammatory cytokines differentially regulate adipocyte mitochondrial metabolism, oxidative stress, and dynamics", American Journal of Physiology—Endocrinology and Metabolism, vol. 306, No. 9, May 2014, pp. E1033-E1045, doi: https://doi.org/10.1152/ajpendo.00422.2013.
Hemminki et al., "Subsequent Type 2 Diabetes in Patients with Autoimmune Disease", Scientific Reports, vol. 5, 13871, 2015, 8 pgs., doi: 10.1038/srep13871.
Knowles et al., "Measurement of insulin-mediated glucose uptake: Direct comparison of the modified insulin suppression test and the euglycemic, hyperinsulinemic clamp", Metabolism, vol. 62, No. 4, Apr. 1, 2013, pp. 548-553, doi: https://doi.org/10.1016/j.metabol.2012.10.002.
Latvala et al., "Distribution of FcRn Across Species and Tissues", Journal of Histochemistry & Cytochemistry, vol. 65, No. 6, Jun. 2017, pp. 321-333, doi: 10.1369/0022155417705095.
Li et al., "Hematopoietic-Derived Galectin-3 Causes Cellular and Systemic Insulin Resistance", Cell, vol. 167, No. 4, Nov. 3, 2016, pp. 973-984.e12, doi: 10.1016/j.cell.2016.10.025.
Liu et al., "The Neonatal FcR-Mediated Presentation of Immune-Complexed Antigen Is Associated with Endosomal and Phagosomal pH and Antigen Stability in Macrophages and Dendritic Cells", The Journal of Immunology, vol. 186, No. 8, Apr. 15, 2011, pp. 4674-4686, doi: https://doi.org/10.4049/jimmunol.1003584.
Maynard et al., "Defective mitochondrial respiration, altered dNTP pools and reduced AP endonuclease 1 activity in peripheral blood mononuclear cells of Alzheimer's disease patients", Aging, vol. 7, No. 10, Oct. 2015, pp. 793-810, doi: 10.18632/aging.100810.
Mcgillicuddy et al., "Interferonγ Attenuates Insulin Signaling, Lipid Storage, and Differentiation in Human Adipocytes via Activation of the JAK/STAT Pathway", Journal of Biological Chemistry, vol. 284, No. 46, Nov. 13, 2009, pp. 31936-31944, first published JBC Papers in Press Sep. 23, 2009, doi:10.1074/jbc.M109.061655.
Mezo et al., "Reduction of IgG in nonhuman primates by a peptide antagonist of the neonatal Fc receptor FcRn", Proceedings of the National Academy of Sciences, vol. 105, No. 7, Feb. 19, 2008, pp. 2337-2342, doi: https://doi.org/10.1073/pnas.0708960105.
Nan et al., "Sialidase expression in activated human T lymphocytes influences production of IFN-γ", Journal of Leukocyte Biology, vol. 81, No. 1, Jan. 2007, pp. 284-296, doi: 10.1189/jlb.1105692.
Olaru et al., "Neonatal Fc Receptor Promotes Immune Complex-Mediated Glomerular Disease", Journal of the American Society of Nephrology, vol. 25, No. 5, May 2014, pp. 918-925, doi: https://doi.org/10.1681/ASN.2013050498.
Pagan et al., "Engineered Sialylation of Pathogenic Antibodies In Vivo Attenuates Autoimmune Disease", Cell, vol. 172, No. 3, Jan. 25, 2018, Electronic Publication: Dec. 21, 2017, pp. 564-577.e13, doi: 10.1016/j.cell.2017.11.041.
Pincetic et al., "Type-I and type-II Fc receptors regulate innate and adaptive immunity", Nature Immunology, vol. 15, No. 8, Aug. 2014, pp. 707-716, doi:10.1038/ni.2939.
Plomp et al., "Subclass-specific IgG glycosylation is associated with markers of inflammation and metabolic health", Scientific Reports, vol. 7, No. 1, Sep. 26, 2017, 12325, 10 pgs., doi: 10.1038/s41598-017-12495-0.

(56) References Cited

OTHER PUBLICATIONS

Pyzik et al., "Hepatic FcRn regulates albumin homeostasis and susceptibility to liver injury", Proceedings of the National Academy of Sciences, vol. 114, No. 14, Apr. 4, 2017, Electronic Publication: Mar. 22, 2017, pp. E2862-E2871, doi: 10.1073/pnas.1618291114.

Rose et al., "A longitudinal big data approach for precision health", Nature Medicine, vol. 25, May 8, 2019, pp. 792-804, doi: https://doi.org/10.1038/s41591-019-0414-6.

Sebastian et al., "Glycan Biomarkers for Rheumatoid Arthritis and Its Remission Status in Han Chinese Patients", Omics: A Journal of Integrative Biology, vol. 20, No. 6, Jun. 16, 2016, pp. 343-351, doi: https://doi.org/10.1089/omi.2016.0050.

Senn et al., "Interleukin-6 Induces Cellular Insulin Resistance in Hepatocytes", Diabetes, vol. 51, No. 12, Dec. 2002, pp. 3391-3399, doi: https://doi.org/10.2337/diabetes.51.12.3391.

Shen et al., "B-1a Lymphocytes Attenuate Insulin Resistance", Diabetes, vol. 64, No. 2, Feb. 2015, Electronic Publication: Sep. 22, 2014, pp. 593-603, doi: 10.2337/db14-0554.

Tanigaki et al., "Hyposialylated IgG activates endothelial IgG receptor FcγRIIB to promote obesity-induced insulin resistance", Journal of Clinical Investigation, vol. 128, No. 1, Jan. 2018, Online Publication: Nov. 27, 2017, pp. 309-322, doi: 10.1172/JCI89333.

Tonsawan et al., "Knockout of the neonatal Fc receptor in cultured podocytes alters IL-6 signaling and the actin cytoskeleton", American Journal of Physiology—Cell Physiology, vol. 317, No. 5, Nov. 5, 2019, pp. C1048-C1060, doi: https://doi.org/10.1152/ajpcell.00235.2019.

Vidarsson et al., "FcRn: an IgG receptor on phagocytes with a novel role in phagocytosis", Blood, vol. 108, No. 10, Nov. 15, 2006, pp. 3573-3579, doi: https://doi.org/10.1182/blood-2006-05-024539.

Vuckovic et al., "Association of Systemic Lupus Erythematosus With Decreased Immunosuppressive Potential of the IgG Glycome", Arthritis & Rheumatology, vol. 67, No. 11, Nov. 2015, pp. 2978-2989, doi: https://doi.org/10.1002/art.39273.

Winer et al., "B Lymphocytes Promote Insulin Resistance through Modulation of T Lymphocytes and Production of Pathogenic IgG Antibody", Nature Medicine, vol. 17, Apr. 17, 2011, pp. 610-617, doi: 10.1038/nm.2353.

Yeni-Komshian et al., "Relationship Between Several Surrogate Estimates of Insulin Resistance and Quantification of Insulin-Mediated Glucose Disposal in 490 Healthy Nondiabetic Volunteers", Diabetes Care, vol. 23, No. 2, Feb. 2000, pp. 171-175, doi: https://doi.org/10.2337/diacare.23.2.171.

Yip et al., "Resistance to Insulin-Mediated Glucose Disposal as a Predictor of Cardiovascular Disease", The Journal of Clinical Endocrinology & Metabolism, vol. 83, No. 8, Aug. 1, 1998, pp. 2773-2776, doi: https://doi.org/10.1210/jcem.83.8.5005.

\* cited by examiner

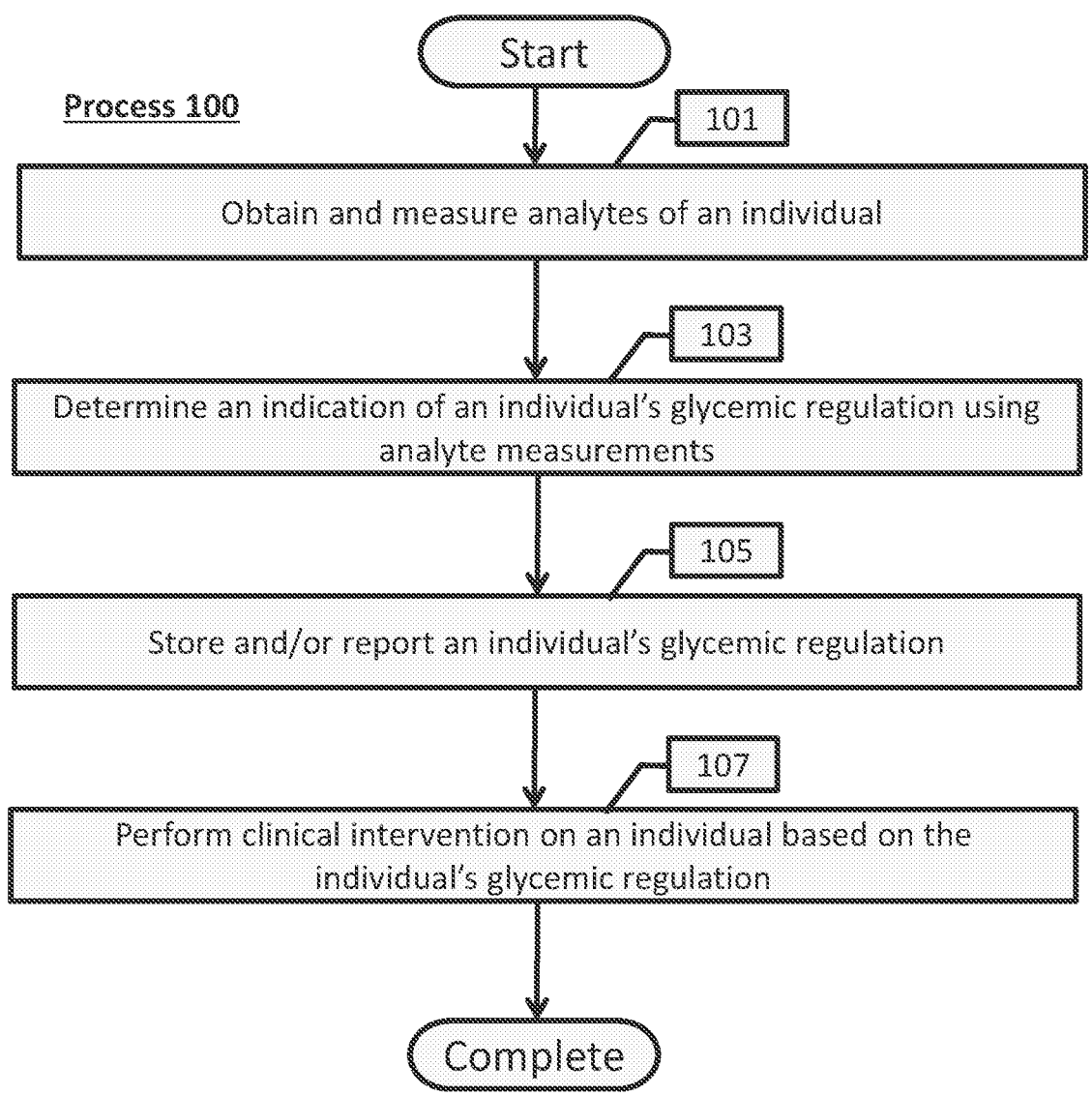

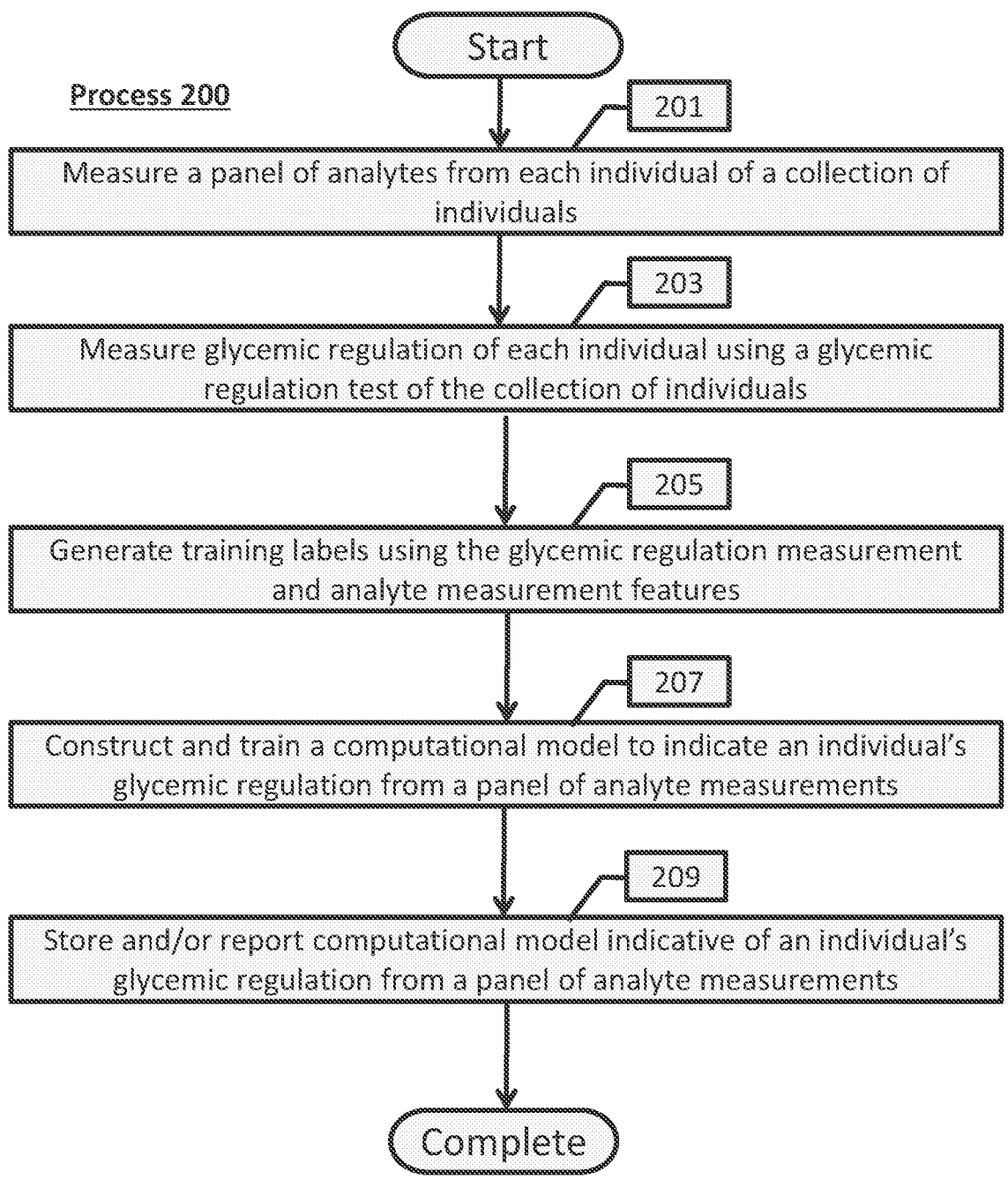

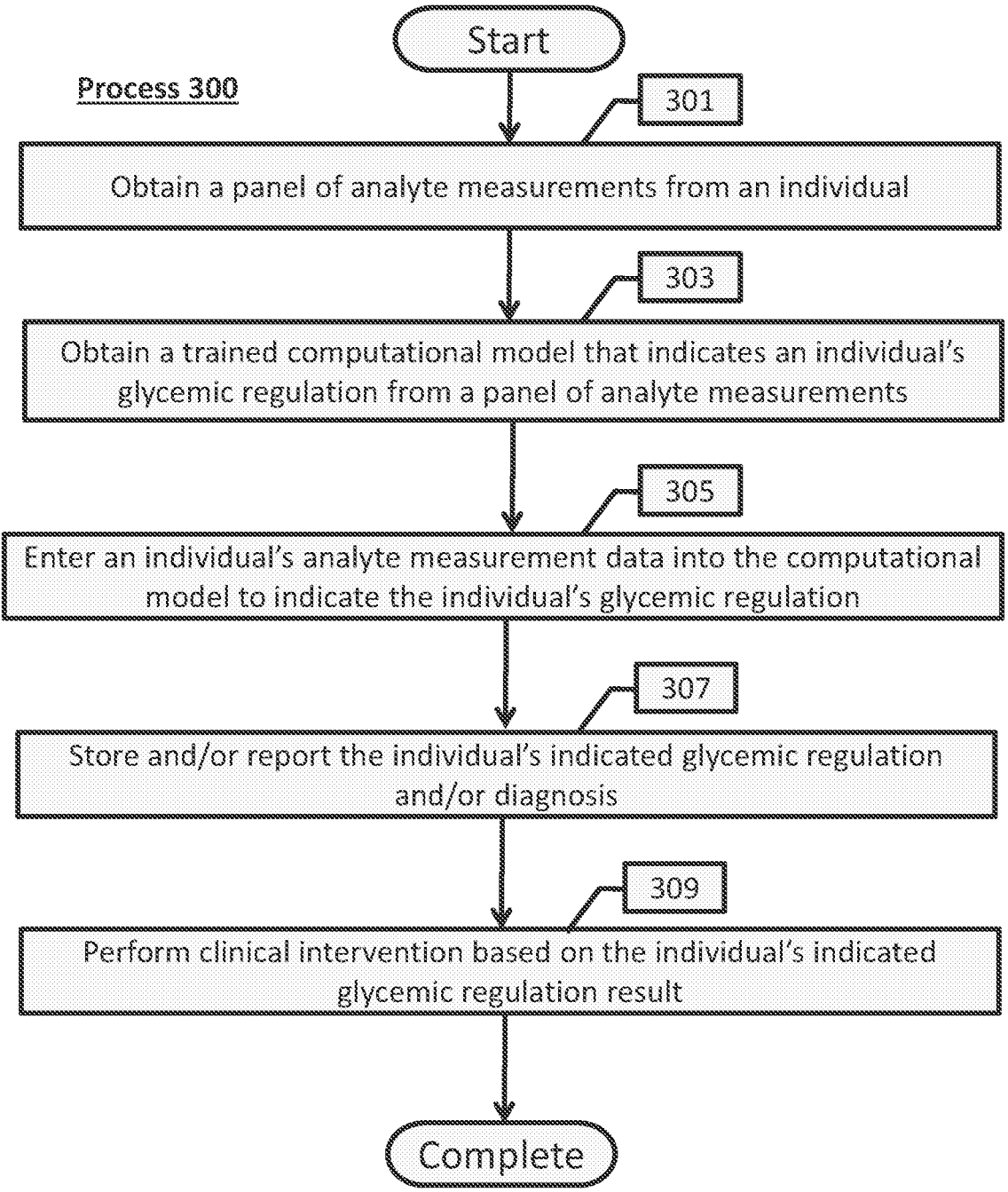

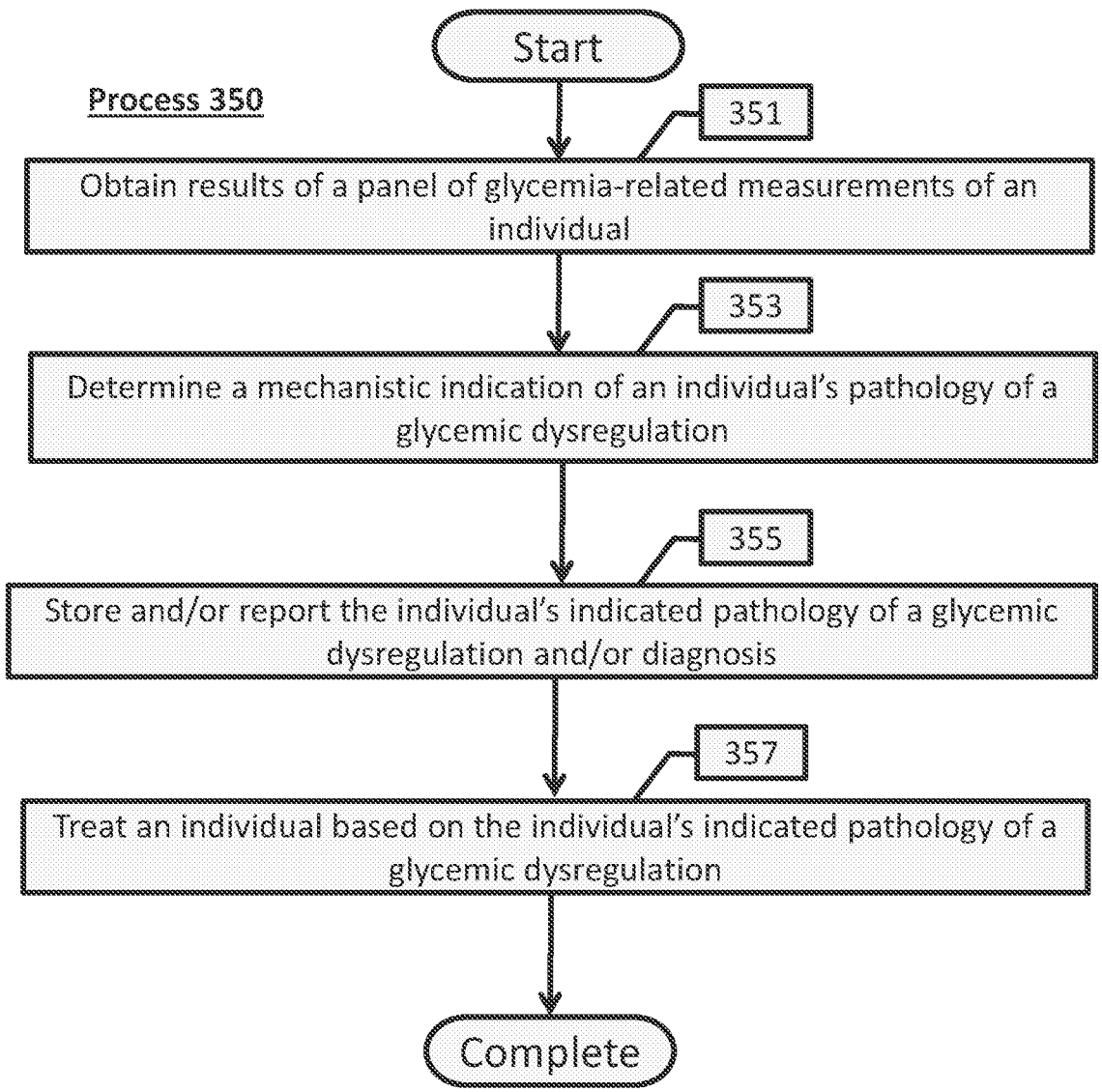

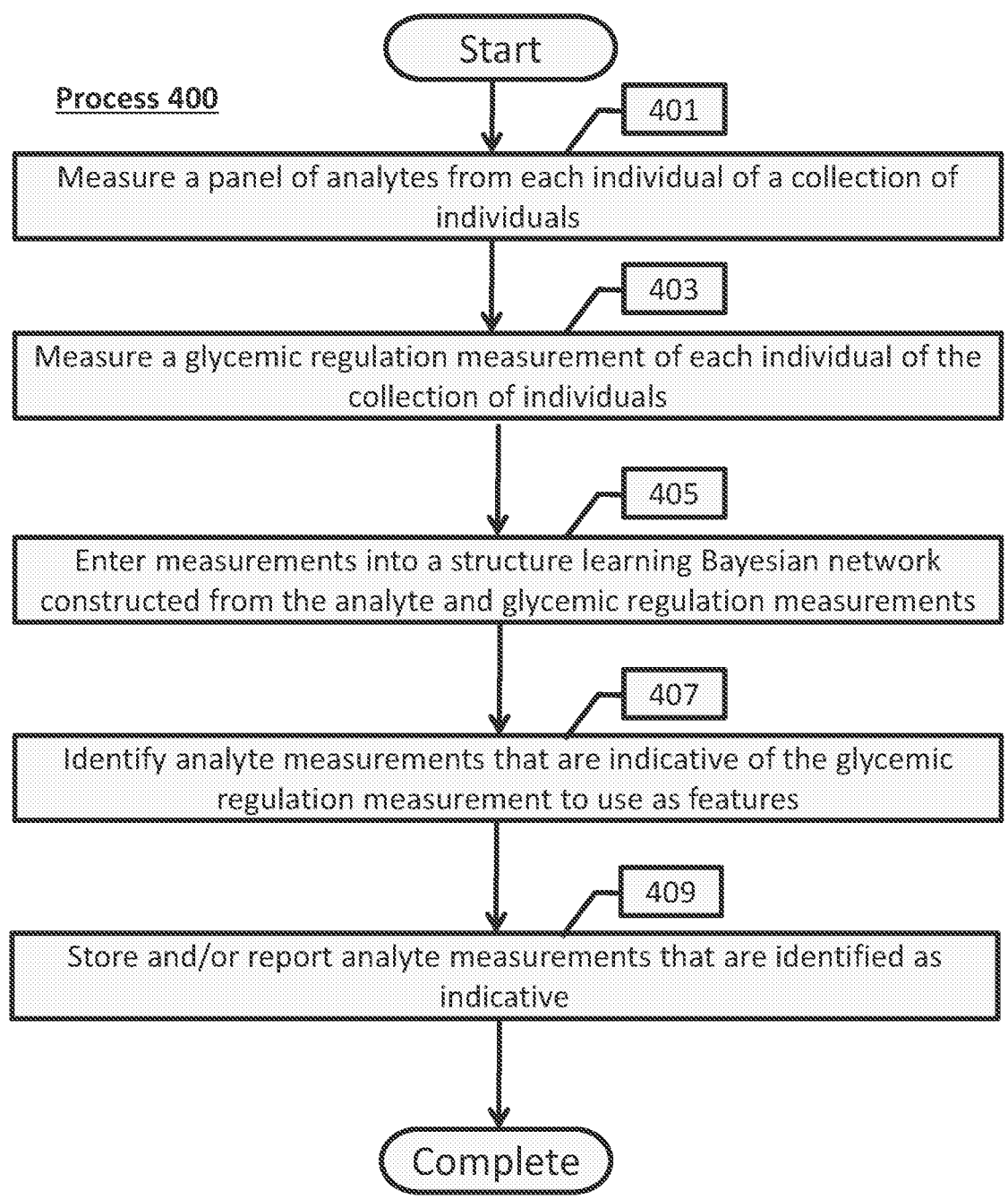

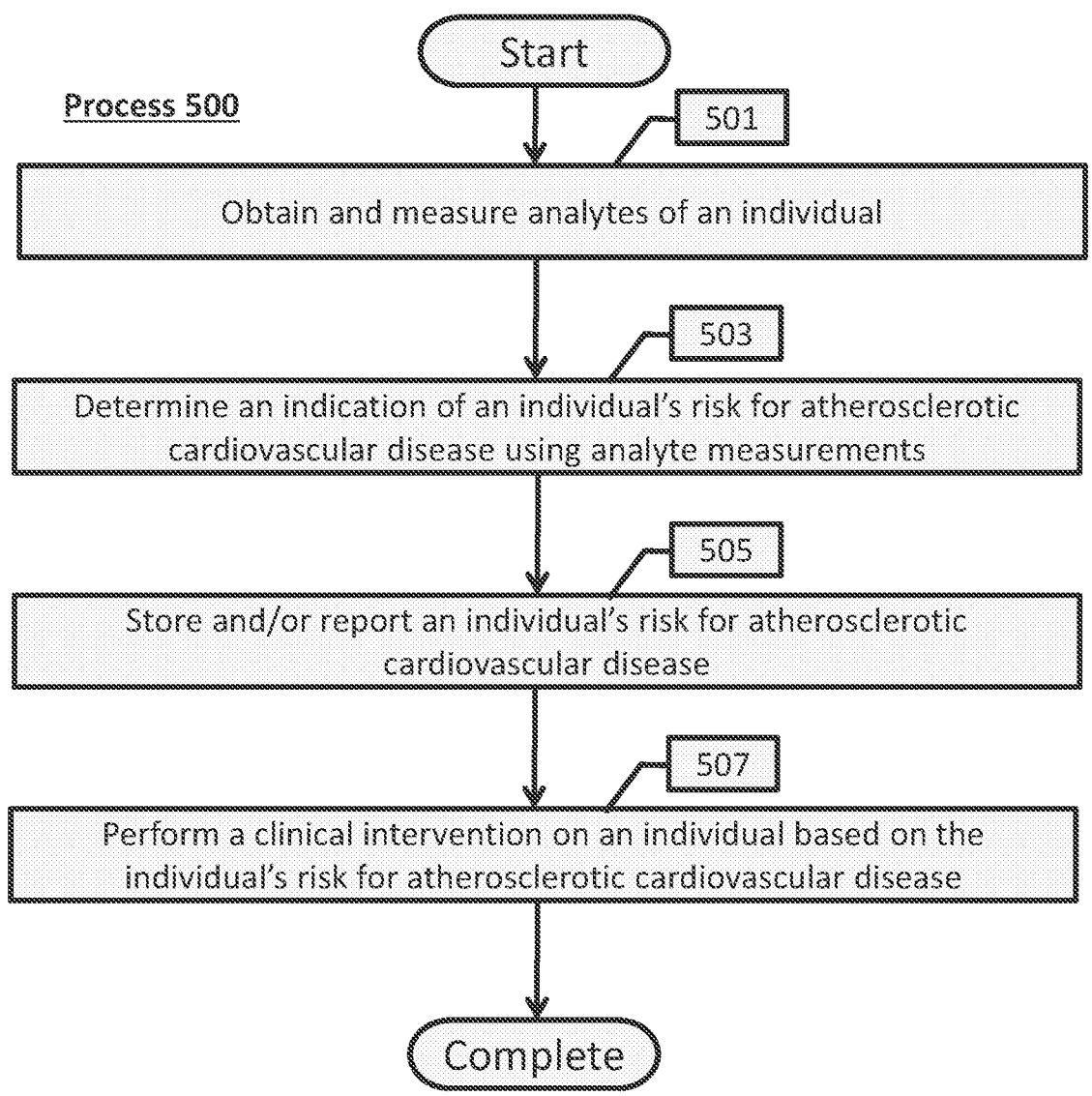

Integrated Personalized Omics Cohort Study (iPOP) Participant Flow Diagram

Fig. 16
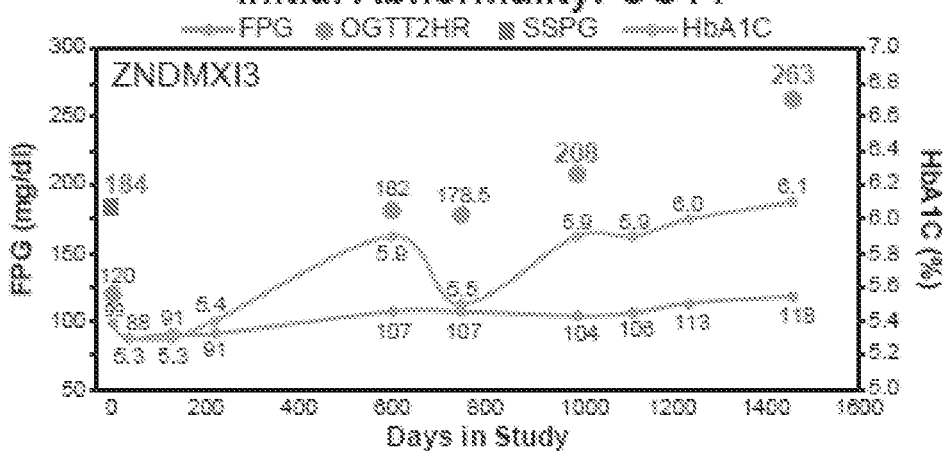
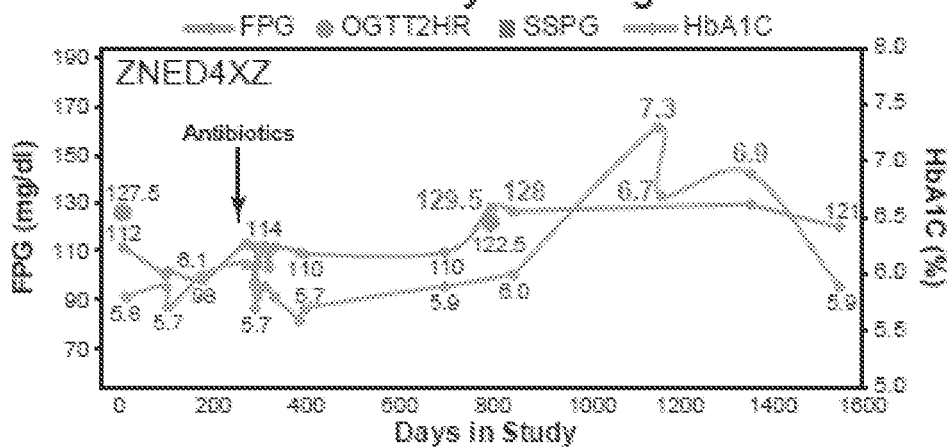
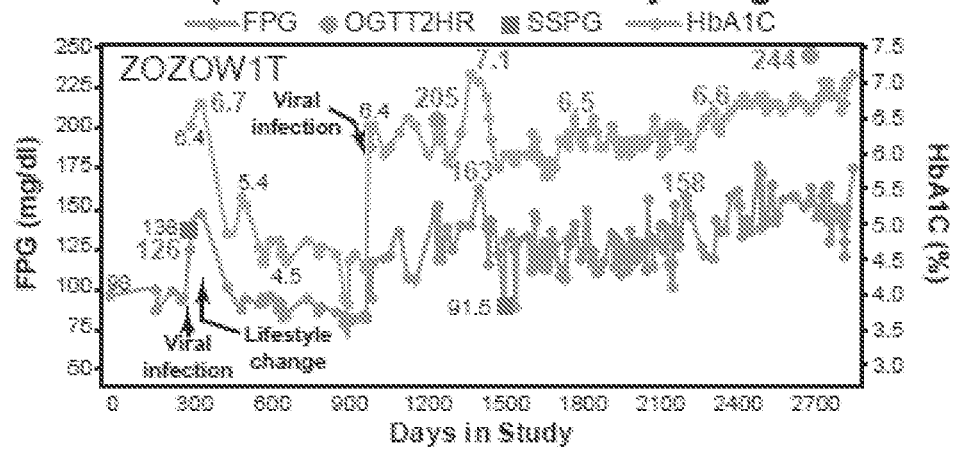

Fig. 18
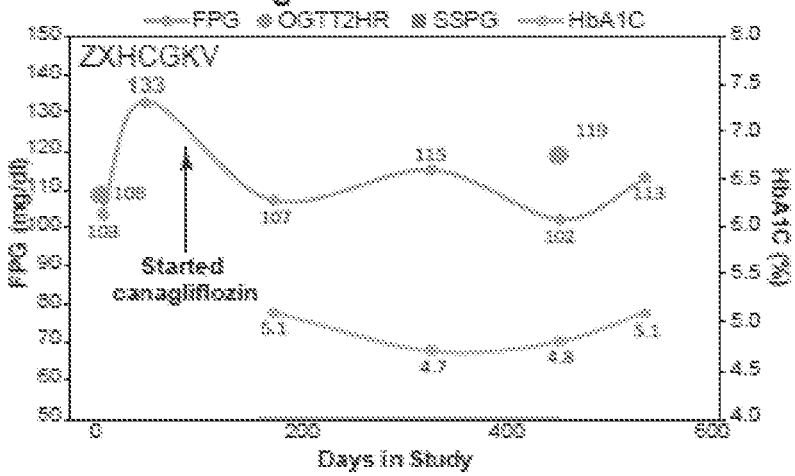
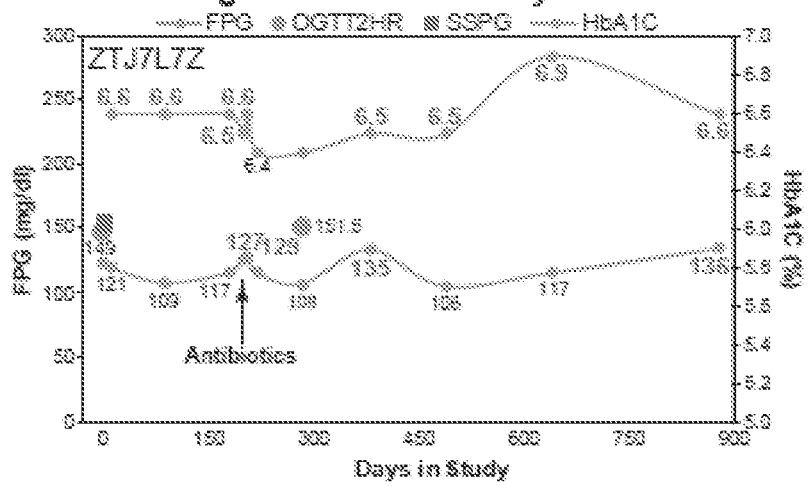
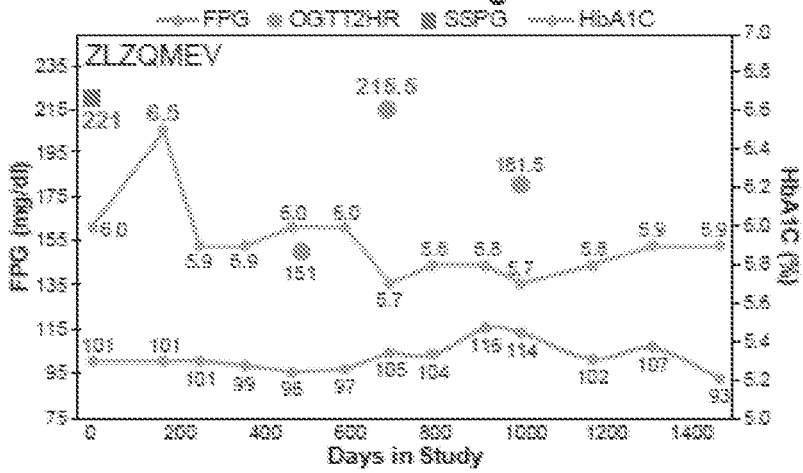

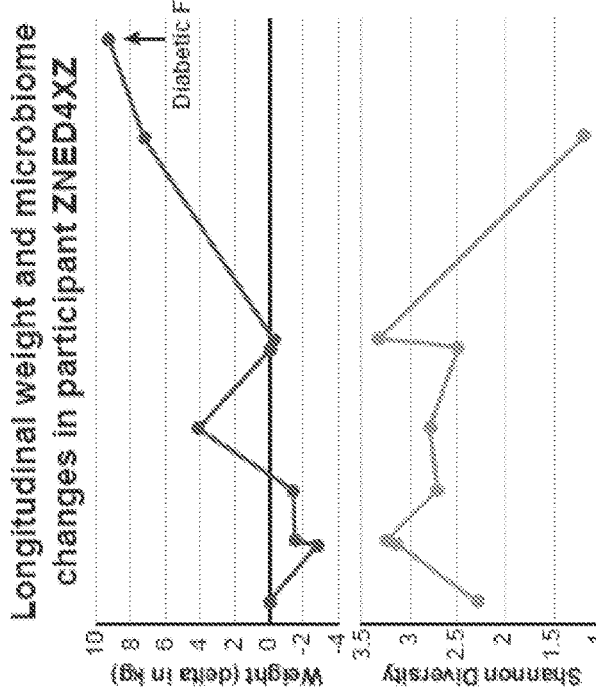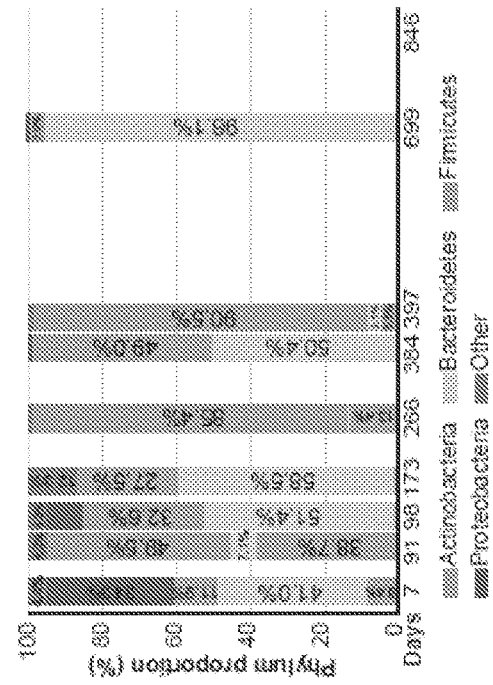
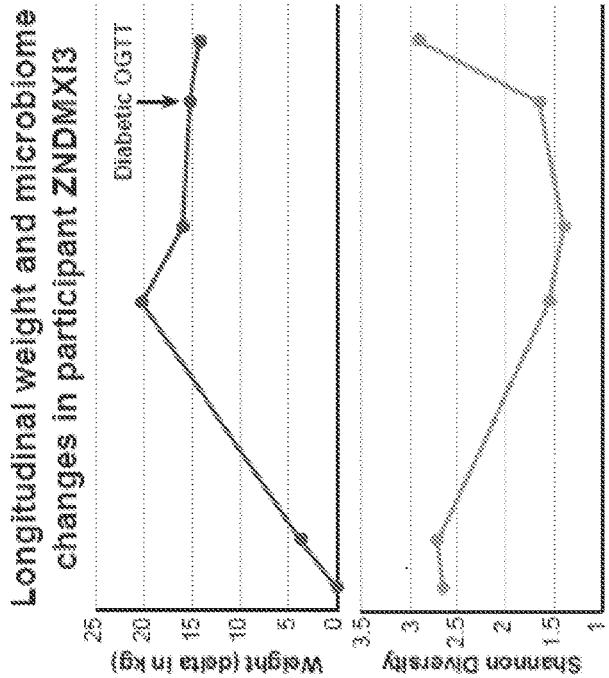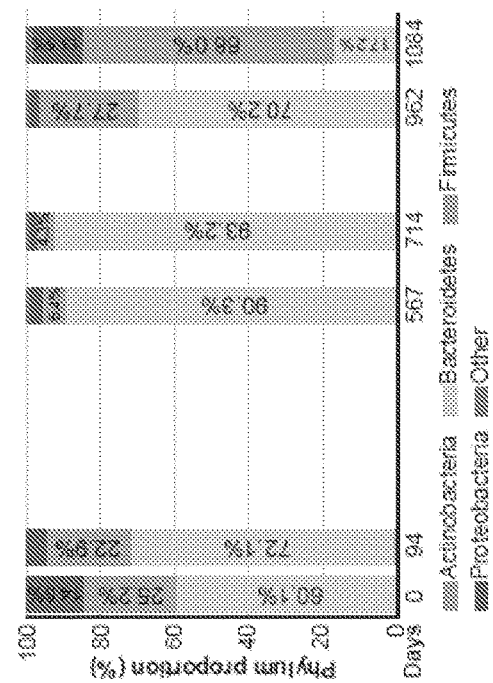
Fig. 19

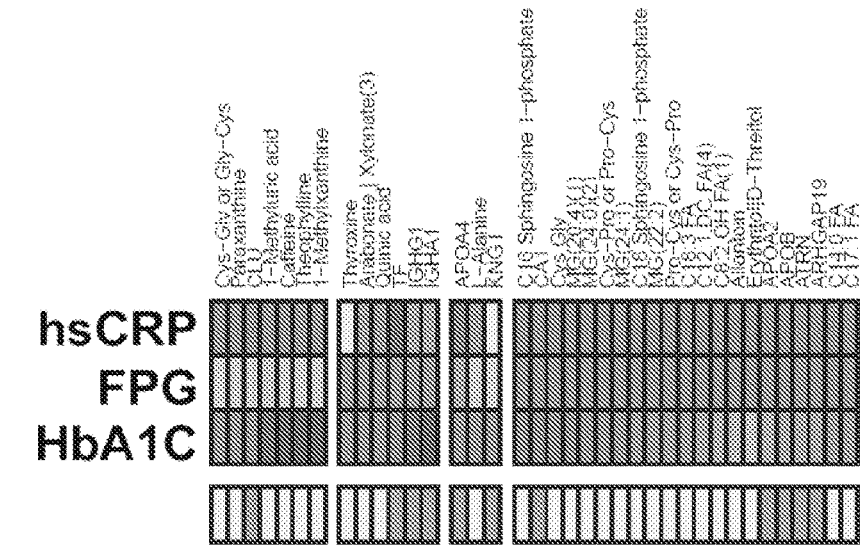
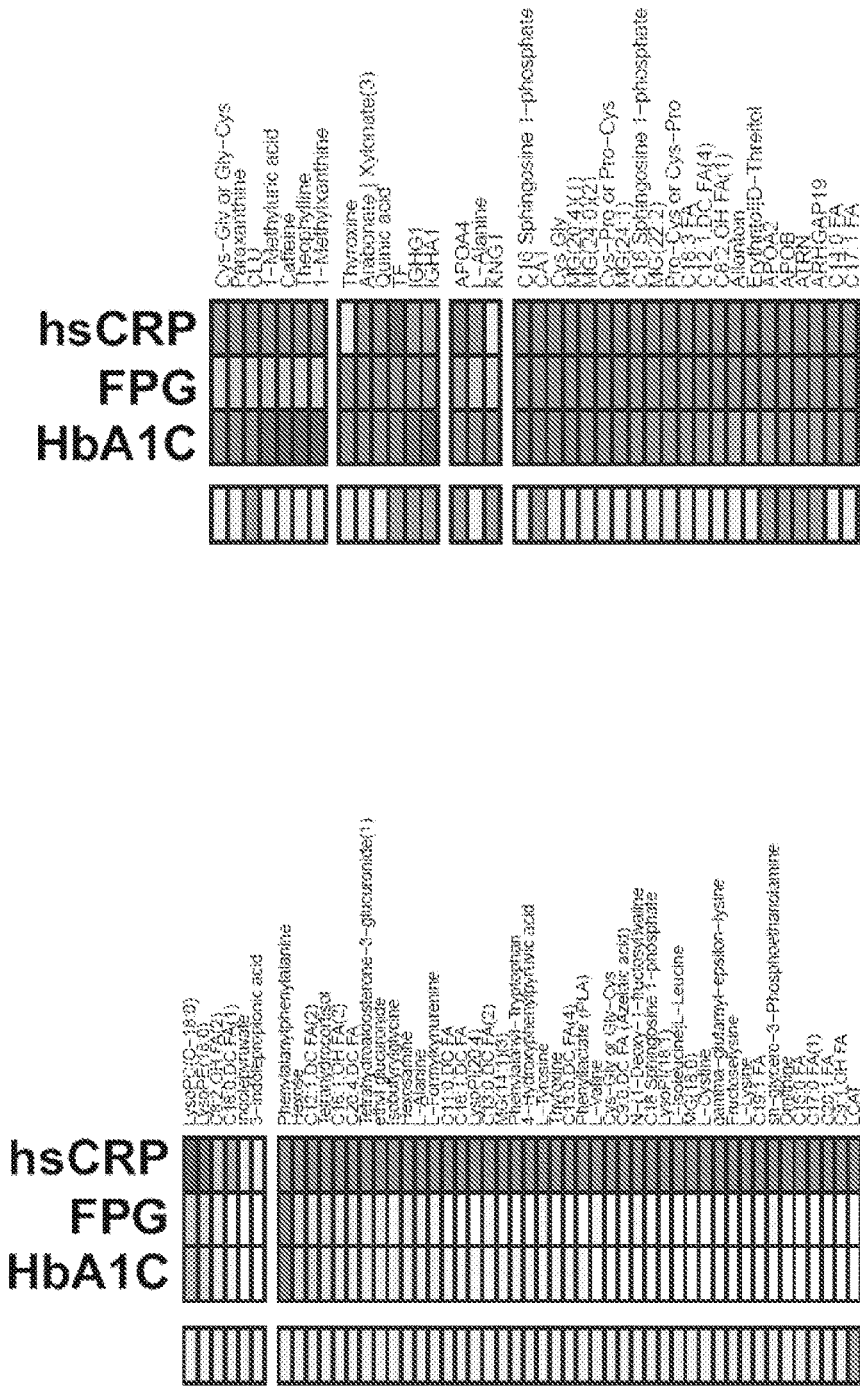
Fig. 22

ASCVD risk profiles

Transitions in dyslipidemia profiles

Fig. 29
Carotid artery profiling
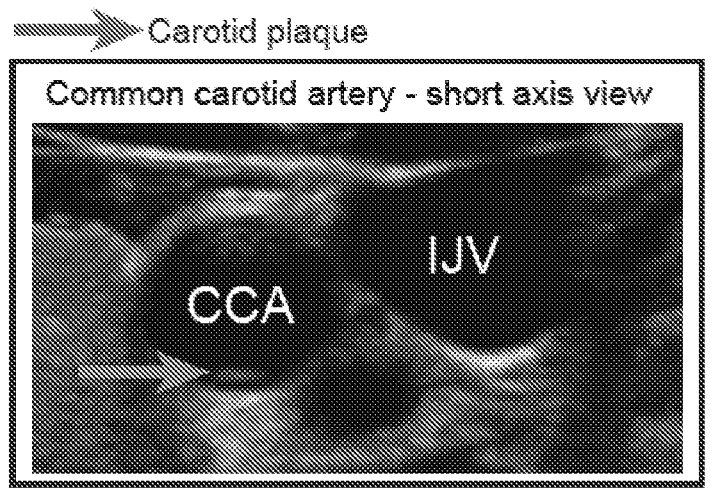
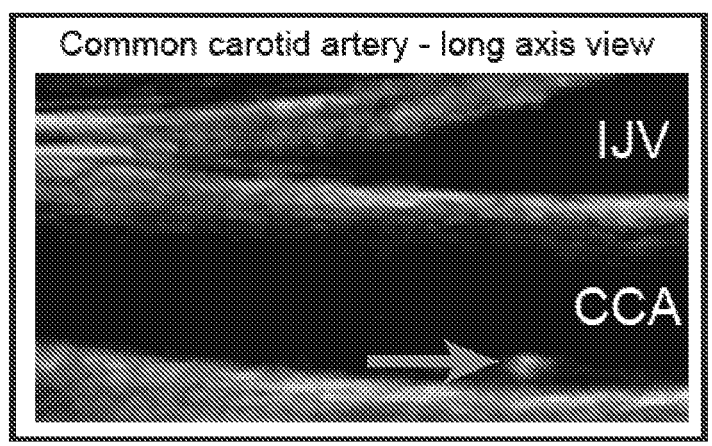
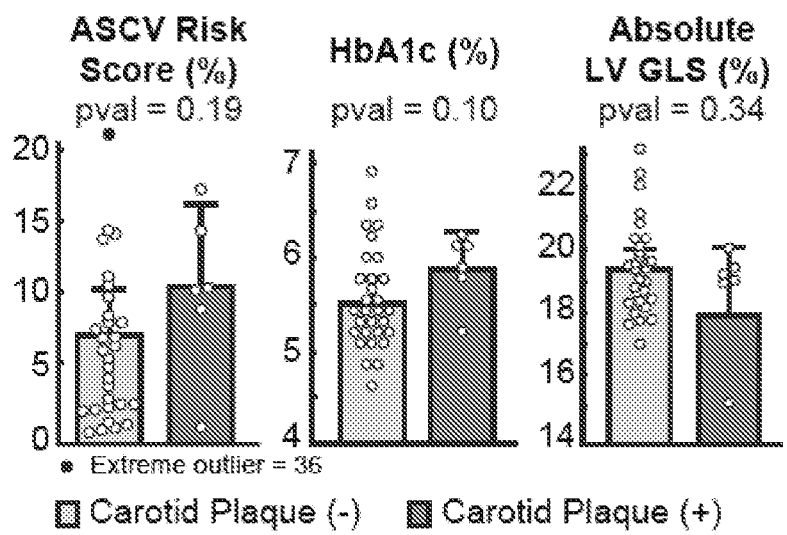

Correlation network of CVD markers

Fig. 33

Major clinically actionable health discoveries

| Metabolic | n |
|---|---|
| MODY mutation (gene) | 1 |
| ABCC8 Mutation (gene) | 1 |
| New DM Labs (clinical) | 14 |
| New PreDM Labs (clinical) | 55 |

| Cardiovascular | n |
|---|---|
| Genetic Cardiomyopathy (gene/imaging) | 1 |
| Arrhythmia (afib, SVT) (wearable) | 2 |
| Actionable Pharmacogenomics (gene) | 3 |
| Early Stage CV Profile (imaging) | 9 |
| Stage II hypertension (vitals) | 18 |

| Heme/Oncological | n |
|---|---|
| Lymphoma (imaging) | 1 |
| MGUS (clinical) | 1 |
| Smoldering Myeloma (clinical) | 1 |
| Oncologic Risk Gene (1x Thyroid Cancer) | 7 |
| α Thalassemia (clinical) | 1 |
| β Thalassemia (gene/clinical) | 1 |
| Pros1 Mutation (gene) | 1 |

| Infectious | n |
|---|---|
| Lyme Disease (wearable) | 1 |

| Others | n |
|---|---|
| Obstructive sleep apnea (wearable) | 1 |
| SLC7A9 mutation (cystinuria risk) (gene) | 1 |
| Macroalbuminuria (clinical) | 2 |

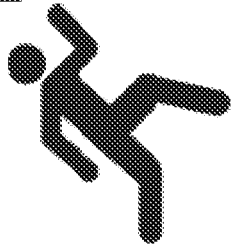

Fig. 34
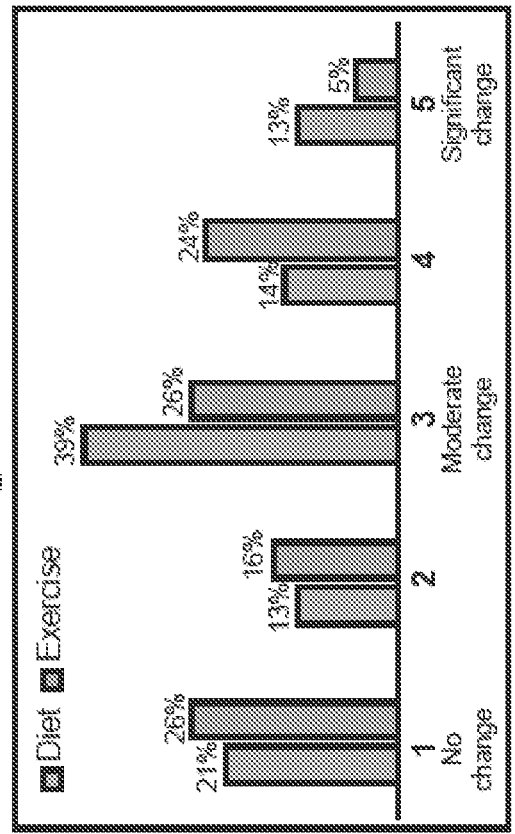
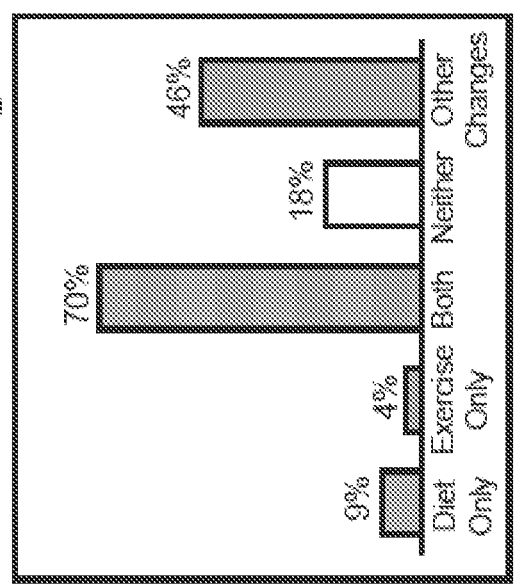

METHODS FOR EVALUATION AND TREATMENT OF GLYCEMIC DYSREGULATION AND ATHEROSCLEROTIC CARDIOVASCULAR DISEASE AND APPLICATIONS THEREOF

CROSS-REFERENCE TO RELATED APPLICATIONS

This application claims priority to U.S. Provisional Patent Application No. 62/747,488 entitled "Longitudinal Big Data Approach for Precision Diagnostics and Treatments," filed Oct. 18, 2018, to U.S. Provisional Patent Application No. 62/757,629 entitled "Methods for Evaluation and Treatment of Glycemic Dysregulation and Applications Thereof," filed Nov. 8, 2018, to U.S. Provisional Patent Application No. 62/814,746 entitled "Methods for Evaluation and Treatment of Glycemic Dysregulation and Applications Thereof," filed Mar. 6, 2019, and to U.S. Provisional Patent Application No. 62/845,161 entitled "Methods for Evaluation and Treatment of Atherosclerotic Cardiovascular Disease and Applications Thereof," filed May 8, 2019, the disclosures of which are each incorporated herein by reference.

STATEMENT REGARDING FEDERALLY SPONSORED RESEARCH OR DEVELOPMENT

This invention was made with Government support under contracts DE023789, DK102556, ES028825, and DK110186 awarded by the National Institutes of Health. The Government has certain rights in the invention.

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Mar. 31, 2020, is named "05737 Seq List_ST25.txt" and is 605 bytes in size.

FIELD OF THE INVENTION

The invention is generally directed to processes that evaluate glycemic regulation and atherosclerotic cardiovascular disease and applications thereof, and more specifically to methods and systems for evaluating glycemia and atherosclerosis including clinical assessments and treatments of diabetes mellitus, insulin resistance, cardiovascular disease and other glycemia related phenotypes.

BACKGROUND

One in ten individuals are affected by diabetes, a condition involving abnormal regulation of glycemia (i.e., the level of sugar or glucose in blood). Standard assessments of glycemia typically utilize single time or average measurements of blood glucose. A few common methods to assess glycemia include measuring fasting plasma glucose (FPG), glycated hemoglobin (HbA1c test), and oral glucose tolerance test (OGTT). In addition, individuals can be tested for their insulin resistance using an insulin suppression test that characterizes the steady-state plasma glucose (SSPG).

Each glycemia assessment yields different insight. FPG is a measure of glucose levels at a steady state where production of glucose by the liver and kidney needs to match glucose uptake by tissues. Impaired FPG typically results from a mismatch between glucose production and glucose utilization. In contrast, OGTT measures a dynamic response to a glucose load which leads to increased plasma insulin which suppresses hepatic glucose release and stimulates glucose uptake in the peripheral tissues. Impaired pancreatic beta cell function and peripheral insulin resistance, particularly in skeletal muscle, can lead to impaired glucose tolerance (IGT). The ambient glucose concentration determines the rate of formation of HbA1C in erythrocytes which have a lifespan of ~120 days. Accordingly, HbA1C reflects average blood glucose levels over the past 3-4 months.

Insulin resistance is a pathological condition in which cells fail to respond to insulin. Healthy individuals respond to insulin by using the glucose available in the blood stream and inhibit the use of fat for energy, which allows blood glucose to return to the normal range. To perform an insulin suppression test, both glucose and insulin are suppressed from an individual's bloodstream by intravenous infusion of octreotide. Then, insulin and glucose are infused into the bloodstream at a particular rate and blood glucose concentrations are measured at a number of time checkpoints to determine the ability of the individual to respond to insulin, resulting in a determination of SSPG levels. Subjects with an SSPG of 150 mg/dL or greater are considered insulin-resistant; however, this cutoff can vary depending upon the interpreter.

Atherosclerotic cardiovascular disease (ASCVD or atherosclerosis) is a pathological process that thickens and stiffens arteries throughout the mammalian body due to accumulation of fats and cholesterol. ASCVD can result in a restricting of blood flow and oxygen to the organs, which can trigger a heart attack or stroke. Typically, the outward physical symptoms of ASCVD are difficult to detect in the early stages, and thus there is a need to develop tests for early detection.

SUMMARY OF THE INVENTION

Many embodiments are directed to methods of treatment and performing clinical assessments based on a steady-state plasma glucose or glucose tolerance test result, as indicated by measuring a panel of analytes.

In an embodiment to perform a treatment on an individual, a panel of analytes extracted from an individual is measured. The measurements of analytes are utilized in a computational predictive model to indicate a steady-state plasma glucose level of the individual. An indication from the results of the computational model is received that the individual has an elevated steady-state plasma glucose level. The individual is treated to lower the individual's elevated steady-state plasma glucose.

In another embodiment, at least one analyte of the panel of measured analytes is clinical data, personal data, metabolites, protein constituents, genomic DNA, transcript expression, lipids, or human microbiota.

In yet another embodiment, at least one analyte of the panel of analytes is triglycerides-to-high density lipoprotein ratio (TGL/HDL), creatine (CR), body mass index (6M1), absolute count of neutrophils (NEUTAB), calcium (CA), interleukin 1 beta (IL1B), interleukin 18 (IL18), angiotensinogen protein (AGT), interleukin 1 receptor accessory protein (IL1RAP), Ig kappa chain V-I region protein (KV116), complement factor H protein (CFH), myosin-binding protein C (MYBPC2), L-lysine (Lys), L-arginine (Arg), L-alanine (Ala), N1-methyladenosine, 4-formyl Indole, 3-Methyl-L-histidine, C7H15N3O2, C14H22N2O9, C12H24N2O3, C26H42O4, C28H46O4, C28H44O4, LysoPG(18:0), C16:3 FA, hexosylceramide HCER(24:0), lactosylceramide LCER(16:0), glycerophosphoethanolamine PE(P-18:0/22:6), PE(P-16:0/22:6) and PE(P-18:1/18:1), triacylglycerol TAG(58:10) containing fatty acid FA(20:5), chromosome 19 open reading frame 66 transcript (C19orf66), chromosome 1 open reading frame 174 transcript (C1orf174), calcineurin like EF-hand protein 1 transcript (CHP1), deoxyguanosine kinase transcript (DGUOK), Disks large-associated protein 1 transcript (DLGAP1), family with sequence similarity 86 member H pseudogene transcript (FAM86HP), family with sequence similarity 185 member A pseudogene transcript (FAM185A), heat shock cognate B transcript (HSCB), IL12A antisense RNA 1 (IL12A-AS1), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), UBAP1-MVB12-associated (UMA) domain containing 1 transcript (RPA3OS), serine/threonine-protein kinase 494 transcript (SGK494), solute carrier family 16 member 12 transcript (SLC16A12), synaptotagmin 9 transcript (SYT9), transmembrane protein 237 transcript (TMEM237), transmembrane protein 253 transcript (TMEM253), transmembrane protein 108 transcript (TMEM108), transmembrane protein 106B transcript (TMEM106B), U2AF homology motif kinase 1 transcript (UHMK1), vacuolar protein sorting 13 homolog A transcript (VPS13A), *Bacteroides* bacteria, Barnesiella bacteria, *Clostridium* bacteria, *Faecalibacterium* bacteria, *Ruminococcus* bacteria, *Bacteroides, Shigella* bacteria, Lachnospiraceae bacteria, or *Odoribacter* bacteria.

In a further embodiment, the panel of analyte measurements utilized in the prediction model is based upon results of a second computational model that determines a relationship between steady-state plasma glucose and the at least one analyte measurement.

In still yet another embodiment, the second computational model is a Bayesian computational model.

In yet a further embodiment, the predictive computational model is a ridge regression.

In an even further embodiment, the computed steady-state glucose level is above a threshold.

In yet an even further embodiment, the individual is treated with insulin, alpha-glucosidase inhibitors, biguanides, dopamine agonists, DPP-4 inhibitors, GLP-1 receptor agonists, meglitinides, sodium glucose transporter 2 inhibitors, sulfonylureas, or thiazolidinediones.

In still yet an even further embodiment, the predictive computational model was trained utilizing steady-state plasma glucose data results of a cohort of individuals, wherein an insulin suppression test was performed on each individual of the cohort.

In still yet an even further embodiment, the insulin suppression test involved infusion of octreotide to suppress insulin in each individual.

In an embodiment to treat an individual, a panel of analytes extracted from an individual is measured. The measurements of analytes are utilized in a computational predictive model to indicate an oral glucose tolerance test result of the individual. An indication from the results of the computational model is received that the individual has an elevated oral glucose tolerance test result. The individual is treated to lower the individual's elevated oral glucose tolerance test result.

In another embodiment, at least one analyte of the panel of measured analytes is clinical data, personal data, metabolites, protein constituents, genomic DNA, transcript expression, lipids, or human microbiota.

In yet another embodiment, at least one analyte of the panel of analytes is hemoglobin A1C (A1C), alanine aminotransferase (ALT), cytokine platelet-derived growth factor subunit B homodimer (PDGFBB), complement factor D protein (CFD), Ig kappa variable 2D-28 protein (KVD28), Ig heavy constant alpha 2 protein (IGHA2), coagulation factor XI protein (F11), Ig kappa variable 310 protein (KV310), Ig heavy variable 2-70 protein (HV270), vitronectin protein (VTN), hexosamine, taurine, hydroxyphenyllactic acid, hippuric acid, ectoine, p-cresol glucuronide, hydroxy-stearic acid (C18:0,OH FA), dihydroxy-palmitic acid (C16:0,2OH), a-linolenic acid (C18:3 FA), chitobiosyldiphosphodolichol beta-mannosyltransferase like 2 transcript (ALG1L2), chromosome 21 open reading frame 119 transcript (C21 orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNF214), unc-93 homolog B1 transcript (UNC93B1), wee1-like protein kinase 2 transcript (WEE2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), macrophage migration inhibitory factor transcript (MIF), zinc finger protein 596 transcript (ZNF596), *Bacteroides* bacteria, Lachnospiraceae bacteria, *Roseburia* bacteria, or *Faecalibacterium* bacteria.

In a further embodiment, the panel of analyte measurements utilized in the prediction model is based upon results of a second computational model that determines a relationship between glucose tolerance and the at least one analyte measurement.

In still yet another embodiment, the second computational model is a Bayesian computational model.

In yet a further embodiment, the predictive computational model is a ridge regression.

In an even further embodiment, the computed oral glucose tolerance test result is above a threshold.

In yet an even further embodiment, the individual is treated with insulin, alpha-glucosidase inhibitors, biguanides, dopamine agonists, DPP-4 inhibitors, GLP-1 receptor agonists, meglitinides, sodium glucose transporter 2 inhibitors, sulfonylureas, or thiazolidinediones.

In still yet an even further embodiment, the predictive computational model was trained utilizing glucose tolerance level data results of a cohort of individuals, wherein an oral glucose tolerance test was performed on each individual of the cohort.

In still yet an even further embodiment, the oral glucose tolerance test involved each individual of the cohort receiving a standardized dose of glucose.

In an embodiment to monitor and clinically assess an individual for glycemia regulation, a panel of analytes extracted from an individual is measured. The measurements of analytes are utilized in a computational predictive model to indicate a glycemia test result of the individual. The glycemia test is determining steady-state plasma glucose or an oral glucose tolerance test. An indication from the results of the computational model is received that the individual has an elevated glycemia test result. A clinical assessment is performed on the individual based on the elevated glycemia test result.

In another embodiment, he panel of analytes are repeatedly obtained with periodicity.

In yet another embodiment, the periodicity is one day, one week, one month, one year, or one decade.

In a further embodiment, the clinical assessment is a blood test, medical imaging, blood pressure measurements, electrocardiogram, stress test, or an angiogram.

In still yet another embodiment, at least one analyte measurement of the panel of analyte measurements clinical data, personal data, metabolites, protein constituents, genomic DNA, transcript expression, lipids, or human microbiota.

In yet a further embodiment, the glycemia test is insulin resistance. One or more analytes of the panel of analytes is triglycerides-to-high density lipoprotein ratio (TGL/HDL), creatine (CR), body mass index (BMI), absolute count of neutrophils (NEUTAB), calcium (CA), interleukin 1 beta (IL1B), interleukin 18 (IL18), angiotensinogen protein (AGT), interleukin 1 receptor accessory protein (IL1RAP), Ig kappa chain V-I region protein (KV116), complement factor H protein (CFH), myosin-binding protein C (MYBPC2), L-lysine (Lys), L-arginine (Arg), L-alanine (Ala), N1-methyladenosine, 4-formyl Indole, 3-Methyl-L-histidine, C7H15N3O2, C14H22N2O9, C12H24N2O3, C26H42O4, C28H46O4, C28H44O4, LysoPG(18:0), C16:3 FA, hexosylceramide HCER(24:0), lactosylceramide LCER (16:0), glycerophosphoethanolamine PE(P-18:0/22:6), PE(P-16:0/22:6) and PE(P-18:1/18:1), triacylglycerol TAG (58:10) containing fatty acid FA(20:5), chromosome 19 open reading frame 66 transcript (C19orf66), chromosome 1 open reading frame 174 transcript (C1orf174), calcineurin like EF-hand protein 1 transcript (CHP1), deoxyguanosine kinase transcript (DGUOK), Disks large-associated protein 1 transcript (DLGAP1), family with sequence similarity 86 member H pseudogene transcript (FAM86HP), family with sequence similarity 185 member A pseudogene transcript (FAM185A), heat shock cognate B transcript (HSCB), IL12A antisense RNA 1 (IL12A-AS1), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), UBAP1-MVB12-associated (UMA) domain containing 1 transcript (RPA3OS), serine/threonine-protein kinase 494 transcript (SGK494), solute carrier family 16 member 12 transcript (SLC16A12), synaptotagmin 9 transcript (SYT9), transmembrane protein 237 transcript (TMEM237), transmembrane protein 253 transcript (TMEM253), transmembrane protein 108 transcript (TMEM108), transmembrane protein 106B transcript (TMEM106B), U2AF homology motif kinase 1 transcript (UHMK1), vacuolar protein sorting 13 homolog A transcript (VPS13A), *Bacteroides* bacteria, Barnesiella bacteria, *Clostridium* bacteria, *Faecalibacterium* bacteria, *Ruminococcus* bacteria, *Bacteroides, Shigella* bacteria, Lachnospiraceae bacteria, or *Odoribacter* bacteria.

In an even further embodiment, the glycemia test is glucose tolerance. One or more analytes of the panel of analytes is hemoglobin A1C (A1C), alanine aminotransferase (ALT), cytokine platelet-derived growth factor subunit B homodimer (PDGFBB), complement factor D protein (CFD), Ig kappa variable 2D-28 protein (KVD28), Ig heavy constant alpha 2 protein (IGHA2), coagulation factor XI protein (F11), Ig kappa variable 310 protein (KV310), Ig heavy variable 2-70 protein (HV270), vitronectin protein (VTN), hexosamine, taurine, hydroxyphenyllactic acid, hippuric acid, ectoine, p-cresol glucuronide, hydroxy-stearic acid (C18:0,OH FA), dihydroxy-palmitic acid (C16:0,2OH), a-linolenic acid (C18:3 FA), chitobiosyldiphosphodolichol beta-mannosyltransferase like 2 transcript (ALG1L2), chromosome 21 open reading frame 119 transcript (C21orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNG214), unc-93 homolog B1 transcript (UNC93B1), wee1-like protein kinase 2 transcript (WEE2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), macrophage migration inhibitory factor transcript (MIF), zinc finger protein 596 transcript (ZNF596), *Bacteroides* bacteria, Lachnospiraceae bacteria, *Roseburia* bacteria, or *Faecalibacterium* bacteria.

In yet an even further embodiment, at least one analyte measurement of the panel of analyte measurements is selected based upon results of a second computational model that determines a relationship between glucose tolerance and the at least one analyte measurement.

In still yet an even further embodiment, the second computation model is a Bayesian computational model.

In still yet an even further embodiment, the first computational model is a ridge regression.

In an embodiment to treat an individual, a panel of a plurality of glycemia-related analytes extracted from an individual is measured. An indication of an individual's pathology of glycemic dysregulation from the panel of glycemia-related analyte measurements is determined. The individual is treated based on the individual's pathology of glycemic dysregulation such that the treatment is directed towards correcting the individual's pathology of glycemic dysregulation.

In another embodiment, the plurality of glycemia-related measurements include fasting plasma glucose, fasting insulin, fasting glucagon, steady-state plasma glucose, hemoglobin A1C, glucose level from oral glucose tolerance test, insulin level from oral glucose tolerance test, insulin secretion rate max, insulin secretion rate longitudinal pattern, Matsuda index, or disposition index.

In yet another embodiment, the indication of an individual pathology of glycemic dysregulation includes steady-state plasma glucose that has been computed by a computational predictive model utilizing a panel of analyte measurements.

In a further embodiment, the indication of an individual pathology of glycemic dysregulation includes glucose tolerance that has been computed by a computational predictive model utilizing a panel of analyte measurements.

In still yet another embodiment, the individual's pathology of glycemic dysregulation is poor insulin secretion. The individual is treated by administering a DPP-4 inhibitor, a sulfonylurea, a GLP-1 receptor agonist, or *panax ginseng*.

In yet a further embodiment, the DPP-4 inhibitor is: alogliptin, linagliptin, saxagliptin, sitagliptin, vildagliptin, gemigliptin, anagliptin, teneligliptin, trelagliptin, omarigliptin, evogliptin, gosogliptin, dutogliptin, or berberine.

In an even further embodiment, the sulfonylurea is glimepiride, gliclazide, glyburide, chlorpropamide, tolazamide, tolbutamide, acetohexamide, carbutamide, metahexamide, glycyclamide, glibornuride, glipizide, gliquidone, glisoxepide, or glyclopyramide.

In yet an even further embodiment, the GLP-1 receptor agonist selected is glucagon-like peptide 1, gastric inhibitory peptide, albiglutide, dulaglutide, exenatide, liraglutide, lixisenatide, or semaglutide.

In still yet an even further embodiment, the individual's pathology of glycemic dysregulation is peripheral insulin resistance. The individual is treated by administering a thiazolidinedione.

In still yet an even further embodiment, the thiazolidinedione is rosiglitazone, pioglitazone, or lobeglitazone.

In still yet an even further embodiment, the individual's pathology of glycemic dysregulation is excessive production of hepatic glucose. The individual is treated by administering a biguanide or thiazolidinedione.

In still yet an even further embodiment, the biguanide is metformin.

In still yet an even further embodiment, the thiazolidinedione rosiglitazone, pioglitazone, or lobeglitazone.

In an embodiment to treat an individual, a panel of analytes extracted from an individual is measured. An indication of an atherosclerotic cardiovascular risk derived from the panel of analyte measurements is determined. The individual is treated based on the individual's indicated atherosclerotic cardiovascular risk.

In another embodiment, at least one analyte measurement of the panel of analyte measurements is clinical data, personal data, metabolites, protein constituents, genomic DNA, transcript expression, lipids, or human microbiota.

In yet another embodiment, at least one analyte measurement of the panel of analyte measurements is triglycerides (TGL), L-Cysteinylglycine disulfide, hemoglobin A1c (A1C), 2,3-Dihydroxyvaleric acid LysoPC(16:0), C10:2 fatty acid, sex hormone binding globulin (SHBG), protein S1 (PROS1), phospholipid transfer protein (PLTP), high density lipoprotein (HDL), L-Proline, cholesterol-to-high density protein ration (CHOLHDL), LysoPC(20:2), Androstenediol (3beta,17beta) disulfate, LysoPC(18:2), Dihydroxyvitamin D3(2), C22:6 fatty acid, C10:0,OH fatty acid, N-Acetylserine, C16:1 fatty acid, complement component 5 (C5), Ig heavy chain V-III region JON, vascular endothelial growth factor (VEGF), serpin family F member 1 (SERPINF1), Bilirubin, matrix Gla-protein (MGP), low density lipoprotein-to-high density lipoprotein ratio (LDLHDL), C10:3 fatty acid, Red cell distribution width (RDW), platelet-derived growth factor BB (PDGFBB), complement factor H (CFH), Dihydroxyvitamin D3, Chenodeoxycholic acid glycine conjugate, 3-Methyl-2-oxovaleric acid, C8:0,OH fatty acid, Ne-Methyl-Lysine, LysoPC(P-18:1), gamma-glutamyl-epsilon-lysine, 1-Methylxanthine, nucleoporin 205 (NUP205), pregnancy zone protein (PZP), Glycosylphosphatidylinositol Specific Phospholipase D1 (GPLD1), LysoPE(P-16:0), L-a-Hydroxyisovaleric acid, LysoPC(18:0), Hypoxanthine, Homoarginine, vitronectin protein (VTN), interleukin 2 (IL2), or absolute monocyte count (MONOAB).

In a further embodiment, the determined atherosclerotic cardiovascular risk is a score above a threshold.

In still yet another embodiment, the individual is treated with statins, bile acid binding resins, cholesterol absorption inhibitors, fibrates, niacin, anticoagulants, antiplatelet medications, beta blockers, ACE inhibitors, calcium channel blockers, or diuretics.

In an embodiment perform a clinical assessment an individual, a panel of analytes extracted from an individual is measured. An indication of an atherosclerotic cardiovascular risk derived from the panel of analyte measurements is determined. A clinical assessment is performed on the individual based on the individual's indicated atherosclerotic cardiovascular risk.

In another embodiment, at least one analyte measurement of the panel of analyte measurements is clinical data, personal data, metabolites, protein constituents, genomic DNA, transcript expression, lipids, or human microbiota.

In yet another embodiment, at least one analyte measurement of the panel of analyte measurements is triglycerides (TGL), L-Cysteinylglycine disulfide, hemoglobin A1c (A1C), 2,3-Dihydroxyvaleric acid LysoPC(16:0), C10:2 fatty acid, sex hormone binding globulin (SHBG), protein S1 (PROS1), phospholipid transfer protein (PLTP), high density lipoprotein (HDL), L-Proline, cholesterol-to-high density protein ration (CHOLHDL), LysoPC(20:2), Androstenediol (3beta,17beta) disulfate, LysoPC(18:2), Dihydroxyvitamin D3(2), C22:6 fatty acid, C10:0,OH fatty acid, N-Acetylserine, C16:1 fatty acid, complement component 5 (C5), Ig heavy chain V-III region JON, vascular endothelial growth factor (VEGF), serpin family F member 1 (SERPINF1), Bilirubin, matrix Gla-protein (MGP), low density lipoprotein-to-high density lipoprotein ratio (LDLHDL), C10:3 fatty acid, Red cell distribution width (RDW), platelet-derived growth factor BB (PDGFBB), complement factor H (CFH), Dihydroxyvitamin D3, Chenodeoxycholic acid glycine conjugate, 3-Methyl-2-oxovaleric acid, C8:0,OH fatty acid, Ne-Methyl-Lysine, LysoPC(P-18:1), gamma-glutamyl-epsilon-lysine, 1-Methylxanthine, nucleoporin 205 (NUP205), pregnancy zone protein (PZP), Glycosylphosphatidylinositol Specific Phospholipase D1 (GPLD1), LysoPE(P-16:0), L-a-Hydroxyisovaleric acid, LysoPC(18:0), Hypoxanthine, Homoarginine, vitronectin protein (VTN), interleukin 2 (IL2), or absolute monocyte count (MONOAB).

In a further embodiment, the determined atherosclerotic cardiovascular risk is a score above a threshold.

In still yet another embodiment, the clinical assessment is a blood test, medical imaging, blood pressure measurements, electrocardiogram, stress test, and an angiogram.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 1 illustrates a process for treating an individual based on their glycemic regulation derived from analyte data in accordance with an embodiment of the invention.

FIG. 2 illustrates a process to construct and train a computational model to determine an individual's glycemic regulation measurement in accordance with an embodiment of the invention.

FIG. 3A illustrates a process to treat an individual based on the individual's computed glycemic regulation indicator in accordance with an embodiment of the invention.

FIG. 3B illustrates a process to treat an individual based on the individual's indicated pathology of a glycemic dysregulation in accordance with an embodiment of the invention.

FIG. 4 illustrates a process to identify analyte measurement features that are predictive of glycemic regulation measurements in accordance with an embodiment of the invention.

FIG. 5 illustrates a diagram of computing systems configured to determine glycemic regulation determinations in accordance with various embodiments of the invention.

FIGS. 16 to 18 detail longitudinal glycemia test results of various individuals within the iPOP population used in a cohort study, utilized in accordance with various embodiments of the invention.

FIG. 19 details the correlation between transition to diabetes and weight and gut microbial Shannon diversity in two individuals within the iPOP population used in a cohort study, utilized in accordance with various embodiments of the invention.

FIG. 29 provides ultrasound images of carotid plaque and relative distribution of ASCVD risk sore, HbA1c, and LV GLS in presences or absence of carotid plaque, utilized in accordance with various embodiments of the invention.

FIG. 33 illustrates a summary of major clinically actionable health discoveries, utilized in accordance with various embodiments of the invention.

FIG. 34 provides health behavior changes of individuals within the iPOP population used in a cohort study, utilized in accordance with various embodiments of the invention.

DETAILED DESCRIPTION

Figure 6:
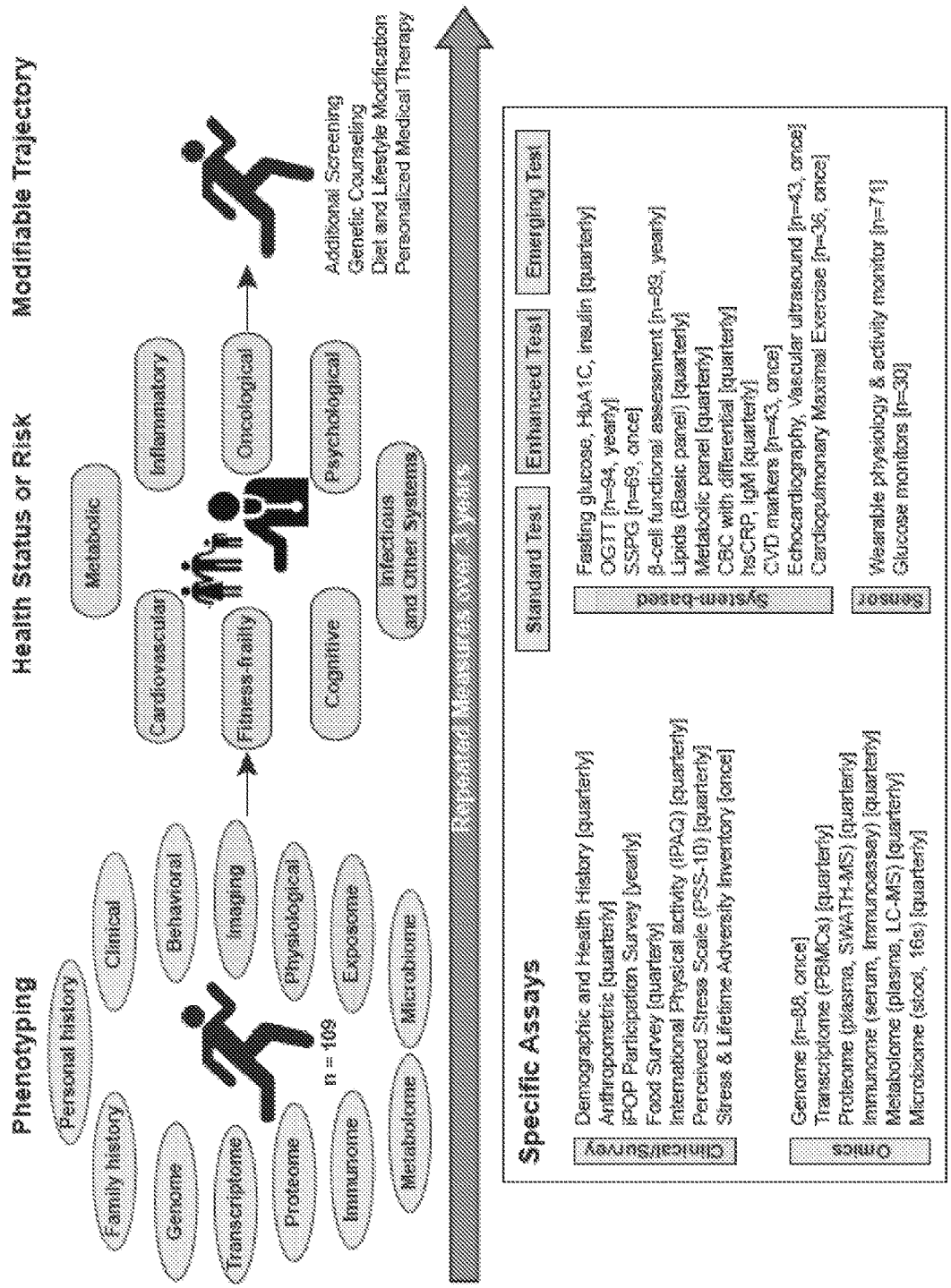
FIG. 6 illustrates an overview of in-depth longitudinal phenotyping used to determine health risk and status in accordance with various embodiments of the invention.

Turning now to the drawings and data, methods and processes to treat individuals based on their glycemic regulation and atherosclerotic disease and applications thereof are described, in accordance with various embodiments of the invention. In several embodiments, analyte measurements of an individual are collected and used to determine an individual's glycemia. In several embodiments, analyte measurements of an individual are collected and used to determine an individual's atherosclerotic cardiovascular disease (ASCVD) risk. In some embodiments, a panel of analyte measurements are used to compute a steady-state plasma glucose level (SSPG) and provide an easily determinable indicator of insulin resistance, which is often currently determined by a modified insulin suppression test. In some embodiments, a panel of analyte measurements are used to compute a glucose tolerance indicator, which in some cases may be used as a surrogate of an oral glucose tolerance test (OGTT). In some embodiments, a panel of analyte measurements are used to compute ASCVD risk utilizing correlation measurements. Many embodiments utilize an individual's glycemic regulation or ASCVD risk determination to perform a treatment upon that individual. In some instances, a treatment can include a medication, a dietary supplement, a dietary alteration, physical exercise, and any combination thereof.

Precision health and medicine are entering a new era where wearable sensors, "omics" technologies and computational methods have the potential to improve health and lead to new discoveries. The value in such approaches is based on identifying new actionable information with a low likelihood of false positive findings. Actionable information can improve risk stratification, facilitate early detection of disease, personalize therapeutic choices, provide insights with genetic counseling, and influence the adoption of a behavior that promotes overall health.

Diabetes mellitus (DM) is a disorder that can benefit greatly from a personalized, longitudinal profiling, and early diagnoses. Early indications of glycemia and/or glycemic dysregulation can be used to treat an individual such that the treatment can mitigate the progression of diabetes and/or insulin resistance. Accordingly, several embodiments utilize actionable data relating to glycemia and/or glycemic regulation to diagnose and/or treat an individual. In many of these embodiments, the actionable data is obtained long before an individual is considered diabetic and/or is symptomatic.

ASCVD is a disorder that can benefit greatly from a personalized, longitudinal profiling, and early diagnoses. Early indications of ASCVD risk can be used to treat an individual such that the treatment can mitigate the progression of atherosclerosis. Accordingly, several embodiments utilize actionable data relating to ASCVD risk to diagnose and/or treat an individual. In many of these embodiments, the actionable data is obtained long before an individual is symptomatic.

Analytes Indicative of Glycemic Dysregulation

A process for determining an individual's glycemic regulation using analyte measurements, in accordance with an embodiment of the invention is shown in FIG. 1. This embodiment is directed to determining an individual's glycemia indicator and applies the knowledge garnered to perform a clinical intervention on an individual. For example, this process can be used to identify an individual having a particular analyte constituency that is indicative of glycemic dysregulation and treat that individual with a medication, a dietary supplement, a dietary alteration, physical exercise, or any combination thereof.

In a number of embodiments, analytes and analyte measurements are to be interpreted broadly as clinical and molecular constituents and measurements that can be captured in medical and/or laboratory setting and are to include clinical data, personal data, metabolites, protein constituents, genomic DNA, transcript expression, lipids, and human microbiota. In some embodiments, clinical data is to include medical patient data such as (for example) weight, height, heart rate, blood pressure, body mass index (BMI), clinical tests and the like. In various embodiments, personal data is to include data captured by an individual such as (for example) wearable data, physical activity, diet, substance abuse and the like. In some embodiments, metabolites are to include intermediates and products of metabolism such as (for example) sugars, amino acids, nucleotides, antioxidants, organic acids, polyols, vitamins, and the like. In various embodiments, protein constituents are chains of amino acids which are to include (but not limited to) peptides, enzymes, receptors, ligands, antibodies, transcription factors, cytokines, hormones, growth factors and the like. In some embodiments, genomic DNA is DNA of an individual and includes (but is not limited to) copy number variant data, single nucleotide variant data, polymorphism data, mutation analysis, insertions, deletions and partial and full genomes. In various embodiments, transcript expression is the evidence of RNA molecules of a particular gene or other RNA transcripts, and is to include (but not limited to) analysis of expression levels of particular transcript targets, splicing variants, a class or pathway of gene targets, and partial and full transcriptomes. In some embodiments, lipids are a broad class of molecules that include (but are not limited to) fatty acid molecules, fat soluble vitamins, glycerolipids, phospholipids, sterols, sphingolipids, prenols, saccharolipids, polyketides, and the like. In various embodiments, human microbiota is the constituency of microbes (especially bacteria) that are found to reside on or within a human, especially in the digestive tract. It is noted that measurements of human microbiota, in accordance with some embodiments, is to include measurements of microbial diversity itself, such as (for example) the Shannon or Simpson diversity indices.

It is now known that a number of analytes have an indication of outcome of various diagnostic tests for diabetes and similar glycemic irregularities. Accordingly, a panel of analytes can be used to assess an individual for glycemic regulation. In some embodiments, analyte measures are used as a surrogate of and in lieu of standard diabetic diagnostic test (e.g., insulin resistance, OGTT). In various embodiments, analyte measures are used to determine whether diabetic diagnostic test, such as insulin resistance or OGTT, should be performed.

Process 100 begins with obtaining and measuring (101) analytes from an individual. In many instances, analytes are measured from a blood extraction, stool sample, urine sample, saliva sample, or biopsy. In some embodiments, an individual's analytes are extracted during fasting, or in a controlled clinical assessment (e.g., OGTT, SSPG). A number of methods are known to extract analytes from an individual and can be used within various embodiments of the invention. In several embodiments, analytes are extracted over a period a time and measured at each time point, resulting in a dynamic analysis of the analytes. In some of these embodiments, analytes are measured with periodicity (e.g., monthly, quarterly, yearly).

In a number of embodiments, an individual is any individual that has their analytes extracted and measured. In some embodiments, an individual has been diagnosed as being diabetic or pre-diabetic. Embodiments are also directed to an individual being one that has not been diagnosed as diabetic. In some of these embodiments, the individual is normoglycemic or diagnosed as normoglycemic, as determined by classical diabetes testing, including (but not limited to) measuring fasting plasma glucose levels, measuring glycated hemoglobin (HbA1C test), and oral glucose tolerance test (OGTT). In a number of these embodiments, normoglycemic, pre-diabetic, and diabetic assessment is determined by standards set forth by a diabetes organization such as the American Diabetes Association.

A number of analytes can be used to indicate glycemic regulation, including (but not limited to) clinical data, personal data, metabolites, protein constituents, genomic DNA, transcript expression, lipids, and human microbiota. Analytes can be detected and measured by a number of methods, including nucleic acid and protein sequencing, mass spectrometry, colorimetric analysis, immunodetection, and the like.

In several embodiments, analyte measurements are performed by taking a single time-point measurement. In many embodiments, the median and/or average of a number time points for participants with multiple time-point measurements are utilized. Various embodiments incorporate correlations, which can be calculated by a number of methods, such as the Spearman correlation method. A number of embodiments utilize a computational model that incorporates analyte measurements, such as linear mixed models and ridge regression models. Significance can be determined by calculating p-values that are corrected for multiple hypothesis. It should be noted however, that there are several correlation, computational models, and statistical methods that can utilize analyte measurements and may also fall within some embodiments of the invention.

In a number of embodiments, dynamic correlations use a ratio of analyte measurements between two time points, a percent change of analyte measurements over a period of time, a rate of change of analyte measurements over a period of time, or any combination thereof. Several other dynamic measurements may also be used in the alternative or in combination in accordance with multiple embodiments.

Using static and/or dynamic measures of analytes, process 100 determines (103) an indication of an individual's glycemic regulation. In many embodiments, the correlations and/or computational models can be used to indicate a result of a glycemia test. In several embodiments, determining analyte correlations or modeling a glycemia test is used to substitute glycemia tests. In various embodiments, measurements of analytes can be used as a precursor indicator to determine whether to perform a glycemia test. Using analyte measurements could potentially prevent the necessity to perform undesirable glycemia tests, such as OGTT and SSPG characterizations, which each can take a considerable amount of an individual's time and is often uncomfortable for the duration of the process. Alternatively, analyte measurements can determine that an individual is likely to be glucose intolerant or insulin resistant and thus confirm whether an OGTT or SSPG characterization should be performed.

Process 100 also outputs (105) a report containing an individual's glycemic regulation result. In some embodiments, these results determine whether an individual is normoglycemic, prediabetic, or diabetic.

Having determined an individual's glycemic regulation, a clinical intervention can be performed (107) on the individual, including performing clinical assessments or treatments. In many embodiments, a clinical assessment includes (but not limited to) a blood test, medical imaging, blood pressure measurements, electrocardiogram, stress test, an angiogram, or any combination thereof. In a number of embodiments, a treatment entails a medication, a dietary supplement, a dietary alteration, physical exercise, or any combination thereof. In some embodiments, an individual is treated by medical professional, such as a doctor, nurse, dietician, or similar. Various embodiments are directed to self-treatment such that an individual having a particular glycemic regulation intakes a medicine, a dietary supplement, alters her diet, or physically exercises based on the knowledge of her indicated glycemic regulation.

While specific examples of determining an individual's glycemic regulation are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for determining an individual's glycemic regulation appropriate to the requirements of a given application can be utilized in accordance with various embodiments of the invention.

Modeling Tests of Glycemic Regulation with Analyte Measurements

Glucose tolerance and steady-state plasma glucose measurements are used to determine an individual's ability to accommodate large loads of glucose and respond to insulin, respectively. Glucose tolerance and SSPG are measured using elaborate time-coursed tests that are uncomfortable or inconvenient for patients and expensive. As such they are often performed infrequently. Accordingly, alternative tests that provide similar results to determine glucose accommodation and insulin response are desired.

The oral glucose tolerance test measures an individual's ability to intake a high dose of glucose, mimicking the intake of sugars during the course of a meal. High sugar intake leads to increased plasma insulin which suppresses hepatic glucose release and stimulates sugar uptake in the peripheral tissues. Impaired pancreatic beta cell function and peripheral insulin resistance, particularly in skeletal muscle, can lead to impaired glucose tolerance (IGT) and/or a diabetic diagnosis where individuals exhibit high levels of glucose in their blood. The inability to regulate glycemia after a meal can lead to spikes of blood glucose, which can result in damage to peripheral tissues.

OGTT requires an individual to fast overnight. In the morning, the individual is first tested for FPG, after which the individual receives a standardized dose of glucose, and then plasma glucose is measured over an extended period of time. High levels of glucose over the time course indicate either the individual has impaired beta cell function (i.e., not producing insulin) or is failing to respond to insulin secretion.

Measurement of SSPG, on the other hand, is a direct indication of an individual's insulin resistance, which occurs when the muscles, fat, and liver are failing to appropriately respond to insulin signaling. The failure to respond results in an inability to take up the glucose from the bloodstream, causing a dysregulation of glycemia.

One exam to determine SSPG is the insulin suppression test, which is an unpleasant, time-consuming, and resource intensive exam. After an overnight fast, glucose and insulin are suppressed in a subject by infusing an appropriate chemical, such as octreotide. Insulin and glucose are then infused into the subject for a period of time and then a number of draws of blood are taken at various intervals to determine blood glucose levels. The mean of the blood glucose levels is the individual's SSPG.

An alternative test to measure glucose tolerance and/or SSPG that is less time-consuming, less expensive and more pleasant on the subject would be of great benefit. One potential alternative would be to measure a panel of analytes and compute an indication of an individual's glucose tolerance and SSPG using a surrogate computational model. Accordingly, various embodiments revolve around constructing, training, and utilizing a computational model to indicate glucose tolerance and SSPG from analyte measurements.

A process for constructing and training a computational model to indicate an individual's glucose tolerance and/or SSPG in accordance with an embodiment of the invention is shown in FIG. 2. Process 200 measures (201) a panel of analytes from each individual of a collection of individuals. In several embodiments, analytes are measured from a blood sample, stool sample, urine sample, saliva sample, or biopsy of an individual. In some embodiments, an individual's analytes are extracted during fasting. A number of methods are known to extract analytes from an individual and can be used within various embodiments of the invention. In several embodiments, analytes are extracted and measured at each time point, resulting in a dynamic analysis of the analytes. In some of these embodiments, analytes are measured with periodicity (e.g., monthly, quarterly, yearly).

A number of analytes can be used to determine glycemic regulation, including (but not limited to) clinical data, personal data, metabolites, protein constituents, genomic DNA, transcript expression, lipids, and human microbiota. Analytes can be detected and measured by a number of methods, including nucleic acid and protein sequencing, mass spectrometry, colorimetric analysis, immunodetection, and the like. It should be noted that static, median, average, and/or dynamic analyte measurements can be used in accordance with various embodiments of the invention.

In numerous embodiments, an individual is any individual that has her analytes extracted and measured. In some embodiments, an individual has been diagnosed as being diabetic or pre-diabetic. Embodiments are also directed to an individual being one that has not been diagnosed as diabetic. In some of these embodiments, the individual is normoglycemic or diagnosed as normoglycemic, as determined by classical diabetes testing, including (but not limited to) measuring fasting glucose levels, measuring glycated hemoglobin (HbA1C test), and oral glucose tolerance test (OGTT). In a number of these embodiments, normoglycemia, pre-diabetic, and diabetic assessment is determined by standards set forth by a Diabetes organization such as the American Diabetes Association.

A collection of individuals, in accordance with many embodiments, is a group of individuals to be measured so that their data can be used to construct and train a computational model. A collection can include individuals that are undiagnosed or diagnosed as diabetic, pre-diabetic, normoglycemic. In some embodiments, it is beneficial to have a diversity of individuals having different glycemic diagnoses, such that a computational model can be trained with an expansive data set. The number of individuals in a collection can vary, and in some embodiments, having a greater number of individuals will increase the prediction power of a trained computer model. The precise number and composition of individuals will vary, depending on the model to be constructed and trained.

Process 200 also measures (203) glycemic regulation of each individual in the collection of individuals. Glycemic regulation tests that can be performed include any glycemic test to be modeled, including OGTT and the insulin suppression test. A few methodologies are known to measure glucose tolerance and SSPG, each of which can be used within various embodiments of the invention.

One methodology to perform OGTT includes fasting overnight to reach a basal steady state of glucose and insulin. Fasting plasma glucose levels are measured before administration of 75 grams of oral glucose. After administration, glucose is measured every hour for two to four hours. In some embodiments, an oximetric method is used to determine blood glucose. IGT is determined if one measurement is elevated above predetermined threshold. It should be understood, however, that other methodologies to determine glucose tolerance can be used and still fall within several embodiments of the invention.

One methodology to perform the insulin suppression test involves administering octreotide (or similar compound) to remove insulin and glucose from the blood stream. In one embodiment, the test is performed after an overnight fast and consists of 180-minute infusion of octreotide (0.27 µg/m2/min), insulin (0.25 µg/m2/min), and glucose (240 µg/m2/min) with blood draws at minutes 150, 160, 170, and 180. In some embodiments, an oximetric method is used to determine blood glucose. SSPG is determined by taking the mean of the glucose measurements. It should be understood, however, that other methodologies to determine SSPG can be used and still fall within several embodiments of the invention.

Using the analyte measurements and glycemic regulation measurements, process 200 generates (205) training labels that provide a correspondence between analyte measurement features and glycemic regulation measurements, such as glucose tolerance and SSPG. In several embodiments, analyte measurements used to generate training labels are predictive of a glycemic regulation measurement. In some embodiments, glycemic regulation measurements and analyte measurements are standardized.

Based on studies performed, it has been found that several analyte measurements provide robust predictive ability, including (but not limited to) particular clinical data, personal data, metabolites, protein constituents, genomic DNA, transcript expression, lipids, and human microbiota. A number of methods can be used to select analyte measurements to be used as features in the training model. In some embodiments, correlation measurements between analyte measurements and glycemic regulation measurements are used to select features. In various embodiments, a computational model is used to determine which analyte measurements are best predictors. For example, a Bayesian network can be used to determine which analyte measurement features represent the outcome of glycemic regulation measurements. In some embodiments, a Max-Min Parents and Child (MMPC) Bayesian network algorithm is used to select features. Use of Bayesian networks to select features is described in greater detail below.

A selection of predictive analyte measurement features are described in the Exemplary Embodiments section. In particular, FIG. 25 and Tables 8 and 9 provide a number of analyte measurement features that are indicative of either SSPG or OGTT results, as determined by MMPC Bayesian network feature selection followed by Ridge Regression.

In various embodiments, analyte measurement features for SSPG include (but not limited to) triglycerides-to-high density lipoprotein ratio (TGL/HDL), creatine (CR), body mass index (BMI), absolute count of neutrophils (NEUTAB), calcium (CA), interleukin 1 beta (IL1B), interleukin 18 (IL18), angiotensinogen protein (AGT), interleukin 1 receptor accessory protein (IL1RAP), Ig kappa chain V-I region protein (KV116), complement factor H protein (CFH), myosin-binding protein C (MYBPC2), L-lysine (Lys), L-arginine (Arg), L-alanine (Ala), N1-methyladenosine, 4-formyl Indole, 3-Methyl-L-histidine, C7H15N3O2, C14H22N2O9, C12H24N2O3, C26H42O4, C28H46O4, C28H44O4, LysoPG(18:0), C16:3 FA, hexosylceramide HCER(24:0), lactosylceramide LCER(16:0), glycerophosphoethanolamine PE(P-18:0/22:6), PE(P-16:0/22:6) and PE(P-18:1/18:1), triacylglycerol TAG(58:10) containing fatty acid FA(20:5), chromosome 19 open reading frame 66 transcript (C19orf66), chromosome 1 open reading frame 174 transcript (C1orf174), calcineurin like EF-hand protein 1 transcript (CHP1), deoxyguanosine kinase transcript (DGUOK), Disks large-associated protein 1 transcript (DLGAP1), family with sequence similarity 86 member H pseudogene transcript (FAM86HP), family with sequence similarity 185 member A pseudogene transcript (FAM185A), heat shock cognate B transcript (HSCB), IL12A antisense RNA 1 (IL12A-AS1), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), UBAP1-MVB12-associated (UMA)

domain containing 1 transcript (RPA3OS), serine/threonine-protein kinase 494 transcript (SGK494), solute carrier family 16 member 12 transcript (SLC16A12), synaptotagmin 9 transcript (SYT9), transmembrane protein 237 transcript (TMEM237), transmembrane protein 253 transcript (TMEM253), transmembrane protein 108 transcript (TMEM108), transmembrane protein 106B transcript (TMEM106B), U2AF homology motif kinase 1 transcript (UHMK1), vacuolar protein sorting 13 homolog A transcript (VPS13A), *Bacteroides* bacteria, *Barnesiella* bacteria, *Clostridium* bacteria, *Faecalibacterium* bacteria, *Ruminococcus* bacteria, *Bacteroides, Shigella* bacteria, *Lachnospiraceae* bacteria, and *Odoribacter* bacteria.

A number of prediction models have been built to predict SSPG with high predictive ability (see Table 8). Various embodiments utilize the features within these models (or similar) to build models to predict SSPG.

In an embodiment, it was found that the analyte measurement features creatine (CR), absolute count of neutrophils (NEUTAB), triglycerides-to-high density lipoprotein ratio (TGL/HDL), and body mass index (BMI) are predictive of SSPG (Table 8). Accordingly, various embodiments are directed towards models that include one or more features selected from: creatine (CR), absolute count of neutrophils (NEUTAB), triglycerides-to-high density lipoprotein ratio (TGL/HDL), and body mass index (BMI). In some embodiments, two or more features described are utilized in a predictive model. In some embodiments, three or more features described are utilized in a predictive model. In some embodiments, four or more features described are utilized in a predictive model.

In an embodiment, it was found that the analyte measurement features creatine (CR), absolute count of neutrophils (NEUTAB), triglycerides-to-high density lipoprotein ratio (TGL/HDL), body mass index (BMI), calcium (CA), interleukin 1 beta (IL1B), and interleukin 18 (IL18) are predictive of SSPG (Table 8). Accordingly, various embodiments are directed towards models that include one or more features selected from: creatine (CR), absolute count of neutrophils (NEUTAB), triglycerides-to-high density lipoprotein ratio (TGL/HDL), body mass index (BMI), calcium (CA), interleukin 1 beta (IL1B), and interleukin 18 (IL18). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model.

In an embodiment, it was found that the analyte measurement features creatine (CR), absolute count of neutrophils (NEUTAB), triglycerides-to-high density lipoprotein ratio (TGL/HDL), body mass index (BMI), angiotensinogen protein (AGT), interleukin 1 receptor accessory protein (IL1RAP), Ig kappa chain V-I region protein (KV116), complement factor H protein (CFH), and myosin-binding protein C (MYBPC2) are predictive of SSPG (Table 8). Accordingly, various embodiments are directed towards models that include one or more features selected from: creatine (CR), absolute count of neutrophils (NEUTAB), triglycerides-to-high density lipoprotein ratio (TGL/HDL), body mass index (BMI), angiotensinogen protein (AGT), interleukin 1 receptor accessory protein (IL1RAP), Ig kappa chain V-I region protein (KV116), complement factor H protein (CFH), and myosin-binding protein C (MYBPC2). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model.

In an embodiment, it was found that the analyte measurement features triglycerides-to-high density lipoprotein ratio (TGL/HDL), N1-methyladenosine, C7H15N3O2, L-lysine (Lys), C14H22N2O9, 4-formyl Indole, C28H46O4, and C26H42O4 are predictive of SSPG (Table 8). Accordingly, various embodiments are directed towards models that include one or more features selected from: triglycerides-to-high density lipoprotein ratio (TGL/HDL), N1-methyladenosine, C7H15N3O2, L-lysine (Lys), C14H22N2O9, 4-formyl Indole, C28H46O4, and C26H42O4. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model.

In an embodiment, it was found that the analyte measurement features creatine (CR), absolute count of neutrophils (NEUTAB), triglycerides-to-high density lipoprotein ratio (TGL/HDL), body mass index (BMI), HCER(24:0), glycerophosphoethanolamine PE(P-18:0/22:6), and triacylglycerol TAG(58:10) containing fatty acid FA(20:5) are predictive of SSPG (Table 8). Accordingly, various embodiments are directed towards models that include one or more features selected from: creatine (CR), absolute count of neutrophils (NEUTAB), triglycerides-to-high density lipoprotein ratio (TGL/HDL), body mass index (BMI), HCER (24:0), glycerophosphoethanolamine PE(P-18:0/22:6), and triacylglycerol TAG(58:10) containing fatty acid FA(20:5). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model.

In an embodiment, it was found that the analyte measurement features absolute count of neutrophils (NEUTAB), triglycerides-to-high density lipoprotein ratio (TGL/HDL), chromosome 19 open reading frame 66 transcript (C19orf66), calcineurin like EF-hand protein 1 transcript (CHP1), family with sequence similarity 86 member H pseudogene transcript (FAM86HP), heat shock cognate B transcript (HSCB), kyphoscoliosis peptidase transcript (KY), mitogen-activated protein kinase kinase kinase 19 transcript (MAP3K19), solute carrier family 16 member 12 transcript (SLC16A12), synaptotagmin 9 transcript (SYT9), transmembrane protein 237 transcript (TMEM237), transmembrane protein 253 transcript (TMEM253), and U2AF homology motif kinase 1 transcript (UHMK1) are predictive of SSPG (Table 8). Accordingly, various embodiments are directed towards models that include one or more features selected from: absolute count of neutrophils (NEUTAB), triglycerides-to-high density lipoprotein ratio (TGL/HDL), chromosome 19 open reading frame 66 transcript (C19orf66), calcineurin like EF-hand protein 1 transcript (CHP1), family with sequence similarity 86 member H pseudogene transcript (FAM86HP), heat shock cognate B transcript (HSCB), kyphoscoliosis peptidase transcript (KY), mitogen-activated protein kinase kinase kinase 19 transcript (MAP3K19), solute carrier family 16 member 12 transcript (SLC16A12), synaptotagmin 9 transcript (SYT9), transmembrane protein 237 transcript (TMEM237), transmembrane protein 253 transcript (TMEM253), and U2AF homology motif kinase 1 transcript (UHMK1). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model.

In an embodiment, it was found that the analyte measurement features triglycerides-to-high density lipoprotein ratio (TGL/HDL), interleukin 1 receptor accessory protein (IL1RAP), L-alanine (Ala), C26H42O4, hexosylceramide HCER(24:0), chromosome 19 open reading frame 66 transcript (C19orf66), Disks large-associated protein 1 transcript (DLGAP1), family with sequence similarity 185 member A pseudogene transcript (FAM185A), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), transmembrane protein 237 transcript (TMEM237), transmembrane protein 253 transcript (TMEM253), and vacuolar protein sorting 13 homolog A transcript (VPS13A) are predictive of SSPG (Table 8). Accordingly, various embodiments are directed towards models that include one or more features selected from: triglycerides-to-high density lipoprotein ratio (TGL/HDL), interleukin 1 receptor accessory protein (IL1RAP), L-alanine (Ala), C26H42O4, hexosylceramide HCER(24:0), chromosome 19 open reading frame 66 transcript (C19orf66), Disks large-associated protein 1 transcript (DLGAP1), family with sequence similarity 185 member A pseudogene transcript (FAM185A), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), transmembrane protein 237 transcript (TMEM237), transmembrane protein 253 transcript (TMEM253), and vacuolar protein sorting 13 homolog A transcript (VPS13A). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model. In some embodiments, fourteen or more features described are utilized in a predictive model. In some embodiments, fifteen or more features described are utilized in a predictive model. In some embodiments, sixteen or more features described are utilized in a predictive model. In some embodiments, seventeen or more features described are utilized in a predictive model.

In an embodiment, it was found that the analyte measurement features triglycerides-to-high density lipoprotein ratio (TGL/HDL), interleukin 1 receptor accessory protein (IL1RAP), L-arginine (Arg), C26H42O4, L-lysine (Lys), chromosome 19 open reading frame 66 transcript (C19orf66), chromosome 1 open reading frame 174 transcript (C1orf174), deoxyguanosine kinase transcript (DGUOK), kyphoscoliosis peptidase transcript (KY), mitogen-activated protein kinase kinase kinase 19 transcript (MAP3K19), UBAP1-MVB12-associated (UMA) domain containing 1 transcript (RPA3OS), serine/threonine-protein kinase 494 transcript (SGK494), transmembrane protein 108 transcript (TMEM108), and *Ruminococcus* bacteria are predictive of SSPG (Table 8). Accordingly, various embodiments are directed towards models that include one or more features selected from: triglycerides-to-high density lipoprotein ratio (TGL/HDL), interleukin 1 receptor accessory protein (IL1RAP), L-arginine (Arg), C26H42O4, L-lysine (Lys), chromosome 19 open reading frame 66 transcript (C19orf66), chromosome 1 open reading frame 174 transcript (C1orf174), deoxyguanosine kinase transcript (DGUOK), kyphoscoliosis peptidase transcript (KY), mitogen-activated protein kinase kinase kinase 19 transcript (MAP3K19), UBAP1-MVB12-associated (UMA) domain containing 1 transcript (RPA3OS), serine/threonine-protein kinase 494 transcript (SGK494), transmembrane protein 108 transcript (TMEM108), and *Ruminococcus* bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model.

In some embodiments, twelve or more features described are utilized in a predictive model. In some embodiments, thirteen or more features described are utilized in a predictive model. In some embodiments, fourteen or more features described are utilized in a predictive model. In some embodiments, fifteen or more features described are utilized in a predictive model.

In an embodiment, it was found that the analyte measurement features L-arginine (Arg), hexosylceramide HCER(24:0), lactosylceramide LCER(16:0), glycerophosphoethanolamine PE(P-18:0/22:6), mitogen-activated protein kinase kinase kinase 19 transcript (MAP3K19), POC5 centriolar protein transcript (POC5), transmembrane protein 106B transcript (TMEM106B), U2AF homology motif kinase 1 transcript (UHMK1), *Ruminococcus* bacteria, *Faecalibacterium* bacteria, and *Clostridium* bacteria are predictive of SSPG (Table 8). Accordingly, various embodiments are directed towards models that include one or more features selected from: L-arginine (Arg), hexosylceramide HCER(24:0), lactosylceramide LCER(16:0), glycerophosphoethanolamine PE(P-18:0/22:6), mitogen-activated protein kinase kinase kinase 19 transcript (MAP3K19), POC5 centriolar protein transcript (POC5), transmembrane protein 106B transcript (TMEM106B), U2AF homology motif kinase 1 transcript (UHMK1), *Ruminococcus* bacteria, *Faecalibacterium* bacteria, and *Clostridium* bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model.

In an embodiment, it was found that the analyte measurement features absolute count of neutrophils (NEUTAB), triglycerides-to-high density lipoprotein ratio (TGL/HDL), body mass index (BMI), *Bacteroides* bacteria, *Faecalibacterium* bacteria, Barnesiella bacteria, *Ruminococcus* bacteria, *Odoribacter* bacteria, and Lachnospiraceae bacteria are predictive of SSPG (Table 8). Accordingly, various embodiments are directed towards models that include one or more features selected from: absolute count of neutrophils (NEUTAB), triglycerides-to-high density lipoprotein ratio (TGL/HDL), body mass index (BMI), *Bacteroides* bacteria, *Faecalibacterium* bacteria, Barnesiella bacteria, *Ruminococcus* bacteria, *Odoribacter* bacteria, and Lachnospiraceae bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model.

In an embodiment, it was found that the analyte measurement features interleukin 1 receptor accessory protein (IL1RAP), L-arginine (Arg), C7H15N3O2, C12H24N2O3, hexosylceramide HCER(24:0), lactosylceramide LCER(16:0), glycerophosphoethanolamine PE(P-16:0/22:6), *Clostridium* bacteria, *Shigella* bacteria, *Ruminococcus* bacteria, and *Faecalibacterium* bacteria are predictive of SSPG (Table 8). Accordingly, various embodiments are directed towards models that include one or more features selected from: interleukin 1 receptor accessory protein (IL1RAP), L-arginine (Arg), C7H15N3O2, C12H24N2O3, hexosylceramide HCER(24:0), lactosylceramide LCER(16:0), glycerophosphoethanolamine PE(P-16:0/22:6), *Clostridium* bacteria, *Shigella* bacteria, *Ruminococcus* bacteria, and *Faecalibacterium* bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model.

In various embodiments, analyte measurement features for OGTT results include (but not limited to) hemoglobin A1C (A1C), alanine aminotransferase (ALT), cytokine platelet-derived growth factor subunit B homodimer (PDGFBB), complement factor D protein (CFD), Ig kappa variable 2D-28 protein (KVD28), Ig heavy constant alpha 2 protein (IGHA2), coagulation factor XI protein (F11), Ig kappa variable 310 protein (KV310), Ig heavy variable 2-70 protein (HV270), vitronectin protein (VTN), hexosamine, taurine, hydroxyphenyllactic acid, hippuric acid, ectoine, p-cresol glucuronide, hydroxy-stearic acid (C18:0,OH FA), dihydroxy-palmitic acid (C16:0,2OH), α-linolenic acid (C18:3 FA), chitobiosyldiphosphodolichol beta-mannosyltransferase like 2 transcript (ALG1L2), chromosome 21 open reading frame 119 transcript (C21 orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNF214), unc-93 homolog B1 transcript (UNC93B1), wee1-like protein kinase 2 transcript (WEE2), ceramide synthase 5 transcript (CERS5), dishevelled associated activator of morphogenesis 1 transcript (DAAM1), family with sequence similarity 86 member H pseudogene transcript (FAM86HP), filaggrin transcript (FLG), macrophage migration inhibitory factor transcript (MIF), zinc finger protein 596 transcript (ZNF596), *Bacteroides* bacteria, Lachnospiraceae bacteria, *Roseburia* bacteria, and *Faecalibacterium* bacteria. Based on the foregoing, it should be understood that a number of combinations of analyte features can be used solitarily or combined in any fashion to be used to train a predictive computational model.

A number of prediction models have been built to predict OGTT results with high predictive ability (see Table 9).

Various embodiments utilize the features within these models (or similar) to build models to predict OGTT results.

In an embodiment, it was found that the analyte measurement features hemoglobin A1C (A1C) and alanine aminotransferase (ALT) are predictive of OGTT results (Table 9). Accordingly, various embodiments are directed towards models that include one or more features selected from: hemoglobin A1C (A1C) and alanine aminotransferase (ALT). In some embodiments, two or more features described are utilized in a predictive model.

In an embodiment, it was found that the analyte measurement features hemoglobin A1C (A1C) and cytokine platelet-derived growth factor subunit B homodimer (PDGFBB) are predictive of OGTT results (Table 9). Accordingly, various embodiments are directed towards models that include one or more features selected from: hemoglobin A1C (A1C) and cytokine platelet-derived growth factor subunit B homodimer (PDGFBB). In some embodiments, two or more features described are utilized in a predictive model.

In an embodiment, it was found that the analyte measurement features hemoglobin A1C (A1C) complement factor D protein (CFD), Ig kappa variable 2D-28 protein (KVD28), Ig heavy constant alpha 2 protein (IGHA2), coagulation factor XI protein (F11), Ig kappa variable 310 protein (KV310), and Ig heavy variable 2-70 protein (HV270) are predictive of OGTT results (Table 9). Accordingly, various embodiments are directed towards models that include one or more features selected from: hemoglobin A1C (A1C) complement factor D protein (CFD), Ig kappa variable 2D-28 protein (KVD28), Ig heavy constant alpha 2 protein (IGHA2), coagulation factor XI protein (F11), Ig kappa variable 310 protein (KV310), and Ig heavy variable 2-70 protein (HV270). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model.

In an embodiment, it was found that the analyte measurement features hemoglobin A1C (A1C), *Bacteroides* bacteria, Lachnospiraceae bacteria, *Roseburia* bacteria, and *Faecalibacterium* bacteria are predictive of OGTT results (Table 9). Accordingly, various embodiments are directed towards models that include one or more features selected from: hemoglobin A1C (A1C), *Bacteroides* bacteria, Lachnospiraceae bacteria, *Roseburia* bacteria, and *Faecalibacterium* bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model.

In an embodiment, it was found that the analyte measurement features hemoglobin A1C (A1C), hexosamine, taurine, hydroxyphenyllactic acid, hippuric acid, p-cresol glucuronide, hydroxy-stearic acid (C18:0,OH FA), and dihydroxy-palmitic acid (C16:0,2OH) are predictive of OGTT results (Table 9). Accordingly, various embodiments are directed towards models that include one or more features selected from: hemoglobin A1C (A1C), hexosamine, taurine, hydroxyphenyllactic acid, hippuric acid, p-cresol glucuronide, hydroxy-stearic acid (C18:0,OH FA), and dihydroxy-palmitic acid (C16:0,2OH). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model.

In an embodiment, it was found that the analyte measurement features hemoglobin A1C (A1C), chitobiosyldiphosphodolichol beta-mannosyltransferase like 2 transcript (ALG1L2), chromosome 21 open reading frame 119 transcript (C21orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNF214), unc-93 homolog B1 transcript (UNC93B1), and wee1-like protein kinase 2 transcript (WEE2) are predictive of OGTT results (Table 9). Accordingly, various embodiments are directed towards models that include one or more features selected from: hemoglobin A1C (A1C), chitobiosyldiphosphodolichol beta-mannosyltransferase like 2 transcript (ALG1L2), chromosome 21 open reading frame 119 transcript (C21orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNF214), unc-93 homolog B1 transcript (UNC93B1), and wee1-like protein kinase 2 transcript (WEE2). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model.

In an embodiment, it was found that the analyte measurement features hemoglobin A1C (A1C), cytokine platelet-derived growth factor subunit B homodimer (PDGFBB), complement factor D protein (CFD), Ig heavy constant alpha 2 protein (IGHA2), vitronectin protein (VTN), Ig kappa variable 2D-28 protein (KVD28), ectoine, taurine, a-linolenic acid (C18:3 FA), p-cresol glucuronide, *Bacteroides* bacteria, Lachnospiraceae bacteria, and *Roseburia* bacteria are predictive of OGTT results (Table 9). Accordingly, various embodiments are directed towards models that include one or more features selected from: hemoglobin A1C (A1C), cytokine platelet-derived growth factor subunit B homodimer (PDGFBB), complement factor D protein (CFD), Ig heavy constant alpha 2 protein (IGHA2), vitronectin protein (VTN), Ig kappa variable 2D-28 protein (KVD28), ectoine, taurine, a-linolenic acid (C18:3 FA), p-cresol glucuronide, *Bacteroides* bacteria, Lachnospiraceae bacteria, and *Roseburia* bacteria. In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model.

In an embodiment, it was found that the analyte measurement features hemoglobin A1C (A1C), cytokine platelet-derived growth factor subunit B homodimer (PDGFBB), complement factor D protein (CFD), Ig heavy constant alpha 2 protein (IGHA2), coagulation factor XI protein (F11), ectoine, taurine, a-linolenic acid (C18:3 FA), p-cresol glucuronide, chitobiosyldiphosphodolichol beta-mannosyltransferase like 2 transcript (ALG1L2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), macrophage migration inhibitory factor transcript (MIF), receptor activity modifying protein 3 transcript (RAMP3), unc-93 homolog B1 transcript (UNC93B1), and zinc finger protein 596 transcript (ZNF596) are predictive of OGTT results (Table 9). Accordingly, various embodiments are directed towards models that include one or more features selected from: hemoglobin A1C (A1C), cytokine platelet-derived growth factor subunit B homodimer (PDGFBB), complement factor D protein (CFD), Ig heavy constant alpha 2 protein (IGHA2), coagulation factor XI protein (F11), ectoine, taurine, a-linolenic acid (C18:3 FA), p-cresol glucuronide, chitobiosyldiphosphodolichol beta-mannosyltransferase like 2 transcript (ALG1L2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), macrophage migration inhibitory factor transcript (MIF), receptor activity modifying protein 3 transcript (RAMP3), unc-93 homolog B1 transcript (UNC93B1), and zinc finger protein 596 transcript (ZNF596). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model. In some embodiments, fourteen or more features described are utilized in a predictive model. In some embodiments, fifteen or more features described are utilized in a predictive model. In some embodiments, sixteen or more features described are utilized in a predictive model. In some embodiments, seventeen or more features described are utilized in a predictive model. In some embodiments, eighteen or more features described are utilized in a predictive model. In some embodiments, nineteen or more features described are utilized in a predictive model.

In an embodiment, it was found that the analyte measurement features hemoglobin A1C (A1C), cytokine platelet-derived growth factor subunit B homodimer (PDGFBB), complement factor D protein (CFD), Ig heavy constant alpha 2 protein (IGHA2), vitronectin protein (VTN), ectoine, taurine, a-linolenic acid (C18:3 FA), p-cresol glucuronide, *Bacteroides* bacteria, Lachnospiraceae bacteria, chitobiosyldiphosphodolichol beta-mannosyltransferase like 2 transcript (ALG1L2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), glutamic-pyruvic transaminase 2 transcript (GPT2), keratin 10 transcript (KRT10), receptor activity modifying protein 3 transcript (RAMP3), unc-93 homolog B1 transcript (UNC93B1), and zinc finger protein 596 transcript (ZNF596) are predictive of OGTT results (Table 9). Accordingly, various embodiments are directed towards models that include one or more features selected from: hemoglobin A1C (A1C), cytokine platelet-derived growth factor subunit B homodimer (PDGFBB), complement factor D protein (CFD), Ig heavy constant alpha 2 protein (IGHA2), vitronectin protein (VTN), ectoine, taurine, a-linolenic acid (C18:3 FA), p-cresol glucuronide, *Bacteroides* bacteria, Lachnospiraceae bacteria, chitobiosyldiphosphodolichol beta-mannosyltransferase like 2 transcript (ALG1L2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), glutamic-pyruvic transaminase 2 transcript (GPT2), keratin 10 transcript (KRT10), receptor activity modifying protein 3 transcript (RAMP3), unc-93 homolog B1 transcript (UNC93B1), and zinc finger protein 596 transcript (ZNF596). In some embodiments, two or more features described are utilized in a predictive model. In some embodiments, three or more features described are utilized in a predictive model. In some embodiments, four or more features described are utilized in a predictive model. In some embodiments, five or more features described are utilized in a predictive model. In some embodiments, six or more features described are utilized in a predictive model. In some embodiments, seven or more features described are utilized in a predictive model. In some embodiments, eight or more features described are utilized in a predictive model. In some embodiments, nine or more features described are utilized in a predictive model. In some embodiments, ten or more features described are utilized in a predictive model. In some embodiments, eleven or more features described are utilized in a predictive model. In some embodiments, twelve or more features described are utilized in a predictive model. In some embodiments, thirteen or more features described are utilized in a predictive model. In some embodiments, fourteen or more features described are utilized in a predictive model. In some embodiments, fifteen or more features described are utilized in a predictive model. In some embodiments, sixteen or more features described are utilized in a predictive model. In some embodiments, seventeen or more features described are utilized in a predictive model. In some embodiments, eighteen or more features described are utilized in a predictive model. In some embodiments, nineteen or more features described are utilized in a predictive model. In some embodiments, twenty or more features described are utilized in a predictive model. In some embodiments, twenty-one or more features described are utilized in a predictive model.

A selection of associative analyte measurement features are described in the Exemplary Embodiments section. In particular, Table 15 provides a number of analyte measurement features that are indicative of SSPG results, as determined by regression analysis with SSPG values and co-association with insulin-sensitive and insulin-resistant individuals. In various embodiments, analyte measurement features for SSPG include (but not limited to) estimated glomerular filtration rate (EGFR), high density lipoprotein (HDL), absolute count of neutrophils (NEUTAB), triglycerides (TGL), white blood cell count (WBC), chemokine (C-X-C motif) ligand 1 (GROA), L-lysine (Lys), L-alanine (Ala), hippuric acid, cinnamoylglycine, 3-phenylpropionate (hydrocinnamate), octadecanedioic acid (C18:0,DC FA), C28H44O4, C27H44O4, C26H42O4, LysoPG(18:0), C16:3 FA, *Anaerovorax* bacteria, *Blautia* bacteria, *Clostridium* bacteria, *Coprococcus* bacteria, *Odoribacter* bacteria, *Oscillibacter* bacteria, *Pseudoflavonifractor* bacteria, vitronectin protein (VTN), apolipoprotein D (APOD), melanoma cell adhesion molecule (MCAM), apolipoprotein C4 (APOC4), phospholipid transfer protein precursor (PLTP), and adiponectin protein (ADIPOQ).

Training labels associating analyte measurement features and glycemic regulation measurements are used to construct and train (207) a computational model to determine an individual's glycemic regulation. In several embodiments, computational models are constructed and trained to determine an individual's glucose tolerance and/or SSPG. Various embodiments construct and train a model to determine whether an individual is normoglycemic, prediabetic, or diabetic. A number of models can be used in accordance with various embodiments, including (but not limited to) ridge regression, K-nearest neighbors, LASSO regression, elastic net, least angle regression (LAR), random forest, and principal components analysis. In some embodiments, ridge regression is kernelized, in which Gaussian or polynomial kernels are utilized. The appropriate model to use can often depend on the glycemia test to be modeled and the corresponding predictive ability of the model.

Ridge regression is a beneficial model for using analyte measurement data to determine glycemic regulation because it is able to analyze multiple measurement regression data that may contain multicollinearity. A common problem with multicollinearity is that they can produce very large variances, however, a ridge regression technique can reduce these variances to better reach the true value. Ridge regression adds a degree of bias to the regression estimates, and thus reduces the standard errors, which should result in estimates that are more reliable.

Ridge regression attempts to find the best set of weights to combine the features for glycemic regulation determination. It minimizes both the error of this prediction as well as the L2 norm of the weights (to avoid overfitting and improve generalizability to other patient populations). In various embodiments, kernel ridge regression can be performed, which is similar to ridge regression but has an addition of using the identified set of features to create polynomial features from them. For example, if TGL/HDL and NEUTAB are features, a polynomial kernel will create features that are TGL/HDL*NEUTAB, TGL/HDL*TGL/HDL, and NEUTAB*NEUTAB.

Models and sets of training labels used to train a model can be evaluated for their ability to accurately determine glucose tolerance and SSPG. By evaluating models, predictive abilities of analyte measurements can be confirmed. In some embodiments, a portion of the analyte/glycemia data is withheld to test the model to determine its efficiency and accuracy. A number of accuracy evaluations can be performed, including (but not limited to) R-square and mean square error analysis. Accordingly, an optimized model can be identified.

Process 200 also outputs (209) the parameters of a computational model indicative of an individual's glycemic regulation measurement from a panel of analyte measurements. Computational models, as will be described in detail below, can be used to determine an individual's glycemic regulation, provide diagnoses, and treat an individual accordingly.

While specific examples of processes for constructing and training a computational model to indicate an individual's glycemic regulation are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for constructing and training a computational model appropriate to the requirements of a given application can be utilized in accordance with various embodiments of the invention.

Determination of an Individual's Glycemic Regulation with Analyte Measurements

Once a computational model has been constructed and trained, it can be used to compute an indicator of an individual's glycemic regulation. As shown in FIG. 3A, a method to determine an individual's glucose tolerance or SSPG using a trained computational model is provided in accordance with an embodiment of the invention. Process 300 obtains (301) a panel of analyte measurements from an individual.

In several embodiments, analytes are measured from a blood sample, stool sample, urine sample, or biopsy of an individual. In some embodiments, an individual's analytes are extracted during fasting. A number of methods are known to extract analytes from an individual and can be used within various embodiments of the invention. In several embodiments, analytes are extracted and measured at each time point, resulting in a dynamic analysis of the analytes. In some of these embodiments, analytes are measured with periodicity (e.g., monthly, quarterly, yearly).

A number of analytes can be used to determine glycemic regulation, including (but not limited to) clinical data, personal data, metabolites, protein constituents, genomic DNA, transcript expression, lipids, and human microbiota. Analytes can be detected and measured by a number of methods, including nucleic acid and protein sequencing, mass spectrometry, colorimetric analysis, immunodetection, and the like. It should be noted that static, median, average, and/or dynamic analyte measurements can be used in accordance with various embodiments of the invention. In many embodiments, the precise panel of analytes to be measured depends on the constructed and trained computational model to be used, as the input analyte measurement data that will be needed to at least partially overlap with the features used to train the model. That is, there should be enough overlap between the feature measurements used to train the model and the individual's analyte measurements obtained such that an SSPG or glucose tolerance can be computed.

In a number of embodiments, an individual is any individual that has their analytes extracted and measured. In some embodiments, an individual has been diagnosed as being diabetic or pre-diabetic. Embodiments are also directed to an individual being one that has not been diagnosed as diabetic. In some of these embodiments, the individual is normoglycemic or diagnosed as normoglycemic, as determined by classical diabetes testing, including (but not limited to) measuring fasting glucose levels, measuring glycated hemoglobin (HbA1C test), and glucose tolerance (OGTT). In a number of these embodiments, normoglycemia, pre-diabetic, and diabetic assessment is determined by standards set forth by a Diabetes organization such as the American Diabetes Association.

Process 300 also obtains (303) a trained computational model that indicates an individual's glycemic regulation (e.g., glucose tolerance, SSPG) from a panel of analyte measurements. Any computational model that can compute an indicator of an individual's SSPG and/or glucose tolerance from a panel of analyte measurements can be used. In some embodiments, the computational model is constructed and trained as described in FIG. 2. In some embodiments, the extraction of analytes and use of a computational model is a surrogate for traditional glycemia tests (e.g., SSPG insulin resistance or OGTT). The computational model, in accordance with various embodiments, has been optimized to accurately and efficiently indicate glucose tolerance and/or SSPG.

In a number of embodiments, the computational model is trained using ridge regression. As stated previously, ridge regression is a beneficial model for using analyte measurement data to compute glycemic regulation because it is able to analyze multiple measurement regression data that may contain multicollinearity. Ridge regression technique can reduce variances to better reach the true value. It should be understood, however, that other models can also be used, including (but not limited to), kernelized ridge regression, K-nearest neighbors, LASSO regression, elastic net, least angle regression (LAR), random forest, and principal components analysis.

Process 300 also enters (305) an individual's analyte measurement data into a computational model to indicate the individual's glycemic regulation. Accordingly, the computational model will provide results indicative of glycemic regulation tests, such as the OGTT or insulin suppression test. In some embodiments, the analyte measurement data is used to compute an individual's glycemic regulation in lieu of performing a traditional glycemic regulation test. Various embodiments utilize the analyte measurement data and computational model in combination with a clinical glycemic regulation test.

Based on studies performed, it has been found that several analyte measurements provide robust predictive ability, including (but not limited to) particular clinical data, personal data, metabolites, protein constituents, genomic DNA, transcript expression, lipids, and human microbiota. A number of methods can be used to select analyte measurements to be used as features in the training model. In some embodiments, correlation measurements between analyte measurements and glycemic regulation measurements are used to select features. In various embodiments, a computational model is used to determine which analyte measurements are best predictors. For example, a Bayesian network can be used to determine which analyte measurement features influence the outcome of glycemic regulation measurements. In some embodiments, a MMPC Bayesian network is used to select features. Use of Bayesian networks to select features is described in greater detail below.

A selection of predictive analyte measurement features are described in the Exemplary Embodiments section. In particular, FIG. 25 and Tables 8 and 9 provide a number of analyte measurement features that are indicative of either SSPG or OGTT results, as determined by MMPC Bayesian network feature selection followed by Ridge Regression. In various embodiments, analyte measurement features for SSPG include (but not limited to) triglycerides-to-high density lipoprotein ratio (TGL/HDL), creatine (CR), body mass index (BMI), absolute count of neutrophils (NEUTAB), interleukin 1 beta (IL1B), interleukin 18 (IL18), angiotensinogen protein (AGT), interleukin 1 receptor accessory protein (IL1RAP), interleukin 26 (IL26), Ig kappa chain V-I region protein (KV116), complement factor H protein (CFH), myosin-binding protein C (MYBPC2), L-lysine (Lys), L-arginine (Arg), L-alanine (Ala), N1-methyladenosine, 4-formyl Indole, 3-Methyl-L-histidineC7H15N3O2, C14H22N2O9, C12H24N2O3, C26H42O4, C28H46O4, C28H44O4, LysoPG(18:0), C16:3 FA, hexosylceramide HCER(24:0), lactosylceramide LCER(16:0), glycerophosphoethanolamine PE(P-18:0/22:6), PE(P-16:0/22:6) and PE(P-18:1/18:1), triacylglycerol TAG(58:10) containing fatty acid FA(20:5), chromosome 19 open reading frame 66 transcript (C19orf66), chromosome 1 open reading frame 174 transcript (C1orf174), calcineurin like EF-hand protein 1 (CHP1), deoxyguanosine kinase transcript (DGUOK), Disks large-associated protein 1 (DLGAP1), family with sequence similarity 86 member H pseudogene transcript (FAM86HP), family with sequence similarity 185 member A pseudogene transcript (FAM185A), heat shock cognate B (HSCB), IL12A antisense RNA 1 (IL12A-AS1), kyphoscoliosis peptidase transcript (KY), mitogen-activated protein kinase kinase kinase 19 transcript (MAP3K19), protein geranylgeranyltransferase type I subunit beta (PGGT1B), POC5 centriolar protein (POC5), UBAP1-MVB12-associated (UMA) domain containing 1 (RPA3OS), serine/threonine-protein kinase 494 transcript (SGK494), solute carrier family 16 member 12 transcript (SLC16A12), synaptotagmin 9 (SYT9), transmembrane protein 237 transcript (TMEM237), transmembrane protein 253 transcript (TMEM253), transmembrane protein 108 transcript (TMEM108), transmembrane protein 106B transcript (TMEM106B), U2AF homology motif kinase 1 transcript (UHMK1), vacuolar protein sorting 13 homolog A (VPS13A), vitronectin protein (VTN), *Bacteroides* bacteria, Barnesiella bacteria, *Clostridium* bacteria, *Faecalibacterium* bacteria, *Ruminococcus* bacteria, *Bacteroides, Shigella* bacteria, Lachnospiraceae bacteria, and *Odoribacter* bacteria.

A number of prediction models have been built to predict SSPG with high predictive ability (see Table 8). Various embodiments utilize the features within these models (or similar) to build models to predict SSPG. Also see description herein for various models that are built and incorporate various features, which can be utilized to predict SSPG for an individual.

In various embodiments, analyte measurement features for OGTT results include (but not limited to) hemoglobin A1C (A1C), alanine aminotransferase (ALT), cytokine platelet-derived growth factor subunit B homodimer (PDGFBB), complement factor D protein (CFD), Ig kappa variable 2D-28 protein (KVD28), Ig heavy constant alpha 2 protein (IGHA2), coagulation factor XI protein (F11), Ig kappa variable 310 protein (KV310), Ig heavy variable 2-70 protein (HV270), vitronectin protein (VTN), hexosamine, taurine, hydroxyphenyllactic acid, hippuric acid, ectoine, p-cresol glucuronide, hydroxy-stearic acid (C18:0,0H FA), dihydroxy-palmitic acid (C16:0,2OH), a-linolenic acid (C18:3 FA), chitobiosyldiphosphodolichol beta-mannosyl-transferase like 2 transcript (ALG1L2), chromosome 21 open reading frame 119 transcript (C21orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMPS), ring finger protein 214 transcript (RNG214), unc-93 homolog B1 transcript (UNC93B1), wee1-like protein kinase 2 transcript (WEE2), ceramide synthase 5 transcript (CERS5), dishevelled associated activator of morphogenesis 1 transcript (DAAM1), family with sequence similarity 86 member H pseudogene transcript (FAM86HP), filaggrin transcript (FLG), macrophage migration inhibitory factor transcript (MIF), zinc finger protein 596 transcript (ZNF596), *Bacteroides* bacteria, Lachnospiraceae bacteria, *Roseburia* bacteria, and *Faecalibacterium* bacteria. Based on the foregoing, it should be understood that a number of combinations of analyte features can be used solitarily or combined in any fashion to be used to train a predictive computational model.

A number of prediction models have been built to predict OGTT results with high predictive ability (see Table 9). Various embodiments utilize the features within these models (or similar) to build models to predict OGTT results. Also see description herein for various models that are built and incorporate various features, which can be utilized to predict OGTT results for an individual.

A computational model can also characterize and/or diagnose an individual. In a number of embodiments, a computational model determines whether the individual has impaired glucose tolerance. Embodiments are also directed to a computational model determining whether the individual is insulin resistant. In various embodiments, a computational model diagnoses the individual as normoglycemic, pre-diabetic, or diabetic.

Process 300 also outputs (307) a report containing an individual's indicated glycemic regulation result and/or diagnosis. Furthermore, based on an individual's indicated glycemic regulation, a clinical intervention is performed (309) on the individual, including clinical assessments and treatment to ameliorate a symptom related to the result and/or diagnosis. In many embodiments, a clinical assessment includes (but not limited to) a blood test, medical imaging, blood pressure measurements, electrocardiogram, stress test, an angiogram, or any combination thereof. In several embodiments, an individual is provided with a personalized treatment plan. Further discussion of treatments that can be utilized in accordance with this embodiment are described in detail below, which may include various medications, dietary supplements, dietary alterations, and physical exercise regimens.

While specific examples of processes for determining an individual's glycemic regulation are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for computing an individual's glycemic regulation appropriate to the requirements of a given application can be utilized in accordance with various embodiments of the invention.

Treatments Utilizing a Pathological Indicator of Glycemic Dysregulation

A number of embodiments of the invention are directed towards determining an underlying mechanistic indication of an individual's pathology of a glycemic dysregulation and treating the individual accordingly. In various embodiments, a number of glycemia-related tests are performed on an individual that illuminate a pathological indicator of glycemic dysregulation. In some embodiments, individuals are treated with medicaments and/or supplements that specifically target an indicated underlying pathology.

In accordance with American Diabetes Association (ADA) "Standard of Medical Care in Diabetes," current practices of treating type 2 diabetes do not utilize indicators of underlying pathology, but instead use a trial-and-error approach (see American Diabetes Association, *Diabetes Care*, 41 (Supplement 1) S73-S85 (January 2018), the disclosure of which is incorporated herein by reference). The ADA recommends beginning treatment with Metformin and further may include treatment with insulin for newly diagnosed patients meeting certain criteria. If the initial mono or dual treatment does not work, then an additional antihyperglycemic agent is added. The ADA further recommends other treatments based on response to the initial treatments, but none of the recommended treatments are actually based on the underlying pathology of glycemic dysregulation.

Provided in FIG. 3B is a process that determines a mechanistic indication of an individual's glycemic dysregulation pathology and utilizes that mechanistic indication to treat the individual. Process 350 can begin by obtaining (351) results of a panel of one or more glycemia-related measurements of an individual. In various embodiment, a panel of glycemia-related measurements include (but are not limited to) fasting plasma glucose (FPG), insulin, glucagon, SSPG, HbA1C, OGTT glucose and insulin response, insulin secretion rate max, insulin secretion rate longitudinal pattern, Matsuda index, disposition index, and combinations thereof. Each measurement provides unique information that can be utilized to get an indication of glycemic dysregulation pathology.

FPG is a measure of steady-state glucose metabolism in which production of glucose by the liver and kidney needs to match glucose uptake by tissues. Impaired FPG typically results from a mismatch between glucose production and glucose utilization with some studies indicating that hepatic glucose production is increased and others reporting that the primary defect is decreased glucose uptake by the liver and other tissues. In addition to hepatic insulin resistance, the liver also appears to be less sensitive to glucose which contributes to abnormal hepatic glucose production in the setting of fasting hyperglycemia.

Fasting insulin is a measure of steady-state insulin production in the body when the glucose metabolism is also at a steady state. Low insulin levels suggest that insulin is not being produced and/or maintained in the body.

Glucagon is a protein secreted by alpha cells of the pancreas and raises glucose levels in the body. Fasting glucagon is a measure of steady-state glucagon production when glucose metabolism is also at a steady state. Glucagon levels can be used to further understand whether a glycemic irregularity is due to a glucagon and/or insulin production and maintenance in the body.

OGTT measures a dynamic response to a glucose load which leads to increased plasma insulin which suppresses hepatic glucose release and stimulates glucose uptake in the peripheral tissues. Impaired pancreatic beta cell function and peripheral insulin resistance, particularly in skeletal muscle, can lead to impaired glucose tolerance (IGT). IGT can indicate impaired insulin secretion, increased insulin resistance, and/or excess hepatic gluconeogenesis. In various embodiments, OGTT results are determined by a computational method, such as one described in FIG. 3A.

SSPG is a measure of peripheral insulin resistance. Thus, SSPG determines whether peripheral tissue (e.g., skeletal muscle) is appropriately responding to insulin when glucose levels are high. A lack of response suggests that glucose is not being absorbed by peripheral tissue despite having adequate levels of insulin to stimulate such a response. In a number of embodiments, SSPG is determined by a computational method, such as one described in FIG. 3A.

The ambient glucose concentration determines the rate of formation of HbA1C. This reaction occurs in erythrocytes and is nonreversible. Since the lifespan of an erythrocyte is ~120 days, HbA1C reflects average blood glucose levels over the past 3-4 months. HbA1C provides less mechanistic information, despite being a primary diagnostic in current treatment regimes.

Insulin secretion rate (max and longitudinal pattern) using c-peptide deconvolution method informs of beta cell function. Impairments in beta cell function results in an insufficient release of insulin in response to glucose load.

The Matsuda index is an estimate of whole-body insulin sensitivity and represents both hepatic and peripheral sensitivity to insulin. The Matsuda index is typically derived utilizing fasting and OGTT measurements, including concentrations of fasting plasma insulin, fasting plasma glucose, mean plasma glucose during OGTT, and mean plasma insulin during OGTT. Peripheral insulin resistance can also be determined by SSPG.

Disposition index is the product of insulin sensitivity times the amount of insulin secreted in response to blood glucose levels. Lower disposition index levels indicate that beta cells are unable to match the output of insulin to compensate for insulin resistance.

Utilizing the results of a panel of glycemia-related measurements, a mechanistic indication of an individual's pathology of a glycemic dysregulation is determined (353). Various combinations measurements can yield underlying mechanistic indicators.

FPG can be combined with tests of insulin resistance (e.g., SSPG, Matsuda index, disposition index) to determine whether an individual with high glucose levels is producing too much glucose or whether the individual's various tissues present defect of glucose utilization.

OGTT can be combined with insulin resistance (e.g., SSPG, Matsuda index, disposition index) and insulin secretion rate to yield an indication of beta cell function. For instance, low insulin secretion combined with high OGTT results indicates poor beta cell function and/or beta cell failure. High OGTT results in combination with high insulin secretion rate and high insulin resistance indicates beta cells cannot fully compensate for the body's insulin resistance. Likewise, high OGTT results combined with relatively normal peripheral insulin resistance (e.g., SSPG) and elevated, yet delayed, insulin secretion rate indicates central insulin resistance and/or decreased beta cell sensitivity to glucose.

Results of various glycemia-related measurements and an individual's indicated pathology of glycemic dysregulation and/or diagnosis is stored and/or reported (355). Based on an individual's indicated pathology of glycemic dysregulation, the individual is treated (357). A number of treatments are described throughout. In particular, an individual can be treated with medicaments and supplements directed at the individuals' indicated pathology. In some embodiments, when an individual has been indicated to have poor insulin secretion, the individual is treated with agents that improve insulin secretion, which may include DPP-4 inhibitors (e.g., alogliptin, linagliptin, saxagliptin, sitagliptin, vildagliptin, gemigliptin, anagliptin, teneligliptin, trelagliptin, omarigliptin, evogliptin, gosogliptin, dutogliptin, berberine), sulfonylureas (e.g., glimepiride, gliclazide, glyburide, chlorpropamide, tolazamide, tolbutamide, acetohexamide, carbutamide, metahexamide, glycyclamide, glibornuride, glipizide, gliquidone, glisoxepide, glyclopyramide), GLP-1 receptor agonists (e.g., glucagon-like peptide 1, gastric inhibitory peptide, albiglutide, dulaglutide, exenatide, liraglutide, lixisenatide, semaglutide), and *panax ginseng*. In various embodiments, when an individual has been indicated to have peripheral insulin resistance, the individual is treated with agents that improve insulin sensitivity, which may include thiazolidinedione (e.g., rosiglitazone, pioglitazone, lobeglitazone). In some embodiments, when an individual has been indicated to excessively produce hepatic glucose, the individual can be treated with agents that decrease hepatic glucose production, which may include biguanides (e.g., metformin) and thiazolidinediones (e.g., rosiglitazone, pioglitazone, lobeglitazone).

Feature Selection

As explained in the previous sections, analyte measurements are used as features to construct a computational model that is then used to indicate an individual's glycemic regulation. Analyte measurement features used to train the model can be selected by a number of ways. In some embodiments, analyte measurement features are determined by which measurements provide strong correlation with the glycemic regulation test. In various embodiments, analyte measurement features are determined using a computational model, such as Bayesian network, which can determine which analyte measurements influence or are influenced by an individual's glycemic regulation. Embodiments also consider practical factors, such as (for example) the ease and/or cost of obtaining the analyte measurement, patient comfort when obtaining the analyte measurement, and current clinical protocols are also considered when selecting features.

Correlation analysis utilizes statistical methods to determine the strength of relationships between two measurements. Accordingly, a strength of relationship between an analyte measurement and a glycemic regulation test measurement can be determined. Many statistical methods are known to determine correlation strength (e.g., correlation coefficient), including linear association (Pearson correlation coefficient), Kendall rank correlation coefficient, and Spearman rank correlation coefficient. Analyte measurements that correlate strongly with a glycemic regulation can then be used as features to construct a computational model to determine an individual's glycemic regulation.

In a number of embodiments, analyte measurement features are identified by a computational model, including (but not limited to) a Bayesian network model, LASSO, and elastic net. Various embodiments utilize an appropriate computational model that results in a number of features that is manageable. For instance, constructing predictive models from hundreds to thousands of analyte measurement features may have overfitting issues. Likewise, too few features can result in less prediction power.

A Bayesian network model is a probabilistic model that can determine whether a set of variables are influential on each other. Using a Bayesian network model, analyte measurements that influence or are influenced by glycemic regulation measurements can be identified as predictive features to train a computational model, such as described in FIG. 2. A number of Bayesian models are known, and several can be used in accordance with various embodiments of the invention. One such Bayesian model is the Max-Min Parents and Children (MMPC), which identifies analyte measurement features that are parents or children of glycemic regulation measurements. Features identified by MMPC are likely to be either direct causes or effects of the glycemic regulation measurements. For example, using an MMPC model, it has been found that an increase/decrease of TGL/HDL is likely to be either a direct cause or effect of an elevated SSPG measurement.

Provided in FIG. 4 is an embodiment of a process to identify analyte measurements that are indicative of a glucose regulation measurement. Process 400 begins by measuring (401) a panel of analytes from each individual of a collection of individuals. In several embodiments, analytes are measured from a blood sample, stool sample, urine sample, or biopsy of an individual. In some embodiments, an individual's analytes are extracted during fasting. A number of methods are known to extract analytes from an individual and can be used within various embodiments of the invention. In several embodiments, analytes are extracted and measured at each time point, resulting in a dynamic analysis of the analytes. In some of these embodiments, analytes are measured with periodicity (e.g., monthly, quarterly, yearly).

A number of analytes can be used to determine glycemic regulation, including (but not limited to) clinical data, personal data, metabolites, protein constituents, genomic DNA, transcript expression, lipids, and human microbiota. Analytes can be detected and measured by a number of methods, including nucleic acid and protein sequencing, mass spectrometry, colorimetric analysis, immunodetection, and the like. It should be noted that static, median, average, and/or dynamic analyte measurements can be used in accordance with various embodiments of the invention.

In numerous embodiments, an individual is any individual that has their analytes extracted and measured. In some embodiments, an individual has been diagnosed as being diabetic or pre-diabetic. Embodiments are also directed to an individual being one that has not been diagnosed as diabetic. In some of these embodiments, the individual is normoglycemic or diagnosed as normoglycemic, as determined by classical diabetes testing, including (but not limited to) measuring fasting glucose levels, measuring glycated hemoglobin (HbA1C test), and oral glucose tolerance test (OGTT). In a number of these embodiments, normoglycemia, pre-diabetic, and diabetic assessment is determined by standards set forth by a Diabetes organization such as the American Diabetes Association.

A collection of individuals, in accordance with many embodiments, is a grouping of individuals to be measured so that their data can be used to construct and train a computational model. A collection can include individuals that are diagnosed as diabetic, pre-diabetic, normoglycemic, or undiagnosed. In some embodiments, it is beneficial to have a diversity of individuals having different glycemic diagnoses, such that a computer model can be trained with an expansive data set. The number of individuals in a collection can vary, and in some embodiments, having a greater number of individuals will increase the prediction power of a trained computer model. The precise number and composition of individuals will vary, depending on the model to be constructed and trained.

Process 400 also measures (403) glycemic regulation of each individual in the collection of individuals. Glycemic regulation tests that can be performed include any glycemic test in which a user desires to find analyte measurements that influence or are influenced by the test, including OGTT and the insulin suppression test. A few methodologies are known to measure glucose tolerance and SSPG, each of which can be used within various embodiments of the invention.

The glycemic regulation test and analyte measures are entered (405) into a structure learning Bayesian network. In some instances, an MMPC network can be used, but any appropriate Bayesian network can be used. Analyte measurement features that are predictive of the glycemic regulation measurement are identified (407), which can be used as features in an indicative computational model, such as described in FIG. 2. A number of methods can be used to identify predictive analyte measurements. In one instance, features are identified by leaving out the measurements of one individual of the collection of individuals and using the rest of the collection as training data. This can be repeated for each individual, resulting in multiple tests to identify features. Features that are repeatedly identified as good candidates can be selected to establish a panel of indicative features. In some instances, a threshold can be used to determine a feature panel (e.g., analyte measurements that are identified in greater than 50% of training sets are selected as features).

Process 400 also outputs (409) the analyte measurements that are identified as indicative. Analyte measurements can be used to construct computational model to indicate an individual's glycemic regulation.

While specific examples of processes for identifying analyte measurements that are indicative of the glycemic regulation measurement are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for identifying analyte measurements appropriate to the requirements of a given application can be utilized in accordance with various embodiments of the invention.

Applications and Treatments Related to Glycemic Regulation

Various embodiments are directed to development of treatments related to glycemic regulation. As described herein, an individual may have their glycemic regulation, including SSPG and glucose tolerance, indicated by various methods. Based on one's glycemic regulation indication, an individual can be treated with various medications, dietary supplements, dietary alterations, and physical exercise regimens.

Medications and Supplements

Several embodiments are directed to the use of medications and/or dietary supplements to treat an individual to lower their SSPG and/or OGTT result. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect. For example, one such amelioration of a symptom could be reduction of SSPG levels or improvement of glucose tolerance. Assessment of glycemic regulation can be performed in many ways, including (but not limited to) assessing SSPG and/or glucose tolerance using analyte measurements. While thresholds of healthy SSPG levels can vary dependent on the assessment, it is typically regarded that healthy SSPG is below one of: 100 mg/dL, 150 mg/dL, or 200 mg/dL. Likewise, healthy OGTT results is typically below one of: 100 mg/dL, 140 mg/dL or 200 mg/dL. Elevated SSPG levels suggest insulin resistance and elevated OGTT results suggest impaired glucose tolerance.

A therapeutically effective amount can be an amount sufficient to prevent reduce, ameliorate or eliminate the symptoms of diseases or pathological conditions susceptible to such treatment, such as, for example, diabetes, heart disease, or other diseases that are affected by elevated glycemia. In some embodiments, a therapeutically effective amount is an amount sufficient to reduce an individual's SSPG and/or improve an individual's glucose tolerance. In similar embodiments, a therapeutically effective amount is an amount sufficient to reduce an individual's SSPG and/or OGTT result below a certain threshold. Various thresholds can be utilized. For instance, a healthy SSPG is below one of: 100 mg/dL, 150 mg/dL, or 200 mg/dL. Likewise, healthy OGTT results is typically below one of: 100 mg/dL, 140 mg/dL or 200 mg/dL.

A number of medications are available to treat elevated glycemia, such as those used to treat type II Diabetes. Medications include (but are not limited to) insulin, alpha-glucosidase inhibitors (e.g., acarbose, miglitol, voglibose), biguanides (e.g., metformin), dopamine agonists (e.g., bromocriptine), DPP-4 inhibitors (e.g., alogliptin, linagliptin, saxagliptin, sitagliptin, vildagliptin, gemigliptin, anagliptin, teneligliptin, trelagliptin, omarigliptin, evogliptin, gosogliptin, dutogliptin, berberine), GLP-1 receptor agonists (e.g., glucagon-like peptide 1, gastric inhibitory peptide, albiglutide, dulaglutide, exenatide, liraglutide, lixisenatide, semaglutide), meglitinides (e.g., nateglinide, repaglinide), sodium glucose transporter 2 inhibitors (e.g., dapagliflozin, canagliflozin, empagliflozin, ertugliflozin, ipragliflozin, luseogliflozin, sotagliflozin, tofogliflozin), sulfonylureas (e.g., glimepiride, gliclazide, glyburide, chlorpropamide, tolazamide, tolbutamide, acetohexamide, carbutamide, metahexamide, glycyclamide, glibornuride, glipizide, gliquidone, glisoxepide, glyclopyramide), and thiazolidinediones (e.g., rosiglitazone, pioglitazone, lobeglitazone). Accordingly, an individual may be treated, in accordance with various embodiments, by a single medication or a combination of medications described herein. Furthermore, several embodiments of treatments further incorporate heart disease medications (e.g., aspirin, cholesterol and high blood pressure medications), dietary supplements, dietary alterations, physical exercise, or a combination thereof.

Numerous dietary supplements may also help to treat elevated glycemia. Various dietary supplements, such as alpha-lipoic acid, chromium, coenzyme Q10, garlic, hydroxychalcone (cinnamon), magnesium, omega-3 fatty acids, *psyllium* and vitamin D have been shown to have beneficial effects on individuals having diabetes and cardiac conditions. Thus, embodiments are directed to the use of dietary supplements, included those listed herein, to be used to treat an individual based on one's SSPG or OGTT result. A number of embodiments are also directed to combining dietary supplements with medications, dietary alterations, and physical exercise to reduce glycemic variability.

Diet and Exercise

Numerous embodiments are directed to dietary alteration and exercise treatments. Altering one's lifestyle, including physical activity and diet, has been shown to improve glycemic regulation. Accordingly, in a number of embodiments, an individual is treated by altering their diet and increasing physical activity in response to a glycemia test result (e.g., SSPG computed from analyte measurements).

There are various diets that will help different individuals in getting better glycemic control. A number of embodiments are directed to treatments to reduce weight, which has been considered by some to be the best approach to control one's glycemia. There are many programs based on the seminal study for a low-fat diet to prevent diabetes (see Diabetes Prevention Program (DPP) Research Group. *Diabetes Care*. 2002 25:2165-71, the disclosure of which is herein incorporated by reference). For others, a diet low in refined carbohydrates and sugars will work better. Numerous embodiments take a more personalized approach such that one can utilize continuous glucose monitoring (CGM) results to determine which foods cause glycemic spikes for an individual and devise a diet to limit these particular foods while maintaining appropriate nutrient intake. Numerous embodiments are directed to treating an individual by substituting saturated fats with monounsaturated and unsaturated fats to help lower the risk for cardiovascular disease, which would be beneficial for many individuals struggling to control their glycemia. Also, embodiments are directed to increasing amounts of fiber in the diet, which would be highly recommended to both help with glycemic regulation and also balance serum lipid levels (cholesterol and triglycerides).

Exercise has a large impact on glycemic regulation. In several embodiments, a treatment would entail a minimum of some minutes of active exercise per week. In some embodiments, treatments would include a minimum of 150 minutes of exercise a week, however, the precise duration of exercise may be dependent on the individual to be treated and their cardiovascular health. It is further noted that cardiovascular exercise is important for the immediate glycemic control and weight training will have a long-term effect by increasing muscle mass, affecting glucose utilization during rest.

In many embodiments, a treatment to help control glucose levels is stress management, as stress increases blood glucose levels. Some proven ways to help control stress include meditation, social support, adequate sleep, journaling, and therapy.

Analytes Indicative of ASCVD Risk

A process for determining an individual's ASCVD risk using analyte measurements, in accordance with an embodiment of the invention is shown in FIG. 5. This embodiment is directed to determining an individual's ASCVD risk indicator and applies the knowledge garnered to perform a clinical intervention on the individual, including clinical assessments and/or treat the individual. For example, this process can be used to identify an individual having a particular analyte constituency that is indicative of ASCVD risk and treat that individual with a medication, a dietary supplement, a dietary alteration, physical exercise, or any combination thereof.

In a number of embodiments, analytes and analyte measurements are to be interpreted broadly as clinical and molecular constituents and measurements that can be captured in medical and/or laboratory setting and are to include clinical data, personal data, metabolites, protein constituents, genomic DNA, transcript expression, lipids, and human microbiota. In some embodiments, clinical data is to include medical patient data such as (for example) weight, height, heart rate, blood pressure, body mass index (BMI), clinical tests and the like. In various embodiments, personal data is to include data captured by an individual such as (for example) wearable data, physical activity, diet, substance abuse and the like. In some embodiments, metabolites are to include intermediates and products of metabolism such as (for example) sugars, amino acids, nucleotides, antioxidants, organic acids, polyols, vitamins, and the like. In various embodiments, protein constituents are chains of amino acids which are to include (but not limited to) peptides, enzymes, receptors, ligands, antibodies, transcription factors, cytokines, hormones, growth factors and the like. In some embodiments, genomic DNA is DNA of an individual and includes (but is not limited to) copy number variant data, single nucleotide variant data, polymorphism data, mutation analysis, insertions, deletions and partial and full genomes. In various embodiments, transcript expression is the evidence of RNA molecules of a particular gene or other RNA transcripts, and is to include (but is not limited to) analysis of expression levels of particular transcript targets, splicing variants, a class or pathway of gene targets, and partial and full transcriptomes. In some embodiments, lipids are a broad class of molecules that include (but are not limited to) fatty acid molecules, fat soluble vitamins, glycerolipids, phospholipids, sterols, sphingolipids, prenols, saccharolipids, polyketides, and the like. In various embodiments, human microbiota is the constituency of microbes (especially bacteria) that are found to reside on or within a human, especially in the digestive tract. It is noted that measurements of human microbiota, in accordance with some embodiments, is to include measurements of microbial diversity itself, such as (for example) the Shannon or Simpson diversity indices.

It is now known that a number of analytes have an indication of ASCVD risk. Accordingly, a panel of analytes can be used to assess an individual for ASCVD risk. In some embodiments, analyte measures are used in lieu of standard ASCVD diagnostic tests. In various embodiments, analyte measures are used to determine whether a further ASCVD risk diagnostic test, such as a coronary artery calcification evaluation, a coronary computed tomographic angiography or a carotid artery ultrasound, should be performed.

Process 500 begins with obtaining and measuring (501) analytes from an individual. In many instances, analytes are measured from a blood extraction, stool sample, urine sample, or biopsy. In some embodiments, an individual's analytes are extracted during fasting, or in a controlled clinical assessment. A number of methods are known to extract analytes from an individual and can be used within various embodiments of the invention. In several embodiments, analytes are extracted over a period a time and measured at each time point, resulting in a dynamic analysis of the analytes. In some of these embodiments, analytes are measured with periodicity (e.g., monthly, quarterly, yearly).

In a number of embodiments, an individual is any individual that has their analytes extracted and measured. In some embodiments, an individual has not been diagnosed as having ASCVD risk. In some of these embodiments, the individual is healthy or diagnosed as healthy, as determined by classical ASCVD testing, including (but not limited to) traditional blood tests, blood pressure, and medical imaging. In a number of these embodiments, blood pressure and ASCVD assessment is determined by standards recognized by a heart organization such as the American Heart Association.

A number of analytes can be used to indicate ASCVD risk, including (but not limited to) clinical data, personal data, metabolites, protein constituents, genomic DNA, transcript expression, lipids, and human microbiota. Analytes can be detected and measured by a number of methods, including nucleic acid and protein sequencing, mass spectrometry, colorimetric analysis, immunodetection, and the like.

In several embodiments, analyte measurements are performed by taking a single time-point measurement. In many embodiments, the median and/or average of a number of time points for participants with multiple time-point measurements are utilized. Various embodiments incorporate correlations, which can be calculated by a number of methods, such as the Spearman correlation method. A number of embodiments utilize a computational model that incorporates analyte measurements, such as linear regression models. Significance can be determined by calculating p-values, and in some instances that are corrected for multiple hypothesis. It should be noted however, that there are several correlation, computational models, and statistical methods that can utilize analyte measurements and may also fall within some embodiments of the invention.

In a number of embodiments, dynamic correlations use a ratio of analyte measurements between two time points, a percent change of analyte measurements over a period of time, a rate of change of analyte measurements over a period of time, or any combination thereof. Several other dynamic measurements may also be used in the alternative or in combination in accordance with multiple embodiments.

Using static and/or dynamic measures of analytes, process 500 determines (503) an indication of an individual's ASCVD risk. In many embodiments, the correlations and/or computational models can be used to indicate a result of ASCVD risk. In several embodiments, determining analyte correlations or modeling ASCVD risk is used for early detection. In various embodiments, measurements of analytes can be used as a precursor indicator to determine whether to perform a further diagnostic.

Based on studies performed, it has been found that several analyte measurements correlate with ASCVD risk and thus can serve a surrogates to determine ASCVD risk. Correlative analytes include (but are not limited to) particular clinical data, personal data, metabolites, protein constituents, genomic DNA, transcript expression, lipids, and human microbiota. A number of methods can be used to select analyte measurements to be used as features in the training model. In some embodiments, correlation measurements between analyte measurements and ASCVD risk measurements are used. In various embodiments, a computational model is used to determine which analyte measurements are best predictors. For example, a linear regression model can be used to determine which analyte measurement features represent a strong correlation between ASCVD risk and analyte measurements.

A selection of correlative analyte measurement features are described in the Exemplary Embodiments section. In particular, FIG. 31 and Tables 17 and 18 provide a number of analyte measurement features that are indicative of ASCVD risk, as determined by Spearman correlation analysis. In various embodiments, analyte measurement features for ASCVD risk include (but not limited to) triglycerides (TGL), L-Cysteinylglycine disulfide, hemoglobin A1c (A1C), 2,3-Dihydroxyvaleric acid LysoPC(16:0), C10:2 fatty acid, sex hormone binding globulin (SHBG), protein S1 (PROS1), phospholipid transfer protein (PLTP), high density lipoprotein (HDL), L-Proline, cholesterol-to-high density protein ration (CHOLHDL), LysoPC(20:2), Androstenediol (3beta,17beta) disulfate, LysoPC(18:2), Dihydroxyvitamin D3(2), C22:6 fatty acid, C10:0,OH fatty acid, N-Acetylserine, C16:1 fatty acid, complement component 5 (C5), Ig heavy chain V-III region JON, vascular endothelial growth factor (VEGF), serpin family F member 1 (SERPINF1), Bilirubin, matrix Gla-protein (MGP), low density lipoprotein-to-high density lipoprotein ratio (LDLHDL), C10:3 fatty acid, Red cell distribution width (RDW), platelet-derived growth factor BB (PDGFBB), complement factor H (CFH), Dihydroxyvitamin D3, Chenodeoxycholic acid glycine conjugate, 3-Methyl-2-oxovaleric acid, C8:0,0H fatty acid, Ne-Methyl-Lysine, LysoPC(P-18:1), gamma-glutamyl-epsilon-lysine, 1-Methylxanthine, nucleoporin 205 (NUP205), pregnancy zone protein (PZP), Glycosylphosphatidylinositol Specific Phospholipase D1 (GPLD1), LysoPE(P-16:0), L-a-Hydroxyisovaleric acid, LysoPC(18:0), Hypoxanthine, Homoarginine, vitronectin protein (VTN), interleukin 2 (IL2), and absolute monocyte count (MONOAB). Based on the foregoing, it should be understood that a number of combinations of analyte features can be used solitarily or combined in any fashion to be used to determine ASCVD risk.

Process 500 also outputs (505) a report containing an individual's ASCVD risk result. In some embodiments, these results determine whether an individual is healthy, has a mild risk, or a great risk of developing ASCVD.

Having determined an individual's ASCVD risk, a clinical intervention, including a clinical assessment or a treatment can be performed on the individual (107). In a number of embodiments, a diagnostic is a blood test, medical imaging, blood pressure measurements, electrocardiogram, stress test, an angiogram, or any combination thereof. In a number of embodiments, a treatment entails a medication, a dietary supplement, a dietary alteration, physical exercise, or any combination thereof. In some embodiments, an individual is treated by medical professional, such as a doctor, nurse, dietician, or similar. Various embodiments are directed to self-treatment such that an individual having a particular ASCVD risk intakes a medicine, a dietary supplement, alters her diet, or physically exercises based on the knowledge of her indicated ASCVD risk.

While specific examples of determining an individual's ASCVD risk are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for determining an individual's ASCVD risk appropriate to the requirements of a given application can be utilized in accordance with various embodiments of the invention.

Biomarkers as Indicators of ASCVD Risk

In several embodiments, biomarkers are detected and measured, and based on the ability to be detected and/or level of the biomarker, ASCVD risk can be determined.

Biomarkers that can be used in the practice of the invention include (but are not limited to) metabolites, protein constituents, genomic DNA, transcript expression, and lipids. As discussed in the Exemplary embodiments, a number of biomarkers have been found to be useful to determine ASCVD risk, including (but not limited to) triglycerides (TGL), L-Cysteinylglycine disulfide, hemoglobin A1c (A1C), 2,3-Dihydroxyvaleric acid LysoPC(16:0), C10:2 fatty acid, sex hormone binding globulin (SHBG), protein S1 (PROS1), phospholipid transfer protein (PLTP), high density lipoprotein (HDL), L-Proline, cholesterol-to-high density protein ration (CHOLHDL), LysoPC(20:2), Androstenediol (3beta,17beta) disulfate, LysoPC(18:2), Dihydroxyvitamin D3(2), C22:6 fatty acid, C10:0,OH fatty acid, N-Acetylserine, C16:1 fatty acid, complement component 5 (C5), Ig heavy chain V-III region JON, vascular endothelial growth factor (VEGF), serpin family F member 1 (SERPINF1), Bilirubin, matrix Gla-protein (MGP), low density lipoprotein-to-high density lipoprotein ratio (LDLHDL), C10:3 fatty acid, Red cell distribution width (RDW), platelet-derived growth factor BB (PDGFBB), complement factor H (CFH), Dihydroxyvitamin D3, Chenodeoxycholic acid glycine conjugate, 3-Methyl-2-oxovaleric acid, C8:0,0H fatty acid, Ne-Methyl-Lysine, LysoPC(P-18:1), gamma-glutamyl-epsilon-lysine, 1-Methylxanthine, nucleoporin 205 (NUP205), pregnancy zone protein (PZP), Glycosylphosphatidylinositol Specific Phospholipase D1 (GPLD1), LysoPE(P-16:0), L-a-Hydroxyisovaleric acid, LysoPC(18:0), Hypoxanthine, Homoarginine, vitronectin protein (VTN), interleukin 2 (IL2), and absolute monocyte count (MONOAB). See Table 5 for a more in depth list of biomarkers that can be utilized to determine ASCVD risk.

Detecting and Measuring Levels of Biomarkers

Analyte biomarkers in a biological sample (e.g., blood extraction, stool sample, urine sample, or biopsy) can be determined by a number of suitable methods. Suitable methods include chromatography (e.g., high-performance liquid chromatography (HPLC), gas chromatography (GC), liquid chromatography (LC)), mass spectrometry (e.g., MS, MS-MS), NMR, enzymatic or biochemical reactions, immunoassay, and combinations thereof. For example, mass spectrometry can be combined with chromatographic methods, such as liquid chromatography (LC), gas chromatography (GC), or electrophoresis to separate the metabolite being measured from other components in the biological sample. See, e.g., Hyotylainen (2012) Expert Rev. Mol. Diagn. 12(5):527-538; Beckonert et al. (2007) Nat. Protoc. 2(11): 2692-2703; O'Connell (2012) Bioanalysis 4(4):431-451; and Eckhart et al. (2012) Clin. Transl. Sci. 5(3):285-288; the disclosures of which are herein incorporated by reference. Alternatively, analytes can be measured with biochemical or enzymatic assays. For example, glucose can be measured with a hexokinase-glucose-6-phosphate dehydrogenase coupled enzyme assay. In another example, biomarkers can be separated by chromatography and relative levels of a biomarker can be determined from analysis of a chromatogram by integration of the peak area for the eluted biomarker.

Immunoassays based on the use of antibodies that specifically recognize a biomarker may be used for measurement of biomarker levels. Such assays include (but are not limited to) enzyme-linked immunosorbent assay (ELISA), radioimmunoassays (RIA), "sandwich" immunoassays, fluorescent immunoassays, enzyme multiplied immunoassay technique (EMIT), capillary electrophoresis immunoassays (CEIA), immunoprecipitation assays, western blotting, immunohistochemistry (IHC), flow cytometry, and cytometry by time of flight (CyTOF).

Antibodies that specifically bind to a biomarker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). A biomarker antigen can be used to immunize a mammal, such as a mouse, rat, rabbit, guinea pig, monkey, or human, to produce polyclonal antibodies. If desired, a biomarker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface-active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a biomarker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 31 42, 1985; Cote et al., Proc. Natl. Acad. Sci. 80, 2026-30, 1983; Cole et al., Mol. Cell Biol. 62, 109-20, 1984).

In addition, techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, Proc. Natl. Acad. Sci. 88, 11120-23, 1991).

Single-chain antibodies also can be constructed using a DNA amplification method, such as PCR, using hybridoma cDNA as a template (Thirion et al., Eur. J. Cancer Prev. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J Cancer 61, 497-501, 1995; Nicholls et al., J. Immunol. Meth. 165, 81-91, 1993).

Antibodies which specifically bind to a biomarker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Antibodies may be used in diagnostic assays to detect the presence or for quantification of the biomarkers in a biological sample. Such a diagnostic assay may comprise at least two steps; (i) contacting a biological sample with the antibody, wherein the sample is blood or plasma, a microchip (e.g., See Kraly et al. (2009) Anal Chim Acta 653(1): 23-35), or a chromatography column with bound biomarkers, etc.; and (ii) quantifying the antibody bound to the substrate. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as $^2H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); David et al., Biochem. 13:1014 (1974); Pain et al., J. Immunol. Methods 40:219 (1981); and Nygren, J. Histochem. and Cytochem. 30:407 (1982).

Immunoassays can be used to determine the presence or absence of a biomarker in a sample as well as the quantity of a biomarker in a sample. First, a test amount of a biomarker in a sample can be detected using the immunoassay methods described above. If a biomarker is present in the sample, it will form an antibody-biomarker complex with an antibody that specifically binds the biomarker under suitable incubation conditions, as described above. The amount of an antibody-biomarker complex can be determined by comparing to a standard. A standard can be, e.g., a known compound or another protein known to be present in a sample. As noted above, the test amount of a biomarker need not be measured in absolute units, as long as the unit of measurement can be compared to a control.

In various embodiments, biomarkers in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate a two-dimensional array of spots for the biomarkers. See, e.g., Jungblut and Thiede, Mass Spectr. Rev. 16:145-162 (1997).

Two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in the one-dimensional array are further separated using a technique generally distinct from that used in the first separation step. For example, in the second dimension, biomarkers separated by isoelectric focusing are further resolved using a polyacrylamide gel by electrophoresis in the presence of sodium dodecyl sulfate (SDS-PAGE). SDS-PAGE allows further separation based on molecular mass. Typically, two-dimensional gel electrophoresis can separate chemically different biomarkers with molecular masses in the range from 1000-200,000 Da, even within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more biomarkers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a biomarker can be analyzed by gas phase ion spectrometry. In gas phase ion spectrometry, the spots can be analyzed using any suitable techniques, such as MALDI or SELDI.

In a number of embodiments, high performance liquid chromatography (HPLC) can be used to separate a mixture of biomarkers in a sample based on their different physical properties, such as polarity, charge and size. HPLC instruments typically consist of a reservoir, the mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers.

After preparation, biomarkers in a sample are typically captured on a substrate for detection. Traditional substrates include antibody-coated 96-well plates or nitrocellulose membranes that are subsequently probed for the presence of biomarkers. Alternatively, metabolite-binding molecules attached to microspheres, microparticles, microbeads, beads, or other particles can be used for capture and detection of biomarkers. The metabolite-binding molecules may be antibodies, peptides, peptoids, aptamers, small molecule ligands or other metabolite-binding capture agents attached to the surface of particles. Each metabolite-binding molecule may comprise a "unique detectable label," which is uniquely coded such that it may be distinguished from other detectable labels attached to other metabolite-binding molecules to allow detection of biomarkers in multiplex assays. Examples include, but are not limited to, color-coded microspheres with known fluorescent light intensities (see e.g., microspheres with xMAP technology produced by Luminex (Austin, TX); microspheres containing quantum dot nanocrystals, for example, having different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by IIlumina (San Diego, CA); chemiluminescent dyes, combinations of dye compounds; and beads of detectably different sizes. See, e.g., U.S. Pat. Nos. 5,981,180, 7,445,844, 6,524,793, Rusling et al. (2010) Analyst 135(10): 2496-2511; Kingsmore (2006) Nat. Rev. Drug Discov. 5(4): 310-320, Proceedings Vol. 5705 Nanobiophotonics and Biomedical Applications II, Alexander N. Cartwright; Marek Osinski, Editors, pp. 114-122; Nanobiotechnology Protocols Methods in Molecular Biology, 2005, Volume 303; herein incorporated by reference in their entireties).

Mass spectrometry, and particularly SELDI mass spectrometry, is useful for detection of biomarkers. Laser desorption time-of-flight mass spectrometer can be used in embodiments of the invention. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting biomarkers. MALDI-MS is a method of mass spectrometry that involves the use of an energy absorbing molecule, frequently called a matrix, for desorbing proteins intact from a probe surface. MALDI is described, for example, in U.S. Pat. No.

5,118,937 (Hillenkamp et al.) and U.S. Pat. No. 5,045,694 (Beavis and Chait). In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art in embodiments of the invention.

The methods for detecting biomarkers in a sample have many applications. For example, the biomarkers are useful in monitoring women during pregnancy, for example to determine gestational age, predict time until delivery, or assess risk of spontaneous abortion.

Kits

In several embodiments, kits are utilized for monitoring individuals for ASCVD risk, wherein the kits can be used to detect analyte biomarkers as described herein. For example, the kits can be used to detect any one or more of the analyte biomarkers described herein, which can be used to determine ASCVD risk. The kit may include one or more agents for detection of one or more metabolite biomarkers, a container for holding a biological sample (e.g., blood or plasma) obtained from a subject; and printed instructions for reacting agents with the biological sample to detect the presence or amount of one or more biomarkers in the sample. The agents may be packaged in separate containers. The kit may further comprise one or more control reference samples and reagents for performing a biochemical assay, enzymatic assay, immunoassay, or chromatography. In various embodiments, a kit may include an antibody that specifically binds to a biomarker. In some embodiments, a kit may contain reagents for performing liquid chromatography (e.g., resin, solvent, and/or column).

A kit can include one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of monitoring women during pregnancy, e.g., to determine gestational age, predict time until delivery, and/or predict imminent spontaneous abortion.

Applications and Treatments Related to ASCVD Risk

Various embodiments are directed to diagnostics and treatments related to ASCVD risk. As described herein, an individual may have their ASCVD risk indicated by various methods. Based on one's ASCVD risk indication, an individual can be subjected to further diagnostics and/or treated with various medications, dietary supplements, dietary alterations, and physical exercise regimens.

Clinical Diagnostics

A number of embodiments are directed towards diagnosing individuals using analyte-based ASCVD risk scores, as determined by methods described herein. In some embodiments, correlation methods or a trained computational model produces an ASCVD risk score indicative of likelihood to develop atherosclerosis, heart attack, or stroke.

In a number of embodiments, diagnostics can be performed as follows:
 a) obtain analyte measurement data of the individual to be diagnosed
 b) determine ASCVD risk score
 c) diagnose the individual based on the ASCVD risk score.

Diagnoses, in accordance with various embodiments, can be performed as portrayed and described in herein, such as portrayed in FIG. 1.

Clinical Assessments, Medications and Supplements

Several embodiments are directed to the use of medications and/or dietary supplements to treat an individual based on her ASCVD risk. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect. A therapeutically effective amount can be an amount sufficient to prevent reduce, ameliorate or eliminate symptoms of ASCVD and/or reduce the risk of ASCVD.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to other tissue and organs and, thereby, reduce side effects.

Data obtained from cell culture assays or animal studies can be used in formulating a range of dosage for use in humans. If the pharmaceutical is provided systemically, the dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition of neoplastic growth) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result.

A number of diagnostic tests are available to further assess ASCVD. Diagnostic tests include (but are not limited to) blood test, medical imaging, blood pressure measurements, electrocardiogram, stress test, and an angiogram. Blood tests can be performed to determine the level cholesterol, blood sugar, or other components involved with ASCVD. Many medical imaging techniques can be performed, including Doppler ultrasound and cardiac catheterization and angiogram. Blood pressure can be measured locally at various extremities, which may be utilized to determine an ankle-brachial index among other measurements. In some embodiments, a coronary artery calcification evaluation, a coronary computed tomographic angiography or a carotid artery ultrasound is performed based on ASCVD risk.

A number of medications are available to treat ASCVD, such as those used to treat bad cholesterol, to reduce platelet formation, beta-blockers, inhibitors of Angiotensin-converting enzyme (ACE), calcium channel blockers, and diuretics. Medications include (but are not limited to) statins (e.g., atorvastatin, fluvastatin, lovastatin, pitavastatin, pravastatin, rosuvastatin, simvastatin), bile acid binding resins (e.g., cholestyramine, colesevelam, colestipol), cholesterol absorption inhibitors (e.g., ezetimibe), fibrates (e.g., fenofibrate, gemfibrozil), niacin (e.g., niacor, niaspan), anticoagulants (e.g., heparin, warfarin, rivaroxaban, dabigatran, apixaban, edoxaban, enoxaparin, fondaparinux), antiplatelet medications (e.g., aspirin, clopidogrel, ticagrelor, prasugrel, dipyridamole, ticlopidine, eptifibatide), beta blockers (e.g., acebutolol, atenolol, bisoprolol, metoprolol, nadolol, nebivolol, propranolol), ACE inhibitors (e.g., benazepril, captopril, enalapril, lisinopril, moexipril, perindopril, quinapril, ramipril, trandolapril), calcium channel blockers (e.g., amlodipine, diltiazem, felodipine, isradipine, nicardipine, nifedipine, nisoldipine, verapamil) and diuretics (e.g., chlorothiazide, chlorthalidone, hydrochlorothiazide, indapamide, metolazone, bumetanide, ethacrynic acid, furosemide, torsemide, amiloride, eplerenone, spironolactone, triamterene). Accordingly, an individual may be treated, in accordance with various embodiments, by a single medication or a combination of medications described herein. Furthermore, several embodiments of treatments further incorporate diabetes medications (e.g., insulin and biguanides), dietary supplements, dietary alterations, physical exercise, or a combination thereof.

Numerous dietary supplements may also help to treat risk of ASCVD. Various dietary supplements, such as alpha-linolenic acid (ALA), barley, beta-sitosterol, black tea, blond *psyllium*, calcium, cocoa, coenzyme Q10, folic acid, garlic, green tea, oat bran, omega-3 fatty acids, sitostanol, and vitamin C have been shown to have beneficial effects on individuals having risk of ASCVD. Thus, embodiments are directed to the use of dietary supplements, included those listed herein, to be used to treat an individual based on one's ASCVD risk result. A number of embodiments are also directed to combining dietary supplements with medications, dietary alterations, and physical exercise to reduce ASCVD risk.

Diet and Exercise

Numerous embodiments are directed to dietary alteration and exercise treatments. Altering one's lifestyle, including physical activity and diet, has been shown to improve ASCVD risk. Accordingly, in a number of embodiments, an individual is treated by altering their diet and increasing physical activity in response to an ASCVD risk result.

There are various diets that will help different individuals in reducing ASCVD risk. A number of embodiments are directed to treatments to reduce weight, which has been considered by some to be the best approach to reduce ASCVD risk. For others, a diet low in refined carbohydrates and sugars will work better. Numerous embodiments are directed to treating an individual by substituting saturated fats with monounsaturated and unsaturated fats to help lower the risk for cardiovascular disease, which would be beneficial for many individuals. Also, embodiments are directed to increasing amounts of fiber in the diet, which would be highly recommended to help balance serum lipid levels (cholesterol and triglycerides).

Exercise has a large impact on ASCVD risk. In several embodiments, a treatment would entail a minimum of some minutes of active exercise per week. In some embodiments, treatments would include a minimum of 150 minutes of exercise a week, however, the precise duration of exercise may be dependent on the individual to be treated and their cardiovascular health. It is further noted that cardiovascular exercise is important for the immediate improvements in cardiac health and weight training will have a long-term effect by increasing muscle mass, affecting cardiac health during rest.

In many embodiments, a treatment to help control glucose levels is stress management, as stress increases ASCVD risk. Some proven ways to help control stress include meditation, social support, adequate sleep, journaling, and therapy.

Exemplary Embodiments

Bioinformatic and biological data support the methods and systems of assessing glycemic regulation and applications thereof. In the ensuing sections, exemplary computational methods and exemplary applications related to analyte panels, correlations, computational models, and glycemic regulation are provided.

Precision health and medicine are entering a new era where wearable sensors, omics technologies, and computational methods have the potential to improve health and lead to mechanistic discoveries. In principle, it is becoming possible to use emerging technologies such as multi-omics profiling along with standard clinical tests to comprehensively assess health, predict disease risk and thereby better manage health. Of particular value is following individuals longitudinally to identify deviations from healthy baselines, ideally before individuals become clinically symptomatic. Connecting longitudinal multi-omics profiling with detailed clinical assessment is also important in developing a new taxonomy of disease based on molecular measures.

Despite the promise of precision health and medicine, very few studies have attempted to leverage emerging technologies and longitudinal profiling to identify disease markers. Accordingly, in the following examples 109 participants at risk for Type 2 diabetes mellitus (DM) were followed for a median of 2.8 years (FIG. 6) and performed quarterly clinical laboratory tests and multi-omics assessments designed to provide information on all molecular levels. In addition, individuals underwent exercise testing, enhanced cardiovascular imaging, wearable sensor monitoring and enhanced clinical physiological testing, and completed various surveys.

The research was designed to capture transitions from normoglycemic to preDM and from preDM to DM and also to capture transitions from healthy to pre-cardiovascular disease to atherosclerosis. Thus, in addition to standard measures such as fasting plasma glucose (FPG, reflects steady state glucose metabolism) and glycated hemoglobin (HbA1C, reflects 3 month average glucose), enhanced measures included the oral glucose tolerance test (OGTT, reflects response to glucose load) with insulin secretion assessment (beta-cell function) and the modified insulin suppression test (SSPG, a measure of peripheral insulin resistance). Data derived from the research was leveraged into improved diagnostics and treatments in the realm of glycemia disorders.

Research Design and Cohort

Figure 7:
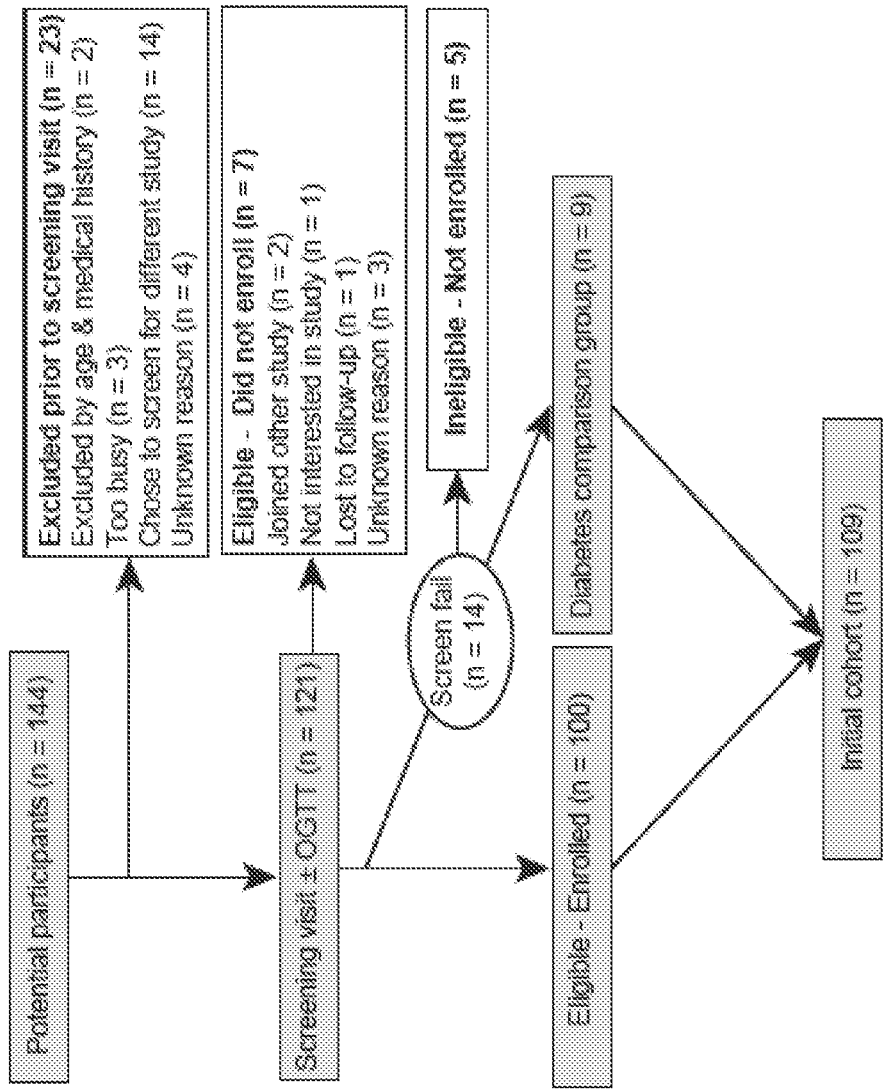
FIG. 7 illustrates a flow diagram of participant inclusion in an integrated personalized Omics cohort study, utilized in accordance with various embodiments of the invention.

A cohort enriched for individuals at risk for DM (n=109, Table 1, FIG. 7) underwent quarterly longitudinal profiling for up to eight years (median 2.8 years) using standard and enhanced clinical measures as well as emerging assays (FIG. 6). Emerging tests included multi-level molecular profiling of the genome, gene expression (transcriptome), proteins (proteome), small molecules (metabolome), immune proteins (immunome) and gut microbes (microbiome). Standard and enhanced tests were focused on glucose regulation and insulin metabolism. Continuous glucose monitoring (CGM) was also used to gain deeper insights into glucose metabolism. The full details of clinical laboratory measures, cytokines, chemokines, growth factors, and emerging cardiovascular laboratory measures are provided in Table 2.

Participants were recruited from the Stanford University surrounding community with the goal of enriching the cohort with individuals at risk for diabetes and thus included individuals who expressed interest in other studies related to diabetes. Participants were enrolled as part of Stanford's iPOP (Integrated Personal Omics Profiling) research study (IRB 23602), which entails longitudinal multi-omics profiling of a cohort of unrelated adult volunteers enriched for pre-diabetics.

The iPOP study is a longitudinal prospective cohort study containing 109 individuals. Inclusion criteria were ages 25 to 75, body mass index (BMI) between 25 and 40 kg/m2 and 2-hour oral glucose tolerance test in the normal or prediabetic range (<200 mg/dl). Exclusions included active eating disorder, hypertriglyceridemia>400 mg/dL, uncontrolled hypertension, heavy alcohol use, pregnancy/lactation, prior bariatric surgery, and active psychiatric disease. After meeting initial recruitment goals, the inclusion criteria was expanded to include people with diabetes and people with normal BMI into the study. Participant demographics can be found in Table 1.

Figure 8:
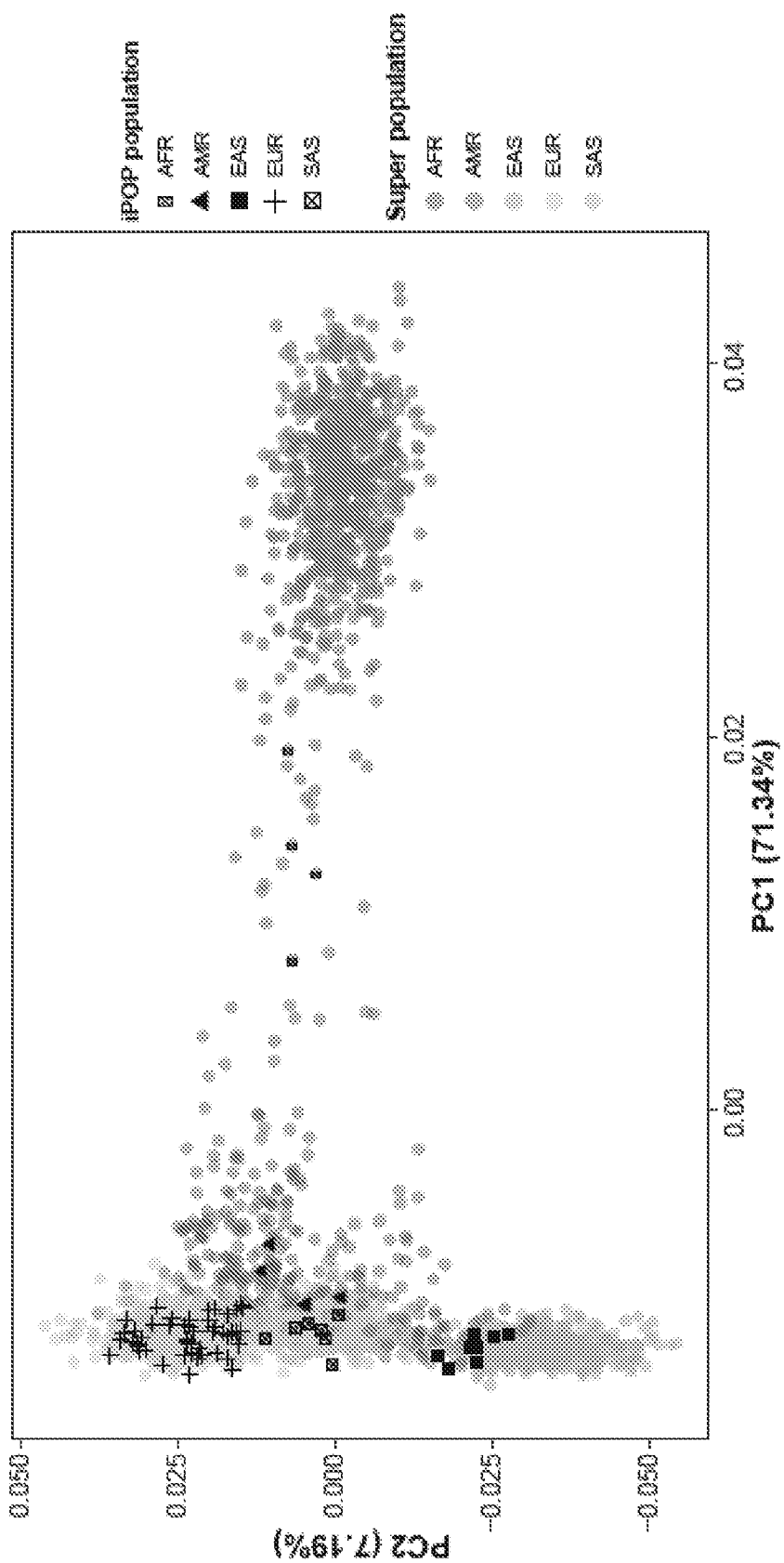
FIG. 8 provides a graphical representation of principal component analysis detailing the genetic ancestry of the iPOP population, utilized in accordance with various embodiments of the invention.

The mean age of iPOP participants at initial enrollment was 53.4±9.2 years old. Demographic, baseline health, and family history characteristics are shown in Table 1. Genetic ancestry was mapped (n=72) using the 1000 Genomes data and shows that the majority of iPOP participants mapped to expected ancestral populations (i.e., super populations) using principal component analysis (FIG. 8).

The cohort was recruited over a number of years with the first participant starting in 2010. Participants were asked to donate samples (i.e. fasted blood and stool) quarterly when healthy and more frequently when sick (viral infection), after immunization and various other events such as after taking antibiotics and going through colonoscopy. Samples collected through December 2016 were used for multi-omics analysis and corresponds to a median participation duration of 2.8 years. Standard and enhanced clinical lab data and participant surveys were available through January 2018. Most analysis were performed using healthy time points only.

All blood samples were collected after an overnight fast and were used to perform standard and enhanced clinical tests as well as emerging assays (FIG. 6). Standard tests included: FPG, HbA1C, fasted insulin, basic lipid panel, complete metabolic panel, CBC with differential and others. In addition, participants were asked to complete various surveys in relation to demographics and current and past medical history, medications, smoking history, and family history, anthropometry, diet and physical activity as well as stress. Enhanced tests included: OGTT, SSPG, beta-cell function assessment, hsCRP, IgM, cardiovascular imaging (echocardiography, vascular ultrasound), cardiopulmonary exercise, cytokines/growth factors, CVD markers and wearable devices (physiology and activity monitor, CGM). In addition, multi-level molecular profiling were performed (emerging tests) including genome, gene expression (transcriptome), proteins (proteome), small molecules (metabolome), immune proteins (immunome) and gut microbes (microbiome). Clinical and cytokine measures are detailed in Table 2.

Overall, during the course of the study, over 67 major clinically actionable health discoveries were found spanning metabolism, cardiovascular disease, oncology and hematology, and infectious disease using clinical, enhanced, and emerging technologies (Table 3).

Methods of Testing and Measurements

Modified Insulin Suppression Test

Sixty-nine participants underwent the modified insulin suppression test to determine steady-state plasma glucose (SSPG) levels. The test was performed after an overnight fast and consists of 180-minute infusion of octreotide (0.27 µg/m2/min), insulin (0.25 µg/m2/min), and glucose (240 µg/m2/min) with blood draws at minutes 150, 160, 170, and 180. The oximetric method was used to determine blood glucose and steady-state plasma glucose (SSPG) was determined by taking the mean of the four measurements. Reasons for not participating in this test included medical contraindications (n=9), refusal (n=5) and dropped out of study (n=11) and not yet performed (n=15).

Genomics

Whole Exome Sequencing (n=88) was performed by an accredited facility and variant calling was performed using the HugeSeq pipeline (see H. Y. K. Lam, et al, *Nat. Biotechnol.* 30, 226-229 (2012), the disclosure of which is herein incorporated by reference). Exomes were assessed for pathogenic variants according to the American College of Medical Genetics Guidelines. The Online Mendelian Inheritance in Man (OMIM) database was used.

Peripheral Blood Mononuclear Cell (PBMC) RNA Sequencing

RNA sequencing from bulk PBMCs was performed using the TruSeq Stranded total RNA LT/HT Sample Prep Kit (Illumine, San Diego, CA) and sequenced on Illumine HiSeq 2000 instrument. The TopHat package in R was used to align the reads to personal genomes, followed by HTseq and DESEQ2 for transcript assembly and RNA expression quantification.

Plasma SWATH-Mass Spectroscopy Proteomics

Tryptic peptides of plasma samples were separated on a NanoLC 425 System (SCIEX, Framingham, MA). MS analyses were performed with randomized samples using SWATH Acquisition on a TripleTOF 6600 System equipped with a DuoSpray Source and 25 µm I.D. electrode (SCIEX, Framingham, MA). A final data matrix was produced with 1% FDR at peptide level and 10% FDR at protein level. Protein abundances were computed as the sum of the three most abundant peptides (top3 method).

Serum Cytokines and Growth Factors Measurements

The 62 plex-Luminex antibody-conjugated bead capture assay (Affymetrix, Santa Clara, CA) was used to characterize blood levels of cytokines, chemokines and growth factors. The assay was performed by the Stanford Human Immune Monitoring Center (Palo Alto, CA).

Plasma Liquid Chromatography-Mass Spectrometry (LC-MS) Metabolomics

Untargeted plasma metabolomics was performed using a broad spectrum LC-MS platform. This analytical platform has been optimized to maximize metabolome coverage and involves complementary reverse-phase liquid chromatography (RPLC) and hydrophilic interaction liquid chromatography (HILIC) separations. Data were acquired on a Q Exactive plus mass spectrometer (Thermo Scientific, Waltham, MA) for HILIC and a Thermo Q Exactive mass spectrometer (Thermo Scientific, Waltham, MA) for RPLC. Both instruments were equipped with a HESI-II probe and operated in full MS scan mode. MS/MS data were acquired at various collision energies on pooled samples. LC-MS data were processed using Progenesis QI (Nonlinear Dynamics, Newcastle upon Tyne, UK) and metabolic features were annotated by matching retention time and fragmentation spectra to authentic standards or to public repositories. Some metabolites elute in multiple peaks and are indicated with a number in parenthesis following the metabolite name ordered by elution time.

Plasma Lipidomics Analysis

Lipids were extracted and analyzed using a mixture of MTBE, methanol and water to extract lipids from 40 µl of plasma following biphasic separation. Lipids were then analyzed with the Lipidyzer platform consisting in a DMS device (SelexION Technology of SCIEX, Framingham, MA) and a QTRAP 5500 (SCIEX, Framingham, MA). Lipids were quantified using a mixture of 58 labeled internal standards provided with the platform.

16S Microbiome Sequencing

DNA was extracted from stool in line with the Human Microbiome Project's (HMP) Core Sampling Protocol A (hmpdacc.org). Targeted rRNA gene amplification of the V1 through V3 hypervariable regions of the 16S rRNA gene was performed using primers 27F and 534R (27F:5'-AGAGTTT-GATCCTGGCTCAG-3' (SEQ. ID No. 1) and 534R: 5'-ATTACCGCGGCTGCTGG-3' (SEQ. ID No. 2)), and subsequently sequenced using 2×300 bp paired-end sequencing (MiSeq of Illumina, San Diego, CA). Illumina's software handles initial processing of all the raw sequencing data. A standard of one mismatch in primer and zero mismatch in barcode was applied to assign read pairs to the appropriate sample within a pool of samples. Barcodes and primers were removed prior to analysis. The microbiome 16S reads were processed in two ways, depending on subsequent use. In the first approach, amplicon sequences were clustered and Operational Taxonomic Units (OTU) picking by Usearch against GreenGenes database (May 2013 version) and final taxonomic assignment were performed using RDP-classifier. This approach was used for all microbiome analyses except the prediction models. In the second approach, 16S reads were processed using QIIME 2 (see J. G. Caporaso, et al., *Nat. Methods* 7, 335-336 (2010), the disclosure of which is herein incorporated by reference; see also https://qiime2.org) and the DADA2 denoising plugin (see J. B. Callahan, et al., *Nat. Methods* 13, 581-583 (2016), the disclosure of which is herein incorporated by reference). DADA2 facilitates cross-study comparison by providing DNA sequences of features thus making it more appropriate for prediction models. The resulting read depth was 18,885±11,852 (mean±SD) following paired end joining, removal of chimeric reads, and removal of samples with <7000 read depth. Taxonomic assignment was carried out using a naïve bayes classifier trained on primers with the 99% 13_8 Greengenes OTU data set as reference sequences (see N. A. Bokulich, et al., *Microbiome* 6, 90 (2018), the disclosure of which is herein incorporated by reference).

Continuous Glucose Monitoring

Continuous glucose monitoring (CGM) was performed with the Dexcom G4 CGM system (Dexcom, San Diego, CA). Participants wore the monitors for 2-4 weeks with interstitial glucose concentrations recorded every 5 minutes. They were also given glucose meters (AccuCheck Nano SmartView of Roche Diabetes Car, Inc., Indianapolis, IN) to measure finger prick blood glucose concentrations twice a day for the purpose of calibration.

Calculation of Insulin Secretion Rate and Disposition Index

The ISEC program (see R. Hovorka, P. A. Soons, and M. A. Young, *Comput. Methods Programs Biomed.* 50, 253-264 (1996), the disclosure of which is herein incorporated by reference) was used to calculate the insulin secretion rate (ISR) from deconvolution of c-peptide measurements from plasma sampled at various time points during the OGTT (at minutes 0, 30 and 120). The deconvolution method uses population-based kinetic parameters for c-peptide clearance to estimate insulin secretion rates at other timepoints. ISR was reported in pmol/kg/min at every 15-minute time interval between 0 and 120 minutes. The disposition index (DI) was calculated as the ISR at 30 minutes (ISR30) times the Matsuda index, which was calculated as previous reported (see E. Cersosimo, et al, *Curr. Diabetes Rev.* 10, 2-42 (2014), the disclosure of which is herein incorporated by reference). DI was reported as (pmol/kg/min)/(mg/dL*µU/mL). It is noted that DI can also be calculated using SSPG.

For association with multi-omics measures, insulin secretion rates were row standardized across the 9 time points from an OGTT sample and then clustered via the k-means clustering algorithm in R (v. 3.5) (function 'kmeans'), with k=4. Simple linear models were used to associate the disposition index with each multi-omics analyte. Values for multi-omics analytes were from the time point closest to the OGTT date. Adjustment of p-values for multiple testing was performed using the Benjamini-Hochberg method, with an adjusted p-value of <0.10 used to identify analytes significantly associated with the disposition index.

ASCVD Circulating Markers

Millipore immunoassays human cardiovascular disease panels 1 to 4 (HCVD1MAG-67K, HCVD2MAG-67K, HCVD3MAG-67K, HCVD4MAG-67K) were used to characterize blood ASCVD circulating markers. The assays were performed by the Stanford Human Immune Monitoring Center.

Echocardiography

Baseline rest echocardiography was performed using commercially available echo systems (iE33; Philips Medical Imaging, Eindhoven, the Netherlands). Post-stress images were acquired immediately post-exercise, as per international consensus. Digitized echocardiographic studies were analyzed by the Stanford Cardiovascular Institute Biomarker and Phenotypic Core Laboratory on Xcelera workstations in accordance with published guidelines of the American Society of Echocardiography (see M. R. Lang, et al., *J. Am. Soc. Echocardiogr.* 28, 1-39.e14 (2015), the disclosure of which is herein incorporated by reference). Regarding specific echocardiographic variables, left ventricular ejection fraction (LVEF) was calculated by manual contouring of apical imaging (see P. W. F. Wilson, et al., *Circulation* 97, 1837-1847 (1998), the disclosure of which is herein incorporated by reference). Left ventricular global longitudinal strain (LV GLS) was calculated from triplane apical imaging on manual tracings of the mid wall with the formula for LaGrangian Strain %=100×(L1−L0)/L0), as previously described (see A. D. Smith, *Ann. Intern. Med.* 164, JC35 (2016), the disclosure of which is herein incorporated by reference). With tissue Doppler imaging, peak myocardial early diastolic velocity was used at the lateral mitral annulus and the assessment of trans mitral to tissue Doppler imaging early diastolic velocity ratio (E/e') (see T. L. McClelland, *J. Am. Coll. Cardiol.* 66, 1643-1653 (2015); and K. K. Lee, et al., *Circulation* 122, 1478-1487 (2010); the disclosure of which are each the disclosure of which is herein incorporated by reference).

Vascular Ultrasound

Screening for subclinical atherosclerosis was performed using vascular ultrasound of the carotid and femoral artery using a 9.0 MHz Philips linear array probe and iE33 xMATRIX echocardiography System manufactured by Philips (Andover, MA, USA). Vascular stiffness was assessed using central pulse wave velocity (PWV).

Cardiopulmonary Exercise Testing

Symptom-limited cardiopulmonary exercise (CPX) ventilatory expired gas analysis was completed with an individualized RAMP treadmill protocol. Participants were encouraged to exercise to maximal exercise capacity. In addition, the respiratory exchange ratio (RER) was monitored during exercise and considered an RER ratio<1.05 as representing sub-optimal or limitations associated with fatigue. Ventilatory efficiency (VE), oxygen consumption (V02), volume of carbon dioxide production ($VCO_2$) and other CPX variables were acquired breath by breath and averaged over 10 second intervals using CareFusion Oxygen Pro (San Diego, California) or CosMEd Quark (Rome, Italy) metabolic system. VE and $VCO_2$ responses throughout exercise were used to calculate the $VE/VCO_2$ slope via least squares linear regression (y=mx+b, m=slope). Percent predicted maximal oxygen consumption was derived using the Fitness Registry and the Importance of Exercise: a National Database (FRIEND) registry equation, derived from a large cohort of healthy US individuals who completed cardiopulmonary exercise testing (see L. A. Kaminsky, et al., Mayo Clin. Proc. 92, 228-233 (2017), the disclosure of which is herein incorporated by reference).

ACSVD and Adjusted ASCVD Risk Score Calculation

The ASCVD Pooled Cohort Risk Equations were implemented according to the instructions in the 2013 ACC/AHA Guideline on the Assessment of Cardiovascular Risk, using SAS 9.4 statistical software (see D. C. Goff, Jr., et al., *Circulation* 129, S49-73 (2014), the disclosure of which is herein incorporated by reference). The baseline time point was used for all participants except those that turned 40 during the study. In these cases, the first time point after age 40 was chosen. Participants under the age of 40 (n=7) for the entire duration of the study were assigned the age of 40 for the purposes of ASCVD risk score calculation. The optimal risk for someone of a particular, age, sex and race, was calculated using a total cholesterol of 170, HDL of 50, and systolic blood pressure of 110 with no blood pressure medications, diabetes, or smoking. Adjusted ASCVD risk score was calculated by subtracting the optimal ASCVD risk score for a person of the same age, gender and race, from the participant's ASCVD risk score.

Stroke Genes Outlier Analysis

Z-scores were calculated as described above for 14 of 32 genes recently identified as being associated with stroke and stroke types. The 14 genes that we detected in our RNA-seq dataset were as follows: CASZ1, CDK6, FURIN, ICA1L, LDLR, LRCH1, PRPF8, SH2B3, SH3PXD2A, SLC22A7, SLC44A2, SMARCA4, ZCCHC14, ZFHX3. A composite Z-score was calculated by summing the individual gene Z-scores.

Association of Multi-omic Analytes and Adjusted ASCVD Risk Score

First, a median value was calculated for each analyte in each participant using healthy time points. A minimum of three healthy visits per participant was required. Spearman correlations were then calculated between adjusted ASCVD risk score and the median value of each multi-omics analytes. Associations were considered significant for analytes with FDR<0.2. FDR correction was performed using the 'qvalue' package (v. 1.36.0) in R (v. 3.0.1).

Correlation Network Analysis

Spearman correlations among molecules significantly associated with disposition index and adjusted ASCVD risk score were calculated using the rcorr function in the 'Hmisc' package (v. 3.15-0) in R (v. 3.0.1) and p-values were corrected for multiple hypothesis using Bonferroni. Correlation networks were plotted using the R package 'igraph' (v. 0.7.1) and the layout used was Fruchterman-Reingold. Edges represent correlations with Bonferroni FDR<0.05 and 0.10 for the disposition index and ASCVD risk score, respectively.

Exercise Sub-Study Analysis

ASCVD risk scores were calculated using cholesterol labs closest to the exercise study date using the same method as that used for the baseline ASCVD risk scores. Correlation analysis was done with 'corrplot' package in R (v. 3.3.2). The network was plotted using Cytoscape 3.4.0, where edges represent correlations with statistically significant Spearman's values (FDR<0.2) (see P. Shannon, et al., Genome Res. 13, 2498-2504 (2003), the disclosure of which is herein incorporated by reference). False discovery rate correction was performed using the 'qvalue' package (v. 1.36.0) in R. The distance between nodes represents the strength of the pull between a node and its connected neighbors. The larger the value, the closer the distance between the two nodes. The system was iterated until dynamic equilibrium using the prefuse force directed layout.

Ethnicity PCA Plot

Ethnicity information for 72 individuals in the study was broadly classified into the five 1000 Genomes Project (1000GP) Consortium super-population definitions, which are namely African (AFR), East Asian (EAS), European (EUR), South Asian (SAS) and admixed American (AMR). Individuals who self-identify as Indians from South Asia were categorized as SAS (n=7), Hispanics and Latinos as AMR (n=3), East Asians as EAS (n=8), Caucasians as EUR (n=50) and African Americans (n=4) as AFR. The ethnicity information from the 2,504 samples, definitions of the populations and super-populations, and genetic information of the 1000GP were obtained from ftp://ftp.1000genomes.ebi.ac.uk/vol1/ftp/release/20130502/ (downloaded in April 2017).

The following filters were first implemented for each individual genome for the study: (a) removed indels, leaving only the SNVs, (b) removed SNVs without the "PASS" tag, (c) kept SNVs with a minimum read depth of 1, and (d) removed SNVs with missing genotypes. The genetic loci from 72 individuals and the samples from the 1000GP were then intersected to obtain 6,653 SNVs common to both datasets. In order to reduce the chance of linkage disequilibrium and dependency between SNVs due to close proximity, the SNV set was further reduced by taking every third SNV. Finally, a combined set of 2,576 samples and 2,318 SNVs were use for PCA. The smartpca tool in the PLINK2 suite was used to generate the PCA (See C. C. Chang, et al., Gigascience 4, 7 (2015); and S. Purcell, et al., *Am. J. Hum. Genet.* 81, 559-575 (2007); the disclosures of which are each herein incorporated by reference).

Profiling Metabolic Health

Figure 9:
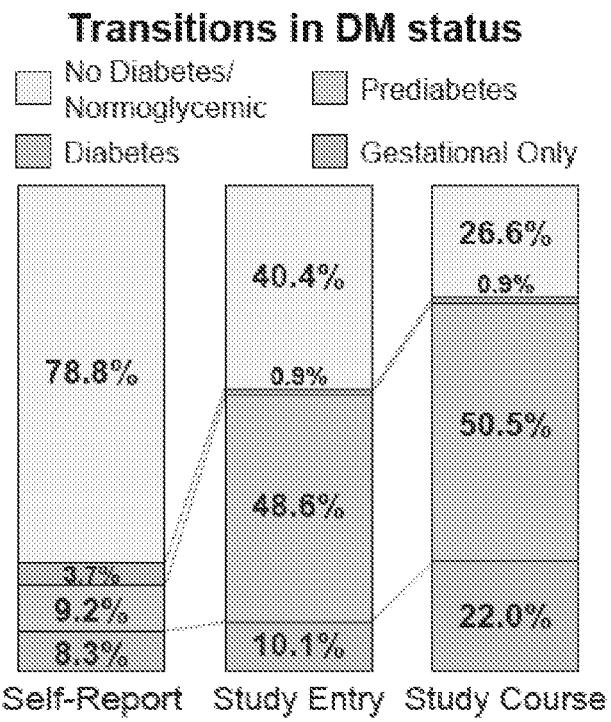
FIG. 9 provides a graphical representation of transitions in diabetes mellitus status of the iPOP population, utilized in accordance with various embodiments of the invention.

Upon enrollment in the study, all participants (n=109) were asked about their DM status. Twenty-five participants (20.1%) self-reported of having DM, being pre-DM or had gestational DM. Of the 86 participants (78.9%) who did not report pre-DM or DM, one had a diagnosis of DM in their health records, one had a DM-range HbA1C and 43 individuals (39.4%) had labs in the pre-diabetic range at study entry (FIG. 9). Over the course of the study, eight individuals converted to DM as assessed by a clinical diagnosis of DM (n=4), starting a diabetic medication after a diabetic range laboratory result (n=3), and/or if they had labs in the diabetic range (n=6) at more than one time point. Five additional participants developed laboratory abnormalities in the diabetic range at one time point, and 12 developed abnormalities in the prediabetic range. In addition, 2 participants had diabetic range CGM measurements (>200 mg/dL) who were normoglycemic on FPG, HbA1C and OGTT indicating that these individuals have glucose dysregulation that is most easily assessed using CGM.

Exome sequencing provided relevant metabolic information for 4 study participants (Table 3). The most notable was a participant classified Type 2 DM at initial enrollment, who was discovered to have a hepatic nuclear factor 1A (HNF1A) mutation, pathogenic for Maturity-Onset Diabetes of the Young (MODY). This discovery has implications for medication management and the individual decided to have the children tested. A second participant had a personal and family history compatible with MODY but no causative mutation was found. Thus, in some cases genomics and in other cases metabolic measurements contributed to valuable diagnostic information for participants and their families.

Figure 10:
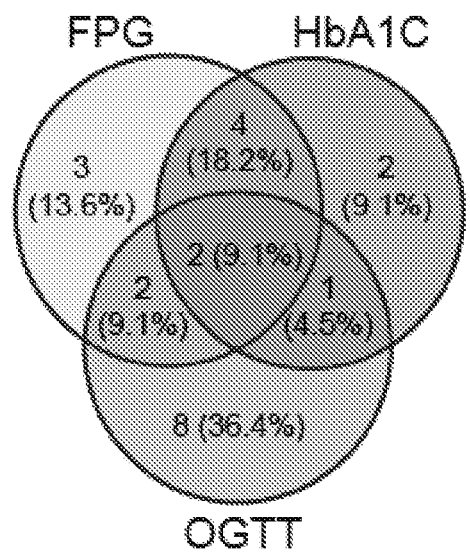
FIG. 10 details the overlap of diabetic range test results by participant over the course of a study, utilized in accordance with various embodiments of the invention.
Figure 11:
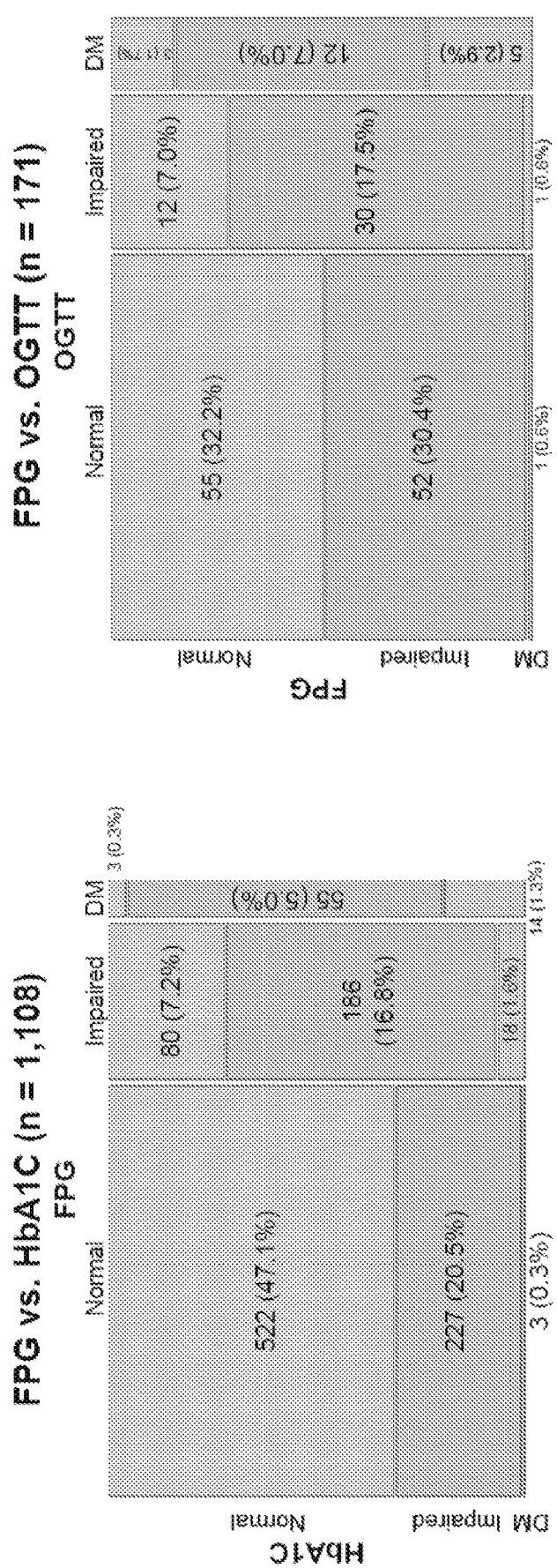
FIG. 11 details the direct comparison of various diabetes test results indicating a diabetic status of various individuals within the iPOP population used in a cohort study, utilized in accordance with various embodiments of the invention.
Figure 12:
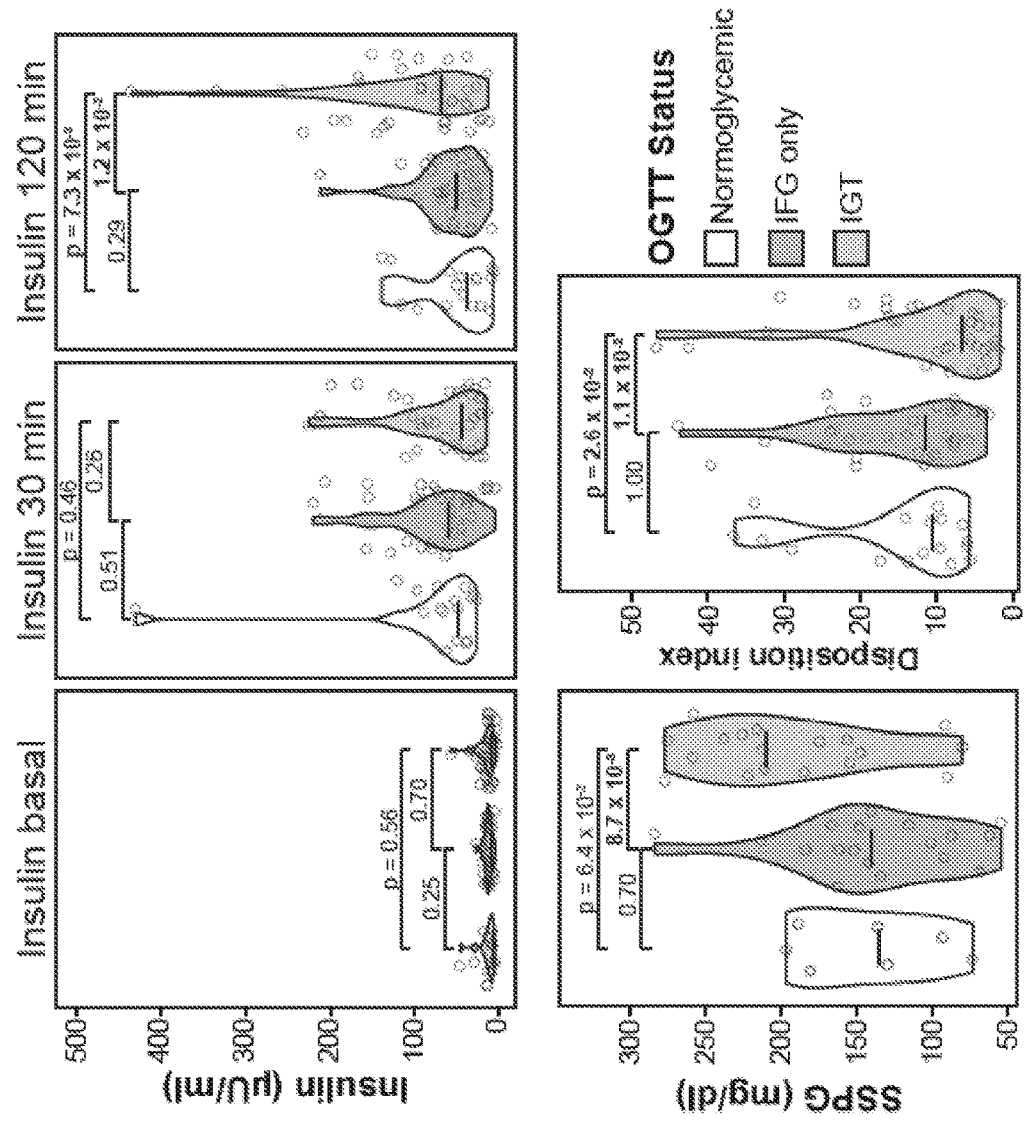
FIG. 12 details insulin secretion rate, insulin resistance and p-cell function of normoglycemic, impaired fasting glucose only, and impaired glucose tolerance individuals within the iPOP population used in a cohort study, utilized in accordance with various embodiments of the invention.
Figure 13:
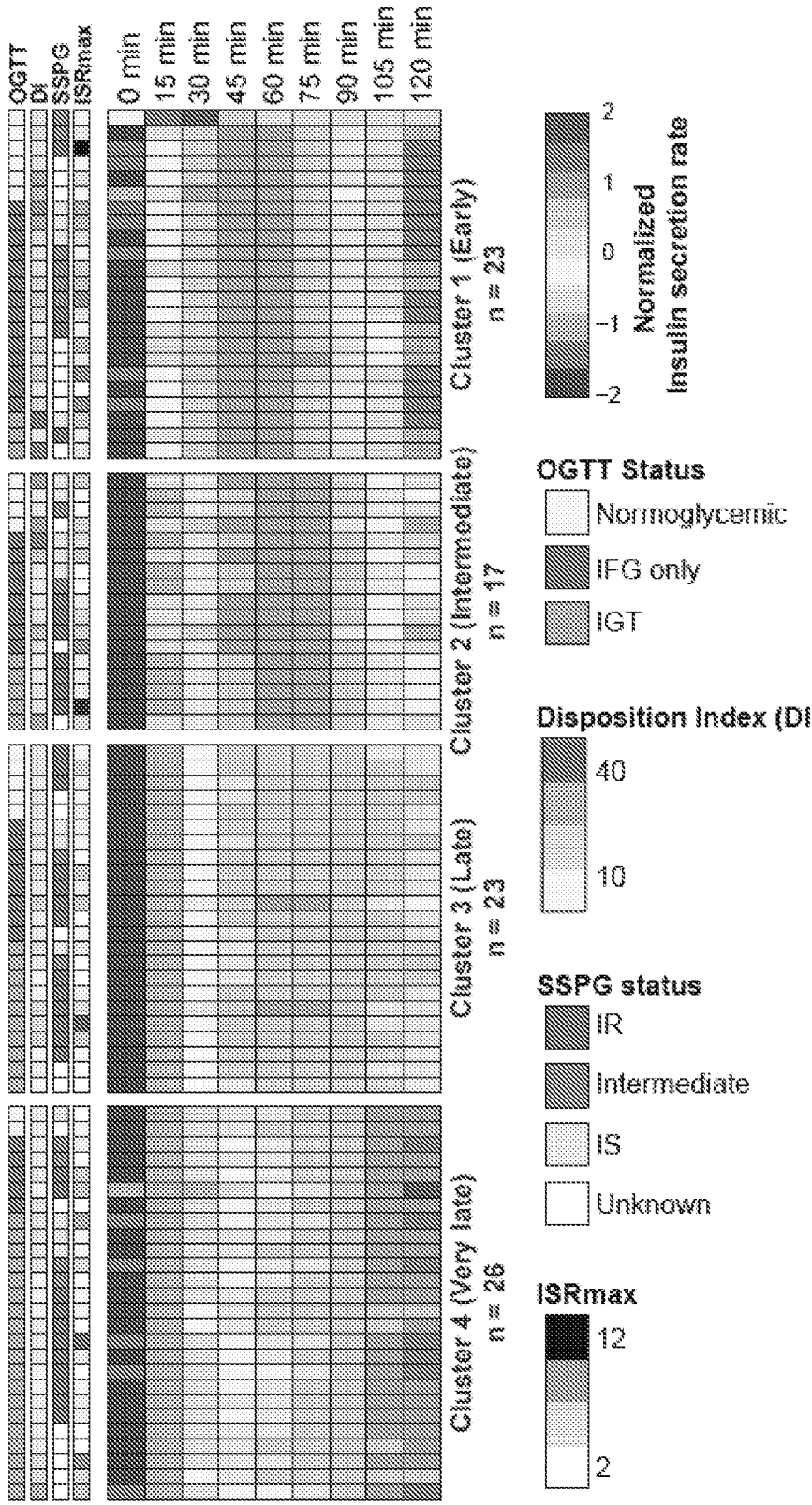
FIG. 13 details insulin secretion rate clustering into four clusters (early, intermediate, late and very late) with clusters ordered by glycemic status of individuals within the iPOP cohort including individuals that are normoglycemic, have impaired fasting glucose only, and have impaired glucose tolerance, utilized in accordance with various embodiments of the invention.

DM is a complex disease with various underlying pathophysiologies including insulin resistance, pancreatic beta-cell dysfunction or abnormal gluconeogenesis, which have a differential effect on standard measures. In this study, 22 participants had at least one test result in the diabetic range over the course of the study (FIG. 10) but few (n=2) had concordance of all three measures. When performed simultaneously, FPG with HbA1C and FPG with OGTT were in agreement 70.4% and 58.5% of the time, respectively (FIG. 11), highlighting that DM status varies depending on the assessment method. Most participants also underwent insulin sensitivity assessment (n=69) among which 55% were found to be resistant (SSPG 150 mg/dl). In addition, beta-cell function was assessed through the glucose disposition index (DI) in 61 participants using a C-peptide deconvolution method (see R. Malik et al., Nat. Genet. 50, 524-537 (2018), the disclosure of which is herein incorporated by reference). Based on OGTT and fasting glucose measurements, participants were categorized into three groups of normoglycemic, impaired fasting glucose only (IFG only) and impaired glucose tolerance (IGT). A large inter-individual variability in insulin levels, insulin resistance and DI between groups was observed (FIG. 12). Participants with IGT had higher insulin levels 120 min post-OGTT test, higher SSPG (more insulin resistant) and a lower DI (impaired beta-cell function). Cluster analysis of the longitudinal pattern of insulin secretion rates during OGTTs demonstrated four insulin secretion groups: early, intermediate, late and very late (FIG. 13). Each cluster was heterogeneous in term of OGTT status, DI, insulin resistance status and maximum insulin level and demonstrated no consistent pattern of molecular enrichment, indicating high heterogeneity in glucose dysregulation.

Figure 14:
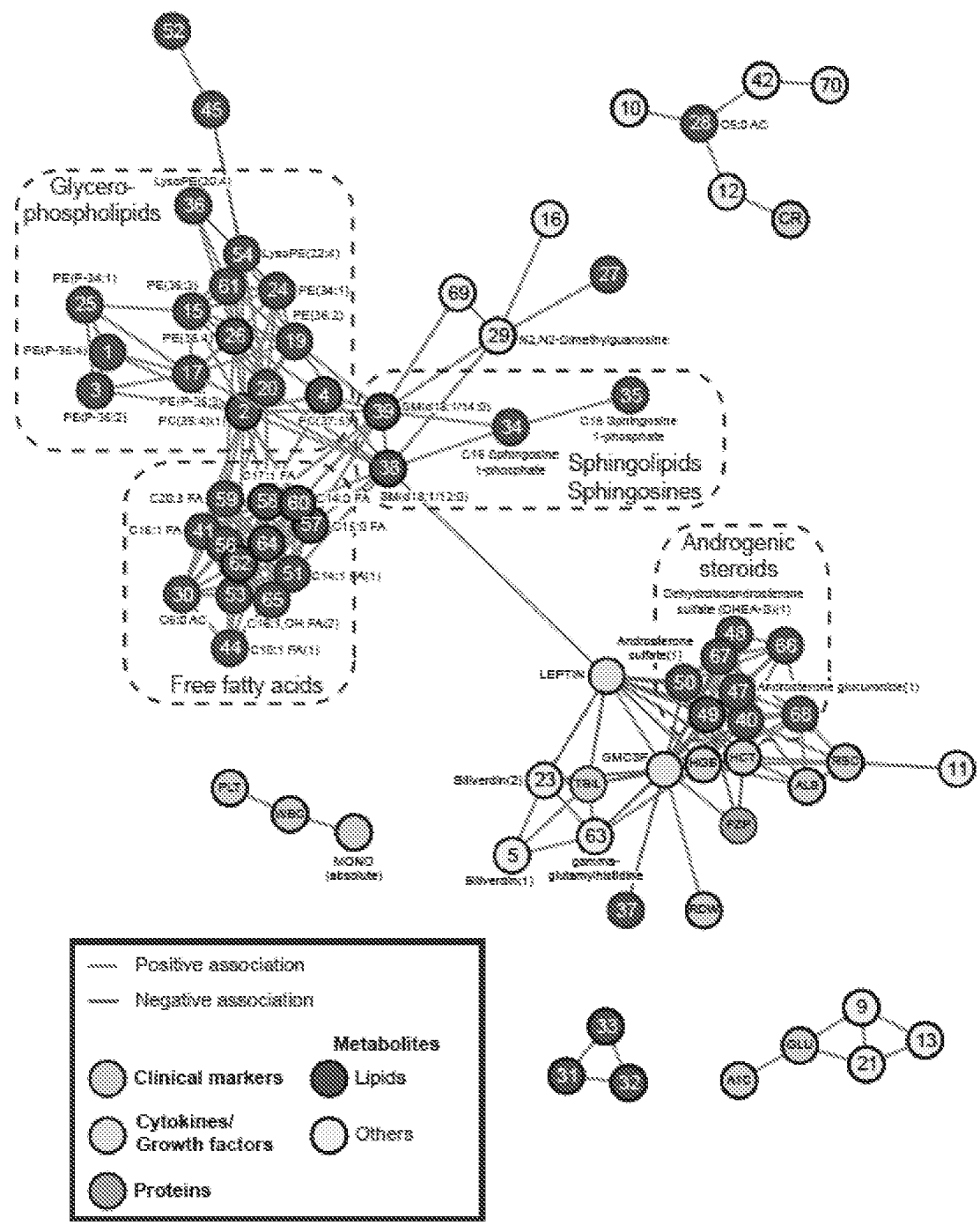
FIG. 14 details a correlation network of molecules associated with disposition index, utilized in accordance with various embodiments of the invention.

Multi-omics molecular associations with disposition index across the revealed 109 significant molecules (FDR<0.1) (Table 4). As expected, HbA1C (FDR=2.0E-03) and FPG (FDR=4.9E-02) were negatively associated with DI in line with previous reports showing association of increased FPG and HbA1C with beta-cell dysfunction. DI was also found to have a strong negative association with leptin (FDR=1.6E-07) and GM-CSF (FDR=7.2E-07). GM-CSF (p=1.5E-07) and leptin (p=3.3E-07) were also the two analytes the most strongly positively associated with BMI in the cohort study and were positively associated with hsCRP, which signifies their connection to obesity and inflammation. In the DI correlation network, leptin and GM-CSF were correlated with various lipid classes including an inverse correlation with androgenic steroids, and a positive correlation with sphingolipids and sphingosines, free fatty acids and glycerophospholipids highlighting their central role in regulating lipid metabolism (FIG. 14).

Longitudinal Course and Mechanistic Insights

Figure 15:
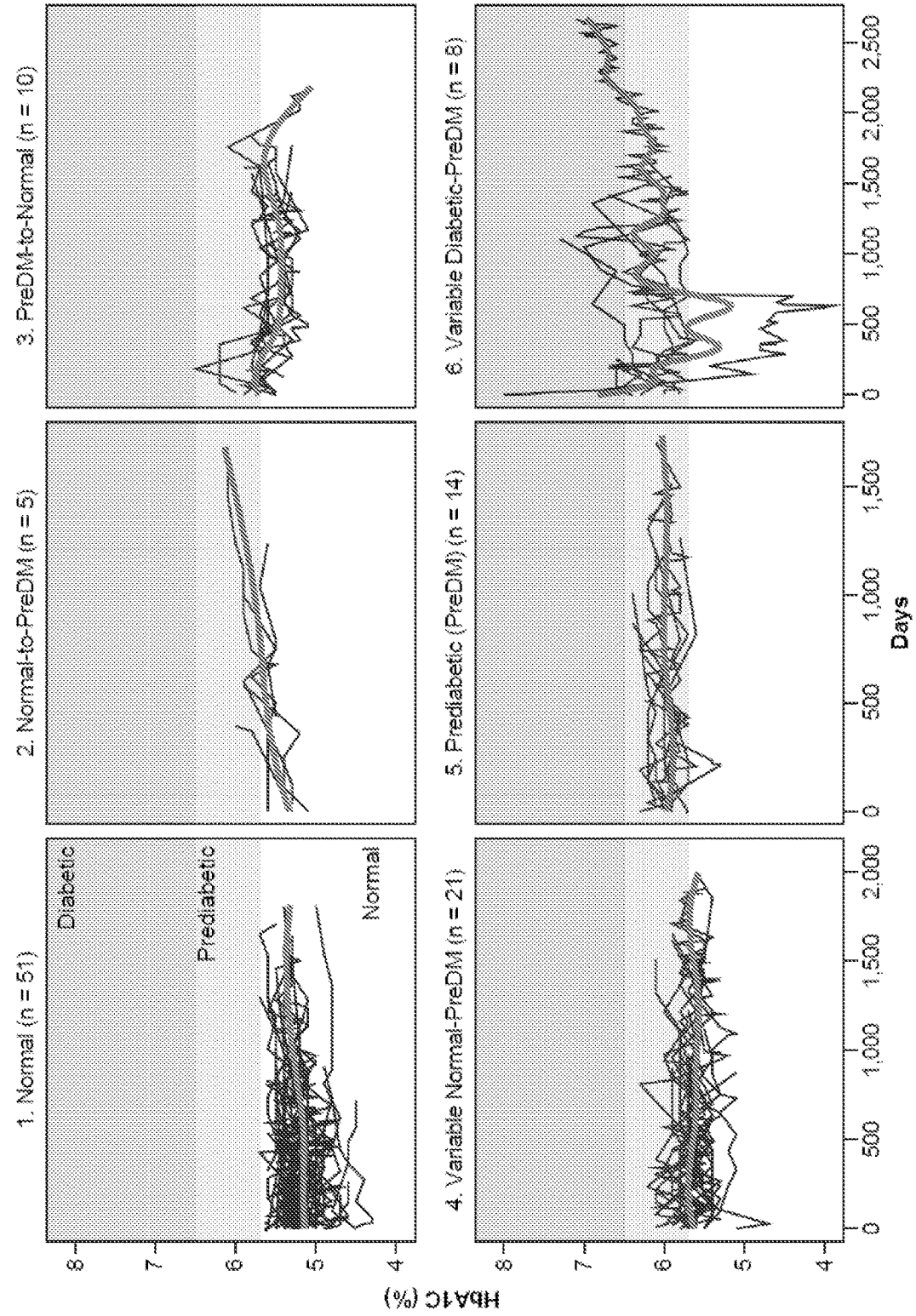
FIG. 15 details HbA1C trajectories of various individuals within the iPOP population used in a cohort study, utilized in accordance with various embodiments of the invention.

One strength of this study lies in the dense longitudinal sampling approximately every 3 months. Based on individual longitudinal HbA1C trajectories, participants were classified in 6 categories as illustrated in FIG. 15. Notably it was common for participants' HbA1C to alternate between normal-preDM (n=22) and preDM-DM range (n=8). No one stayed exclusively within the DM range due to good diabetes control with lifestyle and medications. Consistent transitions from normal to preDM (n=5) and from preDM to normal HbA1C (n=9) were less common.

Figure 17:
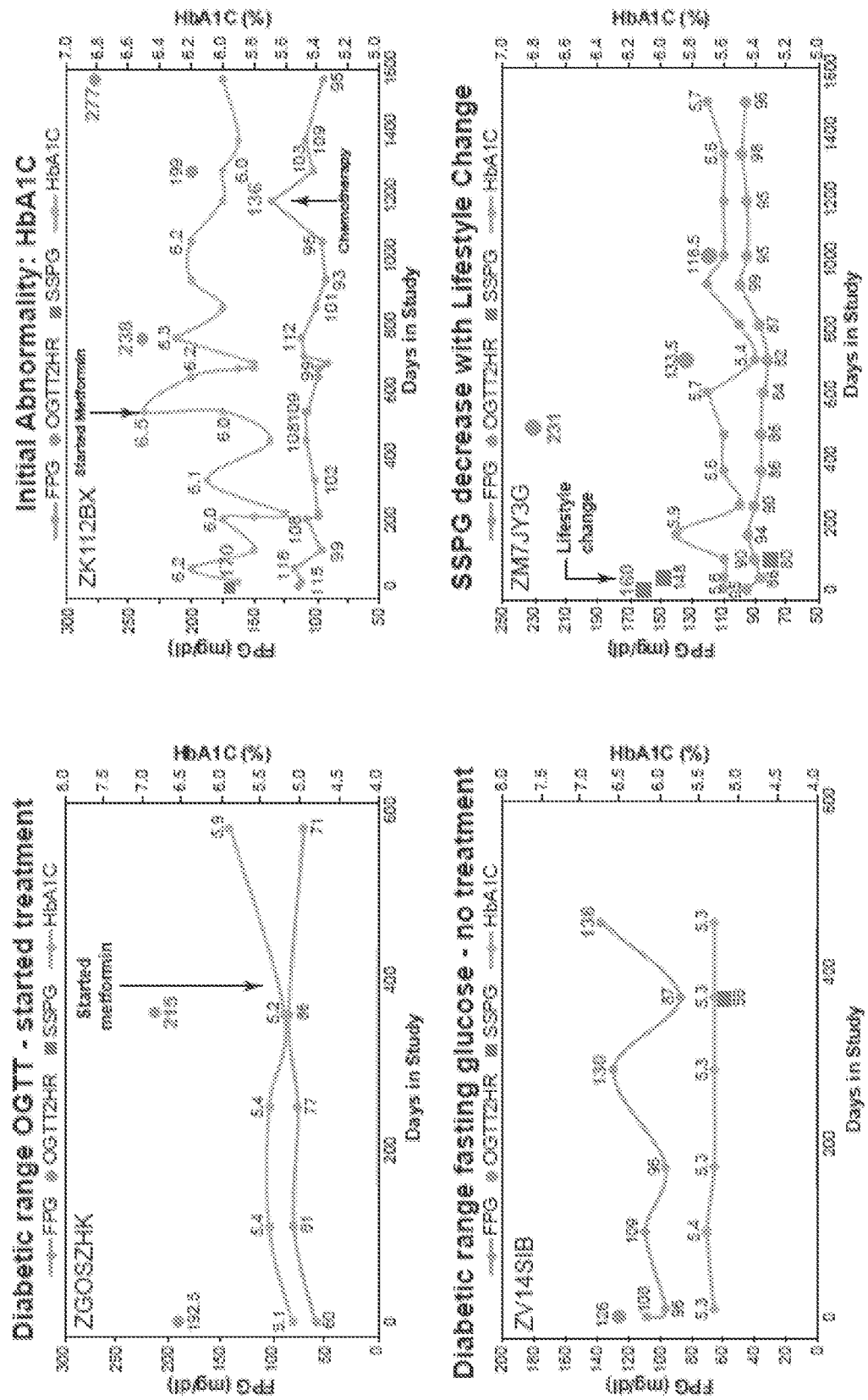

Close evaluation of individual trajectories of participants with new diabetes (n=9) revealed additional insights. All measurements in relation to glucose metabolism were leveraged to understand possible underlying mechanisms of transitions to diabetes (Table 5). Individual trajectory analysis revealed that participants followed multiple pathways to diabetes (FIGS. 16 to 18). Some participants' (n=2) first abnormality was DM-range OGTT, others (n=3) had elevated FPG, the remainder (n=4) had a DM-range HbA1C or abnormalities in multiple measures. Interestingly, diabetic range labs followed viral infections in one participant (see FIG. 16). Also, one participant with a single DM lab improved their SSPG with diet and exercise (see FIG. 17) and never had a second DM range lab during the study.

Figure 20:
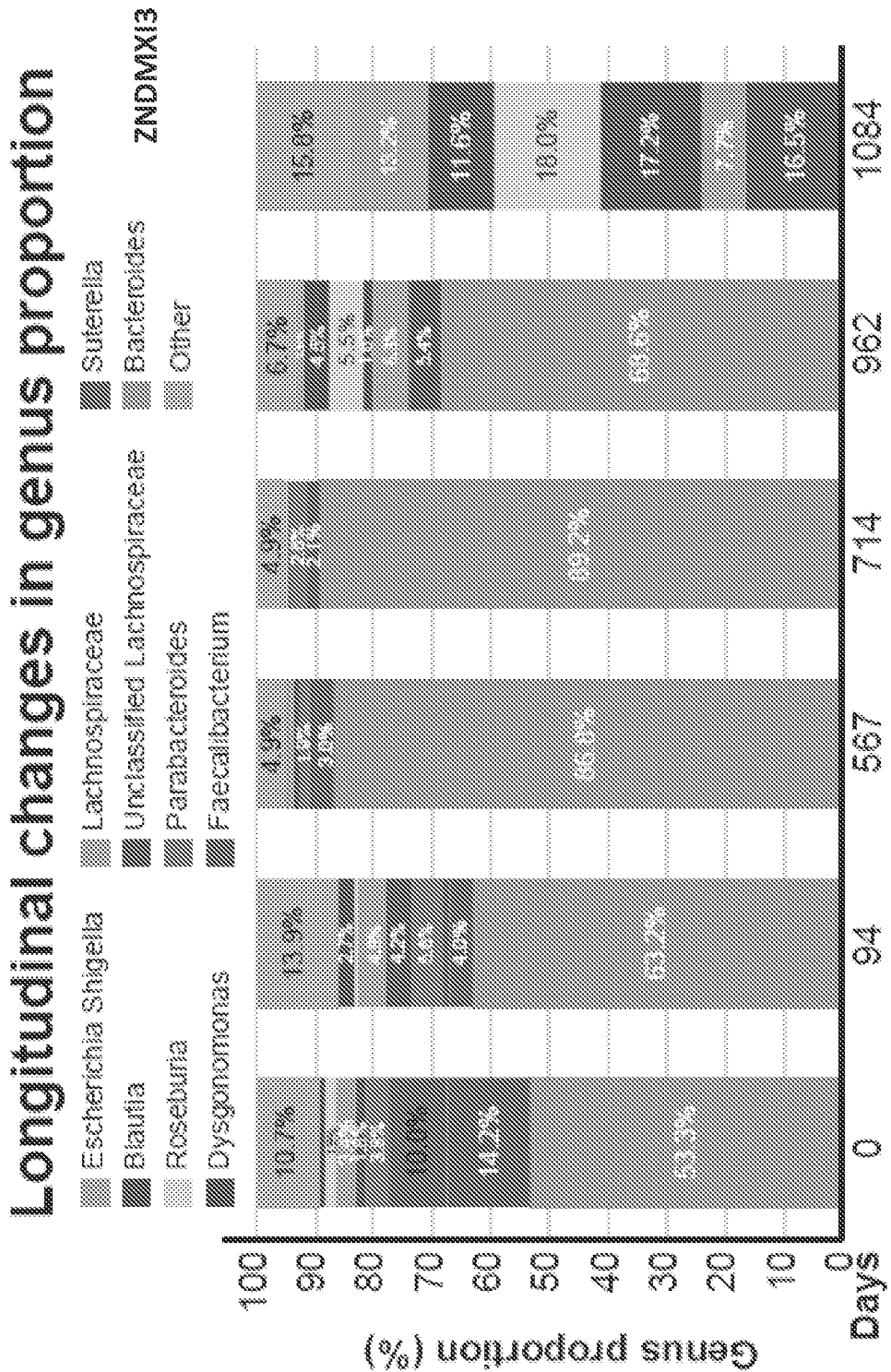
FIG. 20 details longitudinal gut microbial composition changes in an individual within the iPOP population used in a cohort study, utilized in accordance with various embodiments of the invention.

Notably, the progression to DM was associated with weight gain and decreased gut microbiome diversity (Shannon) in 2 of 8 participants (FIG. 16 (top two panels), FIG. 19). To model the change in Shannon diversity over time for individual participants, a general additive model (SAS proc gam) was used, which separates the linear ($\beta$=−0.197, p=0.002) and non-linear (df=3, p=0.0112) components of the trajectory. The F test of the model (p=0.0041) using time as a predictor of Shannon diversity was compared to the null model and was calculated according to SAS usage note 32927: http://support.sas.com/kb/32/927.html (accessed March 2018). In both cases, there was a marked increase in the proportion of the phylum Bacteroidetes at the time point of lowest diversity to the detriment of beneficial bacteria such as the genus *faecalibacterium* (FIG. 20).

Based on the observation of a loss of microbiome diversity in progression to DM, the relationship between microbiome Shannon diversity and SSPG, FPG and HbA1C was further evaluated using linear mixed models to account for repeated measures (Table 6). Shannon diversity was calculated with SAS 9.4 using a code adapted from a previous report (see P. A. Montagna, "Using SAS to Manage Biological Species Data and Calculate Diversity Indices" *SCSUG* (2014), the disclosure of which is herein incorporated by reference). SAS 9.4 Proc Mixed using restricted maximum likelihood estimation the between-within degrees of freedom method was used to model the association of HbA1c, FPG and SSPG and Shannon diversity H' index. Preliminary analyses were done in proc gam which seemed to indicate an 'inverse u' distribution for all 3 measures in relationship to the Shannon diversity index. HbA1C and FPG were modeled using a repeated measures model with spatial power covariance structure. Shannon was entered into the model as a quadratic predictor. SSPG was modeled slightly differently because SSPG was only measured once in participants, while Shannon was calculated for all time points. Shannon was included in the random statement. The strongest relationship was observed for SSPG which had a significant linear inverse relationship with Shannon diversity (p<0.001). SSPG accounted for 28% of the between-person Shannon variance highlighting the importance of insulin resistance in microbiome diversity.

The majority of Shannon diversity variance was intra-individual (76.8%), so longitudinal mixed models were performed to understand what factors contributed within-person Shannon variations (Table 7). To perform the multivariate model (SAS 9.4 Proc Mixed), the full maximum likelihood method of estimation was used to enable comparison between models. The degree of freedom method was the between-within method. An unstructured covariance matrix was used. In addition to the models presented in Table 7, the effect of adding of baseline BMI, consent age, or metformin use to the model was also evaluated. None of these covariates added significantly to the model and thus were left out. In addition, it was evaluated whether use of the Firmicutes/Bacteroidetes ratio in place of the phylum Bacteroidetes would improve the model. However the ratio accounted for substantially less within person variation in Shannon diversity (10.4%) thus the proportion of the phylum Bacteroidetes in the final model was kept. Adding the proportion of the phylum Bacteroidetes to the longitudinal model including its interaction with time accounted for 41% of the remaining within person variance of Shannon diversity, consistent with the relationship observed in the individual profiles between Bacteroidetes proportion and diversity.

Longitudinal evaluation of all data related to glucose and insulin regulation also provided insights into mechanism. For instance, the person in lower panel of FIG. 16 (ZOZOW1T) had a normal SSPG despite a diabetic range OGTT, FPG and HbA1c. Although elevated OGTT is commonly thought to result from increased peripheral resistance or decreased insulin production, this participant had elevated insulin production with a delayed response trajectory, possibly reflecting delayed insulin release.

Based on these results, it was found that participants became diabetic by a variety of different means and the detailed characterization provides potential hypotheses regarding individual underlying mechanisms of glucose dysregulation.

A goal of this study was to better understand the underlying relationships between glucose (FPG, HbA1C) and inflammation (hsCRP) levels and multi-omics measurements at healthy time points (healthy-baseline models) and with relative changes from baseline for all time points (dynamic models) using linear mixed models. The two analyses are complementary since healthy-baseline models highlight the stable relationships between measures and dynamic models highlight common associations with change.

To perform linear mixed model analysis, SAS 9.4 Proc Mixed was used using the full maximum likelihood method of estimation and the between-within method for estimating degrees of freedom. A random intercept model with an unstructured covariance matrix was used for all analytes. The outcome measures (FPG, HbA1C and hsCRP) were log-transformed in all models and the analytes were standardized to a mean of zero and standard deviation of one. All models were controlled for gender and age at consent. The healthy-baseline models used data from healthy quarterly visits. The dynamic analysis used the ratio to the first healthy time point for measures and analytes and used all time points in the study. P-values were corrected for multiple hypothesis testing using the Benjamini-Hochberg procedure. Significant analytes have BH FDR<0.2.

Figure 21:
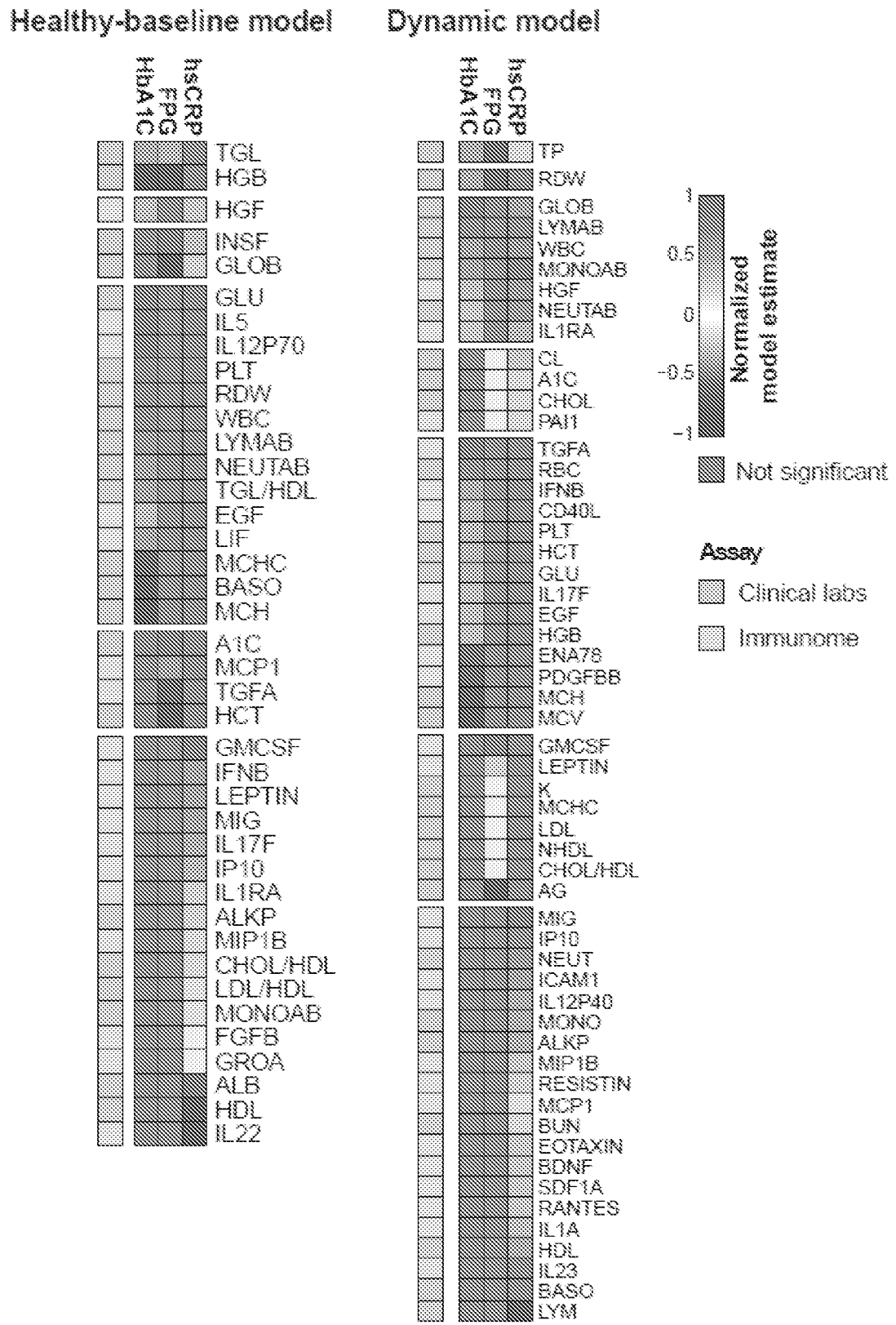
FIGS. 21 and 22 provide analytes associated with various glycemia test results (HbA1C and FPG) and a marker of inflammation (hsCRP) using a healthy baseline and a dynamic model, utilized in accordance with various embodiments of the invention.
Figure 22:
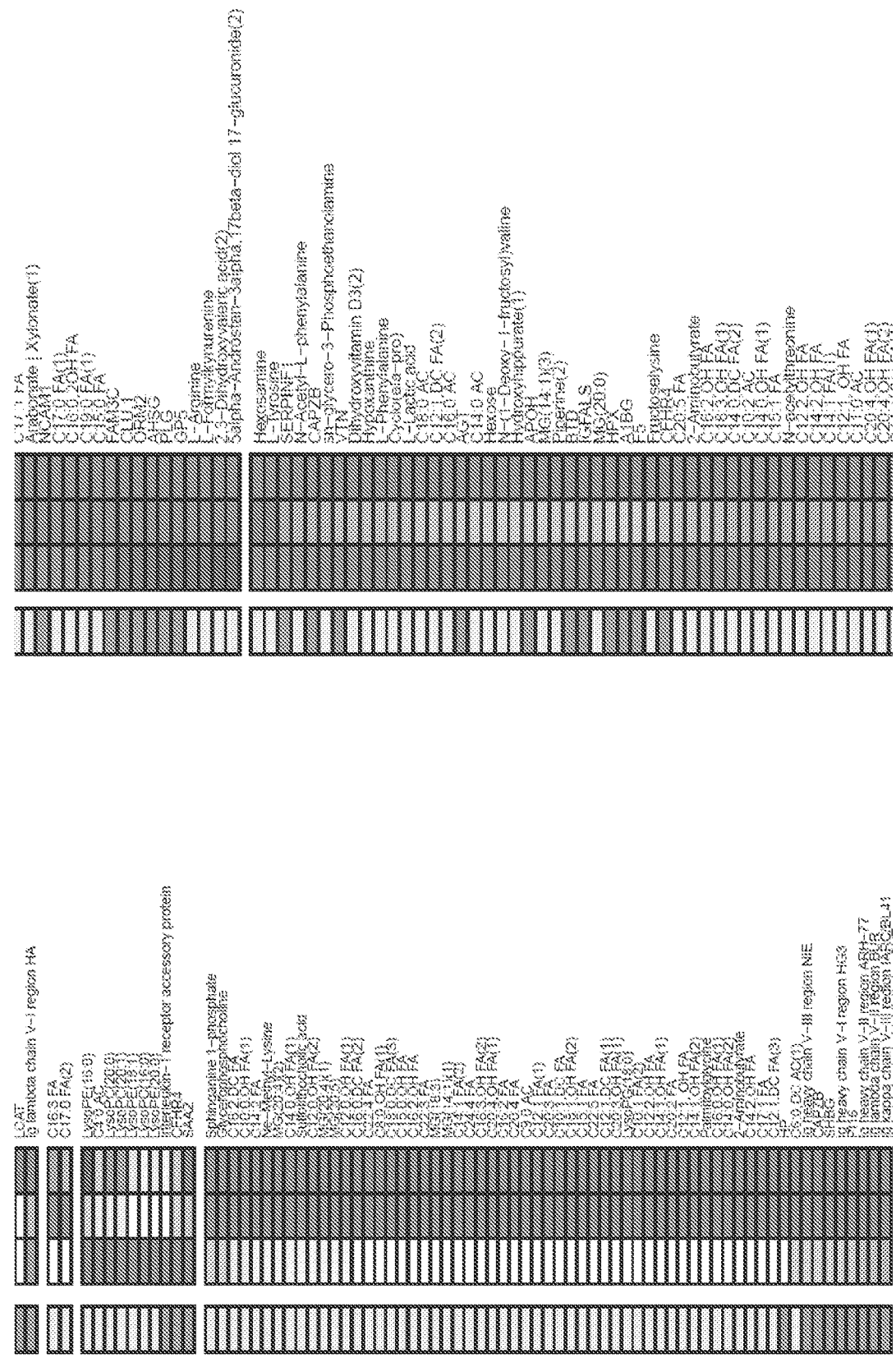
Figure 22:
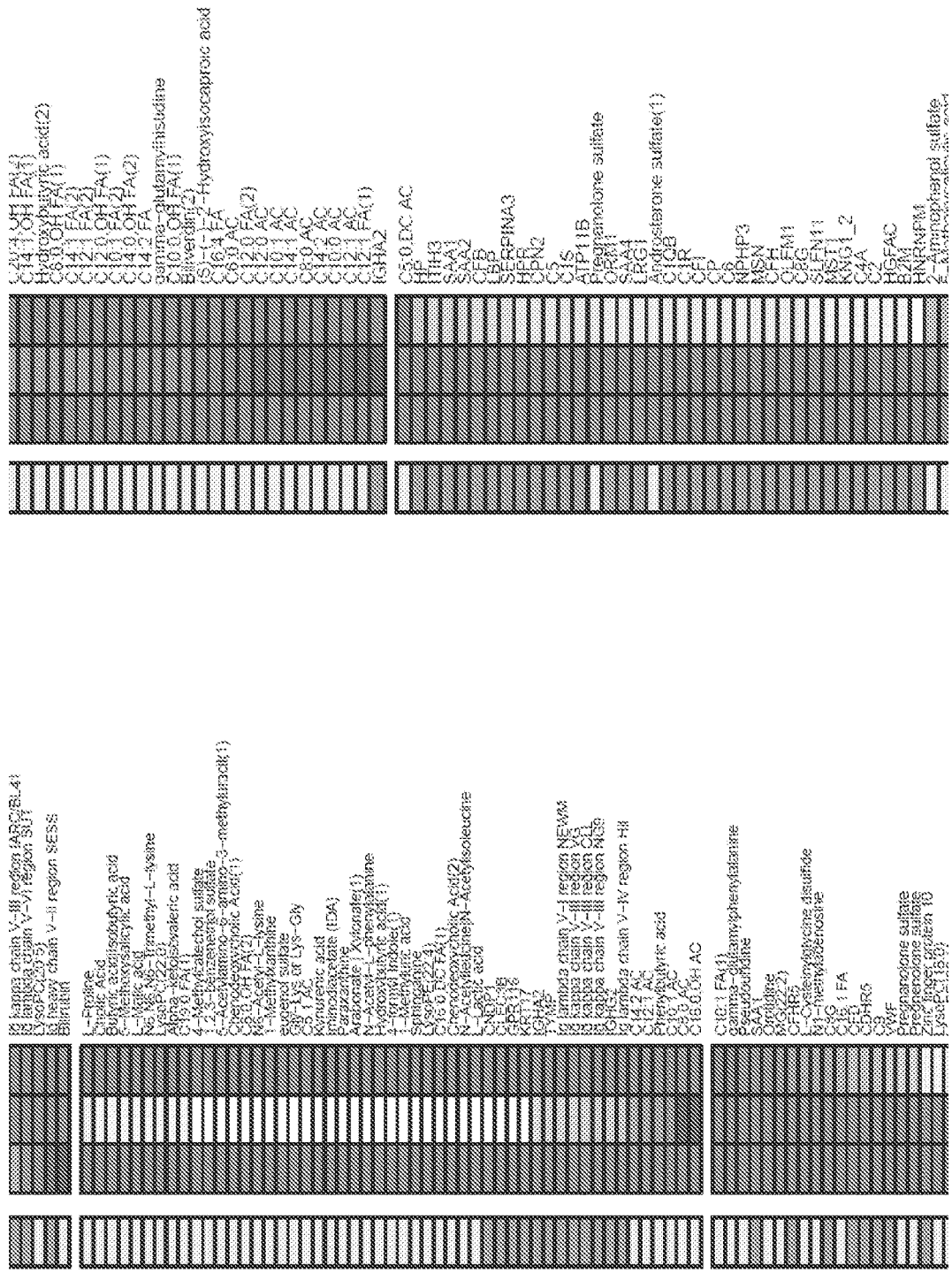
Figure 22:
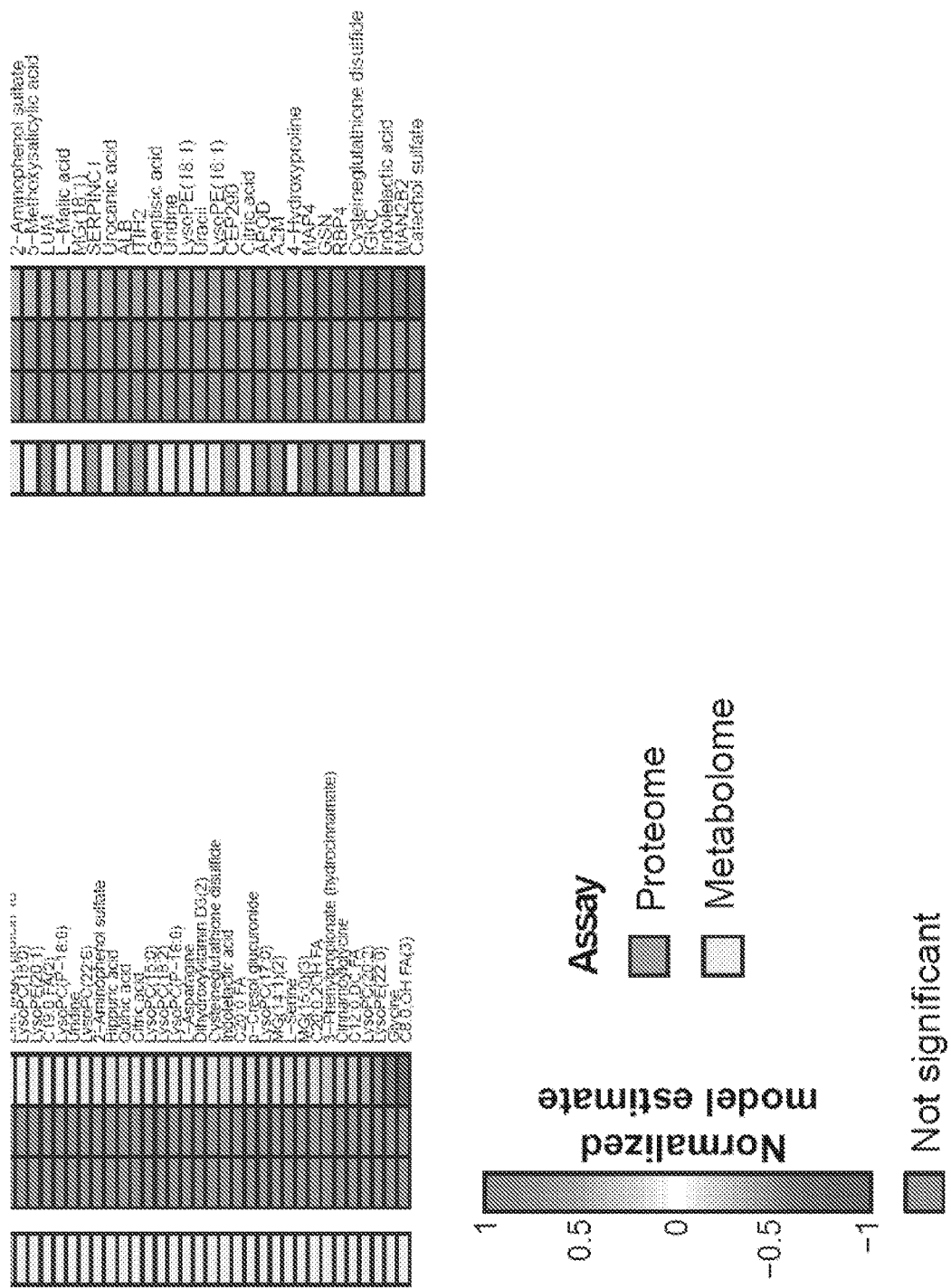
Figure 23:
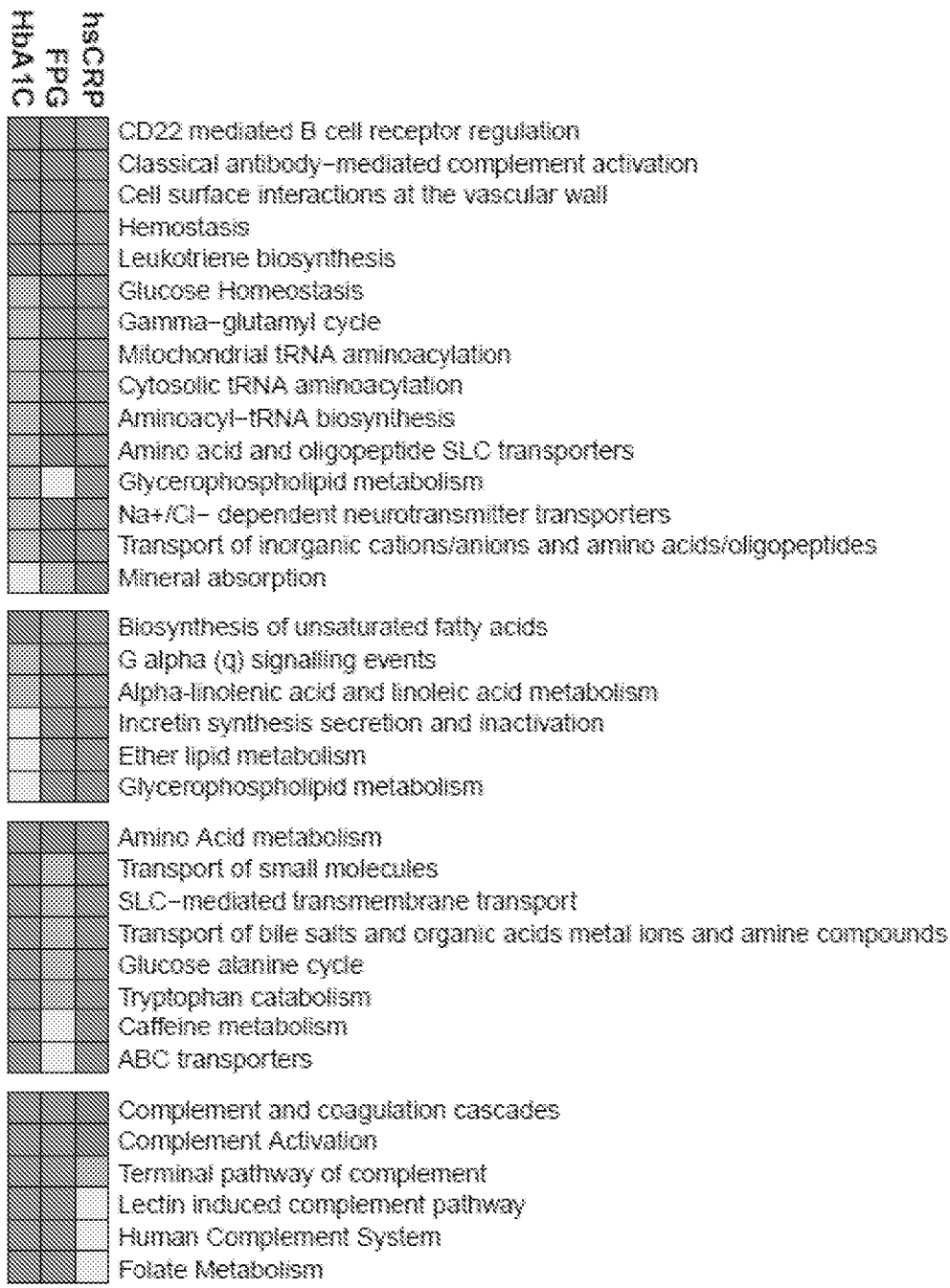
FIGS. 23 and 24 provide pathways enriched from analytes associated with various glycemia test results (HbA1C and FPG) and a marker of inflammation (hsCRP) using a healthy baseline and a dynamic model, utilized in accordance with various embodiments of the invention.
Figure 24:
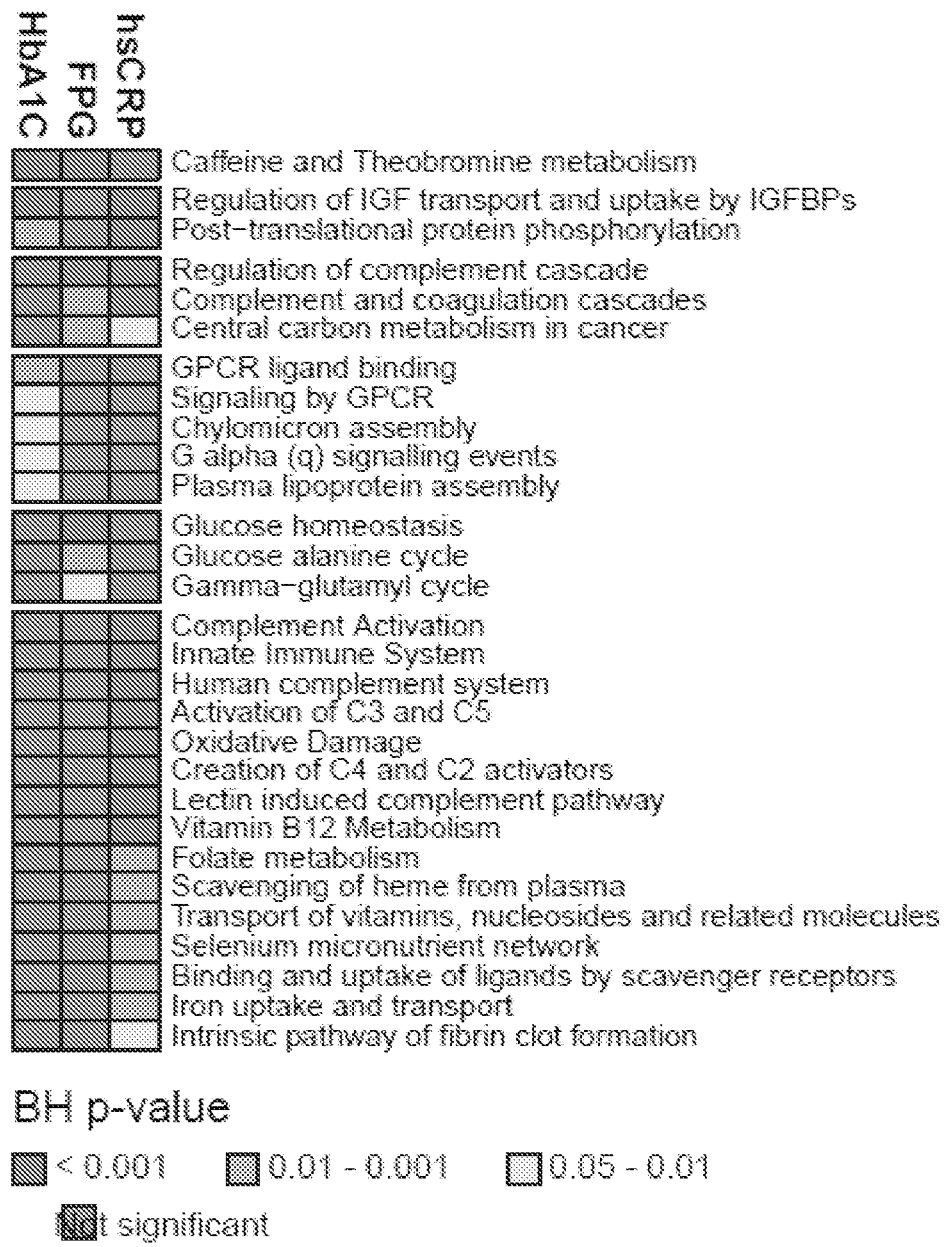

From the models, it was determined that HbA1C, FPG and hsCRP each were significantly associated with a number of analytes (FIGS. 21-22 and Tables 12-14) and pathways (FIGS. 23-24). In addition, FPG was strongly associated with various glucose-related pathways including 'glucose homeostasis' pathway (FIG. 23). Many analytes were associated with both glucose labs and inflammation highlighting the effect of chronic inflammation on blood glucose levels. Both models revealed that HbA1C and hsCRP were positively associated with total white blood cells and subtypes (e.g. monocytes and neutrophils) as well as platelets counts (FIG. 21 and Tables 12 & 14). The association of glucose regulation and inflammation with platelet biology was validated by the significant enrichment of 'response to elevated platelet cytosolic Ca2+' and 'platelet activation signaling and aggregation' pathways using proteins and metabolites associated with HbA1C and hsCRP (FIG. 24). The majority of participants with elevated HbA1C were insulin resistant (61%), which is commonly accompanied by chronic inflammation, which is highlighted by the fact that hsCRP and HbA1C were associated with 'leukotriene biosynthesis,' a pathway that contributes to inflammation and leads to insulin resistance (FIG. 23). In addition, clinical lab lipid measures were found to positively associate with glucose measures and inflammation (e.g., cholesterol/HDL ratio, LDL/HDL ratio and total triglycerides (TGL)) and on the pathway level FPG was associated with 'cholesterol metabolism' demonstrating the intricate relationship between lipid metabolism and glucose regulation and inflammation (FIG. 23). The dynamic model analysis also highlighted that complement and coagulation cascades were deregulated in conjunction with changes in FPG and hsCRP and that hsCRP was associated with inflammatory pathways including 'complement activation', 'innate immune system', and 'oxidative damage' (FIG. 24).

SSPG and OGTT Quantification from Analyte Measurements

The modified insulin suppression test is a clinically important direct measure of peripheral insulin resistance but is expensive, labor-intensive, and requires six-hours. OGTT is a sensitive test for diabetes and is less expensive, however, it is not widely used clinically because of the inconvenience of a two-hour test. Thus, it was evaluated how well multi-omics measurements could quantify the results of these tests.

Highly predictive features were identified using a Bayesian network algorithm. These features were then used in ridge regression modeling to build a prediction model. Features were identified from multi-omics data (clinical data, metabolomics, proteomics, cytokine profile, microbiome, transcriptome, lipidome). To build the model, features were standardized to zero mean with unit variance. Data (including SSPG) were log transformed prior to standardization. The standardized data was used in MXM v0.9.7 R package with the Max-Min Parents and Child algorithm (MMPC) option to identify features that are parents or children of SSPG/OGTT in a Bayesian network constructed from all the available data (see V. Lagani, et al., *Journal of Statistical Software, Articles* 80, 1-25 (2017); L. E. Brown, I. Tsamardinos, and C. F. Aliferis, *Stud. Health Technol. Inform.* 107, 711-715 (2004); I. Tsamardinos, L. E. Brown, and C. F. Aliferis, *Mach. Learn.* 65, 31-78 (2006); the disclosures of which are each herein incorporated by reference). The features selected by the algorithm are likely to be direct causes or effects of SSPG/OGTT in the data, as each feature selected are SSPG/OGTT dependent when conditioned on every possible subset of the other features. These features provide novel information about SSPG/OGTT measurements. There were 45 participants with SSPG values and all multi-omics data. Feature selection was performed using leave-one-out cross validation, where 45 training sets were constructed and each training set excludes the data from a different individual. The MMPC algorithm was run on each training set. Features that were identified by the MMPC algorithm in ≥20% of training sets were selected to be used as features in the ridge regression prediction model. For the OGTT predictive model, there was no lipidomics data available so only clinical, metabolomics, proteomics, cytokine profile, microbiome, and transcriptome data were used in the all omics model.

Ridge Regression was performed using R version 3.4.1. For each -ome, the sample at the closest time point that is equal or prior to the time point of the patient's SSPG/OGTT measurement was used. Leave-one-out cross validation was performed to maximize available training data. For each training set, the hyperparameter was optimized by performing a grid search and selecting the model that minimizes test error. The predicted SSPG/OGTT value is the value from the cross validation iteration in which that SSPG/OGTT data point and its associated features are excluded from the training set. These predicted values were used to calculate mean square error and $R^2$ values. The value of the hyperparameter used was the average of the hyperparameters which minimized test error during cross validation.

Figure 25:
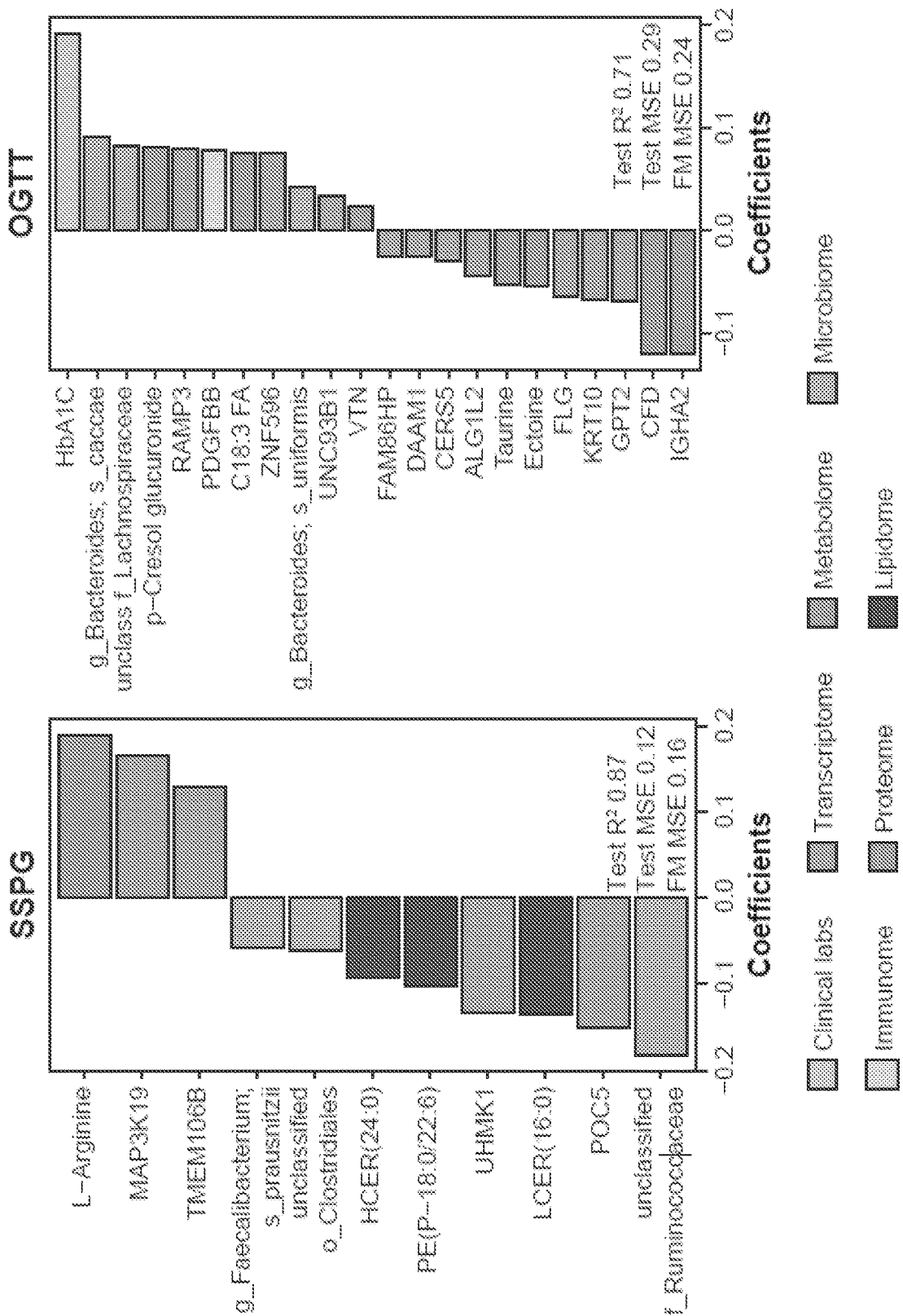
FIG. 25 illustrates the analytes selected from all omics measures using the MMPC feature selection algorithm and the magnitude of the analyte ridge regression coefficients for the SSPG and an OGTT prediction models, utilized in accordance with various embodiments of the invention.

The SSPG prediction model using all omes achieved a cross-validated $R^2$ of (final model mean square error (MSE) 0.16) compared to an $R^2$ of 0.56 (MSE 0.52) using clinical data only (FIG. 25, Table 8). Predictive models using clinical data plus each single ome were also compared and it was found that the transcriptome ($R^2$ 0.84, MSE 0.22) and microbiome model ($R^2$ 0.78; MSE 0.24) had the best predictive accuracy for SSPG. Similarly, the multi-omic prediction model for OGTT ($R^2$ 0.71 (MSE 0.24)) was also superior to the clinical data only model ($R^2$ of 0.42 (MSE 0.71)) (FIG. 25, Table 9). Transcriptome in addition to clinical data had the best predictive accuracy of the single ome models ($R^2$ 0.62, MSE 0.30). Molecules that were found to be consistent across multiple SSPG models included the TGL/HDL ratio the protein IL-1RAP; the lipid HCER (24:0), the MAP3K19 transcript and a microbe from the Ruminococcaceae family. There was little overlap between SSPG and OGTT predictors supporting that these measures reflect different underlying biology. The increased predictive performance with multi-omics measurements compared to clinical labs alone or with single omes illustrates the benefit of multi-omics data.

Cardiovascular Health Profiling and Clinical Discoveries

Atherosclerotic cardiovascular disease (ASCVD) is a major cause of mortality and morbidity associated with insulin resistance and DM. The American Heart Association (AHA) ASCVD risk score was assessed, estimating 10-year risk of heart disease or stroke on all participants at study entry. Longitudinal trajectories of dyslipidemia and systemic hypertension were also followed. Enhanced cardiovascular profiling was performed on 43 participants and included i) vascular ultrasound and echocardiography to assess for subclinical atherosclerosis, arterial stiffness or early stage adverse ventricular remodeling or dysfunction, as well as ii) emerging biomarkers assessment which interrogates oxidative stress, inflammation, immune regulation, myocardial injury and myocardial stress pathways.

Figure 26:
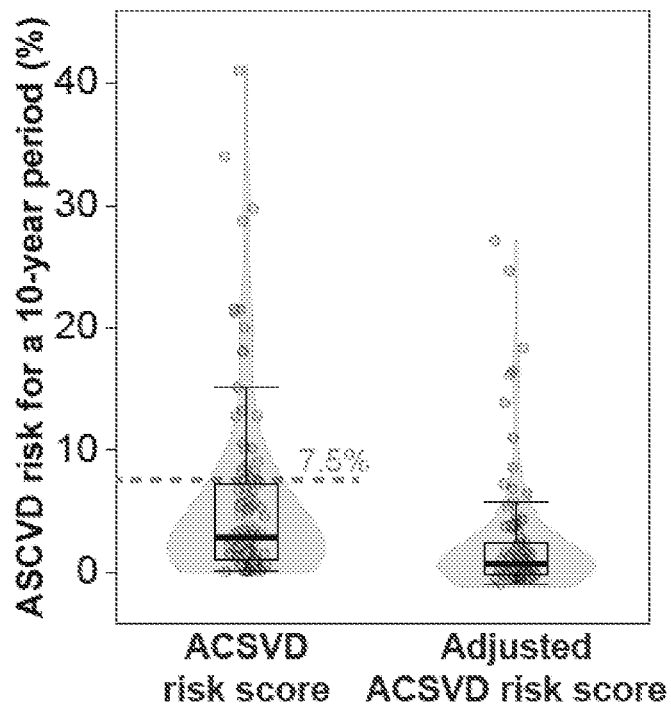
FIG. 26 provides a graphical representation of the distribution of ASCVD risk scores, utilized in in accordance with various embodiments of the invention.
Figure 27:
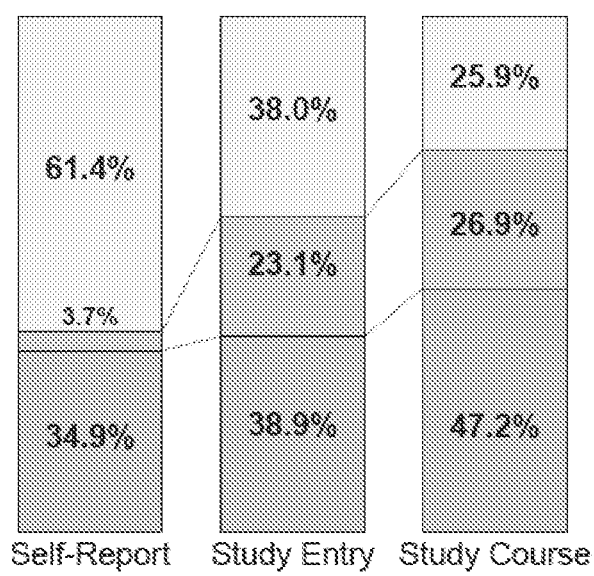
FIG. 27 provides a graphical representation of cholesterol profiles as self-reported, when entered into study, and over study progression, utilized in accordance with various embodiments of the invention.

At study entry, 24 patients (22.6%) had an ASCVD risk score≥7.5%, a threshold often used to guide primary prevention (FIG. 26). Total cholesterol and blood pressure measurements indicate that self-report underestimated the prevalence of dyslipidemia (FIG. 27) and 18 participants learned they had Stage II hypertension during the study.

Figure 28:
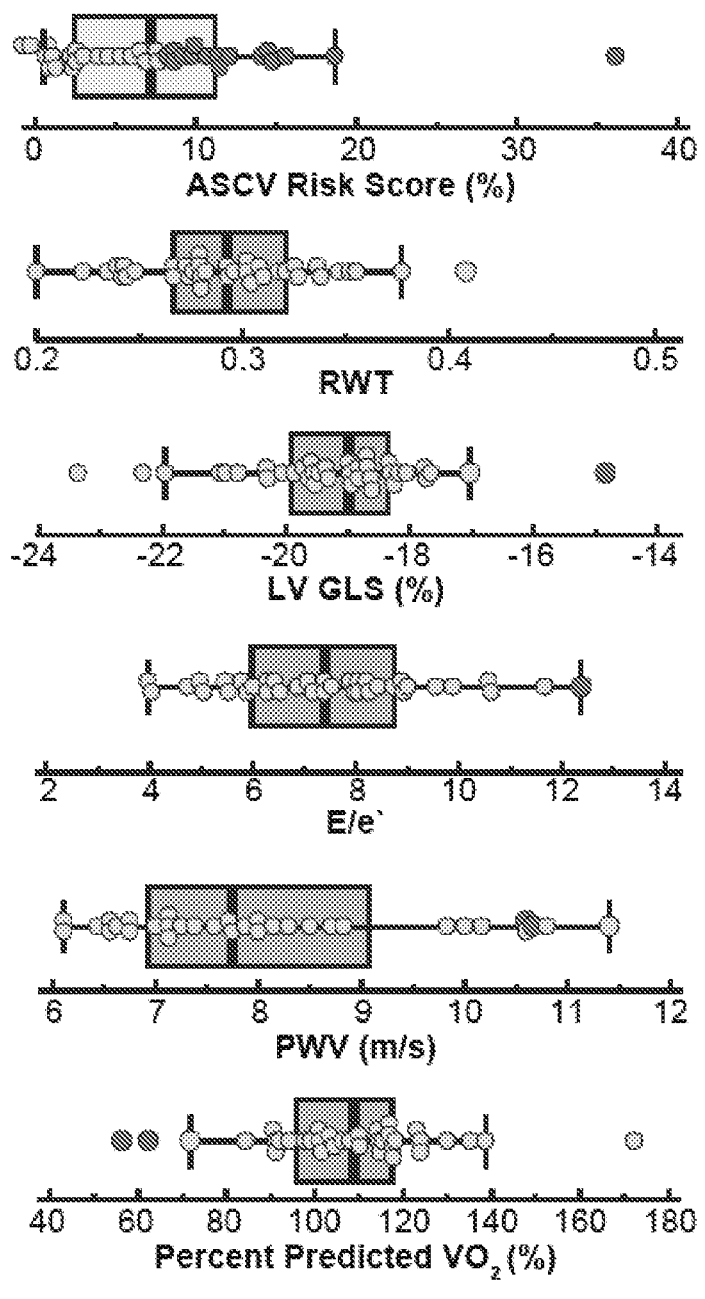
FIG. 28 provides a graphical representation of the distribution of ASCVD risk scores, utilized in accordance with various embodiments of the invention.

Wearable and cardiovascular imaging led to important clinical discoveries. Wearable heart rate monitoring identified two participants with nocturnal supraventricular tachycardia, leading to the diagnosis of obstructive sleep apnea in one and atrial fibrillation secondary to sleep apnea in the other. In the subgroup of participants who had enhanced cardiovascular imaging studies, two major health findings were discovered: one cardiac finding associated with a pathogenic mutation in the RPM20 gene, and one non-cardiac finding (Table 3). Fitness assessment using percent predicted oxygen consumption (maximal oxygen consumption relative to a healthy person of the same age and weight) identified three participants with values below 70% suggestive of a reduction in exercise capacity which has been associated with poorer health outcomes (FIG. 28). Six participants were also found to have subclinical atherosclerosis, leading to a recommendation to increase statin dose (FIG. 29). In all, there were 15 important clinical findings through these enhanced tests (Table 3).

Five participants had cardiovascular events during the course of the study including stroke (n=3), unstable angina (n=1) and stress-induced cardiomyopathy (n=1). All had elevated hsCRP levels prior to their event. Two participants with incident strokes had pharmacogenomic variants that could partially explain suboptimal response to the chosen therapy. One participant on aspirin for stroke prevention had a COMT (catechol-o-methyltransferase) Val/Val genotype (rs4680) which has a 85% increased risk of cardiovascular events in female aspirin users compared to placebo controls (See K. T. Hall, et al., *Arterioscler. Thromb. Vasc. Biol.* 34, 2160-2167 (2014), the disclosure of which is herein incorporated by reference). The other participant with incident stroke was an intermediate clopidogrel metabolizer phenotype (CYP2C19*2 (rs4244285)/CYP2C19*17 (rs12248650) and had a second stroke while on clopidogrel therapy. Intermediate metabolizers of clopidogrel were common in our study (31/88 (35%) are intermediate and 4/88 (4.5%) are poor metabolizers). Additional pharmacogenomic variants related to the common cardiovascular medications statins and coumadin were found in 26 and 30 participants, respectively (Table 16).

Figure 30:
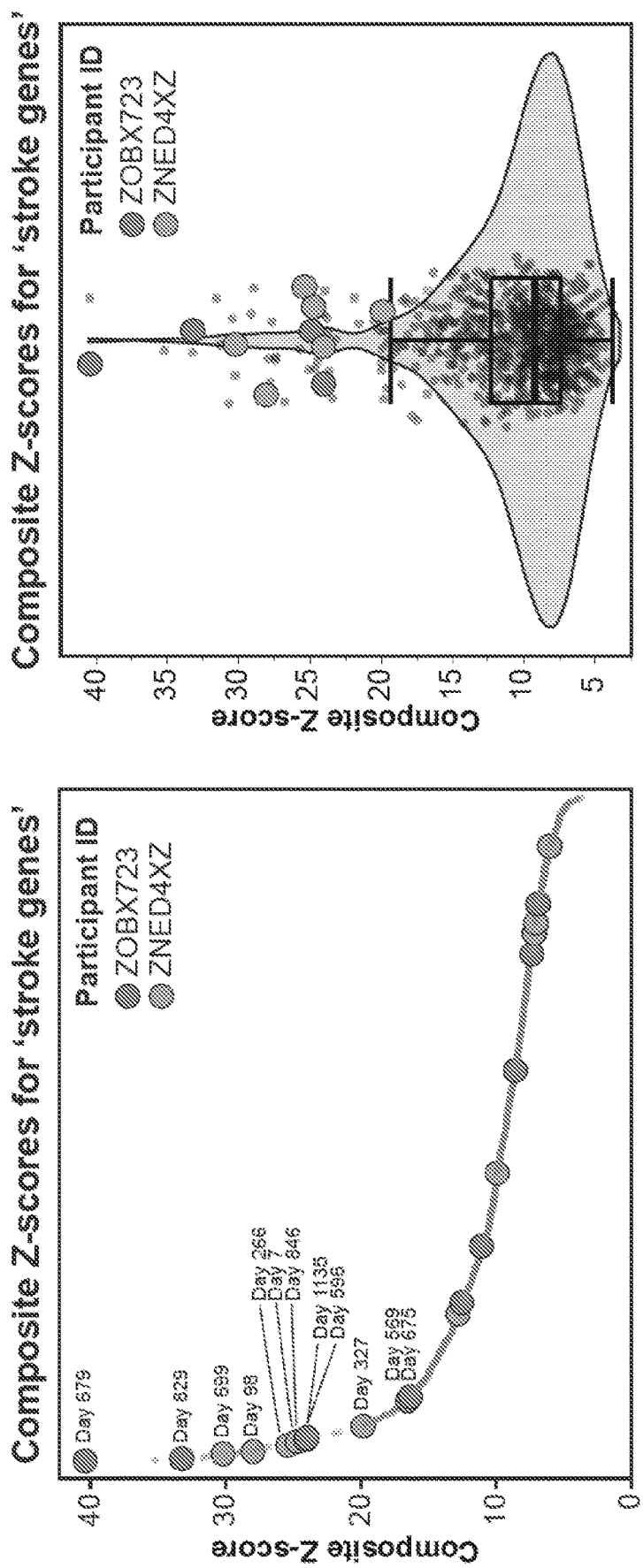
FIG. 30 provides graphical representation of composite Z-scores of two individuals, utilized in accordance with various embodiments of the invention.

Fourteen of thirty two genes associated with stroke and stroke types were also analyzed, which were robustly detected in our RNA-seq dataset (see R. Malik, et al., *Nat. Genet.* 50, 524-537 (2018), the disclosure of which is herein incorporated by reference). Outlier analysis revealed that two of the five participants with cardiovascular events had the highest composite Z-scores at clinically relevant time points (post-stent placement (Z-score=33.2, FDR=6.9E-06), mid-infection (Z-score=40.4, FDR=3.2E-09) for one participant and transition to diabetes (Z-score=30.1 and 24.1) for the other (FIG. 30). Thus, expression levels of genes related to stroke were outliers and associated with significant health issues.

Multi-Omics Analysis of ASCVD Risk

Figure 31:
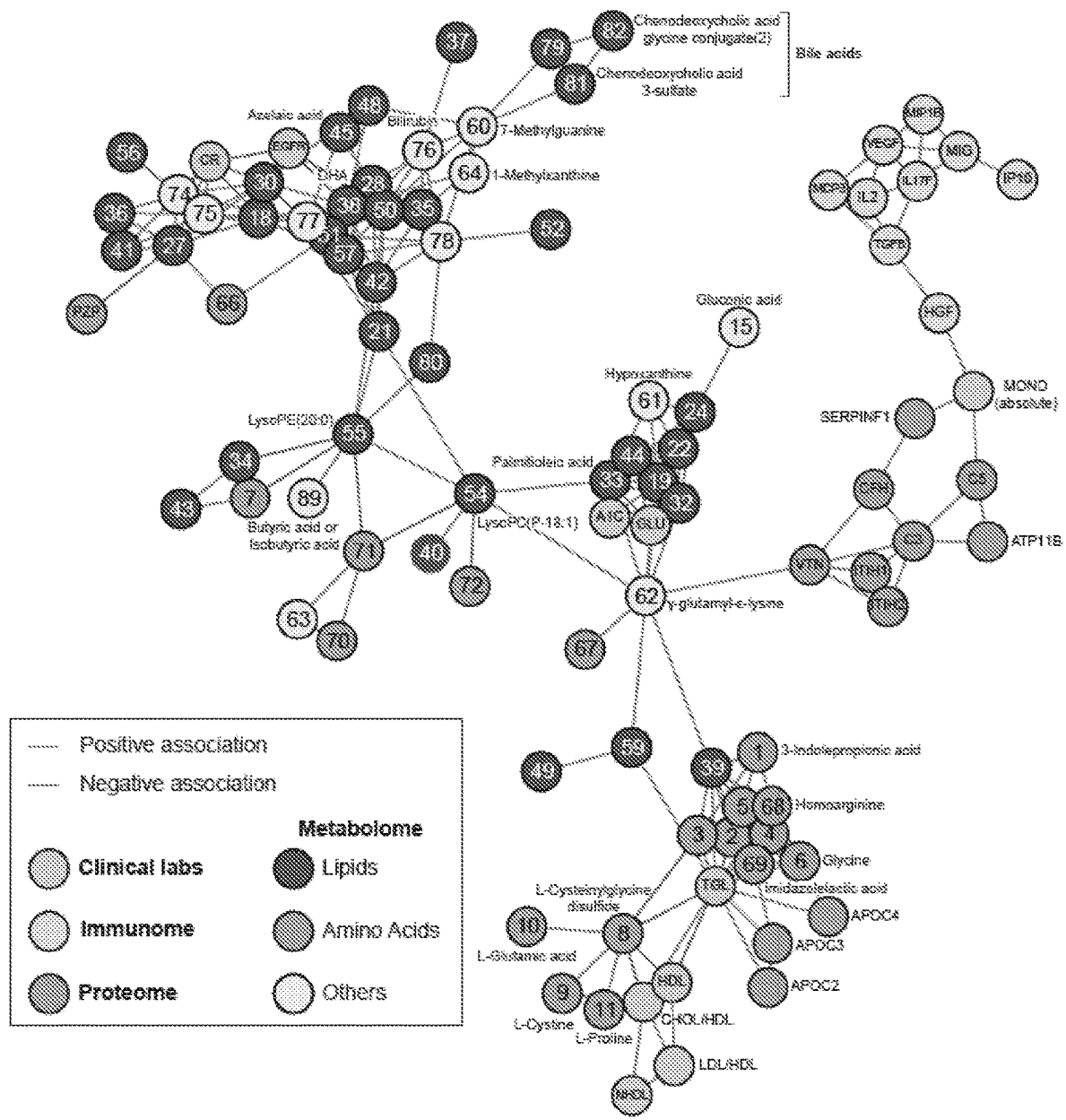
FIG. 31 provides a multi-omics correlation network of molecules associated with adjusted ASCVD risk score, utilized in accordance with various embodiments of the invention.

Multi-omics measures associated with adjusted ASCVD risk score were evaluated using Spearman correlation (Table 17), and a correlation network using all omics and clinical laboratory measures was constructed. This analysis revealed relationships between clinical and omics measures such as monocytes bridging cytokines and complement proteins and triglyceride and cholesterol measures linking to apolipoproteins among others (FIG. 31, Table 18). Among immune proteins, the interferon-gamma pathway [MIG (CXCL9), IP10 (CXCL10)], interleukin-2 (IL-2), vascular endothelial growth factor alpha (VEGF) and hepatic growth factor (HGF) were strongly associated with the ASCVD risk score. The interferon-gamma pathway has been recently found to play a key role in atherosclerosis based on population based studies. IL-2 has been shown to be associated with atherosclerosis through its role in T-cell mediated inflammation. HGF is involved in the survival of endothelial cells and is emerging as an independent risk factor of outcome in several large epidemiological studies. The constructed network also highlighted several molecules that are emerging in cardiovascular disease including complement and free fatty acids as well as y-glutamyl-c-lysine (reported in diabetic nephropathy), hypoxanthine, methylxanthine (associated with coffee consumption) and bile acids.

Figure 32:
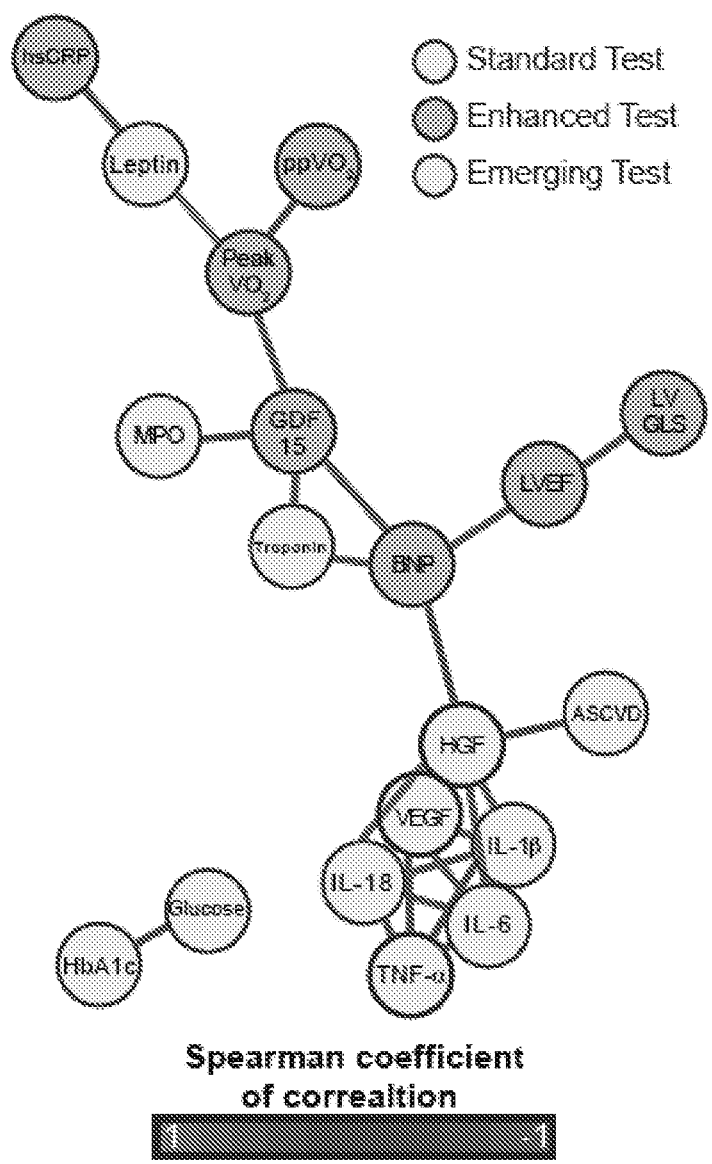
FIG. 32 provides a correlation network of selected metrics collected during cardiovascular assessment, utilized in accordance with various embodiments of the invention.

In participants who underwent cardiovascular imaging, a correlation network analysis was performed to show how ASCVD risk, enhanced imaging and selected circulating protein markers associate together (FIG. 32, Table 2). ASCVD score was closely related to hepatocyte growth factor (HGF), which itself was closely related to selected inflammatory cytokines (IL-1B, IL-18) which are part of the inflammasome complex. Exercise capacity as assessed with peak $VO_2$ was in close proximity to GDF-15, a transforming growth factor which been shown to be associated with cardiovascular mortality risk and leptin, a hormone established in the regulation of appetite. These findings add to the understanding of the interaction between inflammation and ASCVD risk and suggest new opportunities for personalized risk stratification, beyond standard tools available in clinical practice.

Effect of iPOP Participation on Patients

The deep phenotyping profiling had an effect on the majority of the participants by (a) encouraging appropriate risk-based screening including genetic counseling, (b) facilitating clinically meaningful diagnosis, (c) potentially informing therapeutic choices (mechanistic or pharmacogenomic information), and (d) increasing awareness leading to diet and physical activity modifications. Overall, over 67 major clinically actionable health discoveries were found spanning various area including metabolic, cardiovascular, heme/oncological and infectious using standard clinical, enhanced, and emerging technologies (FIG. 33, Table 3).

Fifty-eight participants were surveyed mid to late study about the effect of participating in the study including changes on food and exercise habits, health findings, and their sharing of results with their personal doctors, family and others. Seventy percent reported some change in both diet and exercise habits, 9% diet only, 4% exercise habits only, and only 18% reported no health habit changes (FIG. 34). In addition, almost half reported changing other health behaviors as a result of the study, including improving sleep, reducing stress, adding fiber and supplements to their diet, more careful self-examinations, recording food intake, attending a fitness camp and general lifestyle changes (Table 10). FIG. 34 also shows the amount of change in diet and exercise. Participants also reported that their wearable device kept them accountable for exercising and more mindful to take walking breaks and to break-up long periods of sitting. Others reported using wearables to monitor sleep.

The majority of participants had discussed study results with their family (71%) and physicians (68%). For those who discussed results with physicians, the discussion led to follow-up testing in 29% of the cases. Additional testing included having children tested for gene mutation, colonoscopy, additional eye exams, cardiac calcium scan, PET scan to evaluate lymphoma, repeating study tests (echocardiogram, pulmonary function tests) in the clinical setting, extra screening for macular degeneration risk, and additional tests for diabetes related studies (SSPG and the Quantitative Sudomotor Axon Reflex Test). In addition to the study surveys, participants were also asked about the effect of SSPG testing and CGM monitoring (Table 11). Eight participants who used a CGM monitor reported that it helped them understand how some specific food affect their blood sugar and make different dietary and meal frequency choices. SSPG results motivated at least 2 participants to change their activity and diet (Table 11) and were reassuring to others. Therefore, overall, a myriad of positive behavior modifications and follow-up tests resulted from study participation.

Further Study on Association of Analyte Measurements with SSPG

Figure 35:
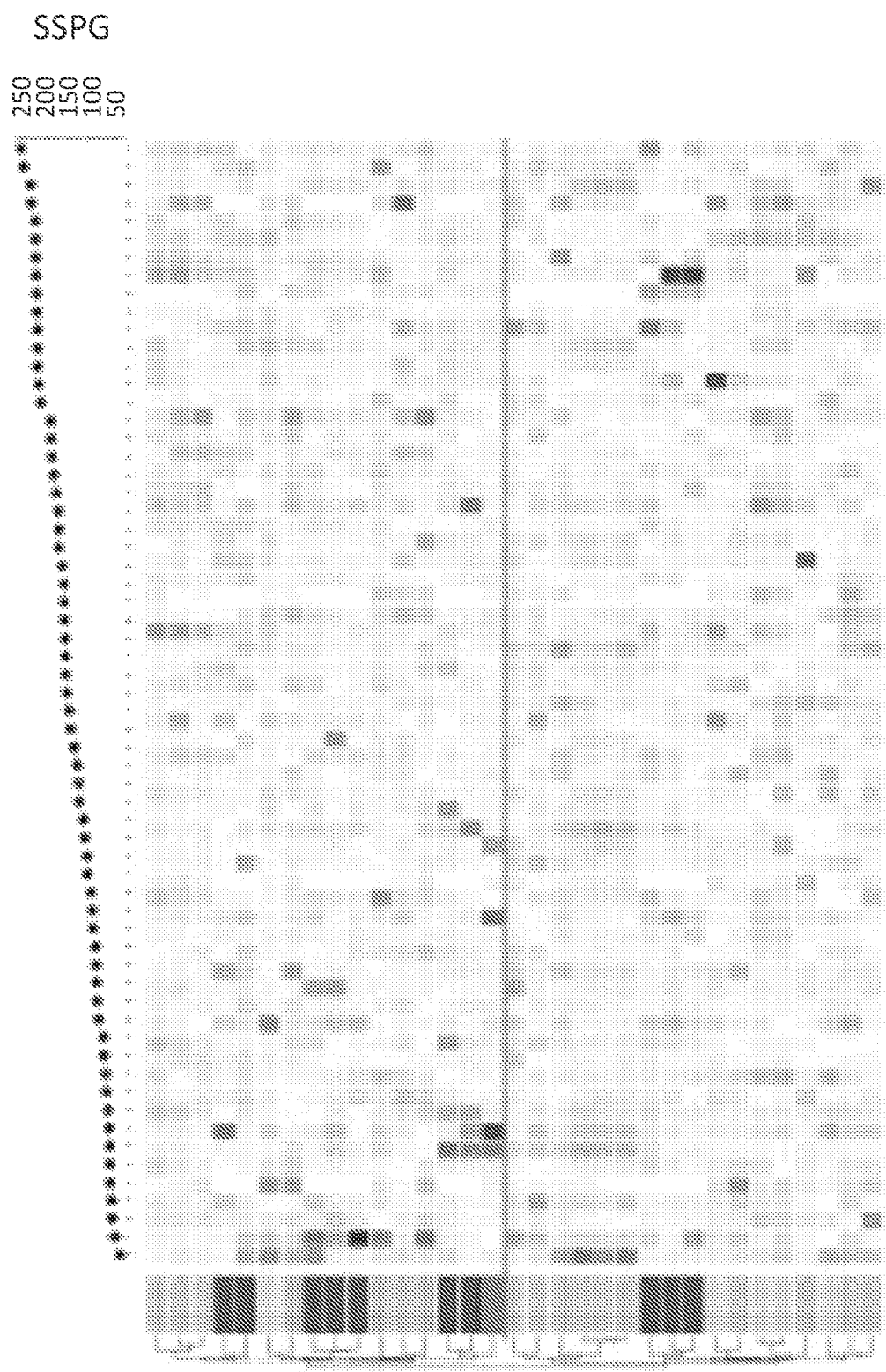
FIG. 35 provides the expression pattern of measurements that significantly associate with SSPG in healthy baselines, utilized in accordance with various embodiments of the invention.

Because many of the participants were well characterized with respect to insulin resistance (as measured by the SSPG assay), it was sought to characterize co-associations using two different approaches: regression analysis with SSPG values and co-association with IS and IR participants. Assuming SSPG values rarely vary per participant no significant changes in BMI and after correcting for BMI, age and sex, 99 omic measurements and clinical labs were found to significantly correlate with SSPG levels (FIG. 35, Table 15, q-value 0.1); 81 were repeatedly observed using correlational analysis with IR/IS classification (Table 15). It was found that triglycerides (TGL) were positively associated with SSPG whereas HDL was inversely correlated with SSPG. It was also found that SSPG positively associated with increased inflammation and immune responses, as evident by neutrophil absolute count (NEUTAB) and white blood cell count (WBC) from clinical laboratory tests. Although these complete blood count values were still in the normal range, these observations highlight the association between inflammation and insulin resistance. Insulin resistance is also associated with altered lipid biology, and several long-chain and polyunsaturated fatty acids we observed to positively correlated with SSPG. Notable metabolites inversely correlated with SSPG or IR/IS classification included indolelactic acid and hippuric acid, which inversely correlate with metabolic syndrome and are strong markers of gut microbiome diversity. In line with the metabolomics data, the genus *Blautia*, which inversely correlates with hippuric acid, was positively correlated with SSPG. In contrast, the genera *Odoribacter*, Oscillibacter, and *Pseudoflavonifractor* were negatively associated with SSPG. Altogether, insulin resistance was found to associate with higher inflammation and altered lipid metabolism, which might cause IR participants impaired responses to additional stresses. For this data, the microbiome analysis were analyzed as follows: Amplicon sequences were clustered and Operational Taxonomic Units (OTU) picked by Usearch against GreenGenes database (May 2013 version) and final taxonomic assignment were performed using RDP-classifier.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

TABLE 1

Demographic and Health Characteristics of the iPOP Cohort

| Mean Age (range) | 53.4 (25-75) | |
|---|---|---|
| | n | % |
| Sex | | |
| Female | 55 | 50.5% |
| Ethnicity | | |
| European | 60 | 55.0% |
| East Asian | 13 | 11.9% |
| South Asian | 11 | 10.1% |
| Jewish | 7 | 6.4% |
| African American | 6 | 5.5% |
| Hispanic | 6 | 5.5% |
| Mixed/Other | 6 | 5.5% |
| Education | | |
| High School/some college/Associates' | 14 | 12.8% |
| Bachelor's Degree | 23 | 21.1% |
| Master's Degree | 39 | 35.8% |

TABLE 1-continued

Demographic and Health Characteristics of the iPOP Cohort

| Mean Age (range) | 53.4 (25-75) | |
|---|---|---|
| | n | % |
| Doctoral Degree | 25 | 22.9% |
| Unknown | 8 | 7.3% |
| Baseline Self-Reported Health | | |
| Past Gestational Diabetes | 4 | 3.7% |
| Prediabetes | 10 | 9.2% |
| Diabetes | 9 | 8.3% |
| Dyslipidemia | 38 | 35.2% |
| Hypertension | 30 | 27.5% |
| Coronary Artery Disease | 5 | 4.6% |
| Family History | | |
| Diabetes | 60 | 55.0% |
| Hypertension | 59 | 54.1% |
| Coronary Artery Disease | 55 | 50.5% |
| Stroke | 26 | 23.9% |
| Baseline BMI | | |
| <25 | 25 | 22.9% |
| 25 to <30 | 56 | 51.4% |
| 30 or higher | 28 | 25.7% |

TABLE 2

Listing of Labs, Cytokines, and Growth Factors Assayed Quarterly

Clinical labs

| Symbol | Full name |
|---|---|
| A1C | Hemoglobin A1C |
| AG | Albumin/Globulin Ratio |
| ALB | Albumin |
| ALCRU | Aluminum/Creatinine Ratio, Random, Urine |
| ALKP | Alkaline Phosphatase |
| ALT | Alanine Aminotransferase |
| AST | Aspartate Aminotransferase |
| BASO | Basophil (percent) |
| BASOAB | Basophil (absolute count) |
| BUN | Blood Urea Nitrogen |
| CA | Calcium |
| CHOL | Total cholesterol |
| CHOLHDL | Cholesterol/HDL ratio |
| CL | Chloride |
| CO2 | Carbon Dioxide |
| CR | Creatinine |
| EOS | Eosinophil (percent) |
| EOSAB | Eosinophil (absolute count) |
| GLOB | Globulin |
| GLU | Glucose |
| HCT | Hematocrit |
| HDL | High-density lipoprotein |
| HGB | Hemoglobin |
| HSCRP | High-Sensitivity C-reactive protein |
| IGM | Immunoglobulin M |
| INSF | Insulin |
| K | Potassium |
| LDL | Low-density lipoprotein |
| LDLHDL | LDL/HDL ratio |
| LYM | Lymphocyte (percent) |
| LYMAB | Lymphocyte (absolute count) |
| MCH | Mean Corpuscular Hemoglobin |
| MCHC | Mean Corpuscular Hemoglobin Concentration |
| MCV | Mean corpuscular Volume |
| MONO | Monocyte (percent) |
| MONOAB | Monocyte (absolute count) |
| NA | Sodium |
| NEUT | Neutrophil (percent) |
| NEUTAB | Neutrophil (absolute count) |

TABLE 2-continued

Listing of Labs, Cytokines, and Growth Factors Assayed Quarterly

| Symbol | Synonym | Full name |
|---|---|---|
| NHDL | | Non-HDL |
| PLT | | Platelet Count |
| RBC | | Red Blood Cell Count |
| RDW | | Red Blood Cell Distribution Width |
| TBIL | | Total Bilirubin |
| TGL | | Total triglyceride |
| TGLHDL | | Triglyceride/HDL ratio |
| TP | | Total Protein |
| UALB | | Urine Albumin |
| WBC | | White Blood Cell Count |

Cytokines/Growth factors

| Symbol | Synonym | Full name |
|---|---|---|
| BDNF | | Brain-derived neurotrophic factor |
| CD40L | | CD40 ligand |
| EGF | | Epidermal growth factor |
| ENA78 | CXCL5 | Epithelial-derived neutrophil-activating protein 78 |
| EOTAXIN | CCL11 | |
| FASL | | Fas ligand |
| FGFB | FGF2 | Basic fibroblast growth factor |
| GCSF | | Granulocyte colony-stimulating factor |
| GMCSF | CSF2 | Granulocyte-macrophage colony-stimulating factor |
| GROA | CXCL1 | Growth-regulated alpha protein |
| HGF | | Hepatocyte growth factor |
| ICAM1 | | Intercellular adhesion molecule 1 |
| IFNA | | Interferon alpha |
| IFNB | | Interferon beta |
| IFNG | | Interferon gamma |
| IL10 | | Interleukin-10 |
| IL12P40 | | Interleukin-12 P40 |
| IL12P70 | | Interleukin-12 P70 |
| IL13 | | Interleukin-13 |
| IL15 | | Interleukin-15 |
| IL17A | | Interleukin-17A |
| IL17F | | Interleukin-17F |
| IL18 | | Interleukin-18 |
| IL1A | | Interleukin-1 alpha |
| IL1B | | Interleukin-1 beta |
| IL1RA | | Interleukin-1 receptor antagonist protein |
| IL2 | | Interleukin-2 |
| IL21 | | Interleukin-21 |
| IL22 | | Interleukin-22 |
| IL23 | | Interleukin-23 |
| IL27 | | Interleukin-27 |
| IL31 | | Interleukin-31 |
| IL4 | | Interleukin-4 |
| IL5 | | Interleukin-5 |
| IL6 | | Interleukin-6 |
| IL7 | | Interleukin-7 |
| IL8 | CXCL8 | Interleukin-8 |
| IL9 | | Interleukin-9 |
| IP10 | CXCL10 | Interferon gamma-induced protein 10 |
| LEPTIN | | LEPTIN |
| LIF | | Leukemia inhibitory factor |
| MCP1 | CCL2 | Monocyte chemoattractant protein 1 |
| MCP3 | CCL7 | Monocyte chemoattractant protein 3 |
| MCSF | CSF1 | Macrophage colony-stimulating factor 1 |
| MIG | CXCL9 | Monokine induced by gamma interferon |
| MIP1A | CCL3 | Macrophage inflammatory protein-1 alpha |
| MIP1B | CCL4 | Macrophage inflammatory protein-1 beta |
| NGF | | Nerve growth factor |
| PAI1 | SERPINE1 | Plasminogen activator inhibitor 1 |
| PDGFBB | CSRP2 | Platelet-derived growth factor-BB |
| RANTES | CCL5 | Regulated on Activation, Normal T Cell Expressed and Secreted |
| RESISTIN | ADSF | RESISTIN |
| SCF | | Stem cell factor |
| SDF1A | | Stromal cell-derived factor-1 alpha |
| TGFA | | Transforming growth factor alpha |
| TGFB | | Transforming growth factor beta |
| TNFA | | Tumor necrosis factor alpha |
| TNFB | | Tumor necrosis factor beta |
| TRAIL | | TNF-related apoptosis-inducing ligand |
| VCAM1 | | Vascular cell adhesion protein 1 |
| VEGF | | Vascular endothelial growth factor A |
| VEGFD | | Vascular endothelial growth factor D |

TABLE 3

All Health-related Discoveries Throughout Course of Study

| Discovery | n | How Discovered | Implication | Clinical Action* |
|---|---|---|---|---|
| Metabolic | | | | |
| HNF1A mutation | 1 | WGS | Pathogenic for MODY; can change medication management | clinical confirmation; testing of family |
| ABCC8 mutation | 1 | WGS | likely pathogenic for hyperinsulinemia | none |
| SLC7A9 mutation | 1 | WGS | Pathogenic for cystinuria | Clinical evaluation |
| New Diabetic Range Labs | 14 | HbA1C/FPG/OGTT | Potential development of diabetes | Life style modification, start medication (n = 3) |
| New Prediabetic range labs | 55 | HbA1C/FPG/OGTT | Risk factor for diabetes development | Life style modification |
| Insulin Resistance status | 68 | SSPG | Weight loss, lifestyle modification if resistant | |
| Elevated liver blood tests (Laboratory criteria) | 21 | ALT | Potential sign of non-alcoholic fatty liver disease; consider hepatic ultrasound in those with elevated BMI, diabetes or metabolic syndrome | Referral for clinical assessment |
| RNAseq Outlier: Liver Pathways | 1 | RNASeq | clinical review of liver labs, travel history; later found to have hepatic steatosis on ultrasound; clinical significance unclear | |
| New albuminuria | 2 | Urine Alb/Cr > 300 | concerning for problems with kidney function | Demonstrated resolution with repeat clinical testing |
| Persistent microalbuminuria | 1 | Urine Alb/Cr > 30 | Microalbinuria can be an early sign of diabetic nephropathy | Eventually diagnosed with smoldering multiple myeloma |
| Hypokalemia | 9 | clinical lab | review medications, supplementation | adjustment of diuretic in 1 participant |
| Hyperkalemia | 9 | clinical lab | monitoring | |
| Hyponatremia | 17 | clinical lab | monitoring; review medications (e.g. diuretics) | |

TABLE 3-continued

All Health-related Discoveries Throughout Course of Study

| Discovery | n | How Discovered | Implication | Clinical Action* |
|---|---|---|---|---|
| Cardiovascular | | | | |
| RBM20 Mutation | 1 | WGS | likely pathogenic for dilated cardiomyopathy | Clinical evaluation & family testing; also had dilated cardiomyopathy on enhanced cardiovascular imaging |
| Reduced LVEF/GLS | 1 | Echocardiography | Early Stage asymptomatic cardiomyopathy | |
| Atrial Fibrillation | 1 | Wearable | increased risk of stroke, | Cardiology evaluation, diagnosis, risk assessment, medication for rate control and anticoagulation |
| Nighttime Supraventricular Tachycardia | 1 | Wearable | | Cardiology evaluation, sleep evaluation; diagnosed with sleep apnea; prescribed cPAP |
| Carotid plaque 10-40% diameter | 6 | Vascular Ultrasound | Lipid and Risk Screening | |
| Dilated left Atrium | 3 | Echocardiography | Blood Pressure review, Screening for atrial fibrillation | |
| Stage II Hypertension (2017 Criteria) | 18 | Measured at Clinic | Lifestyle change, evaluate need for medication | at least 1 participant started on medication |
| 1A Clopidogrel pharmacogenomic variant | 35 | WGS | poor (n = 4) or intermediate (n = 31) metabolizer of clopidogrel; consideration of alternative agents | Knowledge of this variant was relevant for 1 participant with high risk of recurrent stroke |
| SLCO1B1 mutation | 26 | WGS | increased side effects from simvastatin and other statins | reported variant back to participants; unknown if followed up clinically |
| 1A Coumadin pharmacogenomic variant | 30 | WGS | consider alteration in warfarin dosage | at least 1 participant used information to inform coumadin usage |
| Other Pharmacogenomic (rs4680) | 1 | WGS | consider alterative to ASA therapy for stroke prophylaxis in women | participant ended up using coumadin for secondary stroke prophylaxis |
| ASCVD 10 Year risk >7.5% | 24 | Clinical measures | Risk Reduction, Evaluate need for medication | |
| Dyslipidemia | 60 | Cholesterol Panel | Lifestyle change, Evaluate need for medication | |
| >moderate aortic regurgitation | 2 | Echocardiography | Echo Surveillance | |
| >moderate mitral regurgitation | 1 | Echocardiography | Echo Surveillance | |
| Frequent Ectopy | 1 | Electrocardiogram | Further monitoring | |
| elevated hsCRP (>3.0 mg/L) | 49 | hsCRP | Lifestyle change | |
| Oncologic | | | | |
| B cell Lymphoma | 1 | Abdominal Ultrasound | Splenomegaly and paraaortic lymphadenopathy concerning for cancer | Clinical evaluation (PET-CT Scan); LDH, Biopsy; Treatment with chemotherapy; Complete remission after 2 years of follow-up |
| APC mutations | 2 | WGS | Colon Cancer Risk; | Clinical Confirmation, 1 underwent early colonoscopy (results unknown) |
| SDHB mutations | 2 | WGS | Increased risk of paraganglioma and pheochromocytoma; Clinical follow-up includes whole body MRI q2 years and yearly chromogranin and metanephrine screen | in 1 participant revealed papillary thyroid cancer; family member also screened and (+) |
| BRCA1 mutation | 1 | WGS | increased risk for breast cancer, prostate cancer and melanoma | Discussed with clinical genetic counselor and family |
| MUTYH mutation | 1 | WGS | increased Colon Cancer Risk; | Genetics Clinic referral |
| CHEK2 mutation | 1 | WGS | increased Colon & Breast Cancer Risk; | Genetics Clinic referral |
| Hematologic and Immune | | | | |
| Monoclonal Gammopathy of Uncertain Significance | 1 | clinical IgM lab | evaluation for multiple myeloma | Clinical evaluation with labs, MRI, bone marrow biopsy (cytogenetics, FISH, immunophenotyping); Longitudinal clinical monitoring |
| Smoldering IgG Multiple Myeloma | 1 | Low IgM, platelets | recommend full immunoglobulin panel | Clinical evaluation revealed elevated IgG, bone marrow biopsy (cytogenetics, FISH, immunophenotyping), PET-CT |
| PROS1 mutation | 1 | WGS | Pathogenic for Protein S Deficiency | reported to participant |
| Alpha Thalassemia Trait | 1 | Low Hgb | Referral to primary who tested for alpha thalassemia | Found to have -alpha3.7 Alpha(plus)-thalassemia mutation on clinical testing |
| HBB mutation | 1 | WGS | pathogenic for beta thalassemia | participant with known anemia |
| Low IgM | 9 | clinical IgM lab | 4/9 immunoglobulin panel with 1 clinical diagnosis (detailed in Table 1) | 4/9 immunoglobulin panel with 1 clinical diagnosis (see smoldering myeloma) |

TABLE 3-continued

All Health-related Discoveries Throughout Course of Study

| Discovery | n | How Discovered | Implication | Clinical Action* |
|---|---|---|---|---|
| HBD mutation | 1 | WGS | pathogenic, but not disease causing | result not returned to participant |
| New anemia | 27 | Clinical labs | Monitoring, evaluation of iron deficiency, consider supplementation | 1 participant received alpha thalassemia work-up, another ended up being treated with IV Iron |
| thrombocytopenia (platelets < 150) | 14 | platelets | evaluation, work-up if indicated, monitoring | |
| Infectious | | | | |
| Lyme Disease | 1 | wearable | history of tick exposure, concern for infection | clinical diagnosis & antibiotic treatment |

Highlighghted findings are included in FIG. 6 of major clinically actionable health discoveries
*No information about clinical actions taken as a result of returned findings for all participants.
Abbreviations:
WGS—Whole genome sequencing;
FPG—fasting plasma glucose;
OGTT—oral glucose tolerance test;
HbA1C—Hemoglobin A1C;
HNFA1—hepatocyte nuclear factor 1 homeobox A gene;
MODY—maturity onset of diabetes of the young;
ABCC8—ATP binding cassette subfamily C member 8 gene;
SLC7A9—solute carrier family 7 member 9 gene;
SLCO1B1—solute carrier organic anion transporter family, member 1B1 gene;
SSPG—steady-state plasma glucose;
alb—albumin;
cr—creatinine;
ASCVD—atherosclerotic cardiovascular disease;
cPAP—continuous positive airway pressure;
hsCRP—high sensitivity c-reactive protein;
APC—Adenomatous polyposis coli gene;
SDHB—succinate dehydrogenase complex iron sulfur subunit B gene;
BRCA1—BRCA1, DNA repair associated gene;
MUTYH—mutY DNA glycosylase gene;
CHEK2—checkpoint kinase 2 gene;
MRI—magnetic resonance imaging;
IgG—immunoglobulin G;
IgM—immunoglobulin M;
FISH—Fluorescence in situ hybridization;
PET-CT—Positon Emission Tomography-Computed Tomography;
PROS1—Protein S;
HBB—hemoglobin subunit beta gene;
HBD—hemoglobin subunit delta gene;

TABLE 4

Molecules Associated with the Disposition Index

| Molecule Name | Estimate | p-value | FDR | Assay | KEGG | HMDB | Super pathway | Sub-pathway |
|---|---|---|---|---|---|---|---|---|
| LEPTIN | -3.94 | 1.80E-10 | 1.64E-07 | Immunome | | | | |
| GMCSF | -6.87 | 1.58E-09 | 7.18E-07 | Immunome | | | | |
| N6, N6, N6-Trimethyl-L-lysine | 8.19 | 2.48E-06 | 7.51E-04 | Metabolome | C03793 | HMDB01325 | Amino Acid | Lysine Metabolism |
| IL7 | 6.78 | 4.33E-06 | 9.84E-04 | Immunome | | | | |
| Androsterone sulfate(1) | 4.18 | 1.09E-05 | 1.93E-03 | Metabolome | | HMDB02759 | Lipid | Androgenic Steroids |
| TBIL | 14.90 | 1.39E-05 | 1.93E-03 | Clinical labs | | | | |
| 5alpha-Androstan-3alpha,17alpha-diol | 2.83 | 1.49E-05 | 1.93E-03 | Metabolome | | | Lipid | Androgenic Steroids |
| Creatine | -6.38 | 3.09E-05 | 2.01E-03 | Metabolome | C00300 | HMDB00064 | Amino Acid | Creatine Metabolism |
| SM(d18:1/12:0) | -5.10 | 2.18E-05 | 2.01E-03 | Metabolome | C00550 | HMDB12096 | | |
| A1C | -11.81 | 2.99E-05 | 2.01E-03 | Clinical labs | | | | |
| HCT | 1.47 | 2.82E-05 | 2.01E-03 | Clinical labs | | | | |
| HGB | 3.98 | 2.73E-05 | 2.01E-03 | Clinical labs | | | | |
| 5alpha-Androstan-3alpha,17alpha-diol | 3.40 | 2.84E-05 | 2.01E-03 | Metabolome | | | Lipid | Androgenic Steroids |
| PC(35:4)(1) | -6.08 | 2.27E-05 | 2.01E-03 | Metabolome | | | | |
| PPBP | -3.71 | 5.74E-05 | 3.48E-03 | Proteome | | | | |
| 5alpha-Androstan-3alpha,17beta-diol 1 | 2.95 | 1.02E-04 | 5.79E-03 | Metabolome | | | Lipid | Androgenic Steroids |
| LysoPE(22:5) | -6.56 | 2.78E-04 | 1.40E-02 | Metabolome | | HMDB11494 | Lipid | Phospholipid Metabolism |
| RBC | 10.51 | 2.72E-04 | 1.40E-02 | Clinical labs | | | | |
| C16:1 FA | -5.00 | 3.94E-04 | 1.89E-02 | Metabolome | C08362 | HMDB03229 | Lipid | Long Chain Fatty Acid |
| C13:0, DC FA(3) | 3.37 | 4.46E-04 | 2.03E-02 | Metabolome | | | Lipid | Fatty Acid, Dicarboxylate |
| (S)-(-)-2-Hydroxyisocaproic acid | 9.73 | 6.00E-04 | 2.48E-02 | Metabolome | | HMDB00746 | Amino Acid | Leucine, Isoleucine and Valine Metabolism |
| C8G | -5.82 | 5.86E-04 | 2.48E-02 | Proteome | | | | |
| C16:3 FA | -5.57 | 7.06E-04 | 2.67E-02 | Metabolome | | | Lipid | Long Chain Fatty Acid |
| C10:3 AC(1) | -4.96 | 6.98E-04 | 2.67E-02 | Metabolome | | | Lipid | Fatty Acid Metabolism(Acyl Carnitine) |
| C14:1 FA(1) | -4.31 | 7.72E-04 | 2.75E-02 | Metabolome | C08322 | | Lipid | Long Chain Fatty Acid |
| 5alpha-Androstan-3alpha,17alpha-diol | 2.92 | 7.88E-04 | 2.75E-02 | Metabolome | | HMDB02000 | Lipid | Androgenic Steroids |
| C8:1 AC | -4.58 | 8.20E-04 | 2.76E-02 | Metabolome | | HMDB13324 | Lipid | Fatty Acid Metabolism(Acyl Carnitine) |
| C20:0, 2OH FA | 4.01 | 1.06E-03 | 3.17E-02 | Metabolome | | HMDB31923 | Lipid | Fatty Acid, Dihydroxy |
| MST1 | -3.31 | 1.02E-03 | 3.17E-02 | Proteome | | | | |
| C16:2 FA | -5.22 | 1.01E-03 | 3.17E-02 | Metabolome | | | Lipid | Long Chain Fatty Acid |
| gamma-glutamylhistidine | 5.39 | 1.08E-03 | 3.17E-02 | Metabolome | | | Peptide | Gamma-glutamyl Amino Acid |
| C13:0, DC FA(2) | -3.80 | 1.18E-03 | 3.35E-02 | Metabolome | | | Lipid | Fatty Acid, Dicarboxylate |
| Biliverdin(1) | 4.55 | 1.36E-03 | 3.74E-02 | Metabolome | C00500 | HMDB01008 | Cofactors and Vitamins | Hemoglobin and Porphyrin Metabolism |
| Androsterone sulfate(2) | 3.16 | 1.48E-03 | 3.84E-02 | Metabolome | | HMDB02759 | Lipid | Androgenic Steroids |
| Androsterone glucuronide(1) | 4.70 | 1.45E-03 | 3.84E-02 | Metabolome | | HMDB02829 | Lipid | Androgenic Steroids |
| HV348 | 4.93 | 1.81E-03 | 4.51E-02 | Proteome | | | | |
| C10:1 FA(1) | -6.53 | 1.84E-03 | 4.51E-02 | Metabolome | C11135 | | Lipid | Medium Chain Fatty Acid |
| LysoPE(20:4) | -8.09 | 1.90E-03 | 4.55E-02 | Metabolome | | HMDB11487 | Lipid | Phospholipid Metabolism |
| N2, N2-Dimethylguanosine | -10.03 | 2.03E-03 | 4.74E-02 | Metabolome | | HMDB04824 | Nucleotide | Purine Metabolism, Guanine containing |
| PI(34:2) | -4.27 | 2.11E-03 | 4.79E-02 | Metabolome | | | | |
| GLU | -0.21 | 2.39E-03 | 4.94E-02 | Clinical labs | | | | |
| C10:3 AC(2) | -3.85 | 2.24E-03 | 4.94E-02 | Metabolome | | | Lipid | Fatty Acid Metabolism(Acyl Carnitine) |
| PE(36:4) | -3.52 | 2.35E-03 | 4.94E-02 | Metabolome | | | | |
| PE(36:2) | -3.35 | 2.35E-03 | 4.94E-02 | Metabolome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| Dehydroisoandrosterone sulfate (DHE-S)(1) | 3.50 | 2.626-03 | 5.06E-02 | Metabolome | C04555 | HMDB01032 | Lipid | Androgenic Steroids |
| C17:1 FA | -4.79 | 2.52E-03 | 5.06E-02 | Metabolome | | HMDB60038 | Lipid | Long Chain Fatty Acid |
| IL6 | 14.68 | 2.61E-03 | 5.06E-02 | Immunome | | | | |
| SERPINC1 | 8.82 | 2.68E-03 | 5.08E-02 | Proteome | | | | |
| CEP290 | 2.59 | 2.87E-03 | 5.33E-02 | Proteome | | | | |
| LysoPE(22:4) | -3.08 | 2.97E-03 | 5.40E-02 | Metabolome | | HMDB11493 | Lipid | Phospholipid Metabolism |
| C16 Sphingosine 1-phosphate | -5.83 | 3.36E-03 | 5.87E-02 | Metabolome | | HMDB60061 | Lipid | Sphingolipid Metabolism |
| C17:0 FA(2) | -6.44 | 3.34E-03 | 5.87E-02 | Metabolome | | | Lipid | Long Chain Fatty Acid |
| Biliverdin(2) | 2.07 | 3.65E-03 | 6.26E-02 | Metabolome | C00500 | HMDB01008 | Cofactors and Vitamins | Hemoglobin and Porphyrin Metabolism |
| ALB | 11.56 | 3.89E-03 | 6.42E-02 | Clinical labs | | | | |
| PE(P-36:4) | -4.29 | 3.83E-03 | 6.42E-02 | Metabolome | | | | |
| LysoPC(20:1) | 4.44 | 4.16E-03 | 6.75E-02 | Metabolome | C04230 | HMDB10391 | Lipid | Phospholipid Metabolism |
| ethyl glucuronide | -1.71 | 4.38E-03 | 6.86E-02 | Metabolome | | HMDB10325 | Xenobiotics | Chemical |
| TTR | 3.99 | 4.36E-03 | 6.86E-02 | Proteome | | | | |
| APOD | 5.26 | 4.58E-03 | 6.99E-02 | Proteome | | | | |
| C4H6O2 | -13.70 | 4.62E-03 | 6.99E-02 | Metabolome | | | | |
| PE(P-36:3) | -4.07 | 5.00E-03 | 7.46E-02 | Metabolome | | | | |
| L-Hydroxyisovaleric acid | 5.41 | 5.44E-03 | 7.89E-02 | Metabolome | | HMDB00407 | Amino Acid | Leucine, Isoleucine and Valine Metabolism |
| SERPING1 | 3.23 | 5.53E-03 | 7.89E-02 | Proteome | | | | |
| PAI1 | 5.94 | 5.55E-03 | 7.89E-02 | Immunome | | | | |
| C18:0, DC FA(1) | -7.70 | 6.27E-03 | 8.15E-02 | Metabolome | | HMDB00782 | Lipid | Fatty Acid, Dicarboxylate |
| C14:0 FA | -5.54 | 5.88E-03 | 8.15E-02 | Metabolome | C06424 | HMDB00806 | Lipid | Long Chain Fatty Acid |
| C1R | -5.13 | 6.27E-03 | 8.15E-02 | Proteome | | | | |
| F9 | 4.41 | 6.19E-03 | 8.15E-02 | Proteome | | | | |
| C18:3, OH FA(2) | -7.95 | 6.13E-03 | 8.15E-02 | Metabolome | | | Lipid | Fatty Acid, Monohydroxy |
| PE(36:3) | -2.63 | 5.99E-03 | 8.15E-02 | Metabolome | | | | |
| C14:0, DC FA(1) | 3.36 | 6.67E-03 | 8.32E-02 | Metabolome | | HMDB00872 | Lipid | Fatty Acid, Dicarboxylate |
| IV319 | 5.01 | 6.54E-03 | 8.32E-02 | Proteome | | | | |
| MONOAB | -23.60 | 6.68E-03 | 8.32E-02 | Clinical labs | | | | |
| L-Cystine | -5.89 | 6.85E-03 | 8.36E-02 | Metabolome | C00491 | HMDB00192 | Amino Acid | Methionine, Cysteine, SAM and Taurine Metabolism |
| C6:0 AC | -5.19 | 6.90E-03 | 8.36E-02 | Metabolome | | HMDB00705 | Lipid | Fatty Acid Metabolism(Acyl Carnitine) |
| C18 Sphingosine 1-phosphate | -7.52 | 7.24E-03 | 8.42E-02 | Metabolome | C06124 | HMDB00277 | Lipid | Sphingolipid Metabolism |
| N6-Carbamoyl-L-threonyladenosine | -10.21 | 7.34E-03 | 8.42E-02 | Metabolome | | HMDB41623 | Nucleotide | Purine Metabolism, Adenine containing |
| Hexose | -1.26 | 7.41E-03 | 8.42E-02 | Metabolome | C00503|C16884 | HMDB02994|HMDB04136 | Carbohydrate | Glycolysis, Gluconeogenesis, and Pyruvate Metabolism |
| C5:0 AC | 5.65 | 7.38E-03 | 8.42E-02 | Metabolome | | HMDB04827 | Lipid | Fatty Acid Metabolism(Acyl Carnitine) |
| PE(34:1) | -1.70 | 7.12E-03 | 8.42E-02 | Metabolome | | | | |
| Proline betaine | 2.05 | 7.58E-03 | 8.42E-02 | Metabolome | C10172 | | Xenobiotics | Food Component/Plant |
| Ectoine | 2.73 | 7.87E-03 | 8.42E-02 | Metabolome | C06231 | | Xenobiotics | Chemical |
| SEPP1 | 4.00 | 7.80E-03 | 8.42E-02 | Proteome | | | | |
| IL1B | 6.86 | 7.76E-03 | 8.42E-02 | Immunome | | | | |
| PE(P-36:2) | -4.31 | 7.72E-03 | 8.42E-02 | Metabolome | | | | |
| Dihydroxyvitamin D3(2) | 3.85 | 8.24E-03 | 8.71E-02 | Metabolome | | HMDB00430 | Cofactors and Vitamins | Vitamin D Metabolism |
| Erythritol|D-Threitol | -1.66 | 8.44E-03 | 8.82E-02 | Metabolome | | HMDB02302 | Xenobiotics | Food Component/Plant |
| 3-Indolepropionic acid | 2.01 | 9.64E-03 | 9.20E-02 | Metabolome | | HMDB02925 | Amino Acid | Tryptophan Metabolism |
| C20:3 FA | -5.04 | 9.26E-03 | 9.20E-02 | Metabolome | | | Lipid | Polyunsaturated Fatty Acid (n3 and n6) |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| N1-methyladenosine | −7.73 | 9.46E-03 | 9.20E-02 | Metabolome | C02494 | HMDB03331 | Nucleotide | Purine Metabolism, Adenine containing |
| SM(d18:1/14:0) | −4.64 | 9.72E-03 | 9.20E-02 | Metabolome | | HMDB12097 | | |
| IGHA2 | 1.62 | 9.50E-03 | 9.20E-02 | Proteome | | | | |
| PRG4.1 | −1.96 | 9.82E-03 | 9.20E-02 | Proteome | | | | |
| PLT | −0.06 | 9.07E-03 | 9.20E-02 | Clinical labs | | | | |
| C15:0 FA | −5.44 | 9.54E-03 | 9.20E-02 | Metabolome | | | Lipid | Long Chain Fatty Acid |
| C16:1, OH FA(2) | −5.50 | 9.22E-03 | 9.20E-02 | Metabolome | | | Lipid | Fatty Acid, Monohydroxy |
| PE(P-34:1) | −2.09 | 9.92E-03 | 9.20E-02 | Metabolome | | | | |
| PC(37:6) | −3.83 | 9.17E-03 | 9.20E-02 | Metabolome | | | | |
| ZNF10 | 2.66 | 1.04E-02 | 9.39E-02 | Proteome | | | | |
| N-methylproline | 4.52 | 1.04E-02 | 9.39E-02 | Metabolome | | | Amino Acid | Urea cycle; Arginine and Proline Metabolism |
| Hexosamine | −6.41 | 1.04E-02 | 9.39E-02 | Metabolome | | | Carbohydrate | Glycolysis, Gluconeogenesis, and Pyruvate Metabolism |
| PZP | −3.15 | 1.06E-02 | 9.43E-02 | Proteome | | | | |
| VASN | 3.14 | 1.07E-02 | 9.43E-02 | Proteome | | | | |
| SDF1A | 12.05 | 1.09E-02 | 9.49E-02 | Proteome | | | | |
| RDW | −2.96 | 1.13E-02 | 9.67E-02 | Clinical labs | | | | |
| WBC | −2.08 | 1.13E-02 | 9.67E-02 | Clinical labs | | | | |
| C5:0, DC AC | −3.41 | 1.14E-02 | 9.67E-02 | Metabolome | | HMDB00243 | Lipid | Fatty Acid Metabolism(Acyl Carnitine) |
| Pyruvic acid | −1.14 | 1.16E-02 | 9.70E-02 | Metabolome | | | Carbohydrate | Glycolysis, Gluconeogenesis, and Pyruvate Metabolism |
| CR | 16.66 | 1.16E-02 | 9.70E-02 | Clinical labs | | | | |
| L-Lactic acid | −1.09 | 1.27E-02 | 1.03E-01 | Metabolome | C00186 | HMDB00190 | Carbohydrate | Glycolysis, Gluconeogenesis, and Pyruvate Metabolism |
| IGKC | 4.91 | 1.27E-02 | 1.03E-01 | Proteome | | | | |
| THBS1 | −1.41 | 1.27E-02 | 1.03E-01 | Proteome | | | | |
| ENA78 | −2.87 | 1.34E-02 | 1.07E-01 | Immunome | | | | |
| Pantothenic acid | −3.63 | 1.41E-02 | 1.12E-01 | Metabolome | C00864 | HMDB00210 | Cofactors and Vitamins | Pantothenate and CoA Metabolism |
| MCP3 | 7.81 | 1.41E-02 | 1.12E-01 | Immunome | | | | |
| IGLL5 | 2.75 | 1.45E-02 | 1.13E-01 | Proteome | | | | |
| BCHE | 4.56 | 1.51E-02 | 1.18E-01 | Proteome | | | | |
| HV313 | 3.85 | 1.59E-02 | 1.21E-01 | Proteome | | | | |
| C10:3 FA(1) | −3.30 | 1.57E-02 | 1.21E-01 | Metabolome | | | Lipid | Medium Chain Fatty Acid |
| Pregnanolone sulfate | 2.60 | 1.60E-02 | 1.21E-01 | Metabolome | | | Lipid | Progestin Steroids |
| Alpha-ketoisovaleric acid | 6.64 | 1.65E-02 | 1.23E-01 | Metabolome | C00141 | HMDB00019 | Amino Acid | Leucine, Isoleucine and Valine Metabolism |
| C18:1, OH FA(2) | −5.38 | 1.64E-02 | 1.23E-01 | Metabolome | | | Lipid | Fatty Acid, Monohydroxy |
| N-formylmethionine | −6.06 | 1.75E-02 | 1.28E-01 | Metabolome | C03145 | HMDB01015 | Amino Acid | Methionine, Cysteine, SAM and Taurine Metabolism |
| TGL | −0.05 | 1.75E-02 | 1.28E-01 | Clinical labs | | | | |
| Acetylcarnosine | 4.29 | 1.82E-02 | 1.32E-01 | Metabolome | | HMDB12881 | Amino Acid | Hisltidine Metabolism |
| C12:1 FA(2) | −2.99 | 1.85E-02 | 1.33E-01 | Metabolome | | HMDB00529 | Lipid | Medium Chain Fatty Acid |
| SM(d18:1/22:1) | −4.88 | 1.91E-02 | 1.37E-01 | Metabolome | C00550 | HMDB12104 | | |
| C8:0 AC(1) | −4.41 | 1.94E-02 | 1.38E-01 | Metabolome | C02838 | HMDB00791 | Lipid | Fatty Acid Metabolism(Acyl Carnitine) |
| IL1RAP | 3.76 | 1.97E-02 | 1.39E-01 | Proteome | | | | |
| PF4 | −1.72 | 2.09E-02 | 1.45E-01 | Proteome | | | | |
| EGFR | 0.17 | 2.08E-02 | 1.45E-01 | Clinical labs | | | | |
| FAM161B | 2.79 | 2.14E-02 | 1.47E-01 | Proteome | | | | |
| Ethylmalonate | −1.41 | 2.17E-02 | 1.47E-01 | Metabolome | | HMDB00622 | Amino Acid | Leucine, Isoleucine and Valine Metabolism |
| ACAA2 | 2.61 | 2.16E-02 | 1.47E-01 | Proteome | | | | |
| GPX3 | 3.76 | 2.22E-02 | 1.48E-01 | Proteome | | | | |
| PI(34:1) | −3.37 | 2.21E-02 | 1.48E-01 | Metabolome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| LV321.1 | 2.55 | 2.26E-02 | 1.50E-01 | Proteome | | | | |
| Androsterone glucuronide(2) | 3.61 | 2.33E-02 | 1.51E-01 | Metabolome | C11135 | HMDB02829 | Lipid | Androgenic Steroids |
| C10:1 AC | -4.11 | 2.31E-02 | 1.51E-01 | Metabolome | | HMDB13205 | Lipid | Fatty Acid Metabolism(Acyl Carnitine) |
| C8B | -4.37 | 2.33E-02 | 1.51E-01 | Proteome | | | | |
| ITIH1 | 7.44 | 2.46E-02 | 1.58E-01 | Clinical labs | | | | |
| ALKP | -0.11 | 2.47E-02 | 1.58E-01 | Clinical labs | | | | |
| APOC4 | -2.06 | 2.49E-02 | 1.58E-01 | Proteome | | | | |
| LysoPE(20:3) | -3.05 | 2.53E-02 | 1.60E-01 | Metabolome | | HMDB11484 | Lipid | Phospholipid Metabolism |
| C22:3 FA | -3.37 | 2.59E-02 | 1.60E-01 | Metabolome | | HMDB02823 | Lipid | Polyunsaturated Fatty Acid (n3 and n6) |
| LysoPI(20:4) | -3.87 | 2.58E-02 | 1.60E-01 | Metabolome | | HMDB61690 | Lipid | Phospholipid Metabolism |
| TNFB | 6.49 | 2.58E-02 | 1.60E-01 | Immunome | | | | |
| 4-Hydroxyphenylpyruvic acid | -2.59 | 2.66E-02 | 1.64E-01 | Metabolome | C01179 | HMDB00707 | Amino Acid | Tyrosine Metabolism |
| IGM | -0.05 | 2.70E-02 | 1.65E-01 | Clinical labs | | | | |
| C18:4 FA | -2.81 | 2.79E-02 | 1.69E-01 | Metabolome | C16300 | HMDB06547 | Lipid | Long Chain Fatty Acid |
| HV307 | 3.68 | 2.91E-02 | 1.75E-01 | Proteome | | | | |
| L-Alanine | -7.20 | 2.99E-02 | 1.75E-01 | Metabolome | C00041 | HMDB00161 | Amino Acid | Alanine and Aspartate Metabolism |
| Phenyllaclate (PLA) | 4.30 | 2.96E-02 | 1.75E-01 | Metabolome | C05607 | HMDB00779 | Amino Acid | Phenylalanine Metabolism |
| Phenol sulphate | -2.20 | 2.94E-02 | 1.75E-01 | Metabolome | C00850 | HMDB60015 | Amino Acid | Tyrosine Metabolism |
| MCAM | 2.11 | 2.99E-02 | 1.75E-01 | Proteome | | | | |
| C16:0, DC FA(1) | 3.62 | 3.12E-02 | 1.75E-01 | Metabolome | C19615 | HMDB00672 | Lipid | Fatty Acid, Dicarboxylate |
| C22:4 FA | -3.53 | 3.11E-02 | 1.75E-01 | Metabolome | C16527 | HMDB02226 | Lipid | Polyunsaturated Fatty Acid (n3 and n6) |
| Indolepyruvate | 1.08 | 3.14E-02 | 1.75E-01 | Metabolome | C00331 | HMDB60484 | Amino Acid | Tryptophan Metabolism |
| IL17F | -3.08 | 3.14E-02 | 1.75E-01 | Proteome | | | | |
| KVD33_2 | 3.07 | 3.13E-02 | 1.75E-01 | Proteome | | | | |
| TGFBI | 2.30 | 3.01E-02 | 1.75E-01 | Proteome | | | | |
| LV140 | 1.95 | 3.14E-02 | 1.75E-01 | Proteome | | | | |
| C9:0 AC | 2.79 | 3.14E-02 | 1.75E-01 | Metabolome | | | Lipid | Fatty Acid Metabolism(Acyl Carnitine) |
| HV102 | 1.95 | 3.19E-02 | 1.75E-01 | Proteome | | | | |
| PE(P-38:4) | -3.61 | 3.19E-02 | 1.78E-01 | Metabolome | | | | |
| 11-beta-Hydroxyandrosterone-3-glucuronide | -2.79 | 3.26E-02 | 1.78E-01 | Metabolome | | HMDB10351 | Lipid | Androgenic Steroids |
| LysoPC(22:6) | 4.08 | 3.27E-02 | 1.78E-01 | Metabolome | C04230 | HMDB10404 | Lipid | Phospholipid Metabolism |
| Androstenediol (3beta, 17beta) disulfate | 1.94 | 3.32E-02 | 1.78E-01 | Metabolome | C04295 | HMDB03818 | Lipid | Androgenic Steroids |
| RBP4 | 3.59 | 3.30E-02 | 1.78E-01 | Proteome | | | | |
| PE(34:2) | -2.32 | 3.34E-02 | 1.78E-01 | Metabolome | | | | |
| SM(d18:1/18:0) | -3.63 | 3.40E-02 | 1.81E-01 | Metabolome | C00550 | HMDB12088 | Lipid | Fatty Acid, Monohydroxy |
| C18:0, OH FA(1) | -5.13 | 3.50E-02 | 1.84E-01 | Metabolome | C03045 | | | |
| HPR | -3.17 | 3.51E-02 | 1.84E-01 | Proteome | | | | |
| ITIH2 | 6.55 | 3.52E-02 | 1.84E-01 | Proteome | | | | |
| TNFA | 6.82 | 3.54E-02 | 1.84E-01 | Immunome | | | | |
| C18:3 FA | -2.21 | 3.58E-02 | 1.85E-01 | Metabolome | C06426 | HMDB03073 | Lipid | Polyunsaturated Fatty Acid (n3 and n6) |
| 3-Methyl-2-oxovaleric acid | 7.72 | 3.76E-02 | 1.93E-01 | Metabolome | C00671 | HMDB03736 | Amino Acid | Leucine, Isoleucine and Valine Metabolism |
| 2-Hydroxyphenylacetate | -1.14 | 3.86E-02 | 1.96E-01 | Metabolome | C05852 | HMDB00669 | Amino Acid | Tyrosine Metabolism |
| SERPINA5 | 0.84 | 3.87E-02 | 1.96E-01 | Proteome | | | | |
| C16:0, OH FA(2) | -5.16 | 3.92E-02 | 1.98E-01 | Metabolome | | HMDB31057 | Lipid | Fatty Acid, Monohydroxy |
| IL1RAP.1 | 2.58 | 3.95E-02 | 1.98E-01 | Proteome | | | | |
| C15:0, OH FA | 5.63 | 3.98E-02 | 1.99E-01 | Metabolome | | | Lipid | Fatty Acid, Monohydroxy |
| Urocanic acid | 4.25 | 4.04E-02 | 2.01E-01 | Metabolome | C00785 | HMDB00301 | Amino Acid | Histidine Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| C16:2, OH FA | -4.34 | 4.15E-02 | 2.05E-01 | Metabolome | | | Lipid | Fatty Acid, Monohydroxy |
| APCS | 2.31 | 4.20E-02 | 2.06E-01 | Proteome | | | | |
| SERPINF2 | 6.79 | 4.25E-02 | 2.08E-01 | Proteome | | | | |
| PC(33:4)(1) | -2.45 | 4.27E-02 | 2.08E-01 | Metabolome | | | | |
| TRAIL | 6.28 | 4.36E-02 | 2.10E-01 | Immunome | | | | |
| C12:1, DC FA(4) | -1.82 | 4.35E-02 | 2.10E-01 | Metabolome | | | Lipid | Fatty Acid, Dicarboxylate |
| CLU.1 | 5.69 | 4.45E-02 | 2.12E-01 | Proteome | | | | |
| MBL2 | 1.41 | 4.43E-02 | 2.12E-01 | Proteome | | | | |
| Tetrahydroaldosterone-3-glucuronide(2) | -1.02 | 4.49E-02 | 2.13E-01 | Metabolome | | HMDB10357 | Lipid | Androgenic Steroids |
| VCAM1 | 4.85 | 4.55E-02 | 2.14E-01 | Immunome | | | | |
| GSN | 7.03 | 4.61E-02 | 2.15E-01 | Proteome | | | | |
| IGHG1 | 3.55 | 4.59E-02 | 2.15E-01 | Proteome | | | | |
| ACTBL2 | -1.40 | 4.77E-02 | 2.21E-01 | Proteome | | | | |
| HBB | 1.97 | 4.84E-02 | 2.22E-01 | Proteome | | | | |
| IFNB | -2.09 | 4.84E-02 | 2.22E-01 | Immunome | | | | |
| LysoPC(18:2) | 4.99 | 4.90E-02 | 2.23E-01 | Metabolome | C04230 | | Lipid | Phospholipid Metabolism |
| TGFA | -3.10 | 4.89E-02 | 2.23E-01 | Proteome | | | | |
| LCAT | -4.92 | 4.98E-02 | 2.25E-01 | Proteome | | | | |
| KV310 | 1.41 | 5.04E-02 | 2.25E-01 | Proteome | | | | |
| GLOB | -5.96 | 5.06E-02 | 2.25E-01 | Clinical labs | | | | |
| C14:1, OH FA(2) | -4.10 | 5.05E-02 | 2.25E-01 | Metabolome | | HMDB10386 | Lipid | Fatty Acid, Monohydroxy |
| C18:0 AC | 3.46 | 5.11E-02 | 2.26E-01 | Metabolome | | HMDB00848 | Lipid | Fatty Acid Metabolism(Acyl Carnitine) |
| MMRN1 | 2.82 | 5.16E-02 | 2.28E-01 | Proteome | | | | |
| SERPINA3 | 6.31 | 5.19E-02 | 2.28E-01 | Proteome | | | | |
| HP | -2.38 | 5.26E-02 | 2.30E-01 | Proteome | | | | |
| C18:2, DC FA | 2.05 | 5.32E-02 | 2.31E-01 | Metabolome | | HMDB00943 | Lipid | Fatty Acid, Dicarboxylate |
| Threonic acid | -6.27 | 5.37E-02 | 2.32E-01 | Metabolome | C01620 | | Cofactors and Vitamins | Ascorbate and Aldarate Metabolism |
| APOB | 3.64 | 5.48E-02 | 2.32E-01 | Proteome | | | | |
| C1S | -9.01 | 5.45E-02 | 2.32E-01 | Proteome | | | | |
| CA1 | 1.76 | 5.49E-02 | 2.32E-01 | Proteome | | | | |
| PSTK | 2.53 | 5.42E-02 | 2.32E-01 | Proteome | | | | |
| Hydroxybutyric acid(2) | -0.93 | 5.42E-02 | 2.32E-01 | Metabolome | | | | |
| C20:0 FA(1) | -3.17 | 5.52E-02 | 2.35E-01 | Metabolome | | | | |
| EOTAXIN | 2.48 | 5.62E-02 | 2.35E-01 | Immunome | | | | |
| LYMAB | 4.00 | 5.65E-02 | 2.36E-01 | Clinical labs | | | | |
| LysoPC(14:0) | -3.02 | 5.79E-02 | 2.38E-01 | Metabolome | C04230 | HMDB10379 | Lipid | Phospholipid Metabolism |
| APOA1 | 3.53 | 5.74E-02 | 2.38E-01 | Proteome | | | | |
| APOM | 4.75 | 5.85E-02 | 2.38E-01 | Proteome | | | | |
| CLEC3B | 3.54 | 5.88E-02 | 2.38E-01 | Proteome | | | | |
| CLU | 5.67 | 5.88E-02 | 2.38E-01 | Proteome | | | | |
| KV320.1 | -1.86 | 5.76E-02 | 2.38E-01 | Proteome | | | | |
| RANTES | 4.56 | 5.86E-02 | 2.38E-01 | Immunome | | | | |
| N1-Methyl-2-pyridone-5-carboxamide(1) | -3.12 | 6.17E-02 | 2.48E-01 | Metabolome | C05842 | HMDB04193 | Cofactors and Vitamins | Nicolinate and Nicolinamide Metabolism |
| VWF | -1.25 | 6.33E-02 | 2.52E-01 | Proteome | | | | |
| C14:2 FA | -2.56 | 6.31E-02 | 2.52E-01 | Metabolome | | | Lipid | Long Chain Fatty Acid |
| C10:0, OH FA(2) | 3.24 | 6.44E-02 | 2.54E-01 | Metabolome | | HMDB02203 | Lipid | Fatty Acid, Monohydroxy |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| LysoPE(16:1) | -2.03 | 6.41E-02 | 2.54E-01 | Metabolome | | HMDB11474 | Lipid | Phospholipid Metabolism |
| Pregnenolone sulfate | 1.33 | 6.59E-02 | 2.56E-01 | Metabolome | | HMDB00774 | Lipid | Progestin Steroids |
| ATP5A1 | 1.22 | 6.49E-02 | 2.56E-01 | Proteome | | | | |
| PON3 | 4.38 | 6.59E-02 | 2.56E-01 | Proteome | | | | |
| TAGLN2 | -1.58 | 6.61E-02 | 2.56E-01 | Proteome | | | | |
| eugenol sulfate | 1.16 | 6.53E-02 | 2.56E-01 | Metabolome | | | Xenobiotics | Food Component/Plant |
| HBA1 | 2.34 | 6.66E-02 | 2.57E-01 | Proteome | | | | |
| L-Isoleucine/L-Leucine | 6.24 | 7.13E-02 | 2.70E-01 | Metabolome | C00407/C00123 | HMDB00172/HMDB00687 | Amino Acid | Leucine, Isoleucine and Valine Metabolism |
| p-Cresol glucuronide | -0.68 | 7.14E-02 | 2.70E-01 | Metabolome | | HMDB11686 | Amino Acid | Tyrosine Metabolism |
| LPA | 0.87 | 7.14E-02 | 2.70E-01 | Proteome | | | | |
| SLFN11 | 2.01 | 7.16E-02 | 2.70E-01 | Proteome | | | | |
| C18:3, OH FA(1) | -3.49 | 7.09E-02 | 2.70E-01 | Metabolome | | | Lipid | Fatty Acid, Monohydroxy |
| C18:1 FA | -2.67 | 7.26E-02 | 2.73E-01 | Metabolome | C00712 | HMDB00207 | Lipid | Long Chain Fatty Acid |
| Betonicine | 1.15 | 7.38E-02 | 2.76E-01 | Metabolome | C08269 | HMDB29412 | Xenobiotics | Food Component/Plant |
| LysoPC(20:0) | 1.60 | 7.61E-02 | 2.82E-01 | Metabolome | C04230 | HMDB10390 | Lipid | Phospholipid Metabolism |
| HRG | 4.41 | 7.59E-02 | 2.82E-01 | Proteome | | | | |
| Acetylcholine | -3.24 | 7.95E-02 | 2.89E-01 | Metabolome | | HMDB00895 | Lipid | Phospholipid Metabolism |
| CAPZB | 1.56 | 7.88E-02 | 2.89E-01 | Proteome | | | | |
| ECM1 | 3.66 | 7.85E-02 | 2.89E-01 | Proteome | | | | |
| IL10 | 8.17 | 7.89E-02 | 2.89E-01 | Immunome | | | | |
| IL2 | 5.58 | 7.94E-02 | 2.89E-01 | Immunome | | | | |
| Cholic Acid | 1.04 | 8.04E-02 | 2.91E-01 | Metabolome | C00847 | HMDB00619 | Lipid | Primary Bile Acid Metabolism |
| Pyridoxic acid | -1.62 | 8.16E-02 | 194E-01 | Metabolome | | HMDB00017 | Cofactors and Vitamins | Vitamin B6 Metabolism |
| NEUTAB | -1.88 | 8.26E-02 | 2.97E-01 | Clinical labs | | | | |
| C12:2, OH FA | -3.62 | 8.32E-02 | 2.98E-01 | Metabolome | | | Lipid | Fatty Acid, Monohydroxy |
| C12:1 FA(1) | -2.34 | 8.43E-02 | 2.99E-01 | Metabolome | | HMDB00529 | Lipid | Medium Chain Fatty Acid |
| C8:2, OH FA(1) | 2.82 | 8.41E-02 | 2.99E-01 | Metabolome | | | Lipid | Fatty Acid, Monohydroxy |
| Bilirubin | 1.01 | 8.59E-02 | 3.02E-01 | Metabolome | C00486 | HMDB00054 | Cofactors and Vitamins | Hemoglobin and Porphyrin Metabolism |
| SERPINA7 | -3.48 | 8.58E-02 | 3.02E-01 | Proteome | | | | |
| INSF | -0.15 | 8.65E-02 | 3.02E-01 | Clinical labs | | | | |
| PG(36:0) | -1.86 | 8.64E-02 | 3.02E-01 | Metabolome | | | | |
| Dihydrofenulic acid | 1.22 | 8.70E-02 | 3.03E-01 | Metabolome | | | | |
| KVD33_3 | 2.22 | 8.99E-02 | 3.12E-01 | Proteome | | | | |
| TGLHDL | -1.36 | 9.11E-02 | 3.15E-01 | Clinical labs | | | | |
| C18:2 FA | -3.06 | 9.17E-02 | 3.16E-01 | Metabolome | C01595 | HMDB00673 | Lipid | Polyunsaturated Fatty Acid (n3 and n6) |
| MYBPC2 | 2.06 | 9.26E-02 | 3.18E-01 | Proteome | | | | |
| Dihydroxyvitamin D3(1) | 3.90 | 9.37E-02 | 3.19E-01 | Metabolome | | HMDB00430 | Cofactors and Vitamins | Vitamin D Metabolism |
| FCN3 | 3.88 | 9.38E-02 | 3.19E-01 | Proteome | | | | |
| Sphinganine | -3.97 | 9.58E-02 | 3.25E-01 | Metabolome | C00836 | HMDB00269 | Lipid | Sphingolipid Metabolism |
| C12:0, DC FA | 2.25 | 9.66E-02 | 3.26E-01 | Metabolome | C02678 | HMDB00623 | Lipid | Fatty Acid, Dicarboxylate |
| HBD | 1.99 | 9.68E-02 | 3.26E-01 | Proteome | | | | |
| PC(40:6)(2) | 3.04 | 9.71E-02 | 3.26E-01 | Metabolome | | | | |
| PROC | -0.31 | 9.84E-02 | 3.29E-01 | Clinical labs | | | | |
| K | -4.80 | 9.96E-02 | 3.32E-01 | Clinical labs | | | | |
| ITIH4 | 5.11 | 1.01E-01 | 3.34E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| LV743 | 2.64 | 1.01E-01 | 3.34E-01 | Proteome | | | | |
| C19:1 FA | -2.35 | 1.01E-01 | 3.34E-01 | Metabolome | | HMDB13622 | Lipid | Long Chain Fatty Acid |
| ALCRU | 0.03 | 1.02E-01 | 3.35E-01 | Clinical labs | | | | |
| COMP | 2.83 | 1.05E-01 | 3.41E-01 | Proteome | | | | |
| MAP4 | -1.30 | 1.04E-01 | 3.41E-01 | Proteome | | | | |
| Betaine | 6.68 | 1.07E-01 | 3.43E-01 | Metabolome | C00719 | HMDB00043 | Amino Acid | Glycine, Serine and Threonine Metabolism |
| C10:1, DC FA | 2.64 | 1.08E-01 | 3.43E-01 | Metabolome | | HMDB00603 | Lipid | Fatty Acid, Dicarboxylate |
| C24:4 FA | -2.76 | 1.06E-01 | 3.43E-01 | Metabolome | | HMDB06246 | Lipid | Polyunsaturated Fatty Acid (n3 and n6) |
| C1QB | -4.40 | 1.07E-01 | 3.43E-01 | Proteome | | | | |
| FASL | 4.00 | 1.08E-01 | 3.43E-01 | Proteome | | | | |
| IL9 | 5.26 | 1.08E-01 | 3.43E-01 | Immunome | | | | |
| PE(38:6)(1) | -2.17 | 1.06E-01 | 3.43E-01 | Metabolome | | | | |
| LysoPC(20:2) | 3.00 | 1.09E-01 | 3.44E-01 | Metabolome | C04230 | HMDB10392 | Lipid | Phospholipid Metabolism |
| GPLD1 | 3.23 | 1.09E-01 | 3.45E-01 | Proteome | | | | |
| C20:5 FA | 1.83 | 1.11E-01 | 3.46E-01 | Metabolome | C06428 | HMDB01999 | Lipid | Polyunsaturated Fatty Acid (n3 and n6) |
| N1-Methyl-2-pyridone-5-carboxamide(2) | -2.48 | 1.11E-01 | 3.46E-01 | Metabolome | C05842 | HMDB04193 | Cofactors and Vitamins | Nicolinate and Nicolinamide Metabolism |
| SM(d18:1/24:1) | -3.08 | 1.11E-01 | 3.46E-01 | Metabolome | C00550 | HMDB12107 | | |
| C20:2 FA | -2.48 | 1.11E-01 | 3.47E-01 | Metabolome | C16525 | HMDB05060 | Lipid | Polyunsaturated Fatty Acid (n3 and n6) |
| VCL | 1.27 | 1.13E-01 | 3.50E-01 | Proteome | | | | |
| F13B | -3.21 | 1.15E-01 | 3.55E-01 | Proteome | | | | |
| IGHD | 0.64 | 1.15E-01 | 3.55E-01 | Proteome | | | | |
| EFEMP1 | -0.94 | 1.16E-01 | 3.56E-01 | Proteome | | | | |
| FLNA | -0.95 | 1.16E-01 | 3.56E-01 | Proteome | | | | |
| PC(33:4)(2) | -0.68 | 1.17E-01 | 3.56E-01 | Metabolome | | | | |
| CPN1 | 4.55 | 1.18E-01 | 3.58E-01 | Proteome | | | | |
| C20:0 FA | 2.39 | 1.19E-01 | 3.59E-01 | Metabolome | C06425 | HMDB02212 | Lipid | Long Chain Fatty Acid |
| ARHGAP19 | -1.82 | 1.19E-01 | 3.59E-01 | Proteome | | | | |
| CNDP1 | 2.13 | 1.20E-01 | 3.62E-01 | Proteome | | | | |
| Cysteineglutathione disulfide | 1.51 | 1.23E-01 | 3.67E-01 | Metabolome | | HMDB00656 | Amino Acid | Glutathione Metabolism |
| CD40L | -1.93 | 1.23E-01 | 3.67E-01 | Immunome | | | | |
| C15:1 FA | -3.24 | 1.23E-01 | 3.67E-01 | Metabolome | | HMDB00329 | Lipid | Long Chain Fatty Acid |
| Phenylbutyric acid | 2.14 | 1.24E-01 | 3.67E-01 | Metabolome | | | Xenobiotics | Benzoate Metabolism |
| Hydroxybenzoic acid | -0.69 | 1.24E-01 | 3.67E-01 | Metabolome | | | Xenobiotics | Benzoate Metabolism |
| C16:0 AC | 4.61 | 1.24E-01 | 3.67E-01 | Metabolome | C02990 | HMDB00222 | Lipid | Fatty Acid Metabolism(Acyl Carnitine) |
| C12:1 AC | -2.88 | 1.25E-01 | 3.67E-01 | Metabolome | | HMDB13326 | Lipid | Fatty Acid Metabolism(Acyl Carnitine) |
| Indolelactic acid | 4.01 | 1.25E-01 | 3.68E-01 | Metabolome | C02043 | HMDB00671 | Amino Acid | Tryptophan Metabolism |
| C22:6 FA | 1.09 | 1.26E-01 | 3.68E-01 | Metabolome | C06429 | HMDB02183 | Lipid | Polyunsaturated Fatty Acid (n3 and n6) |
| ABCF1 | 1.38 | 1.27E-01 | 3.69E-01 | Proteome | | | | |
| RESISTIN | -3.04 | 1.27E-01 | 3.69E-01 | Immunome | | | | |
| Glyceric acid | -4.24 | 1.28E-01 | 3.69E-01 | Metabolome | C00258 | HMDB00139 | Carbohydrate | Glycolysis, Gluconeogenesis, and Pyruvate Metabolism |
| C14:1 FA(2) | -1.80 | 1.28E-01 | 3.69E-01 | Metabolome | C08322 | HMDB02000 | Lipid | Long Chain Fatty Acid |
| F2 | 4.91 | 1.28E-01 | 3.69E-01 | Proteome | | | | |
| Arabonate\|Xylonate(3) | 1.60 | 1.30E-01 | 3.72E-01 | Metabolome | | | Carbohydrate | Pentose Metabolism |
| SERPINA10 | -2.18 | 1.30E-01 | 3.72E-01 | Proteome | | | | |
| HPX | -4.19 | 1.31E-01 | 3.72E-01 | Proteome | | | | |
| PC(P-34:4) | -1.74 | 1.31E-01 | 3.72E-01 | Metabolome | | | | |
| TFRC | 2.37 | 1.32E-01 | 3.73E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| SERPIND1 | −4.42 | 1.36E−01 | 3.81E−01 | Proteome | | | | |
| IL12P70 | 6.41 | 1.35E−01 | 3.81E−01 | Immunome | | | | |
| Tetrahydrocortisol | −10.24 | 1.36E−01 | 3.82E−01 | Metabolome | C05472 | HMDB00949 | Lipid | Androgenic Steroids |
| Hypoxanthine | −2.29 | 1.37E−01 | 3.83E−01 | Metabolome | C00262 | HMDB00157 | Nucleotide | Purine Metabolism, (Hypo)Xanthine/Inosine containing |
| CFHR2 | −1.36 | 1.38E−01 | 3.85E−01 | Proteome | | | | |
| Hydroxyhippurate(3) | −0.61 | 1.38E−01 | 3.85E−01 | Metabolome | | | Xenobiotics | Benzoate Metabolism |
| LysoPC(20:3) | −3.81 | 1.41E−01 | 3.90E−01 | Metabolome | C04230 | HMDB10393 | Lipid | Phospholipid Metabolism |
| APOA2 | 2.50 | 1.41E−01 | 3.90E−01 | Proteome | | | | |
| Hydroxybutyric acid(1) | 3.68 | 1.41E−01 | 3.90E−01 | Metabolome | | | Amino Acid | Glutathione Metabolism |
| IL15 | 4.86 | 1.43E−01 | 3.92E−01 | Immunome | | | | |
| MG(14:1)(2) | 1.47 | 1.43E−01 | 3.92E−01 | Metabolome | | HMDB11531 | Lipid | Monoacylglycerol |
| C16:1 AC | −3.26 | 1.44E−01 | 3.92E−01 | Metabolome | | | Lipid | Fatty Acid Metabolism(Acyl Carnitine) |
| FAM3C | 1.98 | 1.45E−01 | 3.94E−01 | Proteome | | | | |
| C20:4, DC FA | 0.45 | 1.45E−01 | 3.94E−01 | Metabolome | | | Lipid | Fatty Acid, Dicarboxylate |
| APOH | −2.94 | 1.46E−01 | 3.94E−01 | Proteome | | | | |
| gamma-glutamylleucine(1) | 3.33 | 1.46E−01 | 3.95E−01 | Metabolome | | HMDB11171 | Peptide | Gamma-glutamyl Amino Acid |
| FCN2 | 1.56 | 1.47E−01 | 3.95E−01 | Proteome | | | | |
| 3-Phenylpropionate (hydrocinnamate) | 1.04 | 1.52E−01 | 4.00E−01 | Metabolome | C05629 | HMDB00764 | Xenobiotics | Benzoate Metabolism |
| C11:0, DC FA | 1.90 | 1.50E−01 | 4.00E−01 | Metabolome | | HMDB00888 | Lipid | Fatty Acid, Dicarboxylate |
| CFHR1 | −0.94 | 1.51E−01 | 4.00E−01 | Proteome | | | | |
| MYH9 | −0.91 | 1.50E−01 | 4.00E−01 | Proteome | | | | |
| PTPRC | 0.99 | 1.51E−01 | 4.00E−01 | Proteome | | | | |
| HSCRP | −0.23 | 1.51E−01 | 4.00E−01 | Clinical labs | | | | |
| Sphinganine 1-phosphate | −1.18 | 1.54E−01 | 4.03E−01 | Metabolome | C01120 | HMDB01383 | Lipid | Sphingolipid Metabolism |
| KVD28 | 1.76 | 1.54E−01 | 4.03E−01 | Proteome | | | | |
| IV151 | 1.36 | 1.53E−01 | 4.03E−01 | Proteome | | | | |
| C18:1, DC FA | 2.74 | 1.54E−01 | 4.03E−01 | Metabolome | | | Lipid | Fatty Acid, Dicarboxylate |
| Alpha-N-Phenylacetyl-L-glutamine | −1.41 | 1.56E−01 | 4.05E−01 | Metabolome | C04148 | HMDB06344 | Peptide | Acetylated Peptides |
| GC | 4.12 | 1.56E−01 | 4.05E−01 | Proteome | | | | |
| MIP1A | 2.86 | 1.57E−01 | 4.05E−01 | Proteome | | | | |
| Sulfolithocholylglycine | 1.25 | 1.58E−01 | 4.06E−01 | Metabolome | C11301 | HMD602639 | Lipid | Secondary Bile Acid Metabolism |
| Sulfolithocholylglycine | 1.25 | 1.58E−01 | 4.06E−01 | Metabolome | C11301 | HMDB02639 | Lipid | Secondary Bile Acid Metabolism |
| HABP2 | −1.93 | 1.58E−01 | 4.06E−01 | Proteome | | | | |
| LysoPE(20:2) | 1.14 | 1.60E−01 | 4.09E−01 | Metabolome | | HMDB11483 | Lipid | Phospholipid Metabolism |
| C13:0, DC FA(4) | −1.90 | 1.60E−01 | 4.09E−01 | Metabolome | | | Lipid | Fatty Acid, Dicarboxylate |
| C1QC | −2.86 | 1.61E−01 | 4.10E−01 | Proteome | | | | |
| C18:1, OH FA(1) | −4.73 | 1.61E−01 | 4.10E−01 | Metabolome | | | Lipid | Fatty Acid, Monohydroxy |
| CTTNBP2 | 0.89 | 1.63E−01 | 4.13E−01 | Proteome | | | | |
| PC(P-36:5)(2) | −0.37 | 1.64E−01 | 4.13E−01 | Metabolome | | | | |
| Sulfuric acid | −3.38 | 1.66E−01 | 4.16E−01 | Metabolome | C00059 | | Xenobiotics | Chemical |
| Sulfuric acid | −3.38 | 1.66E−01 | 4.16E−01 | Metabolome | C00059 | | Xenobiotics | Chemical |
| C14:0, OH FA(1) | −2.31 | 1.67E−01 | 4.18E−01 | Metabolome | | | Lipid | Fatty Acid, Monohydroxy |
| F11 | −2.81 | 1.68E−01 | 4.19E−01 | Proteome | | | | |
| C12:1, OH FA | −3.07 | 1.69E−01 | 4.20E−01 | Metabolome | | | Lipid | Fatty Acid, Monohydroxy |
| C18:1, 3OH FA | −1.41 | 1.69E−01 | 4.20E−01 | Metabolome | | | Lipid | Fatty Acid, Trihydroxy |
| PC(38:4)(1) | −0.23 | 1.69E−01 | 4.20E−01 | Metabolome | | | | |
| L-Tyrosine | −3.78 | 1.72E−01 | 4.20E−01 | Metabolome | C00082 | HMDB00158 | Amino Acid | Tyrosine Metabolism |
| 3-Methyl-L-histidine | 0.96 | 1.73E−01 | 4.20E−01 | Metabolome | C01152 | HMDB00479 | Amino Acid | Histidine Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| 5-Acetylamino-6-amino-3-methyluracil(2) | 0.97 | 1.73E-01 | 4.20E-01 | Metabolome | C16366 | HMDB04400 | Xenobiotics | Xanthine Metabolism |
| 9-HODE | -3.16 | 1.74E-01 | 4.20E-01 | Metabolome | C14826 | HMDB04702 | Lipid | Long Chain Fatty Acid |
| LysoPC(20:4) | -3.32 | 1.74E-01 | 4.20E-01 | Metabolome | C04230 | HMDB10395 | Lipid | Phospholipid Metabolism |
| Tryptophan betaine | 0.47 | 1.72E-01 | 4.20E-01 | Metabolome | C09213 | HMDB61115 | Amino Acid | Tryptophan Metabolism |
| CD5L | -1.36 | 1.72E-01 | 4.20E-01 | Proteome | | | | |
| F12 | -2.37 | 1.70E-01 | 4.20E-01 | Proteome | | | | |
| IGFBP3 | 2.47 | 1.74E-01 | 4.20E-01 | Proteome | | | | |
| C16:0, 2OH FA(2) | -1.91 | 1.73E-01 | 4.20E-01 | Metabolome | | | Lipid | Fatty Acid, Dihydroxy |
| ATP11B | 4.88 | 1.76E-01 | 4.24E-01 | Proteome | | | | |
| GAPDH | -0.81 | 1.77E-01 | 4.25E-01 | Proteome | | | | |
| IL1RA | 4.42 | 1.78E-01 | 4.26E-01 | Immunome | | | | |
| Palmitoylglycine | -3.61 | 1.79E-01 | 4.27E-01 | Metabolome | | | HMDB13034 | Lipid | Fatty Acid Metabolism(Acyl Glycine) |
| L-Cysteinylglycine disulfide | -3.33 | 1.81E-01 | 4.29E-01 | Metabolome | | HMDB00709 | Amino Acid | Glutathione Metabolism |
| Piperine(2) | -1.01 | 1.80E-01 | 4.29E-01 | Metabolome | C03882 | HMDB629377 | Xenobiotics | Food Component/Plant |
| CA | -4.09 | 1.84E-01 | 4.35E-01 | Clinical labs | | | | |
| C19:0 FA(2) | 2.77 | 1.86E-01 | 4.37E-01 | Metabolome | C16535 | HMDB00772 | Lipid | Long Chain Fatty Acid |
| PROZ | -1.03 | 1.86E-01 | 4.37E-01 | Proteome | | | | |
| BUN | 0.36 | 1.85E-01 | 4.37E-01 | Clinical labs | | | | |
| KRT17 | -0.62 | 1.87E-01 | 4.37E-01 | Proteome | | | | |
| p-Cresol sulfate | -0.98 | 1.87E-01 | 4.38E-01 | Metabolome | | HMDB11635 | Amino Acid | Tyrosine Metabolism |
| C8:0, OH FA(2) | 2.31 | 1.91E-01 | 4.46E-01 | Metabolome | | | Lipid | Fatty Acid, Monohydroxy |
| C10:0, DC FA (Sebacic acid)(2) | 1.98 | 1.93E-01 | 4.50E-01 | Metabolome | C08277 | HMDB00792 | Lipid | Fatty Acid, Dicarboxylate |
| C12:0, OH FA(1) | -2.04 | 1.94E-01 | 4.50E-01 | Metabolome | | HMDB00387 | Lipid | Fatty Acid, Monohydroxy |
| MG(14:1)(3) | -3.00 | 1.95E-01 | 4.50E-01 | Metabolome | | HMDB11531 | Lipid | Monoacylglycerol |
| CFH | -3.97 | 1.96E-01 | 4.53E-01 | Proteome | | | | |
| C14:0 AC | 3.02 | 1.97E-01 | 4.53E-01 | Metabolome | | HMDB05066 | Lipid | Fatty Acid Metabolism(Acyl Carnitine) |
| C10:1 FA(2) | -2.14 | 1.99E-01 | 4.57E-01 | Metabolome | | | Lipid | Medium Chain Fatty Acid |
| AHSG | 3.83 | 2.036-01 | 4.64E-01 | Proteome | | | | |
| Taurine | -4.43 | 2.04E-01 | 4.65E-01 | Metabolome | C00245 | HMDB00251 | Amino Acid | Methionine, Cysteine, SAM and Taurine Metabolism |
| APOF | 2.37 | 2.04E-01 | 4.65E-01 | Proteome | | | | |
| C11:0 AC | 1.70 | 2.06E-01 | 4.69E-01 | Metabolome | | | Lipid | Fatty Acid Metabolism(Acyl Carnitine) |
| IL5 | 4.30 | 2.07E-01 | 4.70E-01 | Immunome | | | | |
| 2, 3-Dihydroxyvaleric acid(1) | 1.15 | 2.09E-01 | 4.70E-01 | Metabolome | C04039 | HMDB00421 | Cofactors and Vitamins | Pantothenate and CoA Metabolism |
| LysoPG(18:0) | -2.77 | 2.09E-01 | 4.70E-01 | Metabolome | | | Lipid | Phospholipid Metabolism |
| PE(P-38:5)(1) | -2.18 | 2.08E-01 | 4.70E-01 | Metabolome | | | | |
| LIF | 3.22 | 2.14E-01 | 4.61E-01 | Immunome | | | | |
| FGFB | 5.06 | 2.16E-01 | 4.63E-01 | Immunome | | | | |
| KVD16 | 1.99 | 2.19E-01 | 4.69E-01 | Proteome | | | | |
| PC(38:6)(2) | -0.21 | 2.21E-01 | 4.92E-01 | Metabolome | | | | |
| IGHG4 | 0.95 | 2.22E-01 | 4.93E-01 | Proteome | | | | |
| Chenodeoxycholic acid 3-sulfate | 0.92 | 2.22E-01 | 4.93E-01 | Metabolome | C11301 | HMDB02639 | Lipid | Secondary Bile Acid Metabolism |
| 3-carboxy-4-methyl-5-propyl-2-furanpropanoate (CMPF) | 0.83 | 2.24E-01 | 4.94E-01 | Metabolome | | HMDB61112 | Lipid | Fatty Acid Dicarboxylate |
| C22:2 FA | -1.80 | 2.27E-01 | 4.97E-01 | Metabolome | | HMDB61714 | Lipid | Polyunsaturated Fatty Acid (n3 and n6) |
| APOC2 | 1.80 | 2.27E-01 | 4.97E-01 | Proteome | | | | |
| CFI | -3.65 | 2.27E-01 | 4.97E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| 25-hydroxyvitamin D3 | 1.31 | 2.26E-01 | 4.97E-01 | Metabolome | C04317 | | Cofactors and Vitamins | Vitamin D Metabolism |
| LysoPC(O-18:0) | 1.93 | 2.28E-01 | 4.98E-01 | Metabolome | | HMDB11149 | Lipid | Phospholipid Metabolism |
| KV315 | 1.69 | 2.28E-01 | 4.98E-01 | Proteome | | | | |
| KV320 | 1.10 | 2.31E-01 | 5.02E-01 | Proteome | | | | |
| L-Valine | 3.51 | 2.32E-01 | 5.03E-01 | Metabolome | C00183 | HMDB00883 | Amino Acid | Leucine, Isoleucine and Valine Metabolism |
| gamma-glutamylthreonine(2) | 2.01 | 2.33E-01 | 5.04E-01 | Metabolome | | HMDB29159 | Peptide | Gamma-glutamyl Amino Acid |
| MCHC | 1.73 | 2.33E-01 | 5.04E-01 | Clinical labs | | | | |
| FERMT3 | 1.04 | 2.35E-01 | 5.07E-01 | Proteome | | | | |
| C13:0, DC FA(1) | 4.20 | 2.36E-01 | 5.07E-01 | Metabolome | | | Lipid | Fatty Acid, Dicarboxylate |
| CPB2 | 3.09 | 2.38E-01 | 5.10E-01 | Proteome | | | | |
| C16:1, OH FA(1) | -3.81 | 2.39E-01 | 5.11E-01 | Metabolome | | | Lipid | Fatty Acid, Monohydroxy |
| Glycine | -4.38 | 2.40E-01 | 5.12E-01 | Metabolome | C00037 | HMDB00123 | Amino Acid | Glycine, Serine and Threonine Metabolism |
| SAA1 | -0.80 | 2.41E-01 | 5.13E-01 | Proteome | | | | |
| C18:2, OH FA | -3.43 | 2.42E-01 | 5.13E-01 | Metabolome | | | Lipid | Fatty Acid, Monohydroxy |
| Fructoselysine | -1.69 | 2.44E-01 | 5.18E-01 | Metabolome | C16488 | | Carbohydrate | Pentose Metabolism |
| TYMP | -0.70 | 2.45E-01 | 5.18E-01 | Proteome | | | | |
| MONO | -0.68 | 2.47E-01 | 5.21E-01 | Clinical labs | | | | |
| IGHM | -1.55 | 2.49E-01 | 5.24E-01 | Proteome | | | | |
| PFN1 | -0.79 | 2.51E-01 | 5.25E-01 | Proteome | | | | |
| RYR2 | 1.50 | 2.51E-01 | 5.25E-01 | Proteome | | | | |
| IL22 | 0.96 | 2.50E-01 | 5.25E-01 | Immunome | | | | |
| Allantoin | 1.08 | 2.54E-01 | 5.29E-01 | Metabolome | C01551 | HMDB00462 | Nucleotide | Purine Metabolism, (Hypo)Xanthine/Inosine containing |
| SERPINA6 | 2.35 | 2.56E-01 | 5.33E-01 | Proteome | | | | |
| LysoPC(20:5) | 0.77 | 2.57E-01 | 5.34E-01 | Metabolome | C04230 | HMDB10397 | Lipid | Phospholipid Metabolism |
| C6 | 3.96 | 2.62E-01 | 5.43E-01 | Proteome | | | | |
| B2M | 1.27 | 2.63E-01 | 5.44E-01 | Proteome | | | | |
| C4B | 1.27 | 2.68E-01 | 5.52E-01 | Proteome | | | | |
| C10:3 FA(2) | -1.69 | 2.70E-01 | 5.55E-01 | Metabolome | | | Lipid | Medium Chain Fatty Acid |
| Taurocholic acid(1) | -0.54 | 2.72E-01 | 5.56E-01 | Metabolome | C05122 | HMDB00036 | Lipid | Primary Bile Acid Metabolism |
| GPR116 | 1.24 | 2.71E-01 | 5.56E-01 | Proteome | | | | |
| Quinic acid | 0.57 | 2.73E-01 | 5.58E-01 | Metabolome | C06746 | HMDB03072 | Xenobiotics | Food Component/Plant |
| gamma-glutamylthreonine(1) | -2.77 | 2.75E-01 | 5.61E-01 | Metabolome | | HMDB29159 | Peptide | Gamma-glutamyl Amino Acid |
| Hydroxyphenyllactic acid | 2.82 | 2.77E-01 | 5.63E-01 | Metabolome | C03672 | HMDB00755 | Amino Acid | Tyrosine Metabolism |
| Piperine(1) | -0.67 | 2.79E-01 | 5.66E-01 | Metabolome | C03882 | HMDB29377 | Xenobiotics | Food Component/Plant |
| ALB.y | 2.56 | 2.82E-01 | 5.71E-01 | Proteome | | | | |
| 2-Piperidinone | -1.16 | 2.83E-01 | 5.72E-01 | Metabolome | | HMDB11749 | Xenobiotics | Food Component/Plant |
| gamma-glutamylleucine(2) | 2.17 | 2.85E-01 | 5.75E-01 | Metabolome | | HMDB11171 | Peptide | Gamma-glutamyl Amino Acid |
| Cys-Gly or Gly-Cys | -2.75 | 2.86E-01 | 5.75E-01 | Metabolome | | | Peptide | Dipeptide |
| GP1BA | 1.46 | 2.86E-01 | 5.75E-01 | Proteome | | | | |
| HV434 | 1.56 | 2.90E-01 | 5.80E-01 | Proteome | | | | |
| C16:4 FA | 1.17 | 2.91E-01 | 5.81E-01 | Metabolome | | | Lipid | Long Chain Fatty Acid |
| Xanthine | -2.40 | 2.95E-01 | 5.87E-01 | Metabolome | C00385 | HMDB00292 | Nucleotide | Purine Metabolism, (Hypo)Xanthine/Inosine containing |
| 4-formyl Indole(1) | -1.94 | 2.96E-01 | 5.88E-01 | Metabolome | | | Amino Acid | Tryptophan Metabolism |
| BDNF | 1.78 | 2.98E-01 | 5.91E-01 | Immunome | | | | |
| 1-Methylxanthine | -0.68 | 2.99E-01 | 5.91E-01 | Metabolome | C16358 | HMDB10738 | Xenobiotics | Xanthine Metabolism |
| IL18 | 4.10 | 2.99E-01 | 5.91E-01 | Immunome | | | | |
| 2-Aminobutyrate | 2.25 | 3.01E-01 | 5.92E-01 | Metabolome | C02261 | HMDB00650 | Amino Acid | Glutathione Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| LysoPC(15:0) | −2.37 | 3.01E−01 | 5.92E−01 | Metabolome | C04230 | HMDB10381 | Lipid | Phospholipid Metabolism |
| C10:0 AC | −1.54 | 3.03E−01 | 5.94E−01 | Metabolome | | HMDB00651 | Lipid | Fatty Acid Metabolism(Acyl Carnitine) |
| Pro-Cys or Cys-Pro | 1.98 | 3.03E−01 | 5.94E−01 | Metabolome | | HMDB28783|HMDB29014 | Peptide | Dipeptide |
| Retinol (Vitamin A) | 2.55 | 3.05E−01 | 5.96E−01 | Metabolome | C00473 | HMDB00305 | Cofactors and Vitamins | Vitamin A Metabolism |
| Gentisic acid | 1.10 | 3.09E−01 | 6.00E−01 | Metabolome | C00628 | HMDB00152 | Amino Acid | Tyrosine Metabolism |
| CDHR5 | −1.63 | 3.09E−01 | 6.00E−01 | Proteome | | | | |
| LV321 | −0.76 | 3.08E−01 | 6.00E−01 | Proteome | | | | |
| Tauroursodeoxycholic acid | −0.57 | 3.12E−01 | 6.04E−01 | Metabolome | | HMDB00874 | Lipid | Secondary Bile Acid Metabolism |
| C12:0, OH FA(2) | 2.29 | 3.13E−01 | 6.06E−01 | Metabolome | | HMDB00387 | Lipid | Fatty Acid, Monohydroxy |
| Creatinine | 4.07 | 3.15E−01 | 6.08E−01 | Metabolome | C00791 | HMDB00562 | Amino Acid | Creatine Metabolism |
| LysoPC(22:0) | 0.56 | 3.18E−01 | 6.12E−01 | Metabolome | C04230 | HMDB10398 | Lipid | Phospholipid Metabolism |
| LysoPC(16:1) | −1.95 | 3.20E−01 | 6.13E−01 | Metabolome | C04230 | HMDB10383 | Lipid | Phospholipid Metabolism |
| EOSAB | −5.86 | 3.20E−01 | 6.13E−01 | Clinical labs | | | | |
| HV169 | 0.98 | 3.21E−01 | 6.14E−01 | Proteome | | | | |
| VTN | −2.59 | 3.22E−01 | 6.14E−01 | Proteome | | | | |
| PC(P-38:6) | −0.19 | 3.22E−01 | 6.14E−01 | Metabolome | | | | |
| Dehydroisoandrosterone sulfate (DHEA-S)(2) | 0.74 | 3.24E−01 | 6.14E−01 | Metabolome | C04555 | HMDB01032 | Lipid | Androgenic Steroids |
| PC(P-36:5)(1) | 0.25 | 3.23E−01 | 6.14E−01 | Metabolome | | | | |
| C25:0, OH FA | −1.31 | 3.25E−01 | 6.15E−01 | Metabolome | | | Lipid | Fatty Acid, Monohydroxy |
| TLN1 | −0.60 | 3.27E−01 | 6.19E−01 | Proteome | | | | |
| TTN | 0.89 | 3.30E−01 | 6.21E−01 | Proteome | | | | |
| MYH7 | −1.07 | 3.36E−01 | 6.33E−01 | Proteome | | | | |
| Uracil | 3.09 | 3.40E−01 | 6.36E−01 | Metabolome | C00106 | HMDB00300 | Nucleotide | Pyrimidine Metabolism, Uracil containing |
| LysoPE(16:0) | 0.81 | 3.40E−01 | 6.36E−01 | Metabolome | | HMDB11473 | Lipid | Phospholipid Metabolism |
| IGHG3 | −0.80 | 3.41E−01 | 6.36E−01 | Proteome | | | | |
| SERPINF1 | −2.18 | 3.39E−01 | 6.36E−01 | Proteome | | | | |
| 4-Hydroxyproline | −1.76 | 3.42E−01 | 6.38E−01 | Metabolome | C01157 | HMDB00725 | Amino Acid | Urea cycle; Arginine and Proline Metabolism |
| 2,3-Dihydroxyvaleric acid(2) | 0.55 | 3.52E−01 | 6.50E−01 | Metabolome | C04039 | HMDB00421 | Cofactors and Vitamins | Pantothenate and CoA Metabolism |
| LysoPC(P-16:0) | 2.73 | 3.52E−01 | 6.50E−01 | Metabolome | C04230 | HMDB10407 | Lipid | Phospholipid Metabolism |
| AZGP1 | 1.02 | 3.51E−01 | 6.50E−01 | Proteome | | | | |
| IL21 | 2.44 | 3.51E−01 | 6.50E−01 | Immunome | | | | |
| IGHG2 | 1.02 | 3.53E−01 | 6.51E−01 | Proteome | | | | |
| LV325 | 1.58 | 3.54E−01 | 6.52E−01 | Proteome | | | | |
| IL4 | 4.75 | 3.55E−01 | 6.52E−01 | Immunome | | | | |
| C5 | −3.92 | 3.57E−01 | 6.54E−01 | Proteome | | | | |
| PRG4 | −1.08 | 3.57E−01 | 6.54E−01 | Proteome | | | | |
| IGF2R | 0.64 | 3.62E−01 | 6.61E−01 | Proteome | | | | |
| PIGR | −0.78 | 3.64E−01 | 6.63E−01 | Proteome | | | | |
| C20:1 FA | −1.26 | 3.66E−01 | 6.64E−01 | Metabolome | C16526 | HMDB02231 | Lipid | Long Chain Fatty Acid |
| C17:0 FA(1) | −1.68 | 3.66E−01 | 6.64E−01 | Metabolome | | | Lipid | Long Chain Fatty Acid |
| HV330 | 0.95 | 3.70E−01 | 6.69E−01 | Proteome | | | | |
| Caffeine | −0.43 | 3.71E−01 | 6.70E−01 | Metabolome | C07481 | HMDB01847 | Xenobiotics | Xanthine Metabolism |
| C4BPA | −1.90 | 3.72E−01 | 6.70E−01 | Proteome | | | | |
| KNG1_2 | 0.90 | 3.72E−01 | 6.70E−01 | Proteome | | | | |
| 5-oxoproline | 2.49 | 3.75E−01 | 6.72E−01 | Metabolome | C01879 | HMDB00267 | Amino Acid | Glutathione Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| C5:1 AC | 0.89 | 3.76E-01 | 6.72E-01 | Metabolome | | HM0B02366 | Lipid | Fatty Acid Metabolism(Acyl Carnitine) |
| MCP1 | 1.41 | 3.75E-01 | 6.72E-01 | Immunome | | | | |
| C10:0, OH FA(1) | -1.62 | 3.78E-01 | 6.74E-01 | Metabolome | | HMDB02203 | Lipid | Fatty Acid, Monohydroxy |
| C14:2, OH FA | -1.63 | 3.78E-01 | 6.74E-01 | Metabolome | | | Lipid | Fatty Acid, Monohydroxy |
| CL | -0.45 | 3.80E-01 | 6.76E-01 | Clinical labs | | | | |
| Alliin | 0.73 | 3.83E-01 | 6.79E-01 | Metabolome | C08265 | HMDB33592 | Xenobiotics | |
| C2 | 3.21 | 3.83E-01 | 6.79E-01 | Proteome | | | | |
| 16a-hydroxy DHEA 3-sulfate | -1.08 | 3.85E-01 | 6.61E-01 | Metabolome | | | Lipid | Androgenic Steroids |
| Sulfolithocholic acid | 0.78 | 3.88E-01 | 6.84E-01 | Metabolome | | | Lipid | Secondary Bile Acid Metabolism |
| L-Lysine | -3.47 | 3.90E-01 | 6.88E-01 | Metabolome | C00047 | HMDB00182 | Amino Acid | Lysine Metabolism |
| INSU | -0.85 | 3.93E-01 | 6.90E-01 | Clinical labs | | | | |
| C20:4, OH FA(1) | -1.73 | 3.94E-01 | 6.91E-01 | Metabolome | | | Lipid | Fatty Acid, Monohydroxy |
| MG(14:1)(1) | 1.53 | 3.94E-01 | 6.91E-01 | Metabolome | | HMDB11531 | Lipid | Monoacylglycerol |
| PCOLCE | 1.06 | 3.97E-01 | 6.94E-01 | Proteome | | | | |
| C18:0, DC FA(3) | 1.23 | 4.02E-01 | 6.96E-01 | Metabolome | | HMDB00782 | Lipid | Fatty Acid, Dicarboxylate |
| LysoPE(22:6) | -1.80 | 4.02E-01 | 6.96E-01 | Metabolome | | HMDB11496 | Lipid | Phospholipid Metabolism |
| FGG | -1.64 | 4.02E-01 | 6.96E-01 | Proteome | | | | |
| KLKB1 | -2.23 | 4.03E-01 | 6.96E-01 | Proteome | | | | |
| NUP205 | -1.11 | 4.02E-01 | 6.96E-01 | Proteome | | | | |
| IL31 | 2.46 | 3.99E-01 | 6.96E-01 | Immunome | | | | |
| Phenylpyruvic acid | 1.77 | 4.05E-01 | 6.99E-01 | Metabolome | C00166 | HMDB00205 | Amino Acid | Phenylalanine Metabolism |
| HV323 | 1.23 | 4.08E-01 | 7.02E-01 | Proteome | | | | |
| C14:2 AC | -1.29 | 4.10E-01 | 7.05E-01 | Metabolome | | HMDB13331 | Lipid | Fatty Acid Metabolism(Acyl Carnitine) |
| Uridine | 2.51 | 4.12E-01 | 7.05E-01 | Metabolome | C00299 | HMDB00296 | Nucleotide | Pyrimidine Metabolism, Uracil containing |
| ALT | 0.07 | 4.12E-01 | 7.05E-01 | Clinical labs | | | | |
| PLG | 2.51 | 4.13E-01 | 7.06E-01 | Proteome | | | | |
| KNG1 | -2.18 | 4.16E-01 | 7.08E-01 | Proteome | | | | |
| IP10 | -1.44 | 4.16E-01 | 7.08E-01 | Immunome | | | | |
| C10:2 FA | 1.04 | 4.17E-01 | 7.08E-01 | Metabolome | | | Lipid | Medium Chain Fatty Acid |
| BASO | 2.77 | 4.19E-01 | 7.10E-01 | Clinical labs | | | | |
| DYNC1H1 | -0.75 | 4.23E-01 | 7.16E-01 | Proteome | | | | |
| IFNA | 3.78 | 4.25E-01 | 7.16E-01 | Immunome | | | | |
| PDGFBB | 1.13 | 4.24E-01 | 7.16E-01 | Immunome | | | | |
| Glycocholic acid | -0.49 | 4.29E-01 | 7.17E-01 | Metabolome | C01921 | HMDB00138 | Lipid | Primary Bile Acid Metabolism |
| L-Serine | 2.56 | 4.26E-01 | 7.17E-01 | Metabolome | C00065 | HMDB00187 | Amino Acid | Glycine, Serine and Threonine Metabolism |
| 5-Acetylamino-6-amino-3-methyluracil(1) | -0.46 | 4.27E-01 | 7.17E-01 | Metabolome | C16366 | HMDB04400 | Xenobiotics | Xanthine Metabolism |
| CDK5RAP2 | 0.70 | 4.29E-01 | 7.17E-01 | Proteome | | | | |
| C9:1, OH FA | -1.62 | 4.27E-01 | 7.17E-01 | Metabolome | | | Lipid | Fatty Acid, Monohydroxy |
| NEUT | 0.11 | 4.34E-01 | 7.20E-01 | Clinical labs | | | | |
| N-acetylthreonine | -0.75 | 4.32E-01 | 7.20E-01 | Metabolome | | | Amino Acid | Glycine, Serine and Threonine Metabolism |
| C20:3, OH FA(2) | -0.95 | 4.33E-01 | 7.20E-01 | Metabolome | | | Lipid | Fatty Acid, Monohydroxy |
| L-Formylkynurenine | 0.83 | 4.35E-01 | 7.21E-01 | Metabolome | C02700 | HMDB60485 | Amino Acid | Tryptophan Metabolism |
| Hydroxyhippurate(2) | 0.99 | 4.35E-01 | 7.21E-01 | Metabolome | | | Xenobiotics | Benzoate Metabolism |
| Tetrahydroaldosterone-3-glucuronide(1) | -1.81 | 4.37E-01 | 7.22E-01 | Metabolome | | HMDB10357 | Lipid | Androgenic Steroids |
| LDHB | -0.39 | 4.39E-01 | 7.22E-01 | Proteome | | | | |
| HGF | -1.89 | 4.39E-01 | 7.22E-01 | Immunome | | | | |
| Aminoadipic acid | 0.85 | 4.43E-01 | 7.23E-01 | Metabolome | C00956 | HMDB00510 | Amino Acid | Lysine Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| 3-indoxyl sulfate | -1.07 | 4.51E-01 | 7.23E-01 | Metabolome | | HMDB00682 | Amino Acid | Tryptophan Metabolism |
| C8:0 AC(2) | -0.85 | 4.44E-01 | 7.23E-01 | Metabolome | C02838 | HMDB00791 | Lipid | Fatty Acid Metabolism(Acyl Carnitine) |
| C14:1 AC | -1.24 | 4.49E-01 | 7.23E-01 | Metabolome | | HMDB02014 | Lipid | Fatty Acid Metabolism(Acyl Carnitine) |
| Epsilon-(gamma-Glutamyl)-lysine | -1.34 | 4.47E-01 | 7.23E-01 | Metabolome | C16513 | HMDB03869 | Peptide | Gamma-glutamyl Amino Acid |
| C22:5 FA | -1.37 | 4.42E-01 | 7.23E-01 | Metabolome | C17337 | HMDB06528 | Lipid | Polyunsaturated Fatty Acid (n3 and n6) |
| 7-alpha-hydroxy-3-oxo-4-cholestenoate (7-Hoca) | -2.02 | 4.51E-01 | 7.23E-01 | Metabolome | | HMDB12458 | Lipid | Sterol |
| Homostachydrine | 0.89 | 4.49E-01 | 7.23E-01 | Metabolome | C08283 | HMDB33433 | Xenobiotics | Food Component/Plant |
| CD14 | -1.04 | 4.49E-01 | 7.23E-01 | Proteome | | | | |
| CFD | 0.63 | 4.44E-01 | 7.23E-01 | Proteome | | | | |
| CFHR5 | 1.00 | 4.40E-01 | 7.23E-01 | Proteome | | | | |
| ENO1 | -1.19 | 4.51E-01 | 7.23E-01 | Proteome | | | | |
| IGHA1 | 1.00 | 4.48E-01 | 7.23E-01 | Proteome | | | | |
| ITIH3 | 1.80 | 4.47E-01 | 7.23E-01 | Proteome | | | | |
| LGALS3BP | -1.06 | 4.48E-01 | 7.23E-01 | Proteome | | | | |
| MG(18:3) | 0.88 | 4.53E-01 | 7.24E-01 | Metabolome | | HMDB11539 | Lipid | Monoacylglycerol |
| FBLN1 | -2.61 | 4.54E-01 | 7.24E-01 | Proteome | | | | |
| PE(P-40:6)(1) | 0.20 | 4.54E-01 | 7.24E-01 | Metabolome | | | | |
| MG(20:0) | -0.50 | 4.55E-01 | 7.25E-01 | Metabolome | | HMDB11542 | Lipid | Monoacylglycerol |
| TPM4 | 0.48 | 4.56E-01 | 7.25E-01 | Proteome | | | | |
| A2M | 1.94 | 4.59E-01 | 7.28E-01 | Proteome | | | | |
| Chenodeoxycholic Acid(1) | -0.69 | 4.71E-01 | 7.39E-01 | Metabolome | C02528 | HMDB00518 | Lipid | Primary Bile Acid Metabolism |
| CFB | -2.26 | 4.70E-01 | 7.39E-01 | Proteome | | | | |
| SERPINA1 | 1.67 | 4.70E-01 | 7.39E-01 | Proteome | | | | |
| IL17A | -1.57 | 4.70E-01 | 7.39E-01 | Immunome | | | | |
| UALB | 0.05 | 4.70E-01 | 7.39E-01 | Clinical labs | | | | |
| C20:4, OH FA(2) | 1.37 | 4.68E-01 | 7.39E-01 | Metabolome | | HMDB01868 | Lipid | Fatty Acid, Monohydroxy |
| 5-Methoxysalicylic acid | -0.91 | 4.74E-01 | 7.40E-01 | Metabolome | | HMDB11756 HMDB61684 | Xenobiotics | Benzoate Metabolism |
| N-Acetylleucine|N-Acetylisoleucine | 1.71 | 4.73E-01 | 7.40E-01 | Metabolome | C02710 | | Amino Acid | Leucine, Isoleucine and Valine Metabolism |
| CRISP3 | 0.63 | 4.75E-01 | 7.40E-01 | Proteome | | | | |
| INPP5E | 0.78 | 4.74E-01 | 7.40E-01 | Proteome | | | | |
| LysoPE(20:1) | 1.56 | 4.77E-01 | 7.43E-01 | Metabolome | | HMDB11482 | Lipid | Phospholipid Metabolism |
| Butyric acid|Isobutyric acid | 1.97 | 4.80E-01 | 7.45E-01 | Metabolome | C00246|C02632 | HMDB00039|HMDB01873 | Energy | Butanoate metabolism |
| PROS1 | -1.38 | 4.81E-01 | 7.45E-01 | Proteome | | | | |
| C8:0, OH FA(3) | -0.46 | 4.83E-01 | 7.45E-01 | Metabolome | | HMDB10382 | Lipid | Fatty Acid, Monohydroxy |
| LysoPC(16:0) | 3.07 | 4.84E-01 | 7.46E-01 | Metabolome | C04230 | HMDB10382 | Lipid | Phospholipid Metabolism |
| Cys Gly | 1.61 | 4.84E-01 | 7.46E-01 | Metabolome | C01419 | HMDB00078 | Amino Acid | Glutathione Metabolism |
| F7 | 0.49 | 4.84E-01 | 7.46E-01 | Proteome | | | | |
| KV320.2 | -0.69 | 4.89E-01 | 7.53E-01 | Proteome | | | | |
| 3-O-Sulfogalactosylceramide (d18:1/24:0) | 0.24 | 4.93E-01 | 7.56E-01 | Metabolome | C06125 | HMDB00024 | Lipid | |
| Dihydro-3-coumaric acid | 0.54 | 4.93E-01 | 7.56E-01 | Metabolome | C11457 | | Xenobiotics | Benzoate Metabolism |
| L-Carnitine | -1.46 | 4.96E-01 | 7.58E-01 | Metabolome | C00318 | HMDB00062 | Lipid | Carnitine Metabolism |
| C4BPB | -1.82 | 4.97E-01 | 7.58E-01 | Proteome | | | | |
| FCGBP | -0.68 | 4.98E-01 | 7.58E-01 | Proteome | | | | |
| CO2 | 0.33 | 4.96E-01 | 7.58E-01 | Clinical labs | | | | |
| KV311 | 0.80 | 5.02E-01 | 7.63E-01 | Proteome | | | | |
| LysoPC(17:0) | 1.53 | 5.03E-01 | 7.63E-01 | Metabolome | C04230 | HMDB12108 | Lipid | Phospholipid Metabolism |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| NCAM1 | 0.41 | 5.04E-01 | 7.63E-01 | Proteome | | | | |
| AFM | -1.05 | 5.05E-01 | 7.64E-01 | Proteome | | | | |
| Thyroxine | -1.06 | 5.08E-01 | 7.67E-01 | Metabolome | C01829 | HMDB01918 | Amino Acid | Tyrosine Metabolism |
| Pipecolic acid | 0.93 | 5.19E-01 | 7.75E-01 | Metabolome | C00408 | HMDB00070 | Amino Acid | Lysine Metabolism |
| N-Acetyl-L-phenylalanine | -1.43 | 5.15E-01 | 7.75E-01 | Metabolome | C03519 | HMDB00512 | Amino Acid | Phenylalanine Metabolism |
| Pseudouridine | -1.23 | 5.14E-01 | 7.75E-01 | Metabolome | C02067 | HMDB00767 | Nucleotide | Pyrimidine Metabolism, Uracil containing |
| AFG3L2 | 0.60 | 5.19E-01 | 7.75E-01 | Proteome | | | | |
| APOL1 | 1.71 | 5.17E-01 | 7.75E-01 | Proteome | | | | |
| KV230 | -0.53 | 5.20E-01 | 7.75E-01 | Proteome | | | | |
| SH3GL3 | -0.43 | 5.16E-01 | 7.75E-01 | Proteome | | | | |
| UALBCR | 0.01 | 5.20E-01 | 7.75E-01 | Clinical labs | | | | |
| MCSF | 1.95 | 5.21E-01 | 7.76E-01 | Immunome | | | | |
| Indoleacetyl glutamine | -0.41 | 5.27E-01 | 7.83E-01 | Metabolome | | HMDB13240 | Amino Acid | Tryptophan Metabolism |
| HDL | -0.05 | 5.33E-01 | 7.90E-01 | Clinical labs | | | | |
| Citric acid | -2.41 | 5.36E-01 | 7.93E-01 | Metabolome | C00158 | HMDB00094 | Energy | TCA Cycle |
| C16:0, OH FA(1) | 1.97 | 5.37E-01 | 7.93E-01 | Metabolome | | HMDB31057 | Lipid | Fatty Acid, Monohyroxy |
| F5 | -1.33 | 5.36E-01 | 7.93E-01 | Proteome | | | | |
| SHBG | -0.73 | 5.38E-01 | 7.93E-01 | Proteome | | | | |
| SCF | 1.92 | 5.39E-01 | 7.93E-01 | Immunome | | | | |
| LV147 | 0.92 | 5.41E-01 | 7.94E-01 | Proteome | | | | |
| Gluconic acid | 0.13 | 5.43E-01 | 7.94E-01 | Metabolome | C00257 | HMDB00625 | Carbohydrate | Pentose Metabolism |
| MAN2B2 | -0.49 | 5.44E-01 | 7.94E-01 | Proteome | | | | |
| LDL | 0.02 | 5.43E-01 | 7.94E-01 | Clinical labs | | | | |
| C12:0 FA(2) | -1.04 | 5.42E-01 | 7.94E-01 | Metabolome | | | Lipid | Medium Chain Fatty Acid |
| 4-Methylcatechol sulfate | -0.58 | 5.49E-01 | 8.00E-01 | Metabolome | C08261 | HMDB00784 | Xenobiotics | Benzoate Metabolism |
| Homoarginine | 1.14 | 5.50E-01 | 8.00E-01 | Metabolome | C01924 | HMDB00670 | Amino Acid | Urea cycle; Arginine and Proline Metabolism |
| C8:2, OH FA(2) | 0.73 | 5.51E-01 | 8.00E-01 | Metabolome | | | Lipid | Fatty Acid, Monohydroxy |
| MG(16:1) | -0.72 | 5.52E-01 | 8.00E-01 | Metabolome | | HMDB11534 | Lipid | Monoacylglycerol |
| APOC1 | 0.92 | 5.53E-01 | 8.01E-01 | Proteome | | | | |
| L-α-glutamyl-L-Lysine | 1.68 | 5.55E-01 | 8.02E-01 | Metabolome | C04700 | HMDB04207 | Peptide | Dipeptide |
| SAA4 | -1.10 | 5.56E-01 | 8.02E-01 | Proteome | | | | |
| KVD33_4 | -0.54 | 5.59E-01 | 8.05E-01 | Proteome | | | | |
| ORM1 | -1.03 | 5.59E-01 | 8.05E-01 | Proteome | | | | |
| C9:0, DC FA (Azelaic acid) | -1.45 | 5.62E-01 | 8.07E-01 | Metabolome | | HMDB00784 | Lipid | Fatty Acid, Dicarboxylate |
| LDLHDL | 0.76 | 5.63E-01 | 8.07E-01 | Clinical labs | | | | |
| IL8 | 1.18 | 5.67E-01 | 8.10E-01 | Immunome | | | | |
| C12:1, DC FA(2) | 0.70 | 5.67E-01 | 8.10E-01 | Metabolome | | | Lipid | Fatty Acid, Dicarboxylate |
| PI16 | -0.57 | 5.69E-01 | 8.12E-01 | Proteome | | | | |
| N6-Acetyl-L-Lysine | -2.06 | 5.71E-01 | 8.13E-01 | Metabolome | C02727 | HMDB00206 | Amino Acid | Lysine Metabolism |
| C16:0, DC FA(2) | 1.36 | 5.78E-01 | 8.16E-01 | Metabolome | C19615 | HMDB00672 | Lipid | Fatty Acid, Dicarboxylate |
| C14:0, DC FA(2) | 1.05 | 5.79E-01 | 8.16E-01 | Metabolome | | HMDB00872 | Lipid | Fatty Acid, Dicarboxylate |
| LysoPE(22:0) | -1.17 | 5.80E-01 | 8.16E-01 | Metabolome | | HMDB11490 | Lipid | Phospholipid Metabolism |
| MG(24:0)(1) | -0.69 | 5.80E-01 | 8.16E-01 | Metabolome | | HMDB11558 | Lipid | Monoacylglycerol |
| LysoPC(P-18:0) | 1.70 | 5.76E-01 | 8.16E-01 | Metabolome | C04230 | HMDB13122 | Lipid | Phospholipid Metabolism |
| 2-Aminophenol sulfate | 0.50 | 5.81E-01 | 8.16E-01 | Metabolome | | HMDB61116 | Xenobiotics | Chemical |
| APOA4 | 1.08 | 5.82E-01 | 8.16E-01 | Proteome | | | | |
| BTD | 1.21 | 5.81E-01 | 8.16E-01 | Proteome | | | | |
| SAA2 | 0.31 | 5.77E-01 | 8.16E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| MCH | 0.41 | 5.74E-01 | 8.16E-01 | Clinical labs | | | | |
| L-Cysteine | 1.25 | 5.83E-01 | 8.17E-01 | Metabolome | C00097 | HMDB00574 | Amino Acid | Methionine, Cysteine, SAM and Taurine Metabolism |
| L-Methionine | -1.47 | 5.88E-01 | 8.22E-01 | Metabolome | C00073 | HMDB00696 | Amino Acid | Methionine, Cysteine, SAM and Taurine Metabolism |
| Orotidine | 1.48 | 5.90E-01 | 8.23E-01 | Metabolome | C01103 | HMDB00788 | Nucleotide | Pyrimidine Metabolism, Orotate containing |
| HV439 | -0.59 | 5.89E-01 | 8.23E-01 | Proteome | | | | |
| SCP2 | 0.47 | 5.91E-01 | 8.23E-01 | Proteome | | | | |
| LysoPC(P-18:1) | -1.24 | 5.93E-01 | 8.23E-01 | Metabolome | C04230 | HMDB10408 | Lipid | Phospholipid Metabolism |
| MG(15:0)(1) | 1.21 | 5.94E-01 | 8.23E-01 | Metabolome | | HMDB11532 | Lipid | Monoacylglycerol |
| AMBP | -1.55 | 5.94E-01 | 8.23E-01 | Proteome | | | | |
| Catechol sulfate | 0.21 | 6.04E-01 | 8.30E-01 | Metabolome | | HMDB59724 | Xenobiotics | Benzoate Metabolism |
| LysoPI(18:1) | -0.51 | 6.03E-01 | 8.30E-01 | Metabolome | | HMDB61693 | Lipid | Phospholipid Metabolism |
| LYZ | 0.68 | 6.03E-01 | 8.30E-01 | Proteome | | | | |
| PON1 | 0.93 | 6.04E-01 | 8.30E-01 | Proteome | | | | |
| N-acetyl-1-1-methylhistidine | 0.55 | 6.01E-01 | 8.30E-01 | Metabolome | | | Amino Acid | Histidine Metabolism |
| PE(P-36:5) | 0.41 | 6.06E-01 | 8.32E-01 | Metabolome | | | | |
| L-Malic acid | 1.73 | 6.11E-01 | 8.32E-01 | Metabolome | C00149 | HMDB00156 | Energy | TCA Cycle |
| Citrulline | -0.98 | 6.11E-01 | 8.32E-01 | Metabolome | C00327 | HMDB00904 | Amino Acid | Urea cycle; Arginine and Proline Metabolism |
| 1-Methyluric acid | -0.48 | 6.08E-01 | 8.32E-01 | Metabolome | C16359 | HMDB03099 | Xenobiotics | Xanthine Metabolism |
| CP | -1.26 | 6.11E-01 | 8.32E-01 | Proteome | | | | |
| FGB | -1.09 | 6.10E-01 | 8.32E-01 | Proteome | | | | |
| Paraxanthine | -0.28 | 6.16E-01 | 8.38E-01 | Metabolome | C13747 | HMDB01860 | Xenobiotics | Xanthine Metabolism |
| FRMPD1 | -0.49 | 6.18E-01 | 8.39E-01 | Proteome | | | | |
| 5-methyluridine (ribothymidine) | -2.32 | 6.23E-01 | 8.45E-01 | Metabolome | | HMDB00884 | Nucleotide | Pyrimidine Metabolism, Uracil containing |
| ASS1 | 0.37 | 6.27E-01 | 8.48E-01 | Proteome | | | | |
| IGJ | 0.70 | 6.27E-01 | 8.48E-01 | Proteome | | | | |
| PS(28:2) | -0.22 | 6.29E-01 | 8.50E-01 | Metabolome | | | | |
| CETP | 0.69 | 6.32E-01 | 8.50E-01 | Proteome | | | | |
| LV144 | 0.58 | 6.31E-01 | 8.50E-01 | Proteome | | | | |
| Cys-Pro or Pro-Cys | 0.99 | 6.34E-01 | 8.53E-01 | Metabolome | | HMDB12342 | Peptide | Dipeptide |
| KV133 | -0.79 | 6.35E-01 | 8.53E-01 | Proteome | | | | |
| C12:0 AC | -0.93 | 6.37E-01 | 8.54E-01 | Metabolome | | HMDB02250 | Lipid | Fatty Acid Metabolism(Acyl Carnitine) |
| Kynurenic acid | -1.09 | 6.46E-01 | 8.60E-01 | Metabolome | C01717 | HMDB00715 | Amino Acid | Tryptophan Metabolism |
| 1-Methylguanosine | -0.98 | 6.45E-01 | 8.60E-01 | Metabolome | C04545 | HMDB01563 | Nucleotide | Pyrimidine Metabolism, Uracil containing |
| Pregnanediol-3-glucuronide | -0.40 | 6.46E-01 | 8.60E-01 | Metabolome | C03033 | HMDB10318 | Lipid | Progestin Steroids |
| HV353 | -0.72 | 6.45E-01 | 8.60E-01 | Proteome | | | | |
| EOS | -0.16 | 6.45E-01 | 8.60E-01 | Clinical labs | | | | |
| C6:0, DC AC(2) | 0.27 | 6.50E-01 | 8.61E-01 | Metabolome | | HMDB61677 | Lipid | Fatty Acid Metabolism(Acyl Carnitine) |
| CPN2 | -1.03 | 6.50E-01 | 8.61E-01 | Proteome | | | | |
| F10 | -0.98 | 6.50E-01 | 8.61E-01 | Proteome | | | | |
| C4:0 AC | 0.58 | 6.53E-01 | 8.63E-01 | Metabolome | C02862 | HMDB02013 | Lipid | Fatty Acid Metabolism (also BCAA Metabolism) |
| FETUB | -1.03 | 6.56E-01 | 8.63E-01 | Proteome | | | | |
| ICAM1 | 0.50 | 6.56E-01 | 8.63E-01 | Immunome | | | | |
| TGFB | 1.53 | 6.56E-01 | 8.63E-01 | Immunome | | | | |
| C20:3, OH FA(1) | -1.48 | 6.54E-01 | 8.63E-01 | Metabolome | | HMDB03869 | Lipid | Fatty Acid, Monohydroxy |
| gamma-glutamyl-epsilon-lysine | -1.30 | 6.59E-01 | 8.65E-01 | Metabolome | | | Peptide | Gamma-glutamyl Amino Acid |
| L-Phenylalanine | -0.71 | 6.64E-01 | 8.68E-01 | Metabolome | C00079 | HMDB00159 | Amino Acid | Phenylalanine Metabolism |
| Gly-Lys or Lys-Gly | -0.77 | 6.62E-01 | 8.68E-01 | Metabolome | | | Peptide | Dipeptide |
| PIP(38:2) | -0.31 | 6.63E-01 | 8.68E-01 | Metabolome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| L-Asparagine | 1.40 | 6.66E-01 | 8.69E-01 | Metabolome | C00152 | HMDB00168 | Amino Acid | Alanine and Aspartate Metabolism |
| LysoPE(18:2) | -0.80 | 6.70E-01 | 8.73E-01 | Metabolome | | HMDB11477 | Lipid | Phospholipid Metabolism |
| ATRN | 1.05 | 6.71E-01 | 8.74E-01 | Proteome | | | | |
| LYM | -0.07 | 6.72E-01 | 8.74E-01 | Clinical labs | | | | |
| C3:1 AC | 0.15 | 6.76E-01 | 8.78E-01 | Metabolome | | HMDB13124 | Lipid | Fatty Acid Metabolism (also BCAA Metabolism) |
| Imidazolelactic acid | 0.83 | 6.80E-01 | 8.81E-01 | Metabolome | C05132 | HMDB02320 | Amino Acid | Histidine Metabolism |
| MG(18:0) | -0.73 | 6.82E-01 | 8.81E-01 | Metabolome | | HMDB11131 | Lipid | Monoacylglycerol |
| MG(15:0)(3) | 0.49 | 6.83E-01 | 8.81E-01 | Metabolome | | HMDB11532 | Lipid | Monoacylglycerol |
| C4A | -0.32 | 6.85E-01 | 8.81E-01 | Proteome | | | | |
| LUM | -1.12 | 6.81E-01 | 8.81E-01 | Proteome | | | | |
| IFNG | 1.46 | 6.84E-01 | 8.81E-01 | Immunome | | | | |
| Oleoyl Ethyl Amide | -0.27 | 6.85E-01 | 8.81E-01 | Metabolome | | | Lipid | Long Chain Fatty Acid |
| PCYOX1 | -0.48 | 6.86E-01 | 8.81E-01 | Proteome | | | | |
| pro-hydroxy-pro(2) | 0.51 | 6.89E-01 | 8.82E-01 | Metabolome | | HMDB06695 | Amino Acid | Urea cycle; Arginine and Proline Metabolism |
| LysoPE(20:0) | -1.02 | 6.88E-01 | 8.82E-01 | Metabolome | | HMDB11481 | Lipid | Phospholipid Metabolism |
| PC(35:4) | -0.14 | 6.90E-01 | 8.82E-01 | Metabolome | | | | |
| LysoPE(18:0) | 0.37 | 6.92E-01 | 8.84E-01 | Metabolome | | HMDB11129 | Lipid | Phospholipid Metabolism |
| Hippuric acid | 0.43 | 7.00E-01 | 8.89E-01 | Metabolome | C01586 | HMDB00714 | Xenobiotics | Benzoate Metabolism |
| Ornithine | 1.18 | 7.01E-01 | 8.89E-01 | Metabolome | C00077 | HMDB03374 | Amino Acid | Urea cycle; Arginine and Proline Metabolism |
| CHOL | -0.01 | 7.01E-01 | 8.89E-01 | Clinical labs | | | | |
| C14:1, OH FA(1) | -0.66 | 6.98E-01 | 8.89E-01 | Metabolome | | | Lipid | Fatty Acid, Monohydroxy |
| PS(30:1) | -0.21 | 7.01E-01 | 8.89E-01 | Metabolome | | | | |
| C11:1 FA | 0.73 | 7.07E-01 | 8.91E-01 | Metabolome | C13910 | HMDB33724 | Lipid | Medium Chain Fatty Acid |
| C8:0, OH FA(1) | 0.79 | 7.05E-01 | 8.91E-01 | Metabolome | | | Lipid | Fatty Acid, Monohydroxy |
| PE(P-38:5)(2) | 0.11 | 7.07E-01 | 8.91E-01 | Metabolome | | | | |
| PC(36:6) | 0.11 | 7.05E-01 | 8.91E-01 | Metabolome | | | | |
| PC(P-40:7) | 0.12 | 7.05E-01 | 8.91E-01 | Metabolome | | | | |
| Choline | -1.73 | 7.10E-01 | 8.91E-01 | Metabolome | C00114 | HMDB00097 | Lipid | Phospholipid Metabolism |
| C10:2 AC | -0.39 | 7.11E-01 | 8.91E-01 | Metabolome | | HMDB13325 | Lipid | Fatty Acid Metabolism(Acyl Carnitine) |
| DSP | 0.35 | 7.10E-01 | 8.91E-01 | Proteome | | | | |
| L-Histidine | -1.62 | 7.13E-01 | 8.91E-01 | Metabolome | C00135 | HMDB00177 | Amino Acid | Histidine Metabolism |
| L-Glutamine | -0.97 | 7.14E-01 | 8.91E-01 | Metabolome | C00064 | HMDB00641 | Amino Acid | Glutamate Metabolism |
| MG(15:0)(2) | -0.72 | 7.14E-01 | 8.91E-01 | Metabolome | | HMDB11532 | Lipid | Monoacylglycerol |
| MG(20:5) | 0.55 | 7.16E-01 | 8.91E-01 | Metabolome | | HMDB11550 | Lipid | Monoacylglycerol |
| C9 | -0.75 | 7.16E-01 | 8.91E-01 | Proteome | | | | |
| FN1 | -0.46 | 7.17E-01 | 8.91E-01 | Proteome | | | | |
| PE(36:5) | 0.17 | 7.22E-01 | 8.96E-01 | Metabolome | | | | |
| LCP1 | 0.22 | 7.26E-01 | 8.97E-01 | Proteome | | | | |
| MASP2 | 0.39 | 7.25E-01 | 8.97E-01 | Proteome | | | | |
| MTHFD1 | 0.20 | 7.25E-01 | 8.97E-01 | Proteome | | | | |
| methyl-4-hydroxybenzoate sulfate | 0.17 | 7.26E-01 | 8.97E-01 | Metabolome | | HMDB00637 | Xenobiotics | Benzoate Metabolism |
| Chenodeoxycholic acid glycine conjugate(2) | -0.20 | 7.29E-01 | 8.99E-01 | Metabolome | C05466 | | Lipid | Primary Bile Acid Metabolism |
| APOE | -0.71 | 7.30E-01 | 8.99E-01 | Proteome | | | | |
| C3:0 AC | -0.41 | 7.41E-01 | 9.03E-01 | Metabolome | C03017 | HMDB00824 | Lipid | Fatty Acid Metabolism (also BCAA Metabolism) |
| C18:0, OH FA(2) | 0.79 | 7.41E-01 | 9.03E-01 | Metabolome | C03045 | | Lipid | Fatty Acid, Monohydroxy |
| CAMP | -0.33 | 7.40E-01 | 9.03E-01 | Proteome | | | | |
| CFP | 0.46 | 7.38E-01 | 9.03E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| IL13 | −1.06 | 7.36E-01 | 9.03E-01 | Immunome | | | | |
| VEGF | −0.88 | 7.37E-01 | 9.03E-01 | Immunome | | | | |
| Arabonate|Xylonate(1) | −0.80 | 7.36E-01 | 9.03E-01 | Metabolome | | | Carbohydrate | Pentose Metabolism |
| PE(P-40:6)(2) | 0.55 | 7.39E-01 | 9.03E-01 | Metabolome | | | | |
| Asp-Asp | −0.40 | 7.46E-01 | 9.08E-01 | Metabolome | | | Peptide | Dipeptide |
| L-Threonine | −0.43 | 7.57E-01 | 9.13E-01 | Metabolome | C00188 | HMDB00167 | Amino Acid | Glycine, Serine and Threonine Metabolism |
| L-Arginine | −0.97 | 7.53E-01 | 9.13E-01 | Metabolome | C00062 | HMDB00517 | Amino Acid | Urea cycle; Arginine and Proline Metabolism |
| Glucaric acid | 0.33 | 7.56E-01 | 9.13E-01 | Metabolome | C00818 | HMDB00663 | Carbohydrate | Ascorbate and aldarate metabolism |
| gamma-CEHC | −0.15 | 7.56E-01 | 9.13E-01 | Metabolome | | HMDB01931 | Cofactors and Vitamins | Tocopherol Metabolism |
| ACTA1 | −0.23 | 7.60E-01 | 9.13E-01 | Proteome | | | | |
| C3 | −1.06 | 7.55E-01 | 9.13E-01 | Proteome | | | | |
| C8A | −1.08 | 7.59E-01 | 9.13E-01 | Proteome | | | | |
| COLEC11 | −0.34 | 7.59E-01 | 9.13E-01 | Proteome | | | | |
| SERPINA4 | 0.63 | 7.55E-01 | 9.13E-01 | Proteome | | | | |
| PC(35:4)(2) | 0.10 | 7.60E-01 | 9.13E-01 | Metabolome | | | | |
| Theophylline | −0.18 | 7.61E-01 | 9.13E-01 | Metabolome | C00209 | HMDB01889 | Xenobiotics | Xanthine Metabolism |
| Oxalate (ethanedioate) | −0.11 | 7.62E-01 | 9.13E-01 | Metabolome | | HMDB02329 | Cofactors and Vitamins | Ascorbate and Aldarate Metabolism |
| C24:5 FA | −0.46 | 7.66E-01 | 9.13E-01 | Metabolome | | HMDB06322 | Lipid | Polyunsaturated Fatty Acid (n3 and n6) |
| ADIPOQ | −0.36 | 7.66E-01 | 9.13E-01 | Proteome | | | | |
| 5alpha-Androstan-3alpha,17beta-diol 1 | 0.16 | 7.66E-01 | 9.13E-01 | Metabolome | | | Lipid | Androgenic Steroids |
| PC(33:1) | 0.08 | 7.66E-01 | 9.13E-01 | Metabolome | | | | |
| LysoPE(P-16:0) | −0.33 | 7.69E-01 | 9.15E-01 | Metabolome | | HMDB11152 | Lipid | Phospholipid Metabolism |
| sn-glycero-3-Phosphoethanolamine | −1.04 | 7.71E-01 | 9.16E-01 | Metabolome | C01233 | HMDB00114 | Lipid | Phospholipid Metabolism |
| KV139 | −0.32 | 7.73E-01 | 9.18E-01 | Proteome | | | | |
| HV307_2 | 0.47 | 7.77E-01 | 9.21E-01 | Proteome | | | | |
| N-(1-Deoxy-1-fructosyl)valine | 0.35 | 7.82E-01 | 9.24E-01 | Metabolome | | HMDB37844 | Amino Acid | Leucine, Isoleucine and Valine Metabolism |
| KV116 | −0.11 | 7.81E-01 | 9.24E-01 | Proteome | | | | |
| PC(32:1) | 0.08 | 7.85E-01 | 9.27E-01 | Metabolome | | | | |
| Arabitol|Xylitol | 0.45 | 7.91E-01 | 9.31E-01 | Metabolome | C01904 | | Carbohydrate | Pentose Metabolism |
| HNRNPM | −0.17 | 7.92E-01 | 9.31E-01 | Proteome | | | | |
| SCLT1 | 0.29 | 7.91E-01 | 9.31E-01 | Proteome | | | | |
| TF | 0.90 | 7.92E-01 | 9.31E-01 | Immunome | | | | |
| GCSE | 1.06 | 7.95E-01 | 9.33E-01 | Proteome | | | | |
| LRG1 | −0.54 | 7.97E-01 | 9.33E-01 | Proteome | | | | |
| LYVE1 | −0.36 | 7.98E-01 | 9.33E-01 | Proteome | | | | |
| MGP | −0.37 | 8.00E-01 | 9.35E-01 | Proteome | | | | |
| Iminodiacetate (IDA) | −0.53 | 8.02E-01 | 9.36E-01 | Metabolome | C19911 | HMDB11753 | Xenobiotics | Chemical |
| IL1A | 0.75 | 8.03E-01 | 9.36E-01 | Immunome | | | | |
| Chenodeoxycholic Acid(3) | −0.16 | 8.06E-01 | 9.38E-01 | Metabolome | | HMDB00518 | Lipid | Primary Bile Acid Metabolism |
| gamma-glutamyl phenylalanine | −0.22 | 8.21E-01 | 9.38E-01 | Metabolome | | HMDB00594 | Peptide | Gamma-glutamyl Amino Acid |
| C18:0, DC FA(2) | 0.61 | 8.22E-01 | 9.38E-01 | Metabolome | | HMDB00782 | Lipid | Fatty Acid, Dicarboxylate |
| pro-hydroxy-pro(1) | −0.44 | 8.13E-01 | 9.38E-01 | Metabolome | C04230 | HMDB06695 | Amino Acid | Urea cycle; Arginine and Proline Metabolism |
| LysoPC(22:4) | 0.26 | 8.10E-01 | 9.38E-01 | Metabolome | | HMDB10401 | Lipid | Phospholipid Metabolism |
| LysoPE(18:1) | −0.47 | 8.22E-01 | 9.38E-01 | Metabolome | | HMDB11475 | Lipid | Phospholipid Metabolism |
| Phenylalanylphenylalanine | −0.44 | 8.16E-01 | 9.38E-01 | Metabolome | | HMDB13302 | Peptide | Dipeptide |
| CST3 | 0.32 | 8.22E-01 | 9.38E-01 | Proteome | | | | |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| HV146 | −0.27 | 8.19E-01 | 9.38E-01 | Proteome | | | | |
| IGHM.1 | −0.12 | 8.24E-01 | 9.38E-01 | Proteome | | | | |
| MASP1 | −0.37 | 8.22E-01 | 9.38E-01 | Proteome | | | | |
| NPHP3 | −0.26 | 8.11E-01 | 9.38E-01 | Proteome | | | | |
| SELL | 0.36 | 8.15E-01 | 9.38E-01 | Immunome | | | | |
| NGF | −1.07 | 8.08E-01 | 9.38E-01 | Immunome | | | | |
| BASOAB | −14.77 | 8.14E-01 | 9.38E-01 | Clinical labs | | | | |
| C10:1, OH FA | 0.43 | 8.23E-01 | 9.38E-01 | Metabolome | | | Lipid | Fatty Acid, Monohydroxy |
| C12:1, DC FA(3) | 0.49 | 8.23E-01 | 9.38E-01 | Metabolome | | | Lipid | Fatty Acid, Dicarboxylate |
| C14:0, OH FA(2) | 0.67 | 8.11E-01 | 9.38E-01 | Metabolome | | | Lipid | Fatty Acid, Monohydroxy |
| C10:0, DC FA (Sebacic acid)(1) | 0.55 | 8.29E-01 | 9.40E-01 | Metabolome | C08277 | | Lipid | Fatty Acid, Dicarboxylate |
| C6:0, DC AC(1) | −0.11 | 8.27E-01 | 9.40E-01 | Metabolome | | HMDB61677 | Lipid | Fatty Acid Metabolism(Acyl Carnitine) |
| IL12P40 | −0.55 | 8.29E-01 | 9.40E-01 | Immunome | | | | |
| Hydroxyhippurate(1) | −0.19 | 8.29E-01 | 9.40E-01 | Metabolome | | | Xenobiotics | Benzoate Metabolism |
| Taurocholic acid(2) | −0.16 | 8.32E-01 | 9.40E-01 | Metabolome | C05122 | HMDB00036 | Lipid | Primary Bile Acid Metabolism |
| ILK | 0.42 | 8.32E-01 | 9.40E-01 | Proteome | | | | |
| LV211 | −0.19 | 8.34E-01 | 9.42E-01 | Proteome | | | | |
| F13A1 | 0.32 | 8.38E-01 | 9.43E-01 | Proteome | | | | |
| IL23 | 0.69 | 8.38E-01 | 9.43E-01 | Immunome | | | | |
| PE(38:6)(2) | 0.08 | 8.38E-01 | 9.43E-01 | Metabolome | | | | |
| IL27 | −0.71 | 8.39E-01 | 9.43E-01 | Immunome | | | | |
| PS(32:3) | −0.11 | 8.41E-01 | 9.43E-01 | Metabolome | | | | |
| PGLYRP2 | 0.51 | 8.46E-01 | 9.44E-01 | Proteome | | | | |
| AG | 0.09 | 8.47E-01 | 9.44E-01 | Clinical labs | | | | |
| 1, 2, 3-benzenetriol sulfate | −0.07 | 8.47E-01 | 9.44E-01 | Metabolome | | | Xenobiotics | Chemical |
| PC(P-34:2) | 0.06 | 8.42E-01 | 9.44E-01 | Metabolome | | | | |
| PC(38:6)(1) | 0.05 | 8.45E-01 | 9.44E-01 | Metabolome | | | | |
| PC(38:4)(2) | −0.05 | 8.44E-01 | 9.44E-01 | Metabolome | | | | |
| C18:1 AC | 0.55 | 8.49E-01 | 9.44E-01 | Metabolome | | HMDB05065 | Lipid | Fatty Acid Metabolism(Acyl Carnitine) |
| C12:1, OH FA | 0.37 | 8.49E-01 | 9.44E-01 | Metabolome | | HMDB00148 | Lipid | Fatty Acid, Monohydroxy |
| L-Glutamic acid | 0.11 | 8.52E-01 | 9.45E-01 | Metabolome | C00025 | HMDB00148 | Amino Acid | Glutamate Metabolism |
| Uric acid | 0.78 | 8.54E-01 | 9.45E-01 | Metabolome | C00366 | HMDB00289 | Nucleotide | Purine Metabolism, (Hypo)Xanthine/Inosine containing |
| C7 | 0.35 | 8.51E-01 | 9.45E-01 | Proteome | | | | |
| Phenylalanylleucine | −0.54 | 8.54E-01 | 9.45E-01 | Metabolome | | | Peptide | Dipeptide |
| C20:4 FA | 0.14 | 8.60E-01 | 9.48E-01 | Metabolome | C00219 | HMDB01043 | Lipid | Polyunsaturated Fatty Acid (n3 and n6) |
| HGFAC | −0.32 | 8.59E-01 | 9.48E-01 | Proteome | | | | |
| C1QA | −0.33 | 8.64E-01 | 9.51E-01 | Proteome | | | | |
| LBP | −0.29 | 8.63E-01 | 9.51E-01 | Proteome | | | | |
| LysoPC(18:0) | −0.50 | 8.67E-01 | 9.51E-01 | Metabolome | C04230 | HMDB10384 | Lipid | Phospholipid Metabolism |
| Phenylalanyl-Tryptophan | −0.18 | 8.66E-01 | 9.51E-01 | Metabolome | | HMDB29006 | Peptide | Dipeptide |
| KVD33 | 0.19 | 8.70E-01 | 9.52E-01 | Proteome | | | | |
| C12:1, DC FA(1) | −0.33 | 8.69E-01 | 9.52E-01 | Metabolome | | | Lipid | Fatty Acid, Dicarboxylate |
| MG(20:4)(1) | −0.19 | 8.72E-01 | 9.53E-01 | Metabolome | | HMDB04666 | Lipid | Monoacylglycerol |
| MG(20:4)(2) | −0.11 | 8.73E-01 | 9.53E-01 | Metabolome | | HMDB04666 | Lipid | Monoacylglycerol |
| GP5 | 0.17 | 8.74E-01 | 9.53E-01 | Proteome | | | | |
| TP | 0.42 | 8.74E-01 | 9.53E-01 | Clinical labs | | | | |
| 7-Methylguanine | −0.17 | 8.88E-01 | 9.61E-01 | Metabolome | C02242 | HMDB00897 | | |
| SM(d18:1/16:0) | 0.16 | 6.84E-01 | 9.61E-01 | Metabolome | C00550 | HMDB13464 | Nucleotide | Purine Metabolism, Guanine containing |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| DBH | -0.10 | 8.86E-01 | 9.61E-01 | Proteome | | | | |
| HV333_2 | 0.15 | 8.88E-01 | 9.61E-01 | Proteome | | | | |
| IGFALS | 0.38 | 8.86E-01 | 9.61E-01 | Proteome | | | | |
| PC(35:2) | 0.04 | 8.86E-01 | 9.61E-01 | Metabolome | | | | |
| AGT | 0.38 | 8.90E-01 | 9.62E-01 | Proteome | | | | |
| KV320_2 | -0.16 | 8.94E-01 | 9.64E-01 | Proteome | | | | |
| GROA | 0.27 | 8.93E-01 | 9.64E-01 | Immunome | | | | |
| C18:2 AC | 0.32 | 8.96E-01 | 9.64E-01 | Metabolome | | HMDB06461 | Lipid | Fatty Acid Metabolism(Acyl Carnitine) |
| MSN | 0.12 | 8.96E-01 | 9.64E-01 | Proteome | | | | |
| PC(40:6)(1) | 0.03 | 8.99E-01 | 9.66E-01 | Metabolome | | | | |
| 1-Methylhistidine | -0.35 | 9.04E-01 | 9.70E-01 | Metabolome | C01152 | HMDB00001 | Amino Acid | Histidine Metabolism |
| Chenodeoxycholic acid glycine conjugate(1) | -0.07 | 9.17E-01 | 9.71E-01 | Metabolome | C05466 | HMDB00637 | Lipid | Primary Bile Acid Metabolism |
| Isobutyrylglycine | -0.08 | 9.16E-01 | 9.71E-01 | Metabolome | | HMDB00730 | Amino Acid | Leucine, Isoleucine and Valine Metabolism |
| MG(24:0)(2) | 0.12 | 9.13E-01 | 9.71E-01 | Metabolome | | HMDB11558 | Lipid | Monoacylglycerol |
| COL6A3 | 0.10 | 9.09E-01 | 9.71E-01 | Proteome | | | | |
| OLFM1 | 0.10 | 9.17E-01 | 9.71E-01 | Proteome | | | | |
| ORM2 | -0.17 | 9.17E-01 | 9.71E-01 | Proteome | | | | |
| PRDX2 | -0.09 | 9.13E-01 | 9.71E-01 | Proteome | | | | |
| EGF | -0.11 | 9.09E-01 | 9.71E-01 | Immunome | | | | |
| VEGFD | 0.18 | 9.08E-01 | 9.71E-01 | Immunome | | | | |
| NHDL | 0.00 | 9.10E-01 | 9.71E-01 | Clinical labs | | | | |
| Arabonate|Xylonate(2) | 0.14 | 9.11E-01 | 9.71E-01 | Metabolome | | | Carbohydrate | Pentose Metabolism |
| C13:1, OH FA | -0.20 | 9.12E-01 | 9.71E-01 | Metabolome | | | Lipid | Fatty Acid, Monohydroxy |
| C18:3, OH FA(3) | -0.21 | 9.20E-01 | 9.73E-01 | Metabolome | | | Lipid | Fatty Acid, Monohydroxy |
| Chenodeoxycholic Acid(2) | -0.10 | 9.27E-01 | 9.78E-01 | Metabolome | C00148 | HMDB00518 | Lipid | Primary Bile Acid Metabolism |
| L-Proline | -0.19 | 9.28E-01 | 9.78E-01 | Metabolome | | HMDB00162 | Amino Acid | Urea cycle; Arginine and Proline Metabolism |
| MIP1B | -0.33 | 9.28E-01 | 9.78E-01 | Immunome | | | | |
| C18:0, OH AC | 0.04 | 9.30E-01 | 9.79E-01 | Metabolome | | HMDB13164 | Lipid | Fatty Acid Metabolism(Acyl Carnitine) |
| A1BG | -0.27 | 9.34E-01 | 9.79E-01 | Proteome | | | | |
| LV657 | -0.05 | 9.33E-01 | 9.79E-01 | Proteome | | | | |
| PC(34:2) | 0.02 | 9.32E-01 | 9.79E-01 | Metabolome | | | | |
| Ala-Leu or Leu-Ala | 0.03 | 9.35E-01 | 9.79E-01 | Metabolome | | HMDB00197 | Peptide | Dipeptide |
| Indoleacetic acid | 0.14 | 9.44E-01 | 9.80E-01 | Metabolome | C00954 | HMDB00772 | Amino Acid | Tryptophan Metabolism |
| C19:0 FA(1) | 0.12 | 9.38E-01 | 9.80E-01 | Metabolome | C16535 | HMDB11553 | Lipid | Long Chain Fatty Acid |
| MG(22:2) | 0.07 | 9.40E-01 | 9.80E-01 | Metabolome | | HMDB11621 | Lipid | Monoacylglycerol |
| Cinnamoylglycine | 0.04 | 9.45E-01 | 9.80E-01 | Metabolome | | | Xenobiotics | Food Component/Plant |
| FBLN1.1 | 0.15 | 9.40E-01 | 9.80E-01 | Proteome | | | | |
| AST | -0.01 | 9.40E-01 | 9.80E-01 | Clinical labs | | | | |
| C20:2, OH FA | 0.17 | 9.45E-01 | 9.80E-01 | Metabolome | | | Lipid | Fatty Acid, Monohydroxy |
| Asp-Glu or Glu-Asp | 0.10 | 9.45E-01 | 9.80E-01 | Metabolome | | | Peptide | Dipeptide |
| PC(36:4) | -0.02 | 9.45E-01 | 9.80E-01 | Metabolome | | | | |
| ATRN.1 | -0.16 | 9.47E-01 | 9.80E-01 | Proteome | | | | |
| IGF2 | -0.12 | 9.50E-01 | 9.80E-01 | Proteome | | | | |
| IGLC2 | -0.06 | 9.49E-01 | 9.80E-01 | Proteome | | | | |
| MCV | 0.02 | 9.48E-01 | 9.80E-01 | Clinical labs | | | | |
| L-Tryptophan | -0.18 | 9.57E-01 | 9.83E-01 | Metabolome | C00078 | HMDB00929 | Amino Acid | Tryptophan Metabolism |
| C24:6 FA | 0.06 | 9.59E-01 | 9.83E-01 | Metabolome | | HMDB02007 | Lipid | Polyunsaturated Fatty Acid (n3 and n6) |

TABLE 4-continued

Molecules Associated with the Disposition Index

| Molecule Name | Estimate | p-value | FDR | Assay | KEGG | HMDB | Super pathway | Sub-pathway |
|---|---|---|---|---|---|---|---|---|
| APOC3 | 0.09 | 9.56E-01 | 9.83E-01 | Proteome | | | | |
| HV270 | -0.03 | 9.55E-01 | 9.83E-01 | Proteome | | | | |
| PE(P-38:6) | 0.10 | 9.58E-01 | 9.83E-01 | Metabolome | | | | |
| PC(34:4) | -0.01 | 9.59E-01 | 9.83E-01 | Metabolome | | | | |
| MG(18:1) | 0.05 | 9.66E-01 | 9.87E-01 | Metabolome | | HMDB11536 | Lipid | Monoacylglycerol |
| C1RL | -0.04 | 9.67E-01 | 9.87E-01 | Proteome | | | | |
| 4-formyl Indole(2) | -0.07 | 9.68E-01 | 9.87E-01 | Metabolome | | | Amino Acid | Tryptophan Metabolism |
| PS(30:2) | 0.03 | 9.65E-01 | 9.87E-01 | Metabolome | | | | |
| Glycerophosphocholine | -0.03 | 9.71E-01 | 9.89E-01 | Metabolome | C00670 | HMDB00086 | Lipid | Phospholipid Metabolism |
| HV333 | -0.03 | 9.72E-01 | 9.89E-01 | Proteome | | | | |
| LV657_2 | -0.02 | 9.73E-01 | 9.89E-01 | Proteome | | | | |
| Ne-Methyl-Lysine | -0.03 | 9.77E-01 | 9.90E-01 | Metabolome | C02728 | HMDB02038 | Amino Acid | Lysine Metabolism |
| MG(24:1) | 0.04 | 9.76E-01 | 9.90E-01 | Metabolome | | HMDB11559 | Lipid | Monoacylglycerol |
| PLTP | -0.05 | 9.77E-01 | 9.90E-01 | Proteome | | | | |
| NA | 0.02 | 9.78E-01 | 9.90E-01 | Clinical labs | | | | |
| FGA | 0.04 | 9.81E-01 | 9.91E-01 | Proteome | | | | |
| PC(P-42:5) | -0.01 | 9.82E-01 | 9.91E-01 | Proteome | | | | |
| Symmetric dimethylarginine | -0.08 | 9.86E-01 | 9.93E-01 | Metabolome | C03626 | HMDB01539 | Amino Acid | Urea cycle; Arginine and Proline Metabolism |
| CFHR4 | -0.01 | 9.87E-01 | 9.93E-01 | Proteome | | | | |
| CHOLHDL | -0.02 | 9.87E-01 | 9.93E-01 | Clinical labs | | | | |
| HV330_2 | -0.01 | 9.88E-01 | 9.94E-01 | Proteome | | | | |
| PC(36:2) | 0.00 | 9.92E-01 | 9.97E-01 | Metabolome | | | | |
| INHBC | 0.01 | 9.94E-01 | 9.97E-01 | Proteome | | | | |
| N-Acetylserine | -0.02 | 9.96E-01 | 9.98E-01 | Metabolome | | HMDB02931 | Amino Acid | Glycine, Serine and Threonine Metabolism |
| Cyclo(ala-pro) | 0.01 | 9.97E-01 | 9.98E-01 | Metabolome | | | Peptide | Dipeptide |
| MIG | 0.00 | 1.00E+00 | 1.00E+00 | Immunome | | | | |

TABLE 5

| | | | | | | | | | | | | | |
|---|---|---|---|---|---|---|---|---|---|---|---|---|---|
| Participant ID Diabetic Converters | Figure | FPG | A1C | 2HR-OGTT | First DM range abnormality | ISR cluster | ISR Max | Matsuda | SSPG (mg/dL) | CGM* | Weight Gain | Potential Mechanisms | Notes |
| ZOZOWIT | 3c | N to D | D to N to D | D to P | unknown | very late | 7.97 | 3.05 | Int (138) to IS (91) | | no | delayed insulin secretion/ impaired beta cell sensitivity to glucose | |
| ZNED4XZ | 3b | P to D | P to D | N | FPG | n/a | n/a | n/a | n/a | n/a | yes (91 to 100 kg) | steady state problem- possibly tissue uptake weight gain leading to possible increased insulin resistance and worsening OGTT | no c-peptide or SSPG available |
| ZNDMXI3 | 3a | N to P | N to P | N to D | OGTT | late to very late | 2.64 | 1.9 | IR (170) | n/a | yes (74 to 94 kg) | steady state problem- likely glucose production > tissue uptake | |
| ZXHCGKV | S3b | P to D | N | N | FPG | late | 1.04 | 13.96 | n/a | | no | Likely insulin resistance is primary | |
| ZLZQMEV | S3f | P | P to D to P | D to P | A1C, OGTT | intermediate | 3.24 | 2.2 | IR (221) | F, R | no | Likely insulin resistance is primary decreased beta cell sensitivity to glucose | |
| ZK112BX | S3e | P | P to D | D | A1C | very late | 3.1 | 3.2 | IR (211) | | no | Likely insulin resistance is primary decreased beta cell sensitivity to glucose | on medication (metformin 250 mg) at time of OGTT ?gluco-corticoid related |
| ZGOSZHK | S3a | N | N to P | P to D | OGTT | very late | 7.36 | 14.96 | IR (160) | n/a | no | steady state problem | |
| ZV14S1B | S3c | P to D | N | N | FPG | n/a | n/a | n/a | IS (58) | n/a | no | | |
| *Undiagnosed at Start of Study* | | | | | | | | | | | | | |
| ZTJ7L7Z | S3d | P | D | P to D | HbA1C | very late to late | 10.7 | 2.1 | IR (155) | F, R | n/a | delayed insulin secretion/ impaired beta cell sensitivity to glucose, decreased peripheral uptake | |
| *Unconfirmed (Only 1 DM Range OGTT or HbA1C)* | | | | | | | | | | | | | |
| ZM7JY3G | S3g | N | P | D to N | OGTT | late | 4.44 | 4.9 | IR (160) to IS (80) | R | weight loss (88.5 to 79 kg) | possible delayed insulin secretion | C-peptide sent during normal OGTT |
| ZMBHIOZ | n/a | N/P | D to P | N to P | HbA1C | intermediate to early | 2.9 to 3.3 | 3.3 to 3.0 | IR (183) | n/a | no | insulin resistance | |
| ZPF36E2 | n/a | P | P | D to P | OGTT | n/a | n/a | n/a | IR (155) | n/a | weight loss (77 to 71 kg) | insulin resistance | no c-peptide available |
| ZUPAQVU | n/a | N | P | N to D | OGTT | intermediate to early | 5.6 to 4.9 | 5.3 to 4.9 | IR (282.2) | n/a | no | insulin resistance predominates | C-peptide sent during normal OGTTs not diabetic one |
| ZUF48YS | n/a | N | N to P | D | OGTT | very late | 1.2 | 6.9 | n/a | n/a | yes (75 to 80 kg) | poor insulin production | |

TABLE 5-continued

Underlying Mechanisms of Glucose Dysregulation

| Participant ID Diabetic Converters | Figure | FPG | A1C | 2HR-OGTT | First DM range abnormality | ISR cluster | ISR Max | Matsuda | SSPG (mg/dL) | CGM* | Weight Gain | Potential Mechanisms | Notes |
|---|---|---|---|---|---|---|---|---|---|---|---|---|---|
| Continuous Glucose Diabetic Range Abnormality Only ||||||||||||||
| ZW61YGW | n/a | N | N | N | CGM | late | 3.48 | 4.34 | IS (69) | F | | | **works night |
| ZVM4N7A | n/a | N | N | N | CGM | late | 1.85 | 5.58 | Int (141) | R, ** | | | shift so no fasting |
| ZQFLIP3 | n/a | P | P | N | CGM | intermediate | 1.58 | 5.96 | IS (62) | F | | | |
| ZL9BTWF | n/a | P | P | P | CGM | very late | 5.11 | 5.98 | Int (147) | R, F | | | |
| ZL63I8R | n/a | P | P | P | CGM | late | 5.81 | 4.77 | IR (154) | F | | | |
| ZKVR426 | n/a | N | P | N to P | CGM | late | 2.42 | 1.79 | IR (215) | R | | | |
| ZKFV71L | n/a | P | P to N | N to P | CGM | very late | 1.5 to 1.9 | 4.2 to 3.6 | Int (115) | R, F | | | |

Abbreviations: FPG-Fasting Plasma Glucose; OGTT-oral glucose tolerance test; HbA1C-Hemoglobin A1C; N-normoglycemic; P-prediabetic range; D-diabetic range; ISR-insulin secretion rate given in pmol/kg/min; CGM-Continuous glucose monitoring; DM-diabetes; SSPG-Steady State plasma glucose; IR-insulin resitant (SSPG ≥ 150) ; Int-Intermediate Insulin Resistance (150 > SSPG ≥ 100); IS-Insulin Sensitive (100 > SSPG); F-fasting; R-Random; kg-kilogram;
*CGM-Diabetic range values were considered random glucose >200 (R); Fasting (F)-was definited as 2 or more days of >30 minutes of glucose >125 during the hours of 3 am and 7 am. We excluded 1 person who worked night shift and another who reported eating during this period.

TABLE 6

Relationship between Shannon and Glucose Metabolism Measures

| | Estimate | 95% Confidence Int. Lower CL | Upper CL | StdErr | DF | p-value |
|---|---|---|---|---|---|---|
| SSPG (Steady State Plasma Glucose) all time points ||||||||
| Intercept | 0.12 | 0.04 | 0.20 | 0.04 | 59 | 0.002653814 |
| Shannon | −0.33 | −0.50 | −0.16 | 0.09 | 599 | 0.00015367 |
| HbA1C (Hemoglobin A1C) all time points ||||||||
| Intercept | −0.06 | −0.19 | 0.06 | 0.06 | 94 | 0.317643379 |
| Shannon | −0.04 | −0.08 | 0.00 | 0.02 | 635 | 0.029986228 |
| Shannon*Shannon | −0.03 | −0.05 | −0.01 | 0.01 | 635 | 0.001139332 |
| FPG (Fasting Plasma Glucose) all time points ||||||||
| Intercept | 0.03 | −0.06 | 0.13 | 0.05 | 94 | 0.479816844 |
| Shannon | −0.07 | −0.14 | 0.01 | 0.04 | 641 | 0.08865918 |
| Shannon*Shannon | −0.08 | −0.11 | −0.04 | 0.02 | 641 | 2.20973E−05 |
| SSPG-Healthy time points ||||||||
| Intercept | 0.23 | 0.13 | 0.34 | 0.05 | 58 | 3.89324E−05 |
| Shannon | −0.40 | −0.60 | −0.20 | 0.10 | 311 | 9.65995E−05 |
| HbA1C Healthy time points ||||||||
| Intercept | −0.11 | −0.27 | 0.05 | 0.08 | 90 | 0.17536848 |
| Shannon | −0.04 | −0.11 | 0.03 | 0.04 | 338 | 0.284117095 |
| Shannon*Shannon | 0.00 | −0.04 | 0.04 | 0.02 | 338 | 0.987950076 |
| FPG Healthy time points ||||||||
| Intercept | −0.05 | −0.19 | 0.08 | 0.07 | 90 | 0.444555923 |
| Shannon | 0.02 | −0.09 | 0.14 | 0.06 | 339 | 0.675568458 |
| Shannon*Shannon | −0.01 | −0.07 | 0.06 | 0.03 | 339 | 0.845528567 |
| SSPG Other than Healthy time points ||||||||
| Intercept | −0.01 | −0.12 | 0.11 | 0.06 | 43 | 0.927574247 |
| Shannon | −0.26 | −0.47 | −0.04 | 0.11 | 244 | 0.019554651 |
| FPG Other than Healthy time points ||||||||
| Intercept | 0.03 | −0.13 | 0.19 | 0.08 | 59 | 0.719128799 |
| Shannon | −0.02 | −0.14 | 0.09 | 0.06 | 244 | 0.697371891 |
| Shannon*Shannon | −0.06 | −0.11 | −0.01 | 0.03 | 244 | 0.014664238 |
| HbAIC other than Healthy time points ||||||||
| Intercept | −0.05 | −0.28 | 0.18 | 0.11 | 59 | 0.669401987 |
| Shannon | −0.02 | −0.08 | 0.04 | 0.03 | 239 | 0.551259944 |
| Shannon*Shannon | −0.02 | −0.05 | 0.00 | 0.01 | 239 | 0.071620587 |

TABLE 7

Multivariate Linear Mixed Effects models of Shannon Diversity

Model A Shannon empty model with random intercept (participants with SSPG (n = 60, obs 660))

| Fixed Effects | | | | | | Covariance Parameter Estimates | | | Pseudo | Model Fit Statistics | |
|---|---|---|---|---|---|---|---|---|---|---|---|
| Effect | Estimate | Lower CI | Upper CI | DF | Pr > \|t\| | Cov Parm | Estimate | S.E. | R-square | −2 Log Likelihood | 1606.3 |
| Intercept | 0.01087 | −0.1571 | 0.1789 | 59 | 0.8974 | UN(1, 1) | 0.3166 | 0.07665 | | AIC | 1612.3 |
| | | | | | | Residual | 0.5756 | 0.0332 | | BIC | 1618.6 |

Model B Shannon = SSPG with random intercept

| Effect | Estimate | Lower CI | Upper CI | DF | Pr > \|t\| | Cov Parm | Estimate | S.E. | | −2 Log Likelihood | 1594.2 |
|---|---|---|---|---|---|---|---|---|---|---|---|
| Intercept | 0.04804 | −0.1011 | 0.1972 | 58 | 0.5217 | UN(1, 1) | 0.2281 | 0.06072 | 0.279533 | AIC | 1602.2 |
| SSPG | −0.2591 | −0.3979 | −0.1202 | 58 | 0.0004 | Residual | 0.5775 | 0.03336 | −0.0033 | BIC | 1610 |

Model C: Shannon = year with random intercept and year

| Effect | Estimate | Lower CI | Upper CI | DF | Pr > \|t\| | Cov Parm | Estimate | S.E. | | −2 Log Likelihood | 1600.0 |
|---|---|---|---|---|---|---|---|---|---|---|---|
| Intercept | 0.07255 | −0.11 | 0.2551 | 59 | 0.4298 | UN(1, 1) | 0.3224 | 0.09246 | | AIC | 1612 |
| year | −0.0711 | −0.1615 | 0.01933 | 599 | 0.1231 | UN(2, 1) | −0.00809 | 0.02971 | | BIC | 1624.5 |
| | | | | | | UN(2, 2) | 0.02247 | 0.01651 | 0.034798 | | |
| | | | | | | Residual | 0.5562 | 0.03298 | | | |

Model D: Shannon = year sspg with random intercept and year

| Effect | Estimate | Lower CI | Upper CI | DF | Pr > \|t\| | Cov Parm | Estimate | S.E. | | −2 Log Likelihood | 1588.5 |
|---|---|---|---|---|---|---|---|---|---|---|---|
| Intercept | 0.097 | −0.06661 | 0.2606 | 58 | 0.2402 | UN(1, 1) | 0.2578 | 0.0802 | 0.200372 | AIC | 1602.5 |
| year | −0.05158 | −0.1178 | 0.01459 | 599 | 0.1263 | UN(2, 1) | −0.02066 | 0.02893 | | BIC | 1617.2 |
| SSPG | −0.2571 | −0.397 | −0.1173 | 58 | 0.0005 | UN(2, 2) | 0.02281 | 0.01685 | −0.01513 | | |
| | | | | | | Residual | 0.5575 | 0.03312 | 0.032466 | | |

**Model E Shannon = sspg year P_bacteroidetes p_bacteroidetes*year with random intercept & year**

| Effect | Estimate | Lower CI | Upper CI | DF | Pr > \|t\| | Cov Parm | Estimate | S.E. | | Fit statistics | |
|---|---|---|---|---|---|---|---|---|---|---|---|
| Intercept | 0.01131 | −0.1278 | 0.1504 | 58 | 0.8713 | UN(1, 1) | 0.1761 | 0.04922 | 0.453784 | −2 Log Likelihood | 1255.0 |
| year | 0.02883 | −0.03611 | 0.09377 | 597 | 0.3836 | UN(2, 1) | −0.02853 | 0.01689 | | AIC | 1273 |
| SSPG | −0.1669 | −0.2727 | −0.06118 | 58 | 0.0025 | UN(2, 2) | 0.01116 | 0.01024 | 0.503338 | BIC | 1291.8 |
| p_Bacteroidetes | −0.4435 | −0.5314 | −0.3556 | 597 | <0.0001 | Residual | 0.3402 | 0.02043 | 0.408965 | | |
| year*p_Bacteroidetes | −0.1127 | −0.1688 | −0.05654 | 597 | <0.0001 | | | | | | |

**Model F: Shannon = SSPG year P_bacteroidetes p_bacteroidetes*year lymab (absolute lymphocyte count) with random intercept and year**

| Effect | Estimate | Lower CI | Upper CI | DF | Pr > \|t\| | Cov Parm | Estimate | S.E. | | Fit Statistics | |
|---|---|---|---|---|---|---|---|---|---|---|---|
| Intercept | 0.2638 | −0.01775 | 0.5454 | 58 | 0.0658 | UN(1, 1) | 0.1489 | 0.0484 | 0.538151 | −2 Log Likelihood | 1077.3 |
| year | 0.02857 | −0.03997 | 0.09712 | 486 | 0.4132 | UN(2, 1) | −0.02079 | 0.01974 | | AIC | 1097.3 |
| SSPG | −0.1659 | −0.2703 | −0.06154 | 58 | 0.0023 | UN(2, 2) | 0.008598 | 0.01196 | 0.617356 | BIC | 1118.2 |
| p_Bacteroidetes | −0.4375 | −0.5355 | −0.3394 | 486 | <.0001 | Residual | 0.3597 | 0.02405 | 0.387265 | | |
| year*p_Bacteroidetes | −0.1258 | −0.1916 | −0.05997 | 486 | 0.0002 | | | | | | |
| LYMAB | −0.1512 | −0.2862 | −0.0162 | 486 | 0.0282 | | | | | | |

Confidence Intervals (CI) represent 95% CI;

Abbreviations: SSPG, Steady-State Plasma Glucose; Cov, Covariance; Parm, Parameter; S.E., standard error; LYMAB, absolute lymphocyte count; DF,

TABLE 8

Steady State Plasma Glucose (insulin resistance) Prediction Models

Steady-State Plasma Glucose (SSPG) Prediction Models

| Clinical labs only (n = 52) | | Clinical labs + Immunome (n = 52) | | Clinical labs + Proteome (n = 52) | |
|---|---|---|---|---|---|
| Test MSE | 0.42 | Test MSE | 0.35 | Test MSE | 0.29 |
| Test R2 | 0.59 | Test R2 | 0.66 | Test R2 | 0.71 |
| FM MSE | 0.55 | FM MSE | 0.44 | FM MSE | 0.36 |
| Clinical Labs | Coefficients | Clinical Labs | Coefficients | Clinical Labs | Coefficients |
| CR | −0.133 | CR | −0.108 | CR | −0.122 |
| NEUTAB | 0.176 | NEUTAB | 0.184 | NEUTAB | 0.193 |
| TGL/HDL | 0.253 | TGL/HDL | 0.246 | TGL/HDL | 0.240 |
| BMI | 0.155 | BMI | 0.164 | BMI | 0.143 |
|  |  | CA | 0.113 |  |  |
|  |  | Immune Prot. | Coefficients | Proteins | Coefficients |
|  |  | IL1B | −0.124 | AGT | −0.136 |
|  |  | IL18 | −0.093 | IL1RAP | −0.133 |
|  |  |  |  | KV116 | 0.142 |
|  |  |  |  | CFH | 0.111 |
|  |  |  |  | MYBPC2 | −0.071 |
|  |  |  |  | P_CFH | 0.115 |
|  |  |  |  | P_MYBPC2 | −0.074 |
| Clinical labs + Metabolome (n = 52) | | Clinical labs + Lipidome (n = 45) | | Clinical labs + Transcriptome (n = 51) | |
| Test MSE | 0.20 | Test MSE | 0.36 | Test MSE | 0.13 |
| Test R2 | 0.80 | Test R2 | 0.62 | Test R2 | 0.88 |
| FM MSE | 0.31 | FM MSE | 0.41 | FM MSE | 0.15 |
| Clinical Labs | Coefficients | Clinical Labs | Coefficients | Clinical Labs | Coefficients |
|  |  | CR | −0.100 |  |  |
|  |  | NEUTAB | 0.157 | NEUTAB | 0.176 |
| TGL/HDL | 0.286 | TGL/HDL | 0.169 | TGL/HDL | 0.222 |
|  |  | BMI | 0.111 |  |  |
| Metabolites | Coefficients | Lipids | Coefficients | Transcripts | Coefficients |
| N1-methyladenosine | 0.147 |  | −0.164 | C19orf66 | −0.110 |
| C7H15N3O2 | 0.190 |  | −0.148 | CHP1 | −0.101 |
| L-Lysine | 0.172 |  | −0.095 | FAM86HP | −0.127 |
| C14H22N2O9 | −0.140 |  |  | HSCB | −0.125 |
| 4-formyl Indole(2) | −0.129 |  |  | KY | 0.110 |
| C28H46O4(1) | 0.061 |  |  | MAP3K19 | 0.158 |
| C26H42O4 | 0.192 |  |  | SLC16A12 | −0.146 |
|  |  |  |  | SYT9 | 0.086 |
|  |  |  |  | TMEM237 | 0.111 |
|  |  |  |  | TMEM253 | 0.131 |
|  |  |  |  | UHMK1 | −0.093 |
| All Omes (no Microbiome) (n = 44) | | All Omes (no Lipidome) (n = 46) | | All Omes including Lipidome (n = 41) | |
| Test MSE | 0.10 | Test MSE | 0.10 | Test MSE | 0.12 |
| Test R2 | 0.89 | Test R2 | 0.89 | Test R2 | 0.87 |
| FM MSE | 0.09 | FM MSE | 0.13 | FM MSE | 0.16 |
| Clinical Labs | Coefficients | Clinical Labs | Coefficients | Clinical Labs | Coefficients |
| lTGL/HDL | 0.177 | TGL/HDL | 0.149 |  |  |
| Multiomes | Coefficients | Multiomes | Coefficients | Multiomes | Coefficients |
| IL1RAP | −0.081 | IL1RAP | −0.102 | L-Arginine | 0.190 |
| L-Alanine | 0.154 | L-Arginine | 0.103 |  | −0.092 |
| C26H42O4 | 0.132 | C26H42O4 | 0.123 |  | −0.136 |
|  | −0.158 | L-Lysine | 0.083 |  | −0.102 |
| MAP3K19 | 0.087 | 3-Methyl-L-histidine | −0.090 | MAP3K19 | 0.165 |
| C19orf66 | −0.103 | MAP3K19 | 0.162 | POC5 | −0.151 |
| DLGAP1 | −0.172 | C19orf66 | −0.170 | TMEM106B | 0.130 |
| FAM185A | 0.128 | C1orf174 | −0.110 | UHMK1 | −0.133 |
| IL12A-AS1 | −0.112 | DGUOK | 0.102 | unclassified f_Ruminococcac | −0.183 |
| IL26 | 0.074 | KY | 0.065 | g_Faecalibacterium; s_praus | −0.058 |
| KY | 0.068 | RPA3OS | −0.078 | unclassified o_Clostridiales | −0.062 |
| PGGT1B | −0.088 | SGK494 | 0.058 |  |  |

TABLE 8-continued

| | | | |
|---|---|---|---|
| POC5 | −0.027 | TMEM108 | 0.162 |
| TMEM237 | 0.060 | unclassified f_Ruminococcaceae | −0.112 |
| TMEM253 | 0.109 | | |
| VPS13A | −0.074 | | |

| Clinical labs + Microbiome (n = 47) | | All Omes (no Transcriptome) (n = 42) | |
|---|---|---|---|
| Test MSE | 0.21 | Test MSE | 0.24 |
| Test R2 | 0.78 | Test R2 | 0.74 |
| FM MSE | 0.26 | FM MSE | 0.25 |

| Clinical Labs | Coefficients | Clinical Labs | Coefficients |
|---|---|---|---|
| NEUTAB | 0.141 | | |
| TGL/HDL | 0.125 | | |
| BMI | 0.159 | | |

| Microbes | Coefficients | Multiomes | Coefficients |
|---|---|---|---|
| g_Bacteroides; s_unclassified | −0.117 | IL1RAP | −0.103 |
| g_Faecalibacterium; s_prausnitzii | 0.117 | L-Arginine | 0.128 |
| g_Barnesiella; s_intestinihominis | 0.093 | C7H15N3O2 | 0.088 |
| g_Ruminococcus; s_unclassified | 0.094 | C12H24N2O3 | 0.108 |
| g_Odoribacter; s_unclassified | −0.183 | | −0.092 |
| unclassified f_Lachnospiraceae | −0.119 | | −0.099 |
| unclassified f_Ruminococcaceae | −0.116 | | −0.091 |
| unclassified o_Clostridiales | −0.164 | unclassified o_Clostridiales | −0.103 |
| | | g_Shigella; s_unclassified | 0.078 |
| | | unclassified f_Ruminococcaceae | −0.176 |
| | | g_Faecalibacterium; s_prausnitzii | −0.085 |

TABLE 9

Two Hour Oral Glucose Tolerance Test (OGTT) Prediction Models

| Clinical Only | | Clinical + Immunone | | Clinical + Proteome | |
|---|---|---|---|---|---|
| Test MSE | 0.58 | Test MSE | 0.52 | Test MSE | 0.35 |
| Test R2 | 0.42 | Test R2 | 0.47 | Test R2 | 0.64 |
| FM MSE | 0.71 | FM MSE | 0.66 | FM MSE | 0.44 |

| Clinical Labs | coefficients | Clinical Labs | coefficients | Clinical Labs | coefficients |
|---|---|---|---|---|---|
| A1C | 0.311 | A1C | 0.342 | A1C | 0.284 |
| ALT | 0.069 | | | | |

| | | Cytokines | coefficients | Other Omes | coefficients |
|---|---|---|---|---|---|
| | | PDGFBB | 0.101 | P_CFD | −0.147 |
| | | | | P_KVD28 | −0.090 |
| | | | | P_IGHA2 | −0.137 |
| | | | | P_F11 | 0.080 |
| | | | | P_KV310 | −0.076 |
| | | | | P_HV270 | −0.071 |

| Clinical + Microbiome | | Clinical + Metabolome | | Clinical + Transcriptome | |
|---|---|---|---|---|---|
| Test MSE | 0.45 | Test MSE | 0.37 | Test MSE | 0.37 |
| Test R2 | 0.54 | Test R2 | 0.62 | Test R2 | 0.62 |
| FM MSE | 0.47 | FM MSE | 0.45 | FM MSE | 0.30 |

| Clinical Labs | coefficients | Clinical Labs | coefficients | Clinical Labs | coefficients |
|---|---|---|---|---|---|
| A1C | 0.288 | A1C | 0.232 | A1C | 0.262 |

| Microbes | coefficients | Metabolites | coefficients | Transcripts | coefficients |
|---|---|---|---|---|---|
| g_Bacteroides; s_uniformis | 0.080 | Hexosamine | 0.110 | ALG1L2 | −0.079 |
| g_Bacteroides; s_unclassified | 0.076 | Taurine | −0.058 | C21orf119 | 0.072 |
| g_Bacteroides; s_caccae | 0.181 | Hydroxyphenyllactic acid | −0.120 | CHST3 | 0.118 |
| unclassified f_Lachnospiraceae | 0.116 | Hippuric acid | −0.099 | DDT | 0.105 |
| g_Roseburia; s_unclassified | −0.116 | p-Cresol glucuronide | 0.132 | FBXO40 | 0.122 |
| g_Faecalibacterium; s_prausnitzii | −0.107 | C18:0, OH FA(2) | 0.131 | GPT2 | −0.224 |
| | | C16:0, 2OH FA | −0.114 | KRT10 | −0.151 |
| | | | | LINC01093 | 0.043 |
| | | | | RAMP3 | 0.070 |
| | | | | RNF214 | 0.117 |

TABLE 9-continued

| | | | | | |
|---|---|---|---|---|---|
| | | | | UNC93B1 | 0.058 |
| | | | | WEE2 | −0.132 |

| All Omes (no Transcriptome) | | All Omes (no Microbiome) | | All Omes (no lipidome) | |
|---|---|---|---|---|---|
| Test MSE | 0.32 | Test MSE | 0.29 | Test MSE | 0.289 |
| Test R2 | 0.68 | Test R2 | 0.72 | Test R2 | 0.71 |
| FM MSE | 0.31 | FM MSE | 0.24 | FM MSE | 0.243 |

| Clinical Labs | coefficients | Clinical Labs | coefficients | Clinical Labs | coefficients |
|---|---|---|---|---|---|
| A1C | 0.246 | A1C | 0.227 | A1C | 0.192 |

| Other Omes | coefficients | Other Omes | coefficients | Other Omes | coefficients |
|---|---|---|---|---|---|
| C_PDGFBB | 0.095 | C_PDGFBB | 0.096 | C_PDGFBB | 0.078 |
| P_CFD | −0.131 | P_CFD | −0.152 | P_CFD | −0.120 |
| P_IGHA2 | −0.129 | P_IGHA2 | −0.145 | P_IGHA2 | −0.120 |
| P_VTN | 0.046 | | | P_VTN | 0.023 |
| P_KVD28 | −0.055 | P_F11 | | | 0.033 |
| Ectoine | −0.078 | Ectoine | −0.029 | Ectoine | −0.055 |
| Taurine | −0.087 | Taurine | −0.061 | Taurine | −0.053 |
| C18:3 FA | 0.097 | C18:3 FA | 0.087 | C18:3 FA | 0.075 |
| p-Cresol glucuronide | 0.079 | p-Cresol glucuronide | 0.090 | p-Cresol glucu | 0.081 |
| g_Bacteroides; s_uniformis | 0.074 | | | g_Bacteroides | 0.042 |
| g_Bacteroides; s_caccae | 0.087 | | | g_Bacteroides | 0.091 |
| unclassified f_Lachnospiraceae | 0.085 | | | unclassified f_ | 0.082 |
| g_Roseburia; s_unclassified | −0.071 | ALG1L2 | −0.052 | ALG1L2 | −0.045 |
| | | CERS5 | −0.010 | CERS5 | −0.029 |
| | | DAAM1 | −0.039 | DAAM1 | −0.026 |
| | | FAM86HP | −0.048 | FAM86HP | −0.026 |
| | | FLG | −0.103 | FLG | −0.065 |
| | | GPT2 | −0.062 | GPT2 | −0.069 |
| | | MIF | −0.054 | KRT10 | −0.067 |
| | | RAMP3 | 0.084 | RAMP3 | 0.079 |
| | | UNC93B1 | 0.054 | UNC93B1 | 0.034 |
| | | ZNF596 | 0.092 | ZNF596 | 0.075 |

TABLE 10

Participant Suvey Comments regarding Study Impact on Health Habits

| Behavioral Change | n |
|---|---|
| Improving Sleep | 5 |
| Stress Reduction | 2 |
| Mindfulness | 2 |
| Yoga | 1 |
| Fitness Camp | 1 |
| More exercise, marathon training, more diet monitoring | 1 |
| Increased Fiber through diet or supplementation | 5 |
| Decreased alcohol intake | 1 |
| Awareness of effects of sweets & decreased intake | 4 |
| Wearable made them feel acountable for exercising | 4 |
| Changed diet to Vegan/Vegetarian | 1 |
| Daily Glucose Checks | 1 |
| Recording Food Intake | 1 |
| Daily weight on internet scale | 1 |
| Walking more | 2 |
| Took probiotic supplement for 1 year | 1 |
| Used frequent data sampling to "fend off statins" | 1 |
| Started supplementing with acetyl-l-carnitine, magnesium and increased alpha lipoic acid for diabetic neuropathy | 1 |
| Engaged 23 & Me for additional data | 1 |
| More concientious about checking for moles and "bumps" | 1 |
| More aware of hypoxia while flying, changed breathing patterns | 1 |
| I started out with some changes but than took a break from the study and these "behaviors" took a break too | 1 |
| Health problems prevented them from making change | 2 |

TABLE 11

Participant-Reported Metabolic Health Discoveries and Behavioral Change

| | Data | Behavioral Change | Effects |
|---|---|---|---|
| Participant Metabolic Discoveries | | | |
| Was less insulin resistant than thought; weightloss paid off | SSPG & CGM | Renewed motivation to continue to work on weight loss | |
| Fruit has more of an effect on her blood sugar than she realized | CGM | Will cut down on portions of fruit | |
| Restaurant meals increase blood sugars much more than she expected | CGM | Is now making very different food choices | Lost 15 pounds (lb) |
| Smaller more frequent meals work better for her | CGM | Including breakfast and snack in the afternoon | |

TABLE 11-continued

Participant-Reported Metabolic Health Discoveries and Behavioral Change

|  | Data | Behavioral Change | Effects |
|---|---|---|---|
| Large portion of starches at night keep blood sugars high through the night | CGM | Cut portions of starches in meals, especially at dinner | |
| cholesterol is above normal range | labs | motivation for weight loss. | achieved 12 lb weight loss |
| blood sugars in diabetic range | OGTT | visited doctor and changed diet | |
| fiber helped in lowering cholesterol. Pt is intolerant to statins | labs | long term fiber | Total cholesterol improved by 20 mg/dL while taking certain fibers |
| lentils cause high blood sugar spikes | CGM | limiting lentils | |
| blood sugars much higher than he thought | CGM | Unknown | |
| learned she is insulin resistant | SSPG | changed diet- paying attention to carbohydrate intake (reducing "quick sugars", exercising | lost 19 pounds, although CGM in diabetic range, clinical labs stayed normoglycemic |
| even though overweight, metabolically very healthy | labs, SSPG | feels less stressed about health, relieved | |
| Learned importance of sleep via activity tracking watch | wearable | sleeping more | |
| Oatmeal made blood sugars very high, but mac & cheese and BBQ did not | CGM | adjusted diet | |
| *Improvement in SSPG* | | | |
| very insulin resistant | SSPG | lost >20 lbs to control this; cut back on sweets; increased exercise | SSPG improved from 160 to 80 |
| Running improved blood glucose measurements | HbA1C, FPG, SSPG | Started running, cut out sugars from diet and had 15 lb weight loss | SSPG improved from 138 to 91, labs from diabetic range to normal |
| *Improvement in HbA1c* | | | |
| Prediabetic HbA1C | HbA1C | Major changes to diet and exercise through study participation | HbA1c improved from prediabetic to normal |
| Prediabetic HbA1C | HbA1C | moderate changes to diet, significant changes to exercise, discused HbA1C with doctor | HbA1c improved from prediabetic to normal |
| Diabetic range HbA1C related to stress and eating out | HbA1C | changed diet (back to home cooking) | HbA1c returned to normal range |
| Prediabetic HbA1c | HbA1C | increased exercise from ~1500 metmin/wk to 3000-4000 metmin/wk | HbA1c returned to normal range |

TABLE 12

Healthy-Baseline 8, Dynamic Models: Molecules Associated with Hemoglobin A1C
Healthy-Baseline Model: Hemoglobin A1C (n = 101, samples 560)

| Molecule | Estimate | StdErr | DF | tValue | p-value | FDR | Assay | Accession ID |
|---|---|---|---|---|---|---|---|---|
| GLU | 0.04 | 0.01 | 456 | 6.78 | 3.74E−11 | 3.15E−08 | Clinical labs | |
| Hexose | 0.08 | 0.01 | 414 | 5.9 | 7.46E−09 | 3.15E−06 | Metabolome | HMDB00122 |
| Hexosamine | 0.03 | 0.01 | 414 | 5.5 | 6.63E−08 | 1.86E−05 | Metabolome | HMDB01514 |
| ethyl glucuronide | 0.04 | 0.01 | 414 | 4.85 | 1.73E−06 | 3.65E−04 | Metabolome | HMD610325 |
| PLT | 0.03 | 0.01 | 452 | 4.03 | 6.44E−05 | 7.50E−03 | Clinical labs | |
| L-Tyrosine | 0.02 | 0.00 | 414 | 4.01 | 7.11E−05 | 7.50E−03 | Metabolome | HMDB00158 |
| C12:1, DC FA(2) | 0.08 | 0.02 | 414 | 4.06 | 5.76E−05 | 7.50E−03 | Metabolome | HMDB00933 |
| C14:0, OH FA(1) | 0.02 | 0.01 | 414 | 4.11 | 4.75E−05 | 7.50E−03 | Metabolome | HMD602261 |
| L-Alanine | 0.03 | 0.01 | 414 | 3.92 | 1.02E−04 | 9.53E−03 | Metabolome | HMDB00161 |
| WBC | 0.03 | 0.01 | 452 | 3.89 | 1.14E−04 | 9.62E−03 | Clinical labs | |
| Tetrahydroaldosterone-3-glucuronide(1) | 0.04 | 0.01 | 414 | 3.84 | 1.44E−04 | 1.03E−02 | Metabolome | HMDB10357 |
| Phenylalanyl-Tryptophan | 0.02 | 0.01 | 414 | 3.83 | 1.47E−04 | 1.03E−02 | Metabolome | HMD629006 |
| LysoPI(20:4) | 0.02 | 0.01 | 414 | 3.77 | 1.89E−04 | 1.22E−02 | Metabolome | HMDB61690 |
| C22:4 FA | 0.02 | 0.00 | 414 | 3.65 | 2.97E−04 | 1.67E−02 | Metabolome | HMDB02226 |
| C18:1, DC FA | 0.02 | 0.01 | 414 | 3.66 | 2.82E−04 | 1.67E−02 | Metabolome | |
| RDW | 0.03 | 0.01 | 452 | 3.59 | 3.67E−04 | 1.87E−02 | Clinical labs | |
| C12:1, DC FA(1) | 0.01 | 0.00 | 414 | 3.56 | 4.13E−04 | 1.87E−02 | Metabolome | HMDB00933 |
| C10:0, OH FA(1) | 0.04 | 0.01 | 414 | 3.56 | 4.11E−04 | 1.87E−02 | Metabolome | HMDB02203 |
| C16:2, OH FA | 0.02 | 0.00 | 414 | 3.55 | 4.22E−04 | 1.87E−02 | Metabolome | |
| C18 Sphingosine 1-phosphate | 0.02 | 0.00 | 414 | 3.51 | 5.06E−04 | 2.03E−02 | Metabolome | HMDB00277 |
| C18:0, DC FA(1) | 0.02 | 0.01 | 414 | 3.51 | 5.06E−04 | 2.03E−02 | Metabolome | HMDB00782 |
| NEUTAB | 0.02 | 0.01 | 452 | 3.47 | 5.78E−04 | 2.12E−02 | Clinical labs | |
| 3-Indolepropionic acid | 0.01 | 0.00 | 414 | 3.48 | 5.63E−04 | 2.12E−02 | Metabolome | HMDB02302 |
| N-(1-Deoxy-1-fructosyl)valine | 0.02 | 0.00 | 414 | 3.35 | 8.81E−04 | 3.10E−02 | Metabolome | HMD537844 |
| C16:0, DC FA(2) | 0.02 | 0.01 | 414 | 3.33 | 9.59E−04 | 3.24E−02 | Metabolome | HMDB00672 |
| C12:0, OH FA(1) | 0.02 | 0.00 | 414 | 3.27 | 1.18E−03 | 3.82E−02 | Metabolome | HMDB00387 |
| Indolepyruvate | 0.01 | 0.00 | 414 | 3.25 | 1.24E−03 | 3.86E−02 | Metabolome | HMDB60484 |
| C16:3 FA | 0.02 | 0.00 | 414 | 3.22 | 1.41E−03 | 4.24E−02 | Metabolome | |
| C11:0, DC FA | 0.02 | 0.01 | 414 | 3.19 | 1.55E−03 | 4.35E−02 | Metabolome | HMDB00888 |

TABLE 12-continued

| | | | | | | | |
|---|---|---|---|---|---|---|---|
| Thyroxine | 0.02 | 0.01 | 414 | 3.19 | 1.55E-03 | 4.35E-02 | Metabolome | HMDB01918 |
| C15:0, OH FA | 0.02 | 0.01 | 414 | 3.16 | 1.69E-03 | 4.61E-02 | Metabolome | |
| MG(14:1)(3) | 0.02 | 0.01 | 414 | 3.11 | 1.99E-03 | 5.10E-02 | Metabolome | HMDB11531 |
| C8:0, OH FA(1) | 0.02 | 0.01 | 414 | 3.12 | 1.94E-03 | 5.10E-02 | Metabolome | |
| TGL | 0.02 | 0.01 | 457 | 3.1 | 2.08E-03 | 5.16E-02 | Clinical labs | |
| MCHC | −0.01 | 0.00 | 452 | −3.09 | 2.15E-03 | 5.18E-02 | Clinical labs | |
| Fructoselysine | 0.01 | 0.00 | 414 | 3.05 | 2.42E-03 | 5.51E-02 | Metabolome | |
| C8:2, OH FA(2) | 0.03 | 0.01 | 414 | 3.05 | 2.41E-03 | 5.51E-02 | Metabolome | |
| Glycerophosphocholine | 0.09 | 0.03 | 414 | 3.04 | 2.49E-03 | 5.54E-02 | Metabolome | HMDB00086 |
| BASO | −0.02 | 0.01 | 451 | −3.02 | 2.71E-03 | 5.73E-02 | Clinical labs | |
| LYMAB | 0.03 | 0.01 | 452 | 3.01 | 2.72E-03 | 5.73E-02 | Clinical labs | |
| C20:3 FA | 0.01 | 0.00 | 414 | 2.99 | 2.91E-03 | 5.85E-02 | Metabolome | HMDB02925 |
| Ig lambda chain V-VI region SUT | −0.01 | 0.00 | 437 | −3 | 2.85E-03 | 5.85E-02 | Proteome | P06317 |
| MG(20:5) | 0.02 | 0.01 | 414 | 2.97 | 3.15E-03 | 6.05E-02 | Metabolome | HMDB11550 |
| C16:1, OH FA(2) | 0.05 | 0.02 | 414 | 2.97 | 3.15E-03 | 6.05E-02 | Metabolome | |
| Cys-Gly or Gly-Cys | 0.02 | 0.01 | 414 | 2.92 | 3.67E-03 | 6.88E-02 | Metabolome | HMDB00078 |
| L-Lysine | 0.01 | 0.00 | 414 | 2.89 | 4.04E-03 | 7.33E-02 | Metabolome | HMDB00182 |
| C13:0, DC FA(2) | 0.02 | 0.01 | 414 | 2.89 | 4.08E-03 | 7.33E-02 | Metabolome | HMDB02327 |
| C14:1 FA(2) | 0.01 | 0.01 | 414 | 2.88 | 4.20E-03 | 7.39E-02 | Metabolome | HMDB02000 |
| C22:3 FA | 0.02 | 0.01 | 414 | 2.86 | 4.43E-03 | 7.53E-02 | Metabolome | HMDB02823 |
| C15:1 FA | 0.01 | 0.00 | 414 | 2.86 | 4.46E-03 | 7.53E-02 | Metabolome | |
| C16:2 FA | 0.01 | 0.01 | 414 | 2.81 | 5.23E-03 | 8.65E-02 | Metabolome | |
| C19:1 FA | 0.01 | 0.00 | 414 | 2.8 | 5.33E-03 | 8.66E-02 | Metabolome | HMD013622 |
| MG(18:3) | 0.02 | 0.01 | 414 | 2.79 | 5.52E-03 | 8.79E-02 | Metabolome | HMDB11539 |
| Isobutyrylglycine | 0.03 | 0.01 | 414 | 2.73 | 6.52E-03 | 9.65E-02 | Metabolome | HMDB00730 |
| C9:0, DC FA (Azelaic acid) | 0.02 | 0.01 | 414 | 2.73 | 6.63E-03 | 9.65E-02 | Metabolome | HMDB00784 |
| C22:5 FA | 0.01 | 0.00 | 414 | 2.75 | 6.19E-03 | 9.65E-02 | Metabolome | HMDB06528 |
| C20:4, OH FA(1) | 0.01 | 0.01 | 414 | 2.75 | 6.31E-03 | 9.65E-02 | Metabolome | |
| C18:3, OH FA(2) | 0.01 | 0.01 | 414 | 2.73 | 6.51E-03 | 9.65E-02 | Metabolome | |
| MG(20:4)(1) | 0.02 | 0.01 | 414 | 2.71 | 6.97E-03 | 9.84E-02 | Metabolome | HMDB04666 |
| Ig kappa chain V-III region IARC/BL41 | −0.01 | 0.00 | 437 | −2.71 | 6.99E-03 | 9.84E-02 | Proteome | P06311 |
| Bilirubin | −0.03 | 0.01 | 414 | −2.69 | 7.46E-03 | 9.95E-02 | Metabolome | HMDB00054 |
| C12:1 FA(1) | 0.01 | 0.01 | 414 | 2.67 | 7.90E-03 | 9.95E-02 | Metabolome | HMDB00529 |
| C10:1, DC FA | 0.01 | 0.00 | 414 | 2.69 | 7.35E-03 | 9.95E-02 | Metabolome | HMDB00603 |
| Sulfolithocholic acid | 0.02 | 0.01 | 414 | 2.68 | 7.62E-03 | 9.95E-02 | Metabolome | HMDB00907 |
| C12:0, OH FA(2) | 0.02 | 0.01 | 414 | 2.7 | 7.22E-03 | 9.95E-02 | Metabolome | HMDB02059 |
| MG(18:0) | 0.02 | 0.01 | 414 | 2.68 | 7.67E-03 | 9.95E-02 | Metabolome | HMDB11131 |
| Ig heavy chain V-II region SESS | 0.02 | 0.01 | 437 | −2.67 | 7.79E-03 | 9.95E-02 | Proteome | P04438 |
| MG(14:1)(1) | 0.02 | 0.01 | 414 | 2.66 | 8.10E-03 | 1.01E-01 | Metabolome | HMDB11531 |
| LIF | −0.01 | 0.00 | 446 | −2.64 | 8.65E-03 | 1.05E-01 | Immunome | |
| sn-glycero-3-Phosphoethanolamine | 0.01 | 0.00 | 414 | 2.63 | 8.92E-03 | 1.05E-01 | Metabolome | HMDB00114 |
| C13:0, DC FA(4) | 0.02 | 0.01 | 414 | 2.64 | 8.70E-03 | 1.05E-01 | Metabolome | HMDB02327 |
| Ig lambda chain V-I region HA | −0.01 | 0.00 | 437 | −2.63 | 8.89E-03 | 1.05E-01 | Proteome | P01700 |
| TGL HDL | 0.02 | 0.01 | 457 | 2.61 | 9.30E-03 | 1.08E-01 | Clinical labs | |
| LysoPC(O-18:0) | 0.15 | 0.06 | 414 | 2.6 | 9.77E-03 | 1.11E-01 | Metabolome | HMDB11149 |
| Palmitoylglycine | 0.01 | 0.00 | 414 | 2.56 | 1.08E-02 | 1.18E-01 | Metabolome | HMDB13034 |
| C9:1, OH FA(2) | 0.01 | 0.00 | 414 | 2.56 | 1.09E-02 | 1.18E-01 | Metabolome | |
| C14:1, OH FA(2) | 0.01 | 0.00 | 414 | 2.56 | 1.09E-02 | 1.18E-01 | Metabolome | |
| C17:0 FA(2) | 0.01 | 0.00 | 414 | 2.57 | 1.06E-02 | 1.18E-01 | Metabolome | |
| Ig lambda chain V-II region BUR | −0.01 | 0.00 | 437 | −2.55 | 1.12E-02 | 1.19E-01 | Proteome | P01708 |
| C20:4 FA | 0.01 | 0.01 | 414 | 2.54 | 1.16E-02 | 1.20E-01 | Metabolome | HMDB01043 |
| C6:0, DC AC(1) | −0.01 | 0.00 | 414 | −2.53 | 1.17E-02 | 1.20E-01 | Metabolome | HMDB61677 |
| C18:1, OH FA(2) | 0.01 | 0.01 | 414 | 2.53 | 1.16E-02 | 1.20E-01 | Metabolome | |
| C20:3, OH FA(1) | 0.01 | 0.01 | 414 | 2.53 | 1.19E-02 | 1.21E-01 | Metabolome | |
| Sphinganine 1-phosphate | 0.09 | 0.03 | 414 | 2.52 | 1.21E-02 | 1.21E-01 | Metabolome | HMDB01383 |
| L-Formylkynurenine | 0.03 | 0.01 | 414 | 2.51 | 1.26E-02 | 1.25E-01 | Metabolome | HMDB60485 |
| L-Isoleucine\|L-Leucine | 0.02 | 0.01 | 414 | 2.5 | 1.29E-02 | 1.27E-01 | Metabolome | HMDB00172\|HMDB00687 |
| PI16 | −0.01 | 0.00 | 437 | −2.49 | 1.32E-02 | 1.28E-01 | Proteome | Q6UXB8 |
| LysoPE(18:0) | 0.09 | 0.03 | 414 | 2.48 | 1.34E-02 | 1.28E-01 | Metabolome | HMDB11129 |
| C12:1, DC FA(3) | 0.01 | 0.00 | 414 | 2.48 | 1.37E-02 | 1.30E-01 | Metabolome | HMDB00933 |
| C12:2, OH FA | 0.01 | 0.01 | 414 | 2.46 | 1.42E-02 | 1.34E-01 | Metabolome | |
| L-Cystine | 0.02 | 0.01 | 414 | 2.45 | 1.47E-02 | 1.34E-01 | Metabolome | HMDB00192 |
| C17:1 FA | 0.01 | 0.01 | 414 | 2.45 | 1.46E-02 | 1.34E-01 | Metabolome | HMDB60038 |
| SHBG | −0.01 | 0.00 | 437 | −2.46 | 1.45E-02 | 1.34E-01 | Proteome | P04278 |
| L-Valine | 0.02 | 0.01 | 414 | 2.44 | 1.49E-02 | 1.34E-01 | Metabolome | HMDB00883 |
| IL12P70 | 0.03 | 0.01 | 446 | 2.42 | 1.58E-02 | 1.38E-01 | Immunome | |
| C18:0, DC FA(3) | 0.02 | 0.01 | 414 | 2.42 | 1.57E-02 | 1.38E-01 | Metabolome | HMDB00782 |
| C10:1 FA(2) | 0.01 | 0.01 | 414 | 2.42 | 1.58E-02 | 1.38E-01 | Metabolome | |
| C14:2 FA | 0.02 | 0.01 | 414 | 2.41 | 1.62E-02 | 1.38E-01 | Metabolome | HMDB00560 |
| 2-Aminobutyrate | 0.01 | 0.00 | 414 | 2.41 | 1.64E-02 | 1.38E-01 | Metabolome | HMD800650 |
| Phenylalanylphenylalanine | 0.35 | 0.15 | 414 | 2.41 | 1.63E-02 | 1.38E-01 | Metabolome | HMDB13302 |
| C20:2 FA | 0.01 | 0.00 | 414 | 2.4 | 1.67E-02 | 1.39E-01 | Metabolome | HMDB05060 |
| MG(20:4)(2) | 0.02 | 0.01 | 414 | 2.38 | 1.78E-02 | 1.46E-01 | Metabolome | HMDB04666 |
| C12:1, OH FA | 0.01 | 0.00 | 414 | 2.38 | 1.78E-02 | 1.46E-01 | Metabolome | |
| LysoPC(20:5) | −0.02 | 0.01 | 414 | −2.37 | 1.81E-02 | 1.47E-01 | Metabolome | HMDB10397 |
| MCH | −0.02 | 0.01 | 452 | −2.36 | 1.88E-02 | 1.48E-01 | Clinical labs | |
| IL5 | 0.04 | 0.02 | 446 | 2.34 | 1.95E-02 | 1.48E-01 | Immunome | |
| 4-Hydroxyphenylpyruvic acid | 0.02 | 0.01 | 414 | 2.34 | 1.98E-02 | 1.48E-01 | Metabolome | HMDB00707 |
| Ne-Methyl-Lysine | 0.02 | 0.01 | 414 | 2.34 | 1.98E-02 | 1.48E-01 | Metabolome | HMD302038 |
| C24:4 FA | 0.01 | 0.01 | 414 | 2.36 | 1.87E-02 | 1.48E-01 | Metabolome | HMDB06246 |

TABLE 12-continued

| | | | | | | | |
|---|---|---|---|---|---|---|---|
| C16:0, OH FA(1) | 0.01 | 0.00 | 414 | 2.35 | 1.95E−02 | 1.48E−01 | Metabolome | HMDB31057 |
| LysoPI(18:1) | 0.02 | 0.01 | 414 | 2.35 | 1.92E−02 | 1.48E−01 | Metabolome | HMDB61693 |
| C14:1, OH FA(1) | 0.01 | 0.01 | 414 | 2.36 | 1.88E−02 | 1.48E−01 | Metabolome | |
| HP | 0.01 | 0.00 | 437 | 2.34 | 2.00E−02 | 1.48E−01 | Proteome | P00738 |
| LCAT | 0.01 | 0.00 | 437 | 2.33 | 2.01E−02 | 1.48E−01 | Proteome | P04180 |
| CAPZB | −0.01 | 0.00 | 437 | −2.33 | 2.02E−02 | 1.48E−01 | Proteome | P47756 |
| C18:2, DC FA | 0.04 | 0.02 | 414 | 2.31 | 2.16E−02 | 1.55E−01 | Metabolome | |
| C15:0 FA | 0.01 | 0.00 | 414 | 2.31 | 2.15E−02 | 1.55E−01 | Metabolome | |
| C17:0 FA(1) | 0.01 | 0.00 | 414 | 2.3 | 2.18E−02 | 1.55E−01 | Metabolome | |
| Ig heavy chain V-III region NIE | −0.01 | 0.00 | 437 | −2.3 | 2.19E−02 | 1.55E−01 | Proteome | P01770 |
| Phenyllactate (PLA) | 0.02 | 0.01 | 414 | 2.29 | 2.22E−02 | 1.56E−01 | Metabolome | HMDB00779 |
| gamma-glutamyl-epsilon-lysine | 0.01 | 0.01 | 414 | 2.29 | 2.24E−02 | 1.56E−01 | Metabolome | HMDB03869 |
| HGF | 0.02 | 0.01 | 446 | 2.27 | 2.36E−02 | 1.63E−01 | Immunome | |
| Ornithine | 0.01 | 0.00 | 414 | 2.27 | 2.38E−02 | 1.63E−01 | Metabolome | HMDB03374 |
| C9:0 AC | 0.01 | 0.01 | 414 | 2.26 | 2.46E−02 | 1.67E−01 | Metabolome | HMDB13288 |
| Tetrahydrocortisol | 0.06 | 0.03 | 414 | 2.25 | 2.50E−02 | 1.69E−01 | Metabolome | HMDB00949 |
| C20:1 FA | 0.01 | 0.01 | 414 | 2.24 | 2.54E−02 | 1.69E−01 | Metabolome | HMDB02231 |
| Ig heavy chain V-I region HG3 | −0.01 | 0.00 | 437 | −2.24 | 2.53E−02 | 1.69E−01 | Proteome | P01743 |
| C14:0, OH FA(2) | 0.01 | 0.01 | 414 | 2.23 | 2.60E−02 | 1.71E−01 | Metabolome | |
| HGB | −0.02 | 0.01 | 452 | −2.22 | 2.66E−02 | 1.73E−01 | Clinical labs | |
| C14:2, OH FA | 0.01 | 0.01 | 414 | 2.23 | 2.64E−02 | 1.73E−01 | Metabolome | |
| Ig heavy chain V-II region ARH-77 | −0.01 | 0.00 | 437 | −2.22 | 2.68E−02 | 1.73E−01 | Proteome | P06331 |
| C20:4, DC FA | 0.04 | 0.02 | 414 | 2.2 | 2.83E−02 | 1.81E−01 | Metabolome | |
| EGF | 0.02 | 0.01 | 446 | 2.19 | 2.88E−02 | 1.83E−01 | Immunome | |
| LysoPG(18:0) | 0.01 | 0.01 | 414 | 2.18 | 3.01E−02 | 1.90E−01 | Metabolome | |
| LysoPE(20:2) | 0.00 | 0.00 | 414 | −2.15 | 3.25E−02 | 2.03E−01 | Metabolome | HMD611483 |
| LysoPC(22:0) | 0.02 | 0.01 | 414 | 2.14 | 3.27E−02 | 2.03E−01 | Metabolome | HMDB10398 |
| C10:0, DC FA (Sebacic acid)(2) | 0.02 | 0.01 | 414 | 2.13 | 3.34E−02 | 2.06E−01 | Metabolome | HMDB00792 |
| methyl-4-hyd roxybenzoate sulfate | 0.03 | 0.02 | 414 | 2.13 | 3.40E−02 | 2.08E−01 | Metabolome | HMDB34172 |
| Hyd roxybutyric acid (1) | 0.01 | 0.01 | 414 | 2.12 | 3.47E−02 | 2.09E−01 | Metabolome | |
| SCLT1 | −0.01 | 0.00 | 437 | −2.12 | 3.45E−02 | 2.09E−01 | Proteome | Q96NL6 |
| gamma-glutamylleucine(2) | 0.01 | 0.01 | 414 | 2.11 | 3.53E−02 | 2.10E−01 | Metabolome | HMDB11171 |
| LysoPE(20:1) | −0.01 | 0.00 | 414 | −2.11 | 3.51E−02 | 2.10E−01 | Metabolome | HMD311482 |
| MAN2B2 | −0.01 | 0.00 | 437 | −2.11 | 3.55E−02 | 2.10E−01 | Proteome | Q9Y2E5 |
| Pipecolic acid | −0.01 | 0.01 | 414 | −2.1 | 3.66E−02 | 2.15E−01 | Metabolome | HMDB00070 |
| L-Malic acid | 0.01 | 0.01 | 414 | 2.09 | 3.73E−02 | 2.16E−01 | Metabolome | HMDB00156 |
| Ig kappa chain V-III region NG9 | −0.01 | 0.00 | 437 | −2.09 | 3.71E−02 | 2.16E−01 | Proteome | P01621 |
| C14:0, DC FA(2) | 0.01 | 0.01 | 414 | 2.09 | 3.76E−02 | 2.16E−01 | Metabolome | HMDB00872 |
| SCF | 0.02 | 0.01 | 446 | 2.06 | 3.95E−02 | 2.25E−01 | Immunome | |
| C20:2, OH FA | 0.01 | 0.01 | 414 | 2.06 | 3.97E−02 | 2.25E−01 | Metabolome | |
| C16:0, DC FA(1) | 0.01 | 0.01 | 414 | 2.05 | 4.09E−02 | 2.30E−01 | Metabolome | HMDB00672 |
| Ig lambda chain V-VI region EB4 | −0.01 | 0.00 | 437 | −2.04 | 4.21E−02 | 2.35E−01 | Proteome | P06319 |
| C12:0 FA(1) | 0.01 | 0.01 | 414 | 2.04 | 4.25E−02 | 2.36E−01 | Metabolome | |
| C12:0, DC FA | 0.03 | 0.01 | 414 | 2.02 | 4.35E−02 | 2.40E−01 | Metabolome | HMDB00623 |
| MG(15:0)(3) | 0.02 | 0.01 | 414 | 2.02 | 4.42E−02 | 2.42E−01 | Metabolome | HMDB11532 |
| N-Acetylleucine\|N-Acetylisoleucine | 0.01 | 0.01 | 414 | 2.01 | 4.48E−02 | 2.42E−01 | Metabolome | HMDB11756\|HMDB61684 |
| 7-alpha-hydroxy-3-oxo-4-cholestenoate (7-Hoca) | 0.01 | 0.01 | 414 | 2.01 | 4.46E−02 | 2.42E−01 | Metabolome | HMDB12458 |
| Ig lambda chain V-V region DEL | −0.02 | 0.01 | 437 | −2.01 | 4.55E−02 | 2.43E−01 | Proteome | P01719 |
| COL6A3 | −0.01 | 0.00 | 437 | −2.01 | 4.55E−02 | 2.43E−01 | Proteome | P12111 |
| C18:3, OH FA(1) | 0.01 | 0.01 | 414 | 2 | 4.62E−02 | 2.45E−01 | Metabolome | |
| IG heavy chain V-III region BUR | −0.01 | 0.00 | 437 | −2 | 4.66E−02 | 2.46E−01 | Proteome | P01773 |
| 4-Methylcatechol sulfate | 0.01 | 0.01 | 414 | 1.99 | 4.69E−02 | 2.46E−01 | Metabolome | |
| SELL | −0.01 | 0.00 | 437 | −1.99 | 4.75E−02 | 2.47E−01 | Proteome | P14151 |
| 5-methyluridine (ribothymidine) | −0.01 | 0.01 | 414 | −1.98 | 4.79E−02 | 2.48E−01 | Metabolome | HMDB00884 |
| C10:3 FA(2) | 0.01 | 0.00 | 414 | 1.96 | 5.04E−02 | 2.59E−01 | Metabolome | |
| MG(14:1)(2) | 0.02 | 0.01 | 414 | 1.95 | 5.19E−02 | 2.64E−01 | Metabolome | HMDB11531 |
| 5alpha-Androstan-3alpha, 17alpha-diol monosulfate(3) | 0.04 | 0.02 | 414 | 1.95 | 5.18E−02 | 2.64E−01 | Metabolome | |
| Phenylbutyric acid | −0.01 | 0.01 | 414 | −1.94 | 5.26E−02 | 2.66E−01 | Metabolome | HMDB00329 |
| 1,2,3-benzenetriol sulfate | 0.02 | 0.01 | 414 | 1.92 | 5.54E−02 | 2.78E−01 | Metabolome | |
| MG(22:2) | 0.02 | 0.01 | 414 | 1.92 | 5.58E−02 | 2.79E−01 | Metabolome | HMDB11553 |
| Betaine | 0.01 | 0.01 | 414 | 1.9 | 5.84E−02 | 2.85E−01 | Metabolome | HMDB00043 |
| C24:5 FA | 0.01 | 0.01 | 414 | 1.9 | 5.80E−02 | 2.85E−01 | Metabolome | HMDB06322 |
| 4-formyl Indole(2) | 0.02 | 0.01 | 414 | 1.9 | 5.82E−02 | 2.85E−01 | Metabolome | |
| Ig lambda chain V-I region NEWM | −0.01 | 0.00 | 437 | −1.9 | 5.75E−02 | 2.85E−01 | Proteome | P01703 |
| CHOLHDL | 0.02 | 0.01 | 457 | 1.89 | 5.92E−02 | 2.86E−01 | Clinical labs | |
| LDHB | −0.01 | 0.00 | 437 | −1.89 | 5.94E−02 | 2.86E−01 | Proteome | P07195 |
| LDLHDL | 0.01 | 0.01 | 456 | 1.88 | 6.03E−02 | 2.89E−01 | Clinical labs | |
| LysoPE(22:0) | 0.04 | 0.02 | 414 | 1.88 | 6.13E−02 | 2.92E−01 | Metabolome | HMDB11490 |
| 5-Acetylamino-6-amino-3-methyluracil(1) | 0.01 | 0.01 | 414 | 1.85 | 6.52E−02 | 3.03E−01 | Metabolome | HMDB04400 |
| LysoPE(22:4) | 0.01 | 0.01 | 414 | 1.84 | 6.60E−02 | 3.03E−01 | Metabolome | HMDB11493 |
| MG(18:1) | 0.02 | 0.01 | 414 | 1.85 | 6.52E−02 | 3.03E−01 | Metabolome | HMDB11536 |
| Ig mu heavy chain disease protein | −0.01 | 0.00 | 437 | −1.85 | 6.53E−02 | 3.03E−01 | Proteome | P04220 |
| C8B | −0.01 | 0.00 | 437 | 1.86 | 6.40E−02 | 3.03E−01 | Proteome | P07358 |
| PROZ | −0.02 | 0.01 | 437 | −1.85 | 6.57E−02 | 3.03E−01 | Proteome | P22891 |
| FETUB | −0.01 | 0.00 | 437 | −1.85 | 6.56E−02 | 3.03E−01 | Proteome | Q9UGM5 |
| C22:2 FA | 0.01 | 0.01 | 414 | 1.83 | 6.75E−02 | 3.08E−01 | Metabolome | HMDB61714 |
| Phenol sulphate | 0.01 | 0.01 | 414 | 1.83 | 6.79E−02 | 3.08E−01 | Metabolome | HMDB60015 |
| C18:1, OH FA(1) | 0.01 | 0.01 | 414 | 1.82 | 6.91E−02 | 3.12E−01 | Metabolome | |

TABLE 12-continued

| | | | | | | | |
|---|---|---|---|---|---|---|---|
| NHDL | 0.01 | 0.01 | 457 | 1.81 | 7.06E−02 | 3.14E−01 | Clinical labs | |
| IL1B | −0.01 | 0.00 | 446 | −1.81 | 7.07E−02 | 3.14E−01 | Immunome | |
| Phenylpyruvic acid | −0.01 | 0.01 | 414 | −1.81 | 7.18E−02 | 3.14E−01 | Metabolome | HMDB00205 |
| Aminoadipic acid | 0.01 | 0.01 | 414 | 1.8 | 7.22E−02 | 3.14E−01 | Metabolome | HMDB00510 |
| 7-Methylguanine | 0.01 | 0.01 | 414 | 1.8 | 7.19E−02 | 3.14E−01 | Metabolome | HMDB00897 |
| MGP | −0.01 | 0.00 | 437 | −1.81 | 7.10E−02 | 3.14E−01 | Proteome | P08493 |
| PON3 | 0.01 | 0.00 | 437 | 1.81 | 7.13E−02 | 3.14E−01 | Proteome | Q15166 |
| C12:1 FA(2) | 0.02 | 0.01 | 414 | 1.79 | 7.38E−02 | 3.14E−01 | Metabolome | HMDB00529 |
| MG(16:1) | 0.01 | 0.01 | 414 | 1.79 | 7.38E−02 | 3.14E−01 | Metabolome | HMDB11534 |
| Oleoyl Ethyl Amide | 0.01 | 0.00 | 414 | 1.8 | 7.31E−02 | 3.14E−01 | Metabolome | |
| C10:1 FA(1) | 0.00 | 0.00 | 414 | 1.8 | 7.27E−02 | 3.14E−01 | Metabolome | |
| ALKP | 0.01 | 0.01 | 456 | 1.78 | 7.57E−02 | 3.21E−01 | Clinical labs | |
| 9-HODE | 0.01 | 0.01 | 414 | 1.78 | 7.66E−02 | 3.23E−01 | Metabolome | HMDB04702 |
| N1-Methyl-2-pyridone-5-carboxamide(1) | 0.02 | 0.01 | 414 | 1.77 | 7.76E−02 | 3.26E−01 | Metabolome | HMDB04193 |
| Ig kappa chain V-I region Scw | −0.01 | 0.00 | 437 | −1.76 | 7.86E−02 | 3.28E−01 | Proteome | P01609 |
| LysoPC(16:1) | −0.01 | 0.00 | 414 | −1.75 | 8.03E−02 | 3.34E−01 | Metabolome | HMDB10383 |
| C10:0, DC FA (Sebacic acid)(1) | 0.02 | 0.01 | 414 | 1.74 | 8.18E−02 | 3.36E−01 | Metabolome | HMDB00792 |
| gamma-glutamylthreonine(1) | 0.01 | 0.00 | 414 | 1.74 | 8.25E−02 | 3.36E−01 | Metabolome | HMDB29159 |
| C18:0, OH FA(2) | 0.01 | 0.01 | 414 | 1.75 | 8.17E−02 | 3.36E−01 | Metabolome | |
| C18:2, OH FA | 0.01 | 0.01 | 414 | 1.74 | 8.23E−02 | 3.36E−01 | Metabolome | |
| Pyruvic acid | −0.01 | 0.01 | 414 | −1.73 | 8.42E−02 | 3.39E−01 | Metabolome | HMDB00243 |
| Hypoxanthine | 0.01 | 0.00 | 414 | 1.73 | 8.44E−02 | 3.39E−01 | Metabolome | HMDB00157 |
| 25-hydroxyvitamin D3 | 0.02 | 0.01 | 414 | 1.73 | 8.38E−02 | 3.39E−01 | Metabolome | |
| C14:0 FA | 0.01 | 0.00 | 414 | 1.71 | 8.71E−02 | 3.46E−01 | Metabolome | HMDB00806 |
| LysoPC(18:0) | 0.01 | 0.01 | 414 | 1.71 | 8.72E−02 | 3.46E−01 | Metabolome | HMDB10384 |
| N-acetylthreonine | 0.02 | 0.01 | 414 | 1.72 | 8.68E−02 | 3.46E−01 | Metabolome | |
| Ig lambda chain V-I region VOR | −0.01 | 0.00 | 437 | −1.71 | 8.76E−02 | 3.46E−01 | Proteome | P01699 |
| Chenodeoxycholic acid 3-sulfate | 0.01 | 0.01 | 414 | 1.69 | 9.08E−02 | 3.57E−01 | Metabolome | HMDB02639 |
| Hydroxybenzoic acid | 0.05 | 0.03 | 414 | 1.69 | 9.22E−02 | 3.60E−01 | Metabolome | HMDB00500 |
| MCP1 | 0.01 | 0.01 | 446 | 1.68 | 9.34E−02 | 3.63E−01 | Immunome | |
| C19:0 FA(2) | 0.01 | 0.01 | 414 | 1.67 | 9.60E−02 | 3.72E−01 | Metabolome | HMDB00772 |
| CL | −0.01 | 0.00 | 456 | −1.66 | 9.66E−02 | 3.72E−01 | Clinical labs | |
| C10:3 AC(2) | 0.01 | 0.01 | 414 | 1.65 | 9.95E−02 | 3.82E−01 | Metabolome | |
| Gly-Lys or Lys-Gly | 0.01 | 0.01 | 414 | 1.64 | 1.01E−01 | 3.83E−01 | Metabolome | HMDB28846 |
| Ig kappa chain V-II region RPMI 6410 | −0.01 | 0.00 | 437 | −1.65 | 1.01E−01 | 3.83E−01 | Proteome | P06310 |
| N-Acetylserine | 0.01 | 0.01 | 414 | 1.64 | 1.02E−01 | 3.84E−01 | Metabolome | HMDB02931 |
| IL13 | 0.03 | 0.02 | 446 | 1.64 | 1.03E−01 | 3.86E−01 | Immunome | |
| C14:1 FA(1) | 0.01 | 0.01 | 414 | 1.62 | 1.05E−01 | 3.94E−01 | Metabolome | HMDB02000 |
| C18:1 FA | 0.01 | 0.00 | 414 | 1.62 | 1.06E−01 | 3.94E−01 | Metabolome | HMDB00207 |
| C4:0 AC | 0.02 | 0.01 | 414 | 1.62 | 1.06E−01 | 3.94E−01 | Metabolome | HMDB02013 |
| NGF | 0.02 | 0.01 | 446 | 1.61 | 1.07E−01 | 3.96E−01 | Immunome | |
| Creatine | 0.01 | 0.01 | 414 | 1.62 | 1.07E−01 | 3.96E−01 | Metabolome | HMDB00064 |
| Ig kappa chain V-I region AU | −0.01 | 0.00 | 437 | −1.61 | 1.08E−01 | 3.96E−01 | Proteome | P01594 |
| C16 Sphingosine 1-phosphate | 0.01 | 0.01 | 414 | 1.6 | 1.10E−01 | 4.00E−01 | Metabolome | HMDB60061 |
| KRT17 | −0.01 | 0.00 | 437 | −1.6 | 1.10E−01 | 4.00E−01 | Proteome | Q04695 |
| Paraxanthine | 0.01 | 0.01 | 414 | 1.6 | 1.11E−01 | 4.02E−01 | Metabolome | HMDB01860 |
| Ig lambda chain V-IV region Hil | −0.01 | 0.00 | 437 | −1.59 | 1.12E−01 | 4.02E−01 | Proteome | P01717 |
| L-Cysteine | 0.01 | 0.00 | 414 | 1.59 | 1.12E−01 | 4.02E−01 | Metabolome | HMDB00574 |
| N1-Methyl-2-pyridone-5-carboxamide(2) | 0.02 | 0.01 | 414 | 1.59 | 1.13E−01 | 4.03E−01 | Metabolome | HMDB04193 |
| (S)-(−)-2-Hydroxyisocaproic acid | 0.01 | 0.01 | 414 | 1.58 | 1.14E−01 | 4.05E−01 | Metabolome | HMDB00746 |
| L-Phenylalanine | 0.01 | 0.01 | 414 | 1.58 | 1.14E−01 | 4.05E−01 | Metabolome | HMDB00159 |
| IP10 | 0.02 | 0.01 | 446 | 1.58 | 1.15E−01 | 4.05E−01 | Immunome | |
| MONOAB | 0.01 | 0.01 | 452 | 1.57 | 1.18E−01 | 4.13E−01 | Clinical labs | |
| Taurocholic acid(2) | 0.11 | 0.07 | 414 | 1.57 | 1.18E−01 | 4.14E−01 | Metabolome | HMDB00036 |
| L-Cysteinylglycine disulfide | 0.01 | 0.01 | 414 | 1.56 | 1.19E−01 | 4.16E−01 | Metabolome | HMDB00709 |
| LDL | 0.01 | 0.01 | 456 | 1.55 | 1.21E−01 | 4.16E−01 | Clinical labs | |
| C19:0 FA(1) | 0.01 | 0.01 | 414 | 1.55 | 1.21E−01 | 4.16E−01 | Metabolome | HMDB00772 |
| Ig kappa chain V-III region VG | −0.01 | 0.00 | 437 | −1.55 | 1.21E−01 | 4.16E−01 | Proteome | P04433 |
| C4A | 0.00 | 0.00 | 437 | −1.55 | 1.21E−01 | 4.16E−01 | Proteome | P0C0L4 |
| L-Proline | 0.01 | 0.01 | 414 | 1.54 | 1.23E−01 | 4.22E−01 | Metabolome | HMDB00162 |
| C18:0, DC FA(2) | 0.01 | 0.01 | 414 | 1.54 | 1.24E−01 | 4.23E−01 | Metabolome | HMD300782 |
| N6-Acetyl-L-lysine | 0.01 | 0.01 | 414 | 1.52 | 1.29E−01 | 4.27E−01 | Metabolome | HMD600206 |
| C18:2 FA | 0.01 | 0.00 | 414 | 1.52 | 1.29E−01 | 4.27E−01 | Metabolome | HMDB00673 |
| LysoPC(P-18:1) | 0.01 | 0.01 | 414 | 1.52 | 1.29E−01 | 4.27E−01 | Metabolome | HMDB10408 |
| IGLC2 | −0.01 | 0.00 | 437 | −1.53 | 1.27E−01 | 4.27E−01 | Proteome | P0CG05 |
| ILK | 0.00 | 0.00 | 437 | −1.52 | 1.28E−01 | 4.27E−01 | Proteome | Q13418 |
| FRMPD1 | −0.01 | 0.00 | 437 | −1.53 | 1.28E−01 | 4.27E−01 | Proteome | Q5SYB0 |
| CNDP1 | 0.01 | 0.00 | 437 | 1.53 | 1.26E−01 | 4.27E−01 | Proteome | Q96KN2 |
| C13:0, DC FA(1) | 0.01 | 0.01 | 414 | 1.52 | 1.30E−01 | 4.28E−01 | Metabolome | HMDB02327 |
| LysoPE(P-16:0) | 0.03 | 0.02 | 414 | 1.52 | 1.30E−01 | 4.28E−01 | Metabolome | HMDB11152 |
| Sphinganine | 0.01 | 0.00 | 414 | 1.51 | 1.32E−01 | 4.30E−01 | Metabolome | HMDB00269 |
| Alliin | 0.00 | 0.00 | 414 | 1.51 | 1.32E−01 | 4.30E−01 | Metabolome | HMDB33592 |
| TF | 0.00 | 0.00 | 437 | 1.5 | 1.34E−01 | 4.36E−01 | Proteome | P02787 |
| FGG | 0.00 | 0.00 | 437 | 1.49 | 1.36E−01 | 4.38E−01 | Proteome | P02679 |
| PROC | −0.01 | 0.00 | 437 | −1.49 | 1.37E−01 | 4.38E−01 | Proteome | P04070 |
| CEHR1 | 0.00 | 0.00 | 437 | −1.49 | 1.36E−01 | 4.38E−01 | Proteome | Q03591 |
| FCN2 | −0.01 | 0.00 | 437 | −1.49 | 1.37E−01 | 4.39E−01 | Proteome | Q15485 |
| Ig kappa chain V-III region GOL | −0.01 | 0.00 | 437 | −1.49 | 1.38E−01 | 4.40E−01 | Proteome | P04206 |
| HCT | −0.01 | 0.00 | 452 | −1.48 | 1.41E−01 | 4.42E−01 | Clinical labs | |
| 2-Piperidinone | 0.02 | 0.01 | 414 | 1.48 | 1.41E−01 | 4.42E−01 | Metabolome | HMDB11749 |

TABLE 12-continued

| | | | | | | | |
|---|---|---|---|---|---|---|---|
| C18:3, OH FA(3) | 0.01 | 0.01 | 414 | 1.48 | 1.41E-01 | 4.42E-01 | Metabolome | |
| N-acetyl-1-methylhistidine | 0.01 | 0.01 | 414 | 1.47 | 1.41E-01 | 4.42E-01 | Metabolome | |
| SCP2 | 0.00 | 0.00 | 437 | -1.48 | 1.41E-01 | 4.42E-01 | Proteome | P22307 |
| VEGFD | -0.01 | 0.01 | 446 | -1.46 | 1.44E-01 | 4.47E-01 | Immunome | |
| Pregnanediol-3-glucuronide | 0.00 | 0.00 | 414 | 1.46 | 1.44E-01 | 4.47E-01 | Metabolome | HMDB10318 |
| MG(15:0)(1) | 0.01 | 0.01 | 414 | 1.45 | 1.47E-01 | 4.53E-01 | Metabolome | HMDB11532 |
| Titin | 0.00 | 0.00 | 437 | -1.45 | 1.48E-01 | 4.56E-01 | Proteome | Q8WZ42_2 |
| C3:1 AC | 0.00 | 0.00 | 414 | -1.44 | 1.50E-01 | 4.62E-01 | Metabolome | HMDB13124 |
| IGHG2 | -0.01 | 0.00 | 437 | -1.43 | 1.54E-01 | 4.70E-01 | Proteome | P01859 |
| ENA78 | -0.02 | 0.02 | 446 | -1.43 | 1.55E-01 | 4.72E-01 | Immunome | |
| Butyric acid|Isobutyric acid | 0.02 | 0.01 | 414 | 1.42 | 1.56E-01 | 4.73E-01 | Metabolome | HMDB00039|HMDB01873 |
| EFEMP1 | 0.00 | 0.00 | 437 | -1.42 | 1.56E-01 | 4.73E-01 | Proteome | Q12805 |
| Kynurenic acid | 0.01 | 0.01 | 414 | 1.42 | 1.57E-01 | 4.74E-01 | Metabolome | HMDB00715 |
| C14:0 AC | -0.01 | 0.01 | 414 | -1.41 | 1.60E-01 | 4.76E-01 | Metabolome | HMDB05066 |
| p-Cresol glucuronide | 0.01 | 0.01 | 414 | 1.41 | 1.59E-01 | 4.76E-01 | Metabolome | HMDB11686 |
| Tryptophan betaine | 0.00 | 0.00 | 414 | -1.41 | 1.60E-01 | 4.76E-01 | Metabolome | HMDB61115 |
| SERPINA10 | 0.00 | 0.00 | 437 | 1.41 | 1.59E-01 | 4.76E-01 | Proteome | Q9UK55 |
| MG(24:1) | 0.01 | 0.01 | 414 | 1.39 | 1.64E-01 | 4.85E-01 | Metabolome | HMDB11559 |
| GPR116 | 0.01 | 0.00 | 437 | 1.39 | 1.64E-01 | 4.85E-01 | Proteome | Q8IZF2 |
| IL21 | -0.03 | 0.02 | 446 | -1.38 | 1.69E-01 | 4.89E-01 | Immunome | |
| L-Carnitine | 0.01 | 0.01 | 414 | 1.38 | 1.69E-01 | 4.89E-01 | Metabolome | HMDB00062 |
| C11:0 AC | 0.01 | 0.01 | 414 | 1.38 | 1.68E-01 | 4.89E-01 | Metabolome | HMDB13321 |
| ATP5A1 | -0.01 | 0.00 | 437 | -1.39 | 1.66E-01 | 4.89E-01 | Proteome | P25705 |
| Microtubule-associated protein 4 | -0.01 | 0.00 | 437 | -1.38 | 1.68E-01 | 4.89E-01 | Proteome | P27816_2 |
| NUP205 | 0.00 | 0.00 | 437 | 1.38 | 1.68E-01 | 4.89E-01 | Proteome | Q92621 |
| C10:0, OH FA(2) | 0.01 | 0.01 | 414 | 1.37 | 1.71E-01 | 4.92E-01 | Metabolome | HMDB02203 |
| CLEC3B | 0.00 | 0.00 | 437 | 1.36 | 1.73E-01 | 4.97E-01 | Proteome | P05452 |
| Citrulline | 0.01 | 0.01 | 414 | 1.36 | 1.75E-01 | 4.99E-01 | Metabolome | HMDB00904 |
| ICAM1 | 0.02 | 0.02 | 446 | 1.36 | 1.76E-01 | 5.00E-01 | Immunome | |
| N2, N2-Dimethylguanosine | 0.01 | 0.01 | 414 | 1.36 | 1.75E-01 | 5.00E-01 | Metabolome | HMDB04824 |
| C18:0, OH AC | -0.02 | 0.02 | 414 | -1.34 | 1.81E-01 | 5.13E-01 | Metabolome | HMDB13164 |
| ALB | 0.01 | 0.01 | 456 | 1.33 | 1.85E-01 | 5.21E-01 | Clinical labs | |
| ALT | 0.01 | 0.01 | 454 | 1.32 | 1.87E-01 | 5.23E-01 | Clinical labs | |
| Dehydroisoandrosterone sulfate (DHEA-S)(1) | 0.01 | 0.01 | 414 | 1.32 | 1.87E-01 | 5.23E-01 | Metabolome | HMDB01032 |
| C5:1 AC | 0.01 | 0.01 | 414 | 1.32 | 1.88E-01 | 5.23E-01 | Metabolome | HMDB02366 |
| LysoPC(18:2) | -0.01 | 0.01 | 414 | -1.32 | 1.88E-01 | 5.23E-01 | Metabolome | HMDB10386 |
| Ig heavy chain V-III region GAL | 0.00 | 0.00 | 437 | -1.32 | 1.88E-01 | 5.23E-01 | Proteome | P01781 |
| VCL | 0.00 | 0.00 | 437 | 1.31 | 1.90E-01 | 5.27E-01 | Proteome | P18206 |
| UALB | 0.00 | 0.00 | 274 | -1.29 | 1.98E-01 | 5.29E-01 | Clinical labs | |
| CD40L | 0.03 | 0.02 | 446 | 1.28 | 2.00E-01 | 5.29E-01 | Immunome | |
| VCAM1 | -0.01 | 0.01 | 446 | -1.29 | 1.98E-01 | 5.29E-01 | Immunome | |
| L-Glutamic acid | 0.01 | 0.01 | 414 | 1.29 | 1.96E-01 | 5.29E-01 | Metabolome | HMDB00148 |
| C18:1 AC | 0.01 | 0.01 | 414 | 1.29 | 1.97E-01 | 5.29E-01 | Metabolome | HMDB05065 |
| pro-hydroxy-pro(1) | -0.01 | 0.01 | 414 | -1.29 | 1.96E-01 | 5.29E-01 | Metabolome | HMDB06695 |
| LysoPE(20:0) | 0.01 | 0.01 | 414 | 1.28 | 2.01E-01 | 5.29E-01 | Metabolome | HMDB11481 |
| LysoPE(22:5) | 0.01 | 0.01 | 414 | 1.31 | 1.92E-01 | 5.29E-01 | Metabolome | HMDB11494 |
| MG(20:0) | 0.01 | 0.01 | 414 | 1.3 | 1.94E-01 | 5.29E-01 | Metabolome | HMDB11542 |
| C13:1, OH FA | 0.01 | 0.00 | 414 | 1.29 | 1.98E-01 | 5.29E-01 | Metabolome | |
| C3 | 0.00 | 0.00 | 437 | 1.29 | 1.97E-01 | 5.29E-01 | Proteome | P01024 |
| Ig kappa chain V-I region BAN | 0.00 | 0.00 | 437 | -1.28 | 2.01E-01 | 5.29E-01 | Proteome | P04430 |
| SERPINA4 | 0.00 | 0.00 | 437 | 1.28 | 2.00E-01 | 5.29E-01 | Proteome | P29622 |
| TPM4 | 0.00 | 0.00 | 437 | 1.29 | 1.97E-01 | 5.29E-01 | Proteome | P67936 |
| cont_000137 | 0.00 | 0.00 | 437 | 1.3 | 1.95E-01 | 5.29E-01 | Proteome | |
| MYBPC2 | 0.00 | 0.00 | 437 | -1.27 | 2.06E-01 | 5.41E-01 | Proteome | Q14324 |
| MCV | -0.01 | 0.01 | 452 | -1.26 | 2.09E-01 | 5.48E-01 | Clinical labs | |
| Hydroxyphenyllactic acid | 0.01 | 0.00 | 414 | 1.25 | 2.12E-01 | 5.55E-01 | Metabolome | HMDB00755 |
| Arabonate | Xylonate(3) | -0.01 | 0.01 | 414 | -1.24 | 2.15E-01 | 5.56E-01 | Metabolome | |
| Phenylalanylleucine | 0.01 | 0.01 | 414 | 1.24 | 2.15E-01 | 5.56E-01 | Metabolome | |
| TYMP | 0.00 | 0.00 | 437 | -1.25 | 2.14E-01 | 5.56E-01 | Proteome | P19971 |
| IL2 | 0.03 | 0.03 | 446 | 1.23 | 2.19E-01 | 5.62E-01 | Immunome | |
| L-Lactic acid | 0.01 | 0.01 | 414 | 1.23 | 2.20E-01 | 5.62E-01 | Metabolome | HMDB00190 |
| LysoPC(20:1) | 0.02 | 0.01 | 414 | 1.23 | 2.20E-01 | 5.62E-01 | Metabolome | HMDB10391 |
| IGLL5 | 0.00 | 0.00 | 437 | 1.23 | 2.18E-01 | 5.62E-01 | Proteome | B9A064 |
| Citric acid | 0.01 | 0.01 | 414 | 1.23 | 2.21E-01 | 5.63E-01 | Metabolome | HMDB00094 |
| EOSAB | 0.01 | 0.01 | 451 | 1.22 | 2.24E-01 | 5.68E-01 | Clinical labs | |
| IL8 | 0.02 | 0.01 | 446 | 1.22 | 2.24E-01 | 5.68E-01 | Immunome | |
| Threonic acid | 0.01 | 0.01 | 414 | 1.21 | 2.26E-01 | 5.69E-01 | Metabolome | HMDB00943 |
| PRG4(1) | 0.00 | 0.00 | 437 | 1.21 | 2.25E-01 | 5.69E-01 | Proteome | Q92954 |
| Glyceric acid | -0.01 | 0.01 | 414 | -1.21 | 2.29E-01 | 5.70E-01 | Metabolome | HMD600139 |
| Cinnamoylglycine | 0.01 | 0.01 | 414 | 1.21 | 2.29E-01 | 5.70E-01 | Metabolome | HMDB11621 |
| APOB | 0.00 | 0.00 | 437 | 1.21 | 2.28E-01 | 5.70E-01 | Proteome | P04114 |
| Ig heavy chain V-I region V35 | 0.00 | 0.00 | 437 | -1.21 | 2.29E-01 | 5.70E-01 | Proteome | P23083 |
| IL9 | 0.03 | 0.02 | 446 | 1.2 | 2.30E-01 | 5.70E-01 | Immunome | |
| 3-Methyl-L-histidine | 0.01 | 0.01 | 414 | 1.2 | 2.30E-01 | 5.70E-01 | Metabolome | HMDB00479 |
| LysoPE(20:3) | 0.02 | 0.01 | 414 | 1.19 | 2.34E-01 | 5.75E-01 | Metabolome | HMDB11484 |
| IGHG4 | 0.01 | 0.01 | 437 | 1.19 | 2.33E-01 | 5.75E-01 | Proteome | P01861 |
| 5-oxoproline | 0.00 | 0.00 | 414 | 1.18 | 2.40E-01 | 5.78E-01 | Metabolome | HMDB00267 |
| pro-hydroxy-pro(2) | -0.01 | 0.01 | 414 | -1.18 | 2.38E-01 | 5.78E-01 | Metabolome | HMDB06695 |
| LysoPC(20:0) | 0.02 | 0.01 | 414 | 1.18 | 2.39E-01 | 5.78E-01 | Metabolome | HMDB10390 |

TABLE 12-continued

| | | | | | | | |
|---|---|---|---|---|---|---|---|
| C8:0, OH FA(2) | 0.01 | 0.01 | 414 | 1.18 | 2.38E−01 | 5.78E−01 | Metabolome | |
| C1QA | 0.00 | 0.00 | 437 | −1.19 | 2.36E−01 | 5.78E−01 | Proteome | P02745 |
| CFHR4 | 0.00 | 0.00 | 437 | −1.18 | 2.39E−01 | 5.78E−01 | Proteome | Q92496 |
| PCYOX1 | 0.00 | 0.00 | 437 | 1.18 | 2.39E−01 | 5.78E−01 | Proteome | Q9UHG3 |
| VTN | 0.00 | 0.00 | 437 | 1.17 | 2.42E−01 | 5.83E−01 | Proteome | P04004 |
| Hydroxybutyric acid(2) | 0.01 | 0.01 | 414 | 1.17 | 2.44E−01 | 5.85E−01 | Metabolome | |
| C7 | 0.00 | 0.00 | 437 | 1.16 | 2.45E−01 | 5.86E−01 | Proteome | P10643 |
| APOC1 | 0.00 | 0.00 | 437 | 1.16 | 2.46E−01 | 5.87E−01 | Proteome | P02654 |
| C8:0, OH FA(3) | 0.00 | 0.00 | 414 | −1.16 | 2.48E−01 | 5.89E−01 | Metabolome | |
| TP | 0.01 | 0.01 | 456 | 1.14 | 2.53E−01 | 5.97E−01 | Clinical labs | |
| Chenodeoxycholic Acid(3) | 0.02 | 0.02 | 414 | 1.14 | 2.54E−01 | 5.97E−01 | Metabolome | HMDB00518 |
| HPX | 0.00 | 0.00 | 437 | 1.14 | 2.54E−01 | 5.97E−01 | Proteome | P02790 |
| NA | −0.01 | 0.00 | 456 | −1.14 | 2.53E−01 | 5.97E−01 | Clinical labs | |
| Dihydroferulic acid | −0.01 | 0.01 | 414 | −1.14 | 2.55E−01 | 5.97E−01 | Metabolome | |
| N-Acetyl-L-phenylalanine | 0.01 | 0.01 | 414 | 1.12 | 2.63E−01 | 6.12E−01 | Metabolome | HMDB00512 |
| F10 | 0.00 | 0.00 | 437 | −1.12 | 2.63E−01 | 6.12E−01 | Proteome | P00742 |
| FGB | 0.00 | 0.00 | 437 | 1.12 | 2.63E−01 | 6.12E−01 | Proteome | P02675 |
| ACAA2 | 0.00 | 0.00 | 437 | −1.12 | 2.65E−01 | 6.15E−01 | Proteome | P42765 |
| 3-carboxy-4-methyl-5-propyl-2-furanpropanoate (CMPF) | 0.01 | 0.01 | 414 | 1.11 | 2.67E−01 | 6.15E−01 | Metabolome | HMDB61112 |
| C10:2 FA | 0.01 | 0.01 | 414 | 1.11 | 2.67E−01 | 6.15E−01 | Metabolome | |
| CRISP3 | 0.00 | 0.00 | 437 | −1.11 | 2.68E−01 | 6.15E−01 | Proteome | P54108 |
| LysoPE(16:0) | 0.04 | 0.03 | 414 | 1.11 | 2.69E−01 | 6.17E−01 | Metabolome | HMDB11473 |
| C18:3 FA | 0.00 | 0.00 | 414 | 1.1 | 2.70E−01 | 6.18E−01 | Metabolome | HMDB03073 |
| 5alpha-Androstan-3alpha,17alpha-diol monosulfate(1) | 0.02 | 0.02 | 414 | 1.1 | 2.71E−01 | 6.18E−01 | Metabolome | |
| cont_000107 | 0.00 | 0.00 | 437 | 1.09 | 2.77E−01 | 6.30E−01 | Proteome | |
| Betonicine | 0.00 | 0.00 | 414 | 1.09 | 2.78E−01 | 6.31E−01 | Metabolome | HMDB29412 |
| Arabonate | Xylonate(2) | −0.01 | 0.01 | 414 | −1.08 | 2.82E−01 | 6.37E−01 | Metabolome | |
| AFM | 0.00 | 0.00 | 437 | 1.08 | 2.82E−01 | 6.37E−01 | Proteome | P43652 |
| Chenodeoxycholic acid glycine conjugate(1) | 0.01 | 0.01 | 414 | 1.06 | 2.89E−01 | 6.43E−01 | Metabolome | HMDB00637 |
| CFB | 0.00 | 0.00 | 437 | 1.06 | 2.88E−01 | 6.43E−01 | Proteome | P00751 |
| Ig heavy chain V-III region KOL | 0.00 | 0.00 | 437 | −1.06 | 2.89E−01 | 6.43E−01 | Proteome | P01772 |
| Ig lambda chain V-I region BL2 | 0.00 | 0.00 | 437 | 1.06 | 2.88E−01 | 6.43E−01 | Proteome | P06316 |
| C4B | 0.00 | 0.00 | 437 | 1.06 | 2.88E−01 | 6.43E−01 | Proteome | P0C0L5 |
| LUM | 0.00 | 0.00 | 437 | 1.07 | 2.87E−01 | 6.43E−01 | Proteome | P51884 |
| PSTK | 0.00 | 0.00 | 437 | −1.06 | 2.90E−01 | 6.43E−01 | Proteome | Q8IV42 |
| K | 0.00 | 0.00 | 456 | 1.06 | 2.91E−01 | 6.43E−01 | Clinical labs | |
| Androsterone sulfate(2) | 0.01 | 0.01 | 414 | 1.05 | 2.94E−01 | 6.45E−01 | Metabolome | HMDB02759 |
| COLEC11 | 0.00 | 0.00 | 437 | 1.05 | 2.94E−01 | 6.45E−01 | Proteome | Q9BWP8 |
| C11:1 FA | 0.01 | 0.01 | 414 | 1.05 | 2.95E−01 | 6.46E−01 | Metabolome | HMDB33724 |
| 11-beta-Hydroxyandrosterone-3-glucuronide | −0.01 | 0.01 | 414 | −1.05 | 2.96E−01 | 6.47E−01 | Metabolome | HMDB10351 |
| FN1 | 0.00 | 0.00 | 437 | 1.04 | 2.97E−01 | 6.47E−01 | Proteome | P02751 |
| HNRNPM | 0.00 | 0.00 | 437 | 1.04 | 2.99E−01 | 6.51E−01 | Proteome | P52272 |
| Pregnanolone sulfate | 0.00 | 0.00 | 414 | −1.04 | 3.00E−01 | 6.52E−01 | Metabolome | |
| Asp-Glu or Glu-Asp | 0.00 | 0.00 | 414 | 1.03 | 3.01E−01 | 6.52E−01 | Metabolome | HMDB28752 |
| MG(24:0)(2) | 0.01 | 0.01 | 414 | 1.03 | 3.02E−01 | 6.52E−01 | Metabolome | HMDB11558 |
| 3-indoxyl sulfate | 0.01 | 0.01 | 414 | 1.03 | 3.06E−01 | 6.55E−01 | Metabolome | HMDB00682 |
| Ig kappa chain V-III region CLL | 0.00 | 0.00 | 437 | −1.03 | 3.05E−01 | 6.55E−01 | Proteome | P04207 |
| LYZ | 0.00 | 0.00 | 437 | −1.03 | 3.04E−01 | 6.55E−01 | Proteome | P61626 |
| C5:0 AC | 0.01 | 0.01 | 414 | 1.02 | 3.09E−01 | 6.60E−01 | Metabolome | |
| C16:1, OH FA(1) | 0.00 | 0.00 | 414 | 1.01 | 3.11E−01 | 6.62E−01 | Metabolome | |
| SERPINA6 | 0.00 | 0.00 | 437 | 1.01 | 3.11E−01 | 6.62E−01 | Proteome | P08185 |
| Attractin | 0.00 | 0.00 | 437 | 1.01 | 3.15E−01 | 6.65E−01 | Proteome | O75882_2 |
| CFHR2 | 0.00 | 0.00 | 437 | −1.01 | 3.15E−01 | 6.65E−01 | Proteome | P36980 |
| OLFM1 | 0.00 | 0.00 | 437 | −1.01 | 3.15E−01 | 6.65E−01 | Proteome | Q99784 |
| SAA2 | 0.00 | 0.00 | 437 | −0.99 | 3.22E−01 | 6.77E−01 | Proteome | P0DJI9 |
| N-Methylproline | −0.01 | 0.01 | 414 | −0.98 | 3.25E−01 | 6.83E−01 | Metabolome | |
| C3:0 AC | −0.01 | 0.01 | 414 | −0.98 | 3.29E−01 | 6.88E−01 | Metabolome | HMDB00824 |
| GLOB | 0.01 | 0.01 | 456 | 0.97 | 3.31E−01 | 6.90E−01 | Clinical labs | |
| SERPIND1 | 0.00 | 0.00 | 437 | 0.97 | 3.30E−01 | 6.90E−01 | Proteome | P05546 |
| Indoleactic acid | −0.01 | 0.01 | 414 | −0.97 | 3.35E−01 | 6.96E−01 | Metabolome | HMDB00375 |
| C10:3 AC(1) | 0.01 | 0.01 | 414 | 0.96 | 3.36E−01 | 6.96E−01 | Metabolome | |
| MCP3 | −0.01 | 0.01 | 446 | −0.95 | 3.43E−01 | 7.07E−01 | Immunome | |
| Dihydro-3-coumaric acid | 0.01 | 0.01 | 414 | 0.95 | 3.43E−01 | 7.07E−01 | Metabolome | HMDB00375 |
| FGA | 0.00 | 0.00 | 437 | 0.94 | 3.45E−01 | 7.10E−01 | Proteome | P02671 |
| DSP | 0.00 | 0.00 | 437 | −0.94 | 3.46E−01 | 7.10E−01 | Proteome | P15924 |
| C14:0, DC FA(1) | −0.01 | 0.01 | 414 | −0.94 | 3.48E−01 | 7.12E−01 | Metabolome | HMDB00872 |
| MONO | −0.01 | 0.01 | 452 | −0.91 | 3.63E−01 | 7.12E−01 | Clinical labs | |
| TBIL | −0.01 | 0.01 | 456 | −0.91 | 3.63E−01 | 7.12E−01 | Clinical labs | |
| GMCSF | 0.02 | 0.02 | 446 | 0.93 | 3.53E−01 | 7.12E−01 | Immunome | |
| MIP1A | −0.02 | 0.02 | 446 | −0.91 | 3.61E−01 | 7.12E−01 | Immunome | |
| C16:0 AC | −0.01 | 0.01 | 414 | −0.94 | 3.49E−01 | 7.12E−01 | Metabolome | HMDB00222 |
| Xanthine | 0.00 | 0.01 | 414 | 0.91 | 3.64E−01 | 7.12E−01 | Metabolome | HMD300292 |
| C16:1 FA | 0.01 | 0.01 | 414 | 0.93 | 3.54E−01 | 7.12E−01 | Metabolome | HMD603229 |
| N1-methyladenosine | 0.00 | 0.00 | 414 | 0.92 | 3.57E−01 | 7.12E−01 | Metabolome | HMD303331 |
| L-a-glutamyl-L-Lysine | 0.01 | 0.01 | 414 | 0.93 | 3.51E−01 | 7.12E−01 | Metabolome | HMDB04207 |
| C18:4 FA | 0.01 | 0.01 | 414 | 0.92 | 3.57E−01 | 7.12E−01 | Metabolome | HMD306547 |

TABLE 12-continued

| | | | | | | | |
|---|---|---|---|---|---|---|---|
| C8:1 AC | 0.00 | 0.01 | 414 | 0.92 | 3.60E−01 | 7.12E−01 | Metabolome | HMDB13324 |
| C16:4 FA | 0.01 | 0.01 | 414 | 0.92 | 3.60E−01 | 7.12E−01 | Metabolome | |
| C8:2, OH FA(1) | −0.01 | 0.01 | 414 | −0.92 | 3.60E−01 | 7.12E−01 | Metabolome | |
| PLG | 0.00 | 0.00 | 437 | 0.92 | 3.56E−01 | 7.12E−01 | Proteome | P00747 |
| KNG1(1) | 0.00 | 0.00 | 437 | 0.92 | 3.60E−01 | 7.12E−01 | Proteome | P01042 |
| Kininogen-1 | 0.00 | 0.00 | 437 | −0.93 | 3.55E−01 | 7.12E−01 | Proteome | P01042_2 |
| IGJ | 0.00 | 0.00 | 437 | −0.92 | 3.57E−01 | 7.12E−01 | Proteome | P01591 |
| APOC2 | 0.00 | 0.00 | 437 | 0.94 | 3.49E−01 | 7.12E−01 | Proteome | P02655 |
| AFG3L2 | 0.00 | 0.00 | 437 | −0.91 | 3.63E−01 | 7.12E−01 | Proteome | Q9Y4W6 |
| IL10 | 0.02 | 0.02 | 446 | 0.9 | 3.67E−01 | 7.12E−01 | Immunome | |
| LysoPC(20:3) | −0.01 | 0.01 | 414 | −0.9 | 3.67E−01 | 7.12E−01 | Metabolome | HMDB10393 |
| CP | 0.00 | 0.00 | 437 | 0.9 | 3.67E−01 | 7.12E−01 | Proteome | P00450 |
| HPR | 0.00 | 0.00 | 437 | 0.9 | 3.66E−01 | 7.12E−01 | Proteome | P00739 |
| APOC4 | 0.00 | 0.00 | 437 | 0.9 | 3.69E−01 | 7.14E−01 | Proteome | P55056 |
| C13:0, DC FA(3) | 0.00 | 0.00 | 414 | 0.89 | 3.73E−01 | 7.20E−01 | Metabolome | HMDB02327 |
| 5alpha-Androstan-3alpha, 17beta-diol 17-glucuronide(1) | −0.01 | 0.01 | 414 | −0.88 | 3.78E−01 | 7.28E−01 | Metabolome | |
| ALCRU | 0.01 | 0.01 | 274 | 0.88 | 3.79E−01 | 7.28E−01 | Clinical labs | |
| Taurine | −0.01 | 0.01 | 414 | −0.88 | 3.80E−01 | 7.29E−01 | Metabolome | HMDB00251 |
| PCOLCE | 0.00 | 0.00 | 437 | −0.88 | 3.81E−01 | 7.29E−01 | Proteome | Q15113 |
| CPB2 | 0.00 | 0.00 | 437 | −0.86 | 3.89E−01 | 7.43E−01 | Proteome | Q96IY4 |
| C6:0 AC | 0.01 | 0.02 | 414 | 0.86 | 3.91E−01 | 7.44E−01 | Metabolome | HMDB00705 |
| C20:5 FA | 0.01 | 0.01 | 414 | 0.86 | 3.92E−01 | 7.44E−01 | Metabolome | HMDB01999 |
| cont_000108 | 0.00 | 0.00 | 437 | 0.86 | 3.92E−01 | 7.44E−01 | Proteome | |
| Pregnenolone sulfate | −0.01 | 0.01 | 414 | −0.85 | 3.95E−01 | 7.47E−01 | Metabolome | HMDB00774 |
| APOM | 0.00 | 0.00 | 437 | −0.84 | 4.00E−01 | 7.55E−01 | Proteome | O95445 |
| LysoPC(20:2) | −0.01 | 0.02 | 414 | −0.84 | 4.04E−01 | 7.60E−01 | Metabolome | HMDB10392 |
| C25:0, OH FA | 0.01 | 0.01 | 414 | 0.84 | 4.04E−01 | 7.60E−01 | Metabolome | |
| BDNF | 0.00 | 0.01 | 446 | −0.83 | 4.07E−01 | 7.61E−01 | Immunome | |
| Acetylcarnosine | 0.01 | 0.01 | 414 | 0.83 | 4.06E−01 | 7.61E−01 | Metabolome | HMD612881 |
| Uracil | 0.00 | 0.00 | 414 | 0.83 | 4.09E−01 | 7.63E−01 | Metabolome | HMDB00300 |
| MG(24:0)(1) | 0.01 | 0.01 | 414 | 0.83 | 4.10E−01 | 7.63E−01 | Metabolome | HMDB11558 |
| L-Arginine | 0.00 | 0.01 | 414 | 0.82 | 4.13E−01 | 7.66E−01 | Metabolome | HMDB00517 |
| 4-formyl Indole(1) | 0.01 | 0.01 | 414 | 0.82 | 4.13E−01 | 7.66E−01 | Metabolome | |
| ITIH2 | 0.00 | 0.00 | 437 | 0.82 | 4.14E−01 | 7.66E−01 | Proteome | P19823 |
| C16:0, OH FA(2) | 0.00 | 0.00 | 414 | 0.82 | 4.15E−01 | 7.67E−01 | Metabolome | HMDB31057 |
| Unknown | 0.00 | 0.00 | 437 | 0.81 | 4.16E−01 | 7.67E−01 | Proteome | |
| CO2 | 0.00 | 0.00 | 456 | 0.8 | 4.23E−01 | 7.72E−01 | Clinical labs | |
| IL6 | 0.03 | 0.03 | 446 | 0.81 | 4.20E−01 | 7.72E−01 | Immunome | |
| C12:1, OH FA | 0.01 | 0.01 | 414 | 0.8 | 4.22E−01 | 7.72E−01 | Metabolome | |
| IGFBP3 | 0.00 | 0.00 | 437 | −0.8 | 4.23E−01 | 7.72E−01 | Proteome | P17936 |
| HGFAC | 0.00 | 0.00 | 437 | −0.8 | 4.23E−01 | 7.72E−01 | Proteome | Q04756 |
| IL17A | −0.01 | 0.01 | 446 | −0.79 | 4.31E−01 | 7.73E−01 | Immunome | |
| Urocanic acid | 0.00 | 0.00 | 414 | −0.79 | 4.27E−01 | 7.73E−01 | Metabolome | HMDB00301 |
| Biliverdin(2) | −0.01 | 0.01 | 414 | −0.79 | 4.30E−01 | 7.73E−01 | Metabolome | HMDB01008 |
| LysoPC(14:0) | 0.00 | 0.00 | 414 | −0.79 | 4.29E−01 | 7.73E−01 | Metabolome | HMD610379 |
| CFH | 0.00 | 0.00 | 437 | 0.79 | 4.30E−01 | 7.73E−01 | Proteome | P08603 |
| GP5 | 0.00 | 0.00 | 437 | −0.79 | 4.30E−01 | 7.73E−01 | Proteome | P40197 |
| CTTNBP2 | 0.00 | 0.00 | 437 | −0.8 | 4.25E−01 | 7.73E−01 | Proteome | Q8WZ74 |
| TNFB | 0.01 | 0.02 | 446 | 0.78 | 4.34E−01 | 7.75E−01 | Immunome | |
| Indoleacetic acid | 0.01 | 0.01 | 414 | 0.78 | 4.34E−01 | 7.75E−01 | Metabolome | HMDB00197 |
| INPP5E | 0.00 | 0.00 | 437 | −0.78 | 4.34E−01 | 7.75E−01 | Proteome | Q9NRR6 |
| Uridine | 0.00 | 0.01 | 414 | 0.78 | 4.38E−01 | 7.78E−01 | Metabolome | HMDB00296 |
| MTHFD1 | 0.00 | 0.00 | 437 | 0.78 | 4.37E−01 | 7.78E−01 | Proteome | P11586 |
| Biliverdin(1) | −0.01 | 0.01 | 414 | −0.77 | 4.41E−01 | 7.82E−01 | Metabolome | HMDB01008 |
| HDL | −0.01 | 0.01 | 457 | −0.77 | 4.43E−01 | 7.83E−01 | Clinical labs | |
| Imidazolelactic acid | −0.01 | 0.01 | 414 | −0.76 | 4.46E−01 | 7.83E−01 | Metabolome | HMDB02320 |
| Pro-Cys or Cys-Pro | 0.00 | 0.00 | 414 | −0.76 | 4.46E−01 | 7.83E−01 | Metabolome | HMD628783\|HMDB29014 |
| CFD | 0.00 | 0.00 | 437 | −0.76 | 4.45E−01 | 7.83E−01 | Proteome | P00746 |
| APOA1 | 0.00 | 0.00 | 437 | 0.77 | 4.44E−01 | 7.83E−01 | Proteome | P02647 |
| SERPINA5 | 0.00 | 0.00 | 437 | 0.76 | 4.49E−01 | 7.86E−01 | Proteome | P05154 |
| BCHE | 0.00 | 0.00 | 437 | 0.76 | 4.51E−01 | 7.87E−01 | Proteome | P06276 |
| IL17F | −0.02 | 0.02 | 446 | −0.75 | 4.54E−01 | 7.92E−01 | Immunome | |
| BUN | 0.00 | 0.01 | 456 | 0.74 | 4.60E−01 | 7.98E−01 | Clinical labs | |
| C10:1 AC | 0.01 | 0.01 | 414 | 0.74 | 4.60E−01 | 7.98E−01 | Metabolome | HMD13205 |
| Ig heavy chain V-III region HIL | 0.00 | 0.01 | 437 | −0.74 | 4.60E−01 | 7.98E−01 | Proteome | P01771 |
| Alpha-ketoisovaleric acid | 0.01 | 0.01 | 414 | 0.74 | 4.63E−01 | 7.99E−01 | Metabolome | HMD00019 |
| Cysteinglutathione disulfide | 0.00 | 0.00 | 414 | −0.73 | 4.66E−01 | 7.99E−01 | Metabolome | HMD00656 |
| gamma-glutamylleucine(1) | 0.00 | 0.01 | 414 | 0.73 | 4.68E−01 | 7.99E−01 | Metabolome | HMD11171 |
| C6:0, DC AC(2) | 0.00 | 0.00 | 414 | −0.73 | 4.68E−01 | 7.99E−01 | Metabolome | HMD61677 |
| C10:1, OH FA | 0.01 | 0.01 | 414 | 0.73 | 4.67E−01 | 7.99E−01 | Metabolome | |
| eugenol sulfate | 0.01 | 0.01 | 414 | 0.73 | 4.64E−01 | 7.99E−01 | Metabolome | |
| MBL2 | 0.00 | 0.00 | 437 | −0.73 | 4.65E−01 | 7.99E−01 | Proteome | P11226 |
| ACTBL2 | 0.00 | 0.00 | 437 | 0.73 | 4.66E−01 | 7.99E−01 | Proteome | Q562R1 |
| TGFA | −0.02 | 0.03 | 446 | −0.72 | 4.74E−01 | 8.00E−01 | Immunome | |
| Hydroxyhippurate(3) | 0.00 | 0.00 | 414 | −0.72 | 4.72E−01 | 8.00E−01 | Metabolome | HMDB00840 |
| N6-Carbamoyl-L-threonyladenosine | 0.01 | 0.01 | 414 | 0.72 | 4.74E−01 | 8.00E−01 | Metabolome | HMD641623 |
| C4BPA | 0.00 | 0.00 | 437 | 0.72 | 4.71E−01 | 8.00E−01 | Proteome | P04003 |
| ITIH1 | 0.00 | 0.00 | 437 | 0.72 | 4.73E−01 | 8.00E−01 | Proteome | P19827 |
| IFNA | 0.01 | 0.01 | 446 | 0.71 | 4.77E−01 | 8.00E−01 | Immunome | |

TABLE 12-continued

| | | | | | | | |
|---|---|---|---|---|---|---|---|
| Ig lambda chain V-III region SH | 0.00 | 0.00 | 437 | 0.71 | 4.75E-01 | 8.00E-01 | Proteome | P01714 |
| F11 | 0.00 | 0.00 | 437 | 0.71 | 4.76E-01 | 8.00E-01 | Proteome | P03951 |
| Asp-Asp | 0.00 | 0.01 | 414 | 0.7 | 4.84E-01 | 8.10E-01 | Metabolome | HMDB28749 |
| F13A1 | 0.00 | 0.00 | 437 | 0.7 | 4.84E-01 | 8.10E-01 | Proteome | P00488 |
| N-formylmethionine | 0.00 | 0.00 | 414 | 0.7 | 4.86E-01 | 8.11E-01 | Metabolome | HMDB01015 |
| IL1A | 0.01 | 0.01 | 446 | 0.68 | 4.94E-01 | 8.12E-01 | Immunome | |
| Tauroursodeoxycholic acid | −0.01 | 0.02 | 414 | −0.69 | 4.90E-01 | 8.12E-01 | Metabolome | HMDB00874 |
| N6,N6,N6-Trimethyl-L-lysine | 0.01 | 0.01 | 414 | 0.69 | 4.93E-01 | 8.12E-01 | Metabolome | HMDB01325 |
| LysoPE(16:1) | 0.00 | 0.01 | 414 | −0.69 | 4.92E-01 | 8.12E-01 | Metabolome | HMD611474 |
| C20:4, OH FA(2) | 0.00 | 0.01 | 414 | 0.68 | 4.94E-01 | 8.12E-01 | Metabolome | |
| C5 | 0.00 | 0.00 | 437 | 0.69 | 4.89E-01 | 8.12E-01 | Proteome | P01031 |
| HBD | 0.00 | 0.00 | 437 | 0.69 | 4.92E-01 | 8.12E-01 | Proteome | P02042 |
| FCGBP | 0.00 | 0.00 | 437 | 0.69 | 4.93E-01 | 8.12E-01 | Proteome | Q9Y6R7 |
| IL15 | −0.01 | 0.02 | 446 | −0.68 | 4.99E-01 | 8.12E-01 | Immunome | |
| Cys Gly | 0.00 | 0.01 | 414 | −0.67 | 5.01E-01 | 8.12E-01 | Metabolome | HMDB00078 |
| L-Threonine | 0.00 | 0.01 | 414 | 0.68 | 4.97E-01 | 8.12E-01 | Metabolome | HMDB00167 |
| Allantoin | 0.04 | 0.06 | 414 | 0.68 | 4.96E-01 | 8.12E-01 | Metabolome | HMD600462 |
| LysoPC(15:0) | 0.00 | 0.00 | 414 | 0.67 | 5.01E-01 | 8.12E-01 | Metabolome | HMDB10381 |
| Ig kappa chain V-I region Ni | 0.00 | 0.00 | 437 | −0.68 | 5.00E-01 | 8.12E-01 | Proteome | P01613 |
| CAMP | 0.00 | 0.00 | 437 | −0.68 | 4.98E-01 | 8.12E-01 | Proteome | P49913 |
| VEGF | 0.01 | 0.01 | 446 | 0.67 | 5.04E-01 | 8.13E-01 | Immunome | |
| Ig heavy chain V-III region BRO | 0.00 | 0.00 | 437 | −0.67 | 5.04E-01 | 8.13E-01 | Proteome | P01766 |
| L-Asparagine | 0.00 | 0.01 | 414 | 0.66 | 5.07E-01 | 8.14E-01 | Metabolome | HMDB00168 |
| LysoPC(22:4) | 0.02 | 0.03 | 414 | 0.67 | 5.06E-01 | 8.14E-01 | Metabolome | HMDB10401 |
| CFP | 0.00 | 0.00 | 437 | −0.67 | 5.05E-01 | 8.14E-01 | Proteome | P27918 |
| IFNB | −0.01 | 0.02 | 446 | −0.65 | 5.14E-01 | 8.14E-01 | Immunome | |
| IL23 | 0.01 | 0.02 | 446 | 0.65 | 5.18E-01 | 8.14E-01 | Immunome | |
| L-Methionine | 0.00 | 0.01 | 414 | 0.65 | 5.14E-01 | 8.14E-01 | Metabolome | HMDB00696 |
| C20:0 FA | 0.00 | 0.01 | 414 | 0.65 | 5.19E-01 | 8.14E-01 | Metabolome | HMDB02212 |
| 5-Acetylamino-6-amino-3-methyluracil(2) | 0.00 | 0.01 | 414 | −0.66 | 5.11E-01 | 8.14E-01 | Metabolome | HMDB04400 |
| SERPINA3 | 0.00 | 0.00 | 437 | 0.65 | 5.19E-01 | 8.14E-01 | Proteome | P01011 |
| AHSG | 0.00 | 0.00 | 437 | 0.64 | 5.20E-01 | 8.14E-01 | Proteome | P02765 |
| ENO1 | 0.00 | 0.00 | 437 | 0.65 | 5.17E-01 | 8.14E-01 | Proteome | P06733 |
| COMP | 0.00 | 0.00 | 437 | −0.66 | 5.09E-01 | 8.14E-01 | Proteome | P49747 |
| FAM3C | 0.00 | 0.00 | 437 | −0.65 | 5.16E-01 | 8.14E-01 | Proteome | Q92520 |
| Ryanodine receptor 2 | 0.00 | 0.00 | 437 | 0.65 | 5.15E-01 | 8.14E-01 | Proteome | Q92736_2 |
| C1RL | 0.00 | 0.00 | 437 | −0.65 | 5.18E-01 | 8.14E-01 | Proteome | Q9NZP8 |
| ALB | 0.00 | 0.00 | 437 | 0.65 | 5.19E-01 | 8.14E-01 | Proteome | P02768 |
| ATRN(1) | 0.00 | 0.00 | 437 | 0.64 | 5.22E-01 | 8.15E-01 | Proteome | O75882 |
| Ethylmalonate | 0.00 | 0.01 | 414 | 0.63 | 5.26E-01 | 8.19E-01 | Metabolome | HMDB00622 |
| NCAM1 | 0.00 | 0.00 | 437 | 0.64 | 5.25E-01 | 8.19E-01 | Proteome | P13591 |
| GCSF | 0.01 | 0.02 | 446 | 0.61 | 5.39E-01 | 8.23E-01 | Immunome | |
| SDF1A | 0.01 | 0.02 | 446 | 0.61 | 5.40E-01 | 8.23E-01 | Immunome | |
| 1-Methylxanthine | 0.00 | 0.01 | 414 | 0.61 | 5.39E-01 | 8.23E-01 | Metabolome | HMDB10738 |
| Iminodiacetate (IDA) | 0.00 | 0.01 | 414 | 0.63 | 5.31E-01 | 8.23E-01 | Metabolome | HMDB11753 |
| Catecholsulfate | 0.08 | 0.12 | 414 | 0.62 | 5.35E-01 | 8.23E-01 | Metabolome | HMDB59724 |
| C1R | 0.00 | 0.00 | 437 | 0.62 | 5.38E-01 | 8.23E-01 | Proteome | P00736 |
| SERPINC1 | 0.00 | 0.00 | 437 | 0.62 | 5.38E-01 | 8.23E-01 | Proteome | P01008 |
| IGHD | −0.01 | 0.01 | 437 | −0.62 | 5.34E-01 | 8.23E-01 | Proteome | P01880 |
| CFI | 0.00 | 0.00 | 437 | 0.61 | 5.40E-01 | 8.23E-01 | Proteome | P05156 |
| MCAM | 0.00 | 0.00 | 437 | −0.62 | 5.38E-01 | 8.23E-01 | Proteome | P43121 |
| VASN | 0.00 | 0.00 | 437 | −0.63 | 5.31E-01 | 8.23E-01 | Proteome | Q6EMK4 |
| SLFN11 | 0.00 | 0.00 | 437 | 0.63 | 5.31E-01 | 8.23E-01 | Proteome | Q7Z7L1 |
| Retinol (Vitamin A) | 0.00 | 0.01 | 414 | 0.61 | 5.44E-01 | 8.23E-01 | Metabolome | HMDB00305 |
| Homoarginine | 0.00 | 0.01 | 414 | 0.6 | 5.51E-01 | 8.23E-01 | Metabolome | HMDB00670 |
| Hippuric acid | 0.00 | 0.01 | 414 | −0.6 | 5.49E-01 | 8.23E-01 | Metabolome | HMDB00714 |
| C24:6 FA | 0.01 | 0.01 | 414 | 0.6 | 5.47E-01 | 8.23E-01 | Metabolome | HMDB02007 |
| Androsterone glucuronide(2) | 0.00 | 0.01 | 414 | 0.6 | 5.49E-01 | 8.23E-01 | Metabolome | HMDB02829 |
| Tetrahydroaldosterone-3-glucoronide(2) | 0.01 | 0.02 | 414 | 0.61 | 5.45E-01 | 8.23E-01 | Metabolome | HMDB10357 |
| ASS1 | 0.00 | 0.00 | 437 | −0.6 | 5.50E-01 | 8.23E-01 | Proteome | P00966 |
| IGF2 | 0.00 | 0.00 | 437 | −0.61 | 5.44E-01 | 8.23E-01 | Proteome | P01344 |
| APOC3 | 0.00 | 0.00 | 437 | 0.61 | 5.44E-01 | 8.23E-01 | Proteome | P02656 |
| PF4 | 0.00 | 0.00 | 437 | −0.61 | 5.44E-01 | 8.23E-01 | Proteome | P02776 |
| C6 | 0.00 | 0.00 | 437 | 0.6 | 5.51E-01 | 8.23E-01 | Proteome | P13671 |
| LysoPC(17:0) | 0.00 | 0.01 | 414 | 0.59 | 5.55E-01 | 8.28E-01 | Metabolome | HMDB12108 |
| A1BG | 0.00 | 0.00 | 437 | 0.59 | 5.58E-01 | 8.31E-01 | Proteome | P02749 |
| Glucaric acid | 0.00 | 0.01 | 414 | −0.58 | 5.60E-01 | 8.31E-01 | Metabolome | HMDB00663 |
| APOH | 0.00 | 0.00 | 437 | 0.58 | 5.60E-01 | 8.31E-01 | Proteome | P02749 |
| IGH3 | 0.00 | 0.00 | 437 | −0.58 | 5.65E-01 | 8.35E-01 | Proteome | P01860 |
| GAPDH | 0.00 | 0.00 | 437 | −0.58 | 5.64E-01 | 8.35E-01 | Proteome | P04406 |
| IL27 | 0.01 | 0.02 | 446 | 0.57 | 5.67E-01 | 8.35E-01 | Immunome | |
| HABP2 | 0.00 | 0.00 | 437 | 0.57 | 5.67E-01 | 8.35E-01 | Proteome | Q14520 |
| Androsterone sulfate(1) | 0.01 | 0.01 | 414 | 0.57 | 5.69E-01 | 8.36E-01 | Metabolome | HMDB02759 |
| LysoPE(18:1) | 0.00 | 0.01 | 414 | 0.57 | 5.70E-01 | 8.36E-01 | Metabolome | HMDB11745 |
| AMBP | 0.00 | 0.00 | 437 | 0.57 | 5.72E-01 | 8.37E-01 | Proteome | P02760 |
| LCP1 | 0.00 | 0.00 | 437 | −0.56 | 5.73E-01 | 8.37E-01 | Proteome | P13796 |
| Interleukin-1 receptor accessory protein | 0.00 | 0.00 | 437 | 0.57 | 5.71E-01 | 8.37E-01 | Proteome | Q9NPH3_5 |
| BASOAB | 0.00 | 0.01 | 451 | 0.56 | 5.77E-01 | 8.37E-01 | Clinical labs | |
| Sulfolithocholylglycine | 0.01 | 0.01 | 414 | 0.56 | 5.78E-01 | 8.37E-01 | Metabolome | HMDB02639 |
| Indoleacetyl glutamine | 0.01 | 0.01 | 414 | 0.56 | 5.77E-01 | 8.37E-01 | Metabolome | HMDB13240 |

TABLE 12-continued

| | | | | | | | | |
|---|---|---|---|---|---|---|---|---|
| Ig kappa chain V-I region AG | 0.00 | 0.00 | 437 | −0.56 | 5.75E−01 | 8.37E−01 | Proteome | P01593 |
| MYH9 | 0.00 | 0.00 | 437 | 0.56 | 5.78E−01 | 8.37E−01 | Proteome | P35579 |
| INSF | 0.01 | 0.01 | 87 | 0.54 | 5.88E−01 | 8.38E−01 | Clinical labs | |
| Chenodeoxycholic Acid (2) | 0.00 | 0.01 | 414 | 0.55 | 5.81E−01 | 8.38E−01 | Metabolome | HMDB00518 |
| gamma-glutamylphenylalanine | 0.00 | 0.01 | 414 | 0.54 | 5.86E−01 | 8.38E−01 | Metabolome | HMDB00594 |
| Pseudouridine | 0.00 | 0.01 | 414 | −0.55 | 5.84E−01 | 8.38E−01 | Metabolome | HMDB00767 |
| C8:0 AC | 0.01 | 0.02 | 414 | 0.55 | 5.84E−01 | 8.38E−01 | Metabolome | HMDB00791 |
| 1-Methyluric acid | 0.00 | 0.01 | 414 | 0.54 | 5.87E−01 | 8.38E−01 | Metabolome | HMDB03099 |
| F2 | 0.00 | 0.00 | 437 | 0.55 | 5.82E−01 | 8.38E−01 | Proteome | P00734 |
| IGHV3-23 | 0.00 | 0.00 | 437 | −0.54 | 5.89E−01 | 8.38E−01 | Proteome | P01764 |
| GP1BA | 0.00 | 0.00 | 437 | −0.55 | 5.85E−01 | 8.38E−01 | Proteome | P07359 |
| MST1 | 0.00 | 0.00 | 437 | −0.54 | 5.86E−01 | 8.38E−01 | Proteome | P26927 |
| Pyridoxic acid | −0.01 | 0.01 | 414 | −0.54 | 5.92E−01 | 8.38E−01 | Metabolome | HMDB00017 |
| APOA2 | 0.00 | 0.00 | 437 | 0.54 | 5.91E−01 | 8.38E−01 | Proteome | P02652 |
| SAA1 | 0.00 | 0.00 | 437 | 0.54 | 5.91E−01 | 8.38E−01 | Proteome | P0DJI8 |
| AST | 0.00 | 0.01 | 454 | −0.53 | 5.99E−01 | 8.40E−01 | Clinical labs | |
| L-Histidine | 0.00 | 0.01 | 414 | −0.53 | 5.98E−01 | 8.40E−01 | Metabolome | HMDB00177 |
| 5-Methoxysalicylic acid | 0.01 | 0.01 | 414 | 0.52 | 6.02E−01 | 8.40E−01 | Metabolome | HMDB01868 |
| 3-Methyl-2-oxovaleric acid | 0.00 | 0.01 | 414 | 0.52 | 6.00E−01 | 8.40E−01 | Metabolome | HMDB03736 |
| 2-Aminophenol sulfate | 0.00 | 0.01 | 414 | 0.52 | 6.02E−01 | 8.40E−01 | Metabolome | HMDB61116 |
| CEP290 | 0.00 | 0.00 | 437 | −0.52 | 6.02E−01 | 8.40E−01 | Proteome | O15078 |
| FCN3 | 0.00 | 0.00 | 437 | −0.52 | 6.03E−01 | 8.40E−01 | Proteome | O75636 |
| RBP4 | 0.00 | 0.00 | 437 | −0.52 | 6.03E−01 | 8.40E−01 | Proteome | P02753 |
| GC | 0.00 | 0.00 | 437 | 0.52 | 6.00E−01 | 8.40E−01 | Proteome | P02774 |
| Fibulin-1 | 0.00 | 0.00 | 437 | 0.52 | 6.02E−01 | 8.40E−01 | Proteome | P23142_4 |
| RESISTIN | 0.00 | 0.01 | 446 | −0.52 | 6.06E−01 | 8.42E−01 | Immunome | |
| C18:0 AC | 0.00 | 0.01 | 414 | 0.51 | 6.08E−01 | 8.42E−01 | Metabolome | HMDB00848 |
| Homostachydrine | −0.01 | 0.01 | 414 | −0.51 | 6.09E−01 | 8.42E−01 | Metabolome | HMDB33433 |
| MSN | 0.00 | 0.00 | 437 | −0.51 | 6.07E−01 | 8.42E−01 | Proteome | P26038 |
| ITIH4 | 0.00 | 0.00 | 437 | 0.51 | 6.10E−01 | 8.42E−01 | Proteome | Q14624 |
| FASL | 0.01 | 0.02 | 446 | 0.5 | 6.15E−01 | 8.46E−01 | Immunome | |
| IL12P40 | 0.01 | 0.01 | 446 | 0.5 | 6.14E−01 | 8.46E−01 | Immunome | |
| DBH | 0.00 | 0.00 | 437 | −0.5 | 6.19E−01 | 8.51E−01 | Proteome | P09172 |
| C16:0, 2OH FA | 0.00 | 0.01 | 414 | 0.5 | 6.21E−01 | 8.52E−01 | Metabolome | |
| IL4 | −0.01 | 0.01 | 446 | −0.48 | 6.29E−01 | 8.57E−01 | Immunome | |
| Cys-Pro or Pro-Cys | 0.00 | 0.01 | 414 | −0.49 | 6.26E−01 | 8.57E−01 | Metabolome | HMDB28783 |
| KLKB1 | 0.00 | 0.00 | 437 | 0.48 | 6.29E−01 | 8.57E−01 | Proteome | P03952 |
| CLU(1) | 0.00 | 0.00 | 437 | 0.48 | 6.29E−01 | 8.57E−01 | Proteome | P10909 |
| BTD | 0.00 | 0.00 | 437 | 0.48 | 6.28E−01 | 8.57E−01 | Proteome | P43251 |
| CHOL | 0.00 | 0.01 | 457 | 0.46 | 6.49E−01 | 8.58E−01 | Clinical labs | |
| Cholic Acid | 0.01 | 0.01 | 414 | 0.45 | 6.56E−01 | 8.58E−01 | Metabolome | HMDB00619 |
| Acetylcholine | 0.00 | 0.01 | 414 | 0.46 | 6.49E−01 | 8.58E−01 | Metabolome | HMDB00895 |
| L-Serine | 0.00 | 0.01 | 414 | 0.46 | 6.47E−01 | 8.58E−01 | Metabolome | HMDB00187 |
| Uric acid | 0.00 | 0.01 | 414 | −0.45 | 6.55E−01 | 8.58E−01 | Metabolome | HMDB00289 |
| Creatinine | 0.00 | 0.01 | 414 | −0.45 | 6.55E−01 | 8.58E−01 | Metabolome | HMDB00562 |
| Gluconic acid | 0.00 | 0.01 | 414 | −0.47 | 6.37E−01 | 8.58E−01 | Metabolome | HMDB00625 |
| Caffeine | 0.00 | 0.01 | 414 | 0.47 | 6.36E−01 | 8.58E−01 | Metabolome | HMDB01847 |
| Androsterone glucuronide(1) | 0.00 | 0.01 | 414 | −0.46 | 6.47E−01 | 8.58E−01 | Metabolome | HMDB02829 |
| gamma-glutamylthreonine(2) | 0.00 | 0.00 | 414 | −0.47 | 6.40E−01 | 8.58E−01 | Metabolome | HMDB29159 |
| C10:3 FA(1) | 0.00 | 0.01 | 414 | 0.46 | 6.48E−01 | 8.58E−01 | Metabolome | |
| F9 | 0.00 | 0.00 | 437 | 0.47 | 6.35E−01 | 8.58E−01 | Proteome | P00740 |
| Ig heavy chain V-III region WEA | 0.00 | 0.00 | 437 | −0.47 | 6.38E−01 | 8.58E−01 | Proteome | P01763 |
| IGKC | 0.00 | 0.00 | 437 | −0.47 | 6.38E−01 | 8.58E−01 | Proteome | P01834 |
| TTR | 0.00 | 0.00 | 437 | −0.46 | 6.46E−01 | 8.58E−01 | Proteome | P02766 |
| APOA4 | 0.00 | 0.00 | 437 | 0.47 | 6.40E−01 | 8.58E−01 | Proteome | P06727 |
| F5 | 0.00 | 0.00 | 437 | 0.46 | 6.48E−01 | 8.58E−01 | Proteome | P12259 |
| LBP | 0.00 | 0.00 | 437 | 0.46 | 6.48E−01 | 8.58E−01 | Proteome | P18428 |
| C4BPB | 0.00 | 0.00 | 437 | 0.45 | 6.55E−01 | 8.58E−01 | Proteome | P20851 |
| PRDX2 | 0.00 | 0.00 | 437 | 0.45 | 6.55E−01 | 8.58E−01 | Proteome | P32119 |
| SEPP1 | 0.00 | 0.00 | 437 | −0.47 | 6.37E−01 | 8.58E−01 | Proteome | P49908 |
| B2M | 0.00 | 0.00 | 437 | 0.45 | 6.56E−01 | 8.58E−01 | Proteome | P61769 |
| Rho GTPase-activating protein 19 | 0.00 | 0.00 | 437 | −0.46 | 6.45E−01 | 8.58E−01 | Proteome | Q14CB8_6 |
| TGEBI | 0.00 | 0.00 | 437 | −0.45 | 6.55E−01 | 8.58E−01 | Proteome | Q15582 |
| CDK5RAP2 | 0.00 | 0.00 | 437 | −0.46 | 6.44E−01 | 8.58E−01 | Proteome | Q965N8 |
| ABCF1 | 0.00 | 0.00 | 437 | −0.44 | 6.58E−01 | 8.60E−01 | Proteome | Q8NE71 |
| MIG | −0.01 | 0.02 | 446 | −0.43 | 6.66E−01 | 8.62E−01 | Immunome | |
| C10:0 AC | 0.01 | 0.01 | 414 | 0.44 | 6.61E−01 | 8.62E−01 | Metabolome | HMDB00651 |
| Ig heavy chain V-III region BUT | 0.00 | 0.00 | 437 | 0.43 | 6.67E−01 | 8.62E−01 | Proteome | P01767 |
| APCS | 0.00 | 0.00 | 437 | −0.43 | 6.66E−01 | 8.62E−01 | Proteome | P02743 |
| HRG | 0.00 | 0.00 | 437 | 0.44 | 6.64E−01 | 8.62E−01 | Proteome | P04196 |
| Ig kappa chain V-III region VH | 0.00 | 0.00 | 437 | −0.43 | 6.66E−01 | 8.62E−01 | Proteome | P04434 |
| MASP1 | 0.00 | 0.00 | 437 | −0.43 | 6.66E−01 | 8.62E−01 | Proteome | P48740 |
| Theophylline | 0.00 | 0.01 | 414 | 0.43 | 6.69E−01 | 8.63E−01 | Metabolome | HMDB01889 |
| PPBP | 0.00 | 0.00 | 437 | 0.43 | 6.70E−01 | 8.64E−01 | Proteome | P02775 |
| INSU | 0.01 | 0.01 | 2 | 0.49 | 6.72E−01 | 8.65E−01 | Clinical labs | |
| MCSF | 0.01 | 0.02 | 446 | 0.41 | 6.84E−01 | 8.72E−01 | Immunome | |
| Pantothenic acid | 0.00 | 0.01 | 414 | 0.41 | 6.80E−01 | 8.72E−01 | Metabolome | HMDB00210 |
| Dihydroxyvitamin D3(2) | 0.00 | 0.01 | 414 | −0.41 | 6.85E−01 | 8.72E−01 | Metabolome | HMDB00430 |
| 4-Hydroxyproline | 0.00 | 0.00 | 414 | −0.41 | 6.81E−01 | 8.72E−01 | Metabolome | HMDB00725 |
| C8G | 0.00 | 0.00 | 437 | 0.41 | 6.84E−01 | 8.72E−01 | Proteome | P07360 |

TABLE 12-continued

| | | | | | | | |
|---|---|---|---|---|---|---|---|
| CETP | 0.00 | 0.00 | 437 | −0.41 | 6.83E−01 | 8.72E−01 | Proteome | P11597 |
| AZGP1 | 0.00 | 0.00 | 437 | −0.41 | 6.85E−01 | 8.72E−01 | Proteome | P25311 |
| EOS | 0.00 | 0.01 | 451 | 0.4 | 6.87E−01 | 8.73E−01 | Clinical labs | |
| C5:0, DC AC | 0.01 | 0.03 | 414 | 0.4 | 6.88E−01 | 8.73E−01 | Metabolome | |
| APOL1 | 0.00 | 0.00 | 437 | −0.4 | 6.91E−01 | 8.76E−01 | Proteome | O14791 |
| IGFALS | 0.00 | 0.00 | 437 | 0.39 | 6.93E−01 | 8.77E−01 | Proteome | P35858 |
| Glycocholic acid | −0.01 | 0.01 | 414 | −0.39 | 6.95E−01 | 8.78E−01 | Metabolome | HMD500138 |
| PON1 | 0.00 | 0.00 | 437 | 0.39 | 6.96E−01 | 8.78E−01 | Proteome | P27169 |
| PDGFBB | 0.00 | 0.01 | 446 | −0.39 | 6.98E−01 | 8.79E−01 | Immunome | |
| IL31 | −0.01 | 0.01 | 446 | −0.39 | 7.00E−01 | 8.81E−01 | Immunome | |
| LysoPC(P-18:0) | 0.00 | 0.01 | 414 | 0.38 | 7.06E−01 | 8.86E−01 | Metabolome | HMD513122 |
| Oxalate (ethanedioate) | 0.00 | 0.00 | 414 | −0.37 | 7.09E−01 | 8.87E−01 | Metabolome | HMDB02329 |
| Hydroxyhippurate(2) | 0.00 | 0.00 | 414 | −0.37 | 7.09E−01 | 8.87E−01 | Metabolome | |
| MMRN1 | 0.00 | 0.00 | 437 | −0.37 | 7.09E−01 | 8.87E−01 | Proteome | Q13201 |
| NPHP3 | 0.00 | 0.00 | 437 | −0.37 | 7.11E−01 | 8.87E−01 | Proteome | Q7Z494 |
| C20:0, 2OH FA | 0.00 | 0.01 | 414 | 0.37 | 7.12E−01 | 8.88E−01 | Metabolome | HMDB31923 |
| PLTP | 0.00 | 0.00 | 437 | −0.37 | 7.13E−01 | 8.88E−01 | Proteome | P55058 |
| IL7 | 0.00 | 0.01 | 446 | 0.36 | 7.21E−01 | 8.90E−01 | Immunome | |
| TRAIL | 0.01 | 0.02 | 446 | 0.34 | 7.31E−01 | 8.90E−01 | Immunome | |
| L-Glutamine | 0.00 | 0.01 | 414 | 0.34 | 7.31E−01 | 8.90E−01 | Metabolome | HMDB00641 |
| 2-Hydroxyphenylacetate | 0.01 | 0.02 | 414 | 0.35 | 7.25E−01 | 8.90E−01 | Metabolome | HMDB00669 |
| LysoPC(22:6) | 0.00 | 0.01 | 414 | −0.34 | 7.32E−01 | 8.90E−01 | Metabolome | HMDB10404 |
| LysoPC(P-16:0) | 0.00 | 0.01 | 414 | −0.35 | 7.24E−01 | 8.90E−01 | Metabolome | HMD510407 |
| C12:1 AC | 0.00 | 0.01 | 414 | −0.35 | 7.28E−01 | 8.90E−01 | Metabolome | HMD313326 |
| C18:0, OH FA(1) | 0.00 | 0.00 | 414 | 0.35 | 7.25E−01 | 8.90E−01 | Metabolome | |
| SERPINA7 | 0.00 | 0.00 | 437 | 0.34 | 7.31E−01 | 8.90E−01 | Proteome | P05543 |
| THBS1 | 0.00 | 0.00 | 437 | 0.34 | 7.31E−01 | 8.90E−01 | Proteome | P07996 |
| PTPRC | 0.00 | 0.00 | 437 | −0.36 | 7.19E−01 | 8.90E−01 | Proteome | P08575 |
| Clusterin | 0.00 | 0.00 | 437 | 0.34 | 7.33E−01 | 8.90E−01 | Proteome | P10909_2 |
| CPN2 | 0.00 | 0.00 | 437 | 0.36 | 7.17E−01 | 8.90E−01 | Proteome | P22792 |
| INHBC | 0.00 | 0.00 | 437 | 0.36 | 7.19E−01 | 8.90E−01 | Proteome | P55103 |
| PGLYRP2 | 0.00 | 0.00 | 437 | 0.35 | 7.26E−01 | 8.90E−01 | Proteome | Q96PD5 |
| CFHR5 | 0.00 | 0.01 | 437 | −0.35 | 7.28E−01 | 8.90E−01 | Proteome | Q9BXR6 |
| cont_000017 | 0.00 | 0.00 | 437 | −0.36 | 7.20E−01 | 8.90E−01 | Proteome | |
| Proline betaine | 0.00 | 0.01 | 414 | 0.33 | 7.40E−01 | 8.93E−01 | Metabolome | HMD604827 |
| Ig kappa chain V-II region FR | 0.00 | 0.00 | 437 | −0.34 | 7.37E−01 | 8.93E−01 | Proteome | P01615 |
| Ig kappa chain V-III region B6 | 0.00 | 0.00 | 437 | −0.33 | 7.40E−01 | 8.93E−01 | Proteome | P01619 |
| FBLN1(1) | 0.00 | 0.00 | 437 | −0.33 | 7.40E−01 | 8.93E−01 | Proteome | P23142 |
| Proteoglycan 4 | 0.00 | 0.00 | 437 | 0.33 | 7.39E−01 | 8.93E−01 | Proteome | Q92954_6 |
| Erythritol|D-Threitol | 0.00 | 0.00 | 414 | −0.33 | 7.42E−01 | 8.93E−01 | Metabolome | HMDB02994|HMDB04136 |
| C8A | 0.00 | 0.00 | 437 | 0.33 | 7.43E−01 | 8.94E−01 | Proteome | P07357 |
| C12:1, DC FA(4) | 0.00 | 0.00 | 414 | −0.32 | 7.46E−01 | 8.94E−01 | Metabolome | HMD300933 |
| Protein FAM161B | 0.00 | 0.00 | 437 | −0.33 | 7.45E−01 | 8.94E−01 | Proteome | Q96MY7 |
| Ig kappa chain V-I region HK101 | 0.00 | 0.00 | 437 | −0.32 | 7.48E−01 | 8.94E−01 | Proteome | P01601 |
| ATP11B | 0.00 | 0.00 | 437 | 0.32 | 7.48E−01 | 8.94E−01 | Proteome | Q9Y2G3 |
| SERPINF2 | 0.00 | 0.00 | 437 | 0.32 | 7.50E−01 | 8.95E−01 | Proteome | P08697 |
| Ig lambda chain V-III region LOI | 0.00 | 0.00 | 437 | 0.32 | 7.50E−01 | 8.95E−01 | Proteome | P80748 |
| Ig kappa chain V-I region Mev | 0.00 | 0.00 | 437 | −0.32 | 7.53E−01 | 8.96E−01 | Proteome | P01612 |
| 16a-hydroxy DHEA 3-sulfate | 0.00 | 0.01 | 414 | −0.31 | 7.54E−01 | 8.96E−01 | Metabolome | |
| IL18 | 0.00 | 0.01 | 446 | 0.3 | 7.61E−01 | 9.00E−01 | Immunome | |
| IL1RA | 0.00 | 0.01 | 446 | 0.31 | 7.60E−01 | 9.00E−01 | Immunome | |
| C14:1 AC | 0.00 | 0.01 | 414 | −0.31 | 7.58E−01 | 9.00E−01 | Metabolome | HMDB02014 |
| Ig lambda chain V region 4A | 0.00 | 0.00 | 437 | 0.3 | 7.62E−01 | 9.00E−01 | Proteome | P04211 |
| 3-Phenylpropionate (hydrocinnamate) | 0.00 | 0.00 | 414 | −0.3 | 7.67E−01 | 9.05E−01 | Metabolome | HMDB00764 |
| TFRC | 0.00 | 0.00 | 437 | −0.3 | 7.68E−01 | 9.05E−01 | Proteome | P02786 |
| CR | 0.00 | 0.01 | 456 | 0.29 | 7.74E−01 | 9.09E−01 | Clinical labs | |
| GROA | 0.01 | 0.02 | 446 | 0.29 | 7.75E−01 | 9.09E−01 | Immunome | |
| RANTES | 0.00 | 0.01 | 446 | −0.29 | 7.75E−01 | 9.09E−01 | Immunome | |
| IGF2R | 0.00 | 0.00 | 437 | −0.29 | 7.73E−01 | 9.09E−01 | Proteome | P11717 |
| LRG1 | 0.00 | 0.00 | 437 | −0.28 | 7.77E−01 | 9.10E−01 | Proteome | P02750 |
| Ig kappa chain V-I region Roy | 0.00 | 0.00 | 437 | −0.28 | 7.79E−01 | 9.10E−01 | Proteome | P01608 |
| MG(15:0)(2) | 0.00 | 0.00 | 414 | 0.28 | 7.82E−01 | 9.11E−01 | Metabolome | HMDB11532 |
| Sulfuric acid | 0.00 | 0.00 | 414 | −0.28 | 7.82E−01 | 9.11E−01 | Metabolome | |
| IGHG1 | 0.00 | 0.00 | 437 | −0.28 | 7.83E−01 | 9.12E−01 | Proteome | P01857 |
| L-Tryptophan | 0.00 | 0.01 | 414 | 0.27 | 7.86E−01 | 9.14E−01 | Metabolome | HMDB00929 |
| 5alpha-Androstan-3alpha, 17alpha-diol monosulfate(2) | 0.00 | 0.01 | 414 | −0.27 | 7.89E−01 | 9.16E−01 | Metabolome | |
| GSN | 0.00 | 0.00 | 437 | 0.27 | 7.91E−01 | 9.17E−01 | Proteome | P06396 |
| C14:2 AC | 0.00 | 0.01 | 414 | 0.26 | 7.96E−01 | 9.21E−01 | Metabolome | HMDB13331 |
| Ig heavy chain V-III region JON | 0.00 | 0.00 | 437 | 0.26 | 7.98E−01 | 9.21E−01 | Proteome | P01780 |
| PZP | 0.00 | 0.00 | 437 | 0.26 | 7.96E−01 | 9.21E−01 | Proteome | P20742 |
| CDHR5 | 0.00 | 0.00 | 437 | −0.26 | 7.98E−01 | 9.21E−01 | Proteome | Q9HBB8 |
| ACTA1 | 0.00 | 0.00 | 437 | −0.25 | 8.00E−01 | 9.22E−01 | Proteome | P68133 |
| Piperine(2) | 0.00 | 0.01 | 414 | 0.25 | 8.07E−01 | 9.27E−01 | Metabolome | HMDB29377 |
| LysoPE(20:4) | 0.00 | 0.01 | 414 | 0.24 | 8.10E−01 | 9.29E−01 | Metabolome | HMDB11487 |
| gamma-glutamylhistidine | 0.00 | 0.01 | 414 | −0.24 | 8.11E−01 | 9.29E−01 | Metabolome | HMDB29151 |
| C18:2 AC | 0.00 | 0.01 | 414 | 0.23 | 8.16E−01 | 9.34E−01 | Metabolome | HMDB06461 |
| LGALS3BP | 0.00 | 0.00 | 437 | 0.23 | 8.16E−01 | 9.34E−01 | Proteome | Q08380 |
| Symmetric dimethylarginine | 0.00 | 0.00 | 414 | −0.23 | 8.19E−01 | 9.35E−01 | Metabolome | HMDB01539 |
| HSCRP | 0.00 | 0.01 | 415 | −0.22 | 8.23E−01 | 9.37E−01 | Clinical labs | |

TABLE 12-continued

| | | | | | | | |
|---|---|---|---|---|---|---|---|
| RBC | 0.00 | 0.01 | 452 | 0.22 | 8.26E-01 | 93.7E-01 | Clinical labs | |
| 1-Methylhistidine | 0.00 | 0.01 | 414 | 0.23 | 8.22E-01 | 9.73E-01 | Metabolome | HMDB00001 |
| Androstenediol (3beta, 17beta) disulfate | 0.00 | 0.01 | 414 | 0.22 | 8.24E-01 | 9.37E-01 | Metabolome | HMDB03818 |
| TLN1 | 0.00 | 0.00 | 437 | −0.22 | 8.25E-01 | 9.37E-01 | Proteome | Q9Y490 |
| CA1 | 0.00 | 0.00 | 437 | 0.22 | 8.27E-01 | 9.37E-01 | Proteome | P00915 |
| CPN1 | 0.00 | 0.00 | 437 | 0.22 | 8.29E-01 | 9.38E-01 | Proteome | P15169 |
| PIGR | 0.00 | 0.00 | 437 | −0.21 | 8.32E-01 | 9.40E-01 | Proteome | P01833 |
| LYM | 0.00 | 0.01 | 452 | 0.2 | 8.39E-01 | 9.44E-01 | Clinical labs | |
| gamma-CEHC | 0.01 | 0.03 | 414 | 0.2 | 8.38E-01 | 9.44E-01 | Metabolome | HMDB01931 |
| C10:2 AC | 0.00 | 0.01 | 414 | −0.2 | 8.41E-01 | 9.44E-01 | Metabolome | HMD313325 |
| Ig heavy chain V-II region WAH | 0.00 | 0.00 | 437 | 0.2 | 8.41E-01 | 9.44E-01 | Proteome | P01824 |
| LYVE1 | 0.00 | 0.00 | 437 | −0.2 | 8.41E-01 | 9.44E-01 | Proteome | Q9Y5Y7 |
| Chenodeoxycholic Acid(1) | 0.00 | 0.01 | 414 | −0.2 | 8.43E-01 | 9.44E-01 | Metabolome | HMDB00518 |
| IL1RAP(1) | 0.00 | 0.00 | 437 | −0.2 | 8.44E-01 | 9.44E-01 | Proteome | Q9NPH3 |
| SERPINA1 | 0.00 | 0.00 | 437 | 0.19 | 8.46E-01 | 9.45E-01 | Proteome | P01009 |
| CST3 | 0.00 | 0.00 | 437 | 0.19 | 8.46E-01 | 9.45E-01 | Proteome | P01034 |
| IGM | 0.00 | 0.01 | 453 | 0.19 | 8.50E-01 | 9.47E-01 | Clinical labs | |
| TNFA | 0.00 | 0.01 | 446 | −0.19 | 8.49E-01 | 9.47E-01 | Immunome | |
| MIP1B | 0.00 | 0.01 | 446 | 0.18 | 8.58E-01 | 9.48E-01 | Immunome | |
| 2,3-Dihydroxyvaleric acid(1) | 0.00 | 0.01 | 414 | −0.17 | 8.65E-01 | 9.48E-01 | Metabolome | HMDB00421 |
| Chenodeoxycholic acid glycine conjugate(2) | 0.00 | 0.02 | 414 | −0.17 | 8.64E-01 | 9.48E-01 | Metabolome | HMDB00637 |
| Cyclo(ala-pro) | 0.00 | 0.01 | 414 | 0.17 | 8.64E-01 | 9.48E-01 | Metabolome | |
| A2M | 0.00 | 0.00 | 437 | 0.18 | 8.58E-01 | 9.48E-01 | Proteome | P01023 |
| Ig heavy chain V-I region EU | 0.00 | 0.00 | 437 | 0.18 | 8.57E-01 | 9.48E-01 | Proteine | P01742 |
| SERPING1 | 0.00 | 0.00 | 437 | 0.18 | 8.59E-01 | 9.48E-01 | Proteome | P05155 |
| PROS1 | 0.00 | 0.00 | 437 | 0.18 | 8.60E-01 | 9.48E-01 | Proteome | P07225 |
| F7 | 0.00 | 0.00 | 437 | 0.18 | 8.56E-01 | 9.48E-01 | Proteome | P08709 |
| HBB | 0.00 | 0.00 | 437 | −0.18 | 8.56E-01 | 9.48E-01 | Proteome | P68871 |
| DYNC1H1 | 0.00 | 0.00 | 437 | −0.17 | 8.65E-01 | 9.48E-01 | Proteome | Q14204 |
| ECM1 | 0.00 | 0.00 | 437 | 0.17 | 8.61E-01 | 9.48E-01 | Proteome | Q16610 |
| FERMT3 | 0.00 | 0.00 | 437 | 0.17 | 8.67E-01 | 9.49E-01 | Proteome | Q86UX7 |
| C12:0 AC | 0.00 | 0.01 | 414 | 0.17 | 8.69E-01 | 9.50E-01 | Metabolome | HMDB02250 |
| IGHA1 | 0.00 | 0.00 | 437 | −0.16 | 8.70E-01 | 9.50E-01 | Proteome | P01876 |
| Taurocholic acid(1) | −0.01 | 0.03 | 414 | −0.16 | 8.71E-01 | 9.50E-01 | Metabolome | HMDB00036 |
| IFNG | 0.00 | 0.01 | 446 | 0.16 | 8.73E-01 | 9.50E-01 | Immunome | |
| AGT | 0.00 | 0.00 | 437 | 0.16 | 8.76E-01 | 9.50E-01 | Proteome | P01019 |
| C1QC | 0.00 | 0.00 | 437 | −0.15 | 8.77E-01 | 9.50E-01 | Proteome | P02747 |
| C1S | 0.00 | 0.00 | 437 | 0.16 | 8.76E-01 | 9.50E-01 | Proteome | P09871 |
| ITIH3 | 0.00 | 0.00 | 437 | −0.16 | 8.74E-01 | 9.50E-01 | Proteome | Q06033 |
| PAI1 | 0.00 | 0.01 | 446 | −0.15 | 8.80E-01 | 9.51E-01 | Immunome | |
| C22:6 FA | 0.00 | 0.00 | 414 | 0.15 | 8.79E-01 | 9.51E-01 | Metabolome | HMDB02183 |
| C12:0 FA(2) | 0.00 | 0.01 | 414 | 0.15 | 8.82E-01 | 9.52E-01 | Metabolome | |
| L-a-Hydroxyisovaleric acid | 0.00 | 0.01 | 414 | −0.14 | 8.86E-01 | 9.54E-01 | Metabolome | HMDB00407 |
| Endophilin-A3 | 0.00 | 0.00 | 437 | −0.14 | 8.86E-01 | 9.54E-01 | Proteome | Q99963_3 |
| MASP2 | 0.00 | 0.00 | 437 | −0.14 | 8.89E-01 | 9.55E-01 | Proteome | O00187 |
| F13B | 0.00 | 0.00 | 437 | −0.14 | 8.88E-01 | 9.55E-01 | Proteome | P05160 |
| Orotidine | 0.00 | 0.01 | 414 | 0.13 | 8.99E-01 | 9.62E-01 | Metabolome | HMDB00788 |
| APOD | 0.00 | 0.00 | 437 | −0.13 | 8.98E-01 | 9.62E-01 | Proteome | P05090 |
| AG | 0.00 | 0.00 | 456 | −0.12 | 9.02E-01 | 9.63E-01 | Clinical labs | |
| Dehydroisoandrosterone sulfate (DHEA-S)(2) | 0.00 | 0.01 | 414 | −0.12 | 9.01E-01 | 9.63E-01 | Metabolome | HMDB01032 |
| VWF | 0.00 | 0.00 | 437 | −0.12 | 9.02E-01 | 9.63E-01 | Proteome | P04275 |
| CA | 0.00 | 0.00 | 456 | 0.12 | 9.04E-01 | 9.64E-01 | Clinical labs | |
| IL22 | 0.00 | 0.01 | 446 | 0.11 | 9.10E-01 | 9.66E-01 | Immunome | |
| Piperine(1) | 0.00 | 0.01 | 414 | −0.11 | 9.09E-01 | 9.66E-01 | Metaboloine | HMDB29377 |
| Arabitol | Xylitol | 0.00 | 0.01 | 414 | 0.11 | 9.12E-01 | 9.66E-01 | Metabolome | |
| CD14 | 0.00 | 0.00 | 437 | 0.11 | 9.11E-01 | 9.66E-01 | Proteome | P08571 |
| HBA1 | 0.00 | 0.00 | 437 | 0.11 | 9.09E-01 | 9.66E-01 | Proteome | P69905 |
| EOTAXIN | 0.00 | 0.01 | 446 | −0.1 | 9.20E-01 | 9.66E-01 | Immunome | |
| p-Cresol sulfate | 0.00 | 0.01 | 414 | −0.1 | 9.21E-01 | 9.66E-01 | Metabolome | HMDB11635 |
| Dihydroxyvitamin D3(1) | 0.00 | 0.01 | 414 | −0.1 | 9.24E-01 | 9.66E-01 | Metabolome | HMDB00430 |
| Alpha-N-Phenylacetyl-L-glutamine | 0.00 | 0.01 | 414 | 0.1 | 9.17E-01 | 9.66E-01 | Metabolome | HMDB06344 |
| C18:1, 3OH FA | 0.00 | 0.00 | 414 | 0.11 | 9.15E-01 | 9.66E-01 | Metabolome | |
| IGHA2 | 0.00 | 0.00 | 437 | −0.1 | 9.24E-01 | 9.66E-01 | Proteome | P01877 |
| APOE | 0.00 | 0.00 | 437 | −0.1 | 9.24E-01 | 9.66E-01 | Proteome | P02649 |
| GPX3 | 0.00 | 0.00 | 437 | 0.1 | 9.23E-01 | 9.66E-01 | Proteome | P22352 |
| SAA4 | 0.00 | 0.00 | 437 | 0.1 | 9.17E-01 | 9.66E-01 | Proteome | P35542 |
| SERPINF1 | 0.00 | 0.00 | 437 | −0.09 | 9.24E-01 | 9.66E-01 | Proteome | P36955 |
| ADIPOQ | 0.00 | 0.00 | 437 | −0.11 | 9.16E-01 | 9.66E-01 | Proteome | Q15848 |
| Ectoine | 0.00 | 0.01 | 414 | 0.09 | 9.28E-01 | 9.68E-01 | Metabolome | |
| F12 | 0.00 | 0.00 | 437 | 0.09 | 9.31E-01 | 9.70E-01 | Proteome | P00748 |
| Gentisic acid | 0.00 | 0.01 | 414 | −0.08 | 9.32E-01 | 9.70E-01 | Metabolome | HMDB00152 |
| TGFB | 0.00 | 0.01 | 446 | 0.08 | 9.38E-01 | 9.71E-01 | Immunome | |
| 1-Methylguanosine | 0.00 | 0.01 | 414 | −0.08 | 9.36E-01 | 9.71E-01 | Metabolome | HMDB01563 |
| C16:1 AC | 0.00 | 0.01 | 414 | −0.08 | 9.40E-01 | 9.71E-01 | Metabolome | HMDB06317 |
| LysoPE(18:2) | 0.00 | 0.01 | 414 | −0.08 | 9.40E-01 | 9.71E-01 | Metabolome | HMDB11477 |
| Ala-Leu or Leu-Ala | 0.00 | 0.01 | 414 | 0.08 | 9.38E-01 | 9.71E-01 | Metabolome | HMDB28691 |
| CD5L | 0.00 | 0.00 | 437 | −0.07 | 9.41E-01 | 9.71E-01 | Proteome | O43866 |
| C9 | 0.00 | 0.00 | 437 | 0.08 | 9.37E-01 | 9.71E-01 | Proteome | P02748 |

TABLE 12-continued

| | | | | | | | | |
|---|---|---|---|---|---|---|---|---|
| Choline | 0.00 | 0.01 | 414 | 0.07 | 9.45E-01 | 9.71E-01 | Metabolome | HMDB00097 |
| LysoPE(22:6) | 0.00 | 0.00 | 414 | -0.07 | 9.42E-01 | 9.71E-01 | Metabolome | HMDB11496 |
| Hydoxyhippurate(1) | 0.00 | 0.01 | 414 | -0.07 | 9.46E-01 | 9.71E-01 | Metabolome | |
| C2 | 0.00 | 0.00 | 437 | 0.07 | 9.46E-01 | 9.71E-01 | Proteome | P06681 |
| FLNA | 0.00 | 0.00 | 437 | -0.07 | 9.47E-01 | 9.71E-01 | Proteome | P21333 |
| IGHM | 0.00 | 0.00 | 437 | 0.06 | 9.48E-01 | 9.71E-01 | Proteome | P01871 |
| LPA | 0.00 | 0.01 | 437 | 0.06 | 9.50E-01 | 9.71E-01 | Proteome | P08519 |
| APOF | 0.00 | 0.00 | 437 | -0.06 | 9.51E-01 | 9.71E-01 | Proteome | Q13790 |
| LysoPC(16:0) | 0.00 | 0.00 | 414 | 0.05 | 9.57E-01 | 9.74E-01 | Metabolome | HMDB10382 |
| C20:3, OH FA(2) | 0.00 | 0.00 | 414 | 0.05 | 9.59E-01 | 9.74E-01 | Metabolome | |
| C1QB | 0.00 | 0.00 | 437 | 0.05 | 9.58E-01 | 9.74E-01 | Proteome | P02746 |
| MYH7 | 0.00 | 0.00 | 437 | 0.05 | 9.58E-01 | 9.74E-01 | Proteome | P12883 |
| ORM2 | 0.00 | 0.00 | 437 | -0.06 | 9.55E-01 | 9.74E-01 | Proteome | P19652 |
| Glycine | 0.00 | 0.03 | 414 | 0.05 | 9.63E-01 | 9.76E-01 | Metabolome | HMDB00123 |
| Zinc finger protein 10 | 0.00 | 0.00 | 437 | -0.05 | 9.63E-01 | 9.76E-01 | Proteome | P21506 |
| PFN1 | 0.00 | 0.00 | 437 | -0.04 | 9.68E-01 | 9.80E-01 | Proteome | P07737 |
| LEPTIN | 0.00 | 0.01 | 446 | -0.03 | 9.74E-01 | 9.84E-01 | Immunome | |
| LysoPC(20:4) | 0.00 | 0.01 | 414 | -0.03 | 9.74E-01 | 9.84E-01 | Metabolome | HMDB10395 |
| Arabonate | Xylonate(1) | 0.00 | 0.01 | 414 | 0.02 | 9.83E-01 | 9.91E-01 | Metabolome | |
| ORM1 | 0.00 | 0.00 | 437 | 0.02 | 9.88E-01 | 9.95E-01 | Proteome | P02763 |
| NEUT | 0.00 | 0.01 | 452 | 0 | 9.97E-01 | 9.98E-01 | Clinical labs | |
| FGFB | 0.00 | 0.02 | 446 | 0 | 9.98E-01 | 9.98E-01 | Immunome | |
| 2,3-Dihydroxyvaleric acid (2) | 0.00 | 0.02 | 414 | 0 | 9.96E-01 | 9.98E-01 | Metabolome | HMDB00421 |
| Quinic acid | 0.00 | 0.01 | 414 | 0.01 | 9.95E-01 | 9.98E-01 | Metabolome | HMDB03072 |
| 5alpha-Androstan-3alpha, 17beta-diol 17-glucuronide(2) | 0.00 | 0.01 | 414 | 0.01 | 9.96E-01 | 9.98E-01 | Metabolome | |
| GPLD1 | 0.00 | 0.00 | 437 | 0.01 | 9.92E-01 | 9.98E-01 | Proteome | P80108 |

Bolded Proteins (n = 12) and metabolites (n = 31) are those that were matched to molecules in known pathways and used in pathway analysis using IMPaLa web tool p-values are derived from the t-test and are two sided; multiple testing correction using Benjamini-Hochberg method was performed and resulting values listed under FDR

| Dynamic Model: Hemoglobin (n = 94, samples 836) | | | | | | | | |
|---|---|---|---|---|---|---|---|---|
| Molecule | Estimate | StdErr | DF | tValue | p-value | FDR | Assay | Accession ID |
| 1-Methylxanthine | -0.010 | 0.002 | 624 | -6.2 | 1.03E-09 | 8.66E-07 | Metabolome | HMDB10738 |
| Theophylline | -0.009 | 0.002 | 624 | -5.66 | 2.27E-08 | 9.52E-06 | Metabolome | HMDB01889 |
| Caffeine | -0.008 | 0.001 | 624 | -5.28 | 1.78E-07 | 3.74E-05 | Metabolome | HMDB01847 |
| RBC | 0.009 | 0.002 | 675 | 5.33 | 1.35E-07 | 3.74E-05 | Clinical labs | |
| GLOB | 0.010 | 0.002 | 726 | 5.21 | 2.43E-07 | 4.07E-05 | Clinical labs | |
| MCV | -0.008 | 0.002 | 675 | -4.82 | 1.78E-06 | 2.49E-04 | Clinical labs | |
| LYMAB | 0.008 | 0.002 | 675 | 4.68 | 3.43E-06 | 4.11E-04 | Clinical labs | |
| IGHA1 | -0.009 | 0.002 | 582 | -4.49 | 8.56E-06 | 8.97E-04 | Proteome | P01876 |
| 1-Methyluric acid | -0.007 | 0.002 | 624 | -4.43 | 1.09E-05 | 1.02E-03 | Metabolome | HMDB03099 |
| 5alpha-Androstan-3alpha, 17beta-diol 17-glucuronide(2) | -0.008 | 0.002 | 624 | -4.29 | 2.11E-05 | 1.77E-03 | Metabolome | |
| 2,3-Dihydroxyvaleric acid(2) | -0.007 | 0.002 | 624 | -4.21 | 2.89E-05 | 2.20E-03 | Metabolome | HMDB00421 |
| WBC | 0.006 | 0.002 | 675 | 4.01 | 6.79E-05 | 4.74E-03 | Clinical labs | |
| MCH | -0.006 | 0.002 | 675 | -3.92 | 9.60E-05 | 6.19E-03 | Clinical labs | |
| C16 Sphingosine 1-phosphate | 0.007 | 0.002 | 624 | 3.74 | 1.98E-04 | 1.19E-02 | Metabolome | HMDB60061 |
| IGHG1 | -0.006 | 0.002 | 582 | -3.66 | 2.72E-04 | 1.52E-02 | Proteome | P01857 |
| RDW | 0.006 | 0.002 | 675 | 3.6 | 3.48E-04 | 1.82E-02 | Clinical labs | |
| GP5 | -0.006 | 0.002 | 582 | -3.58 | 3.69E-04 | 1.82E-02 | Proteome | P40197 |
| L-Arginine | -0.006 | 0.002 | 624 | -3.46 | 5.72E-04 | 2.66E-02 | Metabolome | HMDB00517 |
| PLG | -0.006 | 0.002 | 582 | -3.43 | 6.45E-04 | 2.78E-02 | Proteome | P00747 |
| AHSG | -0.006 | 0.002 | 582 | -3.42 | 6.63E-04 | 2.78E-02 | Proteome | P02765 |
| ORM2 | -0.006 | 0.002 | 582 | -3.3 | 1.04E-03 | 4.14E-02 | Proteome | P19652 |
| MG(20:4)(1) | 0.006 | 0.002 | 624 | 3.24 | 1.26E-03 | 4.82E-02 | Metabolome | HMDB04666 |
| MONOAB | 0.006 | 0.002 | 675 | 3.15 | 1.71E-03 | 6.23E-02 | Clinical labs | |
| Cys Gly | 0.006 | 0.002 | 624 | 3.11 | 1.98E-03 | 6.32E-02 | Metabolome | HMDB00078 |
| C18:3 FA | 0.004 | 0.001 | 624 | 3.11 | 1.96E-03 | 6.32E-02 | Metabolome | HMDB03073 |
| TP | 0.006 | 0.002 | 726 | 3.1 | 1.99E-03 | 6.32E-02 | Clinical labs | |
| CA1 | 0.006 | 0.002 | 582 | 3.1 | 2.04E-03 | 6.32E-02 | Proteome | P00915 |
| IFNB | 0.006 | 0.002 | 607 | 3.06 | 2.34E-03 | 6.55E-02 | Immunome | |
| TF | -0.005 | 0.002 | 582 | -3.07 | 2.26E-03 | 6.55E-02 | Proteome | P02787 |
| CLU.1 | -0.005 | 0.002 | 582 | -3.06 | 2.29E-03 | 6.55E-02 | Proteome | P10909-2 |
| Quinic acid | -0.005 | 0.002 | 624 | -3.01 | 2.73E-03 | 7.16E-02 | Metabolome | HMDB03072 |
| FAM3C | -0.005 | 0.002 | 582 | -3.02 | 2.67E-03 | 7.16E-02 | Proteome | Q92520 |
| C12:1, DC FA(4) | 0.004 | 0.001 | 624 | 2.98 | 2.98E-03 | 7.57E-02 | Metabolome | HMDB00933 |
| C15:0 FA | -0.005 | 0.002 | 624 | -2.97 | 3.07E-03 | 7.57E-02 | Metabolome | |
| PDGFBB | -0.005 | 0.002 | 607 | -2.95 | 3.27E-03 | 7.60E-02 | Immunome | |
| CLU | -0.005 | 0.002 | 582 | -2.96 | 3.24E-03 | 7.60E-02 | Proteome | P10909 |
| Thyroxine | 0.005 | 0.002 | 624 | 2.92 | 3.62E-03 | 8.20E-02 | Metabolome | HMDB01918 |
| C19:0 FA(1) | -0.005 | 0.002 | 624 | -2.84 | 4.68E-03 | 9.99E-02 | Metabolome | HMDB00772 |
| MG(22:2) | 0.005 | 0.002 | 624 | 2.83 | 4.77E-03 | 9.99E-02 | Metabolome | HMDB11553 |
| Cys-Pro or Pro-Cys | 0.005 | 0.002 | 624 | 2.82 | 4.89E-03 | 9.99E-02 | Metabolome | HMD628783 |
| PLT | 0.005 | 0.002 | 675 | 2.83 | 4.83E-03 | 9.99E-02 | Clinical labs | |
| C18 Sphingosine 1-phosphate | 0.005 | 0.002 | 624 | 2.8 | 5.28E-03 | 1.05E-01 | Metabolome | HMDB00277 |
| L-Formylkynurenine | -0.006 | 0.002 | 624 | -2.78 | 5.55E-03 | 1.06E-01 | Metabolome | HMDB60485 |
| C16:0, 2OH FA | -0.005 | 0.002 | 624 | -2.78 | 5.55E-03 | 1.06E-01 | Metabolome | |

TABLE 12-continued

| | | | | | | | |
|---|---|---|---|---|---|---|---|
| HCT | 0.005 | 0.002 | 675 | 2.77 | 5.81E−03 | 1.08E−01 | Clinical labs | |
| ENA78 | −0.005 | 0.002 | 607 | −2.74 | 6.28E−03 | 1.14E−01 | Immunome | |
| Paraxanthine | −0.005 | 0.002 | 624 | −2.72 | 6.72E−03 | 1.19E−01 | Metabolome | HMDB01860 |
| MG(24:1) | 0.005 | 0.002 | 624 | 2.71 | 6.82E−03 | 1.19E−01 | Metabolome | HMDB11559 |
| Arabonate \| Xylonate(3) | −0.005 | 0.002 | 624 | −2.7 | 7.19E−03 | 1.23E−01 | Metabolome | |
| IL17F | 0.005 | 0.002 | 607 | 2.66 | 8.12E−03 | 1.36E−01 | Immunome | |
| Cys-Gly or Gly-Cys | 0.005 | 0.002 | 624 | 2.58 | 9.97E−03 | 1.51E−01 | Metabolome | HMDB00078 |
| Allantoin | 0.003 | 0.001 | 624 | 2.59 | 9.85E−03 | 1.51E−01 | Metabolome | HMDB00462 |
| C14:0 FA | −0.004 | 0.002 | 624 | −2.58 | 1.02E−02 | 1.51E−01 | Metabolome | HMDB00806 |
| NEUTAB | 0.004 | 0.001 | 675 | 2.58 | 1.00E−02 | 1.51E−01 | Clinical labs | |
| HGF | 0.004 | 0.002 | 607 | 2.6 | 9.61E−03 | 1.51E−01 | Immunome | |
| C17:0 FA(1) | −0.005 | 0.002 | 624 | −2.58 | 1.02E−02 | 1.51E−01 | Metabolome | |
| APOA2 | −0.004 | 0.001 | 582 | −2.59 | 9.73E−03 | 1.51E−01 | Proteome | P02652 |
| GLU | 0.005 | 0.002 | 726 | 2.56 | 1.07E−02 | 1.55E−01 | Clinical labs | |
| MG(24:0)(2) | 0.005 | 0.002 | 624 | 2.54 | 1.12E−02 | 1.58E−01 | Metabolome | HMDB11558 |
| TGFA | 0.011 | 0.004 | 607 | 2.54 | 1.13E−02 | 1.58E−01 | Immunome | |
| C17:1 FA | −0.004 | 0.002 | 624 | −2.53 | 1.18E−02 | 1.59E−01 | Metabolome | HMD360038 |
| IL1RA | 0.004 | 0.002 | 607 | 2.53 | 1.16E−02 | 1.59E−01 | Immunome | |
| ATRN | −0.004 | 0.002 | 582 | −2.5 | 1.29E−02 | 1.71E−01 | Proteome | O75882 |
| CD40L | 0.005 | 0.002 | 607 | 2.47 | 1.37E−02 | 1.80E−01 | Immunome | |
| NCAM1 | −0.005 | 0.002 | 582 | −2.45 | 1.44E−02 | 1.86E−01 | Proteome | P13591 |
| Arabonate \| Xylonate(1) | −0.004 | 0.002 | 624 | −2.45 | 1.47E−02 | 1.86E−01 | Metabolome | |
| ARHGAP19 | −0.004 | 0.002 | 582 | −2.43 | 1.54E−02 | 1.92E−01 | Proteome | Q14CB8-6 |
| HGB | 0.004 | 0.002 | 675 | 2.41 | 1.61E−02 | 1.98E−01 | Clinical labs | |
| Pro-Cys or Cys-Pro | 0.005 | 0.002 | 624 | 2.4 | 1.66E−02 | 1.98E−01 | Metabolome | HMDB28783\|HMDB29014 |
| EGF | 0.004 | 0.002 | 607 | 2.41 | 1.65E−02 | 1.98E−01 | Immunome | |
| Erythritol\|D-Threitol | −0.003 | 0.001 | 624 | −2.4 | 1.69E−02 | 1.99E−01 | Metabolome | HMDB02994\|HMDB04136 |
| C8:2, OH FA(1) | 0.004 | 0.002 | 624 | 2.39 | 1.73E−02 | 1.99E−01 | Metabolome | |
| APOB | −0.004 | 0.002 | 582 | −2.39 | 1.72E−02 | 1.99E−01 | Proteome | P04114 |

Bolded Proteins (n = 14) and Metabolites (n = 13) are those that were matched to molecules in known pathways and used in pathway analysis using IMPaLa web tool p-values are derived from the t-test and are two sided; multiple testing correction using Benjamini-Hochberg method was performed and resulting values listed under FDR

TABLE 13

Healthy-Baseline & Dynamic Models: Molecules Associated with Fasting Plasma Glucose
Healthy-Baseline Model: Fasting Plasma Glucose (n = 101, samples 563)

| Molecule | Estimate | StdErr | DF | tValue | p-value | FDR | Assay | Accession ID |
|---|---|---|---|---|---|---|---|---|
| Hexosamine | 0.10 | 0.01 | 417 | 11.8 | 6.41E−28 | 5.41E−25 | Metabolome | HMDB01514 |
| Hexose | 0.22 | 0.02 | 417 | 9.01 | 7.54E−18 | 3.18E−15 | Metabolome | HMDB00122 |
| A1C | 0.07 | 0.01 | 456 | 7.58 | 1.92E−13 | 5.41E−11 | Clinical labs | |
| ethyl glucuronide | 0.11 | 0.01 | 417 | 7.42 | 6.84E−13 | 1.44E−10 | Metabolome | HMDB10325 |
| L-Tyrosine | 0.06 | 0.01 | 417 | 6.36 | 5.45E−10 | 9.21E−08 | Metabolome | HMDB00158 |
| sn-glycero-3-Phosphoethanolamine | 0.06 | 0.01 | 417 | 4.94 | 1.15E−06 | 1.62E−04 | Metabolome | HMDB00114 |
| N-(1-Deoxy-1-fructosyl)valine | 0.05 | 0.01 | 417 | 4.51 | 8.47E−06 | 1.02E−03 | Metabolome | HMDB37844 |
| L-Alanine | 0.06 | 0.01 | 417 | 4.11 | 4.68E−05 | 4.94E−03 | Metabolome | HMDB00161 |
| Fructoselysine | 0.03 | 0.01 | 417 | 4.08 | 5.33E−05 | 5.00E−03 | Metabolome | |
| C12:1, DC FA(2) | 0.13 | 0.03 | 417 | 4.01 | 7.08E−05 | 5.73E−03 | Metabolome | HMDB00933 |
| Tetrahydroaldosterone-3-glucuronide(1) | 0.08 | 0.02 | 417 | 4 | 7.62E−05 | 5.73E−03 | Metabolome | HMDB10357 |
| LysoPE(18:1) | 0.04 | 0.01 | 417 | 3.98 | 8.14E−05 | 5.73E−03 | Metabolome | HMD611475 |
| C8:2, OH FA(2) | 0.06 | 0.02 | 417 | 3.92 | 1.03E−04 | 6.71E−03 | Metabolome | |
| C20:4, DC FA | 0.13 | 0.03 | 417 | 3.73 | 2.20E−04 | 1.32E−02 | Metabolome | |
| C4:0 AC | 0.07 | 0.02 | 417 | 3.55 | 4.31E−04 | 2.42E−02 | Metabolome | HMD802013 |
| TGFA | −0.02 | 0.01 | 449 | −3.47 | 5.74E−04 | 3.03E−02 | Immunome | |
| LysoPE(18:0) | 0.18 | 0.05 | 417 | 3.45 | 6.11E−04 | 3.03E−02 | Metabolome | HMDB11129 |
| L-Malic acid | 0.05 | 0.01 | 417 | 3.39 | 7.68E−04 | 3.60E−02 | Metabolome | HMDB00156 |
| LysoPE(16:0) | 0.19 | 0.06 | 417 | 3.37 | 8.31E−04 | 3.69E−02 | Metabolome | HMD311473 |
| N6-Acetyl-L-lysine | 0.04 | 0.01 | 417 | 3.33 | 9.56E−04 | 4.03E−02 | Metabolome | HMDB00206 |
| MG(18:0) | 0.03 | 0.01 | 417 | 3.29 | 1.07E−03 | 4.31E−02 | Metabolome | HMDB11131 |
| C16:1, OH FA(2) | 0.12 | 0.04 | 417 | 3.22 | 1.36E−03 | 5.22E−02 | Metabolome | |
| L-Valine | 0.04 | 0.01 | 417 | 3.17 | 1.65E−03 | 5.82E−02 | Metabolome | HMDB00883 |
| LysoPI(18:1) | 0.04 | 0.01 | 417 | 3.17 | 1.62E−03 | 5.82E−02 | Metabolome | HMD661693 |
| 4-Methylcatechol sulfate | 0.04 | 0.01 | 417 | 3.07 | 2.30E−03 | 7.77E−02 | Metabolome | |
| Chenodeoxycholic Acid(1) | 0.04 | 0.01 | 417 | 3.05 | 2.43E−03 | 7.79E−02 | Metabolome | HMDB00518 |
| gamma-glutamyl-epsilon-lysine | 0.03 | 0.01 | 417 | 3.04 | 2.49E−03 | 7.79E−02 | Metabolome | HMDB03869 |
| 1-Methylxanthine | 0.03 | 0.01 | 417 | 3.02 | 2.71E−03 | 8.18E−02 | Metabolome | HMDB10738 |
| Ig lambda chain V-IV region Hil | −0.02 | 0.01 | 440 | −2.98 | 3.06E−03 | 8.90E−02 | Proteome | P01717 |
| MCP1 | 0.04 | 0.01 | 449 | 2.93 | 3.55E−03 | 9.99E−02 | Immunome | |
| Alpha-ketoisovaleric acid | 0.04 | 0.02 | 417 | 2.88 | 4.23E−03 | 9.99E−02 | Metabolome | HMDB00019 |
| Cys-Gly or Gly-Cys | 0.03 | 0.01 | 417 | 2.88 | 4.24E−03 | 9.99E−02 | Metabolome | HMDB00078 |
| C19:0 FA(1) | 0.04 | 0.01 | 417 | 2.91 | 3.82E−03 | 9.99E−02 | Metabolome | HMDB00772 |
| C13:0, DC FA(2) | 0.04 | 0.01 | 417 | 2.9 | 3.95E−03 | 9.99E−02 | Metabolome | HMDB02327 |
| LysoPC(22:0) | 0.04 | 0.02 | 417 | 2.9 | 3.92E−03 | 9.99E−02 | Metabolome | HMDB10398 |
| Hydroxybutyric acid (1) | 0.03 | 0.01 | 417 | 2.86 | 4.38E−03 | 9.99E−02 | Metabolome | |

TABLE 13-continued

| | | | | | | | | |
|---|---|---|---|---|---|---|---|---|
| CNDP1 | 0.02 | 0.01 | 440 | 2.87 | 4.35E-03 | 9.99E-02 | Proteome | Q96KN2 |
| C9:1, OH FA | 0.02 | 0.01 | 417 | 2.83 | 4.86E-03 | 1.08E-01 | Metabolome | |
| 5-Acetylamino-6-amino-3-methyluracil(1) | 0.04 | 0.01 | 417 | 2.82 | 5.09E-03 | 1.10E-01 | Metabolome | HMDB04400 |
| L-Cystine | 0.03 | 0.01 | 417 | 2.8 | 5.39E-03 | 1.14E-01 | Metabolome | HMDB00192 |
| Kynurenic acid | 0.03 | 0.01 | 417 | 2.76 | 6.13E-03 | 1.20E-01 | Metabolome | HMDB00715 |
| Tetrahydrocortisol | 0.17 | 0.06 | 417 | 2.75 | 6.17E-03 | 1.20E-01 | Metabolome | HMDB00949 |
| MG(14:1)(3) | 0.03 | 0.01 | 417 | 2.75 | 6.28E-03 | 1.20E-01 | Metabolome | HMDB11531 |
| Phenylalanylphenylalanine | 0.82 | 0.30 | 417 | 2.76 | 6.01E-03 | 1.20E-01 | Metabolome | HMDB13302 |
| C13:0, DC FA(4) | 0.03 | 0.01 | 417 | 2.74 | 6.44E-03 | 1.21E-01 | Metabolome | HMDB02327 |
| Indolepyruvate | 0.03 | 0.01 | 417 | 2.73 | 6.70E-03 | 1.23E-01 | Metabolome | HMD360484 |
| Cholic Acid | 0.05 | 0.02 | 417 | 2.67 | 7.91E-03 | 1.23E-01 | Metabolome | HMDB00619 |
| L-Proline | 0.09 | 0.03 | 417 | 2.69 | 7.53E-03 | 1.23E-01 | Metabolome | HMDB00162 |
| L-Lysine | 0.03 | 0.01 | 417 | 2.67 | 7.93E-03 | 1.23E-01 | Metabolome | HMDB00182 |
| Phenylbutyric acid | −0.04 | 0.01 | 417 | −2.68 | 7.70E-03 | 1.23E-01 | Metabolome | HMDB00329 |
| N-Acetyl-L-phenylalanine | 0.03 | 0.01 | 417 | 2.7 | 7.14E-03 | 1.23E-01 | Metabolome | HMDB00512 |
| Phenyllactate (PLA) | 0.04 | 0.01 | 417 | 2.7 | 7.11E-03 | 1.23E-01 | Metabolome | HMD600779 |
| C11:0, DC FA | 0.04 | 0.01 | 417 | 2.66 | 8.01E-03 | 1.23E-01 | Metabolome | HMD800888 |
| 3-Indolepropionic acid | 0.02 | 0.01 | 417 | 2.68 | 7.63E-03 | 1.23E-01 | Metabolome | HMDB02302 |
| C19:1 FA | 0.03 | 0.01 | 417 | 2.7 | 7.25E-03 | 1.23E-01 | Metabolome | HMDB13622 |
| C9:0, DC FA (Azelaic acid) | 0.03 | 0.01 | 417 | 2.63 | 8.94E-03 | 1.32E-01 | Metabolome | HMDB00784 |
| 4-formyl Indole(1) | 0.03 | 0.01 | 417 | 2.63 | 8.87E-03 | 1.32E-01 | Metabolome | |
| Chenodeoxycholic Acid(2) | 0.02 | 0.01 | 417 | 2.54 | 1.13E-02 | 1.41E-01 | Metabolome | HMDB00518 |
| C18 Sphingosine 1-phosphate | 0.02 | 0.01 | 417 | 2.54 | 1.15E-02 | 1.41E-01 | Metabolome | HMDB00277 |
| 4-Hydroxyphenylpyruvic acid | 0.04 | 0.01 | 417 | 2.52 | 1.20E-02 | 1.41E-01 | Metabolome | HMDB00707 |
| Isobutyrylglycine | 0.05 | 0.02 | 417 | 2.52 | 1.22E-02 | 1.41E-01 | Metabolome | HMDB00730 |
| C5:1 AC | 0.03 | 0.01 | 417 | 2.53 | 1.18E-02 | 1.41E-01 | Metabolome | HMDB02366 |
| 1-Methyluric acid | 0.03 | 0.01 | 417 | 2.5 | 1.28E-02 | 1.41E-01 | Metabolome | HMDB03099 |
| LysoPC(16:0) | 0.02 | 0.01 | 417 | 2.51 | 1.24E-02 | 1.41E-01 | Metabolome | HMDB10382 |
| LysoPC(O-18:0) | 0.29 | 0.11 | 417 | 2.59 | 9.93E-03 | 1.41E-01 | Metabolome | HMDB11149 |
| Iminodiacetate (IDA) | 0.03 | 0.01 | 417 | 2.52 | 1.21E-02 | 1.41E-01 | Metabolome | HMDB11753 |
| N-Acetylleucine\|N-Acetylisoleucine | 0.02 | 0.01 | 417 | 2.52 | 1.22E-02 | 1.41E-01 | Metabolome | HMDB11756\|HMDB61684 |
| C12:1 AC | −0.03 | 0.01 | 417 | −2.51 | 1.26E-02 | 1.41E-01 | Metabolome | HMDB13326 |
| C14:2 AC | −0.03 | 0.01 | 417 | −2.54 | 1.14E-02 | 1.41E-01 | Metabolome | HMDB13331 |
| Gly-Lys or Lys-Gly | 0.03 | 0.01 | 417 | 2.5 | 1.30E-02 | 1.41E-01 | Metabolome | HMDB28846 |
| INSF | 0.07 | 0.03 | 87 | 2.58 | 1.17E-02 | 1.41E-01 | Clinical labs | |
| TGL | 0.03 | 0.01 | 459 | 2.58 | 1.01E-02 | 1.41E-01 | Clinical labs | |
| 1,2,3-benzenetriol sulfate | 0.04 | 0.02 | 417 | 2.57 | 1.05E-02 | 1.41E-01 | Metabolome | |
| IG lambda chain V-I region HA | −0.03 | 0.01 | 440 | −2.5 | 1.29E-02 | 1.41E-01 | Proteome | P01700 |
| IGHG2 | −0.02 | 0.01 | 440 | −2.49 | 1.30E-02 | 1.41E-01 | Proteome | P01859 |
| CLEC3B | 0.02 | 0.01 | 440 | 2.55 | 1.10E-02 | 1.41E-01 | Proteome | P05452 |
| SAA2 | −0.02 | 0.01 | 440 | −2.57 | 1.06E-02 | 1.41E-01 | Proteome | P0DJI9 |
| TYMP | −0.02 | 0.01 | 440 | −2.58 | 1.02E-02 | 1.41E-01 | Proteome | P19971 |
| Thyroxine | 0.03 | 0.01 | 417 | 2.49 | 1.32E-02 | 1.41E-01 | Metabolome | HMDB01918 |
| LysoPC(20:0) | 0.07 | 0.03 | 417 | 2.48 | 1.35E-02 | 1.42E-01 | Metabolome | HMDB10390 |
| L-Lactic acid | 0.02 | 0.01 | 417 | 2.46 | 1.43E-02 | 1.43E-01 | Metabolome | HMDB00190 |
| LysoPC(20:1) | 0.07 | 0.03 | 417 | 2.46 | 1.43E-02 | 1.43E-01 | Metabolome | HMDB10391 |
| Phenylalanyl-Tryptophan | 0.03 | 0.01 | 417 | 2.46 | 1.44E-02 | 1.43E-01 | Metabolome | HMDB29006 |
| L-Formylkynurenine | 0.04 | 0.02 | 417 | 2.47 | 1.37E-02 | 1.43E-01 | Metabolome | HMDB60485 |
| Ig lambda chain V-I region NEWM | −0.02 | 0.01 | 440 | −2.46 | 1.44E-02 | 1.43E-01 | Proteome | P01703 |
| GLOB | −0.03 | 0.01 | 461 | −2.44 | 1.49E-02 | 1.46E-01 | Clinical labs | |
| C18:0, DC FA(1) | 0.02 | 0.01 | 417 | 2.41 | 1.62E-02 | 1.57E-01 | Metabolome | HMDB00782 |
| C10:1 AC | −0.04 | 0.02 | 417 | −2.4 | 1.68E-02 | 1.61E-01 | Metabolome | HMDB13205 |
| Ig kappa chain V-III region NG9 | −0.02 | 0.01 | 440 | −2.38 | 1.76E-02 | 1.67E-01 | Proteome | P01621 |
| L-Isoleucine\|L-Leucine | 0.03 | 0.01 | 417 | 2.35 | 1.92E-02 | 1.70E-01 | Metabolome | HMDB00172\|HMDB00687 |
| Paraxanthine | 0.03 | 0.01 | 417 | 2.36 | 1.90E-02 | 1.70E-01 | Metabolome | HMDB01860 |
| LysoPI(20:4) | 0.03 | 0.01 | 417 | 2.36 | 1.89E-02 | 1.70E-01 | Metabolome | HMDB61690 |
| Arabonate \| Xylonate(1) | 0.03 | 0.01 | 417 | 2.36 | 1.89E-02 | 1.70E-01 | Metabolome | |
| C18:1, DC FA | 0.03 | 0.01 | 417 | 2.35 | 1.94E-02 | 1.70E-01 | Metabolome | |
| C17:0 FA(1) | 0.03 | 0.01 | 417 | 2.35 | 1.91E-02 | 1.70E-01 | Metabolome | |
| IGHA2 | −0.02 | 0.01 | 440 | −2.34 | 1.96E-02 | 1.70E-01 | Proteome | P01877 |
| LCAT | 0.02 | 0.01 | 440 | 2.35 | 1.92E-02 | 1.70E-01 | Proteome | P04180 |
| C18:0, OH AC | −0.09 | 0.04 | 417 | −2.33 | 2.01E-02 | 1.72E-01 | Metabolome | HMDB13164 |
| Ig kappa chain V-III region CLL | −0.02 | 0.01 | 440 | −2.33 | 2.01E-02 | 1.72E-01 | Proteome | P04207 |
| 5-Methoxysalicylic acid | 0.05 | 0.02 | 417 | 2.33 | 2.05E-02 | 1.73E-01 | Metabolome | HMDB01868 |
| HCT | −0.03 | 0.01 | 456 | −2.32 | 2.09E-02 | 1.74E-01 | Clinical labs | |
| CFHR4 | −0.02 | 0.01 | 440 | −2.32 | 2.10E-02 | 1.74E-01 | Proteome | Q92496 |
| Butyric acid\|Isobutyric acid | 0.05 | 0.02 | 417 | 2.3 | 2.18E-02 | 1.74E-01 | Metabolome | HMDB00039\|HMDB01873 |
| Sphinganine | 0.03 | 0.01 | 417 | 2.3 | 2.21E-02 | 1.74E-01 | Metabolome | HMDB00269 |
| Ornithine | 0.02 | 0.01 | 417 | 2.3 | 2.20E-02 | 1.74E-01 | Metabolome | HMDB03374 |
| HGB | −0.03 | 0.01 | 456 | −2.29 | 2.24E-02 | 1.74E-01 | Clinical labs | |
| C8:0, OH FA(2) | 0.04 | 0.02 | 417 | 2.29 | 2.25E-02 | 1.74E-01 | Metabolome | |
| Ig kappa chain V-III region VG | −0.02 | 0.01 | 440 | −2.29 | 2.23E-02 | 1.74E-01 | Proteome | P04433 |
| KRT17 | 0.02 | 0.01 | 440 | 2.31 | 2.14E-02 | 1.74E-01 | Proteome | Q04695 |
| LysoPE(22:4) | 0.03 | 0.01 | 417 | 2.28 | 2.28E-02 | 1.75E-01 | Metabolome | HMDB11493 |
| N6,N6,N6-Trimethyl-L-lysine | 0.04 | 0.02 | 417 | 2.27 | 2.38E-02 | 1.81E-01 | Metabolome | HMDB01325 |
| C8:0 AC | −0.07 | 0.03 | 417 | −2.25 | 2.52E-02 | 1.87E-01 | Metabolome | HMDB00791 |
| C20:1 FA | 0.02 | 0.01 | 417 | 2.25 | 2.48E-02 | 1.87E-01 | Metabolome | HMDB02231 |
| LysoPE(20:0) | 0.02 | 0.01 | 417 | 2.25 | 2.50E-02 | 1.87E-01 | Metabolome | HMDB11481 |
| C16:0, DC FA(1) | 0.03 | 0.01 | 417 | 2.24 | 2.55E-02 | 1.87E-01 | Metabolome | HMDB00672 |

TABLE 13-continued

| | | | | | | | |
|---|---|---|---|---|---|---|---|
| C15:0 FA | 0.02 | 0.01 | 417 | 2.24 | 2.56E-02 | 1.87E-01 | Metabolome | |
| GPR116 | 0.02 | 0.01 | 440 | 2.23 | 2.60E-02 | 1.88E-01 | Proteome | Q8IZF2 |
| Interleukin-1 receptor accessory protein | 0.02 | 0.01 | 440 | 2.23 | 2.65E-02 | 1.89E-01 | Proteome | Q9NPH3_5 |
| eugenol sulfate | 0.03 | 0.02 | 417 | 2.2 | 2.81E-02 | 2.00E-01 | Metabolome | |
| TGLHDL | 0.04 | 0.02 | 459 | 2.2 | 2.84E-02 | 2.00E-01 | Clinical labs | |
| TP | −0.02 | 0.01 | 461 | −2.19 | 2.88E-02 | 2.01E-01 | Clinical labs | |
| LysoPC(18:0) | 0.02 | 0.01 | 417 | 2.18 | 2.98E-02 | 2.01E-01 | Metabolome | HMDB10384 |
| BUN | 0.03 | 0.01 | 461 | 2.19 | 2.90E-02 | 2.01E-01 | Clinical labs | |
| PLT | 0.03 | 0.01 | 456 | 2.18 | 2.95E-02 | 2.01E-01 | Clinical labs | |
| Titin | −0.01 | 0.01 | 440 | −2.18 | 2.98E-02 | 2.01E-01 | Proteome | Q8WZ42_2 |
| C8:0, OH FA(1) | 0.02 | 0.01 | 417 | 2.17 | 3.02E-02 | 2.02E-01 | Metabolome | |
| MASP2 | 0.02 | 0.01 | 440 | 2.17 | 3.05E-02 | 2.03E-01 | Proteome | O00187 |
| Caffeine | 0.03 | 0.01 | 417 | 2.16 | 3.16E-02 | 2.08E-01 | Metabolome | HMDB01847 |
| Bilirubin | −0.05 | 0.03 | 417 | −2.15 | 3.23E-02 | 2.11E-01 | Metabolome | HMDB00054 |
| C14:1 AC | −0.03 | 0.01 | 417 | −2.15 | 3.25E-02 | 2.11E-01 | Metabolome | HMDB02014 |
| C20:0 FA | 0.02 | 0.01 | 417 | 2.14 | 3.28E-02 | 2.12E-01 | Metabolome | HMDB02212 |
| 2,3-Dihydroxyvaleric acid(2) | 0.08 | 0.04 | 417 | 2.14 | 3.32E-02 | 2.12E-01 | Metabolome | HMDB00421 |
| Theophylline | 0.02 | 0.01 | 417 | 2.13 | 3.40E-02 | 2.13E-01 | Metabolome | HMDB01889 |
| Sphinganine 1-phosphate | 0.14 | 0.06 | 417 | 2.13 | 3.37E-02 | 2.13E-01 | Metabolome | HMDB01383 |
| Cyclo(ala-pro) | 0.02 | 0.01 | 417 | 2.12 | 3.44E-02 | 2.13E-01 | Metabolome | |
| Phenylalanylleucine | 0.18 | 0.08 | 417 | 2.12 | 3.43E-02 | 2.13E-01 | Metabolome | |
| MYBPC2 | −0.02 | 0.01 | 440 | −2.12 | 3.48E-02 | 2.15E-01 | Proteome | Q14324 |
| C22:3 FA | 0.02 | 0.01 | 417 | 2.11 | 3.52E-02 | 2.15E-01 | Metabolome | HMDB02823 |
| Citric acid | 0.02 | 0.01 | 417 | 2.11 | 3.58E-02 | 2.17E-01 | Metabolome | HMDB00094 |
| 2,3-Dihydroxyvaleric acid (1) | 0.04 | 0.02 | 417 | 2.09 | 3.68E-02 | 2.20E-01 | Metabolome | HMDB00421 |
| Cys-Pro or Pro-Cys | −0.02 | 0.01 | 417 | −2.09 | 3.68E-02 | 2.20E-01 | Metabolome | HMDB28783 |
| Androsterone glucuronide(2) | 0.03 | 0.01 | 417 | 2.08 | 3.80E-02 | 2.24E-01 | Metabolome | HMDB02829 |
| gamma-glutamylleucine(1) | 0.02 | 0.01 | 417 | 2.08 | 3.79E-02 | 2.24E-01 | Metabolome | HMDB11171 |
| C12:0, OH FA(2) | 0.03 | 0.01 | 417 | 2.07 | 3.89E-02 | 2.25E-01 | Metabolome | HMDB02059 |
| EOS | 0.04 | 0.02 | 455 | 2.07 | 3.89E-02 | 2.25E-01 | Clinical labs | |
| N-acetylthreonine | 0.01 | 0.01 | 417 | 2.07 | 3.88E-02 | 2.25E-01 | Metabolome | |
| L-a-Hydroxyisovaleric acid | 0.03 | 0.02 | 417 | 2.07 | 3.95E-02 | 2.26E-01 | Metabolome | HMDB00407 |
| C10:0, DC FA (Sebacic acid)(2) | 0.03 | 0.02 | 417 | 2.06 | 4.00E-02 | 2.26E-01 | Metabolome | HMDB00792 |
| Ig kappa chain V-I region Scw | −0.02 | 0.01 | 440 | −2.06 | 4.02E-02 | 2.26E-01 | Proteome | P01609 |
| FETUB | −0.02 | 0.01 | 440 | −2.06 | 4.01E-02 | 2.26E-01 | Proteome | Q9UGM5 |
| gamma-glutamylleucine(2) | 0.02 | 0.01 | 417 | 2.04 | 4.17E-02 | 2.33E-01 | Metabolome | HMDB11171 |
| Pantothenic acid | 0.04 | 0.02 | 417 | 2.03 | 4.26E-02 | 2.36E-01 | Metabolome | HMDB00210 |
| PRG4(1) | 0.01 | 0.01 | 440 | 2.03 | 4.28E-02 | 2.36E-01 | Proteome | Q92954 |
| ADIPOQ | 0.02 | 0.01 | 440 | 2.03 | 4.32E-02 | 2.37E-01 | Proteome | Q15848 |
| 1-Methylhistidine | 0.03 | 0.01 | 417 | 2.02 | 4.42E-02 | 2.38E-01 | Metabolome | HMDB00001 |
| Threonic acid | 0.04 | 0.02 | 417 | 2.02 | 4.39E-02 | 2.38E-01 | Metabolome | HMDB00943 |
| Pro-Cys or Cys-Pro | −0.02 | 0.01 | 417 | −2.02 | 4.39E-02 | 2.38E-01 | Metabolome | HMDB28783\|HMDB29014 |
| LysoPE(P-16:0) | 0.07 | 0.03 | 417 | 2 | 4.57E-02 | 2.44E-01 | Metabolome | HMDB11152 |
| Xanthine | −0.02 | 0.01 | 417 | −2 | 4.65E-02 | 2.47E-01 | Metabolome | HMDB00292 |
| C10:0 AC | −0.05 | 0.03 | 417 | −1.99 | 4.73E-02 | 2.49E-01 | Metabolome | HMDB00651 |
| Allantoin | 0.26 | 0.13 | 417 | 1.98 | 4.78E-02 | 2.51E-01 | Metabolome | HMDB00462 |
| C12:1, DC FA(1) | 0.02 | 0.01 | 417 | 1.97 | 4.89E-02 | 2.55E-01 | Metabolome | HMDB00933 |
| Chenodeoxycholic Acid(3) | 0.06 | 0.03 | 417 | 1.96 | 5.06E-02 | 2.60E-01 | Metabolome | HMDB00518 |
| Ig kappa chain V-I region AG | −0.02 | 0.01 | 440 | −1.96 | 5.04E-02 | 2.60E-01 | Proteome | P01593 |
| C14:0 AC | −0.02 | 0.01 | 417 | −1.94 | 5.25E-02 | 2.68E-01 | Metabolome | HMDB05066 |
| L-Glutamic acid | 0.02 | 0.01 | 417 | 1.93 | 5.37E-02 | 2.73E-01 | Metabolome | HMD600148 |
| Kininogen-1 | −0.01 | 0.01 | 440 | −1.93 | 5.48E-02 | 2.77E-01 | Proteome | P01042_2 |
| C12:0, DC FA | 0.03 | 0.02 | 417 | 1.91 | 5.67E-02 | 2.83E-01 | Metabolome | HMDB00623 |
| LysoPE(20:3) | 0.05 | 0.03 | 417 | 1.91 | 5.67E-02 | 2.83E-01 | Metabolome | HMDB11484 |
| Indoleacetic acid | 0.02 | 0.01 | 417 | 1.9 | 5.85E-02 | 2.90E-01 | Metabolome | HMD600197 |
| C18:0, OH FA(1) | 0.02 | 0.01 | 417 | 1.89 | 5.89E-02 | 2.90E-01 | Metabolome | |
| C19:0 FA(2) | 0.02 | 0.01 | 417 | 1.89 | 5.93E-02 | 2.91E-01 | Metabolome | HMDB00772 |
| Indoleacetyl glutamine | 0.03 | 0.01 | 417 | 1.86 | 6.33E-02 | 3.09E-01 | Metabolome | HMDB13240 |
| C16:0, DC FA(2) | 0.02 | 0.01 | 417 | 1.86 | 6.38E-02 | 3.10E-01 | Metabolome | HMD600672 |
| Aminoadipic acid | 0.03 | 0.01 | 417 | 1.85 | 6.48E-02 | 3.10E-01 | Metabolome | HMDB00510 |
| Pregnanediol-3-glucuronide | 0.01 | 0.01 | 417 | 1.85 | 6.49E-02 | 3.10E-01 | Metabolome | HMDB10318 |
| ICAM1 | 0.05 | 0.03 | 449 | 1.85 | 6.50E-02 | 3.10E-01 | Immunome | |
| Arabonate \| Xylonate(3) | 0.02 | 0.01 | 417 | 1.84 | 6.63E-02 | 3.11E-01 | Metabolome | |
| THBS1 | 0.01 | 0.01 | 440 | 1.84 | 6.60E-02 | 3.11E-01 | Proteome | P07996 |
| LPA | −0.04 | 0.02 | 440 | −1.84 | 6.62E-02 | 3.11E-01 | Proteome | P08519 |
| L-Threonine | 0.02 | 0.01 | 417 | 1.83 | 6.77E-02 | 3.16E-01 | Metabolome | HMDB00167 |
| Biliverdin(1) | −0.01 | 0.01 | 417 | −1.82 | 6.96E-02 | 3.21E-01 | Metabolome | HMD601008 |
| ALCRU | 0.02 | 0.01 | 276 | 1.82 | 6.95E-02 | 3.21E-01 | Clinical labs | |
| Ig heavy chain V-I region V35 | −0.02 | 0.01 | 440 | −1.81 | 7.04E-02 | 3.23E-01 | Proteome | P23083 |
| MG(14:1)(1) | 0.02 | 0.01 | 417 | 1.8 | 7.24E-02 | 3.23E-01 | Metabolome | HMDB11531 |
| methyl-4-hydroxybenzoate sulfate | 0.05 | 0.03 | 417 | 1.81 | 7.16E-02 | 3.23E-01 | Metabolome | HMD634172 |
| LYMAB | 0.03 | 0.01 | 456 | 1.81 | 7.15E-02 | 3.23E-01 | Clinical labs | |
| C8:0, OH FA(3) | 0.18 | 0.10 | 417 | 1.8 | 7.27E-02 | 3.23E-01 | Metabolome | |
| IGJ | −0.01 | 0.01 | 440 | −1.81 | 7.13E-02 | 3.23E-01 | Proteome | P01591 |
| BCHE | 0.01 | 0.01 | 440 | 1.8 | 7.25E-02 | 3.23E-01 | Proteome | P06276 |
| C10:1 OH FA | 0.03 | 0.02 | 417 | 1.79 | 7.35E-02 | 3.25E-01 | Metabolome | |
| Ig kappa chain V-I region Ni | −0.01 | 0.01 | 440 | −1.79 | 7.43E-02 | 3.27E-01 | Proteome | P01613 |
| L-Phenylalanine | 0.02 | 0.01 | 417 | 1.77 | 7.70E-02 | 3.33E-01 | Metabolome | HMDB00159 |
| N1-methyladenosine | 0.02 | 0.01 | 417 | 1.78 | 7.63E-02 | 3.33E-01 | Metabolome | HMD603331 |
| C5:0 AC | 0.02 | 0.01 | 417 | 1.77 | 7.67E-02 | 3.33E-01 | Metabolome | |

TABLE 13-continued

| | | | | | | | |
|---|---|---|---|---|---|---|---|
| Ig lambda chain V-II region BUR | −0.01 | 0.01 | 440 | −1.76 | 7.86E−02 | 3.38E−01 | Proteome | P01708 |
| C22:6 FA | −0.01 | 0.01 | 417 | −1.75 | 8.01E−02 | 3.41E−01 | Metabolome | HMDB02183 |
| IL5 | 0.05 | 0.03 | 449 | 1.75 | 8.01E−02 | 3.41E−01 | Immunome | |
| LysoPE(22:0) | 0.08 | 0.05 | 417 | 1.75 | 8.17E−02 | 3.47E−01 | Metabolome | HMDB11490 |
| (S)-(-)-2-Hydroxyisocaproic acid | 0.02 | 0.01 | 417 | 1.73 | 8.39E−02 | 3.52E−01 | Metabolome | HMDB00746 |
| C16:0, OH FA(2) | 0.01 | 0.01 | 417 | 1.73 | 8.42E−02 | 3.52E−01 | Metabolome | HMDB31057 |
| IL1B | −0.01 | 0.01 | 449 | −1.73 | 8.42E−02 | 3.52E−01 | Immunome | |
| GPX3 | 0.01 | 0.01 | 440 | 1.73 | 8.49E−02 | 3.53E−01 | Proteome | P22352 |
| C18:1, OH FA(1) | 0.02 | 0.01 | 417 | 1.72 | 8.58E−02 | 3.55E−01 | Metabolome | |
| EOSAB | 0.03 | 0.02 | 455 | 1.72 | 8.64E−02 | 3.56E−01 | Clinical labs | |
| C14:0, OH FA(1) | 0.02 | 0.01 | 417 | 1.71 | 8.81E−02 | 3.59E−01 | Metabolome | HMDB02261 |
| Arabitol | Xylitol | 0.02 | 0.01 | 417 | 1.71 | 8.77E−02 | 3.59E−01 | Metabolome | |
| C17:1 FA | 0.02 | 0.01 | 417 | 1.7 | 8.90E−02 | 3.61E−01 | Metabolome | HMDB60038 |
| C12:0 FA(2) | −0.02 | 0.01 | 417 | −1.7 | 8.97E−02 | 3.62E−01 | Metabolome | |
| Catechol sulfate | −0.40 | 0.24 | 417 | −1.69 | 9.24E−02 | 3.71E−01 | Metabolome | HMD859724 |
| 2-Aminobutyrate | 0.02 | 0.01 | 417 | 1.68 | 9.46E−02 | 3.76E−01 | Metabolome | HMDB00650 |
| C22:2 FA | 0.02 | 0.01 | 417 | 1.68 | 9.44E−02 | 3.76E−01 | Metabolome | HMDB61714 |
| Proteoglycan 4 | 0.01 | 0.01 | 440 | 1.67 | 9.49E−02 | 3.76E−01 | Proteome | Q92954_6 |
| C12:0 AC | −0.02 | 0.01 | 417 | −1.67 | 9.62E−02 | 3.79E−01 | Metabolome | HMDB02250 |
| Cinnamoylglycine | 0.03 | 0.02 | 417 | 1.66 | 9.77E−02 | 3.84E−01 | Metabolome | HMDB11621 |
| C14:0, DC FA(2) | 0.02 | 0.01 | 417 | 1.65 | 9.97E−02 | 3.87E−01 | Metabolome | HMDB00872 |
| 7-Methylguanine | 0.02 | 0.01 | 417 | 1.65 | 9.99E−02 | 3.87E−01 | Metabolome | HMDB00897 |
| C10:2 AC | −0.03 | 0.02 | 417 | −1.65 | 9.99E−02 | 3.87E−01 | Metabolome | HMDB13325 |
| C18:1, OH FA(2) | 0.02 | 0.01 | 417 | 1.64 | 1.01E−01 | 3.89E−01 | Metabolome | |
| C18:2 AC | −0.02 | 0.01 | 417 | −1.63 | 1.03E−01 | 3.93E−01 | Metabolome | HMDB06461 |
| IGHA1 | −0.01 | 0.01 | 440 | −1.64 | 1.03E−01 | 3.93E−01 | Proteome | P01876 |
| MCHC | 0.01 | 0.01 | 456 | 1.63 | 1.04E−01 | 3.94E−01 | Clinical labs | |
| Ig lambda chain V-I region BL2 | 0.01 | 0.01 | 440 | 1.63 | 1.04E−01 | 3.94E−01 | Proteome | P06316 |
| L-Asparagine | 0.02 | 0.01 | 417 | 1.62 | 1.06E−01 | 4.00E−01 | Metabolome | HMDB00168 |
| C20:3, OH FA(2) | 0.02 | 0.01 | 417 | 1.6 | 1.09E−01 | 4.10E−01 | Metabolome | |
| 3-Methyl-2-oxovaleric acid | 0.02 | 0.01 | 417 | 1.6 | 1.11E−01 | 4.12E−01 | Metabolome | HMD803736 |
| IL23 | 0.05 | 0.03 | 449 | 1.6 | 1.11E−01 | 4.12E−01 | Immunome | |
| PFN1 | 0.01 | 0.01 | 440 | 1.6 | 1.10E−01 | 4.12E−01 | Proteome | P07737 |
| C6:0 AC | −0.05 | 0.03 | 417 | −1.58 | 1.14E−01 | 4.20E−01 | Metabolome | HMDB00705 |
| Alliin | 0.01 | 0.01 | 417 | 1.58 | 1.14E−01 | 4.20E−01 | Metabolome | HMD933592 |
| Cys Gly | −0.02 | 0.01 | 417 | −1.57 | 1.17E−01 | 4.25E−01 | Metabolome | HMDB00078 |
| Androsterone sulfate(2) | 0.02 | 0.02 | 417 | 1.57 | 1.18E−01 | 4.25E−01 | Metabolome | HMDB02759 |
| AG | −0.01 | 0.01 | 461 | −1.56 | 1.18E−01 | 4.25E−01 | Clinical labs | |
| RESISTIN | −0.02 | 0.01 | 449 | −1.57 | 1.17E−01 | 4.25E−01 | Immunome | |
| IGKC | −0.01 | 0.01 | 440 | −1.57 | 1.18E−01 | 4.25E−01 | Proteome | P01834 |
| CD14:0 FA | 0.01 | 0.01 | 417 | 1.56 | 1.20E−01 | 4.29E−01 | Metabolome | HMDB00806 |
| Ethylmalonate | 0.02 | 0.02 | 417 | 1.55 | 1.22E−01 | 4.31E−01 | Metabolome | HMDB00622 |
| 3-indoxyl sulfate | 0.02 | 0.01 | 417 | 1.54 | 1.25E−01 | 4.31E−01 | Metabolome | HMDB00682 |
| N2,N2-Dimethylguanosine | 0.02 | 0.01 | 417 | 1.54 | 1.25E−01 | 4.31E−01 | Metabolome | HMDB04824 |
| LysoPC(22:4) | 0.08 | 0.05 | 417 | 1.54 | 1.25E−01 | 4.31E−01 | Metabolome | HMDB10401 |
| HSCRP | −0.04 | 0.03 | 419 | −1.55 | 1.22E−01 | 4.31E−01 | Clinical labs | |
| PAI1 | 0.02 | 0.01 | 449 | 1.54 | 1.24E−01 | 4.31E−01 | Immunome | |
| 4-formyl Indole(2) | 0.03 | 0.02 | 417 | 1.54 | 1.24E−01 | 4.31E−01 | Metabolome | |
| Ig heavy chain V-III region GAL | −0.01 | 0.01 | 440 | −1.55 | 1.22E−01 | 4.31E−01 | Proteome | P01781 |
| CD14 | 0.01 | 0.01 | 440 | 1.54 | 1.23E−01 | 4.31E−01 | Proteome | P08571 |
| Ectoine | 0.01 | 0.01 | 417 | 1.53 | 1.26E−01 | 4.33E−01 | Metabolome | |
| IL31 | −0.04 | 0.02 | 449 | −1.53 | 1.27E−01 | 4.34E−01 | Immunome | |
| N6-Carbamoyl-L-threonyladenosine | 0.02 | 0.01 | 417 | 1.52 | 1.30E−01 | 4.43E−01 | Metabolome | HMDB41623 |
| Phenol sulphate | 0.02 | 0.01 | 417 | 1.51 | 1.31E−01 | 4.43E−01 | Metabolome | HMDB60015 |
| NEUT | −0.02 | 0.01 | 456 | −1.51 | 1.31E−01 | 4.43E−01 | Clinical labs | |
| AZGP1 | −0.01 | 0.01 | 440 | −1.5 | 1.34E−01 | 4.50E−01 | Proteome | P25311 |
| FLNA | 0.01 | 0.01 | 440 | 1.5 | 1.35E−01 | 4.52E−01 | Proteome | P21333 |
| BID | 0.01 | 0.01 | 440 | 1.5 | 1.35E−01 | 4.52E−01 | Proteome | P43251 |
| LysoPE(20:4) | 0.02 | 0.01 | 417 | 1.49 | 1.37E−01 | 4.56E−01 | Metabolome | HMDB11487 |
| MG(20:4)(2) | 0.03 | 0.02 | 417 | 1.48 | 1.39E−01 | 4.60E−01 | Metabolome | HMDB04666 |
| LysoPC(15:0) | 0.01 | 0.01 | 417 | 1.48 | 1.40E−01 | 4.60E−01 | Metabolome | HMDB10381 |
| C15:1 FA | 0.02 | 0.01 | 417 | 1.48 | 1.40E−01 | 4.60E−01 | Metabolome | |
| Ig kappa chain V-III region GOL | −0.02 | 0.01 | 440 | −1.47 | 1.42E−01 | 4.64E−01 | Proteome | P04206 |
| Dihydroxyvitamin D3(2) | 0.02 | 0.01 | 417 | 1.47 | 1.44E−01 | 4.65E−01 | Metabolome | HMDB00430 |
| Ig heavy chain V-III region BUR | −0.01 | 0.01 | 440 | −1.47 | 1.43E−01 | 4.65E−01 | Proteome | P01773 |
| SERPINA6 | 0.01 | 0.01 | 440 | 1.46 | 1.44E−01 | 4.65E−01 | Proteome | P08185 |
| RBC | −0.02 | 0.01 | 456 | −1.46 | 1.45E−01 | 4.66E−01 | Clinical labs | |
| 3-Methyl-L-histidine | 0.02 | 0.01 | 417 | 1.46 | 1.45E−01 | 4.66E−01 | Metabolome | HMDB00479 |
| C1QA | −0.01 | 0.01 | 440 | −1.46 | 1.46E−01 | 4.68E−01 | Proteome | P02745 |
| Ne-Methyl-Lysine | 0.03 | 0.02 | 417 | 1.45 | 1.48E−01 | 4.70E−01 | Metabolome | HMDB02038 |
| C20:3 FA | 0.01 | 0.01 | 417 | 1.45 | 1.49E−01 | 4.70E−01 | Metabolome | HMDB02925 |
| C16:1 AC | −0.02 | 0.01 | 417 | −1.44 | 1.49E−01 | 4.70E−01 | Metabolome | HMDB06317 |
| IL1RA | −0.03 | 0.02 | 449 | −1.45 | 1.48E−01 | 4.70E−01 | Immunome | |
| TNFA | −0.03 | 0.02 | 449 | −1.44 | 1.50E−01 | 4.70E−01 | Immunome | |
| K | 0.01 | 0.01 | 461 | 1.43 | 1.54E−01 | 4.75E−01 | Clinical labs | |
| WBC | 0.02 | 0.01 | 456 | 1.43 | 1.55E−01 | 4.75E−01 | Clinical labs | |
| IL12P70 | 0.04 | 0.02 | 449 | 1.43 | 1.53E−01 | 4.75E−01 | Immunome | |
| VCL | 0.01 | 0.01 | 440 | 1.43 | 1.54E−01 | 4.75E−01 | Proteome | P18206 |
| PON3 | 0.01 | 0.01 | 440 | 1.43 | 1.55E−01 | 4.75E−01 | Proteome | Q15166 |
| FCN2 | −0.01 | 0.01 | 440 | −1.43 | 1.54E−01 | 4.75E−01 | Proteome | Q15485 |

TABLE 13-continued

| | | | | | | | |
|---|---|---|---|---|---|---|---|
| SCF | 0.03 | 0.02 | 449 | 1.42 | 1.55E−01 | 4.75E−01 | Immunome | |
| C18:3, OH FA(2) | 0.02 | 0.01 | 417 | 1.42 | 1.57E−01 | 4.76E−01 | Metabolome | |
| Ryanodine receptor 2 | 0.01 | 0.01 | 440 | 1.42 | 1.56E−01 | 4.76E−01 | Proteome | Q92736_2 |
| p-Cresol glucuronide | 0.02 | 0.02 | 417 | 1.42 | 1.57E−01 | 4.76E−01 | Metabolome | HMDB11686 |
| Indolelactic acid | 0.02 | 0.01 | 417 | 1.41 | 1.59E−01 | 4.78E−01 | Metabolome | HMDB00671 |
| Glycine | 0.07 | 0.05 | 417 | 1.39 | 1.65E−01 | 4.82E−01 | Metabolome | HMDB00123 |
| gamma-CEHC | −0.07 | 0.05 | 417 | −1.4 | 1.63E−01 | 4.82E−01 | Metabolome | HMDB01931 |
| IL21 | −0.05 | 0.04 | 449 | −1.39 | 1.64E−01 | 4.82E−01 | Immunome | |
| Ig mu heavy chain disease protein | −0.01 | 0.01 | 440 | −1.4 | 1.63E−01 | 4.82E−01 | Proteome | P04220 |
| Fibulin-1 | 0.01 | 0.01 | 440 | 1.39 | 1.64E−01 | 4.82E−01 | Proteome | P23142_4 |
| HBB | −0.01 | 0.01 | 440 | −1.39 | 1.64E−01 | 4.82E−01 | Proteome | P68871 |
| CTTNBP2 | −0.01 | 0.01 | 440 | −1.39 | 1.65E−01 | 4.82E−01 | Proteome | Q8WZ74 |
| NUP205 | 0.01 | 0.01 | 440 | 1.39 | 1.64E−01 | 4.82E−01 | Proteome | Q92621 |
| IL1RAP(1) | 0.01 | 0.01 | 440 | 1.4 | 1.64E−01 | 4.82E−01 | Proteome | Q9NPH3 |
| C10:3 FA(2) | 0.01 | 0.01 | 417 | 1.38 | 1.67E−01 | 4.85E−01 | Metabolome | |
| VASN | 0.01 | 0.01 | 440 | 1.38 | 1.67E−01 | 4.85E−01 | Proteome | Q6EMK4 |
| Retinol (Vitamin A) | 0.01 | 0.01 | 417 | 1.38 | 1.69E−01 | 4.88E−01 | Metabolome | HMDB00305 |
| Tauroursodeoxycholic acid | −0.05 | 0.04 | 417 | −1.38 | 1.69E−01 | 4.88E−01 | Metabolome | HMDB00874 |
| Pyruvic acid | −0.02 | 0.01 | 417 | −1.35 | 1.77E−01 | 4.96E−01 | Metabolome | HMDB00243 |
| Glyceric acid | 0.01 | 0.01 | 417 | 1.36 | 1.76E−01 | 4.96E−01 | Metabolome | HMDB00139 |
| L-Serine | 0.02 | 0.01 | 417 | 1.35 | 1.77E−01 | 4.96E−01 | Metabolome | HMDB00187 |
| Cysteineglutathione disulfide | −0.02 | 0.01 | 417 | −1.36 | 1.75E−01 | 4.96E−01 | Metabolome | HMDB00656 |
| Hydroxyhippurate(3) | −0.08 | 0.06 | 417 | −1.36 | 1.74E−01 | 4.96E−01 | Metabolome | HMDB00840 |
| C20:2 FA | 0.01 | 0.01 | 417 | 1.36 | 1.76E−01 | 4.96E−01 | Metabolome | HMDB05060 |
| CO2 | 0.01 | 0.01 | 461 | 1.35 | 1.78E−01 | 4.96E−01 | Clinical labs | |
| APOC1 | 0.01 | 0.01 | 440 | 1.35 | 1.77E−01 | 4.96E−01 | Proteome | P02654 |
| LBP | 0.01 | 0.01 | 440 | 1.36 | 1.75E−01 | 4.96E−01 | Proteome | P18428 |
| LysoPC(P-18:1) | 0.01 | 0.01 | 417 | 1.34 | 1.80E−01 | 5.01E−01 | Metabolome | HMDB10408 |
| Ig kappa chain V-III region IARC/BL41 | −0.01 | 0.01 | 440 | −1.34 | 1.81E−01 | 5.02E−01 | Proteome | P06311 |
| Hydroxybenzoic acid | −0.07 | 0.05 | 417 | −1.34 | 1.82E−01 | 5.03E−01 | Metabolome | HMDB00500 |
| APOC4 | 0.01 | 0.01 | 440 | 1.34 | 1.82E−01 | 5.03E−01 | Proteome | P55056 |
| LysoPE(18:2) | 0.01 | 0.01 | 417 | 1.33 | 1.84E−01 | 5.04E−01 | Metabolome | HMDB11477 |
| IGM | −0.03 | 0.02 | 456 | −1.33 | 1.84E−01 | 5.04E−01 | Clinical labs | |
| NPHP3 | −0.01 | 0.01 | 440 | −1.33 | 1.85E−01 | 5.04E−01 | Proteome | Q7Z494 |
| LCP1 | 0.01 | 0.01 | 440 | 1.33 | 1.86E−01 | 5.06E−01 | Proteome | P13796 |
| Quinic acid | 0.02 | 0.01 | 417 | 1.32 | 1.87E−01 | 5.09E−01 | Metabolome | HMDB03072 |
| C16:1, OH FA(1) | 0.01 | 0.01 | 417 | 1.31 | 1.90E−01 | 5.12E−01 | Metabolome | |
| MYH7 | 0.01 | 0.01 | 440 | 1.31 | 1.90E−01 | 5.12E−01 | Proteome | P12883 |
| Citrulline | 0.02 | 0.01 | 417 | 1.31 | 1.92E−01 | 5.13E−01 | Metabolome | HMDB00904 |
| Biliverdin(2) | −0.02 | 0.02 | 417 | −1.31 | 1.92E−01 | 5.13E−01 | Metabolome | HMDB01008 |
| Erythritol\|D-Threitol | 0.01 | 0.01 | 417 | 1.3 | 1.93E−01 | 5.13E−01 | Metabolome | HMDB02994\|HMDB04136 |
| C12:0 FA(1) | 0.02 | 0.01 | 417 | 1.31 | 1.92E−01 | 5.13E−01 | Metabolome | |
| L-Tryptophan | 0.01 | 0.01 | 417 | 1.29 | 1.97E−01 | 5.18E−01 | Metabolome | HMDB00929 |
| Androstenediol (3beta, 17beta) disulfate | 0.02 | 0.02 | 417 | 1.29 | 1.96E−01 | 5.18E−01 | Metabolome | HMDB03818 |
| C15:0, OH FA | 0.01 | 0.01 | 417 | 1.29 | 1.98E−01 | 5.18E−01 | Metabolome | |
| Ig kappa chain V-I region BAN | −0.01 | 0.01 | 440 | −1.29 | 1.98E−01 | 5.18E−01 | Proteome | P04430 |
| Ig heavy chain V-II region ARH-77 | −0.01 | 0.01 | 440 | −1.3 | 1.95E−01 | 5.18E−01 | Proteome | P06331 |
| PLTP | 0.01 | 0.01 | 440 | 1.29 | 1.98E−01 | 5.18E−01 | Proteome | P55058 |
| CD40L | 0.04 | 0.03 | 449 | 1.28 | 2.03E−01 | 5.26E−01 | Immunome | |
| DCN3 | −0.01 | 0.01 | 440 | −1.28 | 2.02E−01 | 5.26E−01 | Proteome | O75636 |
| LysoPC(17:0) | 0.01 | 0.01 | 417 | 1.27 | 2.05E−01 | 5.27E−01 | Metabolome | HMDB12108 |
| Piperine(2) | 0.02 | 0.02 | 417 | 1.27 | 2.05E−01 | 5.27E−01 | Metabolome | HMDB29377 |
| HBA1 | −0.01 | 0.01 | 440 | −1.27 | 2.04E−01 | 5.27E−01 | Proteome | P69905 |
| MG(18:3) | 0.01 | 0.01 | 417 | 1.26 | 2.07E−01 | 5.30E−01 | Metabolome | HMDB11539 |
| IGLC2 | −0.01 | 0.01 | 440 | −1.26 | 2.07E−01 | 5.30E−01 | Proteome | P0CG05 |
| ACTBL2 | 0.01 | 0.01 | 440 | 1.25 | 2.12E−01 | 5.40E−01 | Proteome | Q562R1 |
| BASO | −0.01 | 0.01 | 455 | −1.24 | 2.17E−01 | 5.51E−01 | Clinical labs | |
| L-Carnitine | 0.02 | 0.01 | 417 | 1.23 | 2.18E−01 | 5.52E−01 | Metabolome | HMDB00062 |
| TBIL | −0.02 | 0.01 | 461 | −1.23 | 2.19E−01 | 5.54E−01 | Clinical labs | |
| LysoPC (14:0) | 0.01 | 0.01 | 417 | 1.23 | 2.20E−01 | 5.55E−01 | Metabolome | HMDB10379 |
| 5alpha-Androstan-3alpha, 17alpha-diol monosulfate(1) | 0.04 | 0.03 | 417 | 1.22 | 2.23E−01 | 5.59E−01 | Metabolome | |
| IL22 | 0.02 | 0.02 | 449 | 1.21 | 2.25E−01 | 5.64E−01 | Immunome | |
| C16:4 FA | −0.02 | 0.01 | 417 | −1.21 | 2.27E−01 | 5.66E−01 | Metabolome | |
| L-Arginine | 0.01 | 0.01 | 417 | 1.2 | 2.30E−01 | 5.70E−01 | Metabolome | HMDB00517 |
| C22:4 FA | 0.01 | 0.01 | 417 | 1.2 | 2.29E−01 | 5.70E−01 | Metabolome | HMDB02226 |
| IFNB | −0.05 | 0.04 | 449 | −1.2 | 2.31E−01 | 5.71E−01 | Immunome | |
| C18:3, OH FA(3) | 0.01 | 0.01 | 417 | 1.2 | 2.31E−01 | 5.71E−01 | Metabolome | |
| Oleoyl Ethyl Amide | 0.01 | 0.01 | 417 | 1.19 | 2.34E−01 | 5.73E−01 | Metabolome | |
| C10:1 FA(1) | −0.03 | 0.02 | 417 | −1.19 | 2.34E−01 | 5.73E−01 | Metabolome | |
| Ig lambda chain V-VI region SUT | −0.01 | 0.01 | 440 | −1.19 | 2.33E−01 | 5.73E−01 | Proteome | P06317 |
| C10:1, DC FA | 0.01 | 0.01 | 417 | 1.19 | 2.35E−01 | 5.73E−01 | Metabolome | HMDB00603 |
| 5alpha-Androstan-3alpha, 17beta-diol 17-glucuronide(1) | 0.02 | 0.02 | 417 | 1.19 | 2.36E−01 | 5.74E−01 | Metabolome | |
| p-Cresol sulfate | 0.01 | 0.01 | 417 | 1.18 | 2.40E−01 | 5.79E−01 | Metabolome | HMDB11635 |
| Glucaric acid | 0.01 | 0.01 | 417 | 1.18 | 2.40E−01 | 5.79E−01 | Metabolome | HMDB00663 |
| Ig kappa chain V-II region FR | −0.01 | 0.01 | 440 | −1.18 | 2.39E−01 | 5.79E−01 | Proteome | P01615 |
| IGHG1 | −0.01 | 0.01 | 440 | −1.17 | 2.43E−01 | 5.82E−01 | Proteome | P01857 |
| CDHR5 | −0.01 | 0.01 | 440 | −1.17 | 2.42E−01 | 5.82E−01 | Proteome | Q9HBB8 |
| Pregnanolone sulfate | 0.01 | 0.01 | 417 | 1.16 | 2.45E−01 | 5.86E−01 | Metabolome | |

TABLE 13-continued

| | | | | | | | |
|---|---|---|---|---|---|---|---|
| C18:0, DC FA(2) | 0.01 | 0.01 | 417 | 1.16 | 2.46E−01 | 5.87E−01 | Metabolome | HMDB00782 |
| Sulfolithocholylglycine | −0.03 | 0.02 | 417 | −1.16 | 2.47E−01 | 5.87E−01 | Metabolome | HMDB02639 |
| C18:0, DC FA(3) | 0.01 | 0.01 | 417 | 1.14 | 2.56E−01 | 6.04E−01 | Metabolome | HMDB00782 |
| LysoPE(22:6) | −0.01 | 0.01 | 417 | −1.14 | 2.55E−01 | 6.04E−01 | Metabolome | HMDB11496 |
| MGP | −0.01 | 0.01 | 440 | −1.14 | 2.56E−01 | 6.04E−01 | Proteome | P08493 |
| LysoPE(16:1) | 0.02 | 0.01 | 417 | 1.13 | 2.61E−01 | 6.11E−01 | Metabolome | HMDB11474 |
| ORM1 | −0.01 | 0.01 | 440 | −1.13 | 2.61E−01 | 6.11E−01 | Proteome | P02763 |
| Ig kappa chain V-I region Mev | −0.01 | 0.01 | 440 | −1.12 | 2.63E−01 | 6.12E−01 | Proteome | P01612 |
| PCYOX1 | 0.01 | 0.01 | 440 | 1.12 | 2.62E−01 | 6.12E−01 | Proteome | Q9UHG3 |
| Dihydro-3-coumaric acid | 0.02 | 0.02 | 417 | 1.12 | 2.64E−01 | 6.15E−01 | Metabolome | HMDB00375 |
| Asp-Glu or Glu-Asp | 0.01 | 0.01 | 417 | 1.11 | 2.68E−01 | 6.19E−01 | Metabolome | HMDB28752 |
| Ig heavy chain V-II region SESS | −0.01 | 0.01 | 440 | −1.11 | 2.67E−01 | 6.19E−01 | Proteome | P04438 |
| IGEBP3 | −0.01 | 0.01 | 440 | −1.11 | 2.68E−01 | 6.19E−01 | Proteome | P17936 |
| Gentisic acid | 0.02 | 0.01 | 417 | 1.1 | 2.73E−01 | 6.25E−01 | Metabolome | HMDB00152 |
| NEUTAB | 0.01 | 0.01 | 456 | 1.1 | 2.72E−01 | 6.25E−01 | Clinical labs | |
| ENA78 | 0.03 | 0.03 | 449 | 1.09 | 2.77E−01 | 6.33E−01 | Immunome | |
| Ig lambda chain V-III region SH | −0.01 | 0.01 | 440 | −1.09 | 2.78E−01 | 6.33E−01 | Proteome | P01714 |
| ITIH3 | −0.01 | 0.01 | 440 | −1.09 | 2.78E−01 | 6.33E−01 | Proteome | Q06033 |
| Hydroxyphenyllactic acid | 0.01 | 0.01 | 417 | 1.08 | 2.80E−01 | 6.35E−01 | Metabolome | HMDB00755 |
| L-Glutamine | −0.01 | 0.01 | 417 | −1.07 | 2.85E−01 | 6.37E−01 | Metabolome | HMDB00641 |
| 4-Hydroxyproline | 0.01 | 0.01 | 417 | 1.07 | 2.84E−01 | 6.37E−01 | Metabolome | HMDB00725 |
| Pregnenolone sulfate | 0.01 | 0.01 | 417 | 1.07 | 2.84E−01 | 6.37E−01 | Metabolome | HMDB00774 |
| gamma-glutamylhistidine | −0.01 | 0.01 | 417 | −1.07 | 2.85E−01 | 6.37E−01 | Metabolome | HMDB29151 |
| C6:0, DC AC(1) | −0.01 | 0.01 | 417 | −1.08 | 2.82E−01 | 6.37E−01 | Metabolome | HMDB61677 |
| F13A1 | 0.01 | 0.01 | 440 | 1.07 | 2.84E−01 | 6.37E−01 | Proteome | P00488 |
| Asp-Asp | 0.01 | 0.01 | 417 | 1.06 | 2.90E−01 | 6.45E−01 | Metabolome | HMDB28749 |
| C1QB | 0.01 | 0.01 | 440 | 1.06 | 2.90E−01 | 6.45E−01 | Proteome | P02746 |
| C25:0, OH FA | −0.02 | 0.01 | 417 | −1.06 | 2.92E−01 | 6.46E−01 | Metabolome | |
| LYM | 0.01 | 0.01 | 456 | 1.05 | 2.93E−01 | 6.47E−01 | Clinical labs | |
| CFD | −0.01 | 0.01 | 440 | −1.05 | 2.94E−01 | 6.48E−01 | Proteome | P00746 |
| Ig heavy chain V-I region HG3 | −0.01 | 0.01 | 440 | −1.05 | 2.95E−01 | 6.49E−01 | Proteome | P01743 |
| C18:0 AC | 0.01 | 0.01 | 417 | 1.04 | 3.00E−01 | 6.52E−01 | Metabolome | HMDB00848 |
| C14:1 FA(1) | 0.02 | 0.02 | 417 | 1.04 | 2.99E−01 | 6.52E−01 | Metabolome | HMDB02000 |
| C10:0, OH FA(2) | 0.01 | 0.01 | 417 | 1.03 | 3.03E−01 | 6.52E−01 | Metabolome | HMDB02203 |
| C13:0, DC FA(1) | 0.01 | 0.01 | 417 | 1.04 | 3.00E−01 | 6.52E−01 | Metabolome | HMDB02327 |
| MG(15:0)(3) | 0.02 | 0.02 | 417 | 1.03 | 3.02E−01 | 6.52E−01 | Metabolome | HMDB11532 |
| ALKP | 0.01 | 0.01 | 461 | 1.03 | 3.03E−01 | 6.52E−01 | Clinical labs | |
| SAA4 | 0.01 | 0.01 | 440 | 1.04 | 3.00E−01 | 6.52E−01 | Proteome | P35542 |
| ABCF1 | −0.01 | 0.01 | 440 | −1.03 | 3.02E−01 | 6.52E−01 | Proteome | Q8NE71 |
| COLEC11 | 0.01 | 0.01 | 440 | 1.03 | 3.04E−01 | 6.52E−01 | Proteome | Q9BWP8 |
| 5-oxoproline | 0.01 | 0.01 | 417 | 1 | 3.18E−01 | 6.64E−01 | Metabolome | HMDB00267 |
| Sulfolithocholic acid | 0.01 | 0.01 | 417 | 1.01 | 3.13E−01 | 6.64E−01 | Metabolome | HMDB00907 |
| 9-HODE | 0.01 | 0.01 | 417 | 1 | 3.18E−01 | 6.64E−01 | Metabolome | HMDB04702 |
| LysoPC(20:2) | 0.03 | 0.03 | 417 | 1 | 3.17E−01 | 6.64E−01 | Metabolome | HMDB10392 |
| MG(14:1)(2) | 0.02 | 0.01 | 417 | 1.01 | 3.13E−01 | 6.64E−01 | Metabolome | HMDB11531 |
| LysoPC(P-18:0) | 0.01 | 0.01 | 417 | 1 | 3.17E−01 | 6.64E−01 | Metabolome | HMDB13122 |
| C16:0, OH FA(1) | 0.01 | 0.01 | 417 | 1 | 3.19E−01 | 6.64E−01 | Metabolome | HMDB31057 |
| MCH | 0.01 | 0.01 | 456 | 1 | 3.17E−01 | 6.64E−01 | Clinical labs | |
| BDNF | −0.01 | 0.01 | 449 | −1 | 3.16E−01 | 6.64E−01 | Immunome | |
| C14:0, OH FA(2) | 0.01 | 0.01 | 417 | 1 | 3.17E−01 | 6.64E−01 | Metabolome | |
| C18:0, OH FA(2) | 0.01 | 0.01 | 417 | 1 | 3.19E−01 | 6.64E−01 | Metabolome | |
| Attractin | 0.01 | 0.01 | 440 | 1 | 3.16E−01 | 6.64E−01 | Proteome | O75882_2 |
| SCLT1 | −0.01 | 0.01 | 440 | −1.01 | 3.13E−01 | 6.64E−01 | Proteome | Q96NL6 |
| FGFB | −0.03 | 0.03 | 449 | −0.99 | 3.25E−01 | 6.72E−01 | Immunome | |
| SERPINA4 | 0.01 | 0.01 | 440 | 0.99 | 3.24E−01 | 6.72E−01 | Proteome | P29622 |
| Androsterone glucoronide(1) | 0.02 | 0.02 | 417 | 0.98 | 3.27E−01 | 6.72E−01 | Metabolome | HMDB02829 |
| MG(20:5) | 0.01 | 0.01 | 417 | 0.98 | 3.26E−01 | 6.72E−01 | Metabolome | HMDB11550 |
| SERPINA10 | 0.01 | 0.01 | 440 | 0.98 | 3.27E−01 | 6.72E−01 | Proteome | Q9UK55 |
| Alpha-N-Phenylacetyl-L-glutamine | 0.01 | 0.01 | 417 | 0.98 | 3.29E−01 | 6.73E−01 | Metabolome | HMDB06344 |
| C9 | −0.01 | 0.01 | 440 | −0.98 | 3.29E−01 | 6.73E−01 | Proteome | P02748 |
| Betaine | 0.01 | 0.01 | 417 | 0.96 | 3.38E−01 | 6.77E−01 | Metabolome | HMDB00043 |
| C12:1, DC FA(3) | 0.01 | 0.01 | 417 | 0.96 | 3.36E−01 | 6.77E−01 | Metabolome | HMDB00933 |
| N-formylmethionine | 0.01 | 0.01 | 417 | 0.96 | 3.36E−01 | 6.77E−01 | Metabolome | HMDB01015 |
| 1-Methylguanosine | −0.01 | 0.01 | 417 | −0.96 | 3.40E−01 | 6.77E−01 | Metabolome | HMDB01563 |
| IL17A | 0.02 | 0.02 | 449 | 0.96 | 3.37E−01 | 6.77E−01 | Immunome | |
| IL18 | −0.02 | 0.02 | 449 | −0.96 | 3.39E−01 | 6.77E−01 | Immunome | |
| CD5L | −0.01 | 0.01 | 440 | −0.96 | 3.37E−01 | 6.77E−01 | Proteome | O43866 |
| ATRN(1) | 0.01 | 0.01 | 440 | 0.97 | 3.34E−01 | 6.77E−01 | Proteome | O75882 |
| SEPP1 | −0.01 | 0.01 | 440 | −0.97 | 3.34E−01 | 6.77E−01 | Proteome | P49908 |
| ACTA1 | 0.01 | 0.01 | 440 | 0.96 | 3.37E−01 | 6.77E−01 | Proteome | P68133 |
| LysoPE(20:2) | 0.00 | 0.01 | 417 | −0.95 | 3.41E−01 | 6.79E−01 | Metabolome | HMDB11483 |
| COL6A3 | −0.01 | 0.01 | 440 | −0.95 | 3.43E−01 | 6.80E−01 | Proteome | P12111 |
| Uridine | −0.01 | 0.01 | 417 | −0.95 | 3.45E−01 | 6.81E−01 | Metabolome | HMDB00296 |
| MTHFD1 | 0.01 | 0.01 | 440 | 0.94 | 3.45E−01 | 6.81E−01 | Proteome | P11586 |
| CFHR2 | −0.01 | 0.01 | 440 | −0.95 | 3.44E−01 | 6.81E−01 | Proteome | P36980 |
| Ig kappa chain V-III region B6 | −0.01 | 0.01 | 440 | −0.94 | 3.48E−01 | 6.84E−01 | Proteome | P01619 |
| Creatine | 0.01 | 0.01 | 417 | 0.94 | 3.49E−01 | 6.84E−01 | Metabolome | HMDB00064 |
| F10 | −0.01 | 0.01 | 440 | −0.94 | 3.49E−01 | 6.84E−01 | Proteome | P00742 |
| HABP2 | 0.01 | 0.01 | 440 | 0.94 | 3.50E−01 | 6.84E−01 | Proteome | Q14520 |
| Taurocholic acid(1) | −0.06 | 0.06 | 417 | −0.93 | 3.54E−01 | 6.86E−01 | Metabolome | HMDB00036 |

TABLE 13-continued

| | | | | | | | |
|---|---|---|---|---|---|---|---|
| Palmitoylglycine | 0.01 | 0.01 | 417 | 0.93 | 3.55E−01 | 6.86E−01 | Metabolome HMDB13034 |
| EOTAXIN | 0.02 | 0.02 | 449 | 0.93 | 3.52E−01 | 6.86E−01 | Immunome |
| FERMT3 | 0.01 | 0.01 | 440 | 0.93 | 3.54E−01 | 6.86E−01 | Proteome Q86UX7 |
| cont_000107 | −0.01 | 0.01 | 440 | −0.93 | 3.55E−01 | 6.86E−01 | Proteome |
| Uracil | −0.01 | 0.01 | 417 | −0.92 | 3.59E−01 | 6.89E−01 | Metabolome HMDB00300 |
| MG(20:4)(1) | 0.01 | 0.01 | 417 | 0.92 | 3.58E−01 | 6.89E−01 | Metabolome HMDB04666 |
| IGHM | −0.01 | 0.01 | 440 | −0.92 | 3.59E−01 | 6.89E−01 | Proteome P01871 |
| MG(24:0)(2) | −0.01 | 0.01 | 417 | −0.91 | 3.65E−01 | 6.97E−01 | Metabolome HMDB11558 |
| Hydroxybutyric acid(2) | 0.01 | 0.01 | 417 | 0.91 | 3.65E−01 | 6.97E−01 | Metabolome |
| Ig heavy chain V-III region WEA | 0.01 | 0.01 | 440 | 0.9 | 3.68E−01 | 7.01E−01 | Proteome P01763 |
| Dehydroisoandrosterone sulfate (DHEA-S)(1) | 0.01 | 0.01 | 417 | 0.89 | 3.72E−01 | 7.07E−01 | Metabolome HMDB01032 |
| N-Acetylserine | 0.01 | 0.01 | 417 | 0.88 | 3.78E−01 | 7.10E−01 | Metabolome HMDB02931 |
| LysoPE(22:5) | 0.01 | 0.01 | 417 | 0.87 | 3.83E−01 | 7.10E−01 | Metabolome HMDB11494 |
| C3:1 AC | 0.00 | 0.01 | 417 | −0.88 | 3.82E−01 | 7.10E−01 | Metabolome HMDB13124 |
| EGF | 0.01 | 0.01 | 449 | 0.88 | 3.82E−01 | 7.10E−01 | Immunome |
| C5:0, DC AC | −0.04 | 0.05 | 417 | −0.88 | 3.78E−01 | 7.10E−01 | Metabolome |
| 5alpha-Androstan-3alpha, 17alpha-diol monosulfate(2) | 0.02 | 0.02 | 417 | 0.87 | 3.83E−01 | 7.10E−01 | Metabolome |
| 5alpha-Androstan-3alpha, 17beta-diol 17-glucuronide(2) | 0.01 | 0.02 | 417 | 0.88 | 3.82E−01 | 7.10E−01 | Metabolome |
| Ig lambda chain V-I region VOR | −0.01 | 0.01 | 440 | −0.89 | 3.75E−01 | 7.10E−01 | Proteome P01699 |
| HBD | 0.01 | 0.01 | 440 | 0.89 | 3.76E−01 | 7.10E−01 | Proteome P02042 |
| GAPDH | −0.01 | 0.01 | 440 | −0.87 | 3.85E−01 | 7.10E−01 | Proteome P04406 |
| GP1BA | 0.01 | 0.01 | 440 | 0.88 | 3.77E−01 | 7.10E−01 | Proteome P07359 |
| MYH9 | 0.01 | 0.01 | 440 | 0.87 | 3.84E−01 | 7.10E−01 | Proteome P35579 |
| CFHR5 | 0.01 | 0.01 | 440 | 0.88 | 3.80E−01 | 7.10E−01 | Proteome Q9BXR6 |
| C24:4 FA | 0.01 | 0.01 | 417 | 0.86 | 3.88E−01 | 7.15E−01 | Metabolome HMDB06246 |
| IGHG3 | −0.01 | 0.01 | 440 | −0.86 | 3.89E−01 | 7.15E−01 | Proteome P01860 |
| 3-carboxy-4-methyl-5-propyl-2-furanpropanoate (CMPF) | 0.02 | 0.02 | 417 | 0.85 | 3.94E−01 | 7.24E−01 | Metabolome HMDB61112 |
| MONO | −0.01 | 0.01 | 456 | −0.84 | 3.99E−01 | 7.28E−01 | Clinical labs |
| C14:2, OH FA | −0.01 | 0.01 | 417 | −0.85 | 3.99E−01 | 7.28E−01 | Metabolome |
| IGLL5 | 0.01 | 0.01 | 440 | 0.84 | 4.02E−01 | 7.30E−01 | Proteome B9A064 |
| C16:0 AC | −0.01 | 0.01 | 417 | −0.83 | 4.06E−01 | 7.30E−01 | Metabolome HMDB00222 |
| C12:0, OH FA(1) | 0.01 | 0.01 | 417 | 0.83 | 4.06E−01 | 7.30E−01 | Metabolome HMDB00387 |
| Pseudouridine | −0.01 | 0.01 | 417 | −0.83 | 4.05E−01 | 7.30E−01 | Metabolome HMDB00767 |
| LysoPC(20:5) | −0.01 | 0.01 | 417 | −0.83 | 4.04E−01 | 7.30E−01 | Metabolome HMDB10397 |
| Ig heavy chain V-III region HIL | −0.01 | 0.01 | 440 | −0.83 | 4.08E−01 | 7.30E−01 | Proteome P01771 |
| CFP | −0.01 | 0.01 | 440 | −0.83 | 4.07E−01 | 7.30E−01 | Proteome P27918 |
| CAPZB | −0.01 | 0.01 | 440 | −0.83 | 4.07E−01 | 7.30E−01 | Proteome P47756 |
| MAN2B2 | −0.01 | 0.01 | 440 | −0.84 | 4.02E−01 | 7.30E−01 | Proteome Q9Y2E5 |
| MG(24:0)(1) | −0.01 | 0.01 | 417 | −0.82 | 4.10E−01 | 7.30E−01 | Metabolome HMDB11558 |
| C10:3 AC(2) | 0.01 | 0.01 | 417 | 0.83 | 4.09E−01 | 7.30E−01 | Metabolome |
| MASP1 | 0.01 | 0.01 | 440 | 0.82 | 4.10E−01 | 7.30E−01 | Proteome P48740 |
| LRG1 | −0.01 | 0.01 | 440 | −0.82 | 4.11E−01 | 7.31E−01 | Proteome P02750 |
| C7 | 0.01 | 0.01 | 440 | 0.82 | 4.13E−01 | 7.33E−01 | Proteome P10643 |
| C18:2, OH FA | 0.01 | 0.01 | 417 | 0.81 | 4.16E−01 | 7.36E−01 | Metabolome |
| NGF | 0.02 | 0.02 | 449 | 0.81 | 4.18E−01 | 7.38E−01 | Immunome |
| IL17F | −0.03 | 0.04 | 449 | −0.79 | 4.33E−01 | 7.59E−01 | Immunome |
| VEGF | −0.02 | 0.02 | 449 | −0.79 | 4.32E−01 | 7.59E−01 | Immunome |
| Ig heavy chain V-III region BRO | −0.01 | 0.01 | 440 | −0.79 | 4.32E−01 | 7.59E−01 | Proteome P01766 |
| CFHR1 | −0.01 | 0.01 | 440 | −0.78 | 4.36E−01 | 7.63E−01 | Proteome Q03591 |
| C10:0, OH FA(1) | 0.02 | 0.02 | 417 | 0.78 | 4.39E−01 | 7.64E−01 | Metabolome HMDB02203 |
| IL10 | 0.03 | 0.03 | 449 | 0.78 | 4.39E−01 | 7.64E−01 | Immunome |
| F9 | 0.01 | 0.01 | 440 | 0.77 | 4.40E−01 | 7.64E−01 | Proteome P00740 |
| F5 | 0.01 | 0.01 | 440 | 0.77 | 4.39E−01 | 7.64E−01 | Proteome P12259 |
| Ig kappa chain V-I region Roy | −0.01 | 0.01 | 440 | −0.77 | 4.41E−01 | 7.65E−01 | Proteome P01608 |
| Hippuric acid | 0.01 | 0.01 | 417 | 0.76 | 4.46E−01 | 7.65E−01 | Metabolome HMDB00714 |
| IL27 | −0.02 | 0.03 | 449 | −0.77 | 4.44E−01 | 7.65E−01 | Immunome |
| MCP3 | 0.02 | 0.02 | 449 | 0.76 | 4.47E−01 | 7.65E−01 | Immunome |
| TGFB | −0.02 | 0.02 | 449 | −0.76 | 4.45E−01 | 7.65E−01 | Immunome |
| AGT | 0.01 | 0.01 | 440 | 0.76 | 4.47E−01 | 7.65E−01 | Proteome P01019 |
| C8A | −0.01 | 0.01 | 440 | −0.76 | 4.48E−01 | 7.65E−01 | Proteome P07357 |
| Zinc finger protein 10 | −0.01 | 0.01 | 440 | −0.76 | 4.46E−01 | 7.65E−01 | Proteome P21506 |
| IL13 | 0.03 | 0.04 | 449 | 0.76 | 4.50E−01 | 7.67E−01 | Immunome |
| Chenodeoxycholic acid 3-sulfate | 0.01 | 0.01 | 417 | 0.75 | 4.53E−01 | 7.70E−01 | Metabolome HMDB02639 |
| Piperine(1) | 0.01 | 0.01 | 417 | 0.75 | 4.55E−01 | 7.70E−01 | Metabolome HMD329377 |
| CA | 0.01 | 0.01 | 461 | 0.75 | 4.55E−01 | 7.70E−01 | Clinical labs |
| SELL | −0.01 | 0.01 | 440 | −0.75 | 4.54E−01 | 7.70E−01 | Proteome P14151 |
| C16:1 FA | 0.01 | 0.01 | 417 | 0.74 | 4.60E−01 | 7.77E−01 | Metabolome HMDB03229 |
| C11:1 FA | 0.01 | 0.01 | 417 | 0.73 | 4.66E−01 | 7.81E−01 | Metabolome HMDB33724 |
| PDGFBB | 0.01 | 0.01 | 449 | 0.73 | 4.65E−01 | 7.81E−01 | Immunome |
| Ig lambda chain V-V region DEL | −0.01 | 0.01 | 440 | −0.73 | 4.64E−01 | 7.81E−01 | Proteome P01719 |
| MG(16:1) | 0.01 | 0.01 | 417 | 0.72 | 4.70E−01 | 7.82E−01 | Metabolome HMDB11534 |
| C18:2, DC FA | 0.01 | 0.01 | 417 | 0.72 | 4.71E−01 | 7.82E−01 | Metabolome |
| NCAM1 | 0.00 | 0.01 | 440 | 0.73 | 4.68E−01 | 7.82E−01 | Proteome P13591 |
| CPN2 | 0.00 | 0.01 | 440 | 0.72 | 4.71E−01 | 7.82E−01 | Proteome P22792 |
| FCGBP | 0.01 | 0.01 | 440 | 0.72 | 4.71E−01 | 7.82E−01 | Proteome Q9Y6R7 |
| Unknown | 0.00 | 0.01 | 440 | 0.72 | 4.71E−01 | 7.82E−01 | Proteome |

TABLE 13-continued

| | | | | | | | | |
|---|---|---|---|---|---|---|---|---|
| ORM2 | −0.01 | 0.01 | 440 | −0.72 | 4.73E−01 | 7.82E−01 | Proteome | P19652 |
| NHDL | 0.01 | 0.01 | 459 | 0.71 | 4.78E−01 | 7.88E−01 | Clinical labs | |
| F12 | 0.01 | 0.01 | 440 | 0.71 | 4.77E−01 | 7.88E−01 | Proteome | P00748 |
| Dehydroisoandrosterone sulfate (DHEA-S)(2) | −0.01 | 0.02 | 417 | −0.7 | 4.84E−01 | 7.88E−01 | Metabolome | HMDB01032 |
| AST | −0.01 | 0.01 | 459 | −0.7 | 4.84E−01 | 7.88E−01 | Clinical labs | |
| N-acetyl-1-methylhistidine | 0.01 | 0.02 | 417 | 0.7 | 4.82E−01 | 7.88E−01 | Metabolome | |
| KNG1(1) | 0.01 | 0.01 | 440 | 0.7 | 4.85E−01 | 7.88E−01 | Proteome | P01042 |
| IGHV3-23 | 0.00 | 0.01 | 440 | −0.71 | 4.80E−01 | 7.88E−01 | Proteome | P01764 |
| C8B | 0.00 | 0.01 | 440 | 0.7 | 4.83E−01 | 7.88E−01 | Proteome | P07358 |
| AFM | 0.01 | 0.01 | 440 | 0.7 | 4.81E−01 | 7.88E−01 | Proteome | P43652 |
| TRAIL | −0.02 | 0.03 | 449 | −0.69 | 4.87E−01 | 7.91E−01 | Immunome | |
| APOL1 | 0.00 | 0.01 | 440 | −0.69 | 4.90E−01 | 7.93E−01 | Proteome | O14791 |
| CPB2 | −0.01 | 0.01 | 440 | −0.69 | 4.91E−01 | 7.93E−01 | Proteome | Q96IY4 |
| gamma-glutamylphenylalanine | 0.01 | 0.01 | 417 | 0.68 | 4.98E−01 | 7.97E−01 | Metabolome | HMDB00594 |
| L-Methionine | 0.01 | 0.01 | 417 | 0.68 | 5.00E−01 | 7.97E−01 | Metabolome | HMDB00696 |
| LysoPC(20:3) | 0.01 | 0.01 | 417 | 0.68 | 4.98E−01 | 7.97E−01 | Metabolome | HMD610393 |
| LEPTIN | −0.01 | 0.02 | 449 | −0.68 | 4.98E−01 | 7.97E−01 | Immunome | |
| APOM | 0.00 | 0.01 | 440 | −0.68 | 4.95E−01 | 7.97E−01 | Proteome | O95445 |
| IGHD | 0.02 | 0.02 | 440 | 0.68 | 4.98E−01 | 7.97E−01 | Proteome | P01880 |
| SERPING1 | 0.00 | 0.01 | 440 | −0.68 | 4.99E−01 | 7.97E−01 | Proteome | P05155 |
| pro-hydroxy-pro(2) | 0.01 | 0.01 | 417 | 0.66 | 5.07E−01 | 7.97E−01 | Metabolome | HMD606695 |
| GROA | −0.02 | 0.03 | 449 | −0.67 | 5.06E−01 | 7.97E−01 | Immunome | |
| C14:1, OH FA(2) | 0.01 | 0.01 | 417 | 0.67 | 5.03E−01 | 7.97E−01 | Metabolome | |
| 5alpha-Androstan-3alpha, 17alpha-diol monosulfate(3) | 0.02 | 0.03 | 417 | 0.67 | 5.01E−01 | 7.97E−01 | Metabolome | |
| RBP4 | 0.00 | 0.01 | 440 | −0.66 | 5.08E−01 | 7.97E−01 | Proteome | P02753 |
| MSN | 0.01 | 0.01 | 440 | 0.67 | 5.04E−01 | 7.97E−01 | Proteome | P26038 |
| Microtubule-associated protein 4 | −0.01 | 0.01 | 440 | −0.66 | 5.08E−01 | 7.97E−01 | Proteome | P27816_2 |
| IGFALS | 0.00 | 0.01 | 440 | 0.66 | 5.07E−01 | 7.97E−01 | Proteome | P35858 |
| cont_000108 | 0.00 | 0.01 | 440 | −0.66 | 5.07E−01 | 7.97E−01 | Proteome | |
| PIGR | 0.01 | 0.01 | 440 | 0.66 | 5.09E−01 | 7.97E−01 | Proteome | P01833 |
| Imidazolelactic acid | 0.01 | 0.01 | 417 | 0.65 | 5.14E−01 | 7.99E−01 | Metabolome | HMDB02320 |
| 2-Aminophenol sulfate | 0.01 | 0.01 | 417 | 0.65 | 5.16E−01 | 7.99E−01 | Metabolome | HMDB61116 |
| MIP1A | −0.03 | 0.04 | 449 | −0.66 | 5.12E−01 | 7.99E−01 | Immunome | |
| C16:3 FA | 0.01 | 0.01 | 417 | 0.65 | 5.16E−01 | 7.99E−01 | Metabolome | |
| HRG | 0.00 | 0.01 | 440 | −0.65 | 5.14E−01 | 7.99E−01 | Proteome | P04196 |
| SAA1 | −0.01 | 0.01 | 440 | −0.66 | 5.12E−01 | 7.99E−01 | Proteome | P0DJI8 |
| 5-methyluridine (ribothymidine) | −0.01 | 0.01 | 417 | −0.64 | 5.22E−01 | 7.99E−01 | Metabolome | HMD600884 |
| RDW | 0.01 | 0.01 | 456 | 0.64 | 5.23E−01 | 7.99E−01 | Clinical labs | |
| Ig heavy chain V-III region NIE | 0.00 | 0.01 | 440 | −0.64 | 5.23E−01 | 7.99E−01 | Proteome | P01770 |
| APOA1 | 0.00 | 0.01 | 440 | 0.64 | 5.22E−01 | 7.99E−01 | Proteome | P02647 |
| PROC | 0.00 | 0.01 | 440 | −0.64 | 5.21E−01 | 7.99E−01 | Proteome | P04070 |
| Ig lambda chain V-VI region EB4 | −0.01 | 0.01 | 440 | −0.64 | 5.20E−01 | 7.99E−01 | Proteome | P06319 |
| DSP | 0.00 | 0.01 | 440 | −0.65 | 5.19E−01 | 7.99E−01 | Proteome | P15924 |
| SDF1A | −0.02 | 0.03 | 449 | −0.63 | 5.27E−01 | 8.02E−01 | Immunome | |
| F11 | 0.01 | 0.01 | 440 | 0.63 | 5.26E−01 | 8.02E−01 | Proteome | P03951 |
| Ig kappa chain V-II region RPMI 6410 | −0.01 | 0.01 | 440 | −0.63 | 5.27E−01 | 8.02E−01 | Proteome | P06310 |
| C20:0, 2OH FA | 0.01 | 0.01 | 417 | 0.63 | 5.28E−01 | 8.02E−01 | Metabolome | HMDB31923 |
| HPR | 0.00 | 0.01 | 440 | 0.63 | 5.30E−01 | 8.03E−01 | Proteome | P00739 |
| INSU | 0.03 | 0.04 | 3 | 0.7 | 5.33E−01 | 8.05E−01 | Clinical labs | |
| C1R | 0.01 | 0.01 | 440 | 0.62 | 5.32E−01 | 8.05E−01 | Proteome | P00736 |
| 11-beta-Hydroxyandrosterone-3-glucuronide | 0.01 | 0.01 | 417 | 0.62 | 5.35E−01 | 8.05E−01 | Metabolome | HMDB10351 |
| LUM | 0.01 | 0.01 | 440 | 0.62 | 5.35E−01 | 8.05E−01 | Proteome | P51884 |
| C12:1 FA(2) | 0.01 | 0.02 | 417 | 0.62 | 5.37E−01 | 8.07E−01 | Metabolome | HMDB00529 |
| Hypoxanthine | 0.01 | 0.01 | 417 | 0.61 | 5.40E−01 | 8.09E−01 | Metabolome | HMDB00157 |
| MCAM | 0.00 | 0.01 | 440 | −0.61 | 5.40E−01 | 8.09E−01 | Proteome | P43121 |
| SHBG | 0.00 | 0.01 | 440 | 0.61 | 5.43E−01 | 8.11E−01 | Proteome | P04278 |
| Rho GTPase-activating protein 19 | 0.00 | 0.01 | 440 | −0.61 | 5.44E−01 | 8.11E−01 | Proteome | Q14CB8_6 |
| LysoPC(20:4) | 0.01 | 0.01 | 417 | 0.6 | 5.48E−01 | 8.16E−01 | Metabolome | HMDB10395 |
| C1QC | 0.00 | 0.01 | 440 | −0.6 | 5.50E−01 | 8.17E−01 | Proteome | P02747 |
| C20:4 FA | 0.00 | 0.01 | 417 | 0.59 | 5.53E−01 | 8.18E−01 | Metabolome | HMDB01043 |
| HPX | 0.00 | 0.01 | 440 | 0.59 | 5.53E−01 | 8.18E−01 | Proteome | P02790 |
| Acetylcarnosine | 0.01 | 0.01 | 417 | 0.59 | 5.56E−01 | 8.22E−01 | Metabolome | HMDB12881 |
| APOF | 0.00 | 0.01 | 440 | 0.59 | 5.58E−01 | 8.23E−01 | Proteome | Q13790 |
| 3-Phenylpropionate (hydrocinnamate) | 0.01 | 0.02 | 417 | 0.57 | 5.66E−01 | 8.32E−01 | Metabolome | HMDB00764 |
| N1-Methyl-2-pyridone-5-carboxamide(1) | 0.01 | 0.02 | 417 | 0.57 | 5.70E−01 | 8.32E−01 | Metabolome | HMDB04193 |
| gamma-glutamylthreonine(2) | 0.01 | 0.01 | 417 | 0.57 | 5.67E−01 | 8.32E−01 | Metabolome | HMDB29159 |
| C16 Sphingosine 1-phosphate | 0.01 | 0.01 | 417 | 0.57 | 5.70E−01 | 8.32E−01 | Metabolome | HMDB60061 |
| VCAM1 | −0.01 | 0.01 | 449 | −0.57 | 5.70E−01 | 8.32E−01 | Immunome | |
| ASS1 | 0.00 | 0.01 | 440 | −0.58 | 5.65E−01 | 8.32E−01 | Proteome | P00966 |
| IGF2 | 0.00 | 0.01 | 440 | −0.57 | 5.68E−01 | 8.32E−01 | Proteome | P01344 |
| Androsterone sulfate(1) | 0.01 | 0.02 | 417 | 0.57 | 5.72E−01 | 8.32E−01 | Metabolome | HMDB02759 |
| MST1 | 0.00 | 0.01 | 440 | 0.56 | 5.74E−01 | 8.34E−01 | Proteome | P26927 |
| LysoPC(P-16:0) | 0.01 | 0.01 | 417 | 0.56 | 5.75E−01 | 8.34E−01 | Metabolome | HMDB10407 |
| ACAA2 | 0.00 | 0.01 | 440 | 0.56 | 5.77E−01 | 8.35E−01 | Proteome | P42765 |
| PROZ | 0.01 | 0.01 | 440 | 0.55 | 5.80E−01 | 8.38E−01 | Proteome | P22891 |
| Betonicine | 0.01 | 0.02 | 417 | 0.55 | 5.83E−01 | 8.42E−01 | Metabolome | HMDB29412 |
| Glycocholic acid | −0.02 | 0.03 | 417 | −0.54 | 5.86E−01 | 8.42E−01 | Metabolome | HMDB00138 |

TABLE 13-continued

| | | | | | | | |
|---|---|---|---|---|---|---|---|
| C18:1 FA | 0.00 | 0.01 | 417 | 0.54 | 5.87E−01 | 8.42E−01 | Metabolome | HMDB00207 |
| Ig lambda chain V-III region LOI | −0.01 | 0.01 | 440 | −0.55 | 5.86E−01 | 8.42E−01 | Proteome | P80748 |
| IL2 | 0.03 | 0.06 | 449 | 0.54 | 5.90E−01 | 8.45E−01 | Immunome | |
| IF | 0.00 | 0.01 | 440 | 0.54 | 5.90E−01 | 8.45E−01 | Proteome | P02787 |
| C18:1, 3OH FA | 0.00 | 0.01 | 417 | −0.53 | 5.98E−01 | 8.51E−01 | Metabolome | |
| C20:2, OH FA | 0.01 | 0.01 | 417 | 0.53 | 5.98E−01 | 8.51E−01 | Metabolome | |
| ALB | −0.01 | 0.01 | 461 | −0.53 | 5.98E−01 | 8.51E−01 | Clinical labs | |
| Orotidine | 0.01 | 0.01 | 417 | 0.52 | 6.05E−01 | 8.57E−01 | Metabolome | HMDB00788 |
| LysoPC(22:6) | −0.01 | 0.01 | 417 | −0.52 | 6.05E−01 | 8.57E−01 | Metabolome | HMDB10404 |
| IGF2R | 0.00 | 0.01 | 440 | 0.52 | 6.05E−01 | 8.57E−01 | Proteome | P11717 |
| PON1 | 0.00 | 0.01 | 440 | 0.52 | 6.06E−01 | 8.57E−01 | Proteome | P27169 |
| Uric acid | 0.01 | 0.01 | 417 | 0.51 | 6.08E−01 | 8.58E−01 | Metabolome | HMDB00289 |
| ALT | 0.01 | 0.01 | 459 | 0.51 | 6.11E−01 | 8.60E−01 | Clinical labs | |
| APOE | 0.00 | 0.01 | 440 | −0.51 | 6.10E−01 | 8.60E−01 | Proteome | P02649 |
| MG(18:1) | 0.01 | 0.01 | 417 | 0.5 | 6.19E−01 | 8.65E−01 | Metabolome | HMDB11536 |
| CR | 0.01 | 0.01 | 461 | 0.5 | 6.18E−01 | 8.65E−01 | Clinical labs | |
| LDHB | 0.00 | 0.01 | 440 | −0.5 | 6.19E−01 | 8.65E−01 | Proteome | P07195 |
| SCP2 | 0.00 | 0.01 | 440 | −0.5 | 6.17E−01 | 8.65E−01 | Proteome | P22307 |
| MG(20:0) | 0.00 | 0.01 | 417 | 0.49 | 6.27E−01 | 8.68E−01 | Metabolome | HMDB11542 |
| IL7 | 0.01 | 0.01 | 449 | 0.49 | 6.25E−01 | 8.68E−01 | Immunome | |
| A2M | 0.00 | 0.01 | 440 | −0.49 | 6.26E−01 | 8.68E−01 | Proteome | P01023 |
| PF4 | 0.00 | 0.01 | 440 | 0.49 | 6.27E−01 | 8.68E−01 | Proteome | P02776 |
| VTN | 0.00 | 0.01 | 440 | 0.49 | 6.27E−01 | 8.68E−01 | Proteome | P04004 |
| CRISP3 | 0.00 | 0.01 | 440 | −0.49 | 6.26E−01 | 8.68E−01 | Proteome | P54108 |
| DBH | 0.00 | 0.01 | 440 | 0.48 | 6.30E−01 | 8.70E−01 | Proteome | P09172 |
| Homoarginine | −0.01 | 0.01 | 417 | −0.48 | 6.33E−01 | 8.70E−01 | Metabolome | HMDB00670 |
| C20:5 FA | 0.01 | 0.02 | 417 | 0.48 | 6.31E−01 | 8.70E−01 | Metabolome | HMDB01999 |
| C18:4 FA | 0.01 | 0.01 | 417 | 0.48 | 6.32E−01 | 8.70E−01 | Metabolome | HMDB06547 |
| ATP11B | 0.00 | 0.01 | 440 | 0.47 | 6.35E−01 | 8.72E−01 | Proteome | Q9Y2G3 |
| MG(15:0)(1) | 0.01 | 0.02 | 417 | 0.47 | 6.37E−01 | 8.73E−01 | Metabolome | HMDB11532 |
| L-Cysteinylglycine disulfide | 0.00 | 0.01 | 417 | 0.47 | 6.40E−01 | 8.75E−01 | Metabolome | HMDB00709 |
| GMCSF | 0.02 | 0.03 | 449 | 0.46 | 6.43E−01 | 8.78E−01 | Immunome | |
| C8:2, OH FA(1) | 0.00 | 0.01 | 417 | −0.46 | 6.45E−01 | 8.78E−01 | Metabolome | |
| TFRC | 0.00 | 0.01 | 440 | −0.46 | 6.46E−01 | 8.78E−01 | Proteome | P02786 |
| PI16 | 0.00 | 0.01 | 440 | −0.46 | 6.46E−01 | 8.78E−01 | Proteome | Q6UXB8 |
| pro-hydroxy-pro(1) | 0.00 | 0.01 | 417 | 0.46 | 6.49E−01 | 8.81E−01 | Metabolome | HMDB06695 |
| Ig lambda chain V region 4A | 0.00 | 0.01 | 440 | 0.45 | 6.51E−01 | 8.82E−01 | Proteome | P04211 |
| Oxalate (ethanedioate) | 0.00 | 0.01 | 417 | −0.45 | 6.53E−01 | 8.83E−01 | Metabolome | HMDB02329 |
| LDL | 0.01 | 0.01 | 458 | 0.45 | 6.56E−01 | 8.86E−01 | Clinical labs | |
| FRMPD1 | 0.00 | 0.01 | 440 | 0.44 | 6.61E−01 | 8.91E−01 | Proteome | Q5SYB0 |
| 25-hydroxyvitamin D3 | 0.01 | 0.02 | 417 | 0.44 | 6.63E−01 | 8.93E−01 | Metabolome | |
| C14:2 FA | −0.01 | 0.02 | 417 | −0.43 | 6.65E−01 | 8.94E−01 | Metabolome | HMDB00560 |
| SERPINA5 | 0.00 | 0.01 | 440 | 0.42 | 6.71E−01 | 9.01E−01 | Proteome | P05154 |
| APOC3 | 0.00 | 0.01 | 440 | 0.42 | 6.73E−01 | 9.01E−01 | Proteome | P02656 |
| IFNG | 0.01 | 0.03 | 449 | 0.42 | 6.77E−01 | 9.04E−01 | Immunome | |
| Dihydroferulic acid | 0.01 | 0.02 | 417 | 0.42 | 6.78E−01 | 9.04E−01 | Metabolome | |
| FGA | 0.00 | 0.01 | 440 | −0.42 | 6.76E−01 | 9.04E−01 | Proteome | P02671 |
| Dihydroxyvitamin D3(1) | 0.00 | 0.01 | 417 | −0.41 | 6.85E−01 | 9.04E−01 | Metabolome | HMDB00430 |
| C10:0, DC FA (Sebacic acid)(1) | 0.01 | 0.02 | 417 | 0.41 | 6.82E−01 | 9.04E−01 | Metabolome | HMDB00792 |
| Ala-Leu or Leu-Ala | 0.00 | 0.01 | 417 | −0.41 | 6.82E−01 | 9.04E−01 | Metabolome | HMDB28691 |
| SERPINA1 | 0.00 | 0.01 | 440 | −0.41 | 6.79E−01 | 9.04E−01 | Proteome | P01009 |
| Ig heavy chain V-III region BUT | 0.00 | 0.01 | 440 | −0.41 | 6.85E−01 | 9.04E−01 | Proteome | P01767 |
| ATP5A1 | 0.00 | 0.01 | 440 | −0.41 | 6.84E−01 | 9.04E−01 | Proteome | P25705 |
| B2M | 0.00 | 0.01 | 440 | 0.41 | 6.85E−01 | 9.04E−01 | Proteome | P61769 |
| Taurine | 0.00 | 0.01 | 417 | −0.37 | 7.11E−01 | 9.05E−01 | Metabolome | HMDB00251 |
| C3:0 AC | −0.01 | 0.02 | 417 | −0.38 | 7.06E−01 | 9.05E−01 | Metabolome | HMDB00824 |
| C12:1, DC FA(4) | 0.00 | 0.01 | 417 | −0.35 | 7.24E−01 | 9.05E−01 | Metabolome | HMDB00933 |
| C14:1 FA(2) | 0.00 | 0.01 | 417 | 0.38 | 7.01E−01 | 9.05E−01 | Metabolome | HMDB02000 |
| MG(15:0)(2) | 0.00 | 0.01 | 417 | 0.4 | 6.92E−01 | 9.05E−01 | Metabolome | HMDB11532 |
| C9:0 AC | 0.01 | 0.01 | 417 | 0.39 | 6.99E−01 | 9.05E−01 | Metabolome | HMDB13288 |
| CHOL | 0.00 | 0.01 | 459 | 0.4 | 6.88E−01 | 9.05E−01 | Clinical labs | |
| FASL | −0.02 | 0.05 | 449 | −0.37 | 7.14E−01 | 9.05E−01 | Immunome | |
| IFNA | 0.01 | 0.02 | 449 | 0.36 | 7.18E−01 | 9.05E−01 | Immunome | |
| MIP1B | 0.01 | 0.02 | 449 | −0.37 | 7.13E−01 | 9.05E−01 | Immunome | |
| Arabonate \| Xylonate(2) | 0.00 | 0.01 | 417 | 0.38 | 7.07E−01 | 9.05E−01 | Metabolome | |
| C12:2, OH FA | 0.00 | 0.01 | 417 | −0.38 | 7.06E−01 | 9.05E−01 | Metabolome | |
| C16:2 FA | 0.00 | 0.01 | 417 | 0.39 | 6.96E−01 | 9.05E−01 | Metabolome | |
| C17:0 FA(2) | 0.00 | 0.01 | 417 | 0.37 | 7.14E−01 | 9.05E−01 | Metabolome | |
| CP | 0.00 | 0.01 | 440 | 0.38 | 7.06E−01 | 9.05E−01 | Proteome | P00450 |
| F2 | 0.00 | 0.01 | 440 | −0.36 | 7.15E−01 | 9.05E−01 | Proteome | P00734 |
| Ig kappa chain V-I region HK101 | 0.00 | 0.01 | 440 | 0.39 | 6.99E−01 | 9.05E−01 | Proteome | P01601 |
| Ig heavy chain V-I region EU | 0.00 | 0.01 | 440 | 0.36 | 7.22E−01 | 9.05E−01 | Proteome | P01742 |
| IGH4 | −0.01 | 0.02 | 440 | −0.4 | 6.92E−01 | 9.05E−01 | Proteome | P01861 |
| APOA2 | 0.00 | 0.01 | 440 | 0.36 | 7.22E−01 | 9.05E−01 | Proteome | P02652 |
| PPBP | 0.00 | 0.01 | 440 | 0.37 | 7.11E−01 | 9.05E−01 | Proteome | P02775 |
| APOB | 0.00 | 0.01 | 440 | 0.38 | 7.03E−01 | 9.05E−01 | Proteome | P04114 |
| SERPINA7 | 0.00 | 0.01 | 440 | −0.35 | 7.24E−01 | 9.05E−01 | Proteome | P05543 |
| APOA4 | 0.00 | 0.01 | 440 | 0.38 | 7.05E−01 | 9.05E−01 | Proteome | P06727 |
| ENO1 | 0.00 | 0.01 | 440 | 0.39 | 6.97E−01 | 9.05E−01 | Proteome | P06733 |
| C1S | 0.00 | 0.01 | 440 | −0.36 | 7.22E−01 | 9.05E−01 | Proteome | P09871 |

TABLE 13-continued

| | | | | | | | |
|---|---|---|---|---|---|---|---|
| C4A | 0.00 | 0.01 | 440 | −0.36 | 7.18E−01 | 9.05E−01 | Proteome | P0C0L4 |
| Clusterin | 0.00 | 0.01 | 440 | −0.36 | 7.19E−01 | 9.05E−01 | Proteome | P10909_2 |
| C6 | 0.00 | 0.01 | 440 | −0.39 | 6.94E−01 | 9.05E−01 | Proteome | P13671 |
| PRDX2 | 0.00 | 0.01 | 440 | −0.37 | 7.14E−01 | 9.05E−01 | Proteome | P32119 |
| CAMP | 0.00 | 0.01 | 440 | −0.39 | 6.94E−01 | 9.05E−01 | Proteome | P49913 |
| HNRNPM | 0.00 | 0.01 | 440 | 0.37 | 7.14E−01 | 9.05E−01 | Proteome | P52272 |
| GPLD1 | 0.00 | 0.01 | 440 | 0.39 | 6.99E−01 | 9.05E−01 | Proteome | P80108 |
| OLFM1 | 0.00 | 0.01 | 440 | 0.36 | 7.18E−01 | 9.05E−01 | Proteome | Q99784 |
| NA | 0.00 | 0.01 | 461 | −0.38 | 7.03E−01 | 9.05E−01 | Clinical labs | |
| Chenodeoxycholic acid glycine conjugate(2) | −0.01 | 0.03 | 417 | −0.35 | 7.27E−01 | 9.08E−01 | Metabolome | HMDB00637 |
| N1-Methyl-2-pyridone-5-carboxamide(2) | 0.00 | 0.01 | 417 | −0.35 | 7.28E−01 | 9.08E−01 | Metabolome | HMDB04193 |
| Acetylcholine | 0.00 | 0.01 | 417 | 0.34 | 7.31E−01 | 9.08E−01 | Metabolome | HMDB00895 |
| C18:2 FA | 0.00 | 0.01 | 417 | 0.34 | 7.31E−01 | 9.08E−01 | Metabolome | HMDB00673 |
| GCSF | 0.01 | 0.03 | 449 | 0.34 | 7.33E−01 | 9.10E−01 | Immunome | |
| IL1A | −0.01 | 0.02 | 449 | −0.34 | 7.35E−01 | 9.10E−01 | Immunome | |
| SLFN11 | 0.00 | 0.01 | 440 | 0.34 | 7.35E−01 | 9.10E−01 | Proteome | Q7Z7L1 |
| C24:5 FA | 0.00 | 0.01 | 417 | 0.33 | 7.41E−01 | 9.11E−01 | Metabolome | HMDB06322 |
| C6:0, DC AC(2) | 0.00 | 0.01 | 417 | −0.33 | 7.40E−01 | 9.11E−01 | Metabolome | HMDB61677 |
| C8G | 0.00 | 0.01 | 440 | 0.33 | 7.40E−01 | 9.11E−01 | Proteome | P07360 |
| INHBC | 0.00 | 0.01 | 440 | −0.33 | 7.41E−01 | 9.11E−01 | Proteome | P55103 |
| Endophilin-A3 | 0.00 | 0.01 | 440 | −0.33 | 7.42E−01 | 9.12E−01 | Proteome | Q99963_3 |
| BASOAB | 0.00 | 0.01 | 455 | 0.32 | 7.47E−01 | 9.16E−01 | Clinical labs | |
| CL | 0.00 | 0.01 | 461 | 0.32 | 7.49E−01 | 9.16E−01 | Clinical labs | |
| CEP290 | 0.00 | 0.01 | 440 | −0.32 | 7.49E−01 | 9.16E−01 | Proteome | O15078 |
| CFH | 0.00 | 0.01 | 440 | −0.32 | 7.52E−01 | 9.19E−01 | Proteome | P08603 |
| C18:1 AC | 0.00 | 0.01 | 417 | 0.31 | 7.59E−01 | 9.24E−01 | Metabolome | HMDB05065 |
| C8:1 AC | 0.00 | 0.01 | 417 | 0.3 | 7.62E−01 | 9.24E−01 | Metabolome | HMDB13324 |
| RANTES | 0.00 | 0.01 | 449 | −0.31 | 7.58E−01 | 9.24E−01 | Immunome | |
| C3 | 0.00 | 0.01 | 440 | 0.3 | 7.61E−01 | 9.24E−01 | Proteome | P01024 |
| TPM4 | 0.00 | 0.01 | 440 | 0.3 | 7.62E−01 | 9.24E−01 | Proteome | P67936 |
| HP | 0.00 | 0.01 | 440 | 0.3 | 7.66E−01 | 9.26E−01 | Proteome | P00738 |
| LYZ | 0.00 | 0.01 | 440 | −0.3 | 7.67E−01 | 9.26E−01 | Proteome | P61626 |
| LYVE1 | 0.00 | 0.01 | 440 | 0.3 | 7.66E−01 | 9.26E−01 | Proteome | Q9Y5Y7 |
| C13:0, DC FA(3) | 0.00 | 0.01 | 417 | −0.29 | 7.68E−01 | 9.27E−01 | Metabolome | HMDB02327 |
| LysoPE(20:1) | 0.00 | 0.01 | 417 | −0.28 | 7.77E−01 | 9.31E−01 | Metabolome | HMDB11482 |
| gamma-glutamylthreonine(1) | 0.00 | 0.01 | 417 | −0.28 | 7.79E−01 | 9.31E−01 | Metabolome | HMDB29159 |
| IL15 | −0.01 | 0.04 | 449 | −0.28 | 7.78E−01 | 9.31E−01 | Immunome | |
| VEGFD | 0.00 | 0.02 | 449 | 0.29 | 7.73E−01 | 9.31E−01 | Immunome | |
| PROS1 | 0.00 | 0.01 | 440 | −0.28 | 7.79E−01 | 9.31E−01 | Proteome | P07225 |
| PSTK | 0.00 | 0.01 | 440 | 0.28 | 7.77E−01 | 9.31E−01 | Proteome | Q8IV42 |
| N-methylproline | 0.00 | 0.02 | 417 | 0.28 | 7.81E−01 | 9.32E−01 | Metabolome | |
| L-Histidine | 0.00 | 0.01 | 417 | 0.27 | 7.90E−01 | 9.37E−01 | Metabolome | HMDB00177 |
| Gluconic acid | 0.00 | 0.01 | 417 | 0.26 | 7.93E−01 | 9.37E−01 | Metabolome | HMDB00625 |
| 2-Piperidinone | 0.00 | 0.02 | 417 | −0.26 | 7.93E−01 | 9.37E−01 | Metabolome | HMDB11749 |
| 7-alpha-hydroxy-3-oxo-4-cholestenoate (7-Hoca) | 0.00 | 0.01 | 417 | 0.26 | 7.92E−01 | 9.37E−01 | Metabolome | HMDB12458 |
| C13:1, OH FA | 0.00 | 0.01 | 417 | −0.27 | 7.88E−01 | 9.37E−01 | Metabolome | |
| FGB | 0.00 | 0.01 | 440 | −0.26 | 7.91E−01 | 9.37E−01 | Proteome | P02675 |
| SERPIND1 | 0.00 | 0.01 | 440 | 0.27 | 7.88E−01 | 9.37E−01 | Proteome | P05546 |
| PGLYRP2 | 0.00 | 0.01 | 440 | −0.26 | 7.92E−01 | 9.37E−01 | Proteome | Q96PD5 |
| CST3 | 0.00 | 0.01 | 440 | 0.26 | 7.95E−01 | 9.37E−01 | Proteome | P01034 |
| L-Cysteine | 0.00 | 0.01 | 417 | 0.26 | 7.97E−01 | 9.38E−01 | Metabolome | HMDB00574 |
| APOD | 0.00 | 0.01 | 440 | −0.26 | 7.98E−01 | 9.38E−01 | Proteome | P05090 |
| Taurocholic acid(2) | 0.03 | 0.13 | 417 | 0.25 | 8.02E−01 | 9.39E−01 | Metabolome | HMDB00036 |
| Symmetric dimethylarginine | 0.00 | 0.01 | 417 | −0.24 | 8.08E−01 | 9.39E−01 | Metabolome | HMDB01539 |
| Tryptophan betaine | 0.00 | 0.01 | 417 | −0.24 | 8.09E−01 | 9.39E−01 | Metabolome | HMDB61115 |
| IL8 | −0.01 | 0.02 | 449 | −0.25 | 8.01E−01 | 9.39E−01 | Immunome | |
| MIG | −0.01 | 0.04 | 449 | −0.24 | 8.08E−01 | 9.39E−01 | Immunome | |
| C18:3, OH FA(1) | 0.00 | 0.01 | 417 | 0.24 | 8.14E−01 | 9.39E−01 | Metabolome | |
| FN1 | 0.00 | 0.01 | 440 | 0.24 | 8.13E−01 | 9.39E−01 | Proteome | P02751 |
| CPN1 | 0.00 | 0.01 | 440 | 0.24 | 8.13E−01 | 9.39E−01 | Proteome | P15169 |
| C4BPB | 0.00 | 0.01 | 440 | 0.25 | 8.03E−01 | 9.39E−01 | Proteome | P20851 |
| HGFAC | 0.00 | 0.01 | 440 | 0.24 | 8.09E−01 | 9.39E−01 | Proteome | Q04756 |
| MMRN1 | 0.00 | 0.01 | 440 | 0.24 | 8.12E−01 | 9.39E−01 | Proteome | Q13201 |
| FAM3C | 0.00 | 0.01 | 440 | 0.24 | 8.10E−01 | 9.39E−01 | Proteome | Q92520 |
| Protein FAM161B | 0.00 | 0.01 | 440 | 0.25 | 8.05E−01 | 9.39E−01 | Proteome | Q96MY7 |
| Urocanic acid | 0.00 | 0.01 | 417 | 0.23 | 8.16E−01 | 9.40E−01 | Metabolome | HMDB00301 |
| Creatinine | 0.00 | 0.01 | 417 | 0.22 | 8.29E−01 | 9.40E−01 | Metabolome | HMDB00562 |
| C22:5 FA | 0.00 | 0.01 | 417 | 0.22 | 8.26E−01 | 9.40E−01 | Metabolome | HMDB06528 |
| CHOLHDL | 0.00 | 0.01 | 459 | 0.23 | 8.21E−01 | 9.40E−01 | Clinical labs | |
| IL4 | 0.01 | 0.03 | 449 | 0.22 | 8.27E−01 | 9.40E−01 | Immunome | |
| IP10 | 0.01 | 0.02 | 449 | 0.22 | 8.24E−01 | 9.40E−01 | Immunome | |
| C20:3, OH FA(1) | 0.00 | 0.01 | 417 | 0.22 | 8.26E−01 | 9.40E−01 | Metabolome | |
| C14:1, OH FA(1) | 0.00 | 0.01 | 417 | 0.23 | 8.20E−01 | 9.40E−01 | Metabolome | |
| 16a-hydroxy DHEA 3-sulfate | 0.00 | 0.02 | 417 | 0.22 | 8.25E−01 | 9.40E−01 | Metabolome | |
| AHSG | 0.00 | 0.01 | 440 | 0.23 | 8.21E−01 | 9.40E−01 | Proteome | P02765 |
| A1BG | 0.00 | 0.01 | 440 | 0.23 | 8.17E−01 | 9.40E−01 | Proteome | P04217 |
| CFI | 0.00 | 0.01 | 440 | −0.22 | 8.26E−01 | 9.40E−01 | Proteome | P05156 |

TABLE 13-continued

| | | | | | | | |
|---|---|---|---|---|---|---|---|
| GP5 | 0.00 | 0.01 | 440 | 0.22 | 8.28E-01 | 9.40E-01 | Proteome | P40197 |
| C20:4, OH FA(1) | 0.00 | 0.01 | 417 | -0.21 | 8.32E-01 | 9.42E-01 | Metabolome | |
| C10:3 FA(1) | 0.00 | 0.01 | 417 | -0.21 | 8.32E-01 | 9.42E-01 | Metabolome | |
| Proline betaine | 0.00 | 0.01 | 417 | -0.2 | 8.41E-01 | 9.43E-01 | Metabolome | HMD604827 |
| MCV | 0.00 | 0.01 | 456 | 0.2 | 8.39E-01 | 9.43E-01 | Clinical labs | |
| UALB | 0.00 | 0.01 | 276 | -0.2 | 8.42E-01 | 9.43E-01 | Clinical labs | |
| IL6 | -0.01 | 0.06 | 449 | -0.2 | 8.45E-01 | 9.43E-01 | Immunome | |
| LIF | -0.01 | 0.06 | 449 | -0.2 | 8.41E-01 | 9.43E-01 | Immunome | |
| MCSF | -0.01 | 0.03 | 449 | -0.19 | 8.46E-01 | 9.43E-01 | Immunome | |
| Hydroxyhippurate(2) | 0.00 | 0.02 | 417 | -0.19 | 8.50E-01 | 9.43E-01 | Metabolome | |
| Ig heavy chain V-III region JON | 0.00 | 0.01 | 440 | 0.21 | 8.36E-01 | 9.43E-01 | Proteome | P01780 |
| AMBP | 0.00 | 0.01 | 440 | -0.2 | 8.39E-01 | 9.43E-01 | Proteome | P02760 |
| Ig kappa chain V-III region VH | 0.00 | 0.01 | 440 | 0.19 | 8.48E-01 | 9.43E-01 | Proteome | P04434 |
| SERPINF2 | 0.00 | 0.01 | 440 | -0.19 | 8.46E-01 | 9.43E-01 | Proteome | P08697 |
| MBL2 | 0.00 | 0.01 | 440 | 0.19 | 8.47E-01 | 9.43E-01 | Proteome | P11226 |
| CETP | 0.00 | 0.01 | 440 | 0.2 | 8.39E-01 | 9.43E-01 | Proteome | P11597 |
| ITIH4 | 0.00 | 0.01 | 440 | -0.19 | 8.47E-01 | 9.43E-01 | Proteome | Q14624 |
| CDK5RAP2 | 0.00 | 0.01 | 440 | -0.19 | 8.50E-01 | 9.43E-01 | Proteome | Q96SN8 |
| LysoPG(18:0) | 0.00 | 0.01 | 417 | 0.18 | 8.54E-01 | 9.46E-01 | Metabolome | |
| Sulfuric acid | 0.00 | 0.01 | 417 | -0.18 | 8.56E-01 | 9.47E-01 | Metabolome | |
| C24:6 FA | 0.00 | 0.01 | 417 | -0.18 | 8.59E-01 | 9.48E-01 | Metabolome | HMDB02007 |
| PCOLCE | 0.00 | 0.01 | 440 | 0.18 | 8.59E-01 | 9.48E-01 | Proteome | Q15113 |
| FBLN1(1) | 0.00 | 0.01 | 440 | -0.18 | 8.61E-01 | 9.48E-01 | Proteome | P23142 |
| Ig heavy chain V-III region KOL | 0.00 | 0.01 | 440 | -0.17 | 8.63E-01 | 9.48E-01 | Proteome | P01772 |
| C1RL | 0.00 | 0.01 | 440 | -0.17 | 8.63E-01 | 9.48E-01 | Proteome | Q9NZP8 |
| Hydroxyhippurate(1) | 0.00 | 0.01 | 417 | 0.17 | 8.67E-01 | 9.49E-01 | Metabolome | |
| C10:3 AC(1) | 0.00 | 0.02 | 417 | -0.17 | 8.65E-01 | 9.49E-01 | Metabolome | |
| ALB | 0.00 | 0.01 | 440 | -0.17 | 8.66E-01 | 9.49E-01 | Proteome | P02768 |
| C18:3 FA | 0.00 | 0.01 | 417 | -0.14 | 8.85E-01 | 9.49E-01 | Metabolome | HMDB03073 |
| C11:0 AC | 0.00 | 0.01 | 417 | -0.16 | 8.71E-01 | 9.49E-01 | Metabolome | HMDB13321 |
| C10:2 FA | 0.00 | 0.02 | 417 | 0.17 | 8.69E-01 | 9.49E-01 | Metabolome | |
| C10:1 FA(2) | 0.00 | 0.01 | 417 | -0.16 | 8.77E-01 | 9.49E-01 | Metabolome | |
| C16:2, OH FA | 0.00 | 0.01 | 417 | 0.15 | 8.80E-01 | 9.49E-01 | Metabolome | |
| PLG | 0.00 | 0.01 | 440 | 0.15 | 8.80E-01 | 9.49E-01 | Proteome | P00747 |
| CA1 | 0.00 | 0.01 | 440 | -0.16 | 8.77E-01 | 9.49E-01 | Proteome | P00915 |
| TTR | 0.00 | 0.01 | 440 | -0.15 | 8.78E-01 | 9.49E-01 | Proteome | P02766 |
| GC | 0.00 | 0.01 | 440 | 0.15 | 8.81E-01 | 9.49E-01 | Proteome | P02774 |
| C4BPA | 0.00 | 0.01 | 440 | 0.16 | 8.76E-01 | 9.49E-01 | Proteome | P04003 |
| C4B | 0.00 | 0.01 | 440 | 0.15 | 8.85E-01 | 9.49E-01 | Proteome | P0C0L5 |
| ITIH2 | 0.00 | 0.01 | 440 | 0.16 | 8.73E-01 | 9.49E-01 | Proteome | P19823 |
| COMP | 0.00 | 0.01 | 440 | 0.15 | 8.82E-01 | 9.49E-01 | Proteome | P49747 |
| EFEMP1 | 0.00 | 0.01 | 440 | -0.15 | 8.84E-01 | 9.49E-01 | Proteome | Q12805 |
| TGEBI | 0.00 | 0.01 | 440 | -0.16 | 8.71E-01 | 9.49E-01 | Proteome | Q15582 |
| cont_000137 | 0.00 | 0.01 | 440 | 0.15 | 8.79E-01 | 9.49E-01 | Proteome | |
| ITIH1 | 0.00 | 0.01 | 440 | 0.14 | 8.87E-01 | 9.50E-01 | Proteome | P19827 |
| Pyridoxic acid | 0.00 | 0.03 | 417 | 0.12 | 9.05E-01 | 9.53E-01 | Metabolome | HMDB00017 |
| L-a-glutamyl-L-Lysine | 0.00 | 0.01 | 417 | 0.13 | 8.98E-01 | 9.53E-01 | Metabolome | HMDB04207 |
| 5-Acetylamino-6-amino-3-methyluracil(2) | 0.00 | 0.01 | 417 | 0.12 | 9.02E-01 | 9.53E-01 | Metabolome | HMDB04400 |
| LysoPC(16:1) | 0.00 | 0.01 | 417 | 0.12 | 9.04E-01 | 9.53E-01 | Metabolome | HMDB10383 |
| LysoPC(18:2) | 0.00 | 0.01 | 417 | 0.12 | 9.05E-01 | 9.53E-01 | Metabolome | HMDB10386 |
| MG(22:2) | 0.00 | 0.01 | 417 | -0.13 | 8.95E-01 | 9.53E-01 | Metabolome | HMDB11553 |
| HDL | 0.00 | 0.01 | 459 | 0.12 | 9.04E-01 | 9.53E-01 | Clinical labs | |
| MONOAB | 0.00 | 0.01 | 456 | -0.13 | 8.99E-01 | 9.53E-01 | Clinical labs | |
| C12:1, OH FA | 0.00 | 0.02 | 417 | 0.13 | 8.98E-01 | 9.53E-01 | Metabolome | |
| C20:4, OH FA(2) | 0.00 | 0.01 | 417 | -0.12 | 9.02E-01 | 9.53E-01 | Metabolome | |
| APOH | 0.00 | 0.01 | 440 | 0.13 | 8.94E-01 | 9.53E-01 | Proteome | P02749 |
| KLKB1 | 0.00 | 0.01 | 440 | 0.13 | 9.00E-01 | 9.53E-01 | Proteome | P03952 |
| GSN | 0.00 | 0.01 | 440 | -0.14 | 8.92E-01 | 9.53E-01 | Proteome | P06396 |
| C2 | 0.00 | 0.01 | 440 | -0.12 | 9.07E-01 | 9.55E-01 | Proteome | P06681 |
| DYNC1H1 | 0.00 | 0.01 | 440 | -0.11 | 9.11E-01 | 9.57E-01 | Proteome | Q14204 |
| C16:0, 2OH FA | 0.00 | 0.01 | 417 | 0.11 | 9.14E-01 | 9.59E-01 | Metabolome | |
| INPP5E | 0.00 | 0.01 | 440 | 0.11 | 9.16E-01 | 9.60E-01 | Proteome | Q9NRR6 |
| IL12P40 | 0.00 | 0.02 | 449 | 0.1 | 9.19E-01 | 9.63E-01 | Immunome | |
| Pipecolic acid | 0.00 | 0.02 | 417 | -0.09 | 9.32E-01 | 9.68E-01 | Metabolome | HMDB00070 |
| MG(24:1) | 0.00 | 0.01 | 417 | -0.09 | 9.27E-01 | 9.68E-01 | Metabolome | HMDB11559 |
| HGF | 0.00 | 0.01 | 449 | 0.09 | 9.29E-01 | 9.68E-01 | Immunome | |
| C12:1, OH FA | 0.00 | 0.01 | 417 | -0.09 | 9.25E-01 | 9.68E-01 | Metabolome | |
| SERPINA3 | 0.00 | 0.01 | 440 | -0.09 | 9.31E-01 | 9.68E-01 | Proteome | P01011 |
| Ig heavy chain V-II region WAH | 0.00 | 0.01 | 440 | -0.09 | 9.31E-01 | 9.68E-01 | Proteome | P01824 |
| cont_000017 | 0.00 | 0.01 | 440 | 0.09 | 9.31E-01 | 9.68E-01 | Proteome | |
| C14:0, OH FA(1) | 0.00 | 0.01 | 417 | -0.08 | 9.40E-01 | 7.73E-01 | Metabolome | HMDB00872 |
| PTPRC | 0.00 | 0.01 | 440 | -0.08 | 9.39E-01 | 9.73E-01 | Proteome | P08575 |
| IL9 | 0.00 | 0.04 | 449 | -0.07 | 9.43E-01 | 9.75E-01 | Immunome | |
| SERPINF1 | 0.00 | 0.01 | 440 | 0.07 | 9.46E-01 | 9.77E-01 | Proteome | P36955 |
| PZP | 0.00 | 0.01 | 440 | 0.06 | 9.55E-01 | 9.85E-01 | Proteome | P20742 |
| AFG3L2 | 0.00 | 0.01 | 440 | -0.06 | 9.56E-01 | 9.85E-01 | Proteome | Q9Y4W6 |
| CLU(1) | 0.00 | 0.01 | 440 | -0.05 | 9.59E-01 | 9.87E-01 | Proteome | P10909 |
| TLN(1) | 0.00 | 0.01 | 440 | 0.05 | 9.60E-01 | 9.87E-01 | Proteome | Q9Y490 |
| Phenylpyruvic acid | 0.00 | 0.02 | 417 | 0.04 | 9.66E-01 | 9.91E-01 | Metabolome | HMDB00205 |
| Tetrahydroaldosterone-3-glucoronide(2) | 0.00 | 0.03 | 417 | 0.04 | 9.69E-01 | 9.91E-01 | Metabolome | HMDB10357 |

TABLE 13-continued

| | | | | | | | |
|---|---|---|---|---|---|---|---|
| CFB | 0.00 | 0.01 | 440 | 0.04 | 9.66E-01 | 9.91E-01 | Proteome | P00751 |
| C5 | 0.00 | 0.01 | 440 | 0.04 | 9.69E-01 | 9.91E-01 | Proteome | P01031 |
| APOC2 | 0.00 | 0.01 | 440 | -0.04 | 9.69E-01 | 9.91E-01 | Proteome | P02655 |
| Glycerophosphocholine | 0.00 | 0.01 | 417 | -0.02 | 9.81E-01 | 9.91E-01 | Metabolome | HMDB00086 |
| C12:1 FA(1) | 0.00 | 0.01 | 417 | 0.03 | 9.75E-01 | 9.91E-01 | Metabolome | HMDB00529 |
| Chenodeoxycholic acid glycine conjugate(1) | 0.00 | 0.02 | 417 | -0.02 | 9.83E-01 | 9.91E-01 | Metabolome | HMDB00637 |
| Homostachydrine | 0.00 | 0.03 | 417 | 0.03 | 9.79E-01 | 9.91E-01 | Metabolome | HMDB33433 |
| LDLHDL | 0.00 | 0.01 | 458 | 0.02 | 9.84E-01 | 9.91E-01 | Clinical labs | |
| Ig kappa chain V-I region AU | 0.00 | 0.01 | 440 | -0.02 | 9.84E-01 | 9.91E-01 | Proteome | P01594 |
| FGG | 0.00 | 0.01 | 440 | 0.03 | 9.77E-01 | 9.91E-01 | Proteome | P02679 |
| APCS | 0.00 | 0.01 | 440 | -0.03 | 9.80E-01 | 9.91E-01 | Proteome | P02743 |
| VWF | 0.00 | 0.01 | 440 | -0.02 | 9.83E-01 | 9.91E-01 | Proteome | P04275 |
| F13B | 0.00 | 0.01 | 440 | -0.03 | 9.78E-01 | 9.91E-01 | Proteome | P05160 |
| LGALS3BP | 0.00 | 0.01 | 440 | 0.03 | 9.75E-01 | 9.91E-01 | Proteome | Q08380 |
| ILK | 0.00 | 0.01 | 440 | 0.03 | 9.73E-01 | 9.91E-01 | Proteome | Q13418 |
| Choline | 0.00 | 0.01 | 417 | 0.01 | 9.93E-01 | 9.96E-01 | Metabolome | HMDB00097 |
| 2- Hydroxyphenylacetate | 0.00 | 0.03 | 417 | -0.01 | 9.96E-01 | 9.96E-01 | Metabolome | HMDB00669 |
| TNFB | 0.00 | 0.03 | 449 | -0.01 | 9.92E-01 | 9.96E-01 | Immunome | |
| SERPINC1 | 0.00 | 0.01 | 440 | -0.01 | 9.95E-01 | 9.96E-01 | Proteome | P01008 |
| F7 | 0.00 | 0.01 | 440 | 0 | 9.96E-01 | 9.96E-01 | Proteome | P08709 |
| ECM1 | 0.00 | 0.01 | 440 | 0 | 9.96E-01 | 9.96E-01 | Proteome | Q16610 |

Bolded Proteins (n = 17) and metabolites (n = 36) are those that were matched to molecules in known pathways and used in pathway analysis using IMPaLa web tool p-values are derived from the t-test and are two sided; multiple testing correction using Benjamini-Hochberg method was performed and resulting values listed under FDR Dynamic Model: Fasting Plasma Glucose (n = 94, samples 843)

| Molecule | Estimate | StdErr | DF | tValue | p-value | FDR | Assay | Accession ID |
|---|---|---|---|---|---|---|---|---|
| Hexosamine | 0.043 | 0.004 | 631 | 9.73 | 6.16E-21 | 5.16E-18 | Metabolome | HMDB01514 |
| LEPTIN | 0.044 | 0.006 | 616 | 7.6 | 1.13E-13 | 4.75E-11 | Immunome | |
| L-Tyrosine | 0.035 | 0.005 | 631 | 7.25 | 1.21E-12 | 3.39E-10 | Metabolome | HMDB00158 |
| IGHA2 | -0.039 | 0.006 | 590 | -6.23 | 8.72E-10 | 1.83E-07 | Proteome | P01877 |
| C12:1 AC | -0.027 | 0.005 | 631 | -5.51 | 5.16E-08 | 8.65E-06 | Metabolome | HMDB13326 |
| GMCSF | 0.144 | 0.026 | 616 | 5.45 | 7.38E-08 | 1.03E-05 | Immunome | |
| C10:0 AC | -0.025 | 0.005 | 631 | -5.16 | 3.30E-07 | 3.95E-05 | Metabolome | HMDB00651 |
| C8:0 AC | -0.024 | 0.005 | 631 | -5.09 | 4.65E-07 | 4.87E-05 | Metabolome | HMDB00791 |
| C14:2 AC | -0.025 | 0.005 | 631 | -4.94 | 1.03E-06 | 8.59E-05 | Metabolome | HMDB13331 |
| APOA4 | 0.024 | 0.005 | 590 | 4.96 | 9.25E-07 | 8.59E-05 | Proteome | P06727 |
| C12:0 AC | -0.022 | 0.005 | 631 | -4.75 | 2.52E-06 | 1.92E-04 | Metabolome | HMDB02250 |
| C16:4 FA | -0.020 | 0.004 | 631 | -4.53 | 7.01E-06 | 4.89E-04 | Metabolome | |
| C14:1 AC | -0.023 | 0.005 | 631 | -4.42 | 1.16E-05 | 7.46E-04 | Metabolome | HMDB02014 |
| C10:1 AC | -0.022 | 0.005 | 631 | -4.36 | 1.51E-05 | 9.03E-04 | Metabolome | HMDB13205 |
| C12:0 FA(2) | -0.021 | 0.005 | 631 | -4.34 | 1.65E-05 | 9.22E-04 | Metabolome | |
| C6:0 AC | -0.020 | 0.005 | 631 | -4.16 | 3.58E-05 | 1.88E-03 | Metabolome | HMDB00705 |
| C12:1 FA(1) | -0.027 | 0.007 | 631 | -4.11 | 4.41E-05 | 2.17E-03 | Metabolome | HMDB00529 |
| N-Acetyl-L-phenylalanine | 0.020 | 0.005 | 631 | 3.85 | 1.32E-04 | 6.13E-03 | Metabolome | HMDB00512 |
| sn-glycero-3-Phosphoethanolamine | 0.019 | 0.005 | 631 | 3.72 | 2.14E-04 | 9.44E-03 | Metabolome | HMDB00114 |
| CAPZB | 0.020 | 0.005 | 590 | 3.7 | 2.40E-04 | 1.01E-02 | Proteome | P47756 |
| L-Lactic acid | 0.017 | 0.005 | 631 | 3.61 | 3.29E-04 | 1.13E-02 | Metabolome | HMDB00190 |
| C14:2 FA | -0.017 | 0.005 | 631 | -3.62 | 3.19E-04 | 1.13E-02 | Metabolome | HMDB00560 |
| 1-Methyluric acid | 0.016 | 0.004 | 631 | 3.61 | 3.32E-04 | 1.13E-02 | Metabolome | HMDB03099 |
| CL | 0.017 | 0.005 | 748 | 3.6 | 3.37E-04 | 1.13E-02 | Clinical labs | |
| Cyclo(ala-pro) | 0.017 | 0.005 | 631 | 3.6 | 3.38E-04 | 1.13E-02 | Metabolome | |
| Hydroxybutyric acid(2) | -0.016 | 0.004 | 631 | -3.59 | 3.55E-04 | 1.14E-02 | Metabolome | |
| AG | -0.020 | 0.006 | 746 | -3.57 | 3.80E-04 | 1.18E-02 | Clinical labs | |
| Hypoxanthine | 0.017 | 0.005 | 631 | 3.46 | 5.74E-04 | 1.66E-02 | Metabolome | HMDB00157 |
| C14:0, OH FA(2) | -0.017 | 0.005 | 631 | -3.47 | 5.61E-04 | 1.66E-02 | Metabolome | |
| Hexose | 0.013 | 0.004 | 631 | 3.41 | 6.79E-04 | 1.84E-02 | Metabolome | HMDB00122 |
| L-Phenylalanine | 0.017 | 0.005 | 631 | 3.42 | 6.58E-04 | 1.84E-02 | Metabolome | HMDB00159 |
| C12:0, OH FA(1) | -0.017 | 0.005 | 631 | -3.33 | 9.05E-04 | 2.30E-02 | Metabolome | HMDB00387 |
| C12:1 FA(2) | -0.016 | 0.005 | 631 | -3.34 | 9.01E-04 | 2.30E-02 | Metabolome | HMDB00529 |
| (S)-(-)-2-Hydroxyisocaproic acid | -0.018 | 0.005 | 631 | -3.32 | 9.45E-04 | 2.33E-02 | Metabolome | HMDB00746 |
| Caffeine | 0.014 | 0.004 | 631 | 3.25 | 1.22E-03 | 2.93E-02 | Metabolome | HMDB01847 |
| L-Alanine | 0.014 | 0.004 | 631 | 3.21 | 1.39E-03 | 2.99E-02 | Metabolome | HMDB00161 |
| C18:0 AC | 0.016 | 0.005 | 631 | 3.21 | 1.39E-03 | 2.99E-02 | Metabolome | HMD300848 |
| gamma-glutamylhistidine | -0.018 | 0.005 | 631 | -3.22 | 1.36E-03 | 2.99E-02 | Metabolome | HMDB29151 |
| C8:0, OH FA(1) | -0.016 | 0.005 | 631 | -3.22 | 1.34E-03 | 2.99E-02 | Metabolome | |
| C14:1 FA(2) | -0.016 | 0.005 | 631 | -3.2 | 1.44E-03 | 3.02E-02 | Metabolome | HMDB02000 |
| K | 0.015 | 0.005 | 748 | 3.18 | 1.51E-03 | 3.10E-02 | Clinical labs | |
| KNG1 | 0.013 | 0.004 | 590 | 3.11 | 1.97E-03 | 3.93E-02 | Proteome | P01042 |
| C14:1, OH FA(1) | -0.016 | 0.005 | 631 | -3.08 | 2.15E-03 | 4.19E-02 | Metabolome | |
| Theophylline | 0.014 | 0.005 | 631 | 3.07 | 2.20E-03 | 4.20E-02 | Metabolome | HMDB01889 |
| Dihydroxyvitamin D3(2) | 0.018 | 0.006 | 631 | 3.05 | 2.42E-03 | 4.50E-02 | Metabolome | HMDB00430 |
| MCHC | 0.015 | 0.005 | 690 | 3.03 | 2.50E-03 | 4.56E-02 | Clinical labs | |
| KVD33 | -0.021 | 0.007 | 590 | -3 | 2.81E-03 | 5.01E-02 | Proteome | P01780 |
| N-(1-Deoxy-1-fructosyl)valine | 0.013 | 0.004 | 631 | 2.98 | 3.04E-03 | 5.20E-02 | Metabolome | HMDB37844 |
| C20:4, OH FA(2) | -0.014 | 0.005 | 631 | -2.98 | 2.98E-03 | 5.20E-02 | Metabolome | |
| N-acetylthreonine | -0.014 | 0.005 | 631 | -2.94 | 3.43E-03 | 5.75E-02 | Metabolome | |

TABLE 13-continued

| | | | | | | | |
|---|---|---|---|---|---|---|---|
| C10:0, OH FA(1) | −0.018 | 0.006 | 631 | −2.92 | 3.66E−03 | 5.86E−02 | Metabolome | HMD302203 |
| MG(20:0) | 0.012 | 0.004 | 631 | 2.91 | 3.71E−03 | 5.86E−02 | Metabolome | HMDB11542 |
| A1C | 0.014 | 0.005 | 736 | 2.92 | 3.63E−03 | 5.86E−02 | Clinical labs | |
| AGT | 0.014 | 0.005 | 590 | 2.89 | 3.97E−03 | 6.17E−02 | Proteome | P01019 |
| C10:2 AC | −0.014 | 0.005 | 631 | −2.87 | 4.19E−03 | 6.39E−02 | Metabolome | HMDB13325 |
| C12:1, DC FA(2) | 0.015 | 0.005 | 631 | 2.87 | 4.27E−03 | 6.40E−02 | Metabolome | HMDB00933 |
| C14:1 FA(1) | −0.014 | 0.005 | 631 | −2.84 | 4.66E−03 | 6.85E−02 | Metabolome | HMDB02000 |
| C12:1, OH FA | −0.014 | 0.005 | 631 | −2.83 | 4.82E−03 | 6.97E−02 | Metabolome | |
| C16:0 AC | 0.014 | 0.005 | 631 | 2.81 | 5.11E−03 | 7.06E−02 | Metabolome | HMDB00222 |
| 1-Methylxanthine | 0.013 | 0.005 | 631 | 2.79 | 5.39E−03 | 7.06E−02 | Metabolome | HMDB10738 |
| C10:1 FA(2) | −0.017 | 0.006 | 631 | −2.81 | 5.12E−03 | 7.06E−02 | Metabolome | |
| C14:2, OH FA | −0.014 | 0.005 | 631 | −2.8 | 5.33E−03 | 7.06E−02 | Metabolome | |
| C15:1 FA | −0.014 | 0.005 | 631 | −2.8 | 5.30E−03 | 7.06E−02 | Metabolome | |
| C20:4, OH FA(1) | −0.014 | 0.005 | 631 | −2.8 | 5.22E−03 | 7.06E−02 | Metabolome | |
| C14:0, DC FA(2) | −0.013 | 0.005 | 631 | −2.77 | 5.83E−03 | 7.52E−02 | Metabolome | HMD600872 |
| C14:0, OH FA(1) | −0.014 | 0.005 | 631 | −2.76 | 5.94E−03 | 7.54E−02 | Metabolome | HMDB02261 |
| C11:0 AC | −0.014 | 0.005 | 631 | −2.7 | 7.08E−03 | 8.85E−02 | Metabolome | HMDB13321 |
| C14:0 AC | 0.013 | 0.005 | 631 | 2.64 | 8.49E−03 | 1.02E−01 | Metabolome | HMDB05066 |
| MG(14:1)(3) | 0.013 | 0.005 | 631 | 2.65 | 8.34E−03 | 1.02E−01 | Metabolome | HMDB11531 |
| SERPINF1 | 0.022 | 0.008 | 590 | 2.64 | 8.43E−03 | 1.02E−01 | Proteome | P36955 |
| LDL | 0.014 | 0.005 | 728 | 2.63 | 8.69E−03 | 1.03E−01 | Clinical labs | |
| Piperine(2) | 0.012 | 0.005 | 631 | 2.62 | 8.88E−03 | 1.03E−01 | Metabolome | HMD329377 |
| CHOL | 0.013 | 0.005 | 730 | 2.62 | 9.09E−03 | 1.03E−01 | Clinical labs | |
| F5 | 0.011 | 0.004 | 590 | 2.62 | 9.01E−03 | 1.03E−01 | Proteome | P12259 |
| Biliverdin(2) | −0.018 | 0.007 | 631 | −2.6 | 9.44E−03 | 1.06E−01 | Metabolome | HMDB01008 |
| NHDL | 0.014 | 0.005 | 730 | 2.57 | 1.05E−02 | 1.16E−01 | Clinical labs | |
| RDW | −0.012 | 0.005 | 690 | −2.55 | 1.11E−02 | 1.21E−01 | Clinical labs | |
| Paraxanthine | 0.014 | 0.005 | 631 | 2.53 | 1.15E−02 | 1.24E−01 | Metabolome | HMDB01860 |
| VTN | 0.018 | 0.007 | 590 | 2.53 | 1.17E−02 | 1.24E−01 | Proteome | P04004 |
| C18:3, OH FA(1) | −0.012 | 0.005 | 631 | −2.52 | 1.20E−02 | 1.25E−01 | Metabolome | |
| APOH | 0.013 | 0.005 | 590 | 2.52 | 1.19E−02 | 1.25E−01 | Proteome | P02749 |
| C12:2, OH FA | −0.014 | 0.006 | 631 | −2.5 | 1.27E−02 | 1.29E−01 | Metabolome | |
| PAI1 | 0.013 | 0.005 | 616 | 2.5 | 1.28E−02 | 1.29E−01 | Immunome | |
| IGFALS | 0.012 | 0.005 | 590 | 2.48 | 1.35E−02 | 1.35E−01 | Proteome | P35858 |
| C16:2, OH FA | −0.012 | 0.005 | 631 | −2.47 | 1.39E−02 | 1.37E−01 | Metabolome | |
| Hydroxyhippurate(1) | 0.013 | 0.005 | 631 | 2.4 | 1.67E−02 | 1.59E−01 | Metabolome | |
| HPX | 0.012 | 0.005 | 590 | 2.4 | 1.66E−02 | 1.59E−01 | Proteome | P02790 |
| A1BG | 0.011 | 0.005 | 590 | 2.41 | 1.64E−02 | 1.59E−01 | Proteome | P04217 |
| HV353 | −0.016 | 0.007 | 590 | −2.38 | 1.77E−02 | 1.67E−01 | Proteome | P01767 |
| CLU | 0.012 | 0.005 | 590 | 2.37 | 1.83E−02 | 1.70E−01 | Proteome | P10909 |
| Fructoselysine | 0.010 | 0.004 | 631 | 2.36 | 1.86E−02 | 1.71E−01 | Metabolome | |
| Cys-Gly or Gly-Cys | 0.013 | 0.006 | 631 | 2.35 | 1.92E−02 | 1.75E−01 | Metabolome | HMDB00078 |
| CFHR4 | −0.012 | 0.005 | 590 | −2.32 | 2.05E−02 | 1.85E−01 | Proteome | Q92496 |
| C20:5 FA | −0.012 | 0.005 | 631 | −2.3 | 2.18E−02 | 1.92E−01 | Metabolome | HMDB01999 |
| CHOLHDL | 0.012 | 0.005 | 730 | 2.3 | 2.20E−02 | 1.92E−01 | Clinical labs | |
| BTD | 0.012 | 0.005 | 590 | 2.3 | 2.16E−02 | 1.92E−01 | Proteome | P43251 |
| TP | −0.012 | 0.005 | 748 | −2.28 | 2.27E−02 | 1.96E−01 | Clinical labs | |
| 2-Aminobutyrate | −0.012 | 0.005 | 631 | −2.27 | 2.33E−02 | 1.99E−01 | Metabolome | HMDB00650 |

Bolded Proteins (n = 17) and Metabolites (11 = 17) are those that were matched to molecules in known pathways and used in pathway analysis using IMPaLa web tool p-values are derived from the t-test and are two sided; multiple testing correction using Benjamini-Hochberg method was performed and resulting values listed under FDR

TABLE 14

Healthy-Baseline & Dynamic Models: Molecules Associated with high sensitivity C-reactive Protein Healthy-Baseline Model: hsCRP (n = 98, samples 518)

| Molecule | Estimate | StdErr | DF | tValue | p-value | FDR | Assay | Accession ID |
|---|---|---|---|---|---|---|---|---|
| LEPTIN | 0.80 | 0.13 | 414 | 6.38 | 4.73E−10 | 3.99E−07 | Immunome | |
| SAA2 | 0.40 | 0.07 | 403 | 5.76 | 1.70E−08 | 7.17E−06 | Proteome | P0DJI9 |
| GMCSF | 1.46 | 0.27 | 414 | 5.42 | 9.94E−08 | 2.80E−05 | Immunome | |
| C20:0, 2OH FA | −0.50 | 0.10 | 382 | −5.09 | 5.70E−07 | 1.20E−04 | Metabolome | HMDB31923 |
| Cinnamoylglycine | −0.63 | 0.13 | 382 | −4.91 | 1.34E−06 | 2.26E−04 | Metabolome | HMDB11621 |
| L-Serine | −0.48 | 0.10 | 382 | −4.8 | 2.29E−06 | 3.22E−04 | Metabolome | HMDB00187 |
| LysoPC(17:0) | −0.38 | 0.08 | 382 | −4.72 | 3.29E−06 | 3.96E−04 | Metabolome | HMDB12108 |
| 3-Phenylpropionate (hydrocinnamate) | −0.60 | 0.13 | 382 | −4.63 | 5.13E−06 | 5.41E−04 | Metabolome | HMDB00764 |
| SAA1 | 0.31 | 0.07 | 403 | 4.56 | 6.80E−06 | 6.38E−04 | Proteome | P0DJI8 |
| LysoPC(20:0) | −0.97 | 0.22 | 382 | −4.41 | 1.34E−05 | 1.13E−03 | Metabolome | HMDB10390 |
| C8:2, OH FA(2) | −0.65 | 0.15 | 382 | −4.32 | 1.98E−05 | 1.52E−03 | Metabolome | |
| HGF | 0.49 | 0.12 | 414 | 4.26 | 2.52E−05 | 1.78E−03 | Immunome | |
| Glycine | −1.46 | 0.36 | 382 | −4.04 | 6.54E−05 | 4.00E−03 | Metabolome | HMDB00123 |
| C20:0 FA | −0.37 | 0.09 | 382 | −4.02 | 7.11E−05 | 4.00E−03 | Metabolome | HMDB02212 |
| LysoPC(20:1) | −0.96 | 0.24 | 382 | −4.03 | 6.72E−05 | 4.00E−03 | Metabolome | HMDB10391 |
| LysoPE(16:0) | −1.82 | 0.47 | 382 | −3.87 | 1.28E−04 | 6.77E−03 | Metabolome | HMDB11473 |
| LysoPC(20:2) | −0.81 | 0.21 | 382 | −3.81 | 1.61E−04 | 8.01E−03 | Metabolome | HMDB10392 |
| L-Asparagine | −0.31 | 0.08 | 382 | −3.79 | 1.75E−04 | 8.20E−03 | Metabolome | HMDB00168 |
| Cysteineglutathione disulfide | −0.34 | 0.09 | 382 | −3.73 | 2.17E−04 | 9.15E−03 | Metabolome | HMDB00656 |

TABLE 14-continued

Healthy-Baseline & Dynamic Models: Molecules Associated with high sensitivity C-reactive Protein

| | | | | | | | | |
|---|---|---|---|---|---|---|---|---|
| LysoPE(18:1) | −0.34 | 0.09 | 382 | −3.74 | 2.11E−04 | 9.15E−03 | Metabolome | HMDB11475 |
| LysoPC(P-16:0) | −0.29 | 0.08 | 382 | −3.71 | 2.37E−04 | 9.51E−03 | Metabolome | HMDB10407 |
| Indolelactic acid | −0.35 | 0.10 | 382 | −3.62 | 3.30E−04 | 1.21E−02 | Metabolome | HMDB00671 |
| GLOB | 0.42 | 0.12 | 419 | 3.62 | 3.25E−04 | 1.21E−02 | Clinical labs | |
| Pseudouridine | 0.33 | 0.09 | 382 | 3.46 | 6.11E−04 | 1.98E−02 | Metabolome | HMDB00767 |
| ALKP | 0.42 | 0.12 | 419 | 3.47 | 5.72E−04 | 1.98E−02 | Clinical labs | |
| HDL | −0.41 | 0.12 | 419 | −3.46 | 6.01E−04 | 1.98E−02 | Clinical labs | |
| gamma-glutamylphenylalanine | 0.39 | 0.11 | 382 | 3.41 | 7.16E−04 | 2.16E−02 | Metabolome | HMDB00594 |
| CFD | 0.18 | 0.05 | 403 | 3.42 | 6.99E−04 | 2.16E−02 | Proteome | P00746 |
| 3-Indolepropionic acid | −0.20 | 0.06 | 382 | −3.4 | 7.51E−04 | 2.18E−02 | Metabolome | HMDB02302 |
| Citric acid | −0.27 | 0.08 | 382 | −3.38 | 8.11E−04 | 2.28E−02 | Metabolome | HMDB00094 |
| MG(14:1)(2) | −0.44 | 0.13 | 382 | −3.34 | 9.19E−04 | 2.50E−02 | Metabolome | HMDB11531 |
| LysoPC(15:0) | −0.27 | 0.08 | 382 | −3.33 | 9.62E−04 | 2.54E−02 | Metabolome | HMDB10381 |
| C12:0, DC FA | −0.64 | 0.20 | 382 | −3.28 | 1.13E−03 | 2.90E−02 | Metabolome | HMDB00623 |
| LysoPC(18:2) | −0.28 | 0.09 | 382 | −3.25 | 1.27E−03 | 3.15E−02 | Metabolome | HMDB10386 |
| Hippuric acid | −0.26 | 0.08 | 382 | −3.14 | 1.83E−03 | 4.42E−02 | Metabolome | HMDB00714 |
| LysoPE(18:0) | −1.48 | 0.47 | 382 | −3.13 | 1.90E−03 | 4.46E−02 | Metabolome | HMDB11129 |
| C4:0 AC | −0.54 | 0.18 | 382 | −3.05 | 2.44E−03 | 5.57E−02 | Metabolome | HMDB02013 |
| Indolepyruvate | −0.24 | 0.08 | 382 | −3.04 | 2.53E−03 | 5.62E−02 | Metabolome | HMDB60484 |
| Dihydroxyvitamin D3(2) | −0.33 | 0.11 | 382 | −3.02 | 2.68E−03 | 5.77E−02 | Metabolome | HMDB00430 |
| Pregnanolone sulfate | 0.12 | 0.04 | 382 | 3.02 | 2.73E−03 | 5.77E−02 | Metabolome | |
| L-Cysteinylglycine disulfide | 0.23 | 0.08 | 382 | 2.99 | 2.95E−03 | 6.07E−02 | Metabolome | HMDB00709 |
| IP10 | 0.67 | 0.23 | 414 | 2.97 | 3.20E−03 | 6.43E−02 | Immunome | |
| ALB | −0.24 | 0.08 | 419 | −2.94 | 3.47E−03 | 6.81E−02 | Clinical labs | |
| Pregnenolone sulfate | 0.11 | 0.04 | 382 | 2.92 | 3.71E−03 | 7.12E−02 | Metabolome | HMDB00774 |
| LysoPC(18:0) | −0.20 | 0.07 | 382 | −2.89 | 4.08E−03 | 7.66E−02 | Metabolome | HMDB10384 |
| GROA | 0.14 | 0.05 | 414 | 2.87 | 4.27E−03 | 7.84E−02 | Immunome | |
| CHOLHDL | 0.33 | 0.12 | 419 | 2.85 | 4.59E−03 | 8.08E−02 | Clinical labs | |
| C8:0, OH FA(3) | −2.40 | 0.84 | 382 | −2.86 | 4.53E−03 | 8.08E−02 | Metabolome | |
| LysoPE(20:0) | −0.22 | 0.08 | 382 | −2.84 | 4.79E−03 | 8.24E−02 | Metabolome | HMDB11481 |
| LysoPC(16:0) | −0.20 | 0.07 | 382 | −2.83 | 4.93E−03 | 8.32E−02 | Metabolome | HMDB10382 |
| Orotidine | 0.30 | 0.11 | 382 | 2.82 | 5.11E−03 | 8.46E−02 | Metabolome | HMDB00788 |
| N1-methyladenosine | 0.22 | 0.08 | 382 | 2.8 | 5.37E−03 | 8.72E−02 | Metabolome | HMDB03331 |
| IL22 | −0.43 | 0.15 | 414 | −2.79 | 5.52E−03 | 8.79E−02 | Immunome | |
| LysoPE(20:1) | −0.20 | 0.07 | 382 | −2.78 | 5.67E−03 | 8.87E−02 | Metabolome | HMDB11482 |
| MG(15:0)(3) | −0.49 | 0.18 | 382 | −2.76 | 6.11E−03 | 9.35E−02 | Metabolome | HMDB11532 |
| IL1RA | 0.42 | 0.15 | 414 | 2.75 | 6.21E−03 | 9.35E−02 | Immunome | |
| LysoPE(22:0) | −1.19 | 0.44 | 382 | −2.73 | 6.64E−03 | 9.84E−02 | Metabolome | HMDB11490 |
| LysoPC(22:6) | −0.25 | 0.09 | 382 | −2.72 | 6.91E−03 | 1.01E−01 | Metabolome | HMDB10404 |
| C9 | 0.18 | 0.07 | 403 | 2.7 | 7.25E−03 | 1.04E−01 | Proteome | P02748 |
| MIG | 0.80 | 0.30 | 414 | 2.69 | 7.51E−03 | 1.04E−01 | Immunome | |
| CDHR5 | 0.18 | 0.07 | 403 | 2.69 | 7.48E−03 | 1.04E−01 | Proteome | Q9HBB8 |
| LysoPC(P-18:0) | −0.22 | 0.08 | 382 | −2.67 | 7.98E−03 | 1.09E−01 | Metabolome | HMDB13122 |
| C16:1 FA | 0.20 | 0.07 | 382 | 2.64 | 8.61E−03 | 1.15E−01 | Metabolome | HMDB03229 |
| IFNB | 0.85 | 0.32 | 414 | 2.63 | 8.86E−03 | 1.17E−01 | Immunome | |
| LDLHDL | 0.29 | 0.11 | 418 | 2.61 | 9.51E−03 | 1.24E−01 | Clinical labs | |
| C19:0 FA(2) | −0.22 | 0.08 | 382 | −2.58 | 1.02E−02 | 1.30E−01 | Metabolome | HMDB00772 |
| C17:0 FA(2) | 0.17 | 0.07 | 382 | 2.57 | 1.05E−02 | 1.32E−01 | Metabolome | |
| C8G | 0.20 | 0.08 | 403 | 2.53 | 1.18E−02 | 1.47E−01 | Proteome | P07360 |
| 2-Aminophenol sulfate | −0.26 | 0.10 | 382 | −2.52 | 1.22E−02 | 1.49E−01 | Metabolome | HMDB61116 |
| LysoPC(O-18:0) | −2.50 | 1.01 | 382 | −2.47 | 1.40E−02 | 1.67E−01 | Metabolome | HMDB11149 |
| Zinc finger protein 10 | −0.12 | 0.05 | 403 | −2.47 | 1.39E−02 | 1.67E−01 | Proteome | P21506 |
| C18:0, DC FA(1) | 0.22 | 0.09 | 382 | 2.45 | 1.47E−02 | 1.72E−01 | Metabolome | HMDB00782 |
| C16:3 FA | 0.22 | 0.09 | 382 | 2.44 | 1.51E−02 | 1.75E−01 | Metabolome | |
| Uridine | −0.23 | 0.09 | 382 | −2.38 | 1.76E−02 | 1.88E−01 | Metabolome | HMDB00296 |
| Quinic acid | −0.26 | 0.11 | 382 | −2.38 | 1.80E−02 | 1.88E−01 | Metabolome | HMDB03072 |
| INSF | 0.57 | 0.23 | 85 | 2.44 | 1.66E−02 | 1.88E−01 | Clinical labs | |
| MONOAB | 0.28 | 0.12 | 417 | 2.37 | 1.83E−02 | 1.88E−01 | Clinical labs | |
| FGFB | 0.16 | 0.07 | 414 | 2.4 | 1.70E−02 | 1.88E−01 | Immunome | |
| IL17F | 0.75 | 0.31 | 414 | 2.4 | 1.69E−02 | 1.88E−01 | Immunome | |
| MIP1B | 0.38 | 0.16 | 414 | 2.39 | 1.75E−02 | 1.88E−01 | Immunome | |
| C10:1 FA(1) | 0.43 | 0.18 | 382 | 2.36 | 1.86E−02 | 1.88E−01 | Metabolome | |
| VWF | 0.13 | 0.06 | 403 | 2.36 | 1.88E−02 | 1.88E−01 | Proteome | P04275 |
| CFHR4 | 0.13 | 0.05 | 403 | 2.38 | 1.79E−02 | 1.88E−01 | Proteome | Q92496 |
| CFHR5 | 0.24 | 0.10 | 403 | 2.37 | 1.81E−02 | 1.88E−01 | Proteome | Q9BXR6 |
| Interleukin-1 receptor accessory protein | −0.12 | 0.05 | 403 | −2.36 | 1.89E−02 | 1.88E−01 | Proteome | Q9NPH3_5 |
| MG(22:2) | 0.29 | 0.12 | 382 | 2.33 | 2.01E−02 | 1.97E−01 | Metabolome | HMDB11553 |
| p-Cresol glucuronide | −0.38 | 0.16 | 382 | −2.33 | 2.04E−02 | 1.98E−01 | Metabolome | HMDB11686 |
| TGFB | 0.47 | 0.21 | 414 | 2.29 | 2.23E−02 | 2.12E−01 | Immunome | |
| TNFA | 0.41 | 0.18 | 414 | 2.29 | 2.23E−02 | 2.12E−01 | Immunome | |
| LysoPE(P-16:0) | −0.73 | 0.32 | 382 | −2.28 | 2.29E−02 | 2.14E−01 | Metabolome | HMDB11152 |
| L-Malic acid | −0.25 | 0.11 | 382 | −2.27 | 2.36E−02 | 2.19E−01 | Metabolome | HMDB00156 |
| C22:4 FA | 0.20 | 0.09 | 382 | 2.26 | 2.46E−02 | 2.22E−01 | Metabolome | HMDB02226 |
| IGM | 0.41 | 0.18 | 418 | 2.25 | 2.50E−02 | 2.22E−01 | Clinical labs | |
| C20:4, DC FA | −0.72 | 0.32 | 382 | −2.25 | 2.48E−02 | 2.22E−01 | Metabolome | |
| NEUTAB | 0.25 | 0.11 | 417 | 2.25 | 2.47E−02 | 2.22E−01 | Clinical labs | |
| LysoPC(22:4) | −1.06 | 0.48 | 382 | −2.23 | 2.63E−02 | 2.27E−01 | Metabolome | HMDB10401 |
| IL1B | 0.12 | 0.05 | 414 | 2.23 | 2.63E−02 | 2.27E−01 | Immunome | |

TABLE 14-continued

Healthy-Baseline & Dynamic Models: Molecules Associated with high sensitivity C-reactive Protein

| | | | | | | | | |
|---|---|---|---|---|---|---|---|---|
| TGLHDL | 0.30 | 0.13 | 419 | 2.24 | 2.58E-02 | 2.27E-01 | Clinical labs | |
| Uracil | -0.19 | 0.08 | 382 | -2.22 | 2.73E-02 | 2.28E-01 | Metabolome | HMDB00300 |
| Hydroxyphenyllactic acid | 0.20 | 0.09 | 382 | 2.22 | 2.67E-02 | 2.28E-01 | Metabolome | HMDB00755 |
| 5-Methoxysalicylic acid | -0.35 | 0.16 | 382 | -2.21 | 2.75E-02 | 2.28E-01 | Metabolome | HMDB01868 |
| TNFB | 0.12 | 0.05 | 414 | 2.21 | 2.73E-02 | 2.28E-01 | Immunome | |
| 3-carboxy-4-methyl-5-propyl-2-furanpropanoate (CMPF) | -0.40 | 0.18 | 382 | -2.2 | 2.81E-02 | 2.30E-01 | Metabolome | HMDB61112 |
| IL9 | 0.13 | 0.06 | 414 | 2.2 | 2.83E-02 | 2.30E-01 | Immunome | |
| Uric acid | 0.21 | 0.10 | 382 | 2.2 | 2.86E-02 | 2.30E-01 | Metabolome | HMDB00289 |
| C14:0, DC FA(1) | -0.20 | 0.09 | 382 | -2.19 | 2.94E-02 | 2.30E-01 | Metabolome | HMDB00872 |
| WBC | 0.25 | 0.12 | 417 | 2.18 | 2.97E-02 | 2.30E-01 | Clinical labs | |
| HP | 0.11 | 0.05 | 403 | 2.18 | 2.96E-02 | 2.30E-01 | Proteome | P00738 |
| Ig heavy chain V-III region JON | -0.10 | 0.05 | 403 | -2.18 | 2.97E-02 | 2.30E-01 | Proteome | P01780 |
| IL15 | 0.84 | 0.38 | 414 | 2.17 | 3.05E-02 | 2.34E-01 | Immunome | |
| Phenylalanyl-Tryptophan | 0.20 | 0.09 | 382 | 2.14 | 3.26E-02 | 2.48E-01 | Metabolome | HMDB29006 |
| 1-Methylguanosine | 0.17 | 0.08 | 382 | 2.13 | 3.39E-02 | 2.53E-01 | Metabolome | HMDB01563 |
| LRG1 | 0.12 | 0.06 | 403 | 2.13 | 3.38E-02 | 2.53E-01 | Proteome | P02750 |
| LysoPE(18:2) | -0.17 | 0.08 | 382 | -2.11 | 3.56E-02 | 2.61E-01 | Metabolome | HMDB11477 |
| TBIL | -0.26 | 0.12 | 419 | -2.11 | 3.54E-02 | 2.61E-01 | Clinical labs | |
| C9:0 AC | -0.24 | 0.11 | 382 | -2.09 | 3.69E-02 | 2.69E-01 | Metabolome | HMDB13288 |
| TGL | 0.22 | 0.11 | 419 | 2.07 | 3.87E-02 | 2.79E-01 | Clinical labs | |
| KRT17 | -0.11 | 0.06 | 403 | -2.07 | 3.92E-02 | 2.81E-01 | Proteome | Q04695 |
| C16:2 FA | 0.16 | 0.08 | 382 | 2.03 | 4.29E-02 | 3.02E-01 | Metabolome | |
| 4-Methylcatechol sulfate | -0.24 | 0.12 | 382 | -2.03 | 4.26E-02 | 3.02E-01 | Metabolome | |
| C20:3, OH FA(2) | 0.09 | 0.04 | 382 | 2.01 | 4.47E-02 | 3.09E-01 | Metabolome | |
| SERPINF1 | 0.13 | 0.06 | 403 | 2.02 | 4.44E-02 | 3.09E-01 | Proteome | P36955 |
| 1-Methylhistidine | 0.23 | 0.11 | 382 | 2 | 4.67E-02 | 3.21E-01 | Metabolome | HMDB00001 |
| IL17A | 0.42 | 0.21 | 414 | 1.99 | 4.76E-02 | 3.24E-01 | Immunome | |
| Creatine | -0.19 | 0.10 | 382 | -1.98 | 4.81E-02 | 3.25E-01 | Metabolome | HMDB00064 |
| L-Glutamic acid | 0.19 | 0.10 | 382 | 1.98 | 4.88E-02 | 3.27E-01 | Metabolome | HMDB00148 |
| C18:0 AC | -0.20 | 0.10 | 382 | -1.96 | 5.04E-02 | 3.32E-01 | Metabolome | HMDB00848 |
| LysoPC(22:0) | -0.34 | 0.17 | 382 | -1.96 | 5.02E-02 | 3.32E-01 | Metabolome | HMDB10398 |
| RANTES | -0.25 | 0.13 | 414 | -1.95 | 5.18E-02 | 3.39E-01 | Immunome | |
| IL10 | 0.14 | 0.07 | 414 | 1.94 | 5.31E-02 | 3.45E-01 | Immunome | |
| Butyric acid\|Isobutyric acid | -0.37 | 0.19 | 382 | -1.93 | 5.47E-02 | 3.50E-01 | Metabolome | HMDB00039\|HMDB01873 |
| C18:0, OH AC | -2.20 | 1.15 | 382 | -1.92 | 5.55E-02 | 3.50E-01 | Metabolome | HMDB13164 |
| LysoPI(20:4) | 0.17 | 0.09 | 382 | 1.92 | 5.55E-02 | 3.50E-01 | Metabolome | HMDB61690 |
| MCSF | 0.11 | 0.06 | 414 | 1.92 | 5.49E-02 | 3.50E-01 | Immunome | |
| VEGF | 0.32 | 0.17 | 414 | 1.91 | 5.69E-02 | 3.56E-01 | Immunome | |
| LysoPC(P-18:1) | -0.15 | 0.08 | 382 | -1.9 | 5.87E-02 | 3.62E-01 | Metabolome | HMDB10408 |
| C18:3, OH FA(2) | 0.18 | 0.09 | 382 | 1.9 | 5.87E-02 | 3.62E-01 | Metabolome | |
| Pyridoxic acid | 0.37 | 0.20 | 382 | 1.87 | 6.20E-02 | 3.68E-01 | Metabolome | HMDB00017 |
| Taurocholic acid(1) | 0.99 | 0.53 | 382 | 1.87 | 6.24E-02 | 3.68E-01 | Metabolome | HMDB00036 |
| p-Cresol sulfate | -0.21 | 0.11 | 382 | -1.88 | 6.04E-02 | 3.68E-01 | Metabolome | HMDB11635 |
| INHBC | 0.10 | 0.05 | 403 | 1.88 | 6.14E-02 | 3.68E-01 | Proteome | P55103 |
| IL1RAP(1) | -0.11 | 0.06 | 403 | -1.87 | 6.22E-02 | 3.68E-01 | Proteome | Q9NPH3 |
| FETUB | 0.10 | 0.06 | 403 | 1.87 | 6.22E-02 | 3.68E-01 | Proteome | Q9UGM5 |
| C12:2, OH FA | 0.17 | 0.09 | 382 | 1.86 | 6.30E-02 | 3.69E-01 | Metabolome | |
| C8:1 AC | 0.18 | 0.10 | 382 | 1.85 | 6.46E-02 | 3.76E-01 | Metabolome | HMDB13324 |
| CR | 0.18 | 0.10 | 419 | 1.83 | 6.80E-02 | 3.85E-01 | Clinical labs | |
| IL12P40 | 0.30 | 0.17 | 414 | 1.83 | 6.80E-02 | 3.85E-01 | Immunome | |
| C10:2 FA | -0.39 | 0.21 | 382 | -1.83 | 6.80E-02 | 3.85E-01 | Metabolome | |
| Titin | 0.09 | 0.05 | 403 | 1.83 | 6.73E-02 | 3.85E-01 | Proteome | Q8WZ42_2 |
| C18:2 FA | 0.14 | 0.08 | 382 | 1.83 | 6.87E-02 | 3.86E-01 | Metabolome | HMDB00673 |
| Indoleacetic acid | -0.20 | 0.11 | 382 | -1.82 | 6.96E-02 | 3.86E-01 | Metabolome | HMDB00197 |
| IL21 | 0.64 | 0.35 | 414 | 1.82 | 6.96E-02 | 3.86E-01 | Immunome | |
| C18:3 FA | 0.12 | 0.07 | 382 | 1.8 | 7.31E-02 | 4.03E-01 | Metabolome | HMDB03073 |
| TLN1 | 0.10 | 0.06 | 403 | 1.79 | 7.46E-02 | 4.09E-01 | Proteome | Q9Y490 |
| Androsterone glucuronide(2) | -0.20 | 0.11 | 382 | -1.78 | 7.64E-02 | 4.16E-01 | Metabolome | HMDB02829 |
| Citrulline | -0.17 | 0.10 | 382 | -1.75 | 8.09E-02 | 4.19E-01 | Metabolome | HMDB00904 |
| Biliverdin(2) | -0.28 | 0.16 | 382 | -1.76 | 7.99E-02 | 4.19E-01 | Metabolome | HMDB01008 |
| LysoPE(20:4) | -0.15 | 0.09 | 382 | -1.76 | 7.87E-02 | 4.19E-01 | Metabolome | HMDB11487 |
| CO2 | -0.12 | 0.07 | 419 | -1.75 | 8.09E-02 | 4.19E-01 | Clinical labs | |
| IL7 | 0.23 | 0.13 | 414 | 1.76 | 7.94E-02 | 4.19E-01 | Immunome | |
| C10:3 AC(1) | 0.29 | 0.17 | 382 | 1.75 | 8.09E-02 | 4.19E-01 | Metabolome | |
| PF4 | 0.11 | 0.06 | 403 | 1.77 | 7.78E-02 | 4.19E-01 | Proteome | P02776 |
| FLNA | 0.10 | 0.05 | 403 | 1.76 | 7.91E-02 | 4.19E-01 | Proteome | P21333 |
| EOTAXIN | -0.25 | 0.15 | 414 | -1.74 | 8.22E-02 | 4.23E-01 | Immunome | |
| VEGFD | -0.27 | 0.16 | 414 | -1.74 | 8.34E-02 | 4.24E-01 | Immunome | |
| COL6A3 | 0.10 | 0.06 | 403 | 1.74 | 8.33E-02 | 4.24E-01 | Proteome | P12111 |
| NCAM1 | -0.09 | 0.05 | 403 | -1.73 | 8.40E-02 | 4.25E-01 | Proteome | P13591 |
| Chenodeoxycholic Acid(2) | -0.18 | 0.11 | 382 | -1.72 | 8.54E-02 | 4.26E-01 | Metabolome | HMDB00518 |
| 2,3-Dihydroxyvaleric acid(2) | -0.56 | 0.33 | 382 | -1.72 | 8.58E-02 | 4.26E-01 | Metabolome | HMDB00421 |
| LYM | -0.17 | 0.10 | 417 | -1.72 | 8.55E-02 | 4.26E-01 | Clinical labs | |
| C13:0, DC FA(3) | -0.25 | 0.15 | 382 | -1.7 | 8.93E-02 | 4.41E-01 | Metabolome | HMDB02327 |
| Arabonate \| Xylonate(3) | -0.18 | 0.10 | 382 | -1.7 | 8.98E-02 | 4.41E-01 | Metabolome | |
| Glycocholic acid | 0.40 | 0.24 | 382 | 1.69 | 9.17E-02 | 4.44E-01 | Metabolome | HMDB00138 |
| C13:0, DC FA(1) | -0.13 | 0.08 | 382 | -1.69 | 9.26E-02 | 4.44E-01 | Metabolome | HMDB02327 |

TABLE 14-continued

Healthy-Baseline & Dynamic Models: Molecules Associated with high sensitivity C-reactive Protein

| | | | | | | | | |
|---|---|---|---|---|---|---|---|---|
| ethyl glucuronide | −0.14 | 0.08 | 382 | −1.69 | 9.18E−02 | 4.44E−01 | Metabolome | HMDB10325 |
| ACAA2 | −0.09 | 0.05 | 403 | −1.69 | 9.26E−02 | 4.44E−01 | Proteome | P42765 |
| N2,N2-Dimethylguanosine | 0.21 | 0.12 | 382 | 1.68 | 9.37E−02 | 4.47E−01 | Metabolome | HMDB04824 |
| Retinol (Vitamin A) | −0.14 | 0.08 | 382 | −1.67 | 9.58E−02 | 4.54E−01 | Metabolome | HMDB00305 |
| N1-Methyl-2-pyridone-5-carboxamide(1) | 0.22 | 0.13 | 382 | 1.65 | 1.00E−01 | 4.55E−01 | Metabolome | HMDB04193 |
| gamma-glutamylleucine(1) | 0.18 | 0.11 | 382 | 1.67 | 9.66E−02 | 4.55E−01 | Metabolome | HMDB11171 |
| LysoPE(22:6) | −0.13 | 0.08 | 382 | −1.64 | 1.01E−01 | 4.55E−01 | Metabolome | HMDB11496 |
| MG(24:1) | 0.16 | 0.10 | 382 | 1.65 | 9.90E−02 | 4.55E−01 | Metabolome | HMDB11559 |
| RESISTIN | 0.25 | 0.15 | 414 | 1.65 | 9.88E−02 | 4.55E−01 | Immunome | |
| TGFA | 0.71 | 0.43 | 414 | 1.65 | 9.94E−02 | 4.55E−01 | Immunome | |
| ORM1 | 0.08 | 0.05 | 403 | 1.66 | 9.76E−02 | 4.55E−01 | Proteome | P02763 |
| LBP | 0.11 | 0.07 | 403 | 1.66 | 9.84E−02 | 4.55E−01 | Proteome | P18428 |
| PZP | 0.09 | 0.05 | 403 | 1.64 | 1.01E−01 | 4.55E−01 | Proteome | P20742 |
| C19:0 FA(1) | −0.19 | 0.11 | 382 | −1.63 | 1.03E−01 | 4.59E−01 | Metabolome | HMDB00772 |
| LysoPC(20:4) | −0.14 | 0.09 | 382 | −1.62 | 1.07E−01 | 4.59E−01 | Metabolome | HMDB10395 |
| Alliin | −0.07 | 0.04 | 382 | −1.61 | 1.08E−01 | 4.59E−01 | Metabolome | HMDB33592 |
| Hydroxyhippurate(2) | 0.10 | 0.06 | 382 | 1.63 | 1.04E−01 | 4.59E−01 | Metabolome | |
| N-acetylthreonine | −0.30 | 0.18 | 382 | −1.62 | 1.06E−01 | 4.59E−01 | Metabolome | |
| 25-hydroxyvitamin D3 | 0.25 | 0.15 | 382 | 1.62 | 1.05E−01 | 4.59E−01 | Metabolome | |
| 5alpha-Androstan-3alpha,17allpha-diol monosulfate(3) | 0.56 | 0.34 | 382 | 1.63 | 1.04E−01 | 4.59E−01 | Metabolome | |
| C12:1, OH FA | 0.15 | 0.09 | 382 | 1.62 | 1.06E−01 | 4.59E−01 | Metabolome | |
| N-methylproline | −0.20 | 0.13 | 382 | −1.61 | 1.07E−01 | 4.59E−01 | Metabolome | |
| MCHC | −0.13 | 0.08 | 417 | −1.62 | 1.07E−01 | 4.59E−01 | Clinical labs | |
| PRG4(1) | 0.09 | 0.06 | 403 | 1.63 | 1.05E−01 | 4.59E−01 | Proteome | Q92954 |
| C10:0, DC FA (Sebacic acid)(1) | 0.37 | 0.23 | 382 | 1.6 | 1.10E−01 | 4.68E−01 | Metabolome | HMDB00792 |
| 2,3-Dihydroxyvaleric acid(1) | −0.26 | 0.16 | 382 | −1.6 | 1.11E−01 | 4.68E−01 | Metabolome | HMDB00421 |
| C4A | 0.08 | 0.05 | 403 | 1.59 | 1.13E−01 | 4.74E−01 | Proteome | P0C0L4 |
| Glyceric acid | −0.18 | 0.11 | 382 | −1.58 | 1.14E−01 | 4.74E−01 | Metabolome | HMDB00139 |
| C18:3, OH FA(1) | 0.20 | 0.13 | 382 | 1.59 | 1.14E−01 | 4.74E−01 | Metabolome | |
| Glucaric acid | −0.13 | 0.08 | 382 | −1.58 | 1.15E−01 | 4.74E−01 | Metabolome | HMDB00663 |
| Hydroxyhippurate(3) | 0.73 | 0.46 | 382 | 1.57 | 1.17E−01 | 4.74E−01 | Metabolome | HMDB00840 |
| gamma-glutamylleucine(2) | 0.18 | 0.11 | 382 | 1.56 | 1.20E−01 | 4.74E−01 | Metabolome | HMDB11171 |
| LIF | 0.78 | 0.50 | 414 | 1.57 | 1.18E−01 | 4.74E−01 | Immunome | |
| Arabonate | Xylonate(1) | −0.17 | 0.11 | 382 | −1.56 | 1.20E−01 | 4.74E−01 | Metabolome | |
| MIP1A | 0.58 | 0.37 | 414 | 1.58 | 1.16E−01 | 4.74E−01 | Immunome | |
| NEUT | 0.14 | 0.09 | 417 | 1.56 | 1.20E−01 | 4.74E−01 | Clinical labs | |
| Ig heavy chain V-III region NIE | −0.08 | 0.05 | 403 | −1.57 | 1.18E−01 | 4.74E−01 | Proteome | P01770 |
| CFI | 0.09 | 0.06 | 403 | 1.55 | 1.21E−01 | 4.74E−01 | Proteome | P05156 |
| PTPRC | 0.08 | 0.05 | 403 | 1.55 | 1.21E−01 | 4.74E−01 | Proteome | P08575 |
| CFHR2 | 0.09 | 0.06 | 403 | 1.57 | 1.18E−01 | 4.74E−01 | Proteome | P36980 |
| CDK5RAP2 | −0.08 | 0.05 | 403 | −1.57 | 1.18E−01 | 4.74E−01 | Proteome | Q96SN8 |
| C12:1, DC FA(4) | −0.06 | 0.04 | 382 | −1.55 | 1.22E−01 | 4.75E−01 | Metabolome | HMDB00933 |
| BUN | −0.15 | 0.10 | 419 | −1.55 | 1.22E−01 | 4.75E−01 | Clinical labs | |
| MG(16:1) | 0.14 | 0.09 | 382 | 1.54 | 1.23E−01 | 4.76E−01 | Metabolome | HMDB11534 |
| gamma-glutamylhistidine | −0.16 | 0.11 | 382 | −1.54 | 1.23E−01 | 4.76E−01 | Metabolome | HMDB29151 |
| Attractin | 0.11 | 0.07 | 403 | 1.53 | 1.26E−01 | 4.82E−01 | Proteome | O75882_2 |
| TPM4 | 0.08 | 0.05 | 403 | 1.53 | 1.26E−01 | 4.83E−01 | Proteome | P67936 |
| C14:0, OH FA(2) | −0.15 | 0.10 | 382 | −1.52 | 1.30E−01 | 4.91E−01 | Metabolome | |
| NHDL | 0.17 | 0.11 | 419 | 1.52 | 1.30E−01 | 4.91E−01 | Clinical labs | |
| PAI1 | −0.20 | 0.13 | 414 | −1.51 | 1.31E−01 | 4.91E−01 | Immunome | |
| PROC | −0.09 | 0.06 | 403 | −1.51 | 1.31E−01 | 4.91E−01 | Proteome | P04070 |
| Ig kappa chain V-II region FR | 0.10 | 0.06 | 403 | 1.51 | 1.32E−01 | 4.93E−01 | Proteome | P01615 |
| L-Phenylalanine | 0.15 | 0.10 | 382 | 1.5 | 1.35E−01 | 4.96E−01 | Metabolome | HMDB00159 |
| FASL | 0.13 | 0.08 | 414 | 1.5 | 1.35E−01 | 4.96E−01 | Immunome | |
| Ig heavy chain V-II region SESS | 0.15 | 0.10 | 403 | 1.5 | 1.34E−01 | 4.96E−01 | Proteome | P04438 |
| 1-Methyluric acid | −0.14 | 0.09 | 382 | −1.49 | 1.36E−01 | 4.99E−01 | Metabolome | HMDB03099 |
| C16:2, OH FA | 0.14 | 0.09 | 382 | 1.48 | 1.39E−01 | 5.07E−01 | Metabolome | |
| INPP5E | 0.08 | 0.05 | 403 | 1.47 | 1.41E−01 | 5.15E−01 | Proteome | Q9NRR6 |
| NUP205 | 0.09 | 0.06 | 403 | 1.46 | 1.44E−01 | 5.22E−01 | Proteome | Q92621 |
| sn-glycero-3-Phosphoethanolamine | −0.11 | 0.08 | 382 | −1.45 | 1.48E−01 | 5.24E−01 | Metabolome | HMDB00114 |
| Gentisic acid | −0.17 | 0.12 | 382 | −1.45 | 1.47E−01 | 5.24E−01 | Metabolome | HMDB00152 |
| Creatinine | 0.17 | 0.12 | 382 | 1.45 | 1.48E−01 | 5.24E−01 | Metabolome | HMDB00562 |
| Erythritol|D-Threitol | −0.06 | 0.04 | 382 | −1.45 | 1.48E−01 | 5.24E−01 | Metabolome | HMDB02994|HMDB04136 |
| APOC4 | 0.08 | 0.05 | 403 | 1.45 | 1.48E−01 | 5.24E−01 | Proteome | P55056 |
| PCYOX1 | −0.08 | 0.06 | 403 | −1.46 | 1.46E−01 | 5.24E−01 | Proteome | Q9UHG3 |
| C12:0, OH FA(2) | −0.19 | 0.13 | 382 | −1.44 | 1.51E−01 | 5.29E−01 | Metabolome | HMDB02059 |
| N1-Methyl-2-pyridone-5-carboxamide(2) | 0.22 | 0.16 | 382 | 1.44 | 1.50E−01 | 5.29E−01 | Metabolome | HMDB04193 |
| 2-Aminobutyrate | −0.11 | 0.08 | 382 | −1.44 | 1.52E−01 | 5.30E−01 | Metabolome | HMDB00650 |
| C25:0, OH FA | 0.17 | 0.12 | 382 | 1.43 | 1.54E−01 | 5.35E−01 | Metabolome | |
| Pro-Cys or Cys-Pro | 0.16 | 0.11 | 382 | 1.42 | 1.56E−01 | 5.40E−01 | Metabolome | HMDB28783|HMDB29014 |
| C5:0, DC AC | 0.61 | 0.43 | 382 | 1.42 | 1.57E−01 | 5.40E−01 | Metabolome | |
| THBS1 | 0.09 | 0.06 | 403 | 1.41 | 1.58E−01 | 5.43E−01 | Proteome | P07996 |
| CFB | 0.07 | 0.05 | 403 | 1.41 | 1.60E−01 | 5.47E−01 | Proteome | P00751 |
| C20:5 FA | −0.22 | 0.16 | 382 | −1.4 | 1.61E−01 | 5.48E−01 | Metabolome | HMDB01999 |
| C18:1, OH FA(2) | 0.12 | 0.08 | 382 | 1.4 | 1.62E−01 | 5.48E−01 | Metabolome | |
| GP5 | −0.09 | 0.06 | 403 | −1.39 | 1.65E−01 | 5.58E−01 | Proteome | P40197 |
| L-Isoleucine|L-Leucine | 0.14 | 0.10 | 382 | 1.38 | 1.68E−01 | 5.64E−01 | Metabolome | HMDB00172|HMDB00687 |

TABLE 14-continued

Healthy-Baseline & Dynamic Models: Molecules Associated with high sensitivity C-reactive Protein

| | | | | | | | | |
|---|---|---|---|---|---|---|---|---|
| IL8 | −0.31 | 0.23 | 414 | −1.36 | 1.73E−01 | 5.73E−01 | Immunome | |
| C18:1, OH FA(1) | −0.10 | 0.07 | 382 | −1.37 | 1.73E−01 | 5.73E−01 | Metabolome | |
| RDW | 0.18 | 0.13 | 417 | 1.36 | 1.74E−01 | 5.73E−01 | Clinical labs | |
| Ig heavy chain V-III region KOL | −0.07 | 0.05 | 403 | −1.36 | 1.74E−01 | 5.73E−01 | Proteome | P01772 |
| IGHG3 | 0.08 | 0.06 | 403 | 1.37 | 1.73E−01 | 5.73E−01 | Proteome | P01860 |
| IGHV3-23 | 0.07 | 0.05 | 403 | 1.36 | 1.75E−01 | 5.74E−01 | Proteome | P01764 |
| C9:0, DC FA (Azelaic acid) | 0.13 | 0.09 | 382 | 1.35 | 1.79E−01 | 5.74E−01 | Metabolome | HMDB00784 |
| Tauroursodeoxycholic acid | 0.41 | 0.30 | 382 | 1.35 | 1.78E−01 | 5.74E−01 | Metabolome | HMDB00874 |
| Biliverdin(1) | −0.16 | 0.12 | 382 | −1.33 | 1.83E−01 | 5.74E−01 | Metabolome | HMDB01008 |
| 5-Acetylamino-6-amino-3-methyluracil(2) | −0.14 | 0.11 | 382 | −1.34 | 1.82E−01 | 5.74E−01 | Metabolome | HMDB04400 |
| 9-HODE | 0.10 | 0.08 | 382 | 1.35 | 1.77E−01 | 5.74E−01 | Metabolome | HMDB04702 |
| C20:2 FA | 0.11 | 0.08 | 382 | 1.33 | 1.86E−01 | 5.74E−01 | Metabolome | HMDB05060 |
| Tetrahydroaldosterone-3-glucuronide(1) | −0.24 | 0.18 | 382 | −1.34 | 1.82E−01 | 5.74E−01 | Metabolome | HMDB10357 |
| Acetylcarnosine | 0.17 | 0.12 | 382 | 1.35 | 1.77E−01 | 5.74E−01 | Metabolome | HMDB12881 |
| C10:2 AC | 0.17 | 0.13 | 382 | 1.32 | 1.87E−01 | 5.74E−01 | Metabolome | HMDB13325 |
| ALCRU | 0.13 | 0.10 | 270 | 1.33 | 1.83E−01 | 5.74E−01 | Clinical labs | |
| C10:3 AC(2) | 0.13 | 0.10 | 382 | 1.33 | 1.84E−01 | 5.74E−01 | Metabolome | |
| C9:1, OH FA | 0.07 | 0.06 | 382 | 1.33 | 1.84E−01 | 5.74E−01 | Metabolome | |
| C18:3, OH FA(3) | 0.09 | 0.07 | 382 | 1.33 | 1.84E−01 | 5.74E−01 | Metabolome | |
| PLT | 0.17 | 0.13 | 417 | 1.32 | 1.87E−01 | 5.74E−01 | Clinical labs | |
| Kininogen-1 | 0.07 | 0.05 | 403 | 1.32 | 1.87E−01 | 5.74E−01 | Proteome | P01042_2 |
| Ig lambda chain V-I region VOR | −0.09 | 0.06 | 403 | −1.34 | 1.82E−01 | 5.74E−01 | Proteome | P01699 |
| C1QA | 0.07 | 0.05 | 403 | 1.32 | 1.87E−01 | 5.74E−01 | Proteome | P02745 |
| F5 | 0.07 | 0.05 | 403 | 1.35 | 1.79E−01 | 5.74E−01 | Proteome | P12259 |
| EFEMP1 | 0.07 | 0.05 | 403 | 1.32 | 1.88E−01 | 5.74E−01 | Proteome | Q12805 |
| CFH | 0.07 | 0.05 | 403 | 1.32 | 1.89E−01 | 5.76E−01 | Proteome | P08603 |
| Hexose | −0.27 | 0.21 | 382 | −1.3 | 1.93E−01 | 5.82E−01 | Metabolome | HMDB00122 |
| Pantothenic acid | 0.21 | 0.16 | 382 | 1.31 | 1.92E−01 | 5.82E−01 | Metabolome | HMDB00210 |
| C20:3 FA | 0.11 | 0.08 | 382 | 1.3 | 1.94E−01 | 5.82E−01 | Metabolome | HMDB02925 |
| 16a-hydroxy DHEA 3-sulfate | 0.20 | 0.16 | 382 | 1.3 | 1.93E−01 | 5.82E−01 | Metabolome | |
| L-Alanine | −0.16 | 0.12 | 382 | −1.29 | 1.97E−01 | 5.87E−01 | Metabolome | HMDB00161 |
| Ethylmalonate | −0.17 | 0.13 | 382 | −1.29 | 1.96E−01 | 5.87E−01 | Metabolome | HMDB00622 |
| 3-indoxyl sulfate | −0.13 | 0.10 | 382 | −1.29 | 1.97E−01 | 5.87E−01 | Metabolome | HMDB00682 |
| AST | 0.14 | 0.11 | 417 | 1.29 | 1.99E−01 | 5.88E−01 | Clinical labs | |
| Homoarginine | 0.15 | 0.12 | 382 | 1.28 | 2.00E−01 | 5.91E−01 | Metabolome | HMDB00670 |
| MG(14:1)(3) | 0.16 | 0.12 | 382 | 1.28 | 2.01E−01 | 5.92E−01 | Metabolome | HMDB11531 |
| BDNF | 0.12 | 0.10 | 414 | 1.28 | 2.02E−01 | 5.92E−01 | Immunome | |
| Oxalate (ethanedioate) | −0.13 | 0.10 | 382 | −1.27 | 2.03E−01 | 5.92E−01 | Metabolome | HMDB02329 |
| IL4 | −0.25 | 0.20 | 414 | −1.27 | 2.05E−01 | 5.92E−01 | Immunome | |
| MYH9 | 0.07 | 0.06 | 403 | 1.27 | 2.05E−01 | 5.92E−01 | Proteome | P35579 |
| ADIPOQ | −0.07 | 0.06 | 403 | −1.27 | 2.04E−01 | 5.92E−01 | Proteome | Q15848 |
| MG(24:0)(2) | 0.14 | 0.11 | 382 | 1.26 | 2.08E−01 | 5.92E−01 | Metabolome | HMDB11558 |
| C11:0 AC | −0.14 | 0.11 | 382 | −1.26 | 2.08E−01 | 5.92E−01 | Metabolome | HMDB13321 |
| ALT | 0.14 | 0.11 | 417 | 1.26 | 2.08E−01 | 5.92E−01 | Clinical labs | |
| C20:4, OH FA(1) | 0.12 | 0.10 | 382 | 1.27 | 2.06E−01 | 5.92E−01 | Metabolome | |
| SHBG | −0.06 | 0.05 | 403 | −1.26 | 2.07E−01 | 5.92E−01 | Proteome | P04278 |
| 4-formyl Indole(1) | −0.14 | 0.12 | 382 | −1.25 | 2.10E−01 | 5.96E−01 | Metabolome | |
| Ig heavy chain V-I region V35 | −0.06 | 0.05 | 403 | −1.24 | 2.17E−01 | 6.11E−01 | Proteome | P23083 |
| Theophylline | −0.12 | 0.10 | 382 | −1.22 | 2.22E−01 | 6.22E−01 | Metabolome | HMDB01889 |
| C12:0 FA(1) | 0.14 | 0.12 | 382 | 1.23 | 2.21E−01 | 6.22E−01 | Metabolome | |
| C18:2, OH FA | 0.11 | 0.09 | 382 | 1.22 | 2.23E−01 | 6.24E−01 | Metabolome | |
| C10:3 FA(1) | 0.13 | 0.11 | 382 | 1.22 | 2.25E−01 | 6.25E−01 | Metabolome | |
| B2M | 0.07 | 0.05 | 403 | 1.21 | 2.25E−01 | 6.25E−01 | Proteome | P61769 |
| C18:4 FA | 0.11 | 0.09 | 382 | 1.21 | 2.28E−01 | 6.32E−01 | Metabolome | HMDB06547 |
| Catechol sulfate | −0.38 | 0.32 | 382 | −1.2 | 2.30E−01 | 6.34E−01 | Metabolome | HMDB59724 |
| MG(24:0)(1) | 0.12 | 0.10 | 382 | 1.2 | 2.33E−01 | 6.37E−01 | Metabolome | HMDB11558 |
| C16:1, OH FA(2) | 0.05 | 0.04 | 382 | 1.2 | 2.32E−01 | 6.37E−01 | Metabolome | |
| N6-Carbamoyl-L-threonyladenosine | 0.15 | 0.13 | 382 | 1.18 | 2.37E−01 | 6.45E−01 | Metabolome | HMDB41623 |
| Dihydroferulic acid | −0.21 | 0.17 | 382 | −1.19 | 2.37E−01 | 6.45E−01 | Metabolome | |
| UALB | 0.06 | 0.05 | 270 | 1.18 | 2.38E−01 | 6.45E−01 | Clinical labs | |
| APOA1 | −0.06 | 0.05 | 403 | −1.18 | 2.39E−01 | 6.47E−01 | Proteome | P02647 |
| F13B | 0.06 | 0.05 | 403 | 1.16 | 2.45E−01 | 6.61E−01 | Proteome | P05160 |
| Allantoin | −1.24 | 1.07 | 382 | −1.15 | 2.50E−01 | 6.71E−01 | Metabolome | HMDB00462 |
| (S)-(−)-2-Hydroxyisocapric acid | 0.15 | 0.13 | 382 | 1.14 | 2.54E−01 | 6.77E−01 | Metabolome | HMDB00746 |
| Cys Gly | 0.12 | 0.11 | 382 | 1.14 | 2.54E−01 | 6.77E−01 | Metabolome | HMDB00078 |
| Ig kappa chain V-III region IARC/BL41 | 0.08 | 0.07 | 403 | 1.14 | 2.54E−01 | 6.77E−01 | Proteome | P06311 |
| C12:1 AC | 0.13 | 0.11 | 382 | 1.14 | 2.56E−01 | 6.79E−01 | Metabolome | HMDB13326 |
| FGG | 0.06 | 0.05 | 403 | 1.14 | 2.56E−01 | 6.79E−01 | Proteome | P02679 |
| AG | 0.07 | 0.06 | 419 | 1.13 | 2.58E−01 | 6.82E−01 | Clinical labs | |
| FGA | 0.06 | 0.05 | 403 | 1.13 | 2.60E−01 | 6.84E−01 | Proteome | P02671 |
| 5alpha-Androstan-3alpha,17beta-diol 17-glucuronide(1) | 0.20 | 0.18 | 382 | 1.13 | 2.61E−01 | 6.85E−01 | Metabolome | |
| L-a-Hydroxysovaleric acid | 0.20 | 0.18 | 382 | 1.11 | 2.67E−01 | 6.95E−01 | Metabolome | HMDB00407 |
| Isobutyrylglycine | −0.22 | 0.20 | 382 | −1.11 | 2.67E−01 | 6.95E−01 | Metabolome | HMDB00730 |
| FGB | 0.06 | 0.05 | 403 | 1.11 | 2.69E−01 | 6.99E−01 | Proteome | P02675 |
| C13:1, OH FA | −0.10 | 0.09 | 382 | −1.09 | 2.75E−01 | 7.09E−01 | Metabolome | |
| Ig kappa chain V-III region B6 | 0.06 | 0.05 | 403 | 1.09 | 2.75E−01 | 7.09E−01 | Proteome | P01619 |
| ATP11B | 0.06 | 0.05 | 403 | 1.09 | 2.74E−01 | 7.09E−01 | Proteome | Q9Y2G3 |

TABLE 14-continued

Healthy-Baseline & Dynamic Models: Molecules Associated with high sensitivity C-reactive Protein

| | | | | | | | | |
|---|---|---|---|---|---|---|---|---|
| Ig lambda chain V-IV region Hil | 0.06 | 0.06 | 403 | 1.09 | 2.78E−01 | 7.13E−01 | Proteome | P01717 |
| LysoPC(14:0) | −0.09 | 0.09 | 382 | −1.08 | 2.80E−01 | 7.13E−01 | Metabolome | HMDB10379 |
| NPHP3 | 0.06 | 0.06 | 403 | 1.08 | 2.80E−01 | 7.13E−01 | Proteome | Q7Z494 |
| MYH7 | 0.06 | 0.06 | 403 | 1.08 | 2.81E−01 | 7.15E−01 | Proteome | P12883 |
| ICAM1 | 0.26 | 0.24 | 414 | 1.07 | 2.83E−01 | 7.17E−01 | Immunome | |
| Homostachydrine | −0.22 | 0.21 | 382 | −1.07 | 2.85E−01 | 7.20E−01 | Metabolome | HMDB33433 |
| C10:1 AC | 0.15 | 0.14 | 382 | 1.06 | 2.89E−01 | 7.25E−01 | Metabolome | HMD313205 |
| Ig lambda chain V-VI region EB4 | −0.08 | 0.07 | 403 | −1.06 | 2.90E−01 | 7.25E−01 | Proteome | P06319 |
| NA | −0.08 | 0.07 | 419 | −1.06 | 2.88E−01 | 7.25E−01 | Clinical labs | |
| N-Acetyl-L-phenylalanine | 0.10 | 0.10 | 382 | 1.05 | 2.92E−01 | 7.27E−01 | Metabolome | HMDB00512 |
| MCV | −0.16 | 0.15 | 417 | −1.05 | 2.93E−01 | 7.27E−01 | Clinical labs | |
| FRMPD1 | 0.06 | 0.06 | 403 | 1.05 | 2.92E−01 | 7.27E−01 | Proteome | Q5SYB0 |
| BCHE | 0.06 | 0.06 | 403 | 1.05 | 2.94E−01 | 7.28E−01 | Proteome | P06276 |
| IGF2R | 0.06 | 0.06 | 403 | 1.05 | 2.95E−01 | 7.28E−01 | Proteome | P11717 |
| N-Acetylleucine|N-Acetylisoleucine | 0.08 | 0.08 | 382 | 1.04 | 2.98E−01 | 7.30E−01 | Metabolome | HMDB11756|HMDB61684 |
| Arabonate | Xylonate(2) | −0.09 | 0.08 | 382 | −1.04 | 2.97E−01 | 7.30E−01 | Metabolome | |
| C20:3, OH FA(1) | 0.11 | 0.11 | 382 | 1.04 | 2.99E−01 | 7.30E−01 | Metabolome | |
| APOC2 | 0.05 | 0.05 | 403 | 1.04 | 3.00E−01 | 7.33E−01 | Proteome | P02655 |
| Chenodeoxycholic Acid(1) | −0.15 | 0.15 | 382 | −1.03 | 3.05E−01 | 7.34E−01 | Metabolome | HMDB00518 |
| C12:1 FA(1) | 0.10 | 0.10 | 382 | 1 | 3.18E−01 | 7.34E−01 | Metabolome | HMDB00529 |
| C10:1, DC FA | 0.12 | 0.12 | 382 | 1.01 | 3.14E−01 | 7.34E−01 | Metabolome | HMDB00603 |
| N6,N6,N6-Trimethyl-L-lysine | 0.18 | 0.18 | 382 | 0.99 | 3.24E−01 | 7.34E−01 | Metabolome | HMDB01325 |
| C10:0, OH FA(2) | −0.13 | 0.13 | 382 | −0.99 | 3.21E−01 | 7.34E−01 | Metabolome | HMDB02203 |
| Androsterone sulfate(1) | 0.17 | 0.17 | 382 | 0.99 | 3.23E−01 | 7.34E−01 | Metabolome | HMDB02759 |
| LysoPC(20:5) | −0.13 | 0.13 | 382 | −1.01 | 3.11E−01 | 7.34E−01 | Metabolome | HMDB10397 |
| Gly-Lys or Lys-Gly | 0.11 | 0.11 | 382 | 1.01 | 3.11E−01 | 7.34E−01 | Metabolome | HMDB28846 |
| C17:1 FA | 0.08 | 0.08 | 382 | 1 | 3.20E−01 | 7.34E−01 | Metabolome | HMDB60038 |
| GLU | −0.12 | 0.11 | 419 | −1.03 | 3.05E−01 | 7.34E−01 | Clinical labs | |
| IL12P70 | 0.20 | 0.20 | 414 | 1 | 3.16E−01 | 7.34E−01 | Immunome | |
| IL2 | 0.46 | 0.45 | 414 | 1.02 | 3.07E−01 | 7.34E−01 | Immunome | |
| LDL | 0.11 | 0.11 | 418 | 0.99 | 3.23E−01 | 7.34E−01 | Clinical labs | |
| 1,2,3-benzenetriol sulfate | −0.17 | 0.16 | 382 | −1.02 | 3.08E−01 | 7.34E−01 | Metabolome | |
| C10:1 FA(2) | 0.10 | 0.10 | 382 | 1.02 | 3.07E−01 | 7.34E−01 | Metabolome | |
| C15:0 FA | −0.09 | 0.09 | 382 | −1.01 | 3.12E−01 | 7.34E−01 | Metabolome | |
| C15:0, OH FA | −0.09 | 0.09 | 382 | −0.99 | 3.22E−01 | 7.34E−01 | Metabolome | |
| C14:2, OH FA | 0.08 | 0.08 | 382 | 1.01 | 3.13E−01 | 7.34E−01 | Metabolome | |
| NGF | 0.20 | 0.19 | 414 | 1.03 | 3.06E−01 | 7.34E−01 | Immunome | |
| VCAM1 | 0.09 | 0.09 | 414 | 0.99 | 3.22E−01 | 7.34E−01 | Immunome | |
| CST3 | 0.06 | 0.06 | 403 | 1 | 3.18E−01 | 7.34E−01 | Proteome | P01034 |
| TFRC | 0.06 | 0.05 | 403 | 1.03 | 3.02E−01 | 7.34E−01 | Proteome | P02786 |
| APOD | −0.05 | 0.05 | 403 | −1 | 3.17E−01 | 7.34E−01 | Proteome | P05090 |
| CETP | −0.05 | 0.05 | 403 | −0.99 | 3.22E−01 | 7.34E−01 | Proteome | P11597 |
| ORM2 | 0.05 | 0.05 | 403 | 0.99 | 3.22E−01 | 7.34E−01 | Proteome | P19652 |
| OLFM1 | −0.05 | 0.05 | 403 | −1.02 | 3.07E−01 | 7.34E−01 | Proteome | Q99784 |
| Cholic Acid | −0.25 | 0.26 | 382 | −0.97 | 3.32E−01 | 7.35E−01 | Metabolome | HMDB00619 |
| Dehydroisoandrosterone sulfate (DHEA-S)(1) | −0.11 | 0.12 | 382 | −0.98 | 3.30E−01 | 7.35E−01 | Metabolome | HMDB01032 |
| Sphinganine 1-phosphate | −0.48 | 0.49 | 382 | −0.97 | 3.32E−01 | 7.35E−01 | Metabolome | HMDB01383 |
| TP | 0.08 | 0.08 | 419 | 0.97 | 3.32E−01 | 7.35E−01 | Clinical labs | |
| TRAIL | 0.27 | 0.28 | 414 | 0.97 | 3.30E−01 | 7.35E−01 | Immunome | |
| IGF2 | 0.05 | 0.05 | 403 | 0.97 | 3.33E−01 | 7.35E−01 | Proteome | P01344 |
| Ig heavy chain V-I region HG3 | −0.05 | 0.05 | 403 | −0.97 | 3.34E−01 | 7.35E−01 | Proteome | P01743 |
| APOC3 | 0.05 | 0.05 | 403 | 0.98 | 3.28E−01 | 7.35E−01 | Proteome | P02656 |
| C1QB | 0.05 | 0.05 | 403 | 0.97 | 3.32E−01 | 7.35E−01 | Proteome | P02746 |
| PPBP | 0.05 | 0.05 | 403 | 0.97 | 3.31E−01 | 7.35E−01 | Proteome | P02775 |
| CFP | 0.05 | 0.06 | 403 | 0.97 | 3.33E−01 | 7.35E−01 | Proteome | P27918 |
| C12:1 FA(2) | 0.04 | 0.04 | 382 | 0.96 | 3.38E−01 | 7.42E−01 | Metabolome | HMDB00529 |
| CRISP3 | 0.05 | 0.06 | 403 | 0.96 | 3.39E−01 | 7.42E−01 | Proteome | P54108 |
| Sphinganine | 0.07 | 0.07 | 382 | 0.95 | 3.41E−01 | 7.42E−01 | Metabolome | HMDB00269 |
| C10:3 FA(2) | 0.10 | 0.11 | 382 | 0.95 | 3.41E−01 | 7.42E−01 | Metabolome | |
| Ig heavy chain V-II region WAH | 0.05 | 0.05 | 403 | 0.95 | 3.42E−01 | 7.42E−01 | Proteome | P01824 |
| C8A | 0.05 | 0.05 | 403 | 0.95 | 3.41E−01 | 7.42E−01 | Proteome | P07357 |
| N-formylmethionine | −0.09 | 0.09 | 382 | −0.94 | 3.47E−01 | 7.44E−01 | Metabolome | HMDB01015 |
| Androsterone sulfate(2) | −0.14 | 0.14 | 382 | −0.95 | 3.45E−01 | 7.44E−01 | Metabolome | HMDB02759 |
| Phenylalanylleucine | −0.65 | 0.69 | 382 | −0.94 | 3.47E−01 | 7.44E−01 | Metabolome | |
| MCH | −0.12 | 0.13 | 417 | −0.95 | 3.45E−01 | 7.44E−01 | Clinical labs | |
| TTR | −0.05 | 0.05 | 403 | −0.94 | 3.47E−01 | 7.44E−01 | Proteome | P02766 |
| IFNA | 0.17 | 0.18 | 414 | 0.94 | 3.48E−01 | 7.44E−01 | Immunome | |
| MASP1 | 0.06 | 0.06 | 403 | 0.93 | 3.51E−01 | 7.48E−01 | Proteome | P48740 |
| Taurocholic acid(2) | −1.02 | 1.11 | 382 | −0.92 | 3.59E−01 | 7.48E−01 | Metabolome | HMDB00036 |
| gamma-CEHC | 0.37 | 0.40 | 382 | 0.93 | 3.55E−01 | 7.48E−01 | Metabolome | HMDB01931 |
| 1-Methylxanthine | −0.10 | 0.11 | 382 | −0.92 | 3.59E−01 | 7.48E−01 | Metabolome | HMDB10738 |
| gamma-glutamylthreonine(1) | −0.06 | 0.07 | 382 | −0.93 | 3.52E−01 | 7.48E−01 | Metabolome | HMDB29159 |
| Oleoyl Ethyl Amide | −0.05 | 0.06 | 382 | −0.92 | 3.58E−01 | 7.48E−01 | Metabolome | |
| C20:2, OH FA | 0.12 | 0.13 | 382 | 0.93 | 3.53E−01 | 7.48E−01 | Metabolome | |
| F13A1 | −0.05 | 0.05 | 403 | −0.92 | 3.57E−01 | 7.48E−01 | Proteome | P00488 |
| Ig kappa chain V-I region Scw | 0.06 | 0.06 | 403 | 0.92 | 3.58E−01 | 7.48E−01 | Proteome | P01609 |
| PSTK | −0.05 | 0.06 | 403 | −0.93 | 3.55E−01 | 7.48E−01 | Proteome | Q8IV42 |

TABLE 14-continued

Healthy-Baseline & Dynamic Models: Molecules Associated with high sensitivity C-reactive Protein

| | | | | | | | | |
|---|---|---|---|---|---|---|---|---|
| 3-Methyl-L-histidine | −0.10 | 0.11 | 382 | −0.91 | 3.62E−01 | 7.52E−01 | Metabolome | HMDB00479 |
| Ig heavy chain V-III region BUR | 0.06 | 0.06 | 403 | 0.91 | 3.63E−01 | 7.53E−01 | Proteome | P01773 |
| Hydroxybenzoic acid | 0.41 | 0.46 | 382 | 0.9 | 3.68E−01 | 7.54E−01 | Metabolome | HMDB00500 |
| C14:2 FA | 0.15 | 0.17 | 382 | 0.91 | 3.66E−01 | 7.54E−01 | Metabolome | HMDB00560 |
| C6:0 AC | 0.21 | 0.23 | 382 | 0.9 | 3.67E−01 | 7.54E−01 | Metabolome | HMDB00705 |
| C18:1, 3OH FA | 0.04 | 0.04 | 382 | 0.9 | 3.68E−01 | 7.54E−01 | Metabolome | |
| FCN2 | −0.05 | 0.05 | 403 | −0.9 | 3.67E−01 | 7.54E−01 | Proteome | Q15485 |
| Cys-Pro or Pro-Cys | 0.10 | 0.11 | 382 | 0.89 | 3.72E−01 | 7.61E−01 | Metabolome | HMDB28783 |
| C18:1 AC | −0.08 | 0.09 | 382 | −0.89 | 3.74E−01 | 7.61E−01 | Metabolome | HMDB05065 |
| C15:1 FA | −0.09 | 0.10 | 382 | −0.89 | 3.75E−01 | 7.61E−01 | Metabolome | |
| SERPINA5 | −0.07 | 0.08 | 403 | −0.89 | 3.75E−01 | 7.61E−01 | Proteome | P05154 |
| Fibulin-1 | 0.05 | 0.05 | 403 | 0.88 | 3.77E−01 | 7.63E−01 | Proteome | P23142_4 |
| EOS | −0.15 | 0.17 | 416 | −0.87 | 3.82E−01 | 7.70E−01 | Clinical labs | |
| IGJ | 0.05 | 0.05 | 403 | 0.88 | 3.82E−01 | 7.70E−01 | Proteome | P01591 |
| CD14 | 0.05 | 0.06 | 403 | 0.87 | 3.84E−01 | 7.70E−01 | Proteome | P08571 |
| SAA4 | 0.04 | 0.05 | 403 | 0.87 | 3.83E−01 | 7.70E−01 | Proteome | P35542 |
| C16:0, DC FA(1) | 0.09 | 0.10 | 382 | 0.85 | 3.94E−01 | 7.84E−01 | Metabolome | HMDB00672 |
| C16:1, OH FA(1) | −0.06 | 0.07 | 382 | −0.85 | 3.94E−01 | 7.84E−01 | Metabolome | |
| ASS1 | 0.04 | 0.05 | 403 | 0.85 | 3.95E−01 | 7.84E−01 | Proteome | P00966 |
| Ig heavy chain V-I region EU | 0.05 | 0.06 | 403 | 0.86 | 3.92E−01 | 7.84E−01 | Proteome | P01742 |
| Ig heavy chain V-III region BRO | −0.07 | 0.09 | 403 | −0.85 | 3.97E−01 | 7.85E−01 | Proteome | P01766 |
| MSN | 0.05 | 0.05 | 403 | 0.85 | 3.97E−01 | 7.85E−01 | Proteome | P26038 |
| C18:1 FA | 0.06 | 0.08 | 382 | 0.84 | 4.00E−01 | 7.87E−01 | Metabolome | HMDB00207 |
| Ig kappa chain V-I region AG | 0.04 | 0.05 | 403 | 0.84 | 4.00E−01 | 7.87E−01 | Proteome | P01593 |
| RBP4 | −0.04 | 0.05 | 403 | −0.84 | 4.03E−01 | 7.89E−01 | Proteome | P02753 |
| CFHR1 | 0.06 | 0.07 | 403 | 0.84 | 4.02E−01 | 7.89E−01 | Proteome | Q03591 |
| C24:4 FA | 0.08 | 0.10 | 382 | 0.83 | 4.09E−01 | 7.92E−01 | Metabolome | HMDB06246 |
| LysoPC(16:1) | −0.08 | 0.10 | 382 | −0.83 | 4.10E−01 | 7.92E−01 | Metabolome | HMDB10383 |
| LysoPC(20:3) | −0.07 | 0.09 | 382 | −0.82 | 4.10E−01 | 7.92E−01 | Metabolome | HMDB10393 |
| MG(18:3) | 0.07 | 0.09 | 382 | 0.83 | 4.07E−01 | 7.92E−01 | Metabolome | HMDB11539 |
| C1R | 0.05 | 0.06 | 403 | 0.83 | 4.09E−01 | 7.92E−01 | Proteome | P00736 |
| GAPDH | 0.05 | 0.05 | 403 | 0.83 | 4.10E−01 | 7.92E−01 | Proteome | P04406 |
| Ig mu heavy chain disease protein | 0.04 | 0.05 | 403 | 0.82 | 4.12E−01 | 7.94E−01 | Proteome | P04220 |
| SERPINA7 | −0.04 | 0.05 | 403 | −0.82 | 4.13E−01 | 7.94E−01 | Proteome | P05543 |
| COLEC11 | −0.04 | 0.05 | 403 | −0.82 | 4.14E−01 | 7.94E−01 | Proteome | Q9BWP8 |
| C22:3 FA | 0.07 | 0.09 | 382 | 0.81 | 4.16E−01 | 7.94E−01 | Metabolome | HMDB02823 |
| ENA78 | 0.20 | 0.24 | 414 | 0.82 | 4.15E−01 | 7.94E−01 | Immunome | |
| Piperine(1) | −0.11 | 0.13 | 382 | −0.81 | 4.19E−01 | 7.99E−01 | Metabolome | HMDB29377 |
| ENO1 | 0.04 | 0.05 | 403 | 0.81 | 4.20E−01 | 7.99E−01 | Proteome | P06733 |
| pro-hydroxy-pro(1) | 0.07 | 0.09 | 382 | 0.81 | 4.21E−01 | 7.99E−01 | Metabolome | HMDB06695 |
| L-Formylkynurenine | −0.13 | 0.16 | 382 | −0.8 | 4.22E−01 | 7.99E−01 | Metabolome | HMDB60485 |
| C16:1 AC | 0.08 | 0.10 | 382 | 0.8 | 4.24E−01 | 8.01E−01 | Metabolome | HMDB06317 |
| VASN | −0.04 | 0.05 | 403 | −0.8 | 4.26E−01 | 8.03E−01 | Proteome | Q6EMK4 |
| Tryptophan betaine | −0.03 | 0.04 | 382 | −0.79 | 4.30E−01 | 8.06E−01 | Metabolome | HMDB61115 |
| BTD | 0.05 | 0.06 | 403 | 0.79 | 4.29E−01 | 8.06E−01 | Proteome | P43251 |
| Cys-Gly or Gly-Cys | 0.09 | 0.12 | 382 | 0.79 | 4.33E−01 | 8.09E−01 | Metabolome | HMDB00078 |
| ITIH3 | 0.07 | 0.08 | 403 | 0.78 | 4.35E−01 | 8.12E−01 | Proteome | Q06033 |
| CPB2 | 0.04 | 0.06 | 403 | 0.78 | 4.37E−01 | 8.14E−01 | Proteome | Q96IY4 |
| F9 | 0.04 | 0.05 | 403 | 0.78 | 4.38E−01 | 8.15E−01 | Proteome | P00740 |
| C16:0, OH FA(1) | −0.07 | 0.09 | 382 | −0.77 | 4.41E−01 | 8.17E−01 | Metabolome | HMDB31057 |
| APCS | −0.04 | 0.05 | 403 | −0.77 | 4.43E−01 | 8.17E−01 | Proteome | P02743 |
| Ig lambda chain V-I region BL2 | −0.04 | 0.05 | 403 | −0.77 | 4.42E−01 | 8.17E−01 | Proteome | P06316 |
| C18 Sphingosine 1-phosphate | −0.05 | 0.07 | 382 | −0.76 | 4.45E−01 | 8.19E−01 | Metabolome | HMDB00277 |
| VTN | 0.04 | 0.05 | 403 | 0.76 | 4.45E−01 | 8.19E−01 | Proteome | P04004 |
| L-Carnitine | −0.09 | 0.12 | 382 | −0.76 | 4.51E−01 | 8.24E−01 | Metabolome | HMDB00062 |
| Gluconic acid | −0.03 | 0.04 | 382 | −0.73 | 4.68E−01 | 8.24E−01 | Metabolome | HMDB00625 |
| C18:0, DC FA(3) | −0.06 | 0.09 | 382 | −0.74 | 4.61E−01 | 8.24E−01 | Metabolome | HMDB00782 |
| 7-Methylguanine | 0.06 | 0.08 | 382 | 0.74 | 4.60E−01 | 8.24E−01 | Metabolome | HMDB00897 |
| C24:6 FA | −0.11 | 0.15 | 382 | −0.73 | 4.67E−01 | 8.24E−01 | Metabolome | HMDB02007 |
| C10:0, OH FA(1) | 0.15 | 0.21 | 382 | 0.74 | 4.59E−01 | 8.24E−01 | Metabolome | HMDB02203 |
| LysoPE(22:5) | −0.06 | 0.09 | 382 | −0.73 | 4.67E−01 | 8.24E−01 | Metabolome | HMDB11494 |
| GCSF | 0.19 | 0.26 | 414 | 0.73 | 4.66E−01 | 8.24E−01 | Immunome | |
| Hydroxyhippurate(1) | 0.05 | 0.06 | 382 | 0.75 | 4.53E−01 | 8.24E−01 | Metabolome | |
| APOL1 | 0.04 | 0.05 | 403 | 0.74 | 4.60E−01 | 8.24E−01 | Proteome | O14791 |
| APOE | 0.04 | 0.05 | 403 | 0.74 | 4.63E−01 | 8.24E−01 | Proteome | P02649 |
| APOC1 | −0.04 | 0.05 | 403 | −0.73 | 4.66E−01 | 8.24E−01 | Proteome | P02654 |
| AMBP | 0.04 | 0.05 | 403 | 0.74 | 4.58E−01 | 8.24E−01 | Proteome | P02760 |
| Ig kappa chain V-III region GOL | 0.05 | 0.07 | 403 | 0.73 | 4.66E−01 | 8.24E−01 | Proteome | P04206 |
| A1BG | 0.04 | 0.05 | 403 | 0.76 | 4.50E−01 | 8.24E−01 | Proteome | P04217 |
| C4BPB | 0.04 | 0.05 | 403 | 0.73 | 4.64E−01 | 8.24E−01 | Proteome | P02851 |
| Microtubule-associated protein 4 | 0.05 | 0.06 | 403 | 0.74 | 4.62E−01 | 8.24E−01 | Proteome | P27816_2 |
| LYZ | 0.04 | 0.06 | 403 | 0.73 | 4.65E−01 | 8.24E−01 | Proteome | P61626 |
| MMRN1 | −0.04 | 0.06 | 403 | −0.73 | 4.67E−01 | 8.24E−01 | Proteome | Q13201 |
| Rho GTPase-activating protein 19 | 0.04 | 0.06 | 403 | 0.74 | 4.60E−01 | 8.24E−01 | Proteome | Q14CB8_6 |
| IL31 | 0.16 | 0.22 | 414 | 0.71 | 4.75E−01 | 8.31E−01 | Immunome | |
| K | 0.05 | 0.07 | 419 | 0.72 | 4.73E−01 | 8.31E−01 | Clinical labs | |
| CTTNBP2 | 0.04 | 0.05 | 403 | 0.72 | 4.75E−01 | 8.31E−01 | Proteome | Q8WZ74 |
| Endophilin-A3 | −0.04 | 0.05 | 403 | −0.72 | 4.73E−01 | 8.31E−01 | Proteome | Q99963_3 |

TABLE 14-continued

Healthy-Baseline & Dynamic Models: Molecules Associated with high sensitivity C-reactive Protein

| Molecule | | | | | | | |
|---|---|---|---|---|---|---|---|
| Proteoglycan 4 | 0.04 | 0.06 | 403 | 0.71 | 4.79E-01 | 8.35E-01 | Proteome | Q92954_6 |
| Ig lambda chain V-I region NEWM | 0.04 | 0.05 | 403 | 0.7 | 4.82E-01 | 8.39E-01 | Proteome | P01703 |
| IGHD | 0.14 | 0.21 | 403 | 0.7 | 4.84E-01 | 8.40E-01 | Proteome | P01880 |
| MG(20:0) | 0.06 | 0.08 | 382 | 0.7 | 4.86E-01 | 8.40E-01 | Metabolome | HMDB11542 |
| C16:0, OH FA(2) | 0.06 | 0.08 | 382 | 0.69 | 4.89E-01 | 8.40E-01 | Metabolome | HMDB31057 |
| ATRN(1) | 0.03 | 0.05 | 403 | 0.69 | 4.90E-01 | 8.40E-01 | Proteome | O75882 |
| SERPINC1 | −0.04 | 0.05 | 403 | −0.69 | 4.88E-01 | 8.40E-01 | Proteome | P01008 |
| Ig heavy chain V-II region HIL | 0.05 | 0.07 | 403 | 0.69 | 4.89E-01 | 8.40E-01 | Proteome | P01771 |
| DYNC1H1 | −0.04 | 0.05 | 403 | −0.69 | 4.88E-01 | 8.40E-01 | Proteome | Q14204 |
| Dihydroxyvitamin D3(1) | −0.07 | 0.09 | 382 | −0.69 | 4.92E-01 | 8.41E-01 | Metabolome | HMDB00430 |
| Indoleacetyl glutamine | −0.09 | 0.13 | 382 | −0.68 | 4.96E-01 | 8.41E-01 | Metabolome | HMDB13240 |
| Piperine(2) | −0.10 | 0.15 | 382 | −0.68 | 4.96E-01 | 8.41E-01 | Metabolome | HMDB29377 |
| CL | −0.05 | 0.08 | 419 | −0.68 | 4.96E-01 | 8.41E-01 | Clinical labs | |
| Ig kappa chain V-III region NG9 | 0.04 | 0.05 | 403 | 0.69 | 4.93E-01 | 8.41E-01 | Proteome | P01621 |
| C8B | 0.03 | 0.05 | 403 | 0.68 | 4.96E-01 | 8.41E-01 | Proteome | P07358 |
| Betonicine | −0.12 | 0.18 | 382 | −0.67 | 5.03E-01 | 8.45E-01 | Metabolome | HMDB29412 |
| FN1 | 0.03 | 0.05 | 403 | 0.67 | 5.04E-01 | 8.45E-01 | Proteome | P02751 |
| SERPINA4 | −0.04 | 0.05 | 403 | −0.67 | 5.03E-01 | 8.45E-01 | Proteome | P29622 |
| IGFALS | −0.03 | 0.05 | 403 | −0.67 | 5.02E-01 | 8.45E-01 | Proteome | P35858 |
| SEPP1 | −0.03 | 0.05 | 403 | −0.67 | 5.03E-01 | 8.45E-01 | Proteome | P49908 |
| Phenylpyruvic acid | −0.10 | 0.16 | 382 | −0.67 | 5.06E-01 | 8.47E-01 | Metabolome | HMDB00205 |
| Hydroxybutyric acid(1) | 0.07 | 0.10 | 382 | 0.66 | 5.07E-01 | 8.47E-01 | Metabolome | |
| C14:1 FA(1) | 0.08 | 0.13 | 382 | 0.65 | 5.15E-01 | 8.47E-01 | Metabolome | HMDB02000 |
| gamma-glutamyl-epsilon-lysine | −0.07 | 0.10 | 382 | −0.64 | 5.23E-01 | 8.47E-01 | Metabolome | HMDB03869 |
| 7-alpha-hydroxy-3-oxo-4-cholestenoate (7-Hoca) | −0.05 | 0.08 | 382 | −0.64 | 5.23E-01 | 8.47E-01 | Metabolome | HMDB12458 |
| C11:1 FA | −0.07 | 0.10 | 382 | −0.65 | 5.17E-01 | 8.47E-01 | Metabolome | HMDB33724 |
| Arabitol | Xylitol | 0.07 | 0.10 | 382 | 0.66 | 5.12E-01 | 8.47E-01 | Metabolome | |
| MCP1 | −0.08 | 0.13 | 414 | −0.65 | 5.15E-01 | 8.47E-01 | Immunome | |
| Ig kappa chain V-I region AU | 0.04 | 0.06 | 403 | 0.65 | 5.15E-01 | 8.47E-01 | Proteome | P01594 |
| IGHG4 | −0.10 | 0.15 | 403 | −0.65 | 5.18E-01 | 8.47E-01 | Proteome | P01861 |
| Ig kappa chain V-I region BAN | 0.03 | 0.05 | 403 | 0.64 | 5.21E-01 | 8.47E-01 | Proteome | P04430 |
| SERPING1 | −0.03 | 0.05 | 403 | −0.65 | 5.17E-01 | 8.47E-01 | Proteome | P05155 |
| GSN | −0.03 | 0.05 | 403 | −0.65 | 5.18E-01 | 8.47E-01 | Proteome | P06396 |
| PFN1 | 0.04 | 0.06 | 403 | 0.65 | 5.17E-01 | 8.47E-01 | Proteome | P07737 |
| Ryanodine receptor 2 | 0.03 | 0.05 | 403 | 0.64 | 5.20E-01 | 8.47E-01 | Proteome | Q92736_2 |
| PGLYRP2 | 0.03 | 0.05 | 403 | 0.66 | 5.10E-01 | 8.47E-01 | Proteome | Q96PD5 |
| FCGBP | 0.04 | 0.06 | 403 | 0.65 | 5.17E-01 | 8.47E-01 | Proteome | Q9Y6R7 |
| cont_000017 | 0.03 | 0.05 | 403 | 0.65 | 5.19E-01 | 8.47E-01 | Proteome | |
| L-Histidine | 0.03 | 0.05 | 382 | 0.64 | 5.25E-01 | 8.48E-01 | Metabolome | HMDB00177 |
| C8:0, OH FA(2) | −0.09 | 0.14 | 382 | −0.63 | 5.27E-01 | 8.51E-01 | Metabolome | |
| L-Arginine | −0.05 | 0.08 | 382 | −0.63 | 5.31E-01 | 8.52E-01 | Metabolome | HMDB00517 |
| N-Acetylserine | 0.05 | 0.08 | 382 | 0.63 | 5.31E-01 | 8.52E-01 | Metabolome | HMDB02931 |
| C22:5 FA | −0.06 | 0.10 | 382 | −0.63 | 5.30E-01 | 8.52E-01 | Metabolome | HMDB06528 |
| MGP | 0.04 | 0.07 | 403 | 0.61 | 5.41E-01 | 8.66E-01 | Proteome | P08493 |
| CPN2 | −0.03 | 0.05 | 403 | −0.61 | 5.42E-01 | 8.66E-01 | Proteome | P22792 |
| Dehydroisoandrosterone sulfate (DHEA-S)(2) | 0.10 | 0.17 | 382 | 0.61 | 5.45E-01 | 8.66E-01 | Metabolome | HMDB01032 |
| C14:0, OH FA(1) | 0.07 | 0.12 | 382 | 0.61 | 5.43E-01 | 8.66E-01 | Metabolome | HMDB02261 |
| LysoPE(22:4) | −0.06 | 0.10 | 382 | −0.61 | 5.44E-01 | 8.66E-01 | Metabolome | HMDB11493 |
| C14:0 FA | 0.05 | 0.08 | 382 | 0.58 | 5.60E-01 | 8.67E-01 | Metabolome | HMDB00806 |
| C14:1 AC | 0.07 | 0.12 | 382 | 0.6 | 5.49E-01 | 8.67E-01 | Metabolome | HMDB02014 |
| LysoPE(16:1) | 0.07 | 0.11 | 382 | 0.58 | 5.60E-01 | 8.67E-01 | Metabolome | HMDB11474 |
| IL23 | −0.17 | 0.29 | 414 | −0.59 | 5.56E-01 | 8.67E-01 | Immunome | |
| IL5 | 0.15 | 0.26 | 414 | 0.59 | 5.53E-01 | 8.67E-01 | Immunome | |
| CA1 | 0.03 | 0.05 | 403 | 0.59 | 5.58E-01 | 8.67E-01 | Proteome | P00915 |
| Ig lambda chain V-III region SH | −0.03 | 0.05 | 403 | −0.59 | 5.58E-01 | 8.67E-01 | Proteome | P01714 |
| Ig lambda chain V-V region DEL | 0.09 | 0.15 | 403 | 0.6 | 5.51E-01 | 8.67E-01 | Proteome | P01719 |
| C2 | 0.03 | 0.05 | 403 | 0.58 | 5.60E-01 | 8.67E-01 | Proteome | P06681 |
| GPX3 | 0.04 | 0.06 | 403 | 0.59 | 5.56E-01 | 8.67E-01 | Proteome | P22352 |
| PROZ | −0.04 | 0.06 | 403 | −0.6 | 5.51E-01 | 8.67E-01 | Proteome | P22891 |
| ATP5A1 | −0.04 | 0.06 | 403 | −0.59 | 5.57E-01 | 8.67E-01 | Proteome | P25705 |
| COMP | −0.03 | 0.05 | 403 | −0.6 | 5.50E-01 | 8.67E-01 | Proteome | P49747 |
| LGALS3BP | 0.03 | 0.05 | 403 | 0.59 | 5.57E-01 | 8.67E-01 | Proteome | Q08380 |
| ILK | 0.03 | 0.05 | 403 | 0.58 | 5.61E-01 | 8.67E-01 | Proteome | Q13418 |
| 5-methyluridine (ribothymidine) | 0.06 | 0.11 | 382 | 0.58 | 5.64E-01 | 8.69E-01 | Metabolome | HMDB00884 |
| Thyroxine | 0.06 | 0.11 | 382 | 0.58 | 5.64E-01 | 8.69E-01 | Metabolome | HMDB01918 |
| PIGR | 0.03 | 0.06 | 403 | 0.57 | 5.66E-01 | 8.70E-01 | Proteome | P01833 |
| Ig kappa chain V-I region Ni | 0.03 | 0.05 | 403 | 0.57 | 5.67E-01 | 8.70E-01 | Proteome | P01613 |
| C10:0 AC | 0.02 | 0.04 | 382 | 0.57 | 5.69E-01 | 8.70E-01 | Metabolome | HMDB00651 |
| Ig kappa chain V-II region RPMI 6410 | −0.04 | 0.07 | 403 | −0.57 | 5.69E-01 | 8.70E-01 | Proteome | P06310 |
| C3 | 0.03 | 0.05 | 403 | 0.57 | 5.70E-01 | 8.70E-01 | Proteome | P01024 |
| Chenodeoxycholic acid glycine conjugate(2) | 0.18 | 0.32 | 382 | 0.56 | 5.77E-01 | 8.74E-01 | Metabolome | HMDB00637 |
| Chenodeoxycholic acid 3-sulfate | −0.06 | 0.11 | 382 | −0.55 | 5.79E-01 | 8.74E-01 | Metabolome | HMDB02639 |
| 2-Piperidinone | −0.09 | 0.17 | 382 | −0.56 | 5.74E-01 | 8.74E-01 | Metabolome | HMDB11749 |
| Cyclo(ala-pro) | −0.05 | 0.09 | 382 | −0.56 | 5.75E-01 | 8.74E-01 | Metabolome | |
| 5alpha-Androstan-3alpha,17beta-diol | −0.08 | 0.14 | 382 | −0.56 | 5.78E-01 | 8.74E-01 | Metabolome | |

TABLE 14-continued

Healthy-Baseline & Dynamic Models: Molecules Associated with high sensitivity C-reactive Protein

| | | | | | | | | |
|---|---|---|---|---|---|---|---|---|
| 17-glucuronide(2) | | | | | | | | |
| HPR | −0.03 | 0.05 | 403 | −0.55 | 5.80E−01 | 8.74E−01 | Proteome | P00739 |
| cont_000107 | 0.03 | 0.06 | 403 | 0.55 | 5.80E−01 | 8.74E−01 | Proteome | |
| Urocanic acid | −0.05 | 0.08 | 382 | −0.55 | 5.82E−01 | 8.75E−01 | Metabolome | HMDB00301 |
| 5alpha-Androstan-3alpha,17alpha-diol monosulfate(2) | 0.11 | 0.21 | 382 | 0.55 | 5.84E−01 | 8.75E−01 | Metabolome | |
| Ig kappa chain V-I region Roy | 0.04 | 0.08 | 403 | 0.55 | 5.85E−01 | 8.75E−01 | Proteome | P01608 |
| APOH | 0.03 | 0.05 | 403 | 0.54 | 5.86E−01 | 8.75E−01 | Proteome | P02749 |
| C6 | 0.03 | 0.05 | 403 | 0.55 | 5.85E−01 | 8.75E−01 | Proteome | P13671 |
| Paraxanthine | 0.07 | 0.13 | 382 | 0.54 | 5.88E−01 | 8.76E−01 | Metabolome | HMDB01860 |
| C5 | 0.03 | 0.05 | 403 | 0.54 | 5.89E−01 | 8.77E−01 | Proteome | P01031 |
| Glycerophophocholine | 0.03 | 0.06 | 382 | 0.52 | 6.02E−01 | 8.81E−01 | Metabolome | HMDB00086 |
| C16:0, DC FA(2) | −0.05 | 0.10 | 382 | −0.53 | 5.99E−01 | 8.81E−01 | Metabolome | HMDB00672 |
| Phenyllactate (PLA) | 0.07 | 0.13 | 382 | 0.53 | 5.94E−01 | 8.81E−01 | Metabolome | HMDB00779 |
| C8:0 AC | 0.02 | 0.04 | 382 | 0.52 | 6.04E−01 | 8.81E−01 | Metabolome | HMDB00791 |
| L-Valine | 0.06 | 0.12 | 382 | 0.53 | 5.99E−01 | 8.81E−01 | Metabolome | HMDB00883 |
| Palmitoylglycine | −0.05 | 0.09 | 382 | −0.53 | 5.94E−01 | 8.81E−01 | Metabolome | HMDB13034 |
| Phenylalanylphenylalanine | −1.31 | 2.51 | 382 | −0.52 | 6.00E−01 | 8.81E−01 | Metabolome | HMDB13302 |
| HCT | 0.06 | 0.12 | 417 | 0.52 | 6.02E−01 | 8.81E−01 | Clinical labs | |
| C14:0, OH FA(2) | 0.04 | 0.08 | 382 | 0.53 | 5.97E−01 | 8.81E−01 | Metabolome | |
| IGFBP3 | 0.03 | 0.05 | 403 | 0.53 | 5.96E−01 | 8.81E−01 | Proteome | P17936 |
| VCL | 0.03 | 0.06 | 403 | 0.52 | 6.03E−01 | 8.81E−01 | Proteome | P18206 |
| L-Tryptophan | 0.05 | 0.10 | 382 | 0.51 | 6.10E−01 | 8.89E−01 | Metabolome | HMDB00929 |
| CAMP | 0.03 | 0.06 | 403 | 0.51 | 6.11E−01 | 8.89E−01 | Proteome | P49913 |
| C14:0, DC FA(2) | 0.05 | 0.10 | 382 | 0.5 | 6.15E−01 | 8.90E−01 | Metabolome | HMDB00872 |
| HRG | −0.03 | 0.05 | 403 | −0.5 | 6.15E−01 | 8.90E−01 | Proteome | P04196 |
| CNDP1 | 0.03 | 0.06 | 403 | 0.5 | 6.15E−01 | 8.90E−01 | Proteome | Q96KN2 |
| L-Cystine | 0.04 | 0.09 | 382 | 0.5 | 6.20E−01 | 8.96E−01 | Metabolome | HMDB00192 |
| Chenodeoxycholic acid glycine conjugate(1) | 0.08 | 0.17 | 382 | 0.49 | 6.21E−01 | 8.97E−01 | Metabolome | HMDB00637 |
| L-Proline | 0.12 | 0.24 | 382 | 0.49 | 6.23E−01 | 8.97E−01 | Metabolome | HMDB00162 |
| Bilirubin | 0.08 | 0.18 | 382 | 0.46 | 6.49E−01 | 8.98E−01 | Metabolome | HMDB00054 |
| Xanthine | 0.04 | 0.09 | 382 | 0.47 | 6.41E−01 | 8.98E−01 | Metabolome | HMDB00292 |
| C10:0, DC FA (Sebacic acid)(2) | −0.08 | 0.18 | 382 | −0.47 | 6.41E−01 | 8.98E−01 | Metabolome | HMDB00792 |
| C12:1, DC FA(2) | −0.15 | 0.31 | 382 | −0.48 | 6.31E−01 | 8.98E−01 | Metabolome | HMDB00933 |
| Symmetric dimethylarginine | 0.03 | 0.08 | 382 | 0.45 | 6.50E−01 | 8.98E−01 | Metabolome | HMDB01539 |
| Ne-Methyl-Lysine | −0.07 | 0.16 | 382 | −0.47 | 6.41E−01 | 8.98E−01 | Metabolome | HMDB02038 |
| C18:2 AC | −0.05 | 0.10 | 382 | −0.47 | 6.38E−01 | 8.98E−01 | Metabolome | HMDB06461 |
| MG(18:0) | −0.04 | 0.08 | 382 | −0.46 | 6.44E−01 | 8.98E−01 | Metabolome | HMDB11131 |
| LysoPI(18:1) | 0.05 | 0.09 | 382 | 0.49 | 6.27E−01 | 8.98E−01 | Metabolome | HMDB61693 |
| Sulfuric acid | −0.06 | 0.13 | 382 | −0.47 | 6.36E−01 | 8.98E−01 | Metabolome | |
| C18:1, DC FA | −0.05 | 0.11 | 382 | −0.46 | 6.49E−01 | 8.98E−01 | Metabolome | |
| C8:2, OH FA(1) | −0.08 | 0.17 | 382 | −0.45 | 6.50E−01 | 8.98E−01 | Metabolome | |
| N-acetyl-1-methylhistidine | 0.07 | 0.16 | 382 | 0.46 | 6.49E−01 | 8.98E−01 | Metabolome | |
| F2 | 0.02 | 0.05 | 403 | 0.47 | 6.36E−01 | 8.98E−01 | Proteome | P00734 |
| Ig heavy chain V-III region GAL | −0.03 | 0.06 | 403 | −0.46 | 6.43E−01 | 8.98E−01 | Proteome | P01781 |
| APOA2 | −0.02 | 0.05 | 403 | −0.47 | 6.41E−01 | 8.98E−01 | Proteome | P02652 |
| KLKB1 | −0.03 | 0.06 | 403 | −0.48 | 6.33E−01 | 8.98E−01 | Proteome | P03952 |
| Ig kappa chain V-III region CLL | 0.03 | 0.06 | 403 | 0.47 | 6.37E−01 | 8.98E−01 | Proteome | P04207 |
| SERPIND1 | 0.02 | 0.05 | 403 | 0.48 | 6.32E−01 | 8.98E−01 | Proteome | P05546 |
| Ig lambda chain V-VI region SUT | −0.04 | 0.08 | 403 | −0.46 | 6.46E−01 | 8.98E−01 | Proteome | P06317 |
| LDHB | 0.03 | 0.05 | 403 | 0.47 | 6.41E−01 | 8.98E−01 | Proteome | P07195 |
| AZGP1 | −0.02 | 0.05 | 403 | −0.46 | 6.48E−01 | 8.98E−01 | Proteome | P25311 |
| PI16 | 0.03 | 0.06 | 403 | 0.46 | 6.48E−01 | 8.98E−01 | Proteome | Q6UXB8 |
| Protein FAM161B | −0.03 | 0.05 | 403 | −0.49 | 6.27E−01 | 8.98E−01 | Proteome | Q96MY7 |
| INSU | −0.10 | 0.20 | 403 | −0.51 | 6.48E−01 | 8.98E−01 | Clinical labs | |
| APOA4 | −0.02 | 0.05 | 403 | −0.45 | 6.51E−01 | 8.98E−01 | Proteome | P06727 |
| L-Tyrosine | 0.04 | 0.08 | 382 | 0.45 | 6.54E−01 | 8.99E−01 | Metabolome | HMDB00158 |
| C24:5 FA | 0.05 | 0.11 | 382 | 0.45 | 6.54E−01 | 8.99E−01 | Metabolome | HMDB06322 |
| Choline | 0.03 | 0.07 | 382 | 0.45 | 6.56E−01 | 9.00E−01 | Metabolome | HMDB00097 |
| C3:1 AC | −0.02 | 0.04 | 382 | −0.44 | 6.61E−01 | 9.03E−01 | Metabolome | HMDB13124 |
| eugenol sulfate | −0.11 | 0.25 | 382 | −0.44 | 6.61E−01 | 9.03E−01 | Metabolome | |
| F10 | 0.02 | 0.05 | 403 | 0.44 | 6.59E−01 | 9.03E−01 | Proteome | P00742 |
| ITIH2 | −0.02 | 0.05 | 403 | −0.44 | 6.62E−01 | 9.03E−01 | Proteome | P19823 |
| C13:0, DC FA(4) | 0.05 | 0.10 | 382 | 0.43 | 6.64E−01 | 9.04E−01 | Metabolome | HMDB02327 |
| CP | 0.02 | 0.05 | 403 | 0.43 | 6.65E−01 | 9.04E−01 | Proteome | P00450 |
| Chenodeoxycholic Acid(3) | 0.12 | 0.29 | 382 | 0.43 | 6.68E−01 | 9.05E−01 | Metabolome | HMDB00518 |
| C1S | 0.02 | 0.05 | 403 | 0.43 | 6.67E−01 | 9.05E−01 | Proteome | P09871 |
| SCF | 0.06 | 0.15 | 414 | 0.43 | 6.70E−01 | 9.06E−01 | Immunome | |
| C12:1, DC FA(3) | −0.04 | 0.09 | 382 | −0.42 | 6.77E−01 | 9.07E−01 | Metabolome | HMDB00933 |
| N-(1-Deoxy-1-fructosyl)valine | −0.03 | 0.07 | 382 | −0.42 | 6.77E−01 | 9.07E−01 | Metabolome | HMDB37844 |
| C22:2 FA | 0.03 | 0.08 | 382 | 0.42 | 6.75E−01 | 9.07E−01 | Metabolome | HMDB61714 |
| A2M | −0.02 | 0.05 | 403 | −0.42 | 6.76E−01 | 9.07E−01 | Proteome | P01023 |
| C1QC | 0.02 | 0.05 | 403 | 0.42 | 6.75E−01 | 9.07E−01 | Proteome | P02747 |
| CPN1 | 0.02 | 0.05 | 403 | 0.42 | 6.76E−01 | 9.07E−01 | Proteome | P15169 |
| C3:0 AC | −0.07 | 0.17 | 382 | −0.41 | 6.80E−01 | 9.08E−01 | Metabolome | HMDB00824 |
| C7 | −0.02 | 0.05 | 403 | −0.41 | 6.80E−01 | 9.08E−01 | Proteome | P10643 |
| LysoPE(20:2) | 0.02 | 0.04 | 382 | 0.41 | 6.83E−01 | 9.09E−01 | Metabolome | HMDB11483 |

TABLE 14-continued

Healthy-Baseline & Dynamic Models: Molecules Associated with high sensitivity C-reactive Protein

| | | | | | | | | |
|---|---|---|---|---|---|---|---|---|
| C16:0, 2OH FA | 0.04 | 0.09 | 382 | 0.41 | 6.84E-01 | 9.09E-01 | Metabolome | |
| SERPINA3 | 0.02 | 0.05 | 403 | 0.41 | 6.84E-01 | 9.09E-01 | Proteome | P01011 |
| C12:0, OH FA(1) | 0.05 | 0.13 | 382 | 0.4 | 6.88E-01 | 9.11E-01 | Metabolome | HMDB00387 |
| L-Cysteine | 0.02 | 0.05 | 382 | 0.4 | 6.89E-01 | 9.11E-01 | Metabolome | HMDB00574 |
| CD5L | 0.02 | 0.06 | 403 | 0.4 | 6.88E-01 | 9.11E-01 | Proteome | O43866 |
| Ig heavy chain V-III region WEA | 0.02 | 0.06 | 403 | 0.4 | 6.91E-01 | 9.11E-01 | Proteome | P01763 |
| HBA1 | -0.02 | 0.05 | 403 | -0.4 | 6.90E-01 | 9.11E-01 | Proteome | P69905 |
| C8:0, OH FA(1) | -0.04 | 0.10 | 382 | -0.4 | 6.93E-01 | 9.12E-01 | Metabolome | |
| Ig kappa chain V-I region Mev | 0.03 | 0.08 | 403 | 0.39 | 6.95E-01 | 9.13E-01 | Proteome | P01612 |
| L-a-glutamyl-L-Lysine | 0.04 | 0.10 | 382 | 0.39 | 6.98E-01 | 9.14E-01 | Metabolome | HMDB04207 |
| C12:1, OH FA | 0.06 | 0.14 | 382 | 0.39 | 6.98E-01 | 9.14E-01 | Metabolome | |
| C20:1 FA | -0.03 | 0.08 | 382 | -0.39 | 6.99E-01 | 9.14E-01 | Metabolome | HMDB02231 |
| Ig lambda chain V-II region BUR | -0.03 | 0.07 | 403 | -0.39 | 7.00E-01 | 9.14E-01 | Proteome | P01708 |
| AGT | 0.02 | 0.05 | 403 | 0.38 | 7.01E-01 | 9.15E-01 | Proteome | P01019 |
| IGLL5 | -0.02 | 0.05 | 403 | -0.37 | 7.08E-01 | 9.15E-01 | Proteome | B9A064 |
| C22:6 FA | -0.02 | 0.07 | 382 | -0.38 | 7.06E-01 | 9.15E-01 | Metabolome | HMDB02183 |
| C5:1 AC | -0.05 | 0.13 | 382 | -0.36 | 7.17E-01 | 9.15E-01 | Metabolome | HMDB02366 |
| C14:0 AC | 0.04 | 0.11 | 382 | 0.36 | 7.17E-01 | 9.15E-01 | Metabolome | HMDB05066 |
| CD40L | -0.11 | 0.31 | 414 | -0.37 | 7.14E-01 | 9.15E-01 | Immunome | |
| HGB | 0.04 | 0.12 | 417 | 0.37 | 7.14E-01 | 9.15E-01 | Clinical labs | |
| IL27 | 0.09 | 0.24 | 414 | 0.37 | 7.11E-01 | 9.15E-01 | Immunome | |
| C16:4 FA | -0.05 | 0.15 | 382 | -0.36 | 7.17E-01 | 9.15E-01 | Metabolome | |
| 5alpha-Androstan-3alpha,17alpha-diol monosulfate(1) | -0.09 | 0.24 | 382 | -0.37 | 7.14E-01 | 9.15E-01 | Metabolome | |
| PLG | 0.02 | 0.05 | 403 | 0.37 | 7.13E-01 | 9.15E-01 | Proteome | P00747 |
| Ig heavy chain V-III region BUT | -0.02 | 0.05 | 403 | -0.37 | 7.13E-01 | 9.15E-01 | Proteome | P01767 |
| IGHA2 | -0.02 | 0.05 | 403 | -0.37 | 7.10E-01 | 9.15E-01 | Proteome | P01877 |
| SERPINA6 | 0.02 | 0.06 | 403 | 0.37 | 7.15E-01 | 9.15E-01 | Proteome | P08185 |
| PON3 | 0.02 | 0.05 | 403 | 0.38 | 7.06E-01 | 9.15E-01 | Proteome | Q15166 |
| ACTBL2 | -0.02 | 0.05 | 403 | -0.37 | 7.13E-01 | 9.15E-01 | Proteome | Q562R1 |
| IGLC2 | 0.02 | 0.06 | 403 | 0.36 | 7.19E-01 | 9.16E-01 | Proteome | P0CG05 |
| Androsterone glucuronide(1) | -0.05 | 0.14 | 382 | -0.35 | 7.25E-01 | 9.20E-01 | Metabolome | HMDB02829 |
| C14:2 AC | 0.04 | 0.11 | 382 | 0.35 | 7.25E-01 | 9.20E-01 | Metabolome | HMDB13331 |
| FAM3C | 0.02 | 0.06 | 403 | 0.34 | 7.31E-01 | 9.27E-01 | Proteome | Q92520 |
| Pyruvic acid | -0.05 | 0.14 | 382 | -0.32 | 7.46E-01 | 9.28E-01 | Metabolome | HMDB00243 |
| Hexosamine | -0.03 | 0.10 | 382 | -0.32 | 7.48E-01 | 9.28E-01 | Metabolome | HMDB01514 |
| Alpha-ketoisovaleric acid | 0.04 | 0.13 | 382 | 0.31 | 7.55E-01 | 9.28E-01 | Metabolome | HMDB00019 |
| C16:0 AC | 0.03 | 0.10 | 382 | 0.31 | 7.57E-01 | 9.28E-01 | Metabolome | HMDB00222 |
| C11:0, DC FA | 0.05 | 0.17 | 382 | 0.31 | 7.56E-01 | 9.28E-01 | Metabolome | HMDB00888 |
| C20:4 FA | 0.02 | 0.05 | 382 | 0.31 | 7.54E-01 | 9.28E-01 | Metabolome | HMDB01043 |
| C12:0 AC | 0.02 | 0.05 | 382 | 0.33 | 7.41E-01 | 9.28E-01 | Metabolome | HMDB02250 |
| Tetrahydroaldosterone-3-glucuronide(2) | 0.08 | 0.25 | 382 | 0.32 | 7.49E-01 | 9.28E-01 | Metabolome | HMDB10357 |
| MG(18:1) | -0.05 | 0.15 | 382 | -0.32 | 7.48E-01 | 9.28E-01 | Metabolome | HMDB11536 |
| C16 Sphingosine 1-phosphate | 0.03 | 0.09 | 382 | 0.31 | 7.56E-01 | 9.28E-01 | Metabolome | HMDB60061 |
| C6:0, DC AC(2) | 0.02 | 0.06 | 382 | 0.34 | 7.35E-01 | 9.28E-01 | Metabolome | HMDB61677 |
| IFNG | -0.09 | 0.26 | 414 | -0.33 | 7.45E-01 | 9.28E-01 | Immunome | |
| IL13 | -0.08 | 0.26 | 414 | -0.31 | 7.55E-01 | 9.28E-01 | Immunome | |
| MASP2 | 0.02 | 0.06 | 403 | 0.34 | 7.37E-01 | 9.28E-01 | Proteome | O00187 |
| Ig kappa chain V-I region HK101 | -0.02 | 0.06 | 403 | -0.32 | 7.52E-01 | 9.28E-01 | Proteome | P01601 |
| Ig heavy chain V-II region ARH-77 | 0.02 | 0.06 | 403 | 0.31 | 7.57E-01 | 9.28E-01 | Proteome | P06331 |
| PROS1 | 0.02 | 0.05 | 403 | 0.33 | 7.44E-01 | 9.28E-01 | Proteome | P07225 |
| SERPINF2 | -0.02 | 0.05 | 403 | -0.32 | 7.50E-01 | 9.28E-01 | Proteome | P08697 |
| DBH | -0.02 | 0.05 | 403 | -0.33 | 7.45E-01 | 9.28E-01 | Proteome | P09172 |
| MTHFD1 | 0.02 | 0.05 | 403 | 0.33 | 7.39E-01 | 9.28E-01 | Proteome | P11586 |
| TYMP | 0.02 | 0.06 | 403 | 0.33 | 7.44E-01 | 9.28E-01 | Proteome | P19971 |
| MYBPC2 | -0.02 | 0.05 | 403 | -0.33 | 7.40E-01 | 9.28E-01 | Proteome | Q14324 |
| LYVE1 | 0.02 | 0.06 | 403 | 0.32 | 7.51E-01 | 9.28E-01 | Proteome | QY5Y7 |
| Acetylcholine | -0.03 | 0.12 | 382 | -0.28 | 7.81E-01 | 9.32E-01 | Metabolome | HMDB00895 |
| L-Threonine | -0.02 | 0.08 | 382 | -0.29 | 7.70E-01 | 9.32E-01 | Metabolome | HMDB00167 |
| 5-oxoproline | -0.01 | 0.04 | 382 | -0.29 | 7.71E-01 | 9.32E-01 | Metabolome | HMDB00267 |
| C12:1, DC FA(1) | 0.02 | 0.08 | 382 | 0.28 | 7.77E-01 | 9.32E-01 | Metabolome | HMDB00933 |
| Threonic acid | -0.04 | 0.14 | 382 | -0.28 | 7.82E-01 | 9.32E-01 | Metabolome | HMDB00943 |
| Ala-Leu or Leu-Ala | 0.03 | 0.11 | 382 | 0.29 | 7.70E-01 | 9.32E-01 | Metabolome | HMDB28691 |
| IL18 | 0.05 | 0.17 | 414 | 0.28 | 7.81E-01 | 9.32E-01 | Immunome | |
| IL1A | 0.05 | 0.19 | 414 | 0.28 | 7.80E-01 | 9.32E-01 | Immunome | |
| CEP290 | -0.02 | 0.07 | 403 | -0.3 | 7.67E-01 | 9.32E-01 | Proteome | O15078 |
| IGHM | 0.01 | 0.05 | 403 | 0.29 | 7.74E-01 | 9.32E-01 | Proteome | P01871 |
| GC | 0.01 | 0.05 | 403 | 0.3 | 7.65E-01 | 9.32E-01 | Proteome | P02774 |
| TF | -0.01 | 0.05 | 403 | -0.28 | 7.81E-01 | 9.32E-01 | Proteome | P02787 |
| HPX | 0.01 | 0.05 | 403 | 0.29 | 7.69E-01 | 9.32E-01 | Proteome | P02790 |
| Ig kappa chain V-III region VH | 0.02 | 0.06 | 403 | 0.28 | 7.77E-01 | 9.32E-01 | Proteome | P04434 |
| LCP1 | -0.02 | 0.05 | 403 | -0.29 | 7.69E-01 | 9.32E-01 | Proteome | P13796 |
| PON1 | -0.01 | 0.05 | 403 | -0.29 | 7.72E-01 | 9.32E-01 | Proteome | P27169 |
| ECM1 | 0.01 | 0.05 | 403 | 0.28 | 7.79E-01 | 9.32E-01 | Proteome | Q16610 |
| SCLT1 | 0.02 | 0.06 | 403 | 0.28 | 7.78E-01 | 9.32E-01 | Proteome | Q96NL6 |
| MAN2B2 | 0.02 | 0.06 | 403 | 0.28 | 7.82E-01 | 9.32E-01 | Proteome | Q9Y2E5 |
| C13:0, DC FA(2) | -0.03 | 0.12 | 382 | -0.26 | 7.91E-01 | 9.33E-01 | Metabolome | HMDB02327 |
| MG(20:4)(1) | 0.03 | 0.12 | 382 | 0.27 | 7.90E-01 | 9.33E-01 | Metabolome | HMDB04666 |

TABLE 14-continued

Healthy-Baseline & Dynamic Models: Molecules Associated with high sensitivity C-reactive Protein

| | | | | | | | | |
|---|---|---|---|---|---|---|---|---|
| methyl-4-hydroxybenzoate sulfate | −0.05 | 0.18 | 382 | −0.27 | 7.90E−01 | 9.33E−01 | Metabolome | HMDB34172 |
| BASO | 0.03 | 0.11 | 416 | 0.26 | 7.92E−01 | 9.33E−01 | Clinical labs | |
| MCP3 | −0.06 | 0.22 | 414 | −0.27 | 7.85E−01 | 9.33E−01 | Immunome | |
| CLEC3B | 0.02 | 0.06 | 403 | 0.27 | 7.85E−01 | 9.33E−01 | Proteome | P05452 |
| MST1 | 0.01 | 0.05 | 403 | 0.27 | 7.91E−01 | 9.33E−01 | Proteome | P26927 |
| PRDX2 | 0.01 | 0.05 | 403 | 0.27 | 7.89E−01 | 9.33E−01 | Proteome | P32119 |
| GPR116 | 0.01 | 0.05 | 403 | 0.27 | 7.88E−01 | 9.33E−01 | Proteome | Q8IZF2 |
| Kynurenic acid | 0.03 | 0.11 | 382 | 0.25 | 8.01E−01 | 9.40E−01 | Metabolome | HMDB00715 |
| GP1BA | 0.01 | 0.05 | 403 | 0.25 | 8.00E−01 | 9.40E−01 | Proteome | P07359 |
| Pipecolic acid | −0.03 | 0.11 | 382 | −0.24 | 8.10E−01 | 9.43E−01 | Metabolome | HMDB00070 |
| Androstenediol (3beta,17beta) disulfate | 0.04 | 0.16 | 382 | 0.24 | 8.10E−01 | 9.43E−01 | Metabolome | HMDB03818 |
| Alpha-N-Phenylacetyl-L-glutamine | −0.02 | 0.10 | 382 | −0.25 | 8.05E−01 | 9.43E−01 | Metabolome | HMDB06344 |
| C18:0, OH FA(2) | −0.02 | 0.08 | 382 | −0.24 | 8.08E−01 | 9.43E−01 | Metabolome | |
| IGHG1 | 0.01 | 0.05 | 403 | 0.24 | 8.08E−01 | 9.43E−01 | Proteome | P01857 |
| ITIH1 | −0.01 | 0.05 | 403 | −0.24 | 8.10E−01 | 9.43E−01 | Proteome | P19827 |
| Betaine | −0.02 | 0.09 | 382 | −0.24 | 8.12E−01 | 9.44E−01 | Metabolome | HMDB00043 |
| ABCF1 | 0.02 | 0.07 | 403 | 0.24 | 8.14E−01 | 9.45E−01 | Proteome | Q8NE71 |
| BASOAB | 0.03 | 0.12 | 416 | 0.23 | 8.16E−01 | 9.46E−01 | Clinical labs | |
| C20:4, OH FA(2) | 0.03 | 0.14 | 382 | 0.23 | 8.17E−01 | 9.46E−01 | Metabolome | |
| Fructoselysine | 0.01 | 0.07 | 382 | 0.22 | 8.23E−01 | 9.47E−01 | Metabolome | |
| C5:0 Ac | −0.02 | 0.10 | 382 | −0.23 | 8.22E−01 | 9.47E−01 | Metabolome | |
| SERPINA1 | 0.01 | 0.05 | 403 | 0.22 | 8.23E−01 | 9.47E−01 | Proteome | P01009 |
| MBL2 | −0.01 | 0.07 | 403 | −0.23 | 8.20E−01 | 9.47E−01 | Proteome | P11226 |
| PLTP | −0.01 | 0.05 | 403 | −0.23 | 8.20E−01 | 9.47E−01 | Proteome | P55058 |
| C18:0, DC FA(2) | 0.02 | 0.11 | 382 | 0.22 | 8.26E−01 | 9.48E−01 | Metabolome | HMDB00782 |
| HABP2 | 0.01 | 0.06 | 403 | 0.22 | 8.26E−01 | 9.48E−01 | Proteome | Q14520 |
| DSP | 0.01 | 0.05 | 403 | 0.22 | 8.29E−01 | 9.49E−01 | Proteome | P15924 |
| 3-Methyl-2-oxovaleric acid | −0.03 | 0.13 | 382 | −0.21 | 8.31E−01 | 9.50E−01 | Metabolome | HMDB03736 |
| L-Lactic acid | 0.02 | 0.08 | 382 | 0.21 | 8.35E−01 | 9.53E−01 | Metabolome | HMDB00190 |
| Sulfolithocholyglycine | −0.05 | 0.23 | 382 | −0.21 | 8.36E−01 | 9.54E−01 | Metabolome | HMDB02639 |
| Caffeine | 0.02 | 0.11 | 382 | 0.2 | 8.39E−01 | 9.54E−01 | Metabolome | HMDB01847 |
| CLU(1) | −0.01 | 0.05 | 403 | −0.2 | 8.39E−01 | 9.54E−01 | Proteome | P10909 |
| AFM | −0.01 | 0.05 | 403 | −0.2 | 8.38E−01 | 9.54E−01 | Proteome | P43652 |
| Dihydro-3-coumaric acid | 0.02 | 0.08 | 382 | 0.2 | 8.43E−01 | 9.56E−01 | Metabolome | HMDB00375 |
| LPA | 0.03 | 0.17 | 403 | 0.2 | 8.44E−01 | 9.56E−01 | Proteome | P08519 |
| IL6 | 0.11 | 0.56 | 414 | 0.19 | 8.48E−01 | 9.59E−01 | Immunome | |
| Unknown | −0.01 | 0.05 | 403 | −0.19 | 8.49E−01 | 9.59E−01 | Proteome | |
| GPLD1 | 0.01 | 0.05 | 403 | 0.19 | 8.51E−01 | 9.60E−01 | Proteome | P80108 |
| FCN3 | −0.01 | 0.05 | 403 | −0.19 | 8.53E−01 | 9.60E−01 | Proteome | O75636 |
| HGFAC | 0.01 | 0.05 | 403 | 0.19 | 8.53E−01 | 9.60E−01 | Proteome | Q04756 |
| N6-Acetyl-L-lysine | 0.02 | 0.10 | 382 | 0.16 | 8.71E−01 | 9.60E−01 | Metabolome | HMDB00206 |
| Taurine | −0.02 | 0.09 | 382 | −0.17 | 8.66E−01 | 9.60E−01 | Metabolome | HMDB00251 |
| Imidazolelactic acid | 0.02 | 0.11 | 382 | 0.16 | 8.71E−01 | 9.60E−01 | Metabolome | HMDB02320 |
| MG(15:0)(2) | 0.01 | 0.04 | 382 | 0.16 | 8.71E−01 | 9.60E−01 | Metabolome | HMDB11532 |
| EOSAB | 0.03 | 0.18 | 416 | 0.18 | 8.57E−01 | 9.60E−01 | Clinical labs | |
| C18:0, OH FA(1) | −0.02 | 0.09 | 382 | −0.17 | 8.63E−01 | 9.60E−01 | Metabolome | |
| C17:0 FA(1) | −0.02 | 0.09 | 382 | −0.17 | 8.67E−01 | 9.60E−01 | Metabolome | |
| C12:0 FA(2) | 0.01 | 0.04 | 382 | 0.18 | 8.59E−01 | 9.60E−01 | Metabolome | |
| F12 | −0.01 | 0.08 | 403 | −0.18 | 8.55E−01 | 9.60E−01 | Proteome | P00748 |
| Ig lambda chain V-I region HA | −0.01 | 0.09 | 403 | −0.16 | 8.71E−01 | 9.60E−01 | Proteome | P01700 |
| IGHG2 | −0.01 | 0.06 | 403 | −0.18 | 8.59E−01 | 9.60E−01 | Proteome | P01859 |
| F11 | 0.01 | 0.06 | 403 | 0.18 | 8.58E−01 | 9.60E−01 | Proteome | P03951 |
| LCAT | −0.01 | 0.05 | 403 | −0.17 | 8.66E−01 | 9.60E−01 | Proteome | P04180 |
| Ig kappa chain V-III region VG | 0.01 | 0.05 | 403 | 0.17 | 8.64E−01 | 9.60E−01 | Proteome | P04433 |
| C4B | 0.01 | 0.05 | 403 | 0.17 | 8.62E−01 | 9.60E−01 | Proteome | P0C0L5 |
| FERMT3 | 0.01 | 0.05 | 403 | 0.17 | 8.68E−01 | 9.60E−01 | Proteome | Q86UX7 |
| Hypoxanthine | −0.01 | 0.07 | 382 | −0.16 | 8.77E−01 | 9.61E−01 | Metabolome | HMDB00157 |
| Phenylbutyric acid | 0.02 | 0.12 | 382 | 0.15 | 8.79E−01 | 9.61E−01 | Metabolome | HMDB00329 |
| L-Methionine | −0.01 | 0.09 | 382 | −0.15 | 8.78E−01 | 9.61E−01 | Metabolome | HMDB00696 |
| C14:1 FA(2) | 0.01 | 0.09 | 382 | 0.15 | 8.78E−01 | 9.61E−01 | Metabolome | HMDB02000 |
| Pregnanediol-3-glucuronide | 0.01 | 0.04 | 382 | 0.15 | 8.84E−01 | 9.61E−01 | Metabolome | HMDB10318 |
| C19:1 FA | 0.01 | 0.09 | 382 | 0.15 | 8.81E−01 | 9.61E−01 | Metabolome | HMDB13622 |
| Asp-Asp | −0.02 | 0.11 | 382 | −0.15 | 8.83E−01 | 9.61E−01 | Metabolome | HMDB28749 |
| C18:2, DC FA | 0.01 | 0.04 | 382 | 0.15 | 8.78E−01 | 9.61E−01 | Metabolome | |
| IGHA1 | −0.01 | 0.06 | 403 | −0.15 | 8.80E−01 | 9.61E−01 | Proteome | P01876 |
| Ig lambda chain V region 4A | 0.01 | 0.06 | 403 | 0.15 | 8.82E−01 | 9.61E−01 | Proteome | P04211 |
| Clusterin | −0.01 | 0.05 | 403 | −0.14 | 8.85E−01 | 9.61E−01 | Proteome | P10909_2 |
| ACTA1 | 0.01 | 0.05 | 403 | 0.14 | 8.86E−01 | 9.61E−01 | Proteome | P68133 |
| gamma-glutamylthreonine(2) | 0.01 | 0.06 | 382 | 0.14 | 8.88E−01 | 9.61E−01 | Metabolome | HMDB29159 |
| LysoPG(18:0) | 0.01 | 0.09 | 382 | 0.14 | 8.88E−01 | 9.61E−01 | Metabolome | |
| MG(20:5) | 0.01 | 0.10 | 382 | 0.14 | 8.92E−01 | 9.63E−01 | Metabolome | HMDB11550 |
| Aminoadipic acid | −0.02 | 0.12 | 382 | −0.13 | 8.93E−01 | 9.64E−01 | Metabolome | HMDB00510 |
| Tetrahydrocortisol | 0.06 | 0.46 | 382 | 0.13 | 8.99E−01 | 9.68E−01 | Metabolome | HMDB00949 |
| SLEN11 | −0.01 | 0.06 | 403 | −0.13 | 8.99E−01 | 9.68E−01 | Proteome | Q7Z7L1 |
| Ornithine | −0.01 | 0.07 | 382 | −0.12 | 9.01E−01 | 9.69E−01 | Metabolome | HMDB03374 |
| 11-beta-Hydroxyandrosterone-3-glucuronide | 0.01 | 0.12 | 382 | 0.12 | 9.08E−01 | 9.69E−01 | Metabolome | HMDB10351 |
| LysoPE(20:3) | 0.03 | 0.22 | 382 | 0.12 | 9.07E−01 | 9.69E−01 | Metabolome | HMDB11484 |

TABLE 14-continued

Healthy-Baseline & Dynamic Models: Molecules Associated with high sensitivity C-reactive Protein

| Molecule | Estimate | StdErr | DF | tValue | p-value | FDR | Assay | Accession ID |
|---|---|---|---|---|---|---|---|---|
| MG(14:1)(1) | −0.01 | 0.09 | 382 | −0.12 | 9.08E−01 | 9.69E−01 | Metabolome | HMDB11531 |
| C6:0, DC AC(1) | 0.10 | 0.86 | 382 | 0.12 | 9.08E−01 | 9.69E−01 | Metabolome | HMDB61677 |
| SDF1A | −0.03 | 0.22 | 414 | −0.12 | 9.08E−01 | 9.69E−01 | Immunome | |
| AFG3L2 | 0.01 | 0.06 | 403 | 0.12 | 9.04E−01 | 9.69E−01 | Proteome | Q9Y4W6 |
| MCAM | −0.01 | 0.05 | 403 | −0.11 | 9.11E−01 | 9.69E−01 | Proteome | P43121 |
| C1RL | 0.01 | 0.05 | 403 | 0.11 | 9.11E−01 | 9.69E−01 | Proteome | Q9NZP8 |
| PDGFBB | −0.01 | 0.13 | 414 | −0.11 | 9.16E−01 | 9.73E−01 | Immunome | |
| CAPZB | −0.01 | 0.05 | 403 | −0.1 | 9.16E−01 | 9.73E−01 | Proteome | P47756 |
| Asp-Glu or Glu-Asp | 0.00 | 0.04 | 382 | 0.09 | 9.26E−01 | 9.76E−01 | Metabolome | HMDB28752 |
| EGF | −0.01 | 0.09 | 414 | −0.1 | 9.22E−01 | 9.76E−01 | Immunome | |
| LYMAB | −0.01 | 0.14 | 417 | −0.09 | 9.24E−01 | 9.76E−01 | Clinical labs | |
| Hydroxybutyric acid(2) | −0.01 | 0.11 | 382 | −0.1 | 9.22E−01 | 9.76E−01 | Metabolome | |
| 4-formyl Indole(2) | 0.02 | 0.18 | 382 | 0.09 | 9.27E−01 | 9.76E−01 | Metabolome | |
| AHSG | 0.00 | 0.05 | 403 | 0.09 | 9.28E−01 | 9.76E−01 | Proteome | P02765 |
| APOB | 0.00 | 0.05 | 403 | −0.1 | 9.23E−01 | 9.76E−01 | Proteome | P04114 |
| PCOLCE | −0.01 | 0.06 | 403 | −0.09 | 9.28E−01 | 9.76E−01 | Proteome | Q15113 |
| RBC | −0.01 | 0.13 | 417 | −0.09 | 9.30E−01 | 9.76E−01 | Clinical labs | |
| 4-Hydroxyphenylpyruvic acid | −0.01 | 0.14 | 382 | −0.08 | 9.34E−01 | 9.80E−01 | Metabolome | HMDB00707 |
| LUM | 0.00 | 0.05 | 403 | 0.08 | 9.39E−01 | 9.83E−01 | Proteome | P51884 |
| 2-Hydroxyphenylacetate | 0.02 | 0.28 | 382 | 0.07 | 9.44E−01 | 9.83E−01 | Metabolome | HMDB00669 |
| 4-Hydroxyproline | 0.01 | 0.10 | 382 | 0.07 | 9.43E−01 | 9.83E−01 | Metabolome | HMDB00725 |
| Sulfolithocholic acid | −0.01 | 0.12 | 382 | −0.07 | 9.45E−01 | 9.83E−01 | Metabolome | HMDB00907 |
| A1C | −0.01 | 0.12 | 415 | −0.07 | 9.45E−01 | 9.83E−01 | Clinical labs | |
| KNG1(1) | 0.00 | 0.05 | 403 | 0.07 | 9.43E−01 | 9.83E−01 | Proteome | P01042 |
| IGKC | 0.00 | 0.05 | 403 | 0.07 | 9.48E−01 | 9.84E−01 | Proteome | P01834 |
| Ig lambda chain V-III region LOI | 0.00 | 0.05 | 403 | 0.07 | 9.47E−01 | 9.84E−01 | Proteome | P80748 |
| F7 | 0.00 | 0.05 | 403 | 0.06 | 9.50E−01 | 9.85E−01 | Proteome | P08709 |
| L-Glutamine | 0.00 | 0.09 | 382 | −0.05 | 9.57E−01 | 9.86E−01 | Metabolome | HMDB00641 |
| MG(20:4)(2) | −0.01 | 0.17 | 382 | −0.05 | 9.58E−01 | 9.86E−01 | Metabolome | HMDB04666 |
| pro-hydroxy-pro(2) | 0.01 | 0.11 | 382 | 0.06 | 9.52E−01 | 9.86E−01 | Metabolome | HMDB06695 |
| CA | 0.00 | 0.08 | 419 | 0.06 | 9.54E−01 | 9.86E−01 | Clinical labs | |
| CHOL | 0.01 | 0.11 | 419 | 0.05 | 9.58E−01 | 9.86E−01 | Clinical labs | |
| FBLN1(1) | 0.00 | 0.05 | 403 | −0.05 | 9.56E−01 | 9.86E−01 | Proteome | P23142 |
| C10:1, OH FA | 0.01 | 0.15 | 382 | 0.05 | 9.62E−01 | 9.87E−01 | Metabolome | |
| SCP2 | 0.00 | 0.05 | 403 | 0.05 | 9.63E−01 | 9.87E−01 | Proteome | P22307 |
| HBB | 0.00 | 0.06 | 403 | −0.05 | 9.63E−01 | 9.87E−01 | Proteome | P68871 |
| SERPINA10 | 0.00 | 0.05 | 403 | 0.05 | 9.63E−01 | 9.87E−01 | Proteome | Q9UK55 |
| TGPBI | 0.00 | 0.05 | 403 | 0.04 | 9.68E−01 | 9.90E−01 | Proteome | Q15582 |
| Proline betaine | 0.00 | 0.10 | 382 | −0.04 | 9.71E−01 | 9.92E−01 | Metabolome | HMDB04827 |
| Iminodiacetate (IDA) | 0.00 | 0.09 | 382 | −0.03 | 9.79E−01 | 9.99E−01 | Metabolome | HMDB11753 |
| L-Lysine | 0.00 | 0.07 | 382 | 0.01 | 9.95E−01 | 1.00E+00 | Metabolome | HMDB00182 |
| 5-Acetylamino-6-amino-3-methyluracil(1) | 0.00 | 0.10 | 382 | 0.01 | 9.92E−01 | 1.00E+00 | Metabolome | HMDB04400 |
| MG(15:0)(1) | 0.00 | 0.04 | 382 | −0.01 | 9.93E−01 | 1.00E+00 | Metabolome | HMDB11532 |
| Phenol sulphate | 0.00 | 0.11 | 382 | −0.02 | 9.87E−01 | 1.00E+00 | Metabolome | HMDB60015 |
| Ectoine | 0.00 | 0.13 | 382 | 0 | 9.97E−01 | 1.00E+00 | Metabolome | |
| C14:1, OH FA(1) | 0.00 | 0.09 | 382 | −0.01 | 9.91E−01 | 1.00E+00 | Metabolome | |
| MONO | 0.00 | 0.11 | 417 | 0.01 | 9.96E−01 | 1.00E+00 | Clinical labs | |
| APOM | 0.00 | 0.05 | 403 | 0.01 | 9.89E−01 | 1.00E+00 | Proteome | O95445 |
| HBD | 0.00 | 0.06 | 403 | 0.01 | 9.96E−01 | 1.00E+00 | Proteome | P02042 |
| C4BPA | 0.00 | 0.05 | 403 | 0 | 9.99E−01 | 1.00E+00 | Proteome | P04003 |
| SELL | 0.00 | 0.05 | 403 | 0.01 | 9.93E−01 | 1.00E+00 | Proteome | P14151 |
| HNRNPM | 0.00 | 0.05 | 403 | 0 | 9.99E−01 | 1.00E+00 | Proteome | P52272 |
| APOF | 0.00 | 0.05 | 403 | 0.02 | 9.82E−01 | 1.00E+00 | Proteome | Q13790 |
| ITIH4 | 0.00 | 0.05 | 403 | 0.01 | 9.96E−01 | 1.00E+00 | Proteome | Q14624 |
| ALB | 0.00 | 0.05 | 403 | −0.01 | 9.96E−01 | 1.00E+00 | Proteome | P02768 |
| cont_000108 | 0.00 | 0.06 | 403 | 0 | 1.00E+00 | 1.00E+00 | Proteome | |
| cont_000137 | 0.00 | 0.05 | 403 | −0.02 | 9.83E−01 | 1.00E+00 | Proteome | |

Bolded Proteins (n = 10) and Metabolites (n = 24) are those that were matched to molecules in known pathways and used in pathway analysis using IMPaLa web tool
p-values are derived from the t-test and are two sided; multiple testing correction using Benjamini-Hochberg method was performed and resulting values listed under FDR Dynamic Model: hsCRP (n = 92, samples 777)

| Molecule | Estimate | StdErr | DF | tValue | p-value | FDR | Assay | Accession ID |
|---|---|---|---|---|---|---|---|---|
| MONOAB | 0.399 | 0.033 | 677 | 11.97 | 4.00E−30 | 3.35E−27 | Clinical labs | |
| SAA2 | 0.313 | 0.027 | 604 | 11.76 | 6.70E−29 | 2.80E−26 | Proteome | P0DJI9 |
| MIG | 0.473 | 0.042 | 637 | 11.28 | 4.97E−27 | 1.39E−24 | Immunome | |
| LYM | −0.553 | 0.050 | 677 | −11.06 | 2.90E−26 | 6.07E−24 | Clinical labs | |
| IP10 | 0.367 | 0.035 | 637 | 10.6 | 2.78E−24 | 3.88E−22 | Immunome | |
| SAA1 | 0.316 | 0.030 | 604 | 10.63 | 2.66E−24 | 3.88E−22 | Proteome | P0DJI8 |
| NEUTAB | 0.329 | 0.035 | 677 | 9.49 | 3.76E−20 | 4.49E−18 | Clinical labs | |
| HP | 0.473 | 0.050 | 604 | 9.44 | 7.67E−20 | 8.02E−18 | Proteome | P00738 |
| NEUT | 0.315 | 0.039 | 677 | 8.15 | 1.71E−15 | 1.59E−13 | Clinical labs | |
| WBC | 0.297 | 0.037 | 677 | 8.09 | 2.66E−15 | 2.23E−13 | Clinical labs | |
| ITIH3 | 0.323 | 0.041 | 604 | 7.97 | 8.14E−15 | 6.19E−13 | Proteome | Q06033 |
| HGF | 0.294 | 0.039 | 637 | 7.61 | 9.73E−14 | 6.78E−12 | Immunome | |

TABLE 14-continued

Healthy-Baseline & Dynamic Models: Molecules Associated with high sensitivity C-reactive Protein

| | | | | | | | | |
|---|---|---|---|---|---|---|---|---|
| SERPINA3 | 0.262 | 0.036 | 604 | 7.32 | 8.05E−13 | 5.18E−11 | Proteome | P01011 |
| CFB | 0.287 | 0.042 | 604 | 6.9 | 1.35E−11 | 8.07E−10 | Proteome | P00751 |
| LYMAB | −0.271 | 0.040 | 677 | −6.84 | 1.81E−11 | 1.01E−09 | Clinical labs | |
| ALKP | 0.227 | 0.035 | 680 | 6.49 | 1.63E−10 | 8.51E−09 | Clinical labs | |
| C5 | 0.222 | 0.035 | 604 | 6.34 | 4.61E−10 | 2.27E−08 | Proteome | P01031 |
| MONO | 0.233 | 0.038 | 677 | 6.12 | 1.56E−09 | 7.12E−08 | Clinical labs | |
| LBP | 0.274 | 0.045 | 604 | 6.13 | 1.62E−09 | 7.12E−08 | Proteome | P18428 |
| C1S | 0.220 | 0.039 | 604 | 5.68 | 2.08E−08 | 8.71E−07 | Proteome | P09871 |
| GLOB | 0.266 | 0.047 | 680 | 5.65 | 2.34E−08 | 9.33E−07 | Clinical labs | |
| BASO | −0.273 | 0.049 | 672 | −5.59 | 3.37E−08 | 1.28E−06 | Clinical labs | |
| IL12P40 | 0.235 | 0.046 | 637 | 5.1 | 4.59E−07 | 1.67E−05 | Immunome | |
| ATP11B | 0.213 | 0.042 | 604 | 5.08 | 5.06E−07 | 1.76E−05 | Proteome | Q9Y2G3 |
| ICAM1 | 0.288 | 0.057 | 637 | 5.03 | 6.45E−07 | 2.16E−05 | Immunome | |
| IL1RA | 0.214 | 0.043 | 637 | 5 | 7.56E−07 | 2.43E−05 | Immunome | |
| ORM1 | 0.187 | 0.038 | 604 | 4.88 | 1.34E−06 | 4.14E−05 | Proteome | P02763 |
| Catechol sulfate | −0.262 | 0.056 | 587 | −4.67 | 3.65E−06 | 1.09E−04 | Metabolome | HMDB59724 |
| LRG1 | 0.169 | 0.038 | 604 | 4.49 | 8.72E−06 | 2.52E−04 | Proteome | P02750 |
| HDL | −0.209 | 0.047 | 681 | −4.45 | 9.83E−06 | 2.66E−04 | Clinical labs | |
| TF | −0.193 | 0.043 | 604 | −4.46 | 9.86E−06 | 2.66E−04 | Proteome | P02787 |
| C1R | 0.153 | 0.035 | 604 | 4.38 | 1.42E−05 | 3.61E−04 | Proteome | P00736 |
| MAN2B2 | −0.195 | 0.045 | 604 | −4.38 | 1.40E−05 | 3.61E−04 | Proteome | Q9Y2E5 |
| Indolelactic acid | −0.186 | 0.044 | 587 | −4.26 | 2.39E−05 | 5.89E−04 | Metabolome | HMDB00671 |
| CPN2 | 0.223 | 0.055 | 604 | 4.08 | 5.03E−05 | 1.20E−03 | Proteome | P22792 |
| RBP4 | −0.143 | 0.037 | 604 | −3.88 | 1.15E−04 | 2.67E−03 | Proteome | P02753 |
| SAA4 | 0.175 | 0.045 | 604 | 3.87 | 1.19E−04 | 2.70E−03 | Proteome | P35542 |
| RANTES | −0.147 | 0.039 | 637 | −3.73 | 2.12E−04 | 4.44E−03 | Immunome | |
| MIP1B | 0.165 | 0.044 | 637 | 3.73 | 2.07E−04 | 4.44E−03 | Immunome | |
| IGKC | −0.171 | 0.046 | 604 | −3.73 | 2.12E−04 | 4.44E−03 | Proteome | P01834 |
| APOA4 | −0.142 | 0.039 | 604 | −3.68 | 2.57E−04 | 5.24E−03 | Proteome | P06727 |
| GSN | −0.139 | 0.039 | 604 | −3.58 | 3.66E−04 | 7.29E−03 | Proteome | P06396 |
| HPR | 0.227 | 0.063 | 604 | 3.58 | 3.75E−04 | 7.31E−03 | Proteome | P00739 |
| CFI | 0.152 | 0.043 | 604 | 3.51 | 4.83E−04 | 9.19E−03 | Proteome | P05156 |
| CL | −0.137 | 0.040 | 680 | −3.47 | 5.53E−04 | 1.03E−02 | Clinical labs | |
| IL1A | −0.171 | 0.050 | 637 | −3.46 | 5.78E−04 | 1.05E−02 | Immunome | |
| RESISTIN | 0.136 | 0.040 | 637 | 3.41 | 6.97E−04 | 1.24E−02 | Immunome | |
| EOTAXIN | −0.141 | 0.042 | 637 | −3.38 | 7.80E−04 | 1.36E−02 | Immunome | |
| KNG1_2 | 0.099 | 0.029 | 604 | 3.36 | 8.18E−04 | 1.40E−02 | Proteome | P01042 |
| A2M | −0.131 | 0.039 | 604 | −3.33 | 9.12E−04 | 1.53E−02 | Proteome | P01023 |
| Quinic acid | −0.130 | 0.040 | 587 | −3.26 | 1.16E−03 | 1.90E−02 | Metabolome | HMDB03072 |
| OLFM1 | 0.113 | 0.035 | 604 | 3.22 | 1.35E−03 | 2.17E−02 | Proteome | Q99784 |
| KVD33_2 | −0.175 | 0.055 | 604 | −3.2 | 1.46E−03 | 2.27E−02 | Proteome | P01593 |
| C1QB | 0.155 | 0.048 | 604 | 3.2 | 1.47E−03 | 2.27E−02 | Proteome | P02746 |
| L-Alanine | −0.118 | 0.038 | 587 | −3.1 | 2.03E−03 | 3.09E−02 | Metabolome | HMDB00161 |
| NPHP3 | 0.122 | 0.040 | 604 | 3.05 | 2.36E−03 | 3.53E−02 | Proteome | Q7Z494 |
| APOD | −0.126 | 0.042 | 604 | −3.03 | 2.52E−03 | 3.70E−02 | Proteome | P05090 |
| C8G | 0.111 | 0.037 | 604 | 3.02 | 2.61E−03 | 3.77E−02 | Proteome | P07360 |
| MSN | 0.115 | 0.038 | 604 | 2.99 | 2.87E−03 | 4.08E−02 | Proteome | P26038 |
| C4A | 0.094 | 0.032 | 604 | 2.94 | 3.42E−03 | 4.77E−02 | Proteome | P0C0L4 |
| Androsterone sulfate(1) | 0.162 | 0.056 | 587 | 2.92 | 3.60E−03 | 4.94E−02 | Metabolome | HMDB02759 |
| LysoPE(18:1) | −0.114 | 0.040 | 587 | −2.89 | 4.01E−03 | 5.41E−02 | Metabolome | HMDB11475 |
| Citric acid | −0.124 | 0.043 | 587 | −2.88 | 4.08E−03 | 5.42E−02 | Metabolome | HMDB00094 |
| LysoPE(16:1) | −0.117 | 0.041 | 587 | −2.88 | 4.16E−03 | 5.44E−02 | Metabolome | HMDB11474 |
| C5:0; DC AC | 1.455 | 0.508 | 587 | 2.86 | 4.33E−03 | 5.58E−02 | Metabolome | |
| C6 | 0.130 | 0.046 | 604 | 2.82 | 4.94E−03 | 6.27E−02 | Proteome | P13671 |
| IL23 | −0.270 | 0.096 | 637 | −2.81 | 5.08E−03 | 6.35E−02 | Immunome | |
| ITIH2 | −0.104 | 0.037 | 604 | −2.79 | 5.42E−03 | 6.67E−02 | Proteome | P19823 |
| CP | 0.140 | 0.050 | 604 | 2.78 | 5.63E−03 | 6.74E−02 | Proteome | P00450 |
| SLFN11 | 0.103 | 0.037 | 604 | 2.78 | 5.64E−03 | 6.74E−02 | Proteome | Q7Z7L1 |
| IGHG1 | −0.104 | 0.038 | 604 | −2.76 | 5.92E−03 | 6.98E−02 | Proteome | P01857 |
| Pregnanolone sulfate | 0.205 | 0.075 | 587 | 2.73 | 6.56E−03 | 7.63E−02 | Metabolome | |
| MAP4 | −0.132 | 0.049 | 604 | −2.69 | 7.33E−03 | 8.41E−02 | Proteome | P27816 |
| ALB | −0.103 | 0.038 | 604 | −2.67 | 7.72E−03 | 8.73E−02 | Proteome | P02768 |
| CFH | 0.113 | 0.043 | 604 | 2.65 | 8.16E−03 | 9.11E−02 | Proteome | P08603 |
| Gentisic acid | −0.105 | 0.040 | 587 | −2.64 | 8.51E−03 | 9.37E−02 | Metabolome | HMDB00152 |
| CHOL | −0.113 | 0.044 | 681 | −2.6 | 9.58E−03 | 1.03E−01 | Clinical labs | |
| MST1 | 0.101 | 0.039 | 604 | 2.6 | 9.56E−03 | 1.03E−01 | Proteome | P26927 |
| PAI1 | −0.104 | 0.040 | 637 | −2.58 | 1.00E−02 | 1.06E−01 | Immunome | |
| Arabonate \| Xylonate(3) | −0.120 | 0.046 | 587 | −2.58 | 1.01E−02 | 1.06E−01 | Metabolome | |
| 4-Hydroxyproline | −0.131 | 0.051 | 587 | −2.57 | 1.04E−02 | 1.07E−01 | Metabolome | HMDB00725 |
| Urocanic acid | −0.101 | 0.040 | 587 | −2.54 | 1.13E−02 | 1.14E−01 | Metabolome | HMDB00301 |
| BUN | −0.106 | 0.042 | 680 | −2.54 | 1.13E−02 | 1.14E−01 | Clinical labs | |
| Thyroxine | 0.136 | 0.055 | 587 | 2.49 | 1.30E−02 | 1.29E−01 | Metabolome | HMDB01918 |
| BDNF | −0.143 | 0.058 | 637 | −2.48 | 1.33E−02 | 1.29E−01 | Immunome | |
| KNG1 | 0.126 | 0.051 | 604 | 2.48 | 1.33E−02 | 1.29E−01 | Proteome | P01042 |
| TP | 0.105 | 0.043 | 680 | 2.45 | 1.46E−02 | 1.41E−01 | Clinical labs | |
| LUM | −0.093 | 0.038 | 604 | −2.44 | 1.50E−02 | 1.43E−01 | Proteome | P51884 |
| SDF1A | −0.145 | 0.060 | 637 | −2.42 | 1.59E−02 | 1.49E−01 | Immunome | |
| L-Malic acid | −0.097 | 0.040 | 587 | −2.4 | 1.65E−02 | 1.51E−01 | Metabolome | HMDB00156 |

TABLE 14-continued

Healthy-Baseline & Dynamic Models: Molecules Associated with high sensitivity C-reactive Protein

| | | | | | | | | |
|---|---|---|---|---|---|---|---|---|
| A1C | 0.104 | 0.043 | 660 | 2.41 | 1.64E−02 | 1.51E−01 | Clinical labs | |
| IGHA1 | −0.109 | 0.046 | 604 | −2.4 | 1.66E−02 | 1.51E−01 | Proteome | P01876 |
| SERPINC1 | −0.098 | 0.042 | 604 | −2.37 | 1.82E−02 | 1.64E−01 | Proteome | P01008 |
| Cysteineglutathione disulfide | −0.154 | 0.066 | 587 | −2.32 | 2.05E−02 | 1.76E−01 | Metabolome | HMD500656 |
| 5-Methoxysalicylic acid | −0.089 | 0.038 | 587 | −2.33 | 1.99E−02 | 1.76E−01 | Metabolome | HMDB01868 |
| HV307 | −0.190 | 0.082 | 604 | −2.32 | 2.06E−02 | 1.76E−01 | Proteome | P01780 |
| B2M | 0.084 | 0.036 | 604 | 2.32 | 2.06E−02 | 1.76E−01 | Proteome | P61769 |
| HGFAC | 0.087 | 0.037 | 604 | 2.32 | 2.05E−02 | 1.76E−01 | Proteome | Q04756 |
| Uridine | −0.105 | 0.045 | 587 | −2.3 | 2.17E−02 | 1.83E−01 | Metabolome | HMDB00296 |
| Uracil | −0.115 | 0.050 | 587 | −2.29 | 2.21E−02 | 1.84E−01 | Metabolome | HMDB00300 |
| MG(18:1) | −0.098 | 0.043 | 587 | −2.29 | 2.23E−02 | 1.84E−01 | Metabolome | HMDB11536 |
| 2-Aminophenol sulfate | −0.080 | 0.035 | 587 | −2.27 | 2.38E−02 | 1.95E−01 | Metabolome | HMDB61116 |
| C2 | 0.094 | 0.042 | 604 | 2.26 | 2.40E−02 | 1.95E−01 | Proteome | P06681 |
| HNRNPM | 0.072 | 0.032 | 604 | 2.25 | 2.45E−02 | 1.97E−01 | Proteome | P52272 |
| MCP1 | 0.093 | 0.042 | 637 | 2.25 | 2.50E−02 | 1.99E−01 | Immunome | |
| CEP290 | −0.117 | 0.052 | 604 | −2.24 | 2.53E−02 | 2.00E−01 | Proteome | O15078 |

Bolded Proteins (n = 49) and Metabolites (n = 10) are those that were matched to molecules in known pathways and used in pathway analysis using IMPaLa web tool
p-values are derived from the t-test and are two sided; multiple testing correction using Benjamini-Hochberg method was performed and resulting values listed under FDR

TABLE 15

Measurements that Significantly Associated with SSPG in Healthy Baselines

| Measurement | Association with IR/IS? | P-value (FDR) | Association Coefficient |
|---|---|---|---|
| EGFR | YES | 0.0710 | 0.3734 |
| HDL | YES | 0.0074 | −0.4674 |
| NEUTAB | YES | 0.0234 | 0.4137 |
| TGL | YES | 0.0710 | 0.3427 |
| WBC | YES | 0.0542 | 0.3716 |
| GROA | | 0.0529 | −0.4227 |
| L-Lysine | | 0.0341 | 0.4826 |
| L-Alanine | YES | 0.0341 | 0.4852 |
| Hippuric acid | YES | 0.0377 | −0.4692 |
| Cinnamoylglycine | YES | 0.0946 | −0.4198 |
| 3-Phenylpropionate (hydrocinnamate) | | 0.0946 | −0.4039 |
| C18:0, DC FA | | 0.0946 | 0.4083 |
| C28H44O4 | | 0.0946 | 0.4129 |
| C27H44O4 | | 0.0894 | 0.4294 |
| C26H42O4 | | 0.0607 | 0.4477 |
| LysoPG(18:0) | | 0.0946 | 0.4024 |
| C16:3 FA | | 0.0946 | 0.4070 |
| phylum_unclassified_Bacteria | YES | 0.0088 | −0.4137 |
| class_Bacteroidia | YES | 0.0811 | 0.3016 |
| class_unclassified_Bacteria | YES | 0.0088 | −0.4137 |
| class_unclassified_Firmicutes | YES | 0.0001 | −0.5607 |
| order_Bacteroidales | YES | 0.0811 | 0.3016 |
| order_unclassified_Bacteria | YES | 0.0088 | −0.4137 |
| order_unclassified_Firmicutes | YES | 0.0001 | −0.5607 |
| family_Clostridiaceae.1 | YES | 0.0263 | −0.3633 |
| family_Clostridiales_Incertae.Sedis.XIII | YES | 0.0053 | −0.4502 |
| family_Peptostreptococcaceae | YES | 0.0602 | −0.3206 |
| family_unclassified_Bacteria | YES | 0.0088 | −0.4137 |
| family_unclassified_Clostridiales | YES | 0.0006 | −0.5157 |
| family_unclassified_Firmicutes | YES | 0.0001 | −0.5607 |
| genus_*Anaerovorax* | YES | 0.0257 | −0.3662 |
| genus_*Blautia* | YES | 0.0429 | 0.3393 |
| genus_*Clostridium*.XI | YES | 0.0602 | −0.3206 |
| genus_*Clostridium*.XIVa | | 0.0811 | 0.3012 |
| genus_*Clostridium*.XIVb | YES | 0.0176 | 0.3849 |
| genus_*Clostridium*.sensu.stricto | YES | 0.0273 | −0.3599 |
| genus_*Coprococcus* | YES | 0.0088 | −0.4216 |
| genus_*Odoribacter* | YES | 0.0236 | −0.3716 |
| genus_*Oscillibacter* | YES | 0.0096 | −0.4085 |
| genus_*Pseudoflavonifractor* | YES | 0.0006 | −0.5186 |
| genus_unclassified_Bacteria | YES | 0.0088 | −0.4137 |
| genus_unclassified_Clostridiales | YES | 0.0006 | −0.5157 |
| genus_unclassified_Firmicutes | YES | 0.0001 | −0.5607 |
| genus_unclassified_Ruminococcaceae | YES | 0.0065 | −0.4401 |
| VTN | | 0.1213 | 0.3973 |
| APOD | | 0.1555 | −0.3728 |
| MCAM | | 0.1213 | −0.4049 |

TABLE 15-continued

Measurements that Significantly Associated with SSPG in Healthy Baselines

| Measurement | Association with IR/IS? | P-value (FDR) | Association Coefficient |
|---|---|---|---|
| APOC4 | YES | 0.1213 | 0.4306 |
| PLTP | | 0.1213 | −0.3955 |
| ADIPOQ | | 0.1440 | −0.3820 |

TABLE 16

Pharmacogenomic Variants of Common Medications in Cardiovascular Medicine

| n = 88 | Pharmacovariants | | | | | | | | | |
|---|---|---|---|---|---|---|---|---|---|---|
| Medication | Simvastatin | Coumadin | | | | | Clopidogrel | | | |
| Variant | SLCO1B1 | CYP2C9*2 | CYP2C9*1 | VKORC1 | VKORC1 | CYP4F2 | CYP2C19*17 | CYP2C19*4 | CYP2C19*3 | CYP2C19*2 |
| PharmGKB | 1A | 1A | 1A | 1B | 1B | 1A | 1A | 1A | 1A | 1A |
| | rs4149056 | rs1799853 | rs1057910 | rs7294 | rs9934438 | rs2108622 | rs12248560 | rs28399504 | rs4986893 | rs4244285 |
| Heterozygous | 25 | 14 | 6 | 33 | 33 | 38 | 33 | 0 | 2 | 31 |
| Homozygous | 1 | 1 | 0 | 13 | 21 | 9 | 2 | 0 | 0 | 3 |
| Effect | T | T | T | E | T | E | E | E | E | E |

T—Toxicity
E—Efficacy

TABLE 17

Multiomics Associations with Adjusted Atherosclerotic Cardiovascular Disease Risk score

| Molecule | rho | p-value | FDR | Assay | Accession ID |
|---|---|---|---|---|---|
| TGL | 0.52 | 1.32E−06 | 7.01E−04 | Clinical labs | |
| L-Cysteinylglycine disulfide | −0.45 | 3.48E−05 | 7.28E−03 | Metabolome | HMDB00709 |
| A1C | 0.45 | 4.12E−05 | 7.28E−03 | Clinical labs | |
| 2,3-Dihydroxyvaleric acid (1) | 0.43 | 8.76E−05 | 7.89E−03 | Metabolome | HMDB00421 |
| LysoPC(16:0) | 0.42 | 1.42E−04 | 7.89E−03 | Metabolome | HMDB10382 |
| C10:2 FA | 0.42 | 1.49E−04 | 7.89E−03 | Metabolome | |
| SHBG | −0.43 | 9.87E−05 | 7.89E−03 | Proteome | P04278 |
| PROS1 | 0.42 | 1.26E−04 | 7.89E−03 | Proteome | P07225 |
| PLTP | −0.42 | 1.18E−04 | 7.89E−03 | Proteome | P55058 |
| HDL | −0.43 | 9.00E−05 | 7.89E−03 | Clinical labs | |
| L-Proline | −0.41 | 2.50E−04 | 1.21E−02 | Metabolome | HMDB00162 |
| CHOLHDL | 0.40 | 3.37E−04 | 1.49E−02 | Clinical labs | |
| LysoPC(20:2) | 0.39 | 4.87E−04 | 1.99E−02 | Metabolome | HMDB10392 |
| Androstenediol (3beta,17beta) disulfate | 0.38 | 6.66E−04 | 2.52E−02 | Metabolome | HMDB03818 |
| LysoPC(18:2) | 0.37 | 9.43E−04 | 3.33E−02 | Metabolome | HMDB10386 |
| Dihydroxyvitamin D3(2) | 0.35 | 1.56E−03 | 3.52E−02 | Metabolome | HMDB00430 |
| C22:6 FA | 0.36 | 1.45E−03 | 3.52E−02 | Metabolome | HMDB02183 |
| C10:0, OH FA(2) | 0.36 | 1.30E−03 | 3.52E−02 | Metabolome | HMDB02203 |
| N-Acetylserine | 0.36 | 1.10E−03 | 3.52E−02 | Metabolome | HMDB02931 |
| C16:1 FA | 0.35 | 1.59E−03 | 3.52E−02 | Metabolome | HMDB03229 |
| C5 | 0.35 | 1.54E−03 | 3.52E−02 | Proteome | P01031 |
| Ig heavy chain V-III region JON | −0.36 | 1.53E−03 | 3.52E−02 | Proteome | P01780 |
| VEGF | 0.36 | 1.46E−03 | 3.52E−02 | Immunome | P15692 |
| SERPINF1 | 0.36 | 1.22E−03 | 3.52E−02 | Proteome | P36955 |
| Bilirubin | 0.35 | 1.66E−03 | 3.53E−02 | Metabolome | HMDB00054 |
| MGP | 0.35 | 1.89E−03 | 3.81E−02 | Proteome | P08493 |
| LDLHDL | 0.35 | 1.94E−03 | 3.81E−02 | Clinical labs | |
| C10:3 FA(2) | −0.35 | 2.06E−03 | 3.90E−02 | Metabolome | |
| RDW | 0.34 | 2.13E−03 | 3.90E−02 | Clinical labs | |
| PDGFBB | 0.34 | 2.32E−03 | 4.10E−02 | Immunome | P01127 |
| CFH | 0.34 | 2.40E−03 | 4.11E−02 | Proteome | P08603 |
| Dihydroxyvitamin D3(1) | 0.34 | 2.58E−03 | 4.17E−02 | Metabolome | HMDB00430 |
| Chenodeoxycholic acid glycine conjugate(2) | 0.34 | 2.60E−03 | 4.17E−02 | Metabolome | HMDB00637 |
| 3-Methyl-2-oxovaleric acid | 0.34 | 2.69E−03 | 4.19E−02 | Metabolome | HMDB03736 |
| C8:0, OH FA(2) | 0.34 | 2.77E−03 | 4.20E−02 | Metabolome | |
| Ne-Methyl-Lysine | 0.33 | 3.12E−03 | 4.60E−02 | Metabolome | HMDB02038 |
| LysoPC(P-18:1) | 0.33 | 3.21E−03 | 4.60E−02 | Metabolome | HMDB10408 |
| gamma-glutamyl-epsilon-lysine | 0.33 | 3.42E−03 | 4.77E−02 | Metabolome | HMDB03869 |
| 1-Methylxanthine | 0.33 | 3.66E−03 | 4.98E−02 | Metabolome | HMDB10738 |
| NUP205 | −0.32 | 3.97E−03 | 5.26E−02 | Proteome | Q92621 |
| PZP | −0.32 | 4.16E−03 | 5.36E−02 | Proteome | P20742 |
| GPLD1 | 0.32 | 4.24E−03 | 5.36E−02 | Proteome | P80108 |

TABLE 17-continued

Multiomics Associations with Adjusted Atherosclerotic Cardiovascular Disease Risk score

| Molecule | rho | p-value | FDR | Assay | Accession ID |
| --- | --- | --- | --- | --- | --- |
| LysoPE(P-16:0) | 0.32 | 4.57E-03 | 5.63E-02 | Metabolome | HMDB11152 |
| L-a-Hydroxyisovaleric acid | −0.32 | 4.80E-03 | 5.66E-02 | Metabolome | HMDB00709 |
| LysoPC(18:0) | 0.32 | 4.81E-03 | 5.66E-02 | Metabolome | HMDB10384 |
| Hypoxanthine | 0.32 | 5.06E-03 | 5.83E-02 | Metabolome | HMDB00157 |
| Homoarginine | 0.32 | 5.26E-03 | 5.93E-02 | Metabolome | HMDB00670 |
| VTN | 0.31 | 5.51E-03 | 5.96E-02 | Proteome | P04004 |
| IL2 | 0.31 | 5.46E-03 | 5.96E-02 | Immunome | P60568 |
| MONOAB | 0.31 | 5.71E-03 | 6.06E-02 | Clinical labs | |
| Ig kappa chain V-I region HK101 | −0.31 | 6.22E-03 | 6.33E-02 | Proteome | P01601 |
| CAPZB | −0.31 | 6.31E-03 | 6.33E-02 | Proteome | P47756 |
| APOC4 | 0.31 | 6.33E-03 | 6.33E-02 | Proteome | P55056 |
| Ig lambda chain V-VI region SUT | −0.31 | 6.50E-03 | 6.38E-02 | Proteome | P06317 |
| AMBP | 0.31 | 6.98E-03 | 6.72E-02 | Proteome | P02760 |
| C12:1 AC | 0.30 | 7.82E-03 | 7.40E-02 | Metabolome | HMDB13326 |
| L-Formylkynurenine | −0.30 | 8.02E-03 | 7.41E-02 | Metabolome | HMDB60485 |
| IGFALS | −0.30 | 8.11E-03 | 7.41E-02 | Proteome | P35858 |
| A2M | −0.30 | 8.38E-03 | 7.53E-02 | Proteome | P01023 |
| Glycerophosphocholine | 0.30 | 9.18E-03 | 7.73E-02 | Metabolome | HMDB00086 |
| L-Lactic acid | 0.30 | 8.81E-03 | 7.73E-02 | Metabolome | HMDB00190 |
| LysoPC(17:0) | 0.30 | 8.92E-03 | 7.73E-02 | Metabolome | HMDB12108 |
| HGF | 0.30 | 9.14E-03 | 7.73E-02 | Immunome | P14210 |
| ORM2 | 0.29 | 9.47E-03 | 7.73E-02 | Proteome | P19652 |
| PON3 | −0.29 | 9.44E-03 | 7.73E-02 | Proteome | Q15166 |
| ATRN(1) | 0.29 | 1.01E-02 | 8.13E-02 | Proteome | O75882 |
| IGKC | −0.29 | 1.06E-02 | 8.36E-02 | Proteome | P01834 |
| IGF2R | −0.29 | 1.16E-02 | 8.77E-02 | Proteome | P11717 |
| ITIH2 | 0.29 | 1.15E-02 | 8.77E-02 | Proteome | P19823 |
| IGLL5 | −0.28 | 1.23E-02 | 8.78E-02 | Proteome | B9A064 |
| 3-indoxyl sulfate | 0.29 | 1.19E-02 | 8.78E-02 | Metabolome | HMDB00682 |
| LysoPC(P-16:0) | −0.28 | 1.22E-02 | 8.78E-02 | Metabolome | HMDB10407 |
| LGALS3BP | 0.28 | 1.22E-02 | 8.78E-02 | Proteome | Q08380 |
| LRG1 | −0.28 | 1.28E-02 | 9.02E-02 | Proteome | P02750 |
| Creatinine | 0.28 | 1.30E-02 | 9.04E-02 | Metabolome | HMDB00562 |
| C10:1 AC | 0.28 | 1.34E-02 | 9.25E-02 | Metabolome | HMDB13205 |
| LysoPE(20:0) | 0.28 | 1.37E-02 | 9.32E-02 | Metabolome | HMDB11481 |
| IP10 | 0.28 | 1.41E-02 | 9.44E-02 | Immunome | P02778 |
| Tetrahydroaldosterone-3-glucuronide(1) | 0.28 | 1.43E-02 | 9.48E-02 | Metabolome | HMDB10357 |
| APOC3 | 0.27 | 1.55E-02 | 1.02E-01 | Proteome | P02656 |
| gamma-glutamylleucine(1) | −0.27 | 1.58E-02 | 1.02E-01 | Metabolome | HMDB11171 |
| 3-Indolepropionic acid | 0.27 | 1.62E-02 | 1.03E-01 | Metabolome | HMDB02302 |
| Imidazolelactic acid | 0.27 | 1.61E-02 | 1.03E-01 | Metabolome | HMDB02320 |
| gamma-CEHC | 0.27 | 1.65E-02 | 1.03E-01 | Metabolome | HMDB01931 |
| C16:0, OH FA(2) | 0.27 | 1.68E-02 | 1.04E-01 | Metabolome | HMDB31057 |
| C9:0, DC FA (Azelaic acid) | 0.27 | 1.89E-02 | 1.04E-01 | Metabolome | HMDB00784 |
| C10:3 AC(1) | 0.27 | 1.88E-02 | 1.04E-01 | Metabolome | |
| C12:1, DC FA(2) | −0.27 | 1.86E-02 | 1.04E-01 | Metabolome | |
| Dihydroferulic acid | 0.27 | 1.82E-02 | 1.04E-01 | Metabolome | |
| Hexosamine | −0.27 | 1.85E-02 | 1.04E-01 | Metabolome | |
| FCN3 | 0.27 | 1.73E-02 | 1.04E-01 | Proteome | O75636 |
| Ig heavy chain V-I region HG3 | −0.27 | 1.86E-02 | 1.04E-01 | Proteome | P01743 |
| Ig lambda chain V-VI region EB4 | −0.27 | 1.80E-02 | 1.04E-01 | Proteome | P06319 |
| DYNC1H1 | −0.27 | 1.75E-02 | 1.04E-01 | Proteome | Q14204 |
| NHDL | 0.27 | 1.81E-02 | 1.04E-01 | Clinical labs | |
| LysoPI(20:4) | 0.26 | 2.03E-02 | 1.09E-01 | Metabolome | HMDB61690 |
| APOH | 0.26 | 2.03E-02 | 1.09E-01 | Proteome | P02749 |
| PON1 | −0.26 | 2.04E-02 | 1.09E-01 | Proteome | P27169 |
| C11:1 FA | 0.26 | 2.09E-02 | 1.10E-01 | Metabolome | HMDB33724 |
| C3 | 0.26 | 2.11E-02 | 1.10E-01 | Proteome | P01024 |
| SCP2 | 0.26 | 2.11E-02 | 1.10E-01 | Proteome | P22307 |
| IGHG1 | −0.26 | 2.23E-02 | 1.15E-01 | Proteome | P01857 |
| HPX | 0.26 | 2.31E-02 | 1.18E-01 | Proteome | P02790 |
| IL17F | 0.26 | 2.35E-02 | 1.19E-01 | Immunome | Q96PD4 |
| Taurine | −0.26 | 2.44E-02 | 1.22E-01 | Metabolome | HMDB00251 |
| Chenodeoxycholic acid 3-sulfate | 0.26 | 2.47E-02 | 1.22E-01 | Metabolome | HMDB02639 |
| ITIH1 | 0.26 | 2.51E-02 | 1.23E-01 | Proteome | P19827 |
| C12:2, OH FA | 0.25 | 2.54E-02 | 1.23E-01 | Metabolome | |
| LysoPE(20:2) | 0.25 | 2.60E-02 | 1.25E-01 | Metabolome | HMDB11483 |
| Alpha-N-Phenylacetyl-L-glutamine | 0.25 | 2.63E-02 | 1.25E-01 | Metabolome | HMDB06344 |
| C4:0 AC | 0.25 | 2.68E-02 | 1.27E-01 | Metabolome | HMDB02013 |
| C18:3, OH FA(1) | 0.25 | 2.70E-02 | 1.27E-01 | Metabolome | |
| TGFB | 0.25 | 2.77E-02 | 1.28E-01 | Immunome | P01137 |
| APOC2 | 0.25 | 2.76E-02 | 1.28E-01 | Proteome | P02655 |
| C12:0 FA(1) | 0.25 | 2.92E-02 | 1.32E-01 | Metabolome | |
| SERPINA6 | −0.25 | 2.90E-02 | 1.32E-01 | Proteome | P08185 |
| ATP11B | 0.25 | 2.94E-02 | 1.32E-01 | Proteome | Q9Y2G3 |

TABLE 17-continued

Multiomics Associations with Adjusted Atherosclerotic Cardiovascular Disease Risk score

| Molecule | rho | p-value | FDR | Assay | Accession ID |
|---|---|---|---|---|---|
| C8:1 AC | 0.25 | 3.02E−02 | 1.33E−01 | Metabolome | HMDB13324 |
| C8:0, OH FA(1) | 0.25 | 3.02E−02 | 1.33E−01 | Metabolome | |
| IGFBP3 | −0.25 | 3.07E−02 | 1.35E−01 | Proteome | P17936 |
| Ig lambda chain V-IV region Hil | −0.25 | 3.11E−02 | 1.35E−01 | Proteome | P01717 |
| LysoPE(20:1) | 0.25 | 3.17E−02 | 1.37E−01 | Metabolome | HMDB11482 |
| C9:0 AC | 0.24 | 3.29E−02 | 1.40E−01 | Metabolome | |
| C12:0 AC | 0.24 | 3.35E−02 | 1.42E−01 | Metabolome | HMDB02250 |
| L-Cystine | −0.24 | 3.41E−02 | 1.43E−01 | Metabolome | HMDB00192 |
| 7-Methylguanine | 0.24 | 3.39E−02 | 1.43E−01 | Metabolome | HMDB00897 |
| pro-hydroxy-pro(2) | −0.24 | 3.54E−02 | 1.47E−01 | Metabolome | HMDB06695 |
| Ig lambda chain V-III region SH | −0.24 | 3.57E−02 | 1.47E−01 | Proteome | P01714 |
| VCL | 0.24 | 3.71E−02 | 1.51E−01 | Proteome | P18206 |
| ABCF1 | −0.24 | 3.80E−02 | 1.54E−01 | Proteome | Q8NE71 |
| 1-Methylhistidine | 0.23 | 3.99E−02 | 1.59E−01 | Metabolome | HMDB00001 |
| 5alpha-Androstan-3alpha, 17alpha-diol monosulfate(3) | 0.23 | 3.98E−02 | 1.59E−01 | Metabolome | |
| C18:3 FA | 0.23 | 4.11E−02 | 1.61E−01 | Metabolome | HMDB03073 |
| C16:1 AC | 0.23 | 4.15E−02 | 1.61E−01 | Metabolome | |
| Ig kappa chain V-I region Roy | −0.23 | 4.13E−02 | 1.61E−01 | Proteome | P01608 |
| MONO | 0.23 | 4.07E−02 | 1.61E−01 | Clinical labs | |
| L-Glutamic acid | −0.23 | 4.22E−02 | 1.62E−01 | Metabolome | HMDB00148 |
| ENA78 | −0.23 | 4.31E−02 | 1.62E−01 | Immunome | P42830 |
| ILK | 0.23 | 4.29E−02 | 1.62E−01 | Proteome | Q13418 |
| HCT | 0.23 | 4.26E−02 | 1.62E−01 | Clinical labs | |
| SERPING1 | 0.23 | 4.46E−02 | 1.64E−01 | Proteome | P05155 |
| INHBC | 0.23 | 4.40E−02 | 1.64E−01 | Proteome | P55103 |
| GLU | 0.23 | 4.44E−02 | 1.64E−01 | Clinical labs | |
| MIG | 0.23 | 4.61E−02 | 1.69E−01 | Immunome | Q07325 |
| L-Carnitine | 0.23 | 4.72E−02 | 1.71E−01 | Metabolome | HMDB00062 |
| 4-formyl Indole(1) | 0.23 | 4.73E−02 | 1.71E−01 | Metabolome | |
| PRG4(1) | 0.23 | 4.81E−02 | 1.72E−01 | Proteome | Q92954 |
| CR | 0.23 | 4.90E−02 | 1.75E−01 | Clinical labs | |
| Ig heavy chain V-III region WEA | −0.22 | 5.00E−02 | 1.77E−01 | Proteome | P01763 |
| AFM | 0.22 | 5.12E−02 | 1.80E−01 | Proteome | P43652 |
| Ig kappa chain V-I region Scw | −0.22 | 5.18E−02 | 1.81E−01 | Proteome | P01609 |
| Glycine | 0.22 | 5.30E−02 | 1.82E−01 | Metabolome | HMDB00123 |
| L-Cysteine | −0.22 | 5.26E−02 | 1.82E−01 | Metabolome | HMDB00574 |
| Gluconic acid | 0.22 | 5.39E−02 | 1.82E−01 | Metabolome | HMDB00625 |
| Arabonate | Xylonate(3) | 0.22 | 5.39E−02 | 1.82E−01 | Metabolome | |
| PAI1 | 0.22 | 5.33E−02 | 1.82E−01 | Immunome | P05121 |
| HABP2 | −0.22 | 5.43E−02 | 1.82E−01 | Proteome | Q14520 |
| 2-Aminobutyrate | 0.22 | 5.51E−02 | 1.84E−01 | Metabolome | HMDB00650 |
| EOSAB | 0.22 | 5.56E−02 | 1.84E−01 | Clinical labs | |
| SAA2 | 0.22 | 5.69E−02 | 1.87E−01 | Proteome | P0DJI9 |
| C12:1 FA(2) | 0.22 | 5.89E−02 | 1.91E−01 | Metabolome | HMDB00529 |
| gamma-glutamylthreonine(1) | 0.22 | 5.84E−02 | 1.91E−01 | Metabolome | HMDB29159 |
| Dihydro-3-coumaric acid | 0.22 | 5.87E−02 | 1.91E−01 | Metabolome | |
| Acetylcholine | 0.22 | 5.98E−02 | 1.92E−01 | Metabolome | HMDB00895 |
| ADIPOQ | −0.21 | 6.06E−02 | 1.93E−01 | Proteome | Q15848 |
| Butyric acid|Isobutyric acid | 0.21 | 6.19E−02 | 1.97E−01 | Metabolome | HMDB00039|HMDB01873 |
| MIP1B | 0.21 | 6.30E−02 | 1.97E−01 | Immunome | P13236 |
| SERPINA4 | 0.21 | 6.32E−02 | 1.97E−01 | Proteome | P29622 |
| MCP3 | 0.21 | 6.26E−02 | 1.97E−01 | Immunome | P80098 |
| C18:0, DC FA(3) | −0.21 | 6.53E−02 | 1.98E−01 | Metabolome | HMDB00782 |
| C18:0, OH FA(1) | 0.21 | 6.47E−02 | 1.98E−01 | Metabolome | |
| C8:2, OH FA(1) | −0.21 | 6.50E−02 | 1.98E−01 | Metabolome | |
| methyl-4-hydroxybenzoate sulfate | −0.21 | 6.43E−02 | 1.98E−01 | Metabolome | |
| GP1BA | 0.21 | 6.46E−02 | 1.98E−01 | Proteome | P07359 |
| Asp-Asp | 0.21 | 6.60E−02 | 1.99E−01 | Metabolome | |

Spearman correlations were calculated between ASCVD risk scores and the median level of circulating molecules across healthy visits in individuals with at least 3 healthy visits (n = 77). Correlation significance was then calculated and corrected for multiple testing using the q-value package in R.

TABLE 18

Atherosclerotic Cardiovascular Disease Correlation Network Molecule Key

| Metabolites | Number | Super Pathway |
|---|---|---|
| 3-Indolepropionic acid | 1 | Amino Acid |
| 3-indoxyl sulfate | 2 | Amino Acid |
| 3-Methyl-2-oxovaleric acid | 3 | Amino Acid |
| 4-formyl Indole(1) | 4 | Amino Acid |
| Creatinine | 5 | Amino Acid |
| Glycine | 6 | Amino Acid |
| L-Cysteine | 7 | Amino Acid |
| L-Cysteinylglycine disulfide | 8 | Amino Acid |

TABLE 18-continued

Atherosclerotic Cardiovascular Disease
Correlation Network Molecule Key

| Metabolites | Number | Super Pathway |
|---|---|---|
| L-Cystine | 9 | Amino Acid |
| L-Glutamic acid | 10 | Amino Acid |
| L-Proline | 11 | Amino Acid |
| N-Acetylserine | 12 | Amino Acid |
| Ne-Methyl-Lysine | 13 | Amino Acid |
| Taurine | 14 | Amino Acid |
| Gluconic acid | 15 | Carbohydrate |
| Hexosamine | 16 | Carbohydrate |
| L-Lactic acid | 17 | Carbohydrate |
| Acetylcholine | 18 | Lipid |
| C10:0, OH FA(2) | 19 | Lipid |
| C10:1 AC | 20 | Lipid |
| C10:2 FA | 21 | Lipid |
| C10:3 AC(1) | 22 | Lipid |
| C10:3 FA(2) | 23 | Lipid |
| C11:1 FA | 24 | Lipid |
| C12:0 AC | 25 | Lipid |
| C12:0 FA(1) | 26 | Lipid |
| C12:1 AC | 27 | Lipid |
| C12:1 FA(2) | 28 | Lipid |
| C12:1, DC FA(2) | 29 | Lipid |
| C12:2, OH FA | 30 | Lipid |
| C16:0, OH FA(2) | 31 | Lipid |
| C16:1 AC | 32 | Lipid |
| C16:1 FA | 33 | Lipid |
| C18:0, DC FA(3) | 34 | Lipid |
| C18:0, OH FA(1) | 35 | Lipid |
| C18:3 FA | 36 | Lipid |
| C18:3, OH FA(1) | 37 | Lipid |
| C22:6 FA | 38 | Lipid |
| C4:0 AC | 39 | Lipid |
| C8:0, OH FA(1) | 40 | Lipid |
| C8:0, OH FA(2) | 41 | Lipid |
| C8:1 AC | 42 | Lipid |
| C8:2, OH FA(1) | 43 | Lipid |
| C9:0 AC | 44 | Lipid |
| C9:0, DC FA (Azelaic acid) | 45 | Lipid |
| Glycerophosphocholine | 46 | Lipid |
| L-Carnitine | 47 | Lipid |
| LysoPC(16:0) | 48 | Lipid |
| LysoPC(17:0) | 49 | Lipid |
| LysoPC(18:0) | 50 | Lipid |
| LysoPC(18:2) | 51 | Lipid |
| LysoPC(20:2) | 52 | Lipid |
| LysoPC(P-16:0) | 53 | Lipid |
| LysoPC(P-18:1) | 54 | Lipid |
| LysoPE(20:0) | 55 | Lipid |
| LysoPE(20:1) | 56 | Lipid |
| LysoPE(20:2) | 57 | Lipid |
| LysoPE(P-16:0) | 58 | Lipid |
| LysoPI(20:4) | 59 | Lipid |
| 7-Methylguanine | 60 | Nucleotide |
| Hypoxanthine | 61 | Nucleotide |
| gamma-glutamyl-epsilon-lysine | 62 | Peptide |
| gamma-glutamylleucine(1) | 63 | Peptide |
| 1-Methylxanthine | 64 | Xenobiotics |
| Dihydro-3-coumaric acid | 65 | Xenobiotics |
| 1-Methylhistidine | 66 | Amino Acid |
| 2-Aminobutyrate | 67 | Amino Acid |
| Homoarginine | 68 | Amino Acid |
| Imidazolelactic acid | 69 | Amino Acid |
| L-Formylkynurenine | 70 | Amino Acid |
| L-a-Hydroxyisovaleric acid | 71 | Amino Acid |
| pro-hydroxy-pro(2) | 72 | Amino Acid |
| Arabonate \| Xylonate(3) | 73 | Carbohydrate |
| 2,3-Dihydroxyvaleric acid(1) | 74 | Cofactors and Vitamins |
| Bilirubin | 75 | Cofactors and Vitamins |
| Dihydroxyvitamin D3(1) | 76 | Cofactors and Vitamins |
| Dihydroxyvitamin D3(2) | 77 | Cofactors and Vitamins |
| gamma-CEHC | 78 | Cofactors and Vitamins |
| 5alpha-Androstan-3alpha, 17alpha-diol monosulfate(3) | 79 | Lipid |
| Androstenediol (3beta, 17beta) disulfate | 80 | Lipid |
| Chenodeoxycholic acid 3-sulfate | 81 | Lipid |
| Chenodeoxycholic acid glycine conjugate(2) | 82 | Lipid |
| Tetrahydroaldosterone-3-glucuronide(1) | 83 | Lipid |
| Alpha-N-Phenylacetyl-L-glutamine | 84 | Peptide |
| Asp-Asp | 85 | Peptide |
| gamma-glutamylthreonine(1) | 86 | Peptide |
| Dihydroferulic acid | 87 | Xenobiotics |
| methyl-4-hydroxybenzoate sulfate | 88 | Xenobiotics |
| Butyric acid\|Isobutyric acid | 89 | Energy |

What is claimed is:

1. A method to perform a treatment on an individual, comprising:

obtaining a panel of analyte measurements, wherein the analytes have been extracted from an individual;

entering the measurements of analytes as features in a computational predictive model to predict a steady-state plasma glucose level of the individual, wherein the computational predictive model has been trained utilizing data derived from a collection of individuals that have had their steady-state plasma glucose level clinically evaluated and their analytes extracted and measured;

receiving a diagnosis from the computational model that the individual has an elevated steady-state plasma glucose level; and based on the received diagnosis that the individual has an elevated steady-state glucose level, treating the individual to lower the individual's elevated steady-state plasma glucose.

2. The method according to claim 1, wherein at least one analyte measurement of the panel of analyte measurements is a measurement of one of the following: metabolites, protein constituents, genomic DNA, transcript expression, lipids, and human microbiota.

3. The method according to claim 1, wherein at least one analyte measurement of the panel of analyte measurements is a measurement of one of the following: triglycerides-to-high density lipoprotein ratio (TGL/HDL), creatine (CR), body mass index (BMI), absolute count of neutrophils (NEUTAB), calcium (CA), interleukin 1 beta (IL1B), interleukin 18 (IL18), angiotensinogen protein (AGT), interleukin 1 receptor accessory protein (IL1RAP), Ig kappa chain V-I region protein (KV116), complement factor H protein (CFH), myosin-binding protein C (MYBPC2), L-lysine (Lys), L-arginine (Arg), L-alanine (Ala), N1-methyladenosine, 4-formyl Indole, 3-Methyl-L-histidine, C7H15N3O2, C14H22N2O9, C12H24N2O3, C26H42O4, C28H46O4, C28H44O4, LysoPG(18:0), C16:3 FA, hexosylceramide HCER(24:0), lactosylceramide LCER(16:0), glycerophosphoethanolamine PE(P-18:0/22:6), PE(P-16:0/22:6) and PE(P-18:1/18:1), triacylglycerol TAG(58:10) containing fatty acid FA(20:5), chromosome 19 open reading frame 66 transcript (C19orf66), chromosome 1 open reading frame 174 transcript (C1orf174), calcineurin like EF-hand protein 1 transcript (CHP1), deoxyguanosine kinase transcript (DGUOK), Disks large-associated protein 1 transcript (DLGAP1), family with sequence similarity 86 member H pseudogene transcript (FAM86HP), family with sequence similarity 185 member A pseudogene transcript (FAM185A), heat shock cognate B transcript (HSCB), IL12A antisense RNA 1 (IL12A-AS1), interleukin 26 transcript (IL26), kyphoscoliosis peptidase transcript (KY), mitogen-activated protein kinase kinase kinase 19 transcript (MAP3K19), protein geranylgeranyltransferase type I subunit beta transcript (PGGT1B), POC5 centriolar protein transcript (POC5), UBAP1-MVB12-associated (UMA) domain containing 1 transcript (RPA3OS), serine/threonine-protein kinase 494 transcript (SGK494), solute carrier family 16 member 12 transcript (SLC16A12), synaptotagmin 9 transcript (SYT9), transmembrane protein 237 transcript (TMEM237), transmembrane protein 253 transcript (TMEM253), transmembrane protein 108 transcript (TMEM108), transmembrane protein 106B transcript (TMEM106B), U2AF homology motif kinase 1 transcript (UHMK1), vacuolar protein sorting 13 homolog A transcript (VPS13A), *Bacteroides* bacteria, Barnesiella bacteria, *Clostridium* bacteria, *Faecalibacterium* bacteria, *Ruminococcus* bacteria, *Bacteroides*, *Shigella* bacteria, Lachnospiraceae bacteria, and *Odoribacter* bacteria.

4. The method according to claim 1, wherein at least one analyte measurement feature of the analyte measurements features entered in the prediction model is selected as a feature in the predictive model based upon results of a second computational model that determines a relationship between steady-state plasma glucose and the at least one analyte measurement feature.

5. The method according to claim 4, wherein the second computational model is a Bayesian computational model.

6. The method according to claim 1, wherein the predictive computational model is a ridge regression.

7. The method according to claim 1, wherein the computed steady-state glucose level is above a threshold.

8. The method according to claim 1, wherein the treating the individual is administration of a medication selected from the group consisting of: insulin, alpha-glucosidase inhibitors, biguanides, dopamine agonists, DPP-4 inhibitors, GLP-1 receptor agonists, meglitinides, sodium glucose transporter 2 inhibitors, sulfonylureas, and thiazolidinediones.

9. The method according to claim 1, wherein an insulin suppression test was performed on each individual of the collection of individuals to clinically evaluate their steady-state plasma glucose level.

10. The method accordingly to claim 9, wherein the insulin suppression test involved infusion of octreotide to suppress insulin in each individual.

11. A method to treat an individual, comprising:

obtaining a panel of analyte measurements, wherein the analytes have been extracted from an individual;

entering the measurements of analytes as features in a computational predictive model to predict an oral glucose tolerance test result of the individual, wherein the computational predictive model has been trained utilizing data derived from a collection of individuals that have had their oral glucose tolerance clinically evaluated and their analytes extracted and measured;

receiving a diagnosis from the computational model that the individual has an elevated oral glucose tolerance test result; and based on the received diagnosis that the individual has an elevated oral glucose tolerance test result, treating the individual to improve the individual's oral glucose tolerance.

12. The method according to claim 11, wherein at least one analyte measurement of the panel of analyte measurements is a measurement of one of the following: metabolites, protein constituents, genomic DNA, transcript expression, lipids, and human microbiota.

13. The method according to claim 11, wherein at least one analyte measurement of the panel of analyte measurements is a measurement of one of the following: hemoglobin A1C (A1C), alanine aminotransferase (ALT), cytokine platelet-derived growth factor subunit B homodimer (PDGFBB), complement factor D protein (CFD), Ig kappa variable 2D-28 protein (KVD28), Ig heavy constant alpha 2 protein (IGHA2), coagulation factor XI protein (F11), Ig kappa variable 310 protein (KV310), Ig heavy variable 2-70 protein (HV270), vitronectin protein (VTN), hexosamine, taurine, hydroxyphenyllactic acid, hippuric acid, ectoine, p-cresol glucuronide, hydroxy-stearic acid (C18:0,0H FA), dihydroxy-palmitic acid (C16:0,2OH), a-linolenic acid (C18:3 FA), chitobiosyldiphosphodolichol beta-mannosyltransferase like 2 transcript (ALG1L2), chromosome 21 open reading frame 119 transcript (C21orf119), carbohydrate sulfotransferase 3 transcript (CHST3), D-dopachrome tautomerase transcript (DDT), F-box protein 40 transcript (FBXO40), glutamic-pyruvic transaminase 2 transcript (GPT2), keratin 10 transcript (KRT10), LINC01093 transcript, receptor activity modifying protein 3 transcript (RAMP3), ring finger protein 214 transcript (RNF214), unc-93 homolog B1 transcript (UNC93B1), wee1-like protein kinase 2 transcript (WEE2), ceramide synthase 5 transcript (CERS5), disheveled associated activator of morphogenesis 1 transcript (DAAM1), family with sequence similarity 86 member H pseudogene transcript (FAM86HP), filaggrin transcript (FLG), macrophage migration inhibitory factor transcript (MIF), zinc finger protein 596 transcript (ZNF596), *Bacteroides* bacteria, Lachnospiraceae bacteria, *Roseburia* bacteria, and *Faecalibacterium* bacteria.

14. The method according to claim 11, wherein at least one analyte measurement feature of the analyte measurements features entered in the prediction model is selected as a feature in the predictive model based upon results of a second computational model that determines a relationship between glucose tolerance and the at least one analyte measurement feature.

15. The method according to claim 14, wherein the second computation model is a Bayesian computational model.

16. The method according to claim 11, wherein the first computational model is a ridge regression.

17. The method according to claim 11, wherein the computed oral glucose tolerance test result is above a threshold.

18. The method according to claim 11, wherein the treating the individual is administration of a medication selected from the group consisting of: insulin, alpha-glucosidase inhibitors, biguanides, dopamine agonists, DPP-4 inhibitors, GLP-1 receptor agonists, meglitinides, sodium glucose transporter 2 inhibitors, sulfonylureas, and thiazolidinediones.

19. The method according to claim 11, wherein an oral glucose tolerance test was performed on each individual of the collection of individuals to clinically evaluate their oral glucose tolerance.

20. The method accordingly to claim 19, wherein the oral glucose tolerance test involved each individual receiving a standardized dose of glucose.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
agagtttgat cctggctcag                                          20

<210> SEQ ID NO 2
<211> LENGTH: 17
<212> TYPE: DNA
<213> ORGANISM: Homo sapiens

<400> SEQUENCE: 2
attaccgcgg ctgctgg                                             17
```